US011149083B2

(12) United States Patent
Amann et al.

(10) Patent No.: US 11,149,083 B2
(45) Date of Patent: Oct. 19, 2021

(54) ANTIGEN BINDING MOLECULES COMPRISING A TNF FAMILY LIGAND TRIMER AND A TENASCIN BINDING MOIETY

(71) Applicant: Hoffmann—La Roche Inc., Little Falls, NJ (US)

(72) Inventors: Maria Amann, Schlieren (CH); Peter Bruenker, Schlieren (CH); Christina Claus, Schlieren (CH); Claudia Ferrara Koller, Schlieren (CH); Sandra Grau-Richards, Schlieren (CH); Christian Klein, Schlieren (CH); Viktor Levitski, Schlieren (CH); Ekkehard Moessner, Schlieren (CH); Pablo Umana, Schlieren (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/186,443

(22) Filed: Nov. 9, 2018

(65) Prior Publication Data

US 2019/0248877 A1 Aug. 15, 2019

Related U.S. Application Data

(63) Continuation of application No. PCT/EP2017/060870, filed on May 8, 2017.

(30) Foreign Application Priority Data

May 11, 2016 (EP) .................................... 16169244

(51) Int. Cl.

| | |
|---|---|
| ***C07K 16/18*** | (2006.01) |
| ***A61K 47/65*** | (2017.01) |
| ***A61P 35/00*** | (2006.01) |
| ***C07K 14/525*** | (2006.01) |
| ***A61K 47/68*** | (2017.01) |
| ***C07K 14/715*** | (2006.01) |
| ***C07K 16/24*** | (2006.01) |

(52) U.S. Cl.

CPC .............. *C07K 16/18* (2013.01); *A61K 47/65* (2017.08); *A61K 47/6813* (2017.08); *A61K 47/6845* (2017.08); *A61P 35/00* (2018.01); *C07K 14/525* (2013.01); *C07K 14/7151* (2013.01); *C07K 16/241* (2013.01); *C07K 2319/30* (2013.01)

(58) Field of Classification Search

CPC .... C07K 16/18; C07K 16/241; C07K 14/525; C07K 14/7151; C07K 2319/30; A61K 47/6813; A61K 47/6845; A61K 47/65; A61P 35/00

See application file for complete search history.

(56) References Cited

U.S. PATENT DOCUMENTS 7,968,685 B2 6/2011 Brack et al.

FOREIGN PATENT DOCUMENTS

| | | | |
|---|---|---|---|
| EP | 1173766 | B1 | 9/2004 |
| EP | 2 009 022 | A1 | 12/2008 |
| EP | 1817345 | B1 | 5/2009 |
| JP | 2013-543373 | | 12/2013 |
| WO | 2006/050834 | A2 | 5/2006 |
| WO | 2006/050834 | A3 | 5/2006 |
| WO | 2009/000538 | | 12/2008 |
| WO | 2009/089998 | A1 | 7/2009 |
| WO | 2012/020038 | A1 | 2/2012 |
| WO | 2012/130831 | | 10/2012 |
| WO | 2016/075278 | A1 | 5/2016 |

OTHER PUBLICATIONS

Aggarwal et al., "Signalling pathways of the TNF superfamily: a double-edged sword" Nat Rev Immunol 3(9):745-756 (Sep. 2003).
Banner et al., "Crystal Structure of the Soluble Human 55 kd TNF Receptor-Human TNFβ Complex: Implications for TNF Receptor Activation" Cell 73:431-445 ( 1993).
Berg et al., "Enforced covalent trimerization increases the activity of the TNF ligand family members TRAIL and CD95L" Cell Death and Differentiation, Nature 14:2021-2034 ( 2007).
Bodmer et al., "The molecular architecture of the TNF superfamily" Trends Biochem Sci 27(1):19-26 (Jan. 2002).
Borsi et al., "Expression of different tenascin isoforms in normal, hyperplastic and neoplastic human breast tissues" Int J Cancer 52:688-692 ( 1992).
Broll et al., "CD137 Expression in Tumor Vessel Walls High Correlation With Malignant Tumors" Am. J. Chin. Pathol 115:543-549 ( 2001).
Buechele et al., "4-1BB ligand modulates direct and Rituximab-induced NK-cell reactivity in chronic lymphocytic leukemia" Eur. J. Immunol. 42:737-748 ( 2012).
Carnemolla et al., "Comparison of human tenascin expression in normal, Simian-virus-40-transformed and tumor-derived cell lines" Eur J Biochem 205:561-567 ( 1992).
Chiquet-Ehrismann and Chiquet, "Tenascins: regulation and putative functions during pathological stress" J Pathol 200:488-499 ( 2003).

(Continued)

*Primary Examiner* — Robert S Landsman
(74) *Attorney, Agent, or Firm* — Linda Wu

(57) ABSTRACT

The invention relates to novel TNF family ligand trimer-containing antigen binding molecules comprising (a) at least one antigen binding moiety capable of specific binding to Tenascin-C (TnC) and (b) a first and a second polypeptide that are linked to each other by a disulfide bond, wherein the antigen binding molecules are characterized in that the first polypeptide comprises two ectodomains of a TNF ligand family member or two fragments thereof that are connected to each other by a peptide linker and in that the second polypeptide comprises only one ectodomain of said TNF ligand family member or a fragment thereof. The invention further relates to methods of producing these molecules and to methods of using the same.

25 Claims, 27 Drawing Sheets

Specification includes a Sequence Listing.

(56) References Cited

OTHER PUBLICATIONS

Cuadros et al., "Vaccination with dendritic cells pulsed with apoptotic tumors in combination with anti-OX40 and anti-4-1BB monoclonal antibodies induces T cell-mediated protective immunity in Her-2/neu transgenic mice." Int J Cancer 116:934-943 ( 2005).
Curran et al., "Combination CTLA-4 blockade and 4-1BB activation enhances tumor rejection by increasing T-cell infiltration, proliferation, and cytokine production." PLoS One 6(4):e19499. (Apr. 2011).
Diehl et al., "In Vivo Triggering Through 4-1BB Enables Th-Independent Priming of CTL in the Presence of an Intact CD28 Costimulatory Pathway" J Immunol 168:3755-3762 ( 2002).
Dubrot et al., "Treatment with anti-CD137 mAbs causes intense accumulations of liver T cells without selective antitumor immunotherapeutic effects in this organ" Cancer Immunol Immunother 59:1223-1233 ( 2010).
Fischer et al., "A TNF Receptor 2 Selective Agonist Rescues Human Neurons from Oxidative Stress-Induced Cell Death" PLoS One 6(11):e27621, (2011).
Futagawa et al., "Expression and function of 4-1 BB and 4-1BB ligand on murine dendritic cells" International Immonology 14:275-286 ( 2002).
Guo et al., "Combined TIM-3 blockade and CD137 activation affords the long-term protection in a murine model of ovarian cancer." J Transl Med 11:215 ( 2013).
Hanamura et al., "Expression of fibronectin and tenascin-C mRNA by myofibroblasts, vascular cells and epithelial cells in human colon adenomas and carcinomas" Int J Cancer 73:10-15 (1997).
Hsia and Schwarzbauer, "Meet the Tenascins: Multifunctional and Mysterious" J Biol Chem 280(29):26641-26644 ( 2005).
ISR and Written Opinion for PCT/EP2017/060870 (dated Jul. 17, 2017).
Kienzle and von Kempis, "CD137 (ILA/4-1BB), expressed by primary human monocytes, induces monocyte activation and apoptosis of B lymphocytes" International Immonology 12:73-82 ( 2000).
Li and Ravetch, "Inhibitory Fcγ Receptor Engagement Drives Adjuvant and Anti-Tumor Activities of Agonistic CD40 Antibodies" Science 333(6045):1030-1034 ( 2011).
Lin et al., "Fc-dependent expression of CD137 on human NK cells: insights into agonistic effects of anti-CD137 monoclonal antibodies" Blood 112(3):699-707 ( 2008).
Melero et al., "Monoclonal Antibodies Against the 4-1BB T-cell Activation Molecule Eradicate Established Tumors" Nature Medicine 3(6):682-685 ( 1997).
Melero et al., "NK1.1 Cells Express 4-1BB (CDw137) Costimulatory Molecule and Are Required for Tumor Immunity Elicited by Anti-4-1BB Monoclonal Antibodies" Cellular Immunology 190:167-172 ( 1998).
Morales-Kastresana et al., "Essential complicity of perforin-granzyme and FAS-L mechanisms to achieve tumor rejection following treatment with anti-CD137 mAb" Journal for ImmunoTherapy of Cancer 1(3):1-6 ( 2013).
Murillo et al., "Therapeutic Antitumor Efficacy of Anti-CD137 Agonistic Monoclonal Antibody in Mouse Models of Myeloma" Clin Cancer Res 14(21):6895-6906 ( 2003).
Narazaki et al., "CD137 agonist antibody prevents cancer recurrence: contribution of CD137 on both hematopoietic and nonhematopoietic cells" Blood 115:1941-1948 ( 2010).
Nishimoto, et al., "Costimulation of mast cells by 4-1BB, a member of the tumor necrosis factor receptor superfamily, with the high-affinity IgE receptor" Blood 106:4241-4248 ( 2005).
Olofsson, et al., "CD137 Is Expressed in Human Atherosclerosis and Promotes Development of Plaque Inflammation in Hypercholesterolemic Mice" Circulation 117:1292-1301 (2008).
Orend and Chiquet-Ehrismann, "Tenascin-C induced signaling in cancer" Cancer Letters 244:143-163 ( 2006).
Palazon et al., "Agonist Anti-CD137 mAb Act on Tumor Endothelial Cells to Enhance Recruitment of Activated T Lymphocytes" Cancer Research 71:801-811 ( 2011).
Schwarz et al., "ILA, the Human 4-1BB Homologue, Is Inducible in Lymphoid and Other Cell Lineages" Blood 85:1043-1052 ( 1995).
Shao and Schwarz, "CD137 ligand, a member of the tumor necrosis factor family, regulates immune responses via reverse signal transduction." J Leukoc Biol 89:21-29 ( 2011).
Shi and Siemann, "Augmented antitumor effects of radiation therapy by 4-1BB antibody (BMS-469492) treatment." Anticancer Res 26:3445-3453 ( 2006).
Simeone and Ascierto, "Immunomodulating antibodies in the treatment of metastatic melanoma: The experience with anti-CTLA-4, anti-CD137, and anti-PD1" Journal of Immunotoxicology 9:241-247 ( 2012).
Snell et al., "T-cell intrinsic effects of GITR and 4-1BB during viral infection and cancer immunotherapy" Immunological Reviews 244:197-217 ( 2011).
Stagg et al., "Anti-ErbB-2 mAb therapy requires type I and II interferons and synergizes with anti-PD-1 or anti-CD137 mAb therapy" PNAS 108(17):7142-7147 ( 2011).
Trebing et al., "CD70-restricted specific activation of TRAILR1 or TRAILR2 using scFv-targeted TRAIL mutants" Cell Death and Disease 5:e1035 ( 2014).
Von Kempis et al., "Differentiation-dependent and stimulus-specific expression of ILA, the human 4-1BB-homologue, in cells of mesenchymal origin" Osteoarthritis and Cartilage 5:394-406 ( 1997).
Wei et al., "Combinatorial PD-1 blockade and CD137 activation has therapeutic efficacy in murine cancer models and synergizes with cisplatin." PLoS One 8(12):e84927 ( 2013).
Wieckowski et al., "Therapeutic efficacy of the F8-IL2 immunocytokine in a metastaticmouse model of lung adenocarcinoma" Lung Cancer 88:9-15 ( 2015).
Wilcox et al., "Ligation of CD137 receptor prevents and reverses established anergy of $CD8^+$ cytolytic T lymphocytes in vivo" Blood 103:177-184 ( 2004).
Wilcox et al., "Provision of antigen and CD137 signaling breaks immunological ignorance, promoting regression of poorly immunogenic tumors" J Clin Invest. 109:651-659 ( 2002).
Wyzgol et al., "Trimer Stabilization, Oligomerization, and Antibody-Mediated Cell Surface Immobilization Improve the Activity of Soluble Trimers of CD27L, CD40L, 41BBL, and Glucocorticoid-Induced TNF Receptor Ligand" Journal of Immunology 183(3):1851-1861 (2009).
Yoshida et al., "CO-expression of tenascin and fibronectin in epithelial and stromal cells of benign lesions and ductal carcinomas in the human breast" J Pathol 182:421-428 ( 1997).
Zhang et al., "CD137 Promotes Proliferation and Survival of Human B Cells" J Immunol 184:787-795 ( 2010).
Ascierto, P. et al., "Clinical Experiences With Anti-CD137 and Anti-PD1 Therapeutic Antibodies" Semin Oncol 27(5):508-516 (Oct. 1, 2010).
Choi, B., et al., "4-1BB Functions as a Survival Factor in Dendritic Cells" J Immunol 182(7):4107-4115 (Apr. 1, 2009).
Heinisch, I., et al., "CD137 activation abrogates granulocytemacrophage colony-stimulating factor-mediated anti-apoptosis in neutrophils" Eur J Immunol 30(12):3441-3446 (Dec. 1, 2000).
Hornig, N., et al., "Combination of a Bispecific Antibody and Costimulatory Antibody-Ligand Fusion Proteins for Targeted Cancer Immunotherapy" J Immunother 35(5):418-429 (Jun. 1, 2012).
Ju, S., et al., "Eradication of established renal cell carcinoma by a combination of 5-fluorouracil and anti-4-1BB monoclonal antibody in mice." Int J Cancer 122(12):2784-2790 (Jun. 15, 2008).
Kim, D., et al., "4-1BB Engagement Costimulates NKT Cell Activation and Exacerbates NKT Cell Ligand-Induced Airway Hyperresponsiveness and Inflammation" J Immunol 180(4):2062-2068 (Feb. 1, 2008).
Kim, Y. H., et al., "Mechanisms involved in synergistic anticancer effects of anti-4-1BB and cyclophosphamide therapy." Mol Cancer Ther 8(2):469-478 (Feb. 1, 2009).
Kwon, B., et al., "cDNA sequences of two inducible T-cell genes" PNAS USA 86(6):1963-1967 (Mar. 1, 1989).

(56) References Cited

OTHER PUBLICATIONS

Lee, H., et al., "Combinatorial therapy for liver metastatic colon cancer: dendritic cell vaccine and low-dose agonistic anti-4-1BB antibody costimulatory signal" J Surg Res 169(1):e43-50 (Jul. 1, 2011).
Levitsky, V., et al., "The clonal composition of a peptide-specific oligoclonal CTL repertoire selected in response to persistent EBV infection is stable over time." J Immunol 161(2):594-601 (Jun. 30, 1998).
Merchant et al., "An Efficient Route to Human Bispecific IgG" Nat Biotechnol. 16:677-681 (Jul. 1998).
Morales-Kastresana, A., Sanmamed, M.F., Rodriguez, I., Palazon, A., Martinez-Forero, I., Labiano, S., Hervas-Stubbs, S., Sangro, B., Ochoa, C., Rouzaut, A., et al. (2013). Combined immunostimulatory monoclonal antibodies extend survival in an aggressive transgenic hepatocellular carcinoma mouse model. Clin Cancer Res 19, 6151-6162.
Mueller, D. et al., "A Novel Antibody—4-1BBL Fusion Protein for Targeted Costimulation in Cancer Immunotherapy" J Immunother 31(8):714-722 (Oct. 1, 2008).
Murillo, O., et al., "In vivo depletion of DC impairs the anti-tumor effect of agonistic anti-CD137 mAb" Eur J Immunol 39(9):2424-2436 (Sep. 1, 2009).
Teng, M., et al., "CD1d-Based Combination Therapy Eradicates Established Tumors in Mice" J Immunol 183(3):1911-1920 (Aug. 1, 2009).
Wilcox, R., et al., "Cutting Edge: Expression of Functional CD137 Receptor by Dendritic Cells" J Immunol 168(9):4262-4267 (May 1, 2002).
Zhang, N. et al., "Targeted and untargeted CD137L fusion proteins for the immunotherapy of experimental solid tumors." Clin Cancer Res 13(9):2758-2767 (May 1, 2007).
Balza, E., et al., "Production and characterization of monoclonal antibodies specific for different epitopes of human tenascin" FEBS Lett 332(1-2):39-43 (Oct. 1, 1993).
Brack, S., et al., "Tumor-Targeting Properties of Novel Antibodies Specific to the Large Isoform of Tenascin-C" Clin Cancer Res 12(10):3200-3208 (May 15, 2006).
"International Preliminary Report on Patentability—PCT/EP2017/060869":pp. 1-10 (dated Nov. 13, 2018).
"International Search Report—PCT/EP2017/060869 dated Aug. 8, 2017":pp. 1-7 (Aug. 8, 2017).
Joester, A., et al., "Evidence for Combinatorial Variability of Tenascin-C Isoforms and Developmental Regulation in the Mouse Central Nervous System" J Biol Chem 274(24):17144-17151 (Jun. 11, 1999).
Silacci, M., et al., "Human monoclonal antibodies to domain C of tenascin-C selectively target solid tumors in vivo" Protein Eng Des Sel 19(10):471-478 (Oct. 19, 2006).
Wang, Yu-Cai, et al., "Generation and Identification of Monoclonal Antibodies Against FNIII Domain D of Human Tenascin-C" Hybridoma 29(1):13-16 (Jan. 31, 2010).

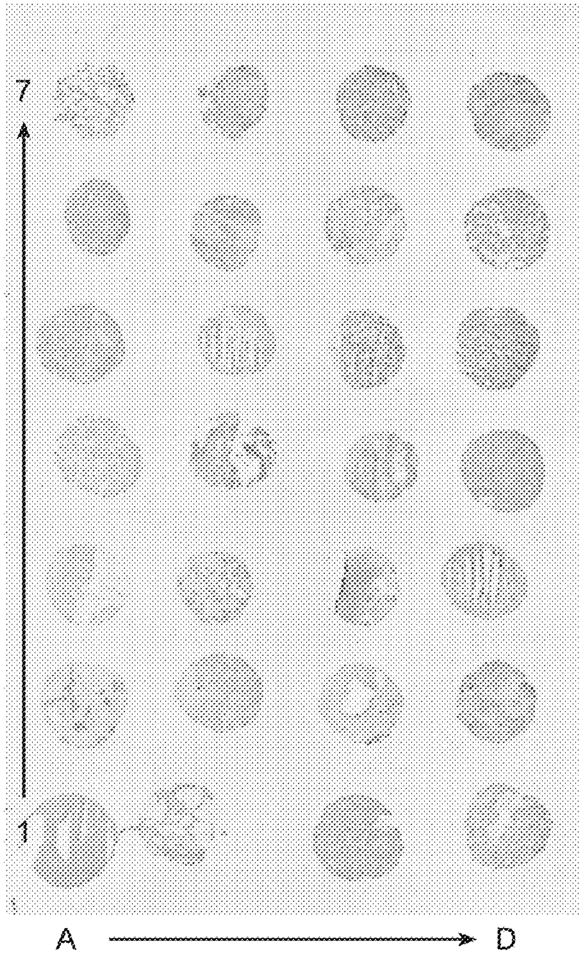

| Position | Tissue Type | Pathological Diagnosis | Isotype Control (0.5 µg/ml) Signal |
|---|---|---|---|
| A1 | Brain | Normal | - |
| B1 | Brain Tumor | Cranionpharyngioma | - |
| A2 | Breast | Normal | - |
| B2 | Breast Tumor | Invasive ductal carcinoma | - |
| A3 | Colon | Normal | - |
| B3 | Colon Tumor | adenocarcinoma | - |
| A4 | Skeletal Muscle | Normal | - |
| B4 | Skeletal Muscle Tumor | Rhabdomyosarcoma | - |
| A5 | Kidney | Normal | - |
| B5 | Kidney Tumor | Renal Cell Carcinoma | - |
| A6 | Liver | Normal | - |
| B6 | Liver Tumor | Hepatocellular Carcinoma | - |
| A7 | Lung | Normal | - |
| B7 | Lung Tumor | squamous cell carcinoma | - |
| C1 | Pancreas | Normal | - |
| D1 | Pancreas Tumor | Adenocarcinoma | - |
| C2 | Prostate | Normal | - |
| D2 | Prostate Tumor | Adenocarcinoma | - |
| C3 | Skin | Normal | - |
| D3 | Skin Tumor | Malignant Melanoma | - |
| C4 | Small Intestine | Normal | - |
| D4 | Small Intestine Tumor | Malignant Mesenchymoma | - |
| C5 | Stomach | Normal | - |
| D5 | Stomach Tumor | adenocarcinomal, ulcer | - |
| C6 | Ovary | Normal | - |
| D6 | Ovary Tumor | Cystadenocarcinoma Serus | - |
| C7 | Uterus | Normal | - |
| D7 | Uterus Tumor | Adenocarcinoma | - |

FIG. 2

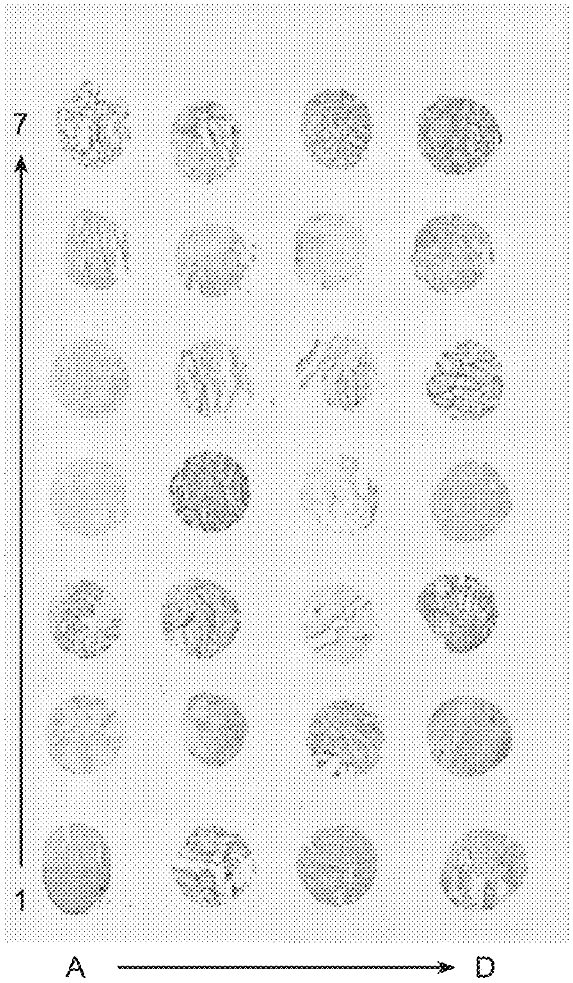

| Position | Tissue Type | Pathological Diagnosis | Tenascin Clone 18D4 (0.5 µg/ml) Expression |
|---|---|---|---|
| A1 | Brain | Normal | - |
| B1 | Brain Tumor | Cranionpharyngioma | ++ |
| A2 | Breast | Normal | - |
| B2 | Breast Tumor | Invasive ductal carcinoma | ++ |
| A3 | Colon | Normal | + |
| B3 | Colon Tumor | adenocarcinoma | ++ |
| A4 | Skeletal Muscle | Normal | - (1/2 +around a vessel) |
| B4 | Skeletal Muscle Tumor | Rhabdomyosarcoma | +++ |
| A5 | Kidney | Normal | 1/2 + around vessels and in glomeruli |
| B5 | Kidney Tumor | Renal Cell Carcinoma | ++ |
| A6 | Liver | Normal | + |
| B6 | Liver Tumor | Hepatocellular Carcinoma | ++ |
| A7 | Lung | Normal | ++ |
| B7 | Lung Tumor | squamous cell carcinoma | ++ |
| C1 | Pancreas | Normal | 1/2 + around a vessels |
| D1 | Pancreas Tumor | Adenocarcinoma | ++ |
| C2 | Prostate | Normal | ++ |
| D2 | Prostate Tumor | Adenocarcinoma | ++ |
| C3 | Skin | Normal | 1/2 + in dermis and around some hair folicules |
| D3 | Skin Tumor | Malignant Melanoma | +++ |
| C4 | Small Intestine | Normal | 1/2 + in conective tissue |
| D4 | Small Intestine Tumor | Malignant Mesenchymoma | 1/2+ |
| C5 | Stomach | Normal | + in muscularis mucosa |
| D5 | Stomach Tumor | adenocarcinomal, ulcer | ++ |
| C6 | Ovary | Normal | - |
| D6 | Ovary Tumor | Cystadenocarcinoma Serus | ++ |
| C7 | Uterus | Normal | ++ |
| D7 | Uterus Tumor | Adenocarcinoma | +++ |

FIG. 3

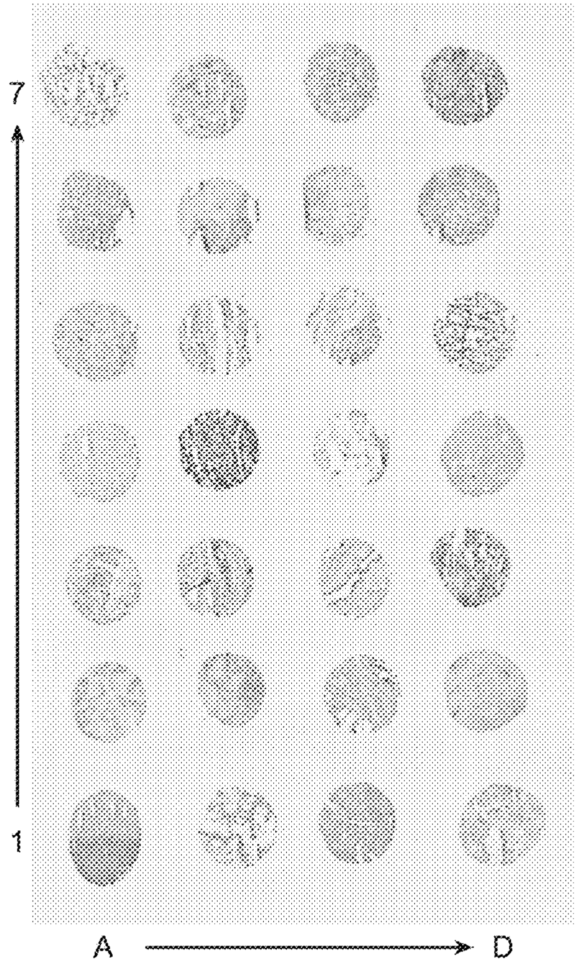

| Position | Tissue Type | Pathological Diagnosis | Tenascin Clone 11C7 (0.5 µg/ml) Expression |
|---|---|---|---|
| A1 | Brain | Normal | - |
| B1 | Brain Tumor | Cranionpharyngioma | + |
| A2 | Breast | Normal | - |
| B2 | Breast Tumor | Invasive ductal carcinoma | ++ |
| A3 | Colon | Normal | + |
| B3 | Colon Tumor | adenocarcinoma | ++ |
| A4 | Skeletal Muscle | Normal | - |
| B4 | Skeletal Muscle Tumor | Rhabdomyosarcoma | +++ |
| A5 | Kidney | Normal | 1/2+ |
| B5 | Kidney Tumor | Renal Cell Carcinoma | + |
| A6 | Liver | Normal | 1/2+ |
| B6 | Liver Tumor | Hepatocellular Carcinoma | 1/2+ |
| A7 | Lung | Normal | + |
| B7 | Lung Tumor | squamous cell carcinoma | + |
| C1 | Pancreas | Normal | - |
| D1 | Pancreas Tumor | Adenocarcinoma | 1/2+ |
| C2 | Prostate | Normal | 1/2+ |
| D2 | Prostate Tumor | Adenocarcinoma | + |
| C3 | Skin | Normal | 1/2+ |
| D3 | Skin Tumor | Malignant Melanoma | +++ |
| C4 | Small Intestine | Normal | 1/2+ |
| D4 | Small Intestine Tumor | Malignant Mesenchymoma | 1/2+ |
| C5 | Stomach | Normal | 1/2+ |
| D5 | Stomach Tumor | adenocarcinomal, ulcer | ++ |
| C6 | Ovary | Normal | - |
| D6 | Ovary Tumor | Cystadenocarcinoma Serus | ++ |
| C7 | Uterus | Normal | + |
| D7 | Uterus Tumor | Adenocarcinoma | +++ |

*FIG. 4*

SEQUENCE LISTING

```
<160> NUMBER OF SEQ ID NOS: 225

<210> SEQ ID NO 1
<211> LENGTH: 3102
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: huTNC

<400> SEQUENCE: 1

atgtccccta tactaggtta ttggaaaatt aagggccttg tgcaacccac tcgacttctt      60

ttggaatatc ttgaagaaaa atatgaagag catttgtatg agcgcgatga aggtgataaa     120

tggcgaaaca aaaagtttga attgggtttg gagtttccca atcttcctta ttatattgat     180

ggtgatgtta aattaacaca gtctatggcc atcatacgtt atatagctga caagcacaac     240

atgttgggtg gttgtccaaa agagcgtgca gagatttcaa tgcttgaagg agcggttttg     300

gatattagat acggtgtttc gagaattgca tatagtaaag actttgaaac tctcaaagtt     360
```

-continued

```
gattttctta gcaagctacc tgaaatgctg aaaatgttcg aagatcgttt atgtcataaa    420
acatatttaa atggtgatca tgtaacccat cctgacttca tgttgtatga cgctcttgat    480
gttgttttat acatggaccc aatgtgcctg gatgcgttcc caaaattagt ttgttttaaa    540
aaacgtattg aagctatccc acaaattgat aagtacttga aatccagcaa gtatatagca    600
tggcctttgc agggctggca agccacgttt ggtggtggcg accatcctcc aaaatcggat    660
ggttcaacta gtggttctgg tcatcaccat caccatcact ccgcgggtct ggtgccacgc    720
ggtagtactg caattggtat gaaagaaacc gctgctgcta aattcgaacg ccagcacatg    780
gacagcccag atctgggtac cggtggtggc tccggtattg agggacgcgg gtccatggga    840
tatcggggat ccgagctgga cacccccaag gacctgcagg tgtccgagac agccgagaca    900
agcctgaccc tgctgtggaa aaccccccctg gccaagttcg accggtacag actgaactac    960
agcctgccca ctggacagtg ggtcggcgtg cagctgcccc ggaacaccac ctcctacgtg   1020
ctgcggggcc tggaacccgg ccaggaatac aacgtcctgc tgacggccga gaagggccgg   1080
cacaagagca agcccgccag agtgaaggcc agcaccgagc aggcccccga gctggaaaac   1140
ctgaccgtga ccgaagtggg ctgggacggc ctgcggctga actggaccgc ggctgaccag   1200
gcctatgagc actttatcat tcaggtgcag gaggccaaca aggtggaggc agctcggaac   1260
ctcaccgtgc ctggcagcct tcgggctgtg gacataccgg gcctcaaggc tgctacgcct   1320
tatacagtct ccatctatgg ggtgatccag ggctatagaa caccagtgct ctctgctgag   1380
gcctccacag gcgaaacacc gaacctgggc gaagtggtgg tggcggaagt gggttgggat   1440
gcgctgaaac tgaactggac cgcgccggaa ggcgcgtatg aatatttttt catccaggtg   1500
caggaagcgg ataccgttga agcggcgcag aacctgaccg ttccgggcgg tctgcgtagc   1560
accgatctgc cgggcctgaa agcggcgacc cattatacca ttaccatccg tggggtgacc   1620
caggacttct ctaccacccc tctgagcgtg gaggtgctga ccgaggaggt acccgacatg   1680
ggcaacctga ccgtgaccga ggtgtcctgg gacgccctgc ggctgaactg gaccaccccc   1740
gacggcacct acgaccagtt cacaatccag gtgcaggaag ccgaccaggt ggaagaagca   1800
cataatctga ccgttccggg tagcctgcgt agcatggaaa ttccgggtct gcgtgcaggc   1860
accccgtata ccgttaccct gcatggtgaa gttcgtggtc atagcacccg tccgctggca   1920
gttgaagttg ttaccgaaga tctgccgcag ctgggtgatc tggcagttag cgaagttggt   1980
tgggatggtc tgcgtctgaa ttggaccgca gcagataatg catatgaaca ttttgtgatc   2040
caggtgcaag aggtgaataa agttgaagca gcccagaatc tgaccctgcc tggttcactg   2100
cgtgcagttg atattccggg actcgaggca gcaaccccgt atcgtgttag catttatggt   2160
gttattcgcg gttatcgtac accggttctg agcgcagaag caagcaccgc aaaagaaccg   2220
gaaattggta atctgaacgt gagcgatatt acaccggaat catttaatct gagctggatg   2280
gcaaccgatg gtatttttga aacctttacc atcgagatca tcgatagcaa tcgtctgctg   2340
gaaaccgtgg aatataatat tagcggtgca gaacgtaccg cacatattag cggtctgcct   2400
ccgagcaccg attttattgt ttatctgagc ggtctggcac cgagcattcg taccaaaacc   2460
attagcgcaa ccgcaaccac cgaagcactg ccgctgctgg aaaatctgac cattagcgat   2520
attaacccgt atggttttac cgtttcatgg atggcaagcg aaaatgcatt tgatagcttt   2580
ctggttacag ttgtggatag cggtaaactg ctggacccgc aagaatttac cctgagcggc   2640
acccagcgca aactggaact gcgtggtctg attaccggta ttggttatga agttatggtg   2700
```

agcggtttta cccagggtca tcagaccaaa ccgctgcgtg cagaaattgt taccgaagca 2760
atgggtagcc cgaaagaagt tattttttcc gatatcaccg agaattcggc aaccgttagc 2820
tggcgtgcac cgaccgcaca ggttgaaagc tttcgtatta cctatgttcc gattaccggt 2880
ggcaccccga gcatggttac agttgatggc accaaaaccc agacccgtct ggttaaactg 2940
attccgggtg ttgaatatct ggttagcatt attgccatga aaggctttga agaaagcgaa 3000
ccggttagcg gtagctttac cacagctagc ggcctgaacg acatcttcga ggctcagaaa 3060
atcgaatggc acgaaggtac ccatcaccat caccaccact aa 3102

<210> SEQ ID NO 2
<211> LENGTH: 2566
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: muTNC

<400> SEQUENCE: 2
tatgtcccct atactaggtt attggaaaat taagggcctt gtgcaaccca ctcgacttct 60
tttggaatat cttgaagaaa aatatgaaga gcatttgtat gagcgcgatg aaggtgataa 120
atggcgaaac aaaaagtttg aattgggttt ggagtttccc aatcttcctt attatattga 180
tggtgatgtt aaattaacac agtctatggc catcatacgt tatatagctg acaagcacaa 240
catgttgggt ggttgtccaa aagagcgtgc agagatttca atgcttgaag gagcggtttt 300
ggatattaga tacggtgttt cgagaattgc atatagtaaa gactttgaaa ctctcaaagt 360
tgattttctt agcaagctac ctgaaatgct gaaaatgttc gaagatcgtt tatgtcataa 420
aacatattta aatggtgatc atgtaaccca tcctgacttc atgttgtatg acgctcttga 480
tgttgtttta tacatggacc caatgtgcct ggatgcgttc ccaaaattag tttgttttaa 540
aaaacgtatt gaagctatcc cacaaattga taagtacttg aaatccagca agtatatagc 600
atggcctttg cagggctggc aagccacgtt tggtggtggc gaccatcctc caaaatcgga 660
tggttcaact agtggttctg gtcatcacca tcaccatcac tccgcgggtc tggtgccacg 720
cggtagtact gcaattggta tgaaagaaac cgctgctgct aaattcgaac gccagcacat 780
ggacagccca gatctgggta ccggtggtgg ctccggtatt gagggacgcg ggtccatggg 840
atatcgggga tccgagctgg acaccccccaa ggacctgcag gtgtccgaga cagccgagac 900
aagcctgacc ctgctgtgga aaaccccccct ggccaagttc gaccggtaca gactgaacta 960
cagcctgccc actggacagt gggtcggcgt gcagctgccc cggaacacca cctcctacgt 1020
gctgcggggc ctggaacccg gccaggaata caacgtcctg ctgacggccg agaagggccg 1080
gcacaagagc aagcccgcca gagtgaaggc cagcaccgag gaagtgccca gcctggaaaa 1140
cctgaccgtg accgaggccg gctgggacgg cctgcggctg aactggaccg ccgacgacct 1200
ggcctacgag tacttcgtga tccaggtgca ggaagccaac aacgtcgaga cagcccacaa 1260
cttcaccgtg cccggcaacc tgagagccgc cgacatcccc ggcctgaagg tggccacatc 1320
ctaccgggtg tccatctacg gcgtggccag gggctaccgg acccccgtgc tgtccgccga 1380
gacaagcacc ggcaccacgc cgaacctggg cgaagtgacc gtggcggaag tgggttggga 1440
tgcgctgacc ctgaattgga ccgcaccgga aggcgcgtat aaaaactttt tcatccaggt 1500
gctggaagcg gataccaccc agaccgtgca gaacctgacc gtgccgggtg gtctgcgtag 1560

```
cgtagatctg cctggtctga aagcagcaac ccgctattac attaccctgc gtggtgttac   1620
ccaggatttt ggcaccgcac cgctgagcgt tgaagttctg accgaggatc tgccgcagct   1680
gggtggtctg agcgttaccg aagttagttg ggatggtctg accctgaatt ggaccaccga   1740
tgatctggca tataaacatt ttgtggtgca ggttcaagag gccaataatg ttgaagcagc   1800
acagaatctg accgttccgg gtagcctgcg tgcagttgat attccgggac tgaaagccga   1860
taccccgtat cgtgttagca tttatggtgt tattcagggt tatcgtaccc cgatgctgag   1920
caccgatgtt agcacagcac gtgaaccgga aattggtaat ctgaatgtta gtgatgtgac   1980
cccgaaatca tttaatctga gctggaccgc aaccgatggt atttttgata tgtttaccat   2040
tgaaattatt gatagcaatc gcctgctgca gaccgcagaa cataacatta gcggtgcaga   2100
acgtaccgca catattagcg gtctgcctcc gagcaccgat tttattgttt atctgagcgg   2160
tattgcaccg agcattcgta ccaaaaccat tagcaccacc gcaaccaccg aagcactgac   2220
cgcaatgggt agcccgaaag aagtgatttt tagcgatatt accgaaaata gcgccaccgt   2280
ttcatggcgt gcaccgaccg cacaggttga aagctttcgt attacctatg ttccgattac   2340
cggtggcacc ccgagcatgg ttaccgttga tggcaccaaa acccagaccc gtctggttaa   2400
actgattccg ggtgttgaat atctggttag cattattgcc atgaaaggct ttgaagaaag   2460
cgaaccggtt agcggtagct ttaccacagc tagcggcctg aacgacatct tcgaggctca   2520
gaaaatcgaa tggcacgaag gtacccatca ccatcaccac cactaa                  2566
```

<210> SEQ ID NO 3
<211> LENGTH: 2565
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: cynoTNC

<400> SEQUENCE: 3

```
atgtccccta tactaggtta ttggaaaatt aagggccttg tgcaacccac tcgacttctt     60
ttggaatatc ttgaagaaaa atatgaagag catttgtatg agcgcgatga aggtgataaa    120
tggcgaaaca aaaagtttga attgggtttg gagtttccca atcttcctta ttatattgat    180
ggtgatgtta aattaacaca gtctatggcc atcatacgtt atatagctga caagcacaac    240
atgttgggtg gttgtccaaa agagcgtgca gagatttcaa tgcttgaagg agcggttttg    300
gatattagat acggtgtttc gagaattgca tatagtaaag actttgaaac tctcaaagtt    360
gattttctta gcaagctacc tgaaatgctg aaaatgttcg aagatcgttt atgtcataaa    420
acatatttaa atggtgatca tgtaacccat cctgacttca tgttgtatga cgctcttgat    480
gttgttttat acatggaccc aatgtgcctg gatgcgttcc caaaattagt ttgttttaaa    540
aaacgtattg aagctatccc acaaattgat aagtacttga aatccagcaa gtatatagca    600
tggcctttgc agggctggca agccacgttt ggtggtggcg accatcctcc aaaatcggat    660
ggttcaacta gtggttctgg tcatcaccat caccatcact ccgcgggtct ggtgccacgc    720
ggtagtactg caattggtat gaaagaaacc gctgctgcta aattcgaacg ccagcacatg    780
gacagcccag atctgggtac cggtggtggc tccggtattg agggacgcgg gtccatggga    840
tatcggggat ccgaactgga taccccgaaa gatctgcgtg ttagcgaaac cgcagaaacc    900
agcctgaccc tgttttggaa aacaccgctg gcaaaatttg atcgttatcg tctgaattat    960
```

-continued

```
agcctgccga ccggtcagtg ggttggtgtt cagctgcctc gtaataccac cagttatgtt   1020

ctgcgtggtc tggaaccggg tcaagaatat aacgttctgc tgaccgcaga aaaaggtcgt   1080

cataaaagca aaccggcacg tgttaaagca agcaccgaac aggcaccgga actggaaaat   1140

ctgaccgtta ccgaagttgg ctgggatggc ctgcgcctga actggacggc tgcggaccag   1200

gcctacgaac acttcgttat ccaggtgcaa gaagccaaca aagtagaagc cgctcagaat   1260

ctgacggttc cgggaaatct gcgtgcagtt gatattccgg gtctgaaagc agcaaccccg   1320

tataccgtta gcatttatgg tgttattcag ggttatcgta caccggttct gagtgccgaa   1380

gccagcaccg gtgaaacccc gaatctgggt gaagttatgg ttagcgaagt gggctgggat   1440

gcactgaaac tgaattggac agttccggaa ggtgcctatg aatacttttt cattcaggtt   1500

caagaagcgg ataccgttga agccgctcag aatcataccg ttccgggtgg tctgcgtagc   1560

accgatctgc ctggcctgaa agccgctacc cattacacca ttaccattcg tggtgttacc   1620

caggatttta gcaccacacc gctgagcgtt gaagttctga cagaagaact gccgcagctg   1680

ggtgatctgg cagttagcga agttggttgg gatggtctgc gtctgaattg gaccgcagca   1740

gatcaggcat atgaacattt tgttatccag gtgcaagaag tgaacaaagt tgaagcagca   1800

cagaatctga ccgttccggg tagcctgcgt gcagttgata ttccgggtct gaaagcagca   1860

accccgtata ccgttagcat ttatggtgtt attcgcggtt atcgtacacc ggttctgagc   1920

gcagaagcaa gcaccgcaaa agaaccggaa attggtaatc tgaacgtgag cgatattaca   1980

ccggaaagtt ttagcctgag ctggaccgca accgatggta tttttgaaac ctttaccatc   2040

gagatcatcg atagcaatcg tctgctggaa atcgtggaat ataacattag cggtgcagaa   2100

cgtaccgcac atattagcgg tctgcctccg agcaccgatt ttattgttta tctgagcggt   2160

ctggcaccga gctttcgtac caaaaccatt agcgcaaccg caaccaccga agcactgacc   2220

gcaatgggta gcccgaaaga agtgattttt agcgatatta ccgaaaatag cgccaccgtt   2280

tcatggcgtg caccgaccgc acaggttgaa agctttcgta ttacctatgt tccgattacc   2340

ggtggcaccc cgagcatggt taccgtggat ggcaccaaaa cccagacccg tctggttaaa   2400

ctggttccgg gtgttgaata tctggtgaat atcattgcca tgaaaggctt tgaagaaagc   2460

gaaccggtta gcggtagctt taccaccgct agcggcctga acgacatctt cgaggctcag   2520

aaaatcgaat ggcacgaagg tacccatcac catcaccacc actaa                   2565
```

<210> SEQ ID NO 4
<211> LENGTH: 1033
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: huTNC

<400> SEQUENCE: 4

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60
```

```
Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Gly Ser Thr Ser
    210                 215                 220

Gly Ser Gly His His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Gly Ser Gly
            260                 265                 270

Ile Glu Gly Arg Gly Ser Met Gly Tyr Arg Gly Ser Glu Leu Asp Thr
        275                 280                 285

Pro Lys Asp Leu Gln Val Ser Glu Thr Ala Glu Thr Ser Leu Thr Leu
    290                 295                 300

Leu Trp Lys Thr Pro Leu Ala Lys Phe Asp Arg Tyr Arg Leu Asn Tyr
305                 310                 315                 320

Ser Leu Pro Thr Gly Gln Trp Val Gly Val Gln Leu Pro Arg Asn Thr
                325                 330                 335

Thr Ser Tyr Val Leu Arg Gly Leu Glu Pro Gly Gln Glu Tyr Asn Val
            340                 345                 350

Leu Leu Thr Ala Glu Lys Gly Arg His Lys Ser Lys Pro Ala Arg Val
        355                 360                 365

Lys Ala Ser Thr Glu Gln Ala Pro Glu Leu Glu Asn Leu Thr Val Thr
    370                 375                 380

Glu Val Gly Trp Asp Gly Leu Arg Leu Asn Trp Thr Ala Ala Asp Gln
385                 390                 395                 400

Ala Tyr Glu His Phe Ile Ile Gln Val Gln Glu Ala Asn Lys Val Glu
                405                 410                 415

Ala Ala Arg Asn Leu Thr Val Pro Gly Ser Leu Arg Ala Val Asp Ile
            420                 425                 430

Pro Gly Leu Lys Ala Ala Thr Pro Tyr Thr Val Ser Ile Tyr Gly Val
        435                 440                 445

Ile Gln Gly Tyr Arg Thr Pro Val Leu Ser Ala Glu Ala Ser Thr Gly
    450                 455                 460

Glu Thr Pro Asn Leu Gly Glu Val Val Val Ala Glu Val Gly Trp Asp
465                 470                 475                 480

Ala Leu Lys Leu Asn Trp Thr Ala Pro Glu Gly Ala Tyr Glu Tyr Phe
```

```
                485                 490                 495

Phe Ile Gln Val Gln Glu Ala Asp Thr Val Glu Ala Ala Gln Asn Leu
            500                 505                 510

Thr Val Pro Gly Gly Leu Arg Ser Thr Asp Leu Pro Gly Leu Lys Ala
        515                 520                 525

Ala Thr His Tyr Thr Ile Thr Ile Arg Gly Val Thr Gln Asp Phe Ser
    530                 535                 540

Thr Thr Pro Leu Ser Val Glu Val Leu Thr Glu Glu Val Pro Asp Met
545                 550                 555                 560

Gly Asn Leu Thr Val Thr Glu Val Ser Trp Asp Ala Leu Arg Leu Asn
                565                 570                 575

Trp Thr Thr Pro Asp Gly Thr Tyr Asp Gln Phe Thr Ile Gln Val Gln
            580                 585                 590

Glu Ala Asp Gln Val Glu Glu Ala His Asn Leu Thr Val Pro Gly Ser
        595                 600                 605

Leu Arg Ser Met Glu Ile Pro Gly Leu Arg Ala Gly Thr Pro Tyr Thr
    610                 615                 620

Val Thr Leu His Gly Glu Val Arg Gly His Ser Thr Arg Pro Leu Ala
625                 630                 635                 640

Val Glu Val Val Thr Glu Asp Leu Pro Gln Leu Gly Asp Leu Ala Val
                645                 650                 655

Ser Glu Val Gly Trp Asp Gly Leu Arg Leu Asn Trp Thr Ala Ala Asp
            660                 665                 670

Asn Ala Tyr Glu His Phe Val Ile Gln Val Gln Glu Val Asn Lys Val
        675                 680                 685

Glu Ala Ala Gln Asn Leu Thr Leu Pro Gly Ser Leu Arg Ala Val Asp
    690                 695                 700

Ile Pro Gly Leu Glu Ala Ala Thr Pro Tyr Arg Val Ser Ile Tyr Gly
705                 710                 715                 720

Val Ile Arg Gly Tyr Arg Thr Pro Val Leu Ser Ala Glu Ala Ser Thr
                725                 730                 735

Ala Lys Glu Pro Glu Ile Gly Asn Leu Asn Val Ser Asp Ile Thr Pro
            740                 745                 750

Glu Ser Phe Asn Leu Ser Trp Met Ala Thr Asp Gly Ile Phe Glu Thr
        755                 760                 765

Phe Thr Ile Glu Ile Ile Asp Ser Asn Arg Leu Leu Glu Thr Val Glu
    770                 775                 780

Tyr Asn Ile Ser Gly Ala Glu Arg Thr Ala His Ile Ser Gly Leu Pro
785                 790                 795                 800

Pro Ser Thr Asp Phe Ile Val Tyr Leu Ser Gly Leu Ala Pro Ser Ile
                805                 810                 815

Arg Thr Lys Thr Ile Ser Ala Thr Ala Thr Thr Glu Ala Leu Pro Leu
            820                 825                 830

Leu Glu Asn Leu Thr Ile Ser Asp Ile Asn Pro Tyr Gly Phe Thr Val
        835                 840                 845

Ser Trp Met Ala Ser Glu Asn Ala Phe Asp Ser Phe Leu Val Thr Val
    850                 855                 860

Val Asp Ser Gly Lys Leu Leu Asp Pro Gln Glu Phe Thr Leu Ser Gly
865                 870                 875                 880

Thr Gln Arg Lys Leu Glu Leu Arg Gly Leu Ile Thr Gly Ile Gly Tyr
                885                 890                 895

Glu Val Met Val Ser Gly Phe Thr Gln Gly His Gln Thr Lys Pro Leu
            900                 905                 910
```

Arg Ala Glu Ile Val Thr Glu Ala Met Gly Ser Pro Lys Glu Val Ile
        915                 920                 925

Phe Ser Asp Ile Thr Glu Asn Ser Ala Thr Val Ser Trp Arg Ala Pro
    930                 935                 940

Thr Ala Gln Val Glu Ser Phe Arg Ile Thr Tyr Val Pro Ile Thr Gly
945                 950                 955                 960

Gly Thr Pro Ser Met Val Thr Val Asp Gly Thr Lys Thr Gln Thr Arg
                965                 970                 975

Leu Val Lys Leu Ile Pro Gly Val Glu Tyr Leu Val Ser Ile Ile Ala
            980                 985                 990

Met Lys Gly Phe Glu Glu Ser Glu  Pro Val Ser Gly Ser  Phe Thr Thr
        995                 1000                1005

Ala Ser  Gly Leu Asn Asp Ile  Phe Glu Ala Gln Lys  Ile Glu Trp
    1010                1015                1020

His Glu  Gly Thr His His His  His His His
    1025                1030

<210> SEQ ID NO 5
<211> LENGTH: 854
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: muTNC

<400> SEQUENCE: 5

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Gly Ser Thr Ser
    210                 215                 220

-continued

```
Gly Ser Gly His His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Gly Ser Gly
            260                 265                 270

Ile Glu Gly Arg Gly Ser Met Gly Tyr Arg Gly Ser Glu Leu Asp Thr
        275                 280                 285

Pro Lys Asp Leu Gln Val Ser Glu Thr Ala Glu Thr Ser Leu Thr Leu
    290                 295                 300

Leu Trp Lys Thr Pro Leu Ala Lys Phe Asp Arg Tyr Arg Leu Asn Tyr
305                 310                 315                 320

Ser Leu Pro Thr Gly Gln Trp Val Gly Val Gln Leu Pro Arg Asn Thr
                325                 330                 335

Thr Ser Tyr Val Leu Arg Gly Leu Glu Pro Gly Gln Glu Tyr Asn Val
            340                 345                 350

Leu Leu Thr Ala Glu Lys Gly Arg His Lys Ser Lys Pro Ala Arg Val
        355                 360                 365

Lys Ala Ser Thr Glu Glu Val Pro Ser Leu Glu Asn Leu Thr Val Thr
    370                 375                 380

Glu Ala Gly Trp Asp Gly Leu Arg Leu Asn Trp Thr Ala Asp Asp Leu
385                 390                 395                 400

Ala Tyr Glu Tyr Phe Val Ile Gln Val Gln Glu Ala Asn Asn Val Glu
                405                 410                 415

Thr Ala His Asn Phe Thr Val Pro Gly Asn Leu Arg Ala Ala Asp Ile
            420                 425                 430

Pro Gly Leu Lys Val Ala Thr Ser Tyr Arg Val Ser Ile Tyr Gly Val
        435                 440                 445

Ala Arg Gly Tyr Arg Thr Pro Val Leu Ser Ala Glu Thr Ser Thr Gly
    450                 455                 460

Thr Thr Pro Asn Leu Gly Glu Val Thr Val Ala Glu Val Gly Trp Asp
465                 470                 475                 480

Ala Leu Thr Leu Asn Trp Thr Ala Pro Glu Gly Ala Tyr Lys Asn Phe
                485                 490                 495

Phe Ile Gln Val Leu Glu Ala Asp Thr Thr Gln Thr Val Gln Asn Leu
            500                 505                 510

Thr Val Pro Gly Gly Leu Arg Ser Val Asp Leu Pro Gly Leu Lys Ala
        515                 520                 525

Ala Thr Arg Tyr Tyr Ile Thr Leu Arg Gly Val Thr Gln Asp Phe Gly
    530                 535                 540

Thr Ala Pro Leu Ser Val Glu Val Leu Thr Glu Asp Leu Pro Gln Leu
545                 550                 555                 560

Gly Gly Leu Ser Val Thr Glu Val Ser Trp Asp Gly Leu Thr Leu Asn
                565                 570                 575

Trp Thr Thr Asp Asp Leu Ala Tyr Lys His Phe Val Val Gln Val Gln
            580                 585                 590

Glu Ala Asn Asn Val Glu Ala Ala Gln Asn Leu Thr Val Pro Gly Ser
        595                 600                 605

Leu Arg Ala Val Asp Ile Pro Gly Leu Lys Ala Asp Thr Pro Tyr Arg
    610                 615                 620

Val Ser Ile Tyr Gly Val Ile Gln Gly Tyr Arg Thr Pro Met Leu Ser
625                 630                 635                 640
```

-continued

Thr Asp Val Ser Thr Ala Arg Glu Pro Glu Ile Gly Asn Leu Asn Val
645 650 655

Ser Asp Val Thr Pro Lys Ser Phe Asn Leu Ser Trp Thr Ala Thr Asp
660 665 670

Gly Ile Phe Asp Met Phe Thr Ile Glu Ile Ile Asp Ser Asn Arg Leu
675 680 685

Leu Gln Thr Ala Glu His Asn Ile Ser Gly Ala Glu Arg Thr Ala His
690 695 700

Ile Ser Gly Leu Pro Pro Ser Thr Asp Phe Ile Val Tyr Leu Ser Gly
705 710 715 720

Ile Ala Pro Ser Ile Arg Thr Lys Thr Ile Ser Thr Thr Ala Thr Thr
725 730 735

Glu Ala Leu Thr Ala Met Gly Ser Pro Lys Glu Val Ile Phe Ser Asp
740 745 750

Ile Thr Glu Asn Ser Ala Thr Val Ser Trp Arg Ala Pro Thr Ala Gln
755 760 765

Val Glu Ser Phe Arg Ile Thr Tyr Val Pro Ile Thr Gly Gly Thr Pro
770 775 780

Ser Met Val Thr Val Asp Gly Thr Lys Thr Gln Thr Arg Leu Val Lys
785 790 795 800

Leu Ile Pro Gly Val Glu Tyr Leu Val Ser Ile Ile Ala Met Lys Gly
805 810 815

Phe Glu Glu Ser Glu Pro Val Ser Gly Ser Phe Thr Thr Ala Ser Gly
820 825 830

Leu Asn Asp Ile Phe Glu Ala Gln Lys Ile Glu Trp His Glu Gly Thr
835 840 845

His His His His His His
850

<210> SEQ ID NO 6
<211> LENGTH: 854
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: cynoTNC

<400> SEQUENCE: 6

Met Ser Pro Ile Leu Gly Tyr Trp Lys Ile Lys Gly Leu Val Gln Pro
1 5 10 15

Thr Arg Leu Leu Leu Glu Tyr Leu Glu Glu Lys Tyr Glu Glu His Leu
20 25 30

Tyr Glu Arg Asp Glu Gly Asp Lys Trp Arg Asn Lys Lys Phe Glu Leu
35 40 45

Gly Leu Glu Phe Pro Asn Leu Pro Tyr Tyr Ile Asp Gly Asp Val Lys
50 55 60

Leu Thr Gln Ser Met Ala Ile Ile Arg Tyr Ile Ala Asp Lys His Asn
65 70 75 80

Met Leu Gly Gly Cys Pro Lys Glu Arg Ala Glu Ile Ser Met Leu Glu
85 90 95

Gly Ala Val Leu Asp Ile Arg Tyr Gly Val Ser Arg Ile Ala Tyr Ser
100 105 110

Lys Asp Phe Glu Thr Leu Lys Val Asp Phe Leu Ser Lys Leu Pro Glu
115 120 125

```
Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Gly Ser Thr Ser
    210                 215                 220

Gly Ser Gly His His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Gly Ser Gly
            260                 265                 270

Ile Glu Gly Arg Gly Ser Met Gly Tyr Arg Gly Ser Glu Leu Asp Thr
        275                 280                 285

Pro Lys Asp Leu Arg Val Ser Glu Thr Ala Glu Thr Ser Leu Thr Leu
    290                 295                 300

Phe Trp Lys Thr Pro Leu Ala Lys Phe Asp Arg Tyr Arg Leu Asn Tyr
305                 310                 315                 320

Ser Leu Pro Thr Gly Gln Trp Val Gly Val Gln Leu Pro Arg Asn Thr
                325                 330                 335

Thr Ser Tyr Val Leu Arg Gly Leu Glu Pro Gly Gln Glu Tyr Asn Val
            340                 345                 350

Leu Leu Thr Ala Glu Lys Gly Arg His Lys Ser Lys Pro Ala Arg Val
        355                 360                 365

Lys Ala Ser Thr Glu Gln Ala Pro Glu Leu Glu Asn Leu Thr Val Thr
    370                 375                 380

Glu Val Gly Trp Asp Gly Leu Arg Leu Asn Trp Thr Ala Ala Asp Gln
385                 390                 395                 400

Ala Tyr Glu His Phe Val Ile Gln Val Gln Glu Ala Asn Lys Val Glu
                405                 410                 415

Ala Ala Gln Asn Leu Thr Val Pro Gly Asn Leu Arg Ala Val Asp Ile
            420                 425                 430

Pro Gly Leu Lys Ala Ala Thr Pro Tyr Thr Val Ser Ile Tyr Gly Val
        435                 440                 445

Ile Gln Gly Tyr Arg Thr Pro Val Leu Ser Ala Glu Ala Ser Thr Gly
    450                 455                 460

Glu Thr Pro Asn Leu Gly Glu Val Met Val Ser Glu Val Gly Trp Asp
465                 470                 475                 480

Ala Leu Lys Leu Asn Trp Thr Val Pro Glu Gly Ala Tyr Glu Tyr Phe
                485                 490                 495

Phe Ile Gln Val Gln Glu Ala Asp Thr Val Glu Ala Ala Gln Asn His
            500                 505                 510

Thr Val Pro Gly Gly Leu Arg Ser Thr Asp Leu Pro Gly Leu Lys Ala
        515                 520                 525

Ala Thr His Tyr Thr Ile Thr Ile Arg Gly Val Thr Gln Asp Phe Ser
    530                 535                 540

Thr Thr Pro Leu Ser Val Glu Val Leu Thr Glu Glu Leu Pro Gln Leu
```

545 550 555 560

Gly Asp Leu Ala Val Ser Glu Val Gly Trp Asp Gly Leu Arg Leu Asn
565 570 575

Trp Thr Ala Ala Asp Gln Ala Tyr Glu His Phe Val Ile Gln Val Gln
580 585 590

Glu Val Asn Lys Val Glu Ala Ala Gln Asn Leu Thr Val Pro Gly Ser
595 600 605

Leu Arg Ala Val Asp Ile Pro Gly Leu Lys Ala Ala Thr Pro Tyr Thr
610 615 620

Val Ser Ile Tyr Gly Val Ile Arg Gly Tyr Arg Thr Pro Val Leu Ser
625 630 635 640

Ala Glu Ala Ser Thr Ala Lys Glu Pro Glu Ile Gly Asn Leu Asn Val
645 650 655

Ser Asp Ile Thr Pro Glu Ser Phe Ser Leu Ser Trp Thr Ala Thr Asp
660 665 670

Gly Ile Phe Glu Thr Phe Thr Ile Glu Ile Ile Asp Ser Asn Arg Leu
675 680 685

Leu Glu Ile Val Glu Tyr Asn Ile Ser Gly Ala Glu Arg Thr Ala His
690 695 700

Ile Ser Gly Leu Pro Pro Ser Thr Asp Phe Ile Val Tyr Leu Ser Gly
705 710 715 720

Leu Ala Pro Ser Phe Arg Thr Lys Thr Ile Ser Ala Thr Ala Thr Thr
725 730 735

Glu Ala Leu Thr Ala Met Gly Ser Pro Lys Glu Val Ile Phe Ser Asp
740 745 750

Ile Thr Glu Asn Ser Ala Thr Val Ser Trp Arg Ala Pro Thr Ala Gln
755 760 765

Val Glu Ser Phe Arg Ile Thr Tyr Val Pro Ile Thr Gly Gly Thr Pro
770 775 780

Ser Met Val Thr Val Asp Gly Thr Lys Thr Gln Thr Arg Leu Val Lys
785 790 795 800

Leu Val Pro Gly Val Glu Tyr Leu Val Asn Ile Ile Ala Met Lys Gly
805 810 815

Phe Glu Glu Ser Glu Pro Val Ser Gly Ser Phe Thr Thr Ala Ser Gly
820 825 830

Leu Asn Asp Ile Phe Glu Ala Gln Lys Ile Glu Trp His Glu Gly Thr
835 840 845

His His His His His His
850

<210> SEQ ID NO 7
<211> LENGTH: 1033
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: GST huTNC fn5 A1234 BC fn6 B

<400> SEQUENCE: 7

Met Ser Pro Ile Leu Gly Tyr Trp Lys Ile Lys Gly Leu Val Gln Pro
1 5 10 15

Thr Arg Leu Leu Leu Glu Tyr Leu Glu Glu Lys Tyr Glu Glu His Leu
20 25 30

Tyr Glu Arg Asp Glu Gly Asp Lys Trp Arg Asn Lys Lys Phe Glu Leu

-continued

```
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Gly Ser Thr Ser
    210                 215                 220

Gly Ser Gly His His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Gly Ser Gly
            260                 265                 270

Ile Glu Gly Arg Gly Ser Met Gly Tyr Arg Gly Ser Glu Leu Asp Thr
        275                 280                 285

Pro Lys Asp Leu Gln Val Ser Glu Thr Ala Glu Thr Ser Leu Thr Leu
    290                 295                 300

Leu Trp Lys Thr Pro Leu Ala Lys Phe Asp Arg Tyr Arg Leu Asn Tyr
305                 310                 315                 320

Ser Leu Pro Thr Gly Gln Trp Val Gly Val Gln Leu Pro Arg Asn Thr
                325                 330                 335

Thr Ser Tyr Val Leu Arg Gly Leu Glu Pro Gly Gln Glu Tyr Asn Val
            340                 345                 350

Leu Leu Thr Ala Glu Lys Gly Arg His Lys Ser Lys Pro Ala Arg Val
        355                 360                 365

Lys Ala Ser Thr Glu Gln Ala Pro Glu Leu Glu Asn Leu Thr Val Thr
    370                 375                 380

Glu Val Gly Trp Asp Gly Leu Arg Leu Asn Trp Thr Ala Ala Asp Gln
385                 390                 395                 400

Ala Tyr Glu His Phe Ile Ile Gln Val Gln Glu Ala Asn Lys Val Glu
                405                 410                 415

Ala Ala Arg Asn Leu Thr Val Pro Gly Ser Leu Arg Ala Val Asp Ile
            420                 425                 430

Pro Gly Leu Lys Ala Ala Thr Pro Tyr Thr Val Ser Ile Tyr Gly Val
        435                 440                 445

Ile Gln Gly Tyr Arg Thr Pro Val Leu Ser Ala Glu Ala Ser Thr Gly
    450                 455                 460
```

Glu Thr Pro Asn Leu Gly Glu Val Val Val Ala Glu Val Gly Trp Asp
465 470 475 480

Ala Leu Lys Leu Asn Trp Thr Ala Pro Glu Gly Ala Tyr Glu Tyr Phe
485 490 495

Phe Ile Gln Val Gln Glu Ala Asp Thr Val Glu Ala Ala Gln Asn Leu
500 505 510

Thr Val Pro Gly Gly Leu Arg Ser Thr Asp Leu Pro Gly Leu Lys Ala
515 520 525

Ala Thr His Tyr Thr Ile Thr Ile Arg Gly Val Thr Gln Asp Phe Ser
530 535 540

Thr Thr Pro Leu Ser Val Glu Val Leu Thr Glu Glu Val Pro Asp Met
545 550 555 560

Gly Asn Leu Thr Val Thr Glu Val Ser Trp Asp Ala Leu Arg Leu Asn
565 570 575

Trp Thr Thr Pro Asp Gly Thr Tyr Asp Gln Phe Thr Ile Gln Val Gln
580 585 590

Glu Ala Asp Gln Val Glu Glu Ala His Asn Leu Thr Val Pro Gly Ser
595 600 605

Leu Arg Ser Met Glu Ile Pro Gly Leu Arg Ala Gly Thr Pro Tyr Thr
610 615 620

Val Thr Leu His Gly Glu Val Arg Gly His Ser Thr Arg Pro Leu Ala
625 630 635 640

Val Glu Val Val Thr Glu Asp Leu Pro Gln Leu Gly Asp Leu Ala Val
645 650 655

Ser Glu Val Gly Trp Asp Gly Leu Arg Leu Asn Trp Thr Ala Ala Asp
660 665 670

Asn Ala Tyr Glu His Phe Val Ile Gln Val Gln Glu Val Asn Lys Val
675 680 685

Glu Ala Ala Gln Asn Leu Thr Leu Pro Gly Ser Leu Arg Ala Val Asp
690 695 700

Ile Pro Gly Leu Glu Ala Ala Thr Pro Tyr Arg Val Ser Ile Tyr Gly
705 710 715 720

Val Ile Arg Gly Tyr Arg Thr Pro Val Leu Ser Ala Glu Ala Ser Thr
725 730 735

Ala Lys Glu Pro Glu Ile Gly Asn Leu Asn Val Ser Asp Ile Thr Pro
740 745 750

Glu Ser Phe Asn Leu Ser Trp Met Ala Thr Asp Gly Ile Phe Glu Thr
755 760 765

Phe Thr Ile Glu Ile Ile Asp Ser Asn Arg Leu Leu Glu Thr Val Glu
770 775 780

Tyr Asn Ile Ser Gly Ala Glu Arg Thr Ala His Ile Ser Gly Leu Pro
785 790 795 800

Pro Ser Thr Asp Phe Ile Val Tyr Leu Ser Gly Leu Ala Pro Ser Ile
805 810 815

Arg Thr Lys Thr Ile Ser Ala Thr Ala Thr Thr Glu Ala Leu Pro Leu
820 825 830

Leu Glu Asn Leu Thr Ile Ser Asp Ile Asn Pro Tyr Gly Phe Thr Val
835 840 845

Ser Trp Met Ala Ser Glu Asn Ala Phe Asp Ser Phe Leu Val Thr Val
850 855 860

Val Asp Ser Gly Lys Leu Leu Asp Pro Gln Glu Phe Thr Leu Ser Gly
865 870 875 880

Thr Gln Arg Lys Leu Glu Leu Arg Gly Leu Ile Thr Gly Ile Gly Tyr
885 890 895

Glu Val Met Val Ser Gly Phe Thr Gln Gly His Gln Thr Lys Pro Leu
900 905 910

Arg Ala Glu Ile Val Thr Glu Ala Met Gly Ser Pro Lys Glu Val Ile
915 920 925

Phe Ser Asp Ile Thr Glu Asn Ser Ala Thr Val Ser Trp Arg Ala Pro
930 935 940

Thr Ala Gln Val Glu Ser Phe Arg Ile Thr Tyr Val Pro Ile Thr Gly
945 950 955 960

Gly Thr Pro Ser Met Val Thr Val Asp Gly Thr Lys Thr Gln Thr Arg
965 970 975

Leu Val Lys Leu Ile Pro Gly Val Glu Tyr Leu Val Ser Ile Ile Ala
980 985 990

Met Lys Gly Phe Glu Glu Ser Glu Pro Val Ser Gly Ser Phe Thr Thr
995 1000 1005

Ala Ser Gly Leu Asn Asp Ile Phe Glu Ala Gln Lys Ile Glu Trp
1010 1015 1020

His Glu Gly Thr His His His His His His
1025 1030

<210> SEQ ID NO 8
<211> LENGTH: 854
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: GST huTNCfn5 mu A124 BC hu fn6 B

<400> SEQUENCE: 8

Met Ser Pro Ile Leu Gly Tyr Trp Lys Ile Lys Gly Leu Val Gln Pro
1 5 10 15

Thr Arg Leu Leu Leu Glu Tyr Leu Glu Glu Lys Tyr Glu Glu His Leu
20 25 30

Tyr Glu Arg Asp Glu Gly Asp Lys Trp Arg Asn Lys Lys Phe Glu Leu
35 40 45

Gly Leu Glu Phe Pro Asn Leu Pro Tyr Tyr Ile Asp Gly Asp Val Lys
50 55 60

Leu Thr Gln Ser Met Ala Ile Ile Arg Tyr Ile Ala Asp Lys His Asn
65 70 75 80

Met Leu Gly Gly Cys Pro Lys Glu Arg Ala Glu Ile Ser Met Leu Glu
85 90 95

Gly Ala Val Leu Asp Ile Arg Tyr Gly Val Ser Arg Ile Ala Tyr Ser
100 105 110

Lys Asp Phe Glu Thr Leu Lys Val Asp Phe Leu Ser Lys Leu Pro Glu
115 120 125

Met Leu Lys Met Phe Glu Asp Arg Leu Cys His Lys Thr Tyr Leu Asn
130 135 140

Gly Asp His Val Thr His Pro Asp Phe Met Leu Tyr Asp Ala Leu Asp
145 150 155 160

Val Val Leu Tyr Met Asp Pro Met Cys Leu Asp Ala Phe Pro Lys Leu
165 170 175

Val Cys Phe Lys Lys Arg Ile Glu Ala Ile Pro Gln Ile Asp Lys Tyr
180 185 190

```
Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Gly Ser Thr Ser
    210                 215                 220

Gly Ser Gly His His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Gly Ser Gly
            260                 265                 270

Ile Glu Gly Arg Gly Ser Met Gly Tyr Arg Gly Ser Glu Leu Asp Thr
        275                 280                 285

Pro Lys Asp Leu Gln Val Ser Glu Thr Ala Glu Thr Ser Leu Thr Leu
    290                 295                 300

Leu Trp Lys Thr Pro Leu Ala Lys Phe Asp Arg Tyr Arg Leu Asn Tyr
305                 310                 315                 320

Ser Leu Pro Thr Gly Gln Trp Val Gly Val Gln Leu Pro Arg Asn Thr
                325                 330                 335

Thr Ser Tyr Val Leu Arg Gly Leu Glu Pro Gly Gln Glu Tyr Asn Val
            340                 345                 350

Leu Leu Thr Ala Glu Lys Gly Arg His Lys Ser Lys Pro Ala Arg Val
        355                 360                 365

Lys Ala Ser Thr Glu Glu Val Pro Ser Leu Glu Asn Leu Thr Val Thr
    370                 375                 380

Glu Ala Gly Trp Asp Gly Leu Arg Leu Asn Trp Thr Ala Asp Asp Leu
385                 390                 395                 400

Ala Tyr Glu Tyr Phe Val Ile Gln Val Gln Glu Ala Asn Asn Val Glu
                405                 410                 415

Thr Ala His Asn Phe Thr Val Pro Gly Asn Leu Arg Ala Ala Asp Ile
            420                 425                 430

Pro Gly Leu Lys Val Ala Thr Ser Tyr Arg Val Ser Ile Tyr Gly Val
        435                 440                 445

Ala Arg Gly Tyr Arg Thr Pro Val Leu Ser Ala Glu Thr Ser Thr Gly
    450                 455                 460

Thr Thr Pro Asn Leu Gly Glu Val Thr Val Ala Glu Val Gly Trp Asp
465                 470                 475                 480

Ala Leu Thr Leu Asn Trp Thr Ala Pro Glu Gly Ala Tyr Lys Asn Phe
                485                 490                 495

Phe Ile Gln Val Leu Glu Ala Asp Thr Thr Gln Thr Val Gln Asn Leu
            500                 505                 510

Thr Val Pro Gly Gly Leu Arg Ser Val Asp Leu Pro Gly Leu Lys Ala
        515                 520                 525

Ala Thr Arg Tyr Tyr Ile Thr Leu Arg Gly Val Thr Gln Asp Phe Gly
    530                 535                 540

Thr Ala Pro Leu Ser Val Glu Val Leu Thr Glu Asp Leu Pro Gln Leu
545                 550                 555                 560

Gly Gly Leu Ser Val Thr Glu Val Ser Trp Asp Gly Leu Thr Leu Asn
                565                 570                 575

Trp Thr Thr Asp Asp Leu Ala Tyr Lys His Phe Val Val Gln Val Gln
            580                 585                 590

Glu Ala Asn Asn Val Glu Ala Ala Gln Asn Leu Thr Val Pro Gly Ser
        595                 600                 605

Leu Arg Ala Val Asp Ile Pro Gly Leu Lys Ala Asp Thr Pro Tyr Arg
```

```
    610                 615                 620

Val Ser Ile Tyr Gly Val Ile Gln Gly Tyr Arg Thr Pro Met Leu Ser
625                 630                 635                 640

Thr Asp Val Ser Thr Ala Arg Glu Pro Glu Ile Gly Asn Leu Asn Val
                645                 650                 655

Ser Asp Val Thr Pro Lys Ser Phe Asn Leu Ser Trp Thr Ala Thr Asp
            660                 665                 670

Gly Ile Phe Asp Met Phe Thr Ile Glu Ile Ile Asp Ser Asn Arg Leu
        675                 680                 685

Leu Gln Thr Ala Glu His Asn Ile Ser Gly Ala Glu Arg Thr Ala His
    690                 695                 700

Ile Ser Gly Leu Pro Pro Ser Thr Asp Phe Ile Val Tyr Leu Ser Gly
705                 710                 715                 720

Ile Ala Pro Ser Ile Arg Thr Lys Thr Ile Ser Thr Thr Ala Thr Thr
                725                 730                 735

Glu Ala Leu Thr Ala Met Gly Ser Pro Lys Glu Val Ile Phe Ser Asp
            740                 745                 750

Ile Thr Glu Asn Ser Ala Thr Val Ser Trp Arg Ala Pro Thr Ala Gln
        755                 760                 765

Val Glu Ser Phe Arg Ile Thr Tyr Val Pro Ile Thr Gly Gly Thr Pro
    770                 775                 780

Ser Met Val Thr Val Asp Gly Thr Lys Thr Gln Thr Arg Leu Val Lys
785                 790                 795                 800

Leu Ile Pro Gly Val Glu Tyr Leu Val Ser Ile Ile Ala Met Lys Gly
                805                 810                 815

Phe Glu Glu Ser Glu Pro Val Ser Gly Ser Phe Thr Thr Ala Ser Gly
            820                 825                 830

Leu Asn Asp Ile Phe Glu Ala Gln Lys Ile Glu Trp His Glu Gly Thr
        835                 840                 845

His His His His His His
    850


<210> SEQ ID NO 9
<211> LENGTH: 668
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GST TNC hu fn5 B-C fn6 B

<400> SEQUENCE: 9

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
```

-continued

```
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Gly Ser Thr Ser
    210                 215                 220

Gly Ser Gly His His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Gly Ser Gly
            260                 265                 270

Ile Glu Gly Arg Gly Ser Met Gly Tyr Arg Gly Ser Glu Leu Asp Thr
        275                 280                 285

Pro Lys Asp Leu Gln Val Ser Glu Thr Ala Glu Thr Ser Leu Thr Leu
    290                 295                 300

Leu Trp Lys Thr Pro Leu Ala Lys Phe Asp Arg Tyr Arg Leu Asn Tyr
305                 310                 315                 320

Ser Leu Pro Thr Gly Gln Trp Val Gly Val Gln Leu Pro Arg Asn Thr
                325                 330                 335

Thr Ser Tyr Val Leu Arg Gly Leu Glu Pro Gly Gln Glu Tyr Asn Val
            340                 345                 350

Leu Leu Thr Ala Glu Lys Gly Arg His Lys Ser Lys Pro Ala Arg Val
        355                 360                 365

Lys Ala Ser Thr Ala Lys Glu Pro Glu Ile Gly Asn Leu Asn Val Ser
    370                 375                 380

Asp Ile Thr Pro Glu Ser Phe Asn Leu Ser Trp Met Ala Thr Asp Gly
385                 390                 395                 400

Ile Phe Glu Thr Phe Thr Ile Glu Ile Ile Asp Ser Asn Arg Leu Leu
                405                 410                 415

Glu Thr Val Glu Tyr Asn Ile Ser Gly Ala Glu Arg Thr Ala His Ile
            420                 425                 430

Ser Gly Leu Pro Pro Ser Thr Asp Phe Ile Val Tyr Leu Ser Gly Leu
        435                 440                 445

Ala Pro Ser Ile Arg Thr Lys Thr Ile Ser Ala Thr Ala Thr Thr Glu
    450                 455                 460

Ala Leu Pro Leu Leu Glu Asn Leu Thr Ile Ser Asp Ile Asn Pro Tyr
465                 470                 475                 480

Gly Phe Thr Val Ser Trp Met Ala Ser Glu Asn Ala Phe Asp Ser Phe
                485                 490                 495

Leu Val Thr Val Val Asp Ser Gly Lys Leu Leu Asp Pro Gln Glu Phe
            500                 505                 510

Thr Leu Ser Gly Thr Gln Arg Lys Leu Glu Leu Arg Gly Leu Ile Thr
        515                 520                 525
```

```
Gly Ile Gly Tyr Glu Val Met Val Ser Gly Phe Thr Gln Gly His Gln
    530                 535                 540

Thr Lys Pro Leu Arg Ala Glu Ile Val Thr Ala Met Gly Ser Pro Lys
545                 550                 555                 560

Glu Val Ile Phe Ser Asp Ile Thr Glu Asn Ser Ala Thr Val Ser Trp
                565                 570                 575

Arg Ala Pro Thr Ala Gln Val Glu Ser Phe Arg Ile Thr Tyr Val Pro
            580                 585                 590

Ile Thr Gly Gly Thr Pro Ser Met Val Thr Val Asp Gly Thr Lys Thr
        595                 600                 605

Gln Thr Arg Leu Val Lys Leu Ile Pro Gly Val Glu Tyr Leu Val Ser
    610                 615                 620

Ile Ile Ala Met Lys Gly Phe Glu Glu Ser Glu Pro Val Ser Gly Ser
625                 630                 635                 640

Phe Thr Thr Ala Ser Gly Leu Asn Asp Ile Phe Glu Ala Gln Lys Ile
                645                 650                 655

Glu Trp His Glu Gly Thr His His His His His His
            660                 665


<210> SEQ ID NO 10
<211> LENGTH: 853
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: GST huTNC fn5 A1234 fn6 B

<400> SEQUENCE: 10

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205
```

```
Thr Phe Gly Gly Gly Asp His Pro Pro Lys Ser Asp Gly Ser Thr Ser
    210                 215                 220

Gly Ser Gly His His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Gly Ser Gly
            260                 265                 270

Ile Glu Gly Arg Gly Ser Met Gly Tyr Arg Gly Ser Glu Leu Asp Thr
        275                 280                 285

Pro Lys Asp Leu Gln Val Ser Glu Thr Ala Glu Thr Ser Leu Thr Leu
    290                 295                 300

Leu Trp Lys Thr Pro Leu Ala Lys Phe Asp Arg Tyr Arg Leu Asn Tyr
305                 310                 315                 320

Ser Leu Pro Thr Gly Gln Trp Val Gly Val Gln Leu Pro Arg Asn Thr
                325                 330                 335

Thr Ser Tyr Val Leu Arg Gly Leu Glu Pro Gly Gln Glu Tyr Asn Val
            340                 345                 350

Leu Leu Thr Ala Glu Lys Gly Arg His Lys Ser Lys Pro Ala Arg Val
        355                 360                 365

Lys Ala Ser Thr Glu Gln Ala Pro Glu Leu Glu Asn Leu Thr Val Thr
    370                 375                 380

Glu Val Gly Trp Asp Gly Leu Arg Leu Asn Trp Thr Ala Ala Asp Gln
385                 390                 395                 400

Ala Tyr Glu His Phe Ile Ile Gln Val Gln Glu Ala Asn Lys Val Glu
                405                 410                 415

Ala Ala Arg Asn Leu Thr Val Pro Gly Ser Leu Arg Ala Val Asp Ile
            420                 425                 430

Pro Gly Leu Lys Ala Ala Thr Pro Tyr Thr Val Ser Ile Tyr Gly Val
        435                 440                 445

Ile Gln Gly Tyr Arg Thr Pro Val Leu Ser Ala Glu Ala Ser Thr Gly
    450                 455                 460

Glu Thr Pro Asn Leu Gly Glu Val Val Val Ala Glu Val Gly Trp Asp
465                 470                 475                 480

Ala Leu Lys Leu Asn Trp Thr Ala Pro Glu Gly Ala Tyr Glu Tyr Phe
                485                 490                 495

Phe Ile Gln Val Gln Glu Ala Asp Thr Val Glu Ala Ala Gln Asn Leu
            500                 505                 510

Thr Val Pro Gly Gly Leu Arg Ser Thr Asp Leu Pro Gly Leu Lys Ala
        515                 520                 525

Ala Thr His Tyr Thr Ile Thr Ile Arg Gly Val Thr Gln Asp Phe Ser
    530                 535                 540

Thr Thr Pro Leu Ser Val Glu Val Leu Thr Glu Glu Val Pro Asp Met
545                 550                 555                 560

Gly Asn Leu Thr Val Thr Glu Val Ser Trp Asp Ala Leu Arg Leu Asn
                565                 570                 575

Trp Thr Thr Pro Asp Gly Thr Tyr Asp Gln Phe Thr Ile Gln Val Gln
            580                 585                 590

Glu Ala Asp Gln Val Glu Glu Ala His Asn Leu Thr Val Pro Gly Ser
        595                 600                 605

Leu Arg Ser Met Glu Ile Pro Gly Leu Arg Ala Gly Thr Pro Tyr Thr
    610                 615                 620
```

Val Thr Leu His Gly Glu Val Arg Gly His Ser Thr Arg Pro Leu Ala
625 630 635 640

Val Glu Val Val Thr Glu Asp Leu Pro Gln Leu Gly Asp Leu Ala Val
645 650 655

Ser Glu Val Gly Trp Asp Gly Leu Arg Leu Asn Trp Thr Ala Ala Asp
660 665 670

Asn Ala Tyr Glu His Phe Val Ile Gln Val Gln Glu Val Asn Lys Val
675 680 685

Glu Ala Ala Gln Asn Leu Thr Leu Pro Gly Ser Leu Arg Ala Val Asp
690 695 700

Ile Pro Gly Leu Glu Ala Ala Thr Pro Tyr Arg Val Ser Ile Tyr Gly
705 710 715 720

Val Ile Arg Gly Tyr Arg Thr Pro Val Leu Ser Ala Glu Ala Ser Thr
725 730 735

Ala Lys Glu Ala Met Gly Ser Pro Lys Glu Val Ile Phe Ser Asp Ile
740 745 750

Thr Glu Asn Ser Ala Thr Val Ser Trp Arg Ala Pro Thr Ala Gln Val
755 760 765

Glu Ser Phe Arg Ile Thr Tyr Val Pro Ile Thr Gly Gly Thr Pro Ser
770 775 780

Met Val Thr Val Asp Gly Thr Lys Thr Gln Thr Arg Leu Val Lys Leu
785 790 795 800

Ile Pro Gly Val Glu Tyr Leu Val Ser Ile Ile Ala Met Lys Gly Phe
805 810 815

Glu Glu Ser Glu Pro Val Ser Gly Ser Phe Thr Thr Ala Ser Gly Leu
820 825 830

Asn Asp Ile Phe Glu Ala Gln Lys Ile Glu Trp His Glu Gly Thr His
835 840 845

His His His His His
850

<210> SEQ ID NO 11
<211> LENGTH: 400
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: huTNC A4 B

<400> SEQUENCE: 11

Met Ser Pro Ile Leu Gly Tyr Trp Lys Ile Lys Gly Leu Val Gln Pro
1 5 10 15

Thr Arg Leu Leu Leu Glu Tyr Leu Glu Glu Lys Tyr Glu Glu His Leu
20 25 30

Tyr Glu Arg Asp Glu Gly Asp Lys Trp Arg Asn Lys Lys Phe Glu Leu
35 40 45

Gly Leu Glu Phe Pro Asn Leu Pro Tyr Tyr Ile Asp Gly Asp Val Lys
50 55 60

Leu Thr Gln Ser Met Ala Ile Ile Arg Tyr Ile Ala Asp Lys His Asn
65 70 75 80

Met Leu Gly Gly Cys Pro Lys Glu Arg Ala Glu Ile Ser Met Leu Glu
85 90 95

Gly Ala Val Leu Asp Ile Arg Tyr Gly Val Ser Arg Ile Ala Tyr Ser
100 105 110

```
Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Gly Ser Thr Ser
    210                 215                 220

Gly Ser Gly His His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Gly Ser Gly
            260                 265                 270

Ile Glu Gly Arg Gly Ser Met Gly Tyr Arg Gly Ser Glu Asp Leu Pro
        275                 280                 285

Gln Leu Gly Asp Leu Ala Val Ser Glu Val Gly Trp Asp Gly Leu Arg
    290                 295                 300

Leu Asn Trp Thr Ala Ala Asp Asn Ala Tyr Glu His Phe Val Ile Gln
305                 310                 315                 320

Val Gln Glu Val Asn Lys Val Glu Ala Ala Gln Asn Leu Thr Leu Pro
                325                 330                 335

Gly Ser Leu Arg Ala Val Asp Ile Pro Gly Leu Glu Ala Ala Thr Pro
            340                 345                 350

Tyr Arg Val Ser Ile Tyr Gly Val Ile Arg Gly Tyr Arg Thr Pro Val
        355                 360                 365

Leu Ser Ala Glu Ala Ser Thr Ala Ser Gly Leu Asn Asp Ile Phe Glu
    370                 375                 380

Ala Gln Lys Ile Glu Trp His Glu Gly Thr His His His His His His
385                 390                 395                 400


<210> SEQ ID NO 12
<211> LENGTH: 400
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: huTNC A1 B

<400> SEQUENCE: 12

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60
```

Leu Thr Gln Ser Met Ala Ile Ile Arg Tyr Ile Ala Asp Lys His Asn
65 70 75 80

Met Leu Gly Gly Cys Pro Lys Glu Arg Ala Glu Ile Ser Met Leu Glu
85 90 95

Gly Ala Val Leu Asp Ile Arg Tyr Gly Val Ser Arg Ile Ala Tyr Ser
100 105 110

Lys Asp Phe Glu Thr Leu Lys Val Asp Phe Leu Ser Lys Leu Pro Glu
115 120 125

Met Leu Lys Met Phe Glu Asp Arg Leu Cys His Lys Thr Tyr Leu Asn
130 135 140

Gly Asp His Val Thr His Pro Asp Phe Met Leu Tyr Asp Ala Leu Asp
145 150 155 160

Val Val Leu Tyr Met Asp Pro Met Cys Leu Asp Ala Phe Pro Lys Leu
165 170 175

Val Cys Phe Lys Lys Arg Ile Glu Ala Ile Pro Gln Ile Asp Lys Tyr
180 185 190

Leu Lys Ser Ser Lys Tyr Ile Ala Trp Pro Leu Gln Gly Trp Gln Ala
195 200 205

Thr Phe Gly Gly Gly Asp His Pro Pro Lys Ser Asp Gly Ser Thr Ser
210 215 220

Gly Ser Gly His His His His His His Ser Ala Gly Leu Val Pro Arg
225 230 235 240

Gly Ser Thr Ala Ile Gly Met Lys Glu Thr Ala Ala Ala Lys Phe Glu
245 250 255

Arg Gln His Met Asp Ser Pro Asp Leu Gly Thr Gly Gly Gly Ser Gly
260 265 270

Ile Glu Gly Arg Gly Ser Met Gly Tyr Arg Gly Ser Glu Gln Ala Pro
275 280 285

Glu Leu Glu Asn Leu Thr Val Thr Glu Val Gly Trp Asp Gly Leu Arg
290 295 300

Leu Asn Trp Thr Ala Ala Asp Gln Ala Tyr Glu His Phe Ile Ile Gln
305 310 315 320

Val Gln Glu Ala Asn Lys Val Glu Ala Ala Arg Asn Leu Thr Val Pro
325 330 335

Gly Ser Leu Arg Ala Val Asp Ile Pro Gly Leu Lys Ala Ala Thr Pro
340 345 350

Tyr Thr Val Ser Ile Tyr Gly Val Ile Gln Gly Tyr Arg Thr Pro Val
355 360 365

Leu Ser Ala Glu Ala Ser Thr Ala Ser Gly Leu Asn Asp Ile Phe Glu
370 375 380

Ala Gln Lys Ile Glu Trp His Glu Gly Thr His His His His His His
385 390 395 400

<210> SEQ ID NO 13
<211> LENGTH: 1614
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: pRJH33 library template DP88-4 library; complete Fab coding region comprising PelB leader sequence + Vk1_5 kappa V-domain + CL constant domain for light chain and PelB + VH1_69 V-domain + CH1 constant domain for heavy chain)

<400> SEQUENCE: 13

-continued

```
atgaaatacc tattgcctac ggcagccgct ggattgttat tactcgcggc ccagccggcc     60

atggccgaca tccagatgac ccagtctcct tccaccctgt ctgcatctgt aggagaccgt    120

gtcaccatca cttgccgtgc cagtcagagt attagtagct ggttggcctg gtatcagcag    180

aaaccaggga aagcccctaa gctcctgatc tatgatgcct ccagtttgga aagtggggtc    240

ccatcacgtt tcagcggcag tggatccggg acagaattca ctctcaccat cagcagcttg    300

cagcctgatg attttgcaac ttattactgc caacagtata atagttattc tacgtttggc    360

cagggcacca aagtcgagat caagcgtacg gtggctgcac catctgtctt catcttcccg    420

ccatctgatg agcagttgaa atctggaact gcctctgttg tgtgcctgct gaataacttc    480

tatcccagag aggccaaagt acagtggaag gtggataacg ccctccaatc gggtaactcc    540

caggagagtg tcacagagca ggacagcaag gacagcacct acagcctcag cagcaccctg    600

acgctgagca aagcagacta cgagaaacac aaagtctacg cctgcgaagt cacccatcag    660

ggcctgagct cgcccgtcac aaagagcttc aacaggggag agtgtggagc cgcagaacaa    720

aaactcatct cagaagagga tctgaatgga gccgcagact acaaggacga cgacgacaag    780

ggtgccgcat aataaggcgc gccaattcta tttcaaggag acagtcatat gaaatacctg    840

ctgccgaccg ctgctgctgg tctgctgctc ctcgctgccc agccggcgat ggcccaggtg    900

caattggtgc agtctggggc tgaggtgaag aagcctgggt cctcggtgaa ggtctcctgc    960

aaggcctccg gaggcacatt cagcagctac gctataagct gggtgcgaca ggcccctgga   1020

caagggctcg agtggatggg agggatcatc cctatctttg gtacagcaaa ctacgcacag   1080

aagttccagg gcagggtcac cattactgca gacaaatcca cgagcacagc ctacatggag   1140

ctgagcagcc tgagatctga ggacaccgcc gtgtattact gtgcgagact atccccaggc   1200

ggttactatg ttatggatgc ctggggccaa gggaccaccg tgaccgtctc ctcagctagc   1260

accaaaggcc catcggtctt ccccctggca ccctcctcca agagcacctc tgggggcaca   1320

gcggccctgg gctgcctggt caaggactac ttccccgaac cggtgacggt gtcgtggaac   1380

tcaggcgccc tgaccagcgg cgtgcacacc ttcccggctg tcctacagtc ctcaggactc   1440

tactccctca gcagcgtggt gaccgtgccc tccagcagct tgggcaccca gacctacatc   1500

tgcaacgtga atcacaagcc cagcaacacc aaagtggaca agaaagttga gcccaaatct   1560

tgtgacgcgg ccgcaagcac tagtgcccat caccatcacc atcacgccgc ggca         1614
```

<210> SEQ ID NO 14
<211> LENGTH: 723
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Fab light chain V1_5

<400> SEQUENCE: 14

```
gacatccaga tgacccagtc tccttccacc ctgtctgcat ctgtaggaga ccgtgtcacc     60

atcacttgcc gtgccagtca gagtattagt agctggttgg cctggtatca gcagaaacca    120

gggaaagccc ctaagctcct gatctatgat gcctccagtt tggaaagtgg ggtcccatca    180

cgtttcagcg gcagtggatc cgggacagaa ttcactctca ccatcagcag cttgcagcct    240

gatgattttg caacttatta ctgccaacag tataatagtt attctacgtt tggccagggc    300

accaaagtcg agatcaagcg tacggtggct gcaccatctg tcttcatctt cccgccatct    360
```

```
gatgagcagt tgaaatctgg aactgcctct gttgtgtgcc tgctgaataa cttctatccc    420

agagaggcca aagtacagtg gaaggtggat aacgccctcc aatcgggtaa ctcccaggag    480

agtgtcacag agcaggacag caaggacagc acctacagcc tcagcagcac cctgacgctg    540

agcaaagcag actacgagaa acacaaagtc tacgcctgcg aagtcaccca tcagggcctg    600

agctcgcccg tcacaaagag cttcaacagg ggagagtgtg gagccgcaga acaaaaactc    660

atctcagaag aggatctgaa tggagccgca gactacaagg acgacgacga caagggtgcc    720

gca                                                                  723
```

<210> SEQ ID NO 15
<211> LENGTH: 720
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Fab heavy chain VH1_69

<400> SEQUENCE: 15

```
caggtgcaat tggtgcagtc tggggctgag gtgaagaagc ctgggtcctc ggtgaaggtc     60

tcctgcaagg cctccggagg cacattcagc agctacgcta taagctgggt gcgacaggcc    120

cctggacaag ggctcgagtg gatgggaggg atcatcccta tctttggtac agcaaactac    180

gcacagaagt tccagggcag ggtcaccatt actgcagaca aatccacgag cacagcctac    240

atggagctga gcagcctgag atctgaggac accgccgtgt attactgtgc gagactatcc    300

ccaggcggtt actatgttat ggatgcctgg ggccaaggga ccaccgtgac cgtctcctca    360

gctagcacca aaggcccatc ggtcttcccc ctggcaccct cctccaagag cacctctggg    420

ggcacagcgg ccctgggctg cctggtcaag gactacttcc ccgaaccggt gacggtgtcg    480

tggaactcag gcgccctgac cagcggcgtg cacaccttcc cggctgtcct acagtcctca    540

ggactctact ccctcagcag cgtggtgacc gtgccctcca gcagcttggg cacccagacc    600

tacatctgca acgtgaatca caagcccagc aacaccaaag tggacaagaa agttgagccc    660

aaatcttgtg acgcggccgc aagcactagt gcccatcacc atcaccatca cgccgcggca    720
```

<210> SEQ ID NO 16
<211> LENGTH: 241
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Fab light chain Vk1_5

<400> SEQUENCE: 16

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80
```

Asp Asp Phe Ala Thr Tyr Tyr Cys Gln Gln Tyr Asn Ser Tyr Ser Thr
85 90 95

Phe Gly Gln Gly Thr Lys Val Glu Ile Lys Arg Thr Val Ala Ala Pro
100 105 110

Ser Val Phe Ile Phe Pro Pro Ser Asp Glu Gln Leu Lys Ser Gly Thr
115 120 125

Ala Ser Val Val Cys Leu Leu Asn Asn Phe Tyr Pro Arg Glu Ala Lys
130 135 140

Val Gln Trp Lys Val Asp Asn Ala Leu Gln Ser Gly Asn Ser Gln Glu
145 150 155 160

Ser Val Thr Glu Gln Asp Ser Lys Asp Ser Thr Tyr Ser Leu Ser Ser
165 170 175

Thr Leu Thr Leu Ser Lys Ala Asp Tyr Glu Lys His Lys Val Tyr Ala
180 185 190

Cys Glu Val Thr His Gln Gly Leu Ser Ser Pro Val Thr Lys Ser Phe
195 200 205

Asn Arg Gly Glu Cys Gly Ala Ala Glu Gln Lys Leu Ile Ser Glu Glu
210 215 220

Asp Leu Asn Gly Ala Ala Asp Tyr Lys Asp Asp Asp Asp Lys Gly Ala
225 230 235 240

Ala

<210> SEQ ID NO 17
<211> LENGTH: 240
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Fab heavy chain VH1_69 (DP88)

<400> SEQUENCE: 17

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Leu Ser Pro Gly Gly Tyr Tyr Val Met Asp Ala Trp Gly Gln
100 105 110

Gly Thr Thr Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro

```
        180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Ala Ala Ala Ser Thr Ser Ala His His His His His His Ala Ala Ala
225                 230                 235                 240


<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: LMB3

<400> SEQUENCE: 18

caggaaacag ctatgaccat gattac                                          26


<210> SEQ ID NO 19
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Vk1_5_L3r_S
<220> FEATURE:
<221> NAME/KEY: misc_feature
<222> LOCATION: (28)..(28)
<223> OTHER INFORMATION: 60% given sequence and 40% m
<220> FEATURE:
<221> NAME/KEY: misc_feature
<222> LOCATION: (29)..(30)
<223> OTHER INFORMATION: 60% given sequence and 40% n
<220> FEATURE:
<221> NAME/KEY: misc_feature
<222> LOCATION: (31)..(31)
<223> OTHER INFORMATION: 60% given sequence and 40% m
<220> FEATURE:
<221> NAME/KEY: misc_feature
<222> LOCATION: (32)..(33)
<223> OTHER INFORMATION: 60% given sequence and 40% n
<220> FEATURE:
<221> NAME/KEY: misc_feature
<222> LOCATION: (34)..(34)
<223> OTHER INFORMATION: 60% given sequence and 40% m
<220> FEATURE:
<221> NAME/KEY: misc_feature
<222> LOCATION: (35)..(36)
<223> OTHER INFORMATION: 60% given sequence and 40% n
<220> FEATURE:
<221> NAME/KEY: misc_feature
<222> LOCATION: (37)..(37)
<223> OTHER INFORMATION: 60% given sequence and 40% m
<220> FEATURE:
<221> NAME/KEY: misc_feature
<222> LOCATION: (38)..(39)
<223> OTHER INFORMATION: 60% given sequence and 40% n
<220> FEATURE:
<221> NAME/KEY: misc_feature
<222> LOCATION: (40)..(40)
<223> OTHER INFORMATION: 60% given sequence and 40% m
<220> FEATURE:
<221> NAME/KEY: misc_feature
<222> LOCATION: (41)..(42)
<223> OTHER INFORMATION: 60% given sequence and 40% n

<400> SEQUENCE: 19
```

ctcgactttg gtgccctggc caaacgtsba atacgaatta tactgttggc agtaataagt 60
tgcaaaatca t 71

<210> SEQ ID NO 20
<211> LENGTH: 74
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Vk1_5_L3r_SY
<220> FEATURE:
<221> NAME/KEY: misc_feature
<222> LOCATION: (28)..(28)
<223> OTHER INFORMATION: 60% given sequence and 40% m
<220> FEATURE:
<221> NAME/KEY: misc_feature
<222> LOCATION: (29)..(30)
<223> OTHER INFORMATION: 60% given sequence and 40% n
<220> FEATURE:
<221> NAME/KEY: misc_feature
<222> LOCATION: (31)..(31)
<223> OTHER INFORMATION: 60% given sequence and 40% m
<220> FEATURE:
<221> NAME/KEY: misc_feature
<222> LOCATION: (32)..(33)
<223> OTHER INFORMATION: 60% given sequence and 40% n
<220> FEATURE:
<221> NAME/KEY: misc_feature
<222> LOCATION: (34)..(34)
<223> OTHER INFORMATION: 60% given sequence and 40% m
<220> FEATURE:
<221> NAME/KEY: misc_feature
<222> LOCATION: (35)..(36)
<223> OTHER INFORMATION: 60% given sequence and 40% n
<220> FEATURE:
<221> NAME/KEY: misc_feature
<222> LOCATION: (37)..(37)
<223> OTHER INFORMATION: 60% given sequence and 40% m
<220> FEATURE:
<221> NAME/KEY: misc_feature
<222> LOCATION: (38)..(39)
<223> OTHER INFORMATION: 60% given sequence and 40% n
<220> FEATURE:
<221> NAME/KEY: misc_feature
<222> LOCATION: (40)..(40)
<223> OTHER INFORMATION: 60% given sequence and 40% m
<220> FEATURE:
<221> NAME/KEY: misc_feature
<222> LOCATION: (41)..(42)
<223> OTHER INFORMATION: 60% given sequence and 40% n
<220> FEATURE:
<221> NAME/KEY: misc_feature
<222> LOCATION: (43)..(43)
<223> OTHER INFORMATION: 60% given sequence and 40% m
<220> FEATURE:
<221> NAME/KEY: misc_feature
<222> LOCATION: (44)..(45)
<223> OTHER INFORMATION: 60% given sequence and 40% n

<400> SEQUENCE: 20
ctcgactttg gtgccctggc caaacgtmhr sgratacgaa ttatactgtt ggcagtaata 60
agttgcaaaa tcat 74

<210> SEQ ID NO 21
<211> LENGTH: 77
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Vk1_5_L3r_SPY
<220> FEATURE:
<221> NAME/KEY: misc_feature
<222> LOCATION: (28)..(28)
<223> OTHER INFORMATION: 60% given sequence and 40% m
<220> FEATURE:
<221> NAME/KEY: misc_feature
<222> LOCATION: (29)..(30)
<223> OTHER INFORMATION: 60% given sequence and 40% n
<220> FEATURE:
<221> NAME/KEY: misc_feature
<222> LOCATION: (31)..(31)
<223> OTHER INFORMATION: 60% given sequence and 40% m
<220> FEATURE:
<221> NAME/KEY: misc_feature
<222> LOCATION: (32)..(33)
<223> OTHER INFORMATION: 60% given sequence and 40% n
<220> FEATURE:
<221> NAME/KEY: misc_feature
<222> LOCATION: (34)..(34)
<223> OTHER INFORMATION: 60% given sequence and 40% m
<220> FEATURE:
<221> NAME/KEY: misc_feature
<222> LOCATION: (35)..(36)
<223> OTHER INFORMATION: 60% given sequence and 40% n
<220> FEATURE:
<221> NAME/KEY: misc_feature
<222> LOCATION: (37)..(37)
<223> OTHER INFORMATION: 60% given sequence and 40% m
<220> FEATURE:
<221> NAME/KEY: misc_feature
<222> LOCATION: (38)..(39)
<223> OTHER INFORMATION: 60% given sequence and 40% n
<220> FEATURE:
<221> NAME/KEY: misc_feature
<222> LOCATION: (40)..(40)
<223> OTHER INFORMATION: 60% given sequence and 40% m
<220> FEATURE:
<221> NAME/KEY: misc_feature
<222> LOCATION: (41)..(42)
<223> OTHER INFORMATION: 60% given sequence and 40% n
<220> FEATURE:
<221> NAME/KEY: misc_feature
<222> LOCATION: (43)..(43)
<223> OTHER INFORMATION: 60% given sequence and 40% m
<220> FEATURE:
<221> NAME/KEY: misc_feature
<222> LOCATION: (44)..(45)
<223> OTHER INFORMATION: 60% given sequence and 40% n
<220> FEATURE:
<221> NAME/KEY: misc_feature
<222> LOCATION: (46)..(46)
<223> OTHER INFORMATION: 60% given sequence and 40% m
<220> FEATURE:
<221> NAME/KEY: misc_feature
<222> LOCATION: (47)..(48)
<223> OTHER INFORMATION: 60% given sequence and 40% n

<400> SEQUENCE: 21
ctcgactttg gtgccctggc caaacgtmhh msssgratac gaattatact gttggcagta 60
ataagttgca aaatcat 77

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: RJH31

<400> SEQUENCE: 22
acgtttggcc agggcaccaa agtcgag 27

<210> SEQ ID NO 23
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: RJH32

<400> SEQUENCE: 23
tctcgcacag taatacacgg cggtgtcc 28

<210> SEQ ID NO 24
<211> LENGTH: 79
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DP88-v4-4
<220> FEATURE:
<221> NAME/KEY: modified_base
<222> LOCATION: (29)..(31)
<223> OTHER INFORMATION: a, c, t, or g
<220> FEATURE:
<221> NAME/KEY: misc_feature
<222> LOCATION: (29)..(31)
<223> OTHER INFORMATION: This region encodes G/D = 20%, E/V/S = 10%,
A/P/R/L/T/Y=5%
<220> FEATURE:
<221> NAME/KEY: modified_base
<222> LOCATION: (32)..(34)
<223> OTHER INFORMATION: a, c, t, or g
<220> FEATURE:
<221> NAME/KEY: misc_feature
<222> LOCATION: (32)..(34)
<223> OTHER INFORMATION: This region encodes G/Y/S=15%,
A/D/T/R/P/L/V/N/W/F/I/E = 4,6%
<220> FEATURE:
<221> NAME/KEY: modified_base
<222> LOCATION: (35)..(37)
<223> OTHER INFORMATION: a, c, t, or g
<220> FEATURE:
<221> NAME/KEY: misc_feature
<222> LOCATION: (35)..(37)
<223> OTHER INFORMATION: This region encodes G/Y/S=15%,
A/D/T/R/P/L/V/N/W/F/I/E = 4,6%
<220> FEATURE:
<221> NAME/KEY: modified_base
<222> LOCATION: (38)..(40)
<223> OTHER INFORMATION: a, c, t, or g
<220> FEATURE:
<221> NAME/KEY: misc_feature
<222> LOCATION: (38)..(40)
<223> OTHER INFORMATION: This region encodes G/A/Y = 20%, P/W/S/D/T = 8%
<220> FEATURE:
<221> NAME/KEY: modified_base
<222> LOCATION: (41)..(43)
<223> OTHER INFORMATION: a, c, t, or g
<220> FEATURE:
<221> NAME/KEY: misc_feature
<222> LOCATION: (41)..(43)
<223> OTHER INFORMATION: This region encodes F = 46%, L/M = 15%, G/I/Y =
8%

<400> SEQUENCE: 24
ggacaccgcc gtgtattact gtgcgagann nnnnnnnnnn nnngactact ggggccaagg 60
gaccaccgtg accgtctcc 79

<210> SEQ ID NO 25
<211> LENGTH: 85
<212> TYPE: DNA

<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DP88-v4-6
<220> FEATURE:
<221> NAME/KEY: modified_base
<222> LOCATION: (29)..(31)
<223> OTHER INFORMATION: a, c, t, or g
<220> FEATURE:
<221> NAME/KEY: misc_feature
<222> LOCATION: (29)..(31)
<223> OTHER INFORMATION: This region encodes G/D = 20%, E/V/S = 10%,
A/P/R/L/T/Y=5%
<220> FEATURE:
<221> NAME/KEY: modified_base
<222> LOCATION: (32)..(34)
<223> OTHER INFORMATION: a, c, t, or g
<220> FEATURE:
<221> NAME/KEY: misc_feature
<222> LOCATION: (32)..(34)
<223> OTHER INFORMATION: This region encodes G/Y/S=15%,
A/D/T/R/P/L/V/N/W/F/I/E = 4,6%
<220> FEATURE:
<221> NAME/KEY: modified_base
<222> LOCATION: (35)..(37)
<223> OTHER INFORMATION: a, c, t, or g
<220> FEATURE:
<221> NAME/KEY: misc_feature
<222> LOCATION: (35)..(37)
<223> OTHER INFORMATION: This region encodes G/Y/S=15%,
A/D/T/R/P/L/V/N/W/F/I/E = 4,6%
<220> FEATURE:
<221> NAME/KEY: modified_base
<222> LOCATION: (38)..(40)
<223> OTHER INFORMATION: a, c, t, or g
<220> FEATURE:
<221> NAME/KEY: misc_feature
<222> LOCATION: (38)..(40)
<223> OTHER INFORMATION: This region encodes G/Y/S=15%,
A/D/T/R/P/L/V/N/W/F/I/E = 4,6%
<220> FEATURE:
<221> NAME/KEY: modified_base
<222> LOCATION: (41)..(43)
<223> OTHER INFORMATION: a, c, t, or g
<220> FEATURE:
<221> NAME/KEY: misc_feature
<222> LOCATION: (41)..(43)
<223> OTHER INFORMATION: This region encodes G/Y/S=15%,
A/D/T/R/P/L/V/N/W/F/I/E = 4,6%
<220> FEATURE:
<221> NAME/KEY: modified_base
<222> LOCATION: (44)..(46)
<223> OTHER INFORMATION: a, c, t, or g
<220> FEATURE:
<221> NAME/KEY: misc_feature
<222> LOCATION: (44)..(46)
<223> OTHER INFORMATION: This region encodes G/A/Y = 20%, P/W/S/D/T = 8%
<220> FEATURE:
<221> NAME/KEY: modified_base
<222> LOCATION: (47)..(49)
<223> OTHER INFORMATION: a, c, t, or g
<220> FEATURE:
<221> NAME/KEY: misc_feature
<222> LOCATION: (47)..(49)
<223> OTHER INFORMATION: This region encodes F = 46%, L/M = 15%, G/I/Y =
8%

<400> SEQUENCE: 25
ggacaccgcc gtgtattact gtgcgagann nnnnnnnnnn nnnnnnnnng actactgggg 60
ccaagggacc accgtgaccg tctcc 85

<210> SEQ ID NO 26
<211> LENGTH: 91
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DP88-v4-8
<220> FEATURE:
<221> NAME/KEY: modified_base
<222> LOCATION: (29)..(31)
<223> OTHER INFORMATION: a, c, t, or g
<220> FEATURE:
<221> NAME/KEY: misc_feature
<222> LOCATION: (29)..(31)
<223> OTHER INFORMATION: This region encodes G/D = 20%, E/V/S = 10%,
      A/P/R/L/T/Y=5%
<220> FEATURE:
<221> NAME/KEY: modified_base
<222> LOCATION: (32)..(34)
<223> OTHER INFORMATION: a, c, t, or g
<220> FEATURE:
<221> NAME/KEY: misc_feature
<222> LOCATION: (32)..(34)
<223> OTHER INFORMATION: This region encodes G/Y/S=15%,
      A/D/T/R/P/L/V/N/W/F/I/E = 4,6%
<220> FEATURE:
<221> NAME/KEY: modified_base
<222> LOCATION: (35)..(37)
<223> OTHER INFORMATION: a, c, t, or g
<220> FEATURE:
<221> NAME/KEY: misc_feature
<222> LOCATION: (35)..(37)
<223> OTHER INFORMATION: This region encodes G/Y/S=15%,
      A/D/T/R/P/L/V/N/W/F/I/E = 4,6%
<220> FEATURE:
<221> NAME/KEY: modified_base
<222> LOCATION: (38)..(40)
<223> OTHER INFORMATION: a, c, t, or g
<220> FEATURE:
<221> NAME/KEY: misc_feature
<222> LOCATION: (38)..(40)
<223> OTHER INFORMATION: This region encodes G/Y/S=15%,
      A/D/T/R/P/L/V/N/W/F/I/E = 4,6%
<220> FEATURE:
<221> NAME/KEY: modified_base
<222> LOCATION: (41)..(43)
<223> OTHER INFORMATION: a, c, t, or g
<220> FEATURE:
<221> NAME/KEY: misc_feature
<222> LOCATION: (41)..(43)
<223> OTHER INFORMATION: This region encodes G/Y/S=15%,
      A/D/T/R/P/L/V/N/W/F/I/E = 4,6%
<220> FEATURE:
<221> NAME/KEY: modified_base
<222> LOCATION: (44)..(46)
<223> OTHER INFORMATION: a, c, t, or g
<220> FEATURE:
<221> NAME/KEY: misc_feature
<222> LOCATION: (44)..(46)
<223> OTHER INFORMATION: This region encodes G/Y/S=15%,
      A/D/T/R/P/L/V/N/W/F/I/E = 4,6%
<220> FEATURE:
<221> NAME/KEY: modified_base
<222> LOCATION: (47)..(49)
<223> OTHER INFORMATION: a, c, t, or g
<220> FEATURE:
<221> NAME/KEY: misc_feature
<222> LOCATION: (47)..(49)
<223> OTHER INFORMATION: This region encodes G/Y/S=15%,
      A/D/T/R/P/L/V/N/W/F/I/E = 4,6%
<220> FEATURE:
<221> NAME/KEY: modified_base
<222> LOCATION: (50)..(52)
<223> OTHER INFORMATION: a, c, t, or g
<220> FEATURE:
<221> NAME/KEY: misc_feature
<222> LOCATION: (50)..(52)
<223> OTHER INFORMATION: This region encodes G/A/Y = 20%, P/W/S/D/T = 8%
<220> FEATURE:
<221> NAME/KEY: modified_base
```

<222> LOCATION: (53)..(55)
<223> OTHER INFORMATION: a, c, t, or g
<220> FEATURE:
<221> NAME/KEY: misc_feature
<222> LOCATION: (53)..(55)
<223> OTHER INFORMATION: This region encodes F = 46%, L/M = 15%, G/I/Y = 8%

<400> SEQUENCE: 26
ggacaccgcc gtgtattact gtgcgagann nnnnnnnnnn nnnnnnnnnn nnnnngacta 60
ctggggccaa gggaccaccg tgaccgtctc c 91

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: fdseqlong

<400> SEQUENCE: 27
gacgttagta aatgaatttt ctgtatgagg 30

<210> SEQ ID NO 28
<211> LENGTH: 1605
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: pRJH53 library template of lambda-DP47 library Vl3_19/VH3_23

<400> SEQUENCE: 28
atgaaatacc tattgcctac ggcagccgct ggattgttat tactcgcggc ccagccggcc 60
atggcctcgt ctgagctgac tcaggaccct gctgtgtctg tggccttggg acagacagtc 120
aggatcacat gccaaggaga cagcctcaga agttattatg caagctggta ccagcagaag 180
ccaggacagg cccctgtact tgtcatctat ggtaaaaaca accggccctc agggatccca 240
gaccgattct ctggctccag ctcaggaaac acagcttcct tgaccatcac tggggctcag 300
gcggaagatg aggctgacta ttactgtaac tcccgtgata gtagcggtaa tcatgtggta 360
ttcggcggag ggaccaagct gaccgtccta ggacaaccca aggctgcccc cagcgtgacc 420
ctgttccccc ccagcagcga ggaattgcag gccaacaagg ccaccctggt ctgcctgatc 480
agcgacttct acccaggcgc cgtgaccgtg gcctggaagg ccgacagcag ccccgtgaag 540
gccggcgtgg agaccaccac ccccagcaag cagagcaaca acaagtacgc cgccagcagc 600
tacctgagcc tgacccccga gcagtggaag agccacaggt cctacagctg ccaggtgacc 660
cacgagggca gcaccgtgga gaaaaccgtg gcccccaccg agtgcagcgg agccgcagaa 720
caaaaactca tctcagaaga ggatctgaat ggagccgcag actacaagga cgacgacgac 780
aagggtgccg cataataagg cgcgccaatt ctatttcaag gagacagtca tatgaaatac 840
ctgctgccga ccgctgctgc tggtctgctg ctcctcgctg cccagccggc gatggccgag 900
gtgcaattgc tggagtctgg gggaggcttg gtacagcctg gggggtccct gagactctcc 960
tgtgcagcct ccggattcac ctttagcagt tatgccatga gctgggtccg ccaggctcca 1020
gggaaggggc tggagtgggt ctcagctatt agtggtagtg gtggtagcac atactacgca 1080

-continued

```
gactccgtga agggccggtt caccatctcc agagacaatt ccaagaacac gctgtatctg   1140

cagatgaaca gcctgagagc cgaggacacg gccgtatatt actgtgcgaa accgtttccg   1200

tattttgact actggggcca aggaaccctg gtcaccgtct cgagtgctag caccaaaggc   1260

ccatcggtct tccccctggc accctcctcc aagagcacct ctgggggcac agcggccctg   1320

ggctgcctgg tcaaggacta cttccccgaa ccggtgacgg tgtcgtggaa ctcaggcgcc   1380

ctgaccagcg gcgtgcacac cttcccggct gtcctacagt cctcaggact ctactccctc   1440

agcagcgtgg tgaccgtgcc ctccagcagc ttgggcaccc agacctacat ctgcaacgtg   1500

aatcacaagc ccagcaacac caaagtggac aagaaagttg agcccaaatc ttgtgacgcg   1560

gccgcaagca ctagtgccca tcaccatcac catcacgccg cggca                   1605
```

<210> SEQ ID NO 29
<211> LENGTH: 726
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Fab light chain Vl3_19

<400> SEQUENCE: 29

```
tcgtctgagc tgactcagga ccctgctgtg tctgtggcct tgggacagac agtcaggatc     60

acatgccaag gagacagcct cagaagttat tatgcaagct ggtaccagca gaagccagga    120

caggcccctg tacttgtcat ctatggtaaa aacaaccggc cctcagggat cccagaccga    180

ttctctggct ccagctcagg aaacacagct tccttgacca tcactggggc tcaggcggaa    240

gatgaggctg actattactg taactcccgt gatagtagcg gtaatcatgt ggtattcggc    300

ggagggacca agctgaccgt cctaggacaa cccaaggctg cccccagcgt gaccctgttc    360

ccccccagca gcgaggaatt gcaggccaac aaggccaccc tggtctgcct gatcagcgac    420

ttctacccag gcgccgtgac cgtggcctgg aaggccgaca gcagccccgt gaaggccggc    480

gtggagacca ccacccccag caagcagagc aacaacaagt acgccgccag cagctacctg    540

agcctgaccc ccgagcagtg gaagagccac aggtcctaca gctgccaggt gacccacgag    600

ggcagcaccg tggagaaaac cgtggccccc accgagtgca gcggagccgc agaacaaaaa    660

ctcatctcag aagaggatct gaatggagcc gcagactaca aggacgacga cgacaagggt    720

gccgca                                                               726
```

<210> SEQ ID NO 30
<211> LENGTH: 708
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Fab heavy chain VH3_23

<400> SEQUENCE: 30

```
gaggtgcaat tgctggagtc tgggggaggc ttggtacagc ctggggggtc cctgagactc     60

tcctgtgcag cctccggatt cacctttagc agttatgcca tgagctgggt ccgccaggct    120

ccagggaagg ggctggagtg ggtctcagct attagtggta gtggtggtag cacatactac    180

gcagactccg tgaagggccg gttcaccatc tccagagaca attccaagaa cacgctgtat    240

ctgcagatga acagcctgag agccgaggac acggccgtat attactgtgc gaaaccgttt    300
```

```
ccgtattttg actactgggg ccaaggaacc ctggtcaccg tctcgagtgc tagcaccaaa    360

ggcccatcgg tcttccccct ggcaccctcc tccaagagca cctctggggg cacagcggcc    420

ctgggctgcc tggtcaagga ctacttcccc gaaccggtga cggtgtcgtg gaactcaggc    480

gccctgacca gcggcgtgca caccttcccg gctgtcctac agtcctcagg actctactcc    540

ctcagcagcg tggtgaccgt gccctccagc agcttgggca cccagaccta catctgcaac    600

gtgaatcaca agcccagcaa caccaaagtg gacaagaaag ttgagcccaa atcttgtgac    660

gcggccgcaa gcactagtgc ccatcaccat caccatcacg ccgcggca                 708
```

```
<210> SEQ ID NO 31
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Fab light chain Vl3_19

<400> SEQUENCE: 31

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser Gly Ala Ala Glu Gln Lys Leu Ile Ser Glu
    210                 215                 220

Glu Asp Leu Asn Gly Ala Ala Asp Tyr Lys Asp Asp Asp Asp Lys Gly
225                 230                 235                 240

Ala Ala


<210> SEQ ID NO 32
<211> LENGTH: 236
<212> TYPE: PRT
```

```
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Fab heavy chain VH3_23 (DP47)

<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Ala Ala Ala Ser
    210                 215                 220

Thr Ser Ala His His His His His His Ala Ala Ala
225                 230                 235


<210> SEQ ID NO 33
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Vl_3_19_L3r_V
<220> FEATURE:
<221> NAME/KEY: misc_feature
<222> LOCATION: (32)..(32)
<223> OTHER INFORMATION: 60% original base and 40% randomization as m
<220> FEATURE:
<221> NAME/KEY: misc_feature
<222> LOCATION: (33)..(34)
<223> OTHER INFORMATION: 60% original base and 40% randomization as n
<220> FEATURE:
<221> NAME/KEY: misc_feature
<222> LOCATION: (35)..(35)
<223> OTHER INFORMATION: 60% original base and 40% randomization as m
<220> FEATURE:
<221> NAME/KEY: misc_feature
<222> LOCATION: (36)..(37)
```

<223> OTHER INFORMATION: 60% original base and 40% randomization as n
<220> FEATURE:
<221> NAME/KEY: misc_feature
<222> LOCATION: (38)..(38)
<223> OTHER INFORMATION: 60% original base and 40% randomization as m
<220> FEATURE:
<221> NAME/KEY: misc_feature
<222> LOCATION: (39)..(40)
<223> OTHER INFORMATION: 60% original base and 40% randomization as n
<220> FEATURE:
<221> NAME/KEY: misc_feature
<222> LOCATION: (41)..(41)
<223> OTHER INFORMATION: 60% original base and 40% randomization as m
<220> FEATURE:
<221> NAME/KEY: misc_feature
<222> LOCATION: (42)..(43)
<223> OTHER INFORMATION: 60% original base and 40% randomization as n
<220> FEATURE:
<221> NAME/KEY: misc_feature
<222> LOCATION: (44)..(44)
<223> OTHER INFORMATION: 60% original base and 40% randomization as m
<220> FEATURE:
<221> NAME/KEY: misc_feature
<222> LOCATION: (45)..(46)
<223> OTHER INFORMATION: 60% original base and 40% randomization as n
<220> FEATURE:
<221> NAME/KEY: misc_feature
<222> LOCATION: (47)..(47)
<223> OTHER INFORMATION: 60% original base and 40% randomization as m
<220> FEATURE:
<221> NAME/KEY: misc_feature
<222> LOCATION: (48)..(49)
<223> OTHER INFORMATION: 60% original base and 40% randomization as n
<220> FEATURE:
<221> NAME/KEY: misc_feature
<222> LOCATION: (50)..(50)
<223> OTHER INFORMATION: 60% original base and 40% randomization as m
<220> FEATURE:
<221> NAME/KEY: misc_feature
<222> LOCATION: (51)..(52)
<223> OTHER INFORMATION: 60% original base and 40% randomization as n

<400> SEQUENCE: 33
ggacggtcag cttggtccct ccgccgaata cvhvattacc gctactatca cgggagttac 60
agtaatagtc agcctcatct tccgc 85

<210> SEQ ID NO 34
<211> LENGTH: 88
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Vl_3_19_L3r_HV
<220> FEATURE:
<221> NAME/KEY: misc_feature
<222> LOCATION: (32)..(32)
<223> OTHER INFORMATION: 60% original base and 40% randomization as m
<220> FEATURE:
<221> NAME/KEY: misc_feature
<222> LOCATION: (33)..(34)
<223> OTHER INFORMATION: 60% original base and 40% randomization as n
<220> FEATURE:
<221> NAME/KEY: misc_feature
<222> LOCATION: (35)..(35)
<223> OTHER INFORMATION: 60% original base and 40% randomization as m
<220> FEATURE:
<221> NAME/KEY: misc_feature
<222> LOCATION: (36)..(37)
<223> OTHER INFORMATION: 60% original base and 40% randomization as n
<220> FEATURE:
<221> NAME/KEY: misc_feature
<222> LOCATION: (38)..(38)
<223> OTHER INFORMATION: 60% original base and 40% randomization as m
<220> FEATURE:

<221> NAME/KEY: misc_feature
<222> LOCATION: (39)..(40)
<223> OTHER INFORMATION: 60% original base and 40% randomization as n
<220> FEATURE:
<221> NAME/KEY: misc_feature
<222> LOCATION: (41)..(41)
<223> OTHER INFORMATION: 60% original base and 40% randomization as m
<220> FEATURE:
<221> NAME/KEY: misc_feature
<222> LOCATION: (42)..(43)
<223> OTHER INFORMATION: 60% original base and 40% randomization as n
<220> FEATURE:
<221> NAME/KEY: misc_feature
<222> LOCATION: (44)..(44)
<223> OTHER INFORMATION: 60% original base and 40% randomization as m
<220> FEATURE:
<221> NAME/KEY: misc_feature
<222> LOCATION: (45)..(46)
<223> OTHER INFORMATION: 60% original base and 40% randomization as n
<220> FEATURE:
<221> NAME/KEY: misc_feature
<222> LOCATION: (47)..(47)
<223> OTHER INFORMATION: 60% original base and 40% randomization as m
<220> FEATURE:
<221> NAME/KEY: misc_feature
<222> LOCATION: (48)..(49)
<223> OTHER INFORMATION: 60% original base and 40% randomization as n
<220> FEATURE:
<221> NAME/KEY: misc_feature
<222> LOCATION: (50)..(50)
<223> OTHER INFORMATION: 60% original base and 40% randomization as m
<220> FEATURE:
<221> NAME/KEY: misc_feature
<222> LOCATION: (51)..(52)
<223> OTHER INFORMATION: 60% original base and 40% randomization as n
<220> FEATURE:
<221> NAME/KEY: misc_feature
<222> LOCATION: (53)..(53)
<223> OTHER INFORMATION: 60% original base and 40% randomization as m
<220> FEATURE:
<221> NAME/KEY: misc_feature
<222> LOCATION: (54)..(55)
<223> OTHER INFORMATION: 60% original base and 40% randomization as n

<400> SEQUENCE: 34
ggacggtcag cttggtccct ccgccgaata ccmmatgatt accgctacta tcacgggagt 60
tacagtaata gtcagcctca tcttccgc 88

<210> SEQ ID NO 35
<211> LENGTH: 91
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Vl_3_19_L3r_HLV
<220> FEATURE:
<221> NAME/KEY: misc_feature
<222> LOCATION: (32)..(32)
<223> OTHER INFORMATION: 60% original base and 40% randomization as m
<220> FEATURE:
<221> NAME/KEY: misc_feature
<222> LOCATION: (33)..(34)
<223> OTHER INFORMATION: 60% original base and 40% randomization as n
<220> FEATURE:
<221> NAME/KEY: misc_feature
<222> LOCATION: (35)..(35)
<223> OTHER INFORMATION: 60% original base and 40% randomization as m
<220> FEATURE:
<221> NAME/KEY: misc_feature
<222> LOCATION: (36)..(37)
<223> OTHER INFORMATION: 60% original base and 40% randomization as n
<220> FEATURE:
<221> NAME/KEY: misc_feature
<222> LOCATION: (38)..(38)

<223> OTHER INFORMATION: 60% original base and 40% randomization as m
<220> FEATURE:
<221> NAME/KEY: misc_feature
<222> LOCATION: (39)..(40)
<223> OTHER INFORMATION: 60% original base and 40% randomization as n
<220> FEATURE:
<221> NAME/KEY: misc_feature
<222> LOCATION: (41)..(41)
<223> OTHER INFORMATION: 60% original base and 40% randomization as m
<220> FEATURE:
<221> NAME/KEY: misc_feature
<222> LOCATION: (42)..(43)
<223> OTHER INFORMATION: 60% original base and 40% randomization as n
<220> FEATURE:
<221> NAME/KEY: misc_feature
<222> LOCATION: (44)..(44)
<223> OTHER INFORMATION: 60% original base and 40% randomization as m
<220> FEATURE:
<221> NAME/KEY: misc_feature
<222> LOCATION: (45)..(46)
<223> OTHER INFORMATION: 60% original base and 40% randomization as n
<220> FEATURE:
<221> NAME/KEY: misc_feature
<222> LOCATION: (47)..(47)
<223> OTHER INFORMATION: 60% original base and 40% randomization as m
<220> FEATURE:
<221> NAME/KEY: misc_feature
<222> LOCATION: (48)..(49)
<223> OTHER INFORMATION: 60% original base and 40% randomization as n
<220> FEATURE:
<221> NAME/KEY: misc_feature
<222> LOCATION: (50)..(50)
<223> OTHER INFORMATION: 60% original base and 40% randomization as m
<220> FEATURE:
<221> NAME/KEY: misc_feature
<222> LOCATION: (51)..(52)
<223> OTHER INFORMATION: 60% original base and 40% randomization as n
<220> FEATURE:
<221> NAME/KEY: misc_feature
<222> LOCATION: (53)..(53)
<223> OTHER INFORMATION: 60% original base and 40% randomization as m
<220> FEATURE:
<221> NAME/KEY: misc_feature
<222> LOCATION: (54)..(55)
<223> OTHER INFORMATION: 60% original base and 40% randomization as n
<220> FEATURE:
<221> NAME/KEY: misc_feature
<222> LOCATION: (56)..(56)
<223> OTHER INFORMATION: 60% original base and 40% randomization as m
<220> FEATURE:
<221> NAME/KEY: misc_feature
<222> LOCATION: (57)..(58)
<223> OTHER INFORMATION: 60% original base and 40% randomization as n

<400> SEQUENCE: 35
ggacggtcag cttggtccct ccgccgaata crhmvwgatg attaccgcta ctatcacggg 60
agttacagta atagtcagcc tcatcttccg c 91

<210> SEQ ID NO 36
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: RJH80

<400> SEQUENCE: 36
ttcggcggag ggaccaagct gaccgtcc 28

<210> SEQ ID NO 37
<211> LENGTH: 25
<212> TYPE: DNA

<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DP47CDR3_ba (mod.)

<400> SEQUENCE: 37
cgcacagtaa tatacggccg tgtcc 25

<210> SEQ ID NO 38
<211> LENGTH: 82
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DP47-v4-4
<220> FEATURE:
<221> NAME/KEY: modified_base
<222> LOCATION: (29)..(31)
<223> OTHER INFORMATION: a, c, t, or g
<220> FEATURE:
<221> NAME/KEY: misc_feature
<222> LOCATION: (29)..(31)
<223> OTHER INFORMATION: This region encodes K=70%, R=30%
<220> FEATURE:
<221> NAME/KEY: modified_base
<222> LOCATION: (32)..(34)
<223> OTHER INFORMATION: a, c, t, or g
<220> FEATURE:
<221> NAME/KEY: misc_feature
<222> LOCATION: (32)..(34)
<223> OTHER INFORMATION: This region encodes G/D=20%, E/V/S=10%,
A/P/R/L/T/Y=5%
<220> FEATURE:
<221> NAME/KEY: modified_base
<222> LOCATION: (35)..(37)
<223> OTHER INFORMATION: a, c, t, or g
<220> FEATURE:
<221> NAME/KEY: misc_feature
<222> LOCATION: (35)..(37)
<223> OTHER INFORMATION: This region encodes G/Y/S=15%,
A/D/T/R/P/L/V/N/W/F/I/E=4,6%
<220> FEATURE:
<221> NAME/KEY: modified_base
<222> LOCATION: (38)..(40)
<223> OTHER INFORMATION: a, c, t, or g
<220> FEATURE:
<221> NAME/KEY: misc_feature
<222> LOCATION: (38)..(40)
<223> OTHER INFORMATION: This region encodes G/Y/S=15%,
A/D/T/R/P/L/V/N/W/F/I/E=4,6%
<220> FEATURE:
<221> NAME/KEY: modified_base
<222> LOCATION: (41)..(43)
<223> OTHER INFORMATION: a, c, t, or g
<220> FEATURE:
<221> NAME/KEY: misc_feature
<222> LOCATION: (41)..(43)
<223> OTHER INFORMATION: This region encodes G/A/Y=20, P/W/S/D/T=8%
<220> FEATURE:
<221> NAME/KEY: modified_base
<222> LOCATION: (44)..(46)
<223> OTHER INFORMATION: a, c, t, or g
<220> FEATURE:
<221> NAME/KEY: misc_feature
<222> LOCATION: (44)..(46)
<223> OTHER INFORMATION: This region encodes F=46%, L/M=15%, G/I/Y=8%

<400> SEQUENCE: 38
cgaggacacg gccgtatatt actgtgcgnn nnnnnnnnnn nnnnnngact actggggcca 60
aggaaccctg gtcaccgtct cg 82

```
<210> SEQ ID NO 39
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DP47-v4-6
<220> FEATURE:
<221> NAME/KEY: modified_base
<222> LOCATION: (29)..(31)
<223> OTHER INFORMATION: a, c, t, or g
<220> FEATURE:
<221> NAME/KEY: misc_feature
<222> LOCATION: (29)..(31)
<223> OTHER INFORMATION: This region encodes K=70%, R=30%
<220> FEATURE:
<221> NAME/KEY: modified_base
<222> LOCATION: (32)..(34)
<223> OTHER INFORMATION: a, c, t, or g
<220> FEATURE:
<221> NAME/KEY: misc_feature
<222> LOCATION: (32)..(34)
<223> OTHER INFORMATION: This region encodes G/D=20%, E/V/S=10%,
      A/P/R/L/T/Y=5%
<220> FEATURE:
<221> NAME/KEY: modified_base
<222> LOCATION: (35)..(37)
<223> OTHER INFORMATION: a, c, t, or g
<220> FEATURE:
<221> NAME/KEY: misc_feature
<222> LOCATION: (35)..(37)
<223> OTHER INFORMATION: This region encodes G/Y/S=15%,
      A/D/T/R/P/L/V/N/W/F/I/E=4,6%
<220> FEATURE:
<221> NAME/KEY: modified_base
<222> LOCATION: (38)..(40)
<223> OTHER INFORMATION: a, c, t, or g
<220> FEATURE:
<221> NAME/KEY: misc_feature
<222> LOCATION: (38)..(40)
<223> OTHER INFORMATION: This region encodes G/Y/S=15%,
      A/D/T/R/P/L/V/N/W/F/I/E=4,6%
<220> FEATURE:
<221> NAME/KEY: modified_base
<222> LOCATION: (41)..(43)
<223> OTHER INFORMATION: a, c, t, or g
<220> FEATURE:
<221> NAME/KEY: misc_feature
<222> LOCATION: (41)..(43)
<223> OTHER INFORMATION: This region encodes G/Y/S=15%,
      A/D/T/R/P/L/V/N/W/F/I/E=4,6%
<220> FEATURE:
<221> NAME/KEY: modified_base
<222> LOCATION: (44)..(46)
<223> OTHER INFORMATION: a, c, t, or g
<220> FEATURE:
<221> NAME/KEY: misc_feature
<222> LOCATION: (44)..(46)
<223> OTHER INFORMATION: This region encodes G/Y/S=15%,
      A/D/T/R/P/L/V/N/W/F/I/E=4,6%
<220> FEATURE:
<221> NAME/KEY: modified_base
<222> LOCATION: (47)..(49)
<223> OTHER INFORMATION: a, c, t, or g
<220> FEATURE:
<221> NAME/KEY: misc_feature
<222> LOCATION: (47)..(49)
<223> OTHER INFORMATION: This region encodes G/A/Y=20, P/W/S/D/T=8%
<220> FEATURE:
<221> NAME/KEY: modified_base
<222> LOCATION: (50)..(52)
<223> OTHER INFORMATION: a, c, t, or g
<220> FEATURE:
<221> NAME/KEY: misc_feature
<222> LOCATION: (50)..(52)
<223> OTHER INFORMATION: This region encodes F=46%, L/M=15%, G/I/Y=8%
```

<400> SEQUENCE: 39
cgaggacacg gccgtatatt actgtgcgnn nnnnnnnnnn nnnnnnnnnn nngactactg     60
gggccaagga accctggtca ccgtctcg                                        88

<210> SEQ ID NO 40
<211> LENGTH: 94
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DP47-v4-8
<220> FEATURE:
<221> NAME/KEY: modified_base
<222> LOCATION: (29)..(31)
<223> OTHER INFORMATION: a, c, t, or g
<220> FEATURE:
<221> NAME/KEY: misc_feature
<222> LOCATION: (29)..(31)
<223> OTHER INFORMATION: This region encodes K=70%, R=30%
<220> FEATURE:
<221> NAME/KEY: modified_base
<222> LOCATION: (32)..(34)
<223> OTHER INFORMATION: a, c, t, or g
<220> FEATURE:
<221> NAME/KEY: misc_feature
<222> LOCATION: (32)..(34)
<223> OTHER INFORMATION: This region encodes G/D=20%, E/V/S=10%,
      A/P/R/L/T/Y=5%
<220> FEATURE:
<221> NAME/KEY: modified_base
<222> LOCATION: (35)..(37)
<223> OTHER INFORMATION: a, c, t, or g
<220> FEATURE:
<221> NAME/KEY: misc_feature
<222> LOCATION: (35)..(37)
<223> OTHER INFORMATION: This region encodes G/Y/S=15%,
      A/D/T/R/P/L/V/N/W/F/I/E=4,6%
<220> FEATURE:
<221> NAME/KEY: modified_base
<222> LOCATION: (38)..(40)
<223> OTHER INFORMATION: a, c, t, or g
<220> FEATURE:
<221> NAME/KEY: misc_feature
<222> LOCATION: (38)..(40)
<223> OTHER INFORMATION: This region encodes G/Y/S=15%,
      A/D/T/R/P/L/V/N/W/F/I/E=4,6%
<220> FEATURE:
<221> NAME/KEY: modified_base
<222> LOCATION: (41)..(43)
<223> OTHER INFORMATION: a, c, t, or g
<220> FEATURE:
<221> NAME/KEY: misc_feature
<222> LOCATION: (41)..(43)
<223> OTHER INFORMATION: This region encodes G/Y/S=15%,
      A/D/T/R/P/L/V/N/W/F/I/E=4,6%
<220> FEATURE:
<221> NAME/KEY: modified_base
<222> LOCATION: (44)..(46)
<223> OTHER INFORMATION: a, c, t, or g
<220> FEATURE:
<221> NAME/KEY: misc_feature
<222> LOCATION: (44)..(46)
<223> OTHER INFORMATION: This region encodes G/Y/S=15%,
      A/D/T/R/P/L/V/N/W/F/I/E=4,6%
<220> FEATURE:
<221> NAME/KEY: modified_base
<222> LOCATION: (47)..(49)
<223> OTHER INFORMATION: a, c, t, or g
<220> FEATURE:
<221> NAME/KEY: misc_feature
<222> LOCATION: (47)..(49)
<223> OTHER INFORMATION: This region encodes G/Y/S=15%,
      A/D/T/R/P/L/V/N/W/F/I/E=4,6%

<220> FEATURE:
<221> NAME/KEY: modified_base
<222> LOCATION: (50)..(52)
<223> OTHER INFORMATION: a, c, t, or g
<220> FEATURE:
<221> NAME/KEY: misc_feature
<222> LOCATION: (50)..(52)
<223> OTHER INFORMATION: This region encodes G/Y/S=15%,
A/D/T/R/P/L/V/N/W/F/I/E=4,6%
<220> FEATURE:
<221> NAME/KEY: modified_base
<222> LOCATION: (53)..(55)
<223> OTHER INFORMATION: a, c, t, or g
<220> FEATURE:
<221> NAME/KEY: misc_feature
<222> LOCATION: (53)..(55)
<223> OTHER INFORMATION: This region encodes G/A/Y=20, P/W/S/D/T=8%
<220> FEATURE:
<221> NAME/KEY: modified_base
<222> LOCATION: (56)..(58)
<223> OTHER INFORMATION: a, c, t, or g
<220> FEATURE:
<221> NAME/KEY: misc_feature
<222> LOCATION: (56)..(58)
<223> OTHER INFORMATION: This region encodes F=46%, L/M=15%, G/I/Y=8%

<400> SEQUENCE: 40
cgaggacacg gccgtatatt actgtgcgnn nnnnnnnnnn nnnnnnnnnn nnnnnnnnga 60
ctactggggc caaggaaccc tggtcaccgt ctcg 94

<210> SEQ ID NO 41
<211> LENGTH: 324
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: 18D4 VL

<400> SEQUENCE: 41
gacatccaga tgacccagtc tccatccacc ctgtctgcat ctgtaggaga ccgtgtcacc 60
atcacttgcc gtgccagtca gagtattagt agctggttgg cctggtatca gcagaaacca 120
gggaaagccc ctaagctcct gatctatgat gcctccagtt tggaaagtgg ggtcccatca 180
cgtttcagcg gcagtggatc cgggacagaa ttcactctca ccatcagcag cttgcagcct 240
gatgattttg caacttatta ctgccaacag aataagaagt ttccttcggg gacgtttggc 300
cagggcacca aagtcgagat caag 324

<210> SEQ ID NO 42
<211> LENGTH: 354
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: 18D4 VH

<400> SEQUENCE: 42
caggtgcaat tggtgcagtc tggggctgag gtgaagaagc ctgggtcctc ggtgaaggtc 60
tcctgcaagg cctccggagg cacattcagc agctacgcta taagctgggt gcgacaggcc 120
cctggacaag ggctcgagtg gatgggaggg atcatcccta tctttggtac agcaaactac 180
gcacagaagt tccagggcag ggtcaccatt actgcagaca aatccacgag cacagcctac 240
atggagctga gcagcctgag atctgaggac accgccgtgt attactgtgc gaaaggtaac 300
ttctacggtg gtctggacta ctggggccaa gggaccaccg tgaccgtctc ctca 354

<210> SEQ ID NO 43
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: 11C7 VL

<400> SEQUENCE: 43
tcgtctgagc tgactcagga ccctgctgtg tctgtggcct tgggacagac agtcagggtc 60
acatgccaag gagacagcct cagaagttat tatgcaagct ggtaccagca gaagccagga 120
caggcccctg tacttgtcat ctatggtaaa aacaaccggc cctcagggat cccagaccga 180
ttctctggct ccagctcagg aaacacagct tccttgacca tcactggggc tcaggcggaa 240
gatgaggctg actattactg taactccatt aatagtactc gtaatgaggt attcggcgga 300
gggaccaagc tgaccgtcct a 321

<210> SEQ ID NO 44
<211> LENGTH: 354
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: 11C7 VH

<400> SEQUENCE: 44
gaggtgcaat tgttggagtc tgggggaggc ttggtacagc ctggggggtc cctgagactc 60
tcctgtgcag cctccggatt cacctttagc agttatgcca tgagctgggt ccgccaggct 120
ccagggaagg ggctggagtg ggtctcagct attagcggta gtggtggtag cacatactac 180
gcagactccg tgaagggccg gttcaccatc tccaaagaca attccaagaa cacgctgtat 240
ctgcagatga acagcctgag agccgaggac acggccgtat attactgtgc gaaaacttct 300
ccgcgtgttc cgctggacta ctggggccaa ggaaccctgg tcaccgtctc gagt 354

<210> SEQ ID NO 45
<211> LENGTH: 108
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: 18D4 VL

<400> SEQUENCE: 45

Asp Ile Gln Met Thr Gln Ser Pro Ser Thr Leu Ser Ala Ser Val Gly
1 5 10 15

Asp Arg Val Thr Ile Thr Cys Arg Ala Ser Gln Ser Ile Ser Ser Trp
20 25 30

Leu Ala Trp Tyr Gln Gln Lys Pro Gly Lys Ala Pro Lys Leu Leu Ile
35 40 45

Tyr Asp Ala Ser Ser Leu Glu Ser Gly Val Pro Ser Arg Phe Ser Gly
50 55 60

Ser Gly Ser Gly Thr Glu Phe Thr Leu Thr Ile Ser Ser Leu Gln Pro 65 70 75 80

Asp Asp Phe Ala Thr Tyr Tyr Cys Gln Gln Asn Lys Lys Phe Pro Ser
85 90 95

Gly Thr Phe Gly Gln Gly Thr Lys Val Glu Ile Lys
100 105

<210> SEQ ID NO 46
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: 18D4 VH

<400> SEQUENCE: 46

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Lys Gly Asn Phe Tyr Gly Gly Leu Asp Tyr Trp Gly Gln Gly Thr
100 105 110

Thr Val Thr Val Ser Ser
115

<210> SEQ ID NO 47
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: 11C7 VL

<400> SEQUENCE: 47

Ser Ser Glu Leu Thr Gln Asp Pro Ala Val Ser Val Ala Leu Gly Gln
1 5 10 15

Thr Val Arg Val Thr Cys Gln Gly Asp Ser Leu Arg Ser Tyr Tyr Ala
20 25 30

Ser Trp Tyr Gln Gln Lys Pro Gly Gln Ala Pro Val Leu Val Ile Tyr
35 40 45

Gly Lys Asn Asn Arg Pro Ser Gly Ile Pro Asp Arg Phe Ser Gly Ser
50 55 60

Ser Ser Gly Asn Thr Ala Ser Leu Thr Ile Thr Gly Ala Gln Ala Glu
65 70 75 80

Asp Glu Ala Asp Tyr Tyr Cys Asn Ser Ile Asn Ser Thr Arg Asn Glu
85 90 95

Val Phe Gly Gly Gly Thr Lys Leu Thr Val Leu
100 105

```
<210> SEQ ID NO 48
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 11C7 VH

<400> SEQUENCE: 48

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Lys Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Ser Pro Arg Val Pro Leu Asp Tyr Trp Gly Gln Gly Thr
            100                 105                 110

Leu Val Thr Val Ser Ser
        115


<210> SEQ ID NO 49
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 18D4 LCDR1

<400> SEQUENCE: 49

cgtgccagtc agagtattag tagctggttg gcc                                  33


<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 18D4 LCDR2

<400> SEQUENCE: 50

gatgcctcca gtttggaaag t                                               21


<210> SEQ ID NO 51
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 18D4 LCDR3

<400> SEQUENCE: 51
```

caacagaata agaagtttcc ttcggggacg 30

<210> SEQ ID NO 52
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: 11C7 LCDR1

<400> SEQUENCE: 52
caaggagaca gcctcagaag ttattatgca agc 33

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: 11C7 LCDR2

<400> SEQUENCE: 53
ggtaaaaaca accggccctc a 21

<210> SEQ ID NO 54
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: 11C7 LCDR3

<400> SEQUENCE: 54
aactccatta atagtactcg taatgaggta 30

<210> SEQ ID NO 55
<211> LENGTH: 11
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: 18D4 LCDR1

<400> SEQUENCE: 55

Arg Ala Ser Gln Ser Ile Ser Ser Trp Leu Ala
1 5 10

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: 18D4 LCDR2

<400> SEQUENCE: 56

Asp Ala Ser Ser Leu Glu Ser
1 5

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: 18D4 LCDR3

<400> SEQUENCE: 57

Gln Gln Asn Lys Lys Phe Pro Ser Gly Thr
1 5 10

<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: 11C7 LCDR1

<400> SEQUENCE: 58

Gln Gly Asp Ser Leu Arg Ser Tyr Tyr Ala Ser
1 5 10

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: 11C7 LCDR2

<400> SEQUENCE: 59

Gly Lys Asn Asn Arg Pro Ser
1 5

<210> SEQ ID NO 60
<211> LENGTH: 10
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: 11C7 LCDR3

<400> SEQUENCE: 60

Asn Ser Ile Asn Ser Thr Arg Asn Glu Val
1 5 10

<210> SEQ ID NO 61
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: 18D4 HCDR1

<400> SEQUENCE: 61
agctacgcta taagc 15

<210> SEQ ID NO 62
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: 18D4 HCDR2

<400> SEQUENCE: 62
gggatcatcc ctatctttgg tacagcaaac tacgcacaga agttccaggg c 51

<210> SEQ ID NO 63
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: 18D4 HCDR3

<400> SEQUENCE: 63
ggtaacttct acggtggtct ggactac 27

<210> SEQ ID NO 64
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: 11C7 HCDR1

<400> SEQUENCE: 64
ggattcacct ttagcagtta tgccatgagc 30

<210> SEQ ID NO 65
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: 11C7 HCDR2

<400> SEQUENCE: 65
gctattagcg gtagtggtgg tagcacatac tacgcagact ccgtgaaggg c 51

<210> SEQ ID NO 66
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: 11C7 HCDR3

<400> SEQUENCE: 66
acttctccgc gtgttccgct ggactac 27

<210> SEQ ID NO 67
<211> LENGTH: 5

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 18D4 HCDR1

<400> SEQUENCE: 67

Ser Tyr Ala Ile Ser
1               5


<210> SEQ ID NO 68
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 18D4 HCDR2

<400> SEQUENCE: 68

Gly Ile Ile Pro Ile Phe Gly Thr Ala Asn Tyr Ala Gln Lys Phe Gln
1               5                   10                  15

Gly


<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 18D4 HCDR3

<400> SEQUENCE: 69

Gly Asn Phe Tyr Gly Gly Leu Asp Tyr
1               5


<210> SEQ ID NO 70
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 11C7 HCDR1

<400> SEQUENCE: 70

Gly Phe Thr Phe Ser Ser Tyr Ala Met Ser
1               5                   10


<210> SEQ ID NO 71
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 11C7 HCDR2

<400> SEQUENCE: 71

Ala Ile Ser Gly Ser Gly Gly Ser Thr Tyr Tyr Ala Asp Ser Val Lys
1               5                   10                  15
```

-continued

Gly

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 11C7 HCDR3

<400> SEQUENCE: 72

Thr Ser Pro Arg Val Pro Leu Asp Tyr
1               5

<210> SEQ ID NO 73
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 18D4 Light chain

<400> SEQUENCE: 73
gacatccaga tgacccagtc tccatccacc ctgtctgcat ctgtaggaga ccgtgtcacc 60
atcacttgcc gtgccagtca gagtattagt agctggttgg cctggtatca gcagaaacca 120
gggaaagccc ctaagctcct gatctatgat gcctccagtt tggaaagtgg ggtcccatca 180
cgtttcagcg gcagtggatc cgggacagaa ttcactctca ccatcagcag cttgcagcct 240
gatgattttg caacttatta ctgccaacag aataagaagt ttccttcggg gacgtttggc 300
cagggcacca aagtcgagat caagcgtacg gtggctgcac catctgtctt catcttcccg 360
ccatctgatg agcagttgaa atctggaact gcctctgttg tgtgcctgct gaataacttc 420
tatcccagag aggccaaagt acagtggaag gtggataacg ccctccaatc gggtaactcc 480
caggagagtg tcacagagca ggacagcaag gacagcacct acagcctcag cagcaccctg 540
acgctgagca aagcagacta cgagaaacac aaagtctacg cctgcgaagt cacccatcag 600
ggcctgagct cgcccgtcac aaagagcttc aacaggggag agtgt 645

<210> SEQ ID NO 74
<211> LENGTH: 1344
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 18D4 Heavy chain

<400> SEQUENCE: 74
caggtgcaat tggtgcagtc tggggctgag gtgaagaagc ctgggtcctc ggtgaaggtc 60
tcctgcaagg cctccggagg cacattcagc agctacgcta taagctgggt gcgacaggcc 120
cctggacaag ggctcgagtg gatgggaggg atcatcccta tctttggtac agcaaactac 180
gcacagaagt tccagggcag ggtcaccatt actgcagaca aatccacgag cacagcctac 240
atggagctga gcagcctgag atctgaggac accgccgtgt attactgtgc gaaaggtaac 300
ttctacggtg gtctggacta ctggggccaa gggaccaccg tgaccgtctc ctcagctagc 360
accaagggcc catcggtctt ccccctggca ccctcctcca agagcacctc tgggggcaca 420
gcggccctgg gctgcctggt caaggactac ttccccgaac cggtgacggt gtcgtggaac 480
tcaggcgccc tgaccagcgg cgtgcacacc ttcccggctg tcctacagtc ctcaggactc 540
tactccctca gcagcgtggt gaccgtgccc tccagcagct tgggcaccca gacctacatc 600
tgcaacgtga atcacaagcc cagcaacacc aaggtggaca agaaagttga gcccaaatct 660
tgtgacaaaa ctcacacatg cccaccgtgc ccagcacctg aactcctggg gggaccgtca 720
gtcttcctct tccccccaaa acccaaggac accctcatga tctcccggac ccctgaggtc 780
acatgcgtgg tggtggacgt gagccacgaa gaccctgagg tcaagttcaa ctggtacgtg 840
gacggcgtgg aggtgcataa tgccaagaca aagccgcggg aggagcagta caacagcacg 900
taccgtgtgg tcagcgtcct caccgtcctg caccaggact ggctgaatgg caaggagtac 960
aagtgcaagg tctccaacaa agccctccca gcccccatcg agaaaaccat ctccaaagcc 1020
aaagggcagc cccgagaacc acaggtgtac accctgcccc catcccggga tgagctgacc 1080
aagaaccagg tcagcctgac ctgcctggtc aaaggcttct atcccagcga catcgccgtg 1140
gagtgggaga gcaatgggca gccggagaac aactacaaga ccacgcctcc cgtgctggac 1200
tccgacggct ccttcttcct ctacagcaag ctcaccgtgg acaagagcag gtggcagcag 1260
gggaacgtct tctcatgctc cgtgatgcat gaggctctgc acaaccacta cacgcagaag 1320
agcctctccc tgtctccggg taaa 1344

<210> SEQ ID NO 75
<211> LENGTH: 639
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: 11C7 Light chain

<400> SEQUENCE: 75
tcgtctgagc tgactcagga ccctgctgtg tctgtggcct tgggacagac agtcagggtc 60
acatgccaag gagacagcct cagaagttat tatgcaagct ggtaccagca gaagccagga 120
caggcccctg tacttgtcat ctatggtaaa aacaaccggc cctcagggat cccagaccga 180
ttctctggct ccagctcagg aaacacagct tccttgacca tcactggggc tcaggcggaa 240
gatgaggctg actattactg taactccatt aatagtactc gtaatgaggt attcggcgga 300
gggaccaagc tgaccgtcct aggtcaaccc aaggctgccc ccagcgtgac cctgttcccc 360
cccagcagcg aggaactgca ggccaacaag gccaccctgg tctgcctgat cagcgacttc 420
tacccaggcg ccgtgaccgt ggcctggaag gccgacagca gccccgtgaa ggccggcgtg 480
gagaccacca cccccagcaa gcagagcaac aacaagtacg ccgccagcag ctacctgagc 540
ctgacccccg agcagtggaa gagccacagg tcctacagct gccaggtgac ccacgagggc 600
agcaccgtgg agaaaaccgt ggcccccacc gagtgcagc 639

<210> SEQ ID NO 76
<211> LENGTH: 1344
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: 11C7 Heavy chain

<400> SEQUENCE: 76

```
gaggtgcaat tgttggagtc tgggggaggc ttggtacagc ctggggggtc cctgagactc      60

tcctgtgcag cctccggatt cacctttagc agttatgcca tgagctgggt ccgccaggct     120

ccagggaagg ggctggagtg ggtctcagct attagcggta gtggtggtag cacatactac     180

gcagactccg tgaagggccg gttcaccatc tccaaagaca attccaagaa cacgctgtat     240

ctgcagatga acagcctgag agccgaggac acggccgtat attactgtgc gaaaacttct     300

ccgcgtgttc cgctggacta ctggggccaa ggaaccctgg tcaccgtctc gagtgctagc     360

accaagggcc catcggtctt ccccctggca ccctcctcca agagcacctc tgggggcaca     420

gcggccctgg gctgcctggt caaggactac ttccccgaac cggtgacggt gtcgtggaac     480

tcaggcgccc tgaccagcgg cgtgcacacc ttcccggctg tcctacagtc ctcaggactc     540

tactccctca gcagcgtggt gaccgtgccc tccagcagct tgggcaccca gacctacatc     600

tgcaacgtga atcacaagcc cagcaacacc aaggtggaca agaaagttga gcccaaatct     660

tgtgacaaaa ctcacacatg cccaccgtgc ccagcacctg aactcctggg gggaccgtca     720

gtcttcctct tccccccaaa acccaaggac accctcatga tctcccggac ccctgaggtc     780

acatgcgtgg tggtggacgt gagccacgaa gaccctgagg tcaagttcaa ctggtacgtg     840

gacggcgtgg aggtgcataa tgccaagaca aagccgcggg aggagcagta caacagcacg     900

taccgtgtgg tcagcgtcct caccgtcctg caccaggact ggctgaatgg caaggagtac     960

aagtgcaagg tctccaacaa agccctccca gcccccatcg agaaaaccat ctccaaagcc    1020

aaagggcagc cccgagaacc acaggtgtac accctgcccc catcccggga tgagctgacc    1080

aagaaccagg tcagcctgac ctgcctggtc aaaggcttct atcccagcga catcgccgtg    1140

gagtgggaga gcaatgggca gccggagaac aactacaaga ccacgcctcc cgtgctggac    1200

tccgacggct ccttcttcct ctacagcaag ctcaccgtgg acaagagcag gtggcagcag    1260

gggaacgtct tctcatgctc cgtgatgcat gaggctctgc acaaccacta cacgcagaag    1320

agcctctccc tgtctccggg taaa                                           1344
```

<210> SEQ ID NO 77
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 18D4 Light chain

<400> SEQUENCE: 77

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Asn Lys Lys Phe Pro Ser
                85                  90                  95
```

Gly Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 78
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 18D4 Heavy chain

<400> SEQUENCE: 78

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Gly Asn Phe Tyr Gly Gly Leu Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

```
His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 79
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 11C7 Light chain

<400> SEQUENCE: 79

Ser Ser Glu Leu Thr Gln Asp Pro Ala Val Ser Val Ala Leu Gly Gln
1               5                   10                  15

Thr Val Arg Val Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Ile Asn Ser Thr Arg Asn Glu
                85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
        115                 120                 125
```

-continued

```
Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210


<210> SEQ ID NO 80
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 11C7 Heavy chain

<400> SEQUENCE: 80

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Lys Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Ser Pro Arg Val Pro Leu Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255
```

-continued

```
Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 81
<211> LENGTH: 1344
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 18D4 Heavy chain PGLALA

<400> SEQUENCE: 81

```
caggtgcaat tggtgcagtc tggggctgag gtgaagaagc ctgggtcctc ggtgaaggtc      60

tcctgcaagg cctccggagg cacattcagc agctacgcta taagctgggt gcgacaggcc     120

cctggacaag ggctcgagtg gatgggaggg atcatcccta tctttggtac agcaaactac     180

gcacagaagt tccagggcag ggtcaccatt actgcagaca aatccacgag cacagcctac     240

atggagctga gcagcctgag atctgaggac accgccgtgt attactgtgc gaaaggtaac     300

ttctacggtg gtctggacta ctggggccaa gggaccaccg tgaccgtctc ctcagctagc     360

accaagggcc catcggtctt ccccctggca ccctcctcca agagcacctc tgggggcaca     420

gcggccctgg gctgcctggt caaggactac ttccccgaac cggtgacggt gtcgtggaac     480

tcaggcgccc tgaccagcgg cgtgcacacc ttcccggctg tcctacagtc ctcaggactc     540

tactccctca gcagcgtggt gaccgtgccc tccagcagct tgggcaccca gacctacatc     600

tgcaacgtga atcacaagcc cagcaacacc aaggtggaca agaaagttga gcccaaatct     660

tgtgacaaaa ctcacacatg cccaccgtgc ccagcacctg aagctgcagg gggaccgtca     720

gtcttcctct tccccccaaa acccaaggac accctcatga tctcccggac ccctgaggtc     780

acatgcgtgg tggtggacgt gagccacgaa gaccctgagg tcaagttcaa ctggtacgtg     840

gacggcgtgg aggtgcataa tgccaagaca aagccgcggg aggagcagta caacagcacg     900
```

-continued

```
taccgtgtgg tcagcgtcct caccgtcctg caccaggact ggctgaatgg caaggagtac    960

aagtgcaagg tctccaacaa agccctcggc gcccccatcg agaaaaccat ctccaaagcc   1020

aaagggcagc cccgagaacc acaggtgtac accctgcccc catcccggga tgagctgacc   1080

aagaaccagg tcagcctgac ctgcctggtc aaaggcttct atcccagcga catcgccgtg   1140

gagtgggaga gcaatgggca gccggagaac aactacaaga ccacgcctcc cgtgctggac   1200

tccgacggct ccttcttcct ctacagcaag ctcaccgtgg acaagagcag gtggcagcag   1260

gggaacgtct tctcatgctc cgtgatgcat gaggctctgc acaaccacta cacgcagaag   1320

agcctctccc tgtctccggg taaa                                          1344
```

<210> SEQ ID NO 82
<211> LENGTH: 1344
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: 11C7 Heavy chain PGLALA

<400> SEQUENCE: 82

```
gaggtgcaat tgttggagtc tgggggaggc ttggtacagc ctggggggtc cctgagactc     60

tcctgtgcag cctccggatt cacctttagc agttatgcca tgagctgggt ccgccaggct    120

ccagggaagg ggctggagtg ggtctcagct attagcggta gtggtggtag cacatactac    180

gcagactccg tgaagggccg gttcaccatc tccaaagaca attccaagaa cacgctgtat    240

ctgcagatga acagcctgag agccgaggac acggccgtat attactgtgc gaaaacttct    300

ccgcgtgttc cgctggacta ctggggccaa ggaaccctgg tcaccgtctc gagtgctagc    360

accaagggcc catcggtctt ccccctggca ccctcctcca agagcacctc tgggggcaca    420

gcggccctgg gctgcctggt caaggactac ttccccgaac cggtgacggt gtcgtggaac    480

tcaggcgccc tgaccagcgg cgtgcacacc ttcccggctg tcctacagtc ctcaggactc    540

tactccctca gcagcgtggt gaccgtgccc tccagcagct tgggcaccca gacctacatc    600

tgcaacgtga atcacaagcc cagcaacacc aaggtggaca agaaagttga gcccaaatct    660

tgtgacaaaa ctcacacatg cccaccgtgc ccagcacctg aagctgcagg gggaccgtca    720

gtcttcctct tccccccaaa acccaaggac accctcatga tctcccggac ccctgaggtc    780

acatgcgtgg tggtggacgt gagccacgaa gaccctgagg tcaagttcaa ctggtacgtg    840

gacggcgtgg aggtgcataa tgccaagaca aagccgcggg aggagcagta caacagcacg    900

taccgtgtgg tcagcgtcct caccgtcctg caccaggact ggctgaatgg caaggagtac    960

aagtgcaagg tctccaacaa agccctcggc gcccccatcg agaaaaccat ctccaaagcc   1020

aaagggcagc cccgagaacc acaggtgtac accctgcccc catcccggga tgagctgacc   1080

aagaaccagg tcagcctgac ctgcctggtc aaaggcttct atcccagcga catcgccgtg   1140

gagtgggaga gcaatgggca gccggagaac aactacaaga ccacgcctcc cgtgctggac   1200

tccgacggct ccttcttcct ctacagcaag ctcaccgtgg acaagagcag gtggcagcag   1260

gggaacgtct tctcatgctc cgtgatgcat gaggctctgc acaaccacta cacgcagaag   1320

agcctctccc tgtctccggg taaa                                          1344
```

<210> SEQ ID NO 83
<211> LENGTH: 448
<212> TYPE: PRT

<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: 18D4 Heavy chain PGLALA

<400> SEQUENCE: 83

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Gly Asn Phe Tyr Gly Gly Leu Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Gly Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
```

```
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 84
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 11C7 Heavy chain PGLALA

<400> SEQUENCE: 84

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Lys Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Ser Pro Arg Val Pro Leu Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
```

275 280 285

Lys Thr Lys Pro Arg Glu Glu Gln Tyr Asn Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Ala Leu Gly Ala Pro Ile Glu Lys Thr
325 330 335

Ile Ser Lys Ala Lys Gly Gln Pro Arg Glu Pro Gln Val Tyr Thr Leu
340 345 350

Pro Pro Ser Arg Asp Glu Leu Thr Lys Asn Gln Val Ser Leu Thr Cys
355 360 365

Leu Val Lys Gly Phe Tyr Pro Ser Asp Ile Ala Val Glu Trp Glu Ser
370 375 380

Asn Gly Gln Pro Glu Asn Asn Tyr Lys Thr Thr Pro Pro Val Leu Asp
385 390 395 400

Ser Asp Gly Ser Phe Phe Leu Tyr Ser Lys Leu Thr Val Asp Lys Ser
405 410 415

Arg Trp Gln Gln Gly Asn Val Phe Ser Cys Ser Val Met His Glu Ala
420 425 430

Leu His Asn His Tyr Thr Gln Lys Ser Leu Ser Leu Ser Pro Gly Lys
435 440 445

<210> SEQ ID NO 85
<211> LENGTH: 163
<212> TYPE: PRT
<213> ORGANISM: Homo sapiens

<400> SEQUENCE: 85

Leu Gln Asp Pro Cys Ser Asn Cys Pro Ala Gly Thr Phe Cys Asp Asn
1 5 10 15

Asn Arg Asn Gln Ile Cys Ser Pro Cys Pro Pro Asn Ser Phe Ser Ser
20 25 30

Ala Gly Gly Gln Arg Thr Cys Asp Ile Cys Arg Gln Cys Lys Gly Val
35 40 45

Phe Arg Thr Arg Lys Glu Cys Ser Ser Thr Ser Asn Ala Glu Cys Asp
50 55 60

Cys Thr Pro Gly Phe His Cys Leu Gly Ala Gly Cys Ser Met Cys Glu
65 70 75 80

Gln Asp Cys Lys Gln Gly Gln Glu Leu Thr Lys Lys Gly Cys Lys Asp
85 90 95

Cys Cys Phe Gly Thr Phe Asn Asp Gln Lys Arg Gly Ile Cys Arg Pro
100 105 110

Trp Thr Asn Cys Ser Leu Asp Gly Lys Ser Val Leu Val Asn Gly Thr
115 120 125

Lys Glu Arg Asp Val Val Cys Gly Pro Ser Pro Ala Asp Leu Ser Pro
130 135 140

Gly Ala Ser Ser Val Thr Pro Pro Ala Pro Ala Arg Glu Pro Gly His
145 150 155 160

Ser Pro Gln

<210> SEQ ID NO 86
<211> LENGTH: 163
<212> TYPE: PRT
<213> ORGANISM: Macaca fascicularis

<400> SEQUENCE: 86

```
Leu Gln Asp Leu Cys Ser Asn Cys Pro Ala Gly Thr Phe Cys Asp Asn
1               5                   10                  15

Asn Arg Ser Gln Ile Cys Ser Pro Cys Pro Pro Asn Ser Phe Ser Ser
            20                  25                  30

Ala Gly Gly Gln Arg Thr Cys Asp Ile Cys Arg Gln Cys Lys Gly Val
        35                  40                  45

Phe Lys Thr Arg Lys Glu Cys Ser Ser Thr Ser Asn Ala Glu Cys Asp
    50                  55                  60

Cys Ile Ser Gly Tyr His Cys Leu Gly Ala Glu Cys Ser Met Cys Glu
65                  70                  75                  80

Gln Asp Cys Lys Gln Gly Gln Glu Leu Thr Lys Lys Gly Cys Lys Asp
                85                  90                  95

Cys Cys Phe Gly Thr Phe Asn Asp Gln Lys Arg Gly Ile Cys Arg Pro
            100                 105                 110

Trp Thr Asn Cys Ser Leu Asp Gly Lys Ser Val Leu Val Asn Gly Thr
        115                 120                 125

Lys Glu Arg Asp Val Val Cys Gly Pro Ser Pro Ala Asp Leu Ser Pro
    130                 135                 140

Gly Ala Ser Ser Ala Thr Pro Pro Ala Pro Ala Arg Glu Pro Gly His
145                 150                 155                 160

Ser Pro Gln
```

<210> SEQ ID NO 87
<211> LENGTH: 164
<212> TYPE: PRT
<213> ORGANISM: Mus musculus

<400> SEQUENCE: 87

```
Val Gln Asn Ser Cys Asp Asn Cys Gln Pro Gly Thr Phe Cys Arg Lys
1               5                   10                  15

Tyr Asn Pro Val Cys Lys Ser Cys Pro Pro Ser Thr Phe Ser Ser Ile
            20                  25                  30

Gly Gly Gln Pro Asn Cys Asn Ile Cys Arg Val Cys Ala Gly Tyr Phe
        35                  40                  45

Arg Phe Lys Lys Phe Cys Ser Ser Thr His Asn Ala Glu Cys Glu Cys
    50                  55                  60

Ile Glu Gly Phe His Cys Leu Gly Pro Gln Cys Thr Arg Cys Glu Lys
65                  70                  75                  80

Asp Cys Arg Pro Gly Gln Glu Leu Thr Lys Gln Gly Cys Lys Thr Cys
                85                  90                  95

Ser Leu Gly Thr Phe Asn Asp Gln Asn Gly Thr Gly Val Cys Arg Pro
            100                 105                 110

Trp Thr Asn Cys Ser Leu Asp Gly Arg Ser Val Leu Lys Thr Gly Thr
        115                 120                 125

Thr Glu Lys Asp Val Val Cys Gly Pro Pro Val Val Ser Phe Ser Pro
    130                 135                 140

Ser Thr Thr Ile Ser Val Thr Pro Glu Gly Gly Pro Gly Gly His Ser
145                 150                 155                 160

Leu Gln Val Leu
```

<210> SEQ ID NO 88
<211> LENGTH: 681
<212> TYPE: DNA
<213> ORGANISM: Artificial Sequence
<220> FEATURE:

<223> OTHER INFORMATION: Description of Artificial Sequence: Synthetic
      polynucleotide
<220> FEATURE:
<223> OTHER INFORMATION: Fc hole chain

<400> SEQUENCE: 88

```
gacaaaactc acacatgccc accgtgccca gcacctgaac tcctgggggg accgtcagtc     60

ttcctcttcc ccccaaaacc caaggacacc ctcatgatct cccggacccc tgaggtcaca    120

tgcgtggtgg tggacgtgag ccacgaagac cctgaggtca agttcaactg gtacgtggac    180

ggcgtggagg tgcataatgc caagacaaag ccgcgggagg agcagtacaa cagcacgtac    240

cgtgtggtca gcgtcctcac cgtcctgcac caggactggc tgaatggcaa ggagtacaag    300

tgcaaggtct ccaacaaagc cctcccagcc cccatcgaga aaaccatctc caaagccaaa    360

gggcagcccc gagaaccaca ggtgtgcacc ctgcccccat cccgggatga gctgaccaag    420

aaccaggtca gcctctcgtg cgcagtcaaa ggcttctatc ccagcgacat cgccgtggag    480

tgggagagca atgggcagcc ggagaacaac tacaagacca cgcctcccgt gctggactcc    540

gacggctcct tcttcctcgt gagcaagctc accgtggaca agagcaggtg gcagcagggg    600

aacgtcttct catgctccgt gatgcatgag gctctgcaca accactacac gcagaagagc    660

ctctccctgt ctccgggtaa a                                              681
```

<210> SEQ ID NO 89
<211> LENGTH: 1266
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: human 4-1BB antigen Fc knob chain

<400> SEQUENCE: 89

```
ctgcaggacc cctgcagcaa ctgccctgcc ggcaccttct gcgacaacaa ccggaaccag     60

atctgcagcc cctgcccccc caacagcttc agctctgccg gcggacagcg gacctgcgac    120

atctgcagac agtgcaaggg cgtgttcaga acccggaaag agtgcagcag caccagcaac    180

gccgagtgcg actgcacccc cggcttccat tgtctgggag ccggctgcag catgtgcgag    240

caggactgca agcagggcca ggaactgacc aagaagggct gcaaggactg ctgcttcggc    300

accttcaacg accagaagcg gggcatctgc cggccctgga ccaactgtag cctggacggc    360

aagagcgtgc tggtcaacgg caccaaagaa cgggacgtcg tgtgcggccc cagccctgct    420

gatctgtctc ctggggccag cagcgtgacc cctcctgccc ctgccagaga gcctggccac    480

tctcctcagg tcgacgaaca gttatatttt cagggcggct cacccaaatc tgcagacaaa    540

actcacacat gcccaccgtg cccagcacct gaactcctgg ggggaccgtc agtcttcctc    600

ttccccccaa aacccaagga caccctcatg atctcccgga cccctgaggt cacatgcgtg    660

gtggtggacg tgagccacga agaccctgag gtcaagttca actggtacgt ggacggcgtg    720

gaggtgcata atgccaagac aaagccgcgg gaggagcagt acaacagcac gtaccgtgtg    780

gtcagcgtcc tcaccgtcct gcaccaggac tggctgaatg gcaaggagta caagtgcaag    840

gtctccaaca aagccctccc agcccccatc gagaaaacca tctccaaagc caaagggcag    900

ccccgagaac cacaggtgta caccctgccc ccatgccggg atgagctgac caagaaccag    960

gtcagcctgt ggtgcctggt caaaggcttc tatcccagcg acatcgccgt ggagtgggag   1020

agcaatgggc agccggagaa caactacaag accacgcctc ccgtgctgga ctccgacggc   1080
```

```
tccttcttcc tctacagcaa gctcaccgtg gacaagagca ggtggcagca ggggaacgtc   1140

ttctcatgct ccgtgatgca tgaggctctg cacaaccact acacgcagaa gagcctctcc   1200

ctgtctccgg gtaaatccgg aggcctgaac gacatcttcg aggcccagaa gattgaatgg   1260

cacgag                                                              1266
```

<210> SEQ ID NO 90
<211> LENGTH: 1266
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: cynomolgus 4-1BB antigen Fc knob chain

<400> SEQUENCE: 90

```
ttgcaggatc tgtgtagtaa ctgcccagct ggtacattct gtgataataa caggagtcag     60

atttgcagtc cctgtcctcc aaatagtttc tccagcgcag gtggacaaag gacctgtgac    120

atatgcaggc agtgtaaagg tgttttcaag accaggaagg agtgttcctc caccagcaat    180

gcagagtgtg actgcatttc agggtatcac tgcctggggg cagagtgcag catgtgtgaa    240

caggattgta aacaaggtca agaattgaca aaaaaaggtt gtaaagactg ttgctttggg    300

acatttaatg accagaaacg tggcatctgt cgcccctgga caaactgttc tttggatgga    360

aagtctgtgc ttgtgaatgg gacgaaggag agggacgtgg tctgcggacc atctccagcc    420

gacctctctc caggagcatc ctctgcgacc ccgcctgccc ctgcgagaga gccaggacac    480

tctccgcagg tcgacgaaca gttatatttt cagggcggct cacccaaatc tgcagacaaa    540

actcacacat gcccaccgtg cccagcacct gaactcctgg ggggaccgtc agtcttcctc    600

ttccccccaa aacccaagga caccctcatg atctcccgga cccctgaggt cacatgcgtg    660

gtggtggacg tgagccacga agaccctgag gtcaagttca actggtacgt ggacggcgtg    720

gaggtgcata atgccaagac aaagccgcgg gaggagcagt acaacagcac gtaccgtgtg    780

gtcagcgtcc tcaccgtcct gcaccaggac tggctgaatg gcaaggagta caagtgcaag    840

gtctccaaca aagccctccc agcccccatc gagaaaacca tctccaaagc caaagggcag    900

ccccgagaac cacaggtgta caccctgccc ccatgccggg atgagctgac caagaaccag    960

gtcagcctgt ggtgcctggt caaaggcttc tatcccagcg acatcgccgt ggagtgggag   1020

agcaatgggc agccggagaa caactacaag accacgcctc ccgtgctgga ctccgacggc   1080

tccttcttcc tctacagcaa gctcaccgtg gacaagagca ggtggcagca ggggaacgtc   1140

ttctcatgct ccgtgatgca tgaggctctg cacaaccact acacgcagaa gagcctctcc   1200

ctgtctccgg gtaaatccgg aggcctgaac gacatcttcg aggcccagaa gattgaatgg   1260

cacgag                                                              1266
```

<210> SEQ ID NO 91
<211> LENGTH: 1269
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: murine 4-1BB antigen Fc knob chain

<400> SEQUENCE: 91

-continued

```
gtgcagaaca gctgcgacaa ctgccagccc ggcaccttct gccggaagta caaccccgtg      60

tgcaagagct gcccccccag caccttcagc agcatcggcg gccagcccaa ctgcaacatc     120

tgcagagtgt gcgccggcta cttccggttc aagaagttct gcagcagcac ccacaacgcc     180

gagtgcgagt gcatcgaggg cttccactgc ctgggccccc agtgcaccag atgcgagaag     240

gactgcagac ccggccagga actgaccaag cagggctgta agacctgcag cctgggcacc     300

ttcaacgacc agaacgggac cggcgtgtgc cggccttgga ccaattgcag cctggacggg     360

agaagcgtgc tgaaaaccgg caccaccgag aaggacgtcg tgtgcggccc tcccgtggtg     420

tccttcagcc ctagcaccac catcagcgtg acccctgaag gcggccctgg cggacactct     480

ctgcaggtcc tggtcgacga acagttatat tttcagggcg gctcacccaa atctgcagac     540

aaaactcaca catgcccacc gtgcccagca cctgaactcc tggggggacc gtcagtcttc     600

ctcttccccc caaaacccaa ggacaccctc atgatctccc ggacccctga ggtcacatgc     660

gtggtggtgg acgtgagcca cgaagaccct gaggtcaagt tcaactggta cgtggacggc     720

gtggaggtgc ataatgccaa gacaaagccg cgggaggagc agtacaacag cacgtaccgt     780

gtggtcagcg tcctcaccgt cctgcaccag gactggctga atggcaagga gtacaagtgc     840

aaggtctcca acaaagccct cccagccccc atcgagaaaa ccatctccaa agccaaaggg     900

cagccccgag aaccacaggt gtacaccctg cccccatgcc gggatgagct gaccaagaac     960

caggtcagcc tgtggtgcct ggtcaaaggc ttctatccca gcgacatcgc cgtggagtgg    1020

gagagcaatg ggcagccgga gaacaactac aagaccacgc ctcccgtgct ggactccgac    1080

ggctccttct tcctctacag caagctcacc gtggacaaga gcaggtggca gcaggggaac    1140

gtcttctcat gctccgtgat gcatgaggct ctgcacaacc actacacgca gaagagcctc    1200

tccctgtctc cgggtaaatc cggaggcctg aacgacatct tcgaggccca gaagattgaa    1260

tggcacgag                                                            1269
```

<210> SEQ ID NO 92
<211> LENGTH: 227
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: Fc hole chain

<400> SEQUENCE: 92

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
```

```
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 93
<211> LENGTH: 422
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: human 4-1BB antigen Fc knob chain

<400> SEQUENCE: 93

Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Pro Asn Ser Phe Ser Ser
            20                  25                  30

Ala Gly Gly Gln Arg Thr Cys Asp Ile Cys Arg Gln Cys Lys Gly Val
        35                  40                  45

Phe Arg Thr Arg Lys Glu Cys Ser Ser Thr Ser Asn Ala Glu Cys Asp
    50                  55                  60

Cys Thr Pro Gly Phe His Cys Leu Gly Ala Gly Cys Ser Met Cys Glu
65                  70                  75                  80

Gln Asp Cys Lys Gln Gly Gln Glu Leu Thr Lys Lys Gly Cys Lys Asp
                85                  90                  95

Cys Cys Phe Gly Thr Phe Asn Asp Gln Lys Arg Gly Ile Cys Arg Pro
            100                 105                 110

Trp Thr Asn Cys Ser Leu Asp Gly Lys Ser Val Leu Val Asn Gly Thr
        115                 120                 125

Lys Glu Arg Asp Val Val Cys Gly Pro Ser Pro Ala Asp Leu Ser Pro
    130                 135                 140

Gly Ala Ser Ser Val Thr Pro Pro Ala Pro Ala Arg Glu Pro Gly His
145                 150                 155                 160

Ser Pro Gln Val Asp Glu Gln Leu Tyr Phe Gln Gly Gly Ser Pro Lys
                165                 170                 175

Ser Ala Asp Lys Thr His Thr Cys Pro Pro Cys Pro Ala Pro Glu Leu
            180                 185                 190

Leu Gly Gly Pro Ser Val Phe Leu Phe Pro Pro Lys Pro Lys Asp Thr
        195                 200                 205

Leu Met Ile Ser Arg Thr Pro Glu Val Thr Cys Val Val Val Asp Val
    210                 215                 220

Ser His Glu Asp Pro Glu Val Lys Phe Asn Trp Tyr Val Asp Gly Val
```

```
225                 230                 235                 240

Glu Val His Asn Ala Lys Thr Lys Pro Arg Glu Glu Gln Tyr Asn Ser
                245                 250                 255

Thr Tyr Arg Val Val Ser Val Leu Thr Val Leu His Gln Asp Trp Leu
            260                 265                 270

Asn Gly Lys Glu Tyr Lys Cys Lys Val Ser Asn Lys Ala Leu Pro Ala
        275                 280                 285

Pro Ile Glu Lys Thr Ile Ser Lys Ala Lys Gly Gln Pro Arg Glu Pro
    290                 295                 300

Gln Val Tyr Thr Leu Pro Pro Cys Arg Asp Glu Leu Thr Lys Asn Gln
305                 310                 315                 320

Val Ser Leu Trp Cys Leu Val Lys Gly Phe Tyr Pro Ser Asp Ile Ala
                325                 330                 335

Val Glu Trp Glu Ser Asn Gly Gln Pro Glu Asn Asn Tyr Lys Thr Thr
            340                 345                 350

Pro Pro Val Leu Asp Ser Asp Gly Ser Phe Phe Leu Tyr Ser Lys Leu
        355                 360                 365

Thr Val Asp Lys Ser Arg Trp Gln Gln Gly Asn Val Phe Ser Cys Ser
    370                 375                 380

Val Met His Glu Ala Leu His Asn His Tyr Thr Gln Lys Ser Leu Ser
385                 390                 395                 400

Leu Ser Pro Gly Lys Ser Gly Gly Leu Asn Asp Ile Phe Glu Ala Gln
                405                 410                 415

Lys Ile Glu Trp His Glu
            420


<210> SEQ ID NO 94
<211> LENGTH: 422
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: cynomolgus 4-1BB antigen Fc knob chain

<400> SEQUENCE: 94

Leu Gln Asp Leu Cys Ser Asn Cys Pro Ala Gly Thr Phe Cys Asp Asn
1               5                   10                  15

Asn Arg Ser Gln Ile Cys Ser Pro Cys Pro Pro Asn Ser Phe Ser Ser
            20                  25                  30

Ala Gly Gly Gln Arg Thr Cys Asp Ile Cys Arg Gln Cys Lys Gly Val
        35                  40                  45

Phe Lys Thr Arg Lys Glu Cys Ser Ser Thr Ser Asn Ala Glu Cys Asp
    50                  55                  60

Cys Ile Ser Gly Tyr His Cys Leu Gly Ala Glu Cys Ser Met Cys Glu
65                  70                  75                  80

Gln Asp Cys Lys Gln Gly Gln Glu Leu Thr Lys Lys Gly Cys Lys Asp
                85                  90                  95

Cys Cys Phe Gly Thr Phe Asn Asp Gln Lys Arg Gly Ile Cys Arg Pro
            100                 105                 110

Trp Thr Asn Cys Ser Leu Asp Gly Lys Ser Val Leu Val Asn Gly Thr
        115                 120                 125

Lys Glu Arg Asp Val Val Cys Gly Pro Ser Pro Ala Asp Leu Ser Pro
    130                 135                 140

Gly Ala Ser Ser Ala Thr Pro Pro Ala Pro Ala Arg Glu Pro Gly His
```

145 150 155 160

Ser Pro Gln Val Asp Glu Gln Leu Tyr Phe Gln Gly Gly Ser Pro Lys
165 170 175

Ser Ala Asp Lys Thr His Thr Cys Pro Pro Cys Pro Ala Pro Glu Leu
180 185 190

Leu Gly Gly Pro Ser Val Phe Leu Phe Pro Pro Lys Pro Lys Asp Thr
195 200 205

Leu Met Ile Ser Arg Thr Pro Glu Val Thr Cys Val Val Val Asp Val
210 215 220

Ser His Glu Asp Pro Glu Val Lys Phe Asn Trp Tyr Val Asp Gly Val
225 230 235 240

Glu Val His Asn Ala Lys Thr Lys Pro Arg Glu Glu Gln Tyr Asn Ser
245 250 255

Thr Tyr Arg Val Val Ser Val Leu Thr Val Leu His Gln Asp Trp Leu
260 265 270

Asn Gly Lys Glu Tyr Lys Cys Lys Val Ser Asn Lys Ala Leu Pro Ala
275 280 285

Pro Ile Glu Lys Thr Ile Ser Lys Ala Lys Gly Gln Pro Arg Glu Pro
290 295 300

Gln Val Tyr Thr Leu Pro Pro Cys Arg Asp Glu Leu Thr Lys Asn Gln
305 310 315 320

Val Ser Leu Trp Cys Leu Val Lys Gly Phe Tyr Pro Ser Asp Ile Ala
325 330 335

Val Glu Trp Glu Ser Asn Gly Gln Pro Glu Asn Asn Tyr Lys Thr Thr
340 345 350

Pro Pro Val Leu Asp Ser Asp Gly Ser Phe Phe Leu Tyr Ser Lys Leu
355 360 365

Thr Val Asp Lys Ser Arg Trp Gln Gln Gly Asn Val Phe Ser Cys Ser
370 375 380

Val Met His Glu Ala Leu His Asn His Tyr Thr Gln Lys Ser Leu Ser
385 390 395 400

Leu Ser Pro Gly Lys Ser Gly Gly Leu Asn Asp Ile Phe Glu Ala Gln
405 410 415

Lys Ile Glu Trp His Glu
420

<210> SEQ ID NO 95
<211> LENGTH: 423
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: murine 4-1BB antigen Fc knob chain

<400> SEQUENCE: 95

Val Gln Asn Ser Cys Asp Asn Cys Gln Pro Gly Thr Phe Cys Arg Lys
1 5 10 15

Tyr Asn Pro Val Cys Lys Ser Cys Pro Pro Ser Thr Phe Ser Ser Ile
20 25 30

Gly Gly Gln Pro Asn Cys Asn Ile Cys Arg Val Cys Ala Gly Tyr Phe
35 40 45

Arg Phe Lys Lys Phe Cys Ser Ser Thr His Asn Ala Glu Cys Glu Cys
50 55 60

Ile Glu Gly Phe His Cys Leu Gly Pro Gln Cys Thr Arg Cys Glu Lys

```
65                  70                  75                  80

Asp Cys Arg Pro Gly Gln Glu Leu Thr Lys Gln Gly Cys Lys Thr Cys
                85                  90                  95

Ser Leu Gly Thr Phe Asn Asp Gln Asn Gly Thr Gly Val Cys Arg Pro
            100                 105                 110

Trp Thr Asn Cys Ser Leu Asp Gly Arg Ser Val Leu Lys Thr Gly Thr
        115                 120                 125

Thr Glu Lys Asp Val Val Cys Gly Pro Pro Val Val Ser Phe Ser Pro
    130                 135                 140

Ser Thr Thr Ile Ser Val Thr Pro Glu Gly Gly Pro Gly Gly His Ser
145                 150                 155                 160

Leu Gln Val Leu Val Asp Glu Gln Leu Tyr Phe Gln Gly Gly Ser Pro
                165                 170                 175

Lys Ser Ala Asp Lys Thr His Thr Cys Pro Pro Cys Pro Ala Pro Glu
            180                 185                 190

Leu Leu Gly Gly Pro Ser Val Phe Leu Phe Pro Pro Lys Pro Lys Asp
        195                 200                 205

Thr Leu Met Ile Ser Arg Thr Pro Glu Val Thr Cys Val Val Val Asp
    210                 215                 220

Val Ser His Glu Asp Pro Glu Val Lys Phe Asn Trp Tyr Val Asp Gly
225                 230                 235                 240

Val Glu Val His Asn Ala Lys Thr Lys Pro Arg Glu Glu Gln Tyr Asn
                245                 250                 255

Ser Thr Tyr Arg Val Val Ser Val Leu Thr Val Leu His Gln Asp Trp
            260                 265                 270

Leu Asn Gly Lys Glu Tyr Lys Cys Lys Val Ser Asn Lys Ala Leu Pro
        275                 280                 285

Ala Pro Ile Glu Lys Thr Ile Ser Lys Ala Lys Gly Gln Pro Arg Glu
    290                 295                 300

Pro Gln Val Tyr Thr Leu Pro Pro Cys Arg Asp Glu Leu Thr Lys Asn
305                 310                 315                 320

Gln Val Ser Leu Trp Cys Leu Val Lys Gly Phe Tyr Pro Ser Asp Ile
                325                 330                 335

Ala Val Glu Trp Glu Ser Asn Gly Gln Pro Glu Asn Asn Tyr Lys Thr
            340                 345                 350

Thr Pro Pro Val Leu Asp Ser Asp Gly Ser Phe Phe Leu Tyr Ser Lys
        355                 360                 365

Leu Thr Val Asp Lys Ser Arg Trp Gln Gln Gly Asn Val Phe Ser Cys
    370                 375                 380

Ser Val Met His Glu Ala Leu His Asn His Tyr Thr Gln Lys Ser Leu
385                 390                 395                 400

Ser Leu Ser Pro Gly Lys Ser Gly Gly Leu Asn Asp Ile Phe Glu Ala
                405                 410                 415

Gln Lys Ile Glu Trp His Glu
            420
```

<210> SEQ ID NO 96
<211> LENGTH: 594
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: human 4-1BB His

<400> SEQUENCE: 96
ctgcaggacc cctgcagcaa ctgccctgcc ggcaccttct gcgacaacaa ccggaaccag 60
atctgcagcc cctgcccccc caacagcttc agctctgccg gcggacagcg gacctgcgac 120
atctgcagac agtgcaaggg cgtgttcaga acccggaaag agtgcagcag caccagcaac 180
gccgagtgcg actgcacccc cggcttccat tgtctgggag ccggctgcag catgtgcgag 240
caggactgca agcagggcca ggaactgacc aagaagggct gcaaggactg ctgcttcggc 300
accttcaacg accagaagcg gggcatctgc cggccctgga ccaactgtag cctggacggc 360
aagagcgtgc tggtcaacgg caccaaagaa cgggacgtcg tgtgcggccc cagccctgct 420
gatctgtctc ctggggccag cagcgtgacc cctcctgccc ctgccagaga gcctggccac 480
tctcctcagg tcgacgaaca gttatatttt cagggcggct caggcctgaa cgacatcttc 540
gaggcccaga agatcgagtg gcacgaggct cgagctcacc accatcacca tcac 594

<210> SEQ ID NO 97
<211> LENGTH: 198
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: human 4-1BB His

<400> SEQUENCE: 97

Leu Gln Asp Pro Cys Ser Asn Cys Pro Ala Gly Thr Phe Cys Asp Asn
1 5 10 15

Asn Arg Asn Gln Ile Cys Ser Pro Cys Pro Pro Asn Ser Phe Ser Ser
20 25 30

Ala Gly Gly Gln Arg Thr Cys Asp Ile Cys Arg Gln Cys Lys Gly Val
35 40 45

Phe Arg Thr Arg Lys Glu Cys Ser Ser Thr Ser Asn Ala Glu Cys Asp
50 55 60

Cys Thr Pro Gly Phe His Cys Leu Gly Ala Gly Cys Ser Met Cys Glu
65 70 75 80

Gln Asp Cys Lys Gln Gly Gln Glu Leu Thr Lys Lys Gly Cys Lys Asp
85 90 95

Cys Cys Phe Gly Thr Phe Asn Asp Gln Lys Arg Gly Ile Cys Arg Pro
100 105 110

Trp Thr Asn Cys Ser Leu Asp Gly Lys Ser Val Leu Val Asn Gly Thr
115 120 125

Lys Glu Arg Asp Val Val Cys Gly Pro Ser Pro Ala Asp Leu Ser Pro
130 135 140

Gly Ala Ser Ser Val Thr Pro Pro Ala Pro Ala Arg Glu Pro Gly His
145 150 155 160

Ser Pro Gln Val Asp Glu Gln Leu Tyr Phe Gln Gly Gly Ser Gly Leu
165 170 175

Asn Asp Ile Phe Glu Ala Gln Lys Ile Glu Trp His Glu Ala Arg Ala
180 185 190

His His His His His His
195

<210> SEQ ID NO 98
<211> LENGTH: 2166
<212> TYPE: DNA
<213> ORGANISM: Artificial Sequence -continued
<220> FEATURE:
<223> OTHER INFORMATION: Description of Artificial Sequence: Synthetic
      polynucleotide
<220> FEATURE:
<223> OTHER INFORMATION: Dimeric ligand (71-254)- CL* Fc knob chain

<400> SEQUENCE: 98

```
agagagggcc ctgagctgag ccccgatgat cctgctggac tgctggacct gcggcagggc     60

atgtttgctc agctggtggc ccagaacgtg ctgctgatcg atggcccct gtcctggtac    120

agcgatcctg gactggctgg cgtgtcactg acaggcggcc tgagctacaa agaggacacc    180

aaagaactgg tggtggccaa ggccggcgtg tactacgtgt tctttcagct ggaactgcgg    240

agagtggtgg ccggcgaagg atctggctct gtgtctctgg ccctgcatct gcagcctctg    300

agaagcgctg ctggcgctgc agctctggca ctgacagtgg atctgcctcc tgccagctcc    360

gaggcccgga atagcgcatt tgggtttcaa ggcaggctgc tgcacctgtc tgccggccag    420

aggctgggag tgcatctgca cacagaggcc agggctagac acgcctggca gctgacacag    480

ggcgctacag tgctgggcct gttcagagtg acccccgaga ttccagccgg cctgccttct    540

ccaagaagcg aaggcggagg cggatctggc ggcggaggat ctagagaggg acccgaactg    600

tcccctgacg atccagccgg gctgctggat ctgagacagg gaatgttcgc ccagctggtg    660

gctcagaatg tgctgctgat tgacggacct ctgagctggt actccgaccc agggctggca    720

ggggtgtccc tgactggggg actgtcctac aaagaagata caaaagaact ggtggtggct    780

aaagctgggg tgtactatgt gttttttcag ctggaactga ggcgggtggt ggctggggag    840

ggctcaggat ctgtgtccct ggctctgcat ctgcagccac tgcgctctgc tgctggcgca    900

gctgcactgg ctctgactgt ggacctgcca ccagcctcta gcgaggccag aaacagcgcc    960

ttcgggttcc aaggacgcct gctgcatctg agcgccggac agcgcctggg agtgcatctg   1020

catactgaag ccagagcccg gcatgcttgg cagctgactc agggggcaac tgtgctggga   1080

ctgtttcgcg tgacacctga gatccctgcc ggactgccaa gccctagatc agaagggggc   1140

ggaggttccg gagggggagg atctcgtacg gtggctgcac catctgtctt tatcttccca   1200

cccagcgacc ggaagctgaa gtctggcaca gccagcgtcg tgtgcctgct gaataacttc   1260

tacccccgcg aggccaaggt gcagtggaag gtggacaatg ccctgcagag cggcaacagc   1320

caggaaagcg tgaccgagca ggacagcaag gactccacct acagcctgag cagcaccctg   1380

accctgagca aggccgacta cgagaagcac aaggtgtacg cctgcgaagt gacccaccag   1440

ggcctgtcta gccccgtgac caagagcttc aaccggggcg agtgcgacaa gacccacacc   1500

tgtcctccat gccctgcccc tgaagctgct ggcggcccta gcgtgttcct gttcccccca   1560

aagcccaagg acaccctgat gatcagccgg acccctgaag tgacctgcgt ggtggtggat   1620

gtgtcccacg aggaccctga agtgaagttc aattggtacg tggacggcgt ggaagtgcac   1680

aatgccaaga ccaagccgcg ggaggagcag tacaacagca cgtaccgtgt ggtcagcgtc   1740

ctcaccgtcc tgcaccagga ctggctgaat ggcaaggagt acaagtgcaa ggtctccaac   1800

aaagccctcg gcgcccccat cgagaaaacc atctccaaag ccaaagggca gccccgagaa   1860

ccacaggtgt acaccctgcc cccatgccgg gatgagctga ccaagaacca ggtcagcctg   1920

tggtgcctgg tcaaaggctt ctatcccagc gacatcgccg tggagtggga gagcaatggg   1980

cagccggaga acaactacaa gaccacgcct cccgtgctgg actccgacgg ctccttcttc   2040

ctctacagca agctcaccgt ggacaagagc aggtggcagc aggggaacgt cttctcatgc   2100

tccgtgatgc atgaggctct gcacaaccac tacacgcaga agagcctctc cctgtctccg   2160
```

ggtaaa 2166

<210> SEQ ID NO 99
<211> LENGTH: 891
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Monomeric ligand (71-254)-CH1*

<400> SEQUENCE: 99
agagagggcc ctgagctgag ccccgatgat cctgctggac tgctggacct gcggcagggc 60
atgtttgctc agctggtggc ccagaacgtg ctgctgatcg atggcccct gtcctggtac 120 agcgatcctg gactggctgg cgtgtcactg acaggcggcc tgagctacaa agaggacacc 180
aaagaactgg tggtggccaa ggccggcgtg tactacgtgt tctttcagct ggaactgcgg 240
agagtggtgg ccggcgaagg atctggctct gtgtctctgg ccctgcatct gcagcctctg 300
agaagcgctg ctggcgctgc agctctggct ctgacagtgg atctgcctcc tgccagctcc 360
gaggcccgga atagcgcatt tgggtttcaa ggccggctgc tgcacctgtc tgccggccag 420
agactgggag tgcatctgca cacagaggcc agagccaggc acgcctggca gctgacacag 480
ggcgctacag tgctgggcct gttcagagtg acccccgaga ttcctgccgg cctgcctagc 540
cctagatctg aaggcggcgg aggttccgga ggcggaggat ctgctagcac aaagggcccc 600
agcgtgttcc ctctggcccc tagcagcaag agcacatctg gcggaacagc cgccctgggc 660
tgcctggtgg aagattactt ccccgagccc gtgaccgtgt cctggaattc tggcgccctg 720
acaagcggcg tgcacacctt tccagccgtg ctgcagagca gcggcctgta ctctctgagc 780
agcgtcgtga cagtgcccag cagctctctg ggcacccaga cctacatctg caacgtgaac 840
cacaagccca gcaacaccaa ggtggacgag aaggtggaac ccaagtcctg c 891

<210> SEQ ID NO 100
<211> LENGTH: 1344
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: anti-TnC(18D4) Fc hole chain

<400> SEQUENCE: 100
caggtgcaat tggtgcagtc tggggctgag gtgaagaagc ctgggtcctc ggtgaaggtc 60
tcctgcaagg cctccggagg cacattcagc agctacgcta taagctgggt gcgacaggcc 120
cctggacaag ggctcgagtg gatgggaggg atcatcccta tctttggtac agcaaactac 180
gcacagaagt tccagggcag ggtcaccatt actgcagaca aatccacgag cacagcctac 240
atggagctga gcagcctgag atctgaggac accgccgtgt attactgtgc gaaaggtaac 300
ttctacggtg gtctggacta ctggggccaa gggaccaccg tgaccgtctc ctcagctagc 360
accaagggcc cctccgtgtt ccccctggcc cccagcagca agagcaccag cggcggcaca 420
gccgctctgg gctgcctggt caaggactac ttccccgagc ccgtgaccgt gtcctggaac 480
agcggagccc tgacctccgg cgtgcacacc ttccccgccg tgctgcagag ttctggcctg 540
tatagcctga gcagcgtggt caccgtgcct tctagcagcc tgggcaccca gacctacatc 600

```
tgcaacgtga accacaagcc cagcaacacc aaggtggaca agaaggtgga gcccaagagc    660

tgcgacaaaa ctcacacatg cccaccgtgc ccagcacctg aagctgcagg gggaccgtca    720

gtcttcctct tccccccaaa acccaaggac accctcatga tctcccggac ccctgaggtc    780

acatgcgtgg tggtggacgt gagccacgaa gaccctgagg tcaagttcaa ctggtacgtg    840

gacggcgtgg aggtgcataa tgccaagaca aagccgcggg aggagcagta caacagcacg    900

taccgtgtgg tcagcgtcct caccgtcctg caccaggact ggctgaatgg caaggagtac    960

aagtgcaagg tctccaacaa agccctcggc gcccccatcg agaaaaccat ctccaaagcc    1020

aaagggcagc cccgagaacc acaggtgtgc accctgcccc catcccggga tgagctgacc    1080

aagaaccagg tcagcctctc gtgcgcagtc aaaggcttct atcccagcga catcgccgtg    1140

gagtgggaga gcaatgggca gccggagaac aactacaaga ccacgcctcc cgtgctggac    1200

tccgacggct ccttcttcct cgtgagcaag ctcaccgtgg acaagagcag gtggcagcag    1260

gggaacgtct tctcatgctc cgtgatgcat gaggctctgc acaaccacta cacgcagaag    1320

agcctctccc tgtctccggg taaa                                            1344
```

<210> SEQ ID NO 101
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Randomized sequence 1
<220> FEATURE:
<221> NAME/KEY: modified_base
<222> LOCATION: (1)..(10)
<223> OTHER INFORMATION: a, c, g, or t

<400> SEQUENCE: 101 nnnnnnnnnn                                                             10

<210> SEQ ID NO 102
<211> LENGTH: 722
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Dimeric ligand (71-254) - CL* Fc knob chain

<400> SEQUENCE: 102

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
    50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110

-continued

```
Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
    130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Pro Ser Pro Arg Ser Glu Gly Gly Gly Gly Ser Gly Gly Gly
            180                 185                 190

Gly Ser Arg Glu Gly Pro Glu Leu Ser Pro Asp Asp Pro Ala Gly Leu
        195                 200                 205

Leu Asp Leu Arg Gln Gly Met Phe Ala Gln Leu Val Ala Gln Asn Val
    210                 215                 220

Leu Leu Ile Asp Gly Pro Leu Ser Trp Tyr Ser Asp Pro Gly Leu Ala
225                 230                 235                 240

Gly Val Ser Leu Thr Gly Gly Leu Ser Tyr Lys Glu Asp Thr Lys Glu
                245                 250                 255

Leu Val Val Ala Lys Ala Gly Val Tyr Tyr Val Phe Phe Gln Leu Glu
            260                 265                 270

Leu Arg Arg Val Val Ala Gly Glu Gly Ser Gly Ser Val Ser Leu Ala
        275                 280                 285

Leu His Leu Gln Pro Leu Arg Ser Ala Ala Gly Ala Ala Ala Leu Ala
    290                 295                 300

Leu Thr Val Asp Leu Pro Pro Ala Ser Ser Glu Ala Arg Asn Ser Ala
305                 310                 315                 320

Phe Gly Phe Gln Gly Arg Leu Leu His Leu Ser Ala Gly Gln Arg Leu
                325                 330                 335

Gly Val His Leu His Thr Glu Ala Arg Ala Arg His Ala Trp Gln Leu
            340                 345                 350

Thr Gln Gly Ala Thr Val Leu Gly Leu Phe Arg Val Thr Pro Glu Ile
        355                 360                 365

Pro Ala Gly Leu Pro Ser Pro Arg Ser Glu Gly Gly Gly Gly Ser Gly
    370                 375                 380

Gly Gly Gly Ser Arg Thr Val Ala Ala Pro Ser Val Phe Ile Phe Pro
385                 390                 395                 400

Pro Ser Asp Arg Lys Leu Lys Ser Gly Thr Ala Ser Val Val Cys Leu
                405                 410                 415

Leu Asn Asn Phe Tyr Pro Arg Glu Ala Lys Val Gln Trp Lys Val Asp
            420                 425                 430

Asn Ala Leu Gln Ser Gly Asn Ser Gln Glu Ser Val Thr Glu Gln Asp
        435                 440                 445

Ser Lys Asp Ser Thr Tyr Ser Leu Ser Ser Thr Leu Thr Leu Ser Lys
    450                 455                 460

Ala Asp Tyr Glu Lys His Lys Val Tyr Ala Cys Glu Val Thr His Gln
465                 470                 475                 480

Gly Leu Ser Ser Pro Val Thr Lys Ser Phe Asn Arg Gly Glu Cys Asp
                485                 490                 495

Lys Thr His Thr Cys Pro Pro Cys Pro Ala Pro Glu Ala Ala Gly Gly
            500                 505                 510

Pro Ser Val Phe Leu Phe Pro Pro Lys Pro Lys Asp Thr Leu Met Ile
        515                 520                 525

Ser Arg Thr Pro Glu Val Thr Cys Val Val Val Asp Val Ser His Glu
```

530 535 540

Asp Pro Glu Val Lys Phe Asn Trp Tyr Val Asp Gly Val Glu Val His
545 550 555 560

Asn Ala Lys Thr Lys Pro Arg Glu Glu Gln Tyr Asn Ser Thr Tyr Arg
565 570 575

Val Val Ser Val Leu Thr Val Leu His Gln Asp Trp Leu Asn Gly Lys
580 585 590

Glu Tyr Lys Cys Lys Val Ser Asn Lys Ala Leu Gly Ala Pro Ile Glu
595 600 605

Lys Thr Ile Ser Lys Ala Lys Gly Gln Pro Arg Glu Pro Gln Val Tyr
610 615 620

Thr Leu Pro Pro Cys Arg Asp Glu Leu Thr Lys Asn Gln Val Ser Leu
625 630 635 640

Trp Cys Leu Val Lys Gly Phe Tyr Pro Ser Asp Ile Ala Val Glu Trp
645 650 655

Glu Ser Asn Gly Gln Pro Glu Asn Asn Tyr Lys Thr Thr Pro Pro Val
660 665 670

Leu Asp Ser Asp Gly Ser Phe Phe Leu Tyr Ser Lys Leu Thr Val Asp
675 680 685

Lys Ser Arg Trp Gln Gln Gly Asn Val Phe Ser Cys Ser Val Met His
690 695 700

Glu Ala Leu His Asn His Tyr Thr Gln Lys Ser Leu Ser Leu Ser Pro
705 710 715 720

Gly Lys

<210> SEQ ID NO 103
<211> LENGTH: 297
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: Monomeric ligand (71-254)-CH1*

<400> SEQUENCE: 103

Arg Glu Gly Pro Glu Leu Ser Pro Asp Asp Pro Ala Gly Leu Leu Asp
1 5 10 15

Leu Arg Gln Gly Met Phe Ala Gln Leu Val Ala Gln Asn Val Leu Leu
20 25 30

Ile Asp Gly Pro Leu Ser Trp Tyr Ser Asp Pro Gly Leu Ala Gly Val
35 40 45

Ser Leu Thr Gly Gly Leu Ser Tyr Lys Glu Asp Thr Lys Glu Leu Val
50 55 60

Val Ala Lys Ala Gly Val Tyr Tyr Val Phe Phe Gln Leu Glu Leu Arg
65 70 75 80

Arg Val Val Ala Gly Glu Gly Ser Gly Ser Val Ser Leu Ala Leu His
85 90 95

Leu Gln Pro Leu Arg Ser Ala Ala Gly Ala Ala Ala Leu Ala Leu Thr
100 105 110

Val Asp Leu Pro Pro Ala Ser Ser Glu Ala Arg Asn Ser Ala Phe Gly
115 120 125

Phe Gln Gly Arg Leu Leu His Leu Ser Ala Gly Gln Arg Leu Gly Val
130 135 140

His Leu His Thr Glu Ala Arg Ala Arg His Ala Trp Gln Leu Thr Gln
145 150 155 160

```
Gly Ala Thr Val Leu Gly Leu Phe Arg Val Thr Pro Glu Ile Pro Ala
                165                 170                 175

Gly Leu Pro Ser Pro Arg Ser Glu Gly Gly Gly Gly Ser Gly Gly Gly
            180                 185                 190

Gly Ser Ala Ser Thr Lys Gly Pro Ser Val Phe Pro Leu Ala Pro Ser
        195                 200                 205

Ser Lys Ser Thr Ser Gly Gly Thr Ala Ala Leu Gly Cys Leu Val Glu
    210                 215                 220

Asp Tyr Phe Pro Glu Pro Val Thr Val Ser Trp Asn Ser Gly Ala Leu
225                 230                 235                 240

Thr Ser Gly Val His Thr Phe Pro Ala Val Leu Gln Ser Ser Gly Leu
                245                 250                 255

Tyr Ser Leu Ser Ser Val Val Thr Val Pro Ser Ser Ser Leu Gly Thr
            260                 265                 270

Gln Thr Tyr Ile Cys Asn Val Asn His Lys Pro Ser Asn Thr Lys Val
        275                 280                 285

Asp Glu Lys Val Glu Pro Lys Ser Cys
    290                 295


<210> SEQ ID NO 104
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: anti-TnC(18D4) Fc hole chain

<400> SEQUENCE: 104

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Gly Asn Phe Tyr Gly Gly Leu Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205
```

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Gly Ala Pro Ile Glu Lys Thr
                325                 330                 335

Ile Ser Lys Ala Lys Gly Gln Pro Arg Glu Pro Gln Val Cys Thr Leu
            340                 345                 350

Pro Pro Ser Arg Asp Glu Leu Thr Lys Asn Gln Val Ser Leu Ser Cys
        355                 360                 365

Ala Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 105
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Randomized sequence 2
<220> FEATURE:
<221> NAME/KEY: modified_base
<222> LOCATION: (1)..(11)
<223> OTHER INFORMATION: a, c, g, or t

<400> SEQUENCE: 105
nnnnnnnnnn n                                                          11

<210> SEQ ID NO 106
<211> LENGTH: 2166
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Dimeric ligand (71-254)- CL Fc knob chain

<400> SEQUENCE: 106
agagagggcc ctgagctgag ccccgatgat cctgctggac tgctggacct gcggcagggc     60
atgtttgctc agctggtggc ccagaacgtg ctgctgatcg atggcccccct gtcctggtac 120 agcgatcctg gactggctgg cgtgtcactg acaggcggcc tgagctacaa agaggacacc 180
aaagaactgg tggtggccaa ggccggcgtg tactacgtgt tctttcagct ggaactgcgg 240
agagtggtgg ccggcgaagg atctggctct gtgtctctgg ccctgcatct gcagcctctg 300
agaagcgctg ctggcgctgc agctctggca ctgacagtgg atctgcctcc tgccagctcc 360
gaggcccgga atagcgcatt tgggtttcaa ggcaggctgc tgcacctgtc tgccggccag 420
aggctgggag tgcatctgca cacagaggcc agggctagac acgcctggca gctgacacag 480
ggcgctacag tgctgggcct gttcagagtg acccccgaga ttccagccgg cctgccttct 540
ccaagaagcg aaggcggagg cggatctggc ggcggaggat ctagagaggg acccgaactg 600
tcccctgacg atccagccgg gctgctggat ctgagacagg gaatgttcgc ccagctggtg 660
gctcagaatg tgctgctgat tgacggacct ctgagctggt actccgaccc agggctggca 720
ggggtgtccc tgactggggg actgtcctac aaagaagata caaaagaact ggtggtggct 780
aaagctgggg tgtactatgt gttttttcag ctggaactga ggcgggtggt ggctggggag 840
ggctcaggat ctgtgtccct ggctctgcat ctgcagccac tgcgctctgc tgctggcgca 900
gctgcactgg ctctgactgt ggacctgcca ccagcctcta gcgaggccag aaacagcgcc 960
ttcgggttcc aaggacgcct gctgcatctg agcgccggac agcgcctggg agtgcatctg 1020
catactgaag ccagagcccg gcatgcttgg cagctgactc agggggcaac tgtgctggga 1080
ctgtttcgcg tgacacctga gatccctgcc ggactgccaa gccctagatc agaagggggc 1140
ggaggttccg gagggggagg atctcgtacg gtggccgctc cctccgtgtt tatctttccc 1200
ccatccgatg aacagctgaa aagcggcacc gcctccgtcg tgtgtctgct gaacaatttt 1260
taccctaggg aagctaaagt gcagtggaaa gtggataacg cactgcagtc cggcaactcc 1320
caggaatctg tgacagaaca ggactccaag gacagcacct actccctgtc ctccaccctg 1380
acactgtcta aggctgatta tgagaaacac aaagtctacg cctgcgaagt cacccatcag 1440
ggcctgagct cgcccgtcac aaagagcttc aacaggggag agtgtgacaa gacccacacc 1500 tgtcccccctt gtcctgcccc tgaagctgct ggcggccctt ctgtgttcct gttcccccca 1560
aagcccaagg acaccctgat gatcagccgg acccccgaag tgacctgcgt ggtggtggat 1620
gtgtcccacg aggaccctga agtgaagttc aattggtacg tggacggcgt ggaagtgcac 1680
aatgccaaga ccaagccgcg ggaggagcag tacaacagca cgtaccgtgt ggtcagcgtc 1740
ctcaccgtcc tgcaccagga ctggctgaat ggcaaggagt acaagtgcaa ggtctccaac 1800
aaagccctcg gcgcccccat cgagaaaacc atctccaaag ccaaagggca gccccgagaa 1860
ccacaggtgt acaccctgcc cccatgccgg gatgagctga ccaagaacca ggtcagcctg 1920
tggtgcctgg tcaaaggctt ctatcccagc gacatcgccg tggagtggga gagcaatggg 1980
cagccggaga acaactacaa gaccacgcct cccgtgctgg actccgacgg ctccttcttc 2040
ctctacagca agctcaccgt ggacaagagc aggtggcagc aggggaacgt cttctcatgc 2100
tccgtgatgc atgaggctct gcacaaccac tacacgcaga agagcctctc cctgtctccg 2160
ggtaaa 2166

<210> SEQ ID NO 107
<211> LENGTH: 891
<212> TYPE: DNA
<213> ORGANISM: Artificial Sequence
<220> FEATURE:

<223> OTHER INFORMATION: Description of Artificial Sequence: Synthetic
      polynucleotide
<220> FEATURE:
<223> OTHER INFORMATION: Monomeric ligand (71-254)-CH1

<400> SEQUENCE: 107
agagagggcc ctgagctgag ccccgatgat cctgctggac tgctggacct gcggcagggc 60
atgtttgctc agctggtggc ccagaacgtg ctgctgatcg atggccccct gtcctggtac 120
agcgatcctg gactggctgg cgtgtcactg acaggcggcc tgagctacaa agaggacacc 180
aaagaactgg tggtggccaa ggccggcgtg tactacgtgt tctttcagct ggaactgcgg 240
agagtggtgg ccggcgaagg atctggctct gtgtctctgg ccctgcatct gcagcctctg 300
agaagcgctg ctggcgctgc agctctggct ctgacagtgg atctgcctcc tgccagctcc 360
gaggcccgga atagcgcatt tgggtttcaa ggccggctgc tgcacctgtc tgccggccag 420
agactgggag tgcatctgca cacagaggcc agagccaggc acgcctggca gctgacacag 480
ggcgctacag tgctgggcct gttcagagtg acccccgaga ttcctgccgg cctgcctagc 540
cctagatctg aaggcggcgg aggttccgga ggcggaggat ctgctagcac caaaggccct 600
tccgtgtttc ctctggctcc tagctccaag tccacctctg gaggcaccgc tgctctcgga 660
tgcctcgtga aggattattt tcctgagcct gtgacagtgt cctggaatag cggagcactg 720
acctctggag tgcatacttt ccccgctgtg ctgcagtcct ctggactgta cagcctgagc 780
agcgtggtga cagtgcccag cagcagcctg ggcacccaga cctacatctg caacgtgaac 840
cacaagccca gcaacaccaa ggtggacaag aaggtggaac ccaagtcttg t 891

<210> SEQ ID NO 108
<211> LENGTH: 722
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Dimeric ligand (71-254) - CL Fc knob chain

<400> SEQUENCE: 108

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
    50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
    130                 135                 140

His Leu His Thr Glu Ala Arg Ala Arg His Ala Trp Gln Leu Thr Gln
145                 150                 155                 160

-continued

Gly Ala Thr Val Leu Gly Leu Phe Arg Val Thr Pro Glu Ile Pro Ala
165 170 175

Gly Leu Pro Ser Pro Arg Ser Glu Gly Gly Gly Gly Ser Gly Gly Gly
180 185 190

Gly Ser Arg Glu Gly Pro Glu Leu Ser Pro Asp Asp Pro Ala Gly Leu
195 200 205

Leu Asp Leu Arg Gln Gly Met Phe Ala Gln Leu Val Ala Gln Asn Val
210 215 220

Leu Leu Ile Asp Gly Pro Leu Ser Trp Tyr Ser Asp Pro Gly Leu Ala
225 230 235 240

Gly Val Ser Leu Thr Gly Gly Leu Ser Tyr Lys Glu Asp Thr Lys Glu
245 250 255

Leu Val Val Ala Lys Ala Gly Val Tyr Tyr Val Phe Phe Gln Leu Glu
260 265 270

Leu Arg Arg Val Val Ala Gly Glu Gly Ser Gly Ser Val Ser Leu Ala
275 280 285

Leu His Leu Gln Pro Leu Arg Ser Ala Ala Gly Ala Ala Ala Leu Ala
290 295 300

Leu Thr Val Asp Leu Pro Pro Ala Ser Ser Glu Ala Arg Asn Ser Ala
305 310 315 320

Phe Gly Phe Gln Gly Arg Leu Leu His Leu Ser Ala Gly Gln Arg Leu
325 330 335

Gly Val His Leu His Thr Glu Ala Arg Ala Arg His Ala Trp Gln Leu
340 345 350

Thr Gln Gly Ala Thr Val Leu Gly Leu Phe Arg Val Thr Pro Glu Ile
355 360 365

Pro Ala Gly Leu Pro Ser Pro Arg Ser Glu Gly Gly Gly Gly Ser Gly
370 375 380

Gly Gly Gly Ser Arg Thr Val Ala Ala Pro Ser Val Phe Ile Phe Pro
385 390 395 400

Pro Ser Asp Glu Gln Leu Lys Ser Gly Thr Ala Ser Val Val Cys Leu
405 410 415

Leu Asn Asn Phe Tyr Pro Arg Glu Ala Lys Val Gln Trp Lys Val Asp
420 425 430

Asn Ala Leu Gln Ser Gly Asn Ser Gln Glu Ser Val Thr Glu Gln Asp
435 440 445

Ser Lys Asp Ser Thr Tyr Ser Leu Ser Ser Thr Leu Thr Leu Ser Lys
450 455 460

Ala Asp Tyr Glu Lys His Lys Val Tyr Ala Cys Glu Val Thr His Gln
465 470 475 480

Gly Leu Ser Ser Pro Val Thr Lys Ser Phe Asn Arg Gly Glu Cys Asp
485 490 495

Lys Thr His Thr Cys Pro Pro Cys Pro Ala Pro Glu Ala Ala Gly Gly
500 505 510

Pro Ser Val Phe Leu Phe Pro Pro Lys Pro Lys Asp Thr Leu Met Ile
515 520 525

Ser Arg Thr Pro Glu Val Thr Cys Val Val Val Asp Val Ser His Glu
530 535 540

Asp Pro Glu Val Lys Phe Asn Trp Tyr Val Asp Gly Val Glu Val His
545 550 555 560

Asn Ala Lys Thr Lys Pro Arg Glu Glu Gln Tyr Asn Ser Thr Tyr Arg
565 570 575

Val Val Ser Val Leu Thr Val Leu His Gln Asp Trp Leu Asn Gly Lys
580 585 590

Glu Tyr Lys Cys Lys Val Ser Asn Lys Ala Leu Gly Ala Pro Ile Glu
595 600 605

Lys Thr Ile Ser Lys Ala Lys Gly Gln Pro Arg Glu Pro Gln Val Tyr
610 615 620

Thr Leu Pro Pro Cys Arg Asp Glu Leu Thr Lys Asn Gln Val Ser Leu
625 630 635 640

Trp Cys Leu Val Lys Gly Phe Tyr Pro Ser Asp Ile Ala Val Glu Trp
645 650 655

Glu Ser Asn Gly Gln Pro Glu Asn Asn Tyr Lys Thr Thr Pro Pro Val
660 665 670

Leu Asp Ser Asp Gly Ser Phe Phe Leu Tyr Ser Lys Leu Thr Val Asp
675 680 685

Lys Ser Arg Trp Gln Gln Gly Asn Val Phe Ser Cys Ser Val Met His
690 695 700

Glu Ala Leu His Asn His Tyr Thr Gln Lys Ser Leu Ser Leu Ser Pro
705 710 715 720

Gly Lys

<210> SEQ ID NO 109
<211> LENGTH: 297
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Monomeric ligand (71-254) -CH1

<400> SEQUENCE: 109

Arg Glu Gly Pro Glu Leu Ser Pro Asp Asp Pro Ala Gly Leu Leu Asp
1 5 10 15

Leu Arg Gln Gly Met Phe Ala Gln Leu Val Ala Gln Asn Val Leu Leu
20 25 30

Ile Asp Gly Pro Leu Ser Trp Tyr Ser Asp Pro Gly Leu Ala Gly Val
35 40 45

Ser Leu Thr Gly Gly Leu Ser Tyr Lys Glu Asp Thr Lys Glu Leu Val
50 55 60

Val Ala Lys Ala Gly Val Tyr Tyr Val Phe Phe Gln Leu Glu Leu Arg
65 70 75 80

Arg Val Val Ala Gly Glu Gly Ser Gly Ser Val Ser Leu Ala Leu His
85 90 95

Leu Gln Pro Leu Arg Ser Ala Ala Gly Ala Ala Ala Leu Ala Leu Thr
100 105 110

Val Asp Leu Pro Pro Ala Ser Ser Glu Ala Arg Asn Ser Ala Phe Gly
115 120 125

Phe Gln Gly Arg Leu Leu His Leu Ser Ala Gly Gln Arg Leu Gly Val
130 135 140

His Leu His Thr Glu Ala Arg Ala Arg His Ala Trp Gln Leu Thr Gln
145 150 155 160

Gly Ala Thr Val Leu Gly Leu Phe Arg Val Thr Pro Glu Ile Pro Ala
165 170 175

Gly Leu Pro Ser Pro Arg Ser Glu Gly Gly Gly Gly Ser Gly Gly Gly
180 185 190

Gly Ser Ala Ser Thr Lys Gly Pro Ser Val Phe Pro Leu Ala Pro Ser

```
        195                 200                 205

Ser Lys Ser Thr Ser Gly Gly Thr Ala Ala Leu Gly Cys Leu Val Lys
    210                 215                 220

Asp Tyr Phe Pro Glu Pro Val Thr Val Ser Trp Asn Ser Gly Ala Leu
225                 230                 235                 240

Thr Ser Gly Val His Thr Phe Pro Ala Val Leu Gln Ser Ser Gly Leu
                245                 250                 255

Tyr Ser Leu Ser Ser Val Val Thr Val Pro Ser Ser Ser Leu Gly Thr
            260                 265                 270

Gln Thr Tyr Ile Cys Asn Val Asn His Lys Pro Ser Asn Thr Lys Val
        275                 280                 285

Asp Lys Lys Val Glu Pro Lys Ser Cys
    290                 295


<210> SEQ ID NO 110
<211> LENGTH: 2505
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: anti-TnC(18D4) Fc hole dimeric ligand (71-254)
      chain

<400> SEQUENCE: 110

caggtgcaat tggtgcagtc tggggctgag gtgaagaagc ctgggtcctc ggtgaaggtc     60

tcctgcaagg cctccggagg cacattcagc agctacgcta taagctgggt gcgacaggcc    120

cctggacaag ggctcgagtg gatgggaggg atcatcccta tctttggtac agcaaactac    180

gcacagaagt tccagggcag ggtcaccatt actgcagaca aatccacgag cacagcctac    240

atggagctga gcagcctgag atctgaggac accgccgtgt attactgtgc gaaaggtaac    300

ttctacggtg gtctggacta ctggggccaa gggaccaccg tgaccgtctc ctcagctagc    360

accaagggcc cctccgtgtt cccccctggcc cccagcagca agagcaccag cggcggcaca    420

gccgctctgg gctgcctggt caaggactac ttccccgagc ccgtgaccgt gtcctggaac    480

agcggagccc tgacctccgg cgtgcacacc ttccccgccg tgctgcagag ttctggcctg    540

tatagcctga gcagcgtggt caccgtgcct tctagcagcc tgggcaccca gacctacatc    600

tgcaacgtga accacaagcc cagcaacacc aaggtggaca agaaggtgga gcccaagagc    660

tgcgacaaaa ctcacacatg cccaccgtgc ccagcacctg aagctgcagg gggaccgtca    720

gtcttcctct tccccccaaa acccaaggac accctcatga tctcccggac ccctgaggtc    780

acatgcgtgg tggtggacgt gagccacgaa gaccctgagg tcaagttcaa ctggtacgtg    840

gacggcgtgg aggtgcataa tgccaagaca aagccgcggg aggagcagta caacagcacg    900

taccgtgtgg tcagcgtcct caccgtcctg caccaggact ggctgaatgg caaggagtac    960

aagtgcaagg tctccaacaa agccctcggc gcccccatcg agaaaaccat ctccaaagcc   1020

aaagggcagc cccgagaacc acaggtgtgc accctgcccc catcccggga tgagctgacc   1080

aagaaccagg tcagcctctc gtgcgcagtc aaaggcttct atcccagcga catcgccgtg   1140

gagtgggaga gcaatgggca gccggagaac aactacaaga ccacgcctcc cgtgctggac   1200

tccgacggct ccttcttcct cgtgagcaag ctcaccgtgg acaagagcag gtggcagcag   1260

gggaacgtct tctcatgctc cgtgatgcat gaggctctgc acaaccacta cacgcagaag   1320

agcctctccc tgtctccggg tggaggcggc ggaagcggag gaggaggatc cagagagggc   1380
```

```
cctgagctga gccccgatga tcctgctgga ctgctggacc tgcggcaggg catgtttgct   1440

cagctggtgg cccagaacgt gctgctgatc gatggccccc tgtcctggta cagcgatcct   1500

ggactggctg gcgtgtcact gacaggcggc ctgagctaca aagaggacac caaagaactg   1560

gtggtggcca aggccggcgt gtactacgtg ttctttcagc tggaactgcg gagagtggtg   1620

gccggcgaag gatctggctc tgtgtctctg gccctgcatc tgcagcctct gagaagcgct   1680

gctggcgctg cagctctggc actgacagtg gatctgcctc ctgccagctc cgaggcccgg   1740

aatagcgcat ttgggtttca aggcaggctg ctgcacctgt ctgccggcca gaggctggga   1800

gtgcatctgc acacagaggc cagggctaga cacgcctggc agctgacaca gggcgctaca   1860

gtgctgggcc tgttcagagt gacccccgag attccagccg gcctgccttc tccaagaagc   1920

gaaggcggag gcggatctgg cggcggagga tctagagagg gacccgaact gtcccctgac   1980

gatccagccg ggctgctgga tctgagacag ggaatgttcg cccagctggt ggctcagaat   2040

gtgctgctga ttgacggacc tctgagctgg tactccgacc cagggctggc aggggtgtcc   2100

ctgactgggg gactgtccta caaagaagat acaaaagaac tggtggtggc taaagctggg   2160

gtgtactatg tgtttttca gctggaactg aggcgggtgg tggctgggga gggctcagga   2220

tctgtgtccc tggctctgca tctgcagcca ctgcgctctg ctgctggcgc agctgcactg   2280

gctctgactg tggacctgcc accagcctct agcgaggcca gaaacagcgc cttcgggttc   2340

caaggacgcc tgctgcatct gagcgccgga cagcgcctgg gagtgcatct gcatactgaa   2400

gccagagccc ggcatgcttg gcagctgact caggggcaa ctgtgctggg actgtttcgc   2460

gtgacacctg agatccctgc cggactgcca agccctagat cagaa                  2505
```

<210> SEQ ID NO 111
<211> LENGTH: 1923
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: anti-TnC(18D4) Fc knob monomeric ligand
(71-254) chain

<400> SEQUENCE: 111

```
caggtgcaat tggtgcagtc tggggctgag gtgaagaagc ctgggtcctc ggtgaaggtc     60

tcctgcaagg cctccggagg cacattcagc agctacgcta taagctgggt gcgacaggcc    120

cctggacaag ggctcgagtg gatgggaggg atcatcccta tctttggtac agcaaactac    180

gcacagaagt tccagggcag ggtcaccatt actgcagaca aatccacgag cacagcctac    240

atggagctga gcagcctgag atctgaggac accgccgtgt attactgtgc gaaaggtaac    300

ttctacggtg gtctggacta ctggggccaa gggaccaccg tgaccgtctc ctcagctagc    360

accaagggcc catcggtctt ccccctggca ccctcctcca agagcacctc tgggggcaca    420

gcggccctgg gctgcctggt caaggactac ttccccgaac cggtgacggt gtcgtggaac    480

tcaggcgccc tgaccagcgg cgtgcacacc ttcccggctg tcctacagtc ctcaggactc    540

tactccctca gcagcgtggt gaccgtgccc tccagcagct tgggcaccca gacctacatc    600

tgcaacgtga atcacaagcc cagcaacacc aaggtggaca agaaagttga gcccaaatct    660

tgtgacaaaa ctcacacatg cccaccgtgc ccagcacctg aagctgcagg gggaccgtca    720

gtcttcctct tcccccaaa acccaaggac accctcatga tctcccggac ccctgaggtc    780
```

```
acatgcgtgg tggtggacgt gagccacgaa gaccctgagg tcaagttcaa ctggtacgtg    840

gacggcgtgg aggtgcataa tgccaagaca aagccgcggg aggagcagta caacagcacg    900

taccgtgtgg tcagcgtcct caccgtcctg caccaggact ggctgaatgg caaggagtac    960

aagtgcaagg tctccaacaa agccctcggc gcccccatcg agaaaaccat ctccaaagcc   1020

aaagggcagc cccgagaacc acaggtgtac accctgcccc cctgcagaga tgagctgacc   1080

aagaaccagg tgtccctgtg gtgtctggtc aagggcttct accccagcga tatcgccgtg   1140

gagtgggaga gcaacggcca gcctgagaac aactacaaga ccaccccccc tgtgctggac   1200

agcgacggca gcttcttcct gtactccaaa ctgaccgtgg acaagagccg gtggcagcag   1260

ggcaacgtgt tcagctgcag cgtgatgcac gaggccctgc acaaccacta cacccagaag   1320

tccctgagcc tgagccccgg cggaggcggc ggaagcggag gaggaggatc cagagagggc   1380

cctgagctga gccccgatga tcctgctgga ctgctggacc tgcggcaggg catgtttgct   1440

cagctggtgg cccagaacgt gctgctgatc gatggccccc tgtcctggta cagcgatcct   1500

ggactggctg gcgtgtcact gacaggcggc ctgagctaca aagaggacac caaagaactg   1560

gtggtggcca aggccggcgt gtactacgtg ttctttcagc tggaactgcg gagagtggtg   1620

gccggcgaag gatctggctc tgtgtctctg gccctgcatc tgcagcctct gagaagcgct   1680

gctggcgctg cagctctggc actgacagtg gatctgcctc ctgccagctc cgaggcccgg   1740

aatagcgcat ttgggtttca aggcaggctg ctgcacctgt ctgccggcca gaggctggga   1800

gtgcatctgc acacagaggc cagggctaga cacgcctggc agctgacaca gggcgctaca   1860

gtgctgggcc tgttcagagt gacccccgag attccagccg gcctgccttc tccaagaagc   1920

gaa                                                                 1923
```

```
<210> SEQ ID NO 112
<211> LENGTH: 835
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: anti-TnC(18D4) Fc hole dimeric ligand (71-254)
      chain

<400> SEQUENCE: 112

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Gly Asn Phe Tyr Gly Gly Leu Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
```

-continued

```
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Gly Ala Pro Ile Glu Lys Thr
                325                 330                 335

Ile Ser Lys Ala Lys Gly Gln Pro Arg Glu Pro Gln Val Cys Thr Leu
            340                 345                 350

Pro Pro Ser Arg Asp Glu Leu Thr Lys Asn Gln Val Ser Leu Ser Cys
        355                 360                 365

Ala Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Gly
        435                 440                 445

Gly Gly Gly Ser Gly Gly Gly Gly Ser Arg Glu Gly Pro Glu Leu Ser
    450                 455                 460

Pro Asp Asp Pro Ala Gly Leu Leu Asp Leu Arg Gln Gly Met Phe Ala
465                 470                 475                 480

Gln Leu Val Ala Gln Asn Val Leu Leu Ile Asp Gly Pro Leu Ser Trp
                485                 490                 495

Tyr Ser Asp Pro Gly Leu Ala Gly Val Ser Leu Thr Gly Gly Leu Ser
            500                 505                 510

Tyr Lys Glu Asp Thr Lys Glu Leu Val Val Ala Lys Ala Gly Val Tyr
        515                 520                 525

Tyr Val Phe Phe Gln Leu Glu Leu Arg Arg Val Val Ala Gly Glu Gly
    530                 535                 540

Ser Gly Ser Val Ser Leu Ala Leu His Leu Gln Pro Leu Arg Ser Ala
545                 550                 555                 560
```

```
Ala Gly Ala Ala Ala Leu Ala Leu Thr Val Asp Leu Pro Pro Ala Ser
                565                 570                 575

Ser Glu Ala Arg Asn Ser Ala Phe Gly Phe Gln Gly Arg Leu Leu His
            580                 585                 590

Leu Ser Ala Gly Gln Arg Leu Gly Val His Leu His Thr Glu Ala Arg
        595                 600                 605

Ala Arg His Ala Trp Gln Leu Thr Gln Gly Ala Thr Val Leu Gly Leu
    610                 615                 620

Phe Arg Val Thr Pro Glu Ile Pro Ala Gly Leu Pro Ser Pro Arg Ser
625                 630                 635                 640

Glu Gly Gly Gly Gly Ser Gly Gly Gly Gly Ser Arg Glu Gly Pro Glu
                645                 650                 655

Leu Ser Pro Asp Asp Pro Ala Gly Leu Leu Asp Leu Arg Gln Gly Met
            660                 665                 670

Phe Ala Gln Leu Val Ala Gln Asn Val Leu Leu Ile Asp Gly Pro Leu
        675                 680                 685

Ser Trp Tyr Ser Asp Pro Gly Leu Ala Gly Val Ser Leu Thr Gly Gly
    690                 695                 700

Leu Ser Tyr Lys Glu Asp Thr Lys Glu Leu Val Val Ala Lys Ala Gly
705                 710                 715                 720

Val Tyr Tyr Val Phe Phe Gln Leu Glu Leu Arg Arg Val Val Ala Gly
                725                 730                 735

Glu Gly Ser Gly Ser Val Ser Leu Ala Leu His Leu Gln Pro Leu Arg
            740                 745                 750

Ser Ala Ala Gly Ala Ala Ala Leu Ala Leu Thr Val Asp Leu Pro Pro
        755                 760                 765

Ala Ser Ser Glu Ala Arg Asn Ser Ala Phe Gly Phe Gln Gly Arg Leu
    770                 775                 780

Leu His Leu Ser Ala Gly Gln Arg Leu Gly Val His Leu His Thr Glu
785                 790                 795                 800

Ala Arg Ala Arg His Ala Trp Gln Leu Thr Gln Gly Ala Thr Val Leu
                805                 810                 815

Gly Leu Phe Arg Val Thr Pro Glu Ile Pro Ala Gly Leu Pro Ser Pro
            820                 825                 830

Arg Ser Glu
        835
```

<210> SEQ ID NO 113
<211> LENGTH: 641
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: anti-TnC(18D4) Fc knob monomeric ligand (71-254) chain

<400> SEQUENCE: 113

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
```

-continued

```
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Gly Asn Phe Tyr Gly Gly Leu Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Gly Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Cys Arg Asp Glu Leu Thr Lys Asn Gln Val Ser Leu Trp Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Gly
        435                 440                 445

Gly Gly Gly Ser Gly Gly Gly Gly Ser Arg Glu Gly Pro Glu Leu Ser
    450                 455                 460

Pro Asp Asp Pro Ala Gly Leu Leu Asp Leu Arg Gln Gly Met Phe Ala
465                 470                 475                 480
```

```
Gln Leu Val Ala Gln Asn Val Leu Leu Ile Asp Gly Pro Leu Ser Trp
                485                 490                 495

Tyr Ser Asp Pro Gly Leu Ala Gly Val Ser Leu Thr Gly Gly Leu Ser
            500                 505                 510

Tyr Lys Glu Asp Thr Lys Glu Leu Val Val Ala Lys Ala Gly Val Tyr
        515                 520                 525

Tyr Val Phe Phe Gln Leu Glu Leu Arg Arg Val Val Ala Gly Glu Gly
    530                 535                 540

Ser Gly Ser Val Ser Leu Ala Leu His Leu Gln Pro Leu Arg Ser Ala
545                 550                 555                 560

Ala Gly Ala Ala Ala Leu Ala Leu Thr Val Asp Leu Pro Pro Ala Ser
                565                 570                 575

Ser Glu Ala Arg Asn Ser Ala Phe Gly Phe Gln Gly Arg Leu Leu His
            580                 585                 590

Leu Ser Ala Gly Gln Arg Leu Gly Val His Leu His Thr Glu Ala Arg
        595                 600                 605

Ala Arg His Ala Trp Gln Leu Thr Gln Gly Ala Thr Val Leu Gly Leu
    610                 615                 620

Phe Arg Val Thr Pro Glu Ile Pro Ala Gly Leu Pro Ser Pro Arg Ser
625                 630                 635                 640

Glu


<210> SEQ ID NO 114
<211> LENGTH: 2130
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Dimeric ligand (71-248) - CL* Fc knob chain

<400> SEQUENCE: 114

agagagggcc ctgagctgag ccccgatgat cctgctggac tgctggacct gcggcagggc     60

atgtttgctc agctggtggc ccagaacgtg ctgctgatcg atggccccct gtcctggtac    120

agcgatcctg gactggctgg cgtgtcactg acaggcggcc tgagctacaa agaggacacc    180

aaagaactgg tggtggccaa ggccggcgtg tactacgtgt tctttcagct ggaactgcgg    240

agagtggtgg ccggcgaagg atctggctct gtgtctctgg ccctgcatct gcagcctctg    300

agatctgctg ctggcgccgc tgctctggca ctgacagtgg atctgcctcc tgccagcagc    360

gaggcccgga atagcgcatt tgggtttcaa ggcaggctgc tgcacctgtc tgccggccag    420

aggctgggag tgcatctgca cacagaggcc agggctagac acgcctggca gctgacacag    480

ggcgctacag tgctgggcct gttcagagtg acccccgaga ttccagccgg actgggaggc    540

ggcggatctg gcggcggagg atctagagaa ggacccgagc tgtcccctga cgatccagcc    600

gggctgctgg atctgagaca gggaatgttc gcccagctgg tggctcagaa tgtgctgctg    660

attgacggac ctctgagctg gtactccgac ccagggctgg caggggtgtc cctgactggg    720

ggactgtcct acaaagaaga tacaaaagaa ctggtggtgg ctaaagctgg ggtgtactat    780

gtgttttttc agctggaact gaggcgggtg gtggctgggg agggctcagg atctgtgtcc    840

ctggctctgc atctgcagcc actgcgctct gcagcagggg ctgcagcact ggccctgact    900

gtggacctgc ccccagcttc ttccgaggcc agaaacagcg ccttcgggtt ccaaggacgc    960

ctgctgcatc tgagcgccgg acagcgcctg ggagtgcatc tgcatactga agccagagcc   1020
```

```
cggcatgctt ggcagctgac tcagggggca actgtgctgg gactgtttcg cgtgacacct   1080
gagatccccg ctggactggg cggaggcggt tccggagggg gaggatctcg tacggtggct   1140
gcaccatctg tctttatctt cccacccagc gaccggaagc tgaagtctgg cacagccagc   1200
gtcgtgtgcc tgctgaataa cttctacccc cgcgaggcca aggtgcagtg gaaggtggac   1260
aatgccctgc agagcggcaa cagccaggaa agcgtgaccg agcaggacag caaggactcc   1320
acctacagcc tgagcagcac cctgaccctg agcaaggccg actacgagaa gcacaaggtg   1380
tacgcctgcg aagtgaccca ccagggcctg tctagccccg tgaccaagag cttcaaccgg   1440
ggcgagtgcg acaagaccca cacctgtcct ccatgccctg cccctgaagc tgctggcggc   1500
cctagcgtgt tcctgttccc cccaaagccc aaggacaccc tgatgatcag ccggacccct   1560
gaagtgacct gcgtggtggt ggatgtgtcc cacgaggacc ctgaagtgaa gttcaattgg   1620
tacgtggacg gcgtggaagt gcacaatgcc aagaccaagc cgcgggagga gcagtacaac   1680
agcacgtacc gtgtggtcag cgtcctcacc gtcctgcacc aggactggct gaatggcaag   1740
gagtacaagt gcaaggtctc caacaaagcc ctcggcgccc ccatcgagaa aaccatctcc   1800
aaagccaaag ggcagccccg agaaccacag gtgtacaccc tgcccccatg ccgggatgag   1860
ctgaccaaga accaggtcag cctgtggtgc ctggtcaaag gcttctatcc cagcgacatc   1920
gccgtggagt gggagagcaa tgggcagccg gagaacaact acaagaccac gcctcccgtg   1980
ctggactccg acggctcctt cttcctctac agcaagctca ccgtggacaa gagcaggtgg   2040
cagcagggga acgtcttctc atgctccgtg atgcatgagg ctctgcacaa ccactacacg   2100
cagaagagcc tctccctgtc tccgggtaaa                                    2130
```

```
<210> SEQ ID NO 115
<211> LENGTH: 873
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Monomeric ligand (71-248)-CH1*

<400> SEQUENCE: 115
```

```
agagagggcc ctgagctgag ccccgatgat cctgctggac tgctggacct gcggcagggc     60
atgtttgctc agctggtggc ccagaacgtg ctgctgatcg atggccccct gtcctggtac    120
agcgatcctg gactggctgg cgtgtcactg acaggcggcc tgagctacaa agaggacacc    180
aaagaactgg tggtggccaa ggccggcgtg tactacgtgt tctttcagct ggaactgcgg    240
agagtggtgg ccggcgaagg atctggctct gtgtctctgg ccctgcatct gcagcctctg    300
agatctgctg ctggcgccgc tgctctggca ctgacagtgg atctgcctcc tgccagcagc    360
gaggcccgga atagcgcatt tgggtttcaa ggcaggctgc tgcacctgtc tgccggccag    420
aggctgggag tgcatctgca cacagaggcc agggctagac acgcctggca gctgacacag    480
ggcgctacag tgctgggcct gttcagagtg acccccgaga ttccagccgg actgggaggc    540
ggaggttccg gaggcggagg atctgctagc acaaagggcc ccagcgtgtt ccctctggcc    600
cctagcagca agagcacatc tggcggaaca gccgccctgg gctgcctggt ggaagattac    660
ttccccgagc ccgtgaccgt gtcctggaat tctggcgccc tgacaagcgg cgtgcacacc    720
tttccagccg tgctgcagag cagcggcctg tactctctga gcagcgtcgt gacagtgccc    780
agcagctctc tgggcaccca gacctacatc tgcaacgtga accacaagcc cagcaacacc    840
```

aaggtggacg agaaggtgga acccaagtcc tgc 873

<210> SEQ ID NO 116
<211> LENGTH: 710
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Dimeric ligand (71-248) - CL* Fc knob chain

<400> SEQUENCE: 116

```
Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
    50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
    130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Gly Gly Gly Gly Ser Gly Gly Gly Gly Ser Arg Glu Gly Pro
            180                 185                 190

Glu Leu Ser Pro Asp Asp Pro Ala Gly Leu Leu Asp Leu Arg Gln Gly
        195                 200                 205

Met Phe Ala Gln Leu Val Ala Gln Asn Val Leu Leu Ile Asp Gly Pro
    210                 215                 220

Leu Ser Trp Tyr Ser Asp Pro Gly Leu Ala Gly Val Ser Leu Thr Gly
225                 230                 235                 240

Gly Leu Ser Tyr Lys Glu Asp Thr Lys Glu Leu Val Val Ala Lys Ala
                245                 250                 255

Gly Val Tyr Tyr Val Phe Phe Gln Leu Glu Leu Arg Arg Val Val Ala
            260                 265                 270

Gly Glu Gly Ser Gly Ser Val Ser Leu Ala Leu His Leu Gln Pro Leu
        275                 280                 285

Arg Ser Ala Ala Gly Ala Ala Ala Leu Ala Leu Thr Val Asp Leu Pro
    290                 295                 300

Pro Ala Ser Ser Glu Ala Arg Asn Ser Ala Phe Gly Phe Gln Gly Arg
305                 310                 315                 320

Leu Leu His Leu Ser Ala Gly Gln Arg Leu Gly Val His Leu His Thr
                325                 330                 335
```

```
Glu Ala Arg Ala Arg His Ala Trp Gln Leu Thr Gln Gly Ala Thr Val
            340                 345                 350

Leu Gly Leu Phe Arg Val Thr Pro Glu Ile Pro Ala Gly Leu Gly Gly
        355                 360                 365

Gly Gly Ser Gly Gly Gly Gly Ser Arg Thr Val Ala Ala Pro Ser Val
    370                 375                 380

Phe Ile Phe Pro Pro Ser Asp Arg Lys Leu Lys Ser Gly Thr Ala Ser
385                 390                 395                 400

Val Val Cys Leu Leu Asn Asn Phe Tyr Pro Arg Glu Ala Lys Val Gln
                405                 410                 415

Trp Lys Val Asp Asn Ala Leu Gln Ser Gly Asn Ser Gln Glu Ser Val
            420                 425                 430

Thr Glu Gln Asp Ser Lys Asp Ser Thr Tyr Ser Leu Ser Ser Thr Leu
        435                 440                 445

Thr Leu Ser Lys Ala Asp Tyr Glu Lys His Lys Val Tyr Ala Cys Glu
    450                 455                 460

Val Thr His Gln Gly Leu Ser Ser Pro Val Thr Lys Ser Phe Asn Arg
465                 470                 475                 480

Gly Glu Cys Asp Lys Thr His Thr Cys Pro Pro Cys Pro Ala Pro Glu
                485                 490                 495

Ala Ala Gly Gly Pro Ser Val Phe Leu Phe Pro Pro Lys Pro Lys Asp
            500                 505                 510

Thr Leu Met Ile Ser Arg Thr Pro Glu Val Thr Cys Val Val Val Asp
        515                 520                 525

Val Ser His Glu Asp Pro Glu Val Lys Phe Asn Trp Tyr Val Asp Gly
    530                 535                 540

Val Glu Val His Asn Ala Lys Thr Lys Pro Arg Glu Glu Gln Tyr Asn
545                 550                 555                 560

Ser Thr Tyr Arg Val Val Ser Val Leu Thr Val Leu His Gln Asp Trp
                565                 570                 575

Leu Asn Gly Lys Glu Tyr Lys Cys Lys Val Ser Asn Lys Ala Leu Gly
            580                 585                 590

Ala Pro Ile Glu Lys Thr Ile Ser Lys Ala Lys Gly Gln Pro Arg Glu
        595                 600                 605

Pro Gln Val Tyr Thr Leu Pro Pro Cys Arg Asp Glu Leu Thr Lys Asn
    610                 615                 620

Gln Val Ser Leu Trp Cys Leu Val Lys Gly Phe Tyr Pro Ser Asp Ile
625                 630                 635                 640

Ala Val Glu Trp Glu Ser Asn Gly Gln Pro Glu Asn Asn Tyr Lys Thr
                645                 650                 655

Thr Pro Pro Val Leu Asp Ser Asp Gly Ser Phe Phe Leu Tyr Ser Lys
            660                 665                 670

Leu Thr Val Asp Lys Ser Arg Trp Gln Gln Gly Asn Val Phe Ser Cys
        675                 680                 685

Ser Val Met His Glu Ala Leu His Asn His Tyr Thr Gln Lys Ser Leu
    690                 695                 700

Ser Leu Ser Pro Gly Lys
705                 710
```

<210> SEQ ID NO 117
<211> LENGTH: 291
<212> TYPE: PRT
<213> ORGANISM: Artificial Sequence
<220> FEATURE:
<223> OTHER INFORMATION: Description of Artificial Sequence: Synthetic

```
      polypeptide
<220> FEATURE:
<223> OTHER INFORMATION: Monomeric ligand (71-248)-CH1*

<400> SEQUENCE: 117

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
    50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
    130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Gly Gly Gly Ser Gly Gly Gly Gly Ser Ala Ser Thr Lys
            180                 185                 190

Gly Pro Ser Val Phe Pro Leu Ala Pro Ser Ser Lys Ser Thr Ser Gly
        195                 200                 205

Gly Thr Ala Ala Leu Gly Cys Leu Val Glu Asp Tyr Phe Pro Glu Pro
    210                 215                 220

Val Thr Val Ser Trp Asn Ser Gly Ala Leu Thr Ser Gly Val His Thr
225                 230                 235                 240

Phe Pro Ala Val Leu Gln Ser Ser Gly Leu Tyr Ser Leu Ser Ser Val
                245                 250                 255

Val Thr Val Pro Ser Ser Ser Leu Gly Thr Gln Thr Tyr Ile Cys Asn
            260                 265                 270

Val Asn His Lys Pro Ser Asn Thr Lys Val Asp Glu Lys Val Glu Pro
        275                 280                 285

Lys Ser Cys
    290


<210> SEQ ID NO 118
<211> LENGTH: 2130
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Dimeric ligand (71-248) - CL Fc knob chain

<400> SEQUENCE: 118

agagagggcc ctgagctgag ccccgatgat cctgctggac tgctggacct gcggcagggc      60

atgtttgctc agctggtggc ccagaacgtg ctgctgatcg atggccccct gtcctggtac     120
```

-continued

```
agcgatcctg gactggctgg cgtgtcactg acaggcggcc tgagctacaa agaggacacc    180
aaagaactgg tggtggccaa ggccggcgtg tactacgtgt tctttcagct ggaactgcgg    240
agagtggtgg ccggcgaagg atctggctct gtgtctctgg ccctgcatct gcagcctctg    300
agatctgctg ctggcgccgc tgctctggca ctgacagtgg atctgcctcc tgccagcagc    360
gaggcccgga atagcgcatt tgggtttcaa ggcaggctgc tgcacctgtc tgccggccag    420
aggctgggag tgcatctgca cacagaggcc agggctagac acgcctggca gctgacacag    480
ggcgctacag tgctgggcct gttcagagtg acccccgaga ttccagccgg actgggaggc    540
ggcggatctg gcggcggagg atctagagaa ggacccgagc tgtcccctga cgatccagcc    600
gggctgctgg atctgagaca gggaatgttc gcccagctgg tggctcagaa tgtgctgctg    660
attgacggac ctctgagctg gtactccgac ccagggctgg caggggtgtc cctgactggg    720
ggactgtcct acaaagaaga tacaaaagaa ctggtggtgg ctaaagctgg ggtgtactat    780
gtgttttttc agctggaact gaggcgggtg gtggctgggg agggctcagg atctgtgtcc    840
ctggctctgc atctgcagcc actgcgctct gcagcagggg ctgcagcact ggccctgact    900
gtggacctgc ccccagcttc ttccgaggcc agaaacagcg ccttcgggtt ccaaggacgc    960
ctgctgcatc tgagcgccgg acagcgcctg ggagtgcatc tgcatactga agccagagcc   1020
cggcatgctt ggcagctgac tcagggggca actgtgctgg gactgtttcg cgtgacacct   1080
gagatccccg ctggactggg cggaggcggt tccggagggg gaggatctcg tacggtggcc   1140
gctccctccg tgtttatctt tcccccatcc gatgaacagc tgaaaagcgg caccgcctcc   1200
gtcgtgtgtc tgctgaacaa tttttaccct agggaagcta aagtgcagtg gaaagtggat   1260
aacgcactgc agtccggcaa ctcccaggaa tctgtgacag aacaggactc caaggacagc   1320
acctactccc tgtcctccac cctgacactg tctaaggctg attatgagaa acacaaagtc   1380
tacgcctgcg aagtcaccca tcagggcctg agctcgcccg tcacaaagag cttcaacagg   1440
ggagagtgtg acaagaccca cacctgtccc ccttgtcctg cccctgaagc tgctggcggc   1500
ccttctgtgt tcctgttccc cccaaagccc aaggacaccc tgatgatcag ccggaccccc   1560
gaagtgacct gcgtggtggt ggatgtgtcc cacgaggacc ctgaagtgaa gttcaattgg   1620
tacgtggacg gcgtggaagt gcacaatgcc aagaccaagc cgcgggagga gcagtacaac   1680
agcacgtacc gtgtggtcag cgtcctcacc gtcctgcacc aggactggct gaatggcaag   1740
gagtacaagt gcaaggtctc caacaaagcc ctcggcgccc ccatcgagaa aaccatctcc   1800
aaagccaaag ggcagccccg agaaccacag gtgtacaccc tgcccccatg ccgggatgag   1860
ctgaccaaga accaggtcag cctgtggtgc ctggtcaaag gcttctatcc cagcgacatc   1920
gccgtggagt gggagagcaa tgggcagccg gagaacaact acaagaccac gcctcccgtg   1980
ctggactccg acggctcctt cttcctctac agcaagctca ccgtggacaa gagcaggtgg   2040
cagcagggga acgtcttctc atgctccgtg atgcatgagg ctctgcacaa ccactacacg   2100
cagaagagcc tctccctgtc tccgggtaaa                                    2130
```

<210> SEQ ID NO 119
<211> LENGTH: 873
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Monomeric ligand (71-248)-CH1

<400> SEQUENCE: 119

```
agagagggcc ctgagctgag ccccgatgat cctgctggac tgctggacct gcggcagggc     60
atgtttgctc agctggtggc ccagaacgtg ctgctgatcg atggccccct gtcctggtac    120
agcgatcctg gactggctgg cgtgtcactg acaggcggcc tgagctacaa agaggacacc    180
aaagaactgg tggtggccaa ggccggcgtg tactacgtgt tctttcagct ggaactgcgg    240
agagtggtgg ccggcgaagg atctggctct gtgtctctgg ccctgcatct gcagcctctg    300
agatctgctg ctggcgccgc tgctctggca ctgacagtgg atctgcctcc tgccagcagc    360
gaggcccgga atagcgcatt tgggtttcaa ggcaggctgc tgcacctgtc tgccggccag    420
aggctgggag tgcatctgca cacagaggcc agggctagac acgcctggca gctgacacag    480
ggcgctacag tgctgggcct gttcagagtg acccccgaga ttccagccgg actgggaggc    540
ggaggttccg gaggcggagg atctgctagc accaaaggcc cttccgtgtt tcctctggct    600
cctagctcca agtccacctc tggaggcacc gctgctctcg gatgcctcgt gaaggattat    660
tttcctgagc ctgtgacagt gtcctggaat agcggagcac tgacctctgg agtgcatact    720
ttccccgctg tgctgcagtc ctctggactg tacagcctga gcagcgtggt gacagtgccc    780
agcagcagcc tgggcaccca gacctacatc tgcaacgtga accacaagcc cagcaacacc    840
aaggtggaca agaaggtgga acccaagtct tgt                                 873
```

<210> SEQ ID NO 120
<211> LENGTH: 710
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Dimeric ligand (71-248) - CL Fc knob chain

<400> SEQUENCE: 120

```
Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
    50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
    130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175
```

```
Gly Leu Gly Gly Gly Gly Ser Gly Gly Gly Gly Ser Arg Glu Gly Pro
            180                 185                 190

Glu Leu Ser Pro Asp Asp Pro Ala Gly Leu Leu Asp Leu Arg Gln Gly
        195                 200                 205

Met Phe Ala Gln Leu Val Ala Gln Asn Val Leu Leu Ile Asp Gly Pro
    210                 215                 220

Leu Ser Trp Tyr Ser Asp Pro Gly Leu Ala Gly Val Ser Leu Thr Gly
225                 230                 235                 240

Gly Leu Ser Tyr Lys Glu Asp Thr Lys Glu Leu Val Val Ala Lys Ala
                245                 250                 255

Gly Val Tyr Tyr Val Phe Phe Gln Leu Glu Leu Arg Arg Val Val Ala
            260                 265                 270

Gly Glu Gly Ser Gly Ser Val Ser Leu Ala Leu His Leu Gln Pro Leu
        275                 280                 285

Arg Ser Ala Ala Gly Ala Ala Ala Leu Ala Leu Thr Val Asp Leu Pro
    290                 295                 300

Pro Ala Ser Ser Glu Ala Arg Asn Ser Ala Phe Gly Phe Gln Gly Arg
305                 310                 315                 320

Leu Leu His Leu Ser Ala Gly Gln Arg Leu Gly Val His Leu His Thr
                325                 330                 335

Glu Ala Arg Ala Arg His Ala Trp Gln Leu Thr Gln Gly Ala Thr Val
            340                 345                 350

Leu Gly Leu Phe Arg Val Thr Pro Glu Ile Pro Ala Gly Leu Gly Gly
        355                 360                 365

Gly Gly Ser Gly Gly Gly Gly Ser Arg Thr Val Ala Ala Pro Ser Val
    370                 375                 380

Phe Ile Phe Pro Pro Ser Asp Glu Gln Leu Lys Ser Gly Thr Ala Ser
385                 390                 395                 400

Val Val Cys Leu Leu Asn Asn Phe Tyr Pro Arg Glu Ala Lys Val Gln
                405                 410                 415

Trp Lys Val Asp Asn Ala Leu Gln Ser Gly Asn Ser Gln Glu Ser Val
            420                 425                 430

Thr Glu Gln Asp Ser Lys Asp Ser Thr Tyr Ser Leu Ser Ser Thr Leu
        435                 440                 445

Thr Leu Ser Lys Ala Asp Tyr Glu Lys His Lys Val Tyr Ala Cys Glu
    450                 455                 460

Val Thr His Gln Gly Leu Ser Ser Pro Val Thr Lys Ser Phe Asn Arg
465                 470                 475                 480

Gly Glu Cys Asp Lys Thr His Thr Cys Pro Pro Cys Pro Ala Pro Glu
                485                 490                 495

Ala Ala Gly Gly Pro Ser Val Phe Leu Phe Pro Pro Lys Pro Lys Asp
            500                 505                 510

Thr Leu Met Ile Ser Arg Thr Pro Glu Val Thr Cys Val Val Val Asp
        515                 520                 525

Val Ser His Glu Asp Pro Glu Val Lys Phe Asn Trp Tyr Val Asp Gly
    530                 535                 540

Val Glu Val His Asn Ala Lys Thr Lys Pro Arg Glu Glu Gln Tyr Asn
545                 550                 555                 560

Ser Thr Tyr Arg Val Val Ser Val Leu Thr Val Leu His Gln Asp Trp
                565                 570                 575

Leu Asn Gly Lys Glu Tyr Lys Cys Lys Val Ser Asn Lys Ala Leu Gly
            580                 585                 590

Ala Pro Ile Glu Lys Thr Ile Ser Lys Ala Lys Gly Gln Pro Arg Glu
```

```
        595                 600                 605

Pro Gln Val Tyr Thr Leu Pro Pro Cys Arg Asp Glu Leu Thr Lys Asn
    610                 615                 620

Gln Val Ser Leu Trp Cys Leu Val Lys Gly Phe Tyr Pro Ser Asp Ile
625                 630                 635                 640

Ala Val Glu Trp Glu Ser Asn Gly Gln Pro Glu Asn Asn Tyr Lys Thr
                645                 650                 655

Thr Pro Pro Val Leu Asp Ser Asp Gly Ser Phe Phe Leu Tyr Ser Lys
            660                 665                 670

Leu Thr Val Asp Lys Ser Arg Trp Gln Gln Gly Asn Val Phe Ser Cys
        675                 680                 685

Ser Val Met His Glu Ala Leu His Asn His Tyr Thr Gln Lys Ser Leu
    690                 695                 700

Ser Leu Ser Pro Gly Lys
705                 710


<210> SEQ ID NO 121
<211> LENGTH: 291
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Monomeric ligand (71-248)-CH1

<400> SEQUENCE: 121

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
    50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
    130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Gly Gly Gly Gly Ser Gly Gly Gly Gly Ser Ala Ser Thr Lys
            180                 185                 190

Gly Pro Ser Val Phe Pro Leu Ala Pro Ser Ser Lys Ser Thr Ser Gly
        195                 200                 205

Gly Thr Ala Ala Leu Gly Cys Leu Val Lys Asp Tyr Phe Pro Glu Pro
    210                 215                 220

Val Thr Val Ser Trp Asn Ser Gly Ala Leu Thr Ser Gly Val His Thr
```

-continued

```
225                 230                 235                 240

Phe Pro Ala Val Leu Gln Ser Ser Gly Leu Tyr Ser Leu Ser Ser Val
                245                 250                 255

Val Thr Val Pro Ser Ser Ser Leu Gly Thr Gln Thr Tyr Ile Cys Asn
            260                 265                 270

Val Asn His Lys Pro Ser Asn Thr Lys Val Asp Lys Lys Val Glu Pro
        275                 280                 285

Lys Ser Cys
    290


<210> SEQ ID NO 122
<211> LENGTH: 2469
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: anti-TnC(18D4) Fc hole dimeric ligand (71-248)
      chain

<400> SEQUENCE: 122

caggtgcaat tggtgcagtc tggggctgag gtgaagaagc ctgggtcctc ggtgaaggtc     60

tcctgcaagg cctccggagg cacattcagc agctacgcta taagctgggt gcgacaggcc    120

cctggacaag ggctcgagtg gatgggaggg atcatcccta tctttggtac agcaaactac    180

gcacagaagt tccagggcag ggtcaccatt actgcagaca aatccacgag cacagcctac    240

atggagctga gcagcctgag atctgaggac accgccgtgt attactgtgc gaaaggtaac    300

ttctacggtg gtctggacta ctggggccaa gggaccaccg tgaccgtctc ctcagctagc    360

accaagggcc cctccgtgtt ccccctggcc cccagcagca agagcaccag cggcggcaca    420

gccgctctgg gctgcctggt caaggactac ttccccgagc ccgtgaccgt gtcctggaac    480

agcggagccc tgacctccgg cgtgcacacc ttccccgccg tgctgcagag ttctggcctg    540

tatagcctga gcagcgtggt caccgtgcct tctagcagcc tgggcaccca gacctacatc    600

tgcaacgtga accacaagcc cagcaacacc aaggtggaca agaaggtgga gcccaagagc    660

tgcgacaaaa ctcacacatg cccaccgtgc ccagcacctg aagctgcagg gggaccgtca    720

gtcttcctct tccccccaaa acccaaggac accctcatga tctcccggac ccctgaggtc    780

acatgcgtgg tggtggacgt gagccacgaa gaccctgagg tcaagttcaa ctggtacgtg    840

gacggcgtgg aggtgcataa tgccaagaca aagccgcggg aggagcagta caacagcacg    900

taccgtgtgg tcagcgtcct caccgtcctg caccaggact ggctgaatgg caaggagtac    960

aagtgcaagg tctccaacaa agccctcggc gcccccatcg agaaaaccat ctccaaagcc   1020

aaagggcagc cccgagaacc acaggtgtgc accctgcccc catcccggga tgagctgacc   1080

aagaaccagg tcagcctctc gtgcgcagtc aaaggcttct atcccagcga catcgccgtg   1140

gagtgggaga gcaatgggca gccggagaac aactacaaga ccacgcctcc cgtgctggac   1200

tccgacggct ccttcttcct cgtgagcaag ctcaccgtgg acaagagcag gtggcagcag   1260

gggaacgtct tctcatgctc cgtgatgcat gaggctctgc acaaccacta cacgcagaag   1320

agcctctccc tgtctccggg tggaggcggc ggaagcggag gaggaggatc cagagagggc   1380

cctgagctga gccctgatga tcctgccgga ctgctggacc tgcggcaggg aatgtttgcc   1440

cagctggtgg cccagaacgt gctgctgatc gatggccccc tgtcctggta cagcgatcct   1500

ggactggctg gcgtgtcact gacaggcggc ctgagctaca aagaggacac caaagaactg   1560
```

-continued gtggtggcca aggccggcgt gtactacgtg ttctttcagc tggaactgcg gagagtggtg 1620
gccggcgaag gatctggctc tgtgtctctg gccctgcatc tgcagcctct gagatctgct 1680
gctggcgccg ctgctctggc actgacagtg gatctgcctc ctgccagcag cgaggcccgg 1740
aatagcgcat ttgggtttca aggcaggctg ctgcacctgt ctgccggcca gaggctggga 1800
gtgcatctgc acacagaggc cagggctaga cacgcctggc agctgacaca gggcgctaca 1860
gtgctgggcc tgttcagagt gacccccgag attccagcag gcctgggagg cggcggatct 1920
ggcggcggag gatctagaga aggacccgag ctgtcccccg acgatcccgc tgggctgctg 1980
gatctgagac agggcatgtt cgctcagctg gtggctcaga atgtgctgct gattgacgga 2040
cctctgagct ggtactccga cccagggctg gcaggggtgt ccctgactgg gggactgtcc 2100
tacaaagaag atacaaaaga actggtggtg gctaaagctg ggtgtacta tgtgtttttt 2160 cagctggaac tgaggcgggt ggtggctggg gagggctcag gatctgtgtc cctggctctg 2220
catctgcagc cactgcgctc tgcagcaggg gctgcagcac tggccctgac tgtggacctg 2280
cccccagctt cttccgaggc cagaaacagc gccttcgggt tccaaggacg cctgctgcat 2340
ctgagcgccg gacagcgcct gggagtgcat ctgcatactg aagccagagc ccggcatgct 2400
tggcagctga ctcagggggc aactgtgctg ggactgtttc gcgtgacacc tgagatccca 2460
gccgggctc 2469

<210> SEQ ID NO 123
<211> LENGTH: 1905
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: anti-TnC(18D4) Fc knob monomeric (71-248)
ligand

<400> SEQUENCE: 123
caggtgcaat tggtgcagtc tggggctgag gtgaagaagc ctgggtcctc ggtgaaggtc 60
tcctgcaagg cctccggagg cacattcagc agctacgcta taagctgggt gcgacaggcc 120
cctggacaag ggctcgagtg gatgggaggg atcatcccta tctttggtac agcaaactac 180
gcacagaagt tccagggcag ggtcaccatt actgcagaca aatccacgag cacagcctac 240
atggagctga gcagcctgag atctgaggac accgccgtgt attactgtgc gaaaggtaac 300
ttctacggtg gtctggacta ctggggccaa gggaccaccg tgaccgtctc ctcagctagc 360
accaagggcc catcggtctt ccccctggca ccctcctcca agagcacctc tgggggcaca 420
gcggccctgg gctgcctggt caaggactac ttccccgaac cggtgacggt gtcgtggaac 480
tcaggcgccc tgaccagcgg cgtgcacacc ttcccggctg tcctacagtc ctcaggactc 540
tactccctca gcagcgtggt gaccgtgccc tccagcagct tgggcaccca gacctacatc 600
tgcaacgtga atcacaagcc cagcaacacc aaggtggaca agaaagttga gcccaaatct 660
tgtgacaaaa ctcacacatg cccaccgtgc ccagcacctg aagctgcagg gggaccgtca 720
gtcttcctct tccccccaaa acccaaggac accctcatga tctcccggac ccctgaggtc 780
acatgcgtgg tggtggacgt gagccacgaa gaccctgagg tcaagttcaa ctggtacgtg 840
gacggcgtgg aggtgcataa tgccaagaca aagccgcggg aggagcagta caacagcacg 900
taccgtgtgg tcagcgtcct caccgtcctg caccaggact ggctgaatgg caaggagtac 960

```
aagtgcaagg tctccaacaa agccctcggc gcccccatcg agaaaaccat ctccaaagcc   1020

aaagggcagc cccgagaacc acaggtgtac accctgcccc cctgcagaga tgagctgacc   1080

aagaaccagg tgtccctgtg gtgtctggtc aagggcttct accccagcga tatcgccgtg   1140

gagtgggaga gcaacggcca gcctgagaac aactacaaga ccaccccccc tgtgctggac   1200

agcgacggca gcttcttcct gtactccaaa ctgaccgtgg acaagagccg gtggcagcag   1260

ggcaacgtgt tcagctgcag cgtgatgcac gaggccctgc acaaccacta cacccagaag   1320

tccctgagcc tgagccccgg cggaggcggc ggaagcggag gaggaggatc cagagagggc   1380

cctgagctga gccctgatga tcctgccgga ctgctggacc tgcggcaggg aatgtttgcc   1440

cagctggtgg cccagaacgt gctgctgatc gatggccccc tgtcctggta cagcgatcct   1500

ggactggctg gcgtgtcact gacaggcggc ctgagctaca aagaggacac caaagaactg   1560

gtggtggcca aggccggcgt gtactacgtg ttctttcagc tggaactgcg gagagtggtg   1620

gccggcgaag gatctggctc tgtgtctctg gccctgcatc tgcagcctct gagatctgct   1680

gctggcgccg ctgctctggc actgacagtg gatctgcctc ctgccagcag cgaggcccgg   1740

aatagcgcat ttgggtttca aggcaggctg ctgcacctgt ctgccggcca gaggctggga   1800

gtgcatctgc acacagaggc cagggctaga cacgcctggc agctgacaca gggcgctaca   1860

gtgctgggcc tgttcagagt gacccccgag attcctgccg ggctc                   1905


<210> SEQ ID NO 124
<211> LENGTH: 823
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: anti-TnC(18D4) Fc hole dimeric ligand (71-248)
      chain

<400> SEQUENCE: 124

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Gly Asn Phe Tyr Gly Gly Leu Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

-continued

```
Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Gly Ala Pro Ile Glu Lys Thr
                325                 330                 335

Ile Ser Lys Ala Lys Gly Gln Pro Arg Glu Pro Gln Val Cys Thr Leu
            340                 345                 350

Pro Pro Ser Arg Asp Glu Leu Thr Lys Asn Gln Val Ser Leu Ser Cys
        355                 360                 365

Ala Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Gly
        435                 440                 445

Gly Gly Gly Ser Gly Gly Gly Gly Ser Arg Glu Gly Pro Glu Leu Ser
    450                 455                 460

Pro Asp Asp Pro Ala Gly Leu Leu Asp Leu Arg Gln Gly Met Phe Ala
465                 470                 475                 480

Gln Leu Val Ala Gln Asn Val Leu Leu Ile Asp Gly Pro Leu Ser Trp
                485                 490                 495

Tyr Ser Asp Pro Gly Leu Ala Gly Val Ser Leu Thr Gly Gly Leu Ser
            500                 505                 510

Tyr Lys Glu Asp Thr Lys Glu Leu Val Val Ala Lys Ala Gly Val Tyr
        515                 520                 525

Tyr Val Phe Phe Gln Leu Glu Leu Arg Arg Val Val Ala Gly Glu Gly
    530                 535                 540

Ser Gly Ser Val Ser Leu Ala Leu His Leu Gln Pro Leu Arg Ser Ala
545                 550                 555                 560

Ala Gly Ala Ala Ala Leu Ala Leu Thr Val Asp Leu Pro Pro Ala Ser
                565                 570                 575

Ser Glu Ala Arg Asn Ser Ala Phe Gly Phe Gln Gly Arg Leu Leu His
            580                 585                 590

Leu Ser Ala Gly Gln Arg Leu Gly Val His Leu His Thr Glu Ala Arg
```

```
        595                 600                 605

Ala Arg His Ala Trp Gln Leu Thr Gln Gly Ala Thr Val Leu Gly Leu
    610                 615                 620

Phe Arg Val Thr Pro Glu Ile Pro Ala Gly Leu Gly Gly Gly Gly Ser
625                 630                 635                 640

Gly Gly Gly Gly Ser Arg Glu Gly Pro Glu Leu Ser Pro Asp Asp Pro
                645                 650                 655

Ala Gly Leu Leu Asp Leu Arg Gln Gly Met Phe Ala Gln Leu Val Ala
            660                 665                 670

Gln Asn Val Leu Leu Ile Asp Gly Pro Leu Ser Trp Tyr Ser Asp Pro
        675                 680                 685

Gly Leu Ala Gly Val Ser Leu Thr Gly Gly Leu Ser Tyr Lys Glu Asp
    690                 695                 700

Thr Lys Glu Leu Val Val Ala Lys Ala Gly Val Tyr Tyr Val Phe Phe
705                 710                 715                 720

Gln Leu Glu Leu Arg Arg Val Val Ala Gly Glu Gly Ser Gly Ser Val
                725                 730                 735

Ser Leu Ala Leu His Leu Gln Pro Leu Arg Ser Ala Ala Gly Ala Ala
            740                 745                 750

Ala Leu Ala Leu Thr Val Asp Leu Pro Pro Ala Ser Ser Glu Ala Arg
        755                 760                 765

Asn Ser Ala Phe Gly Phe Gln Gly Arg Leu Leu His Leu Ser Ala Gly
    770                 775                 780

Gln Arg Leu Gly Val His Leu His Thr Glu Ala Arg Ala Arg His Ala
785                 790                 795                 800

Trp Gln Leu Thr Gln Gly Ala Thr Val Leu Gly Leu Phe Arg Val Thr
                805                 810                 815

Pro Glu Ile Pro Ala Gly Leu
            820


<210> SEQ ID NO 125
<211> LENGTH: 635
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: anti- TnC(18D4) Fc knob monomeric (71-248)
      ligand

<400> SEQUENCE: 125

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Gly Asn Phe Tyr Gly Gly Leu Asp Tyr Trp Gly Gln Gly Thr
            100                 105                 110
```

-continued

```
Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Gly Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Cys Arg Asp Glu Leu Thr Lys Asn Gln Val Ser Leu Trp Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Gly
        435                 440                 445

Gly Gly Gly Ser Gly Gly Gly Gly Ser Arg Glu Gly Pro Glu Leu Ser
    450                 455                 460

Pro Asp Asp Pro Ala Gly Leu Leu Asp Leu Arg Gln Gly Met Phe Ala
465                 470                 475                 480

Gln Leu Val Ala Gln Asn Val Leu Leu Ile Asp Gly Pro Leu Ser Trp
                485                 490                 495

Tyr Ser Asp Pro Gly Leu Ala Gly Val Ser Leu Thr Gly Gly Leu Ser
            500                 505                 510

Tyr Lys Glu Asp Thr Lys Glu Leu Val Val Ala Lys Ala Gly Val Tyr
        515                 520                 525

Tyr Val Phe Phe Gln Leu Glu Leu Arg Arg Val Val Ala Gly Glu Gly
```

```
    530                 535                 540

Ser Gly Ser Val Ser Leu Ala Leu His Leu Gln Pro Leu Arg Ser Ala
545                 550                 555                 560

Ala Gly Ala Ala Ala Leu Ala Leu Thr Val Asp Leu Pro Pro Ala Ser
                565                 570                 575

Ser Glu Ala Arg Asn Ser Ala Phe Gly Phe Gln Gly Arg Leu Leu His
            580                 585                 590

Leu Ser Ala Gly Gln Arg Leu Gly Val His Leu His Thr Glu Ala Arg
        595                 600                 605

Ala Arg His Ala Trp Gln Leu Thr Gln Gly Ala Thr Val Leu Gly Leu
    610                 615                 620

Phe Arg Val Thr Pro Glu Ile Pro Ala Gly Leu
625                 630                 635


<210> SEQ ID NO 126
<211> LENGTH: 1806
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Fc hole dimeric ligand (71-248) chain

<400> SEQUENCE: 126

gacaaaactc acacatgccc accgtgccca gcacctgaag ctgcaggggg accgtcagtc     60

ttcctcttcc ccccaaaacc caaggacacc ctcatgatct cccggacccc tgaggtcaca    120

tgcgtggtgg tggacgtgag ccacgaagac cctgaggtca agttcaactg gtacgtggac    180

ggcgtggagg tgcataatgc caagacaaag ccgcgggagg agcagtacaa cagcacgtac    240

cgtgtggtca gcgtcctcac cgtcctgcac caggactggc tgaatggcaa ggagtacaag    300

tgcaaggtct ccaacaaagc cctcggcgcc cccatcgaga aaaccatctc caaagccaaa    360

gggcagcccc gagaaccaca ggtgtgcacc ctgcccccat cccgggatga gctgaccaag    420

aaccaggtca gcctctcgtg cgcagtcaaa ggcttctatc ccagcgacat cgccgtggag    480

tgggagagca atgggcagcc ggagaacaac tacaagacca cgcctcccgt gctggactcc    540

gacggctcct tcttcctcgt gagcaagctc accgtggaca agagcaggtg gcagcagggg    600

aacgtcttct catgctccgt gatgcatgag gctctgcaca accactacac gcagaagagc    660

ctctccctgt ctccgggtgg aggcggcgga agcggaggag gaggatccag agagggccct    720

gagctgagcc ctgatgatcc tgccggactg ctggacctgc ggcagggaat gtttgcccag    780

ctggtggccc agaacgtgct gctgatcgat ggcccccctgt cctggtacag cgatcctgga    840

ctggctggcg tgtcactgac aggcggcctg agctacaaag aggacaccaa agaactggtg    900

gtggccaagg ccggcgtgta ctacgtgttc tttcagctgg aactgcggag agtggtggcc    960

ggcgaaggat ctggctctgt gtctctggcc ctgcatctgc agcctctgag atctgctgct   1020

ggcgccgctg ctctggcact gacagtggat ctgcctcctg ccagcagcga ggcccggaat   1080

agcgcatttg ggtttcaagg caggctgctg cacctgtctg ccggccagag gctgggagtg   1140

catctgcaca cagaggccag ggctagacac gcctggcagc tgacacaggg cgctacagtg   1200

ctgggcctgt tcagagtgac ccccgagatt ccagcaggcc tgggaggcgg cggatctggc   1260

ggcggaggat ctagagaagg acccgagctg tcccccgacg atcccgctgg gctgctggat   1320

ctgagacagg gcatgttcgc tcagctggtg gctcagaatg tgctgctgat tgacggacct   1380
```

-continued ctgagctggt actccgaccc agggctggca ggggtgtccc tgactggggg actgtcctac 1440
aaagaagata caaaagaact ggtggtggct aaagctgggg tgtactatgt gttttttcag 1500
ctggaactga ggcgggtggt ggctggggag ggctcaggat ctgtgtccct ggctctgcat 1560
ctgcagccac tgcgctctgc agcaggggct gcagcactgg ccctgactgt ggacctgccc 1620
ccagcttctt ccgaggccag aaacagcgcc ttcgggttcc aaggacgcct gctgcatctg 1680
agcgccggac agcgcctggg agtgcatctg catactgaag ccagagcccg gcatgcttgg 1740
cagctgactc agggggcaac tgtgctggga ctgtttcgcg tgacacctga gatcccagcc 1800
gggctc 1806

<210> SEQ ID NO 127
<211> LENGTH: 602
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Fc hole dimeric ligand (71-248) chain

<400> SEQUENCE: 127

Asp Lys Thr His Thr Cys Pro Pro Cys Pro Ala Pro Glu Ala Ala Gly
1 5 10 15

Gly Pro Ser Val Phe Leu Phe Pro Pro Lys Pro Lys Asp Thr Leu Met
20 25 30

Ile Ser Arg Thr Pro Glu Val Thr Cys Val Val Val Asp Val Ser His
35 40 45

Glu Asp Pro Glu Val Lys Phe Asn Trp Tyr Val Asp Gly Val Glu Val
50 55 60

His Asn Ala Lys Thr Lys Pro Arg Glu Glu Gln Tyr Asn Ser Thr Tyr
65 70 75 80

Arg Val Val Ser Val Leu Thr Val Leu His Gln Asp Trp Leu Asn Gly
85 90 95

Lys Glu Tyr Lys Cys Lys Val Ser Asn Lys Ala Leu Gly Ala Pro Ile
100 105 110

Glu Lys Thr Ile Ser Lys Ala Lys Gly Gln Pro Arg Glu Pro Gln Val
115 120 125

Cys Thr Leu Pro Pro Ser Arg Asp Glu Leu Thr Lys Asn Gln Val Ser
130 135 140

Leu Ser Cys Ala Val Lys Gly Phe Tyr Pro Ser Asp Ile Ala Val Glu
145 150 155 160

Trp Glu Ser Asn Gly Gln Pro Glu Asn Asn Tyr Lys Thr Thr Pro Pro
165 170 175

Val Leu Asp Ser Asp Gly Ser Phe Phe Leu Val Ser Lys Leu Thr Val
180 185 190

Asp Lys Ser Arg Trp Gln Gln Gly Asn Val Phe Ser Cys Ser Val Met
195 200 205

His Glu Ala Leu His Asn His Tyr Thr Gln Lys Ser Leu Ser Leu Ser
210 215 220

Pro Gly Gly Gly Gly Gly Ser Gly Gly Gly Gly Ser Arg Glu Gly Pro
225 230 235 240

Glu Leu Ser Pro Asp Asp Pro Ala Gly Leu Leu Asp Leu Arg Gln Gly
245 250 255

Met Phe Ala Gln Leu Val Ala Gln Asn Val Leu Leu Ile Asp Gly Pro
260 265 270

Leu Ser Trp Tyr Ser Asp Pro Gly Leu Ala Gly Val Ser Leu Thr Gly
        275                 280                 285

Gly Leu Ser Tyr Lys Glu Asp Thr Lys Glu Leu Val Val Ala Lys Ala
    290                 295                 300

Gly Val Tyr Tyr Val Phe Phe Gln Leu Glu Leu Arg Arg Val Val Ala
305                 310                 315                 320

Gly Glu Gly Ser Gly Ser Val Ser Leu Ala Leu His Leu Gln Pro Leu
                325                 330                 335

Arg Ser Ala Ala Gly Ala Ala Ala Leu Ala Leu Thr Val Asp Leu Pro
            340                 345                 350

Pro Ala Ser Ser Glu Ala Arg Asn Ser Ala Phe Gly Phe Gln Gly Arg
        355                 360                 365

Leu Leu His Leu Ser Ala Gly Gln Arg Leu Gly Val His Leu His Thr
    370                 375                 380

Glu Ala Arg Ala Arg His Ala Trp Gln Leu Thr Gln Gly Ala Thr Val
385                 390                 395                 400

Leu Gly Leu Phe Arg Val Thr Pro Glu Ile Pro Ala Gly Leu Gly Gly
                405                 410                 415

Gly Gly Ser Gly Gly Gly Gly Ser Arg Glu Gly Pro Glu Leu Ser Pro
            420                 425                 430

Asp Asp Pro Ala Gly Leu Leu Asp Leu Arg Gln Gly Met Phe Ala Gln
        435                 440                 445

Leu Val Ala Gln Asn Val Leu Leu Ile Asp Gly Pro Leu Ser Trp Tyr
    450                 455                 460

Ser Asp Pro Gly Leu Ala Gly Val Ser Leu Thr Gly Gly Leu Ser Tyr
465                 470                 475                 480

Lys Glu Asp Thr Lys Glu Leu Val Val Ala Lys Ala Gly Val Tyr Tyr
                485                 490                 495

Val Phe Phe Gln Leu Glu Leu Arg Arg Val Val Ala Gly Glu Gly Ser
            500                 505                 510

Gly Ser Val Ser Leu Ala Leu His Leu Gln Pro Leu Arg Ser Ala Ala
        515                 520                 525

Gly Ala Ala Ala Leu Ala Leu Thr Val Asp Leu Pro Pro Ala Ser Ser
    530                 535                 540

Glu Ala Arg Asn Ser Ala Phe Gly Phe Gln Gly Arg Leu Leu His Leu
545                 550                 555                 560

Ser Ala Gly Gln Arg Leu Gly Val His Leu His Thr Glu Ala Arg Ala
                565                 570                 575

Arg His Ala Trp Gln Leu Thr Gln Gly Ala Thr Val Leu Gly Leu Phe
            580                 585                 590

Arg Val Thr Pro Glu Ile Pro Ala Gly Leu
        595                 600

<210> SEQ ID NO 128
<211> LENGTH: 1212
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Fc hole monomeric ligand (71-248) chain

<400> SEQUENCE: 128
gacaaaactc acacatgccc accgtgccca gcacctgaag ctgcaggggg accgtcagtc     60

-continued

```
ttcctcttcc ccccaaaacc caaggacacc ctcatgatct cccggacccc tgaggtcaca    120

tgcgtggtgg tggacgtgag ccacgaagac cctgaggtca agttcaactg gtacgtggac    180

ggcgtggagg tgcataatgc caagacaaag ccgcgggagg agcagtacaa cagcacgtac    240

cgtgtggtca gcgtcctcac cgtcctgcac caggactggc tgaatggcaa ggagtacaag    300

tgcaaggtct ccaacaaagc cctcggcgcc cccatcgaga aaaccatctc caaagccaaa    360

gggcagcccc gagaaccaca ggtgtgcacc ctgcccccat cccgggatga gctgaccaag    420

aaccaggtca gcctctcgtg cgcagtcaaa ggcttctatc ccagcgacat cgccgtggag    480

tgggagagca atgggcagcc ggagaacaac tacaagacca cgcctcccgt gctggactcc    540

gacggctcct tcttcctcgt gagcaagctc accgtggaca agagcaggtg gcagcagggg    600

aacgtcttct catgctccgt gatgcatgag gctctgcaca accactacac gcagaagagc    660

ctctccctgt ctccgggtag agagggccct gagctgagcc ctgatgatcc tgccggactg    720

ctggacctgc ggcagggaat gtttgcccag ctggtggccc agaacgtgct gctgatcgat    780

ggccccctgt cctggtacag cgatcctgga ctggctggcg tgtcactgac aggcggcctg    840

agctacaaag aggacaccaa agaactggtg gtggccaagg ccggcgtgta ctacgtgttc    900

tttcagctgg aactgcggag agtggtggcc ggcgaaggat ctggctctgt gtctctggcc    960

ctgcatctgc agcctctgag atctgctgct ggcgccgctg ctctggcact gacagtggat   1020

ctgcctcctg ccagcagcga ggcccggaat agcgcatttg ggtttcaagg caggctgctg   1080

cacctgtctg ccggccagag gctgggagtg catctgcaca cagaggccag ggctagacac   1140

gcctggcagc tgacacaggg cgctacagtg ctgggcctgt tcagagtgac ccccgagatt   1200

cctgccgggc tc                                                       1212
```

```
<210> SEQ ID NO 129
<211> LENGTH: 2439
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: anti-TnC(18D4) Fc knob dimeric ligand (71-248)
      chain

<400> SEQUENCE: 129

caggtgcaat tggtgcagtc tggggctgag gtgaagaagc ctgggtcctc ggtgaaggtc     60

tcctgcaagg cctccggagg cacattcagc agctacgcta taagctgggt gcgacaggcc    120

cctggacaag ggctcgagtg gatgggaggg atcatcccta tctttggtac agcaaactac    180

gcacagaagt tccagggcag ggtcaccatt actgcagaca aatccacgag cacagcctac    240

atggagctga gcagcctgag atctgaggac accgccgtgt attactgtgc gaaaggtaac    300

ttctacggtg gtctggacta ctggggccaa gggaccaccg tgaccgtctc ctcagctagc    360

accaagggcc catcggtctt ccccctggca ccctcctcca agagcacctc tgggggcaca    420

gcggccctgg gctgcctggt caaggactac ttccccgaac cggtgacggt gtcgtggaac    480

tcaggcgccc tgaccagcgg cgtgcacacc ttcccggctg tcctacagtc ctcaggactc    540

tactccctca gcagcgtggt gaccgtgccc tccagcagct tgggcaccca gacctacatc    600

tgcaacgtga atcacaagcc cagcaacacc aaggtggaca agaaagttga gcccaaatct    660

tgtgacaaaa ctcacacatg cccaccgtgc ccagcacctg aagctgcagg gggaccgtca    720

gtcttcctct tcccccaaa acccaaggac accctcatga tctcccggac ccctgaggtc     780
```

```
acatgcgtgg tggtggacgt gagccacgaa gaccctgagg tcaagttcaa ctggtacgtg    840

gacggcgtgg aggtgcataa tgccaagaca aagccgcggg aggagcagta caacagcacg    900

taccgtgtgg tcagcgtcct caccgtcctg caccaggact ggctgaatgg caaggagtac    960

aagtgcaagg tctccaacaa agccctcggc gcccccatcg agaaaaccat ctccaaagcc   1020

aaagggcagc cccgagaacc acaggtgtac accctgcccc cctgcagaga tgagctgacc   1080

aagaaccagg tgtccctgtg gtgtctggtc aagggcttct accccagcga tatcgccgtg   1140

gagtgggaga gcaacggcca gcctgagaac aactacaaga ccaccccccc tgtgctggac   1200

agcgacggca gcttcttcct gtactccaaa ctgaccgtgg acaagagccg gtggcagcag   1260

ggcaacgtgt tcagctgcag cgtgatgcac gaggccctgc acaaccacta cacccagaag   1320

tccctgagcc tgagccccgg cagagagggc cctgagctga gccctgatga tcctgccgga   1380

ctgctggacc tgcggcaggg aatgtttgcc cagctggtgg cccagaacgt gctgctgatc   1440

gatggccccc tgtcctggta cagcgatcct ggactggctg gcgtgtcact gacaggcggc   1500

ctgagctaca aagaggacac caaagaactg gtggtggcca aggccggcgt gtactacgtg   1560

ttctttcagc tggaactgcg gagagtggtg gccggcgaag gatctggctc tgtgtctctg   1620

gccctgcatc tgcagcctct gagatctgct gctggcgccg ctgctctggc actgacagtg   1680

gatctgcctc ctgccagcag cgaggcccgg aatagcgcat ttgggtttca aggcaggctg   1740

ctgcacctgt ctgccggcca gaggctggga gtgcatctgc acacagaggc cagggctaga   1800

cacgcctggc agctgacaca gggcgctaca gtgctgggcc tgttcagagt gacccccgag   1860

attccagcag gcctgggagg cggcggatct ggcggcggag gatctagaga aggacccgag   1920

ctgtcccccg acgatcccgc tgggctgctg gatctgagac agggcatgtt cgctcagctg   1980

gtggctcaga atgtgctgct gattgacgga cctctgagct ggtactccga cccagggctg   2040

gcaggggtgt ccctgactgg gggactgtcc tacaaagaag atacaaaaga actggtggtg   2100

gctaaagctg gggtgtacta tgtgtttttt cagctggaac tgaggcgggt ggtggctggg   2160

gagggctcag gatctgtgtc cctggctctg catctgcagc cactgcgctc tgcagcaggg   2220

gctgcagcac tggccctgac tgtggacctg cccccagctt cttccgaggc cagaaacagc   2280

gccttcgggt tccaaggacg cctgctgcat ctgagcgccg gacagcgcct gggagtgcat   2340

ctgcatactg aagccagagc ccggcatgct tggcagctga ctcagggggc aactgtgctg   2400

ggactgtttc gcgtgacacc tgagatccca gccgggctc                          2439
```

<210> SEQ ID NO 130
<211> LENGTH: 404
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Fc hole monomeric ligand (71-248) chain

<400> SEQUENCE: 130

```
Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45
```

-continued

```
Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Arg Glu Gly Pro Glu Leu Ser Pro Asp Asp Pro Ala Gly Leu
225                 230                 235                 240

Leu Asp Leu Arg Gln Gly Met Phe Ala Gln Leu Val Ala Gln Asn Val
                245                 250                 255

Leu Leu Ile Asp Gly Pro Leu Ser Trp Tyr Ser Asp Pro Gly Leu Ala
            260                 265                 270

Gly Val Ser Leu Thr Gly Gly Leu Ser Tyr Lys Glu Asp Thr Lys Glu
        275                 280                 285

Leu Val Val Ala Lys Ala Gly Val Tyr Tyr Val Phe Phe Gln Leu Glu
    290                 295                 300

Leu Arg Arg Val Val Ala Gly Glu Gly Ser Gly Ser Val Ser Leu Ala
305                 310                 315                 320

Leu His Leu Gln Pro Leu Arg Ser Ala Ala Gly Ala Ala Ala Leu Ala
                325                 330                 335

Leu Thr Val Asp Leu Pro Pro Ala Ser Ser Glu Ala Arg Asn Ser Ala
            340                 345                 350

Phe Gly Phe Gln Gly Arg Leu Leu His Leu Ser Ala Gly Gln Arg Leu
        355                 360                 365

Gly Val His Leu His Thr Glu Ala Arg Ala Arg His Ala Trp Gln Leu
    370                 375                 380

Thr Gln Gly Ala Thr Val Leu Gly Leu Phe Arg Val Thr Pro Glu Ile
385                 390                 395                 400

Pro Ala Gly Leu
```

<210> SEQ ID NO 131
<211> LENGTH: 813
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: anti-TnC(18D4) Fc knob dimeric ligand (71-248)
      chain

<400> SEQUENCE: 131

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Gly Asn Phe Tyr Gly Gly Leu Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Gly Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Cys Arg Asp Glu Leu Thr Lys Asn Gln Val Ser Leu Trp Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser

```
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Arg
        435                 440                 445

Glu Gly Pro Glu Leu Ser Pro Asp Asp Pro Ala Gly Leu Leu Asp Leu
    450                 455                 460

Arg Gln Gly Met Phe Ala Gln Leu Val Ala Gln Asn Val Leu Leu Ile
465                 470                 475                 480

Asp Gly Pro Leu Ser Trp Tyr Ser Asp Pro Gly Leu Ala Gly Val Ser
                485                 490                 495

Leu Thr Gly Gly Leu Ser Tyr Lys Glu Asp Thr Lys Glu Leu Val Val
            500                 505                 510

Ala Lys Ala Gly Val Tyr Tyr Val Phe Phe Gln Leu Glu Leu Arg Arg
        515                 520                 525

Val Val Ala Gly Glu Gly Ser Gly Ser Val Ser Leu Ala Leu His Leu
    530                 535                 540

Gln Pro Leu Arg Ser Ala Ala Gly Ala Ala Ala Leu Ala Leu Thr Val
545                 550                 555                 560

Asp Leu Pro Pro Ala Ser Ser Glu Ala Arg Asn Ser Ala Phe Gly Phe
                565                 570                 575

Gln Gly Arg Leu Leu His Leu Ser Ala Gly Gln Arg Leu Gly Val His
            580                 585                 590

Leu His Thr Glu Ala Arg Ala Arg His Ala Trp Gln Leu Thr Gln Gly
        595                 600                 605

Ala Thr Val Leu Gly Leu Phe Arg Val Thr Pro Glu Ile Pro Ala Gly
    610                 615                 620

Leu Gly Gly Gly Gly Ser Gly Gly Gly Gly Ser Arg Glu Gly Pro Glu
625                 630                 635                 640

Leu Ser Pro Asp Asp Pro Ala Gly Leu Leu Asp Leu Arg Gln Gly Met
                645                 650                 655

Phe Ala Gln Leu Val Ala Gln Asn Val Leu Leu Ile Asp Gly Pro Leu
            660                 665                 670

Ser Trp Tyr Ser Asp Pro Gly Leu Ala Gly Val Ser Leu Thr Gly Gly
        675                 680                 685

Leu Ser Tyr Lys Glu Asp Thr Lys Glu Leu Val Val Ala Lys Ala Gly
    690                 695                 700

Val Tyr Tyr Val Phe Phe Gln Leu Glu Leu Arg Arg Val Val Ala Gly
705                 710                 715                 720

Glu Gly Ser Gly Ser Val Ser Leu Ala Leu His Leu Gln Pro Leu Arg
                725                 730                 735

Ser Ala Ala Gly Ala Ala Ala Leu Ala Leu Thr Val Asp Leu Pro Pro
            740                 745                 750

Ala Ser Ser Glu Ala Arg Asn Ser Ala Phe Gly Phe Gln Gly Arg Leu
        755                 760                 765

Leu His Leu Ser Ala Gly Gln Arg Leu Gly Val His Leu His Thr Glu
    770                 775                 780

Ala Arg Ala Arg His Ala Trp Gln Leu Thr Gln Gly Ala Thr Val Leu
785                 790                 795                 800

Gly Leu Phe Arg Val Thr Pro Glu Ile Pro Ala Gly Leu
                805                 810
```

<210> SEQ ID NO 132

<211> LENGTH: 1242
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Fc knob monomeric ligand (71-248) chain

<400> SEQUENCE: 132
gacaaaactc acacatgccc accgtgccca gcacctgaag ctgcaggggg accgtcagtc 60
ttcctcttcc ccccaaaacc caaggacacc ctcatgatct cccggacccc tgaggtcaca 120
tgcgtggtgg tggacgtgag ccacgaagac cctgaggtca agttcaactg gtacgtggac 180
ggcgtggagg tgcataatgc caagacaaag ccgcgggagg agcagtacaa cagcacgtac 240
cgtgtggtca gcgtcctcac cgtcctgcac caggactggc tgaatggcaa ggagtacaag 300
tgcaaggtct ccaacaaagc cctcggcgcc cccatcgaga aaaccatctc caaagccaaa 360
gggcagcccc gagaaccaca ggtgtacacc ctgccccct gcagagatga gctgaccaag 420
aaccaggtgt ccctgtggtg tctggtcaag ggcttctacc ccagcgatat cgccgtggag 480
tgggagagca acggccagcc tgagaacaac tacaagacca cccccctgt gctggacagc 540 gacggcagct tcttcctgta ctccaaactg accgtggaca agagccggtg gcagcagggc 600
aacgtgttca gctgcagcgt gatgcacgag gccctgcaca accactacac ccagaagtcc 660
ctgagcctga gccccggcgg aggcggcgga agcggaggag gaggatccag agagggccct 720
gagctgagcc ctgatgatcc tgccggactg ctggacctgc ggcagggaat gtttgcccag 780
ctggtggccc agaacgtgct gctgatcgat ggcccctgt cctggtacag cgatcctgga 840
ctggctggcg tgtcactgac aggcggcctg agctacaaag aggacaccaa agaactggtg 900
gtggccaagg ccggcgtgta ctacgtgttc tttcagctgg aactgcggag agtggtggcc 960
ggcgaaggat ctggctctgt gtctctggcc ctgcatctgc agcctctgag atctgctgct 1020
ggcgccgctg ctctggcact gacagtggat ctgcctcctg ccagcagcga ggcccggaat 1080
agcgcatttg ggtttcaagg caggctgctg cacctgtctg ccggccagag gctgggagtg 1140
catctgcaca cagaggccag ggctagacac gcctggcagc tgacacaggg cgctacagtg 1200
ctgggcctgt tcagagtgac ccccgagatt cctgccgggc tc 1242

<210> SEQ ID NO 133
<211> LENGTH: 414
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Fc knob monomeric ligand (71-248) chain

<400> SEQUENCE: 133

Asp Lys Thr His Thr Cys Pro Pro Cys Pro Ala Pro Glu Ala Ala Gly
1 5 10 15

Gly Pro Ser Val Phe Leu Phe Pro Pro Lys Pro Lys Asp Thr Leu Met
20 25 30

Ile Ser Arg Thr Pro Glu Val Thr Cys Val Val Val Asp Val Ser His
35 40 45

Glu Asp Pro Glu Val Lys Phe Asn Trp Tyr Val Asp Gly Val Glu Val
50 55 60

His Asn Ala Lys Thr Lys Pro Arg Glu Glu Gln Tyr Asn Ser Thr Tyr 65 70 75 80

Arg Val Val Ser Val Leu Thr Val Leu His Gln Asp Trp Leu Asn Gly
85 90 95

Lys Glu Tyr Lys Cys Lys Val Ser Asn Lys Ala Leu Gly Ala Pro Ile
100 105 110

Glu Lys Thr Ile Ser Lys Ala Lys Gly Gln Pro Arg Glu Pro Gln Val
115 120 125

Tyr Thr Leu Pro Pro Cys Arg Asp Glu Leu Thr Lys Asn Gln Val Ser
130 135 140

Leu Trp Cys Leu Val Lys Gly Phe Tyr Pro Ser Asp Ile Ala Val Glu
145 150 155 160

Trp Glu Ser Asn Gly Gln Pro Glu Asn Asn Tyr Lys Thr Thr Pro Pro
165 170 175

Val Leu Asp Ser Asp Gly Ser Phe Phe Leu Tyr Ser Lys Leu Thr Val
180 185 190

Asp Lys Ser Arg Trp Gln Gln Gly Asn Val Phe Ser Cys Ser Val Met
195 200 205

His Glu Ala Leu His Asn His Tyr Thr Gln Lys Ser Leu Ser Leu Ser
210 215 220

Pro Gly Gly Gly Gly Gly Ser Gly Gly Gly Gly Ser Arg Glu Gly Pro
225 230 235 240

Glu Leu Ser Pro Asp Asp Pro Ala Gly Leu Leu Asp Leu Arg Gln Gly
245 250 255

Met Phe Ala Gln Leu Val Ala Gln Asn Val Leu Leu Ile Asp Gly Pro
260 265 270

Leu Ser Trp Tyr Ser Asp Pro Gly Leu Ala Gly Val Ser Leu Thr Gly
275 280 285

Gly Leu Ser Tyr Lys Glu Asp Thr Lys Glu Leu Val Val Ala Lys Ala
290 295 300

Gly Val Tyr Tyr Val Phe Phe Gln Leu Glu Leu Arg Arg Val Val Ala
305 310 315 320

Gly Glu Gly Ser Gly Ser Val Ser Leu Ala Leu His Leu Gln Pro Leu
325 330 335

Arg Ser Ala Ala Gly Ala Ala Ala Leu Ala Leu Thr Val Asp Leu Pro
340 345 350

Pro Ala Ser Ser Glu Ala Arg Asn Ser Ala Phe Gly Phe Gln Gly Arg
355 360 365

Leu Leu His Leu Ser Ala Gly Gln Arg Leu Gly Val His Leu His Thr
370 375 380

Glu Ala Arg Ala Arg His Ala Trp Gln Leu Thr Gln Gly Ala Thr Val
385 390 395 400

Leu Gly Leu Phe Arg Val Thr Pro Glu Ile Pro Ala Gly Leu
405 410

<210> SEQ ID NO 134
<211> LENGTH: 1905
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: anti-TnC(18D4) Fc hole monomeric ligand (71-248) chain

<400> SEQUENCE: 134

```
caggtgcaat tggtgcagtc tggggctgag gtgaagaagc ctgggtcctc ggtgaaggtc     60
tcctgcaagg cctccggagg cacattcagc agctacgcta taagctgggt gcgacaggcc    120
cctggacaag ggctcgagtg gatgggaggg atcatcccta tctttggtac agcaaactac    180
gcacagaagt tccagggcag ggtcaccatt actgcagaca aatccacgag cacagcctac    240
atggagctga gcagcctgag atctgaggac accgccgtgt attactgtgc gaaaggtaac    300
ttctacggtg gtctggacta ctggggccaa gggaccaccg tgaccgtctc ctcagctagc    360
accaagggcc cctccgtgtt cccccctggcc cccagcagca agagcaccag cggcggcaca    420
gccgctctgg gctgcctggt caaggactac ttccccgagc ccgtgaccgt gtcctggaac    480
agcggagccc tgacctccgg cgtgcacacc ttccccgccg tgctgcagag ttctggcctg    540
tatagcctga gcagcgtggt caccgtgcct tctagcagcc tgggcaccca gacctacatc    600
tgcaacgtga accacaagcc cagcaacacc aaggtggaca agaaggtgga gcccaagagc    660
tgcgacaaaa ctcacacatg cccaccgtgc ccagcacctg aagctgcagg gggaccgtca    720
gtcttcctct tccccccaaa acccaaggac accctcatga tctcccggac ccctgaggtc    780
acatgcgtgg tggtggacgt gagccacgaa gaccctgagg tcaagttcaa ctggtacgtg    840
gacggcgtgg aggtgcataa tgccaagaca aagccgcggg aggagcagta caacagcacg    900
taccgtgtgg tcagcgtcct caccgtcctg caccaggact ggctgaatgg caaggagtac    960
aagtgcaagg tctccaacaa agccctcggc gcccccatcg agaaaaccat ctccaaagcc   1020
aaagggcagc cccgagaacc acaggtgtgc accctgcccc catcccggga tgagctgacc   1080
aagaaccagg tcagcctctc gtgcgcagtc aaaggcttct atcccagcga catcgccgtg   1140
gagtgggaga gcaatgggca gccggagaac aactacaaga ccacgcctcc cgtgctggac   1200
tccgacggct ccttcttcct cgtgagcaag ctcaccgtgg acaagagcag gtggcagcag   1260
gggaacgtct tctcatgctc cgtgatgcat gaggctctgc acaaccacta cacgcagaag   1320
agcctctccc tgtctccggg tggaggcggc ggaagcggag gaggaggatc cagagagggc   1380
cctgagctga gccctgatga tcctgccgga ctgctggacc tgcggcaggg aatgtttgcc   1440
cagctggtgg cccagaacgt gctgctgatc gatggccccc tgtcctggta cagcgatcct   1500
ggactggctg gcgtgtcact gacaggcggc ctgagctaca aagaggacac caaagaactg   1560
gtggtggcca aggccggcgt gtactacgtg ttctttcagc tggaactgcg gagagtggtg   1620
gccggcgaag gatctggctc tgtgtctctg gccctgcatc tgcagcctct gagatctgct   1680
gctggcgccg ctgctctggc actgacagtg gatctgcctc ctgccagcag cgaggcccgg   1740
aatagcgcat ttgggtttca aggcaggctg ctgcacctgt ctgccggcca gaggctggga   1800
gtgcatctgc acacagaggc cagggctaga cacgcctggc agctgacaca gggcgctaca   1860
gtgctgggcc tgttcagagt gacccccgag attcctgccg ggctc                   1905
```

<210> SEQ ID NO 135
<211> LENGTH: 1806
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Fc knob dimeric ligand (71-248) chain

<400> SEQUENCE: 135

```
gacaaaactc acacatgccc accgtgccca gcacctgaag ctgcaggggg accgtcagtc     60
```

-continued ttcctcttcc ccccaaaacc caaggacacc ctcatgatct cccggacccc tgaggtcaca 120
tgcgtggtgg tggacgtgag ccacgaagac cctgaggtca agttcaactg gtacgtggac 180
ggcgtggagg tgcataatgc caagacaaag ccgcgggagg agcagtacaa cagcacgtac 240
cgtgtggtca gcgtcctcac cgtcctgcac caggactggc tgaatggcaa ggagtacaag 300
tgcaaggtct ccaacaaagc cctcggcgcc cccatcgaga aaaccatctc caaagccaaa 360
gggcagcccc gagaaccaca ggtgtacacc ctgcccccct gcagagatga gctgaccaag 420
aaccaggtgt ccctgtggtg tctggtcaag ggcttctacc ccagcgatat cgccgtggag 480
tgggagagca acggccagcc tgagaacaac tacaagacca cccccccctgt gctggacagc 540 gacggcagct tcttcctgta ctccaaactg accgtggaca agagccggtg gcagcagggc 600
aacgtgttca gctgcagcgt gatgcacgag gccctgcaca accactacac ccagaagtcc 660
ctgagcctga gccccggcgg aggcggcgga agcggaggag gaggatccag agagggccct 720
gagctgagcc ctgatgatcc tgccggactg ctggacctgc ggcagggaat gtttgcccag 780
ctggtggccc agaacgtgct gctgatcgat ggcccctgt cctggtacag cgatcctgga 840
ctggctggcg tgtcactgac aggcggcctg agctacaaag aggacaccaa agaactggtg 900
gtggccaagg ccggcgtgta ctacgtgttc tttcagctgg aactgcggag agtggtggcc 960
ggcgaaggat ctggctctgt gtctctggcc ctgcatctgc agcctctgag atctgctgct 1020
ggcgccgctg ctctggcact gacagtggat ctgcctcctg ccagcagcga ggcccggaat 1080
agcgcatttg ggtttcaagg caggctgctg cacctgtctg ccggccagag gctgggagtg 1140
catctgcaca cagaggccag ggctagacac gcctggcagc tgacacaggg cgctacagtg 1200
ctgggcctgt tcagagtgac cccgagatt ccagcaggcc tgggaggcgg cggatctggc 1260
ggcggaggat ctagagaagg acccgagctg tccccgacg atcccgctgg gctgctggat 1320
ctgagacagg gcatgttcgc tcagctggtg gctcagaatg tgctgctgat tgacggacct 1380
ctgagctggt actccgaccc agggctggca ggggtgtccc tgactggggg actgtcctac 1440
aaagaagata caaaagaact ggtggtggct aaagctgggg tgtactatgt gttttttcag 1500
ctggaactga ggcgggtggt ggctggggag ggctcaggat ctgtgtccct ggctctgcat 1560
ctgcagccac tgcgctctgc agcaggggct gcagcactgg ccctgactgt ggacctgccc 1620
ccagcttctt ccgaggccag aaacagcgcc ttcgggttcc aaggacgcct gctgcatctg 1680
agcgccggac agcgcctggg agtgcatctg catactgaag ccagagcccg gcatgcttgg 1740
cagctgactc agggggcaac tgtgctggga ctgtttcgcg tgacacctga gatcccagcc 1800
gggctc 1806

<210> SEQ ID NO 136
<211> LENGTH: 635
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: anti-TnC(18D4) Fc hole monomeric ligand
(71-248) chain

<400> SEQUENCE: 136

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

-continued

```
Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Gly Asn Phe Tyr Gly Gly Leu Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Gly Ala Pro Ile Glu Lys Thr
                325                 330                 335

Ile Ser Lys Ala Lys Gly Gln Pro Arg Glu Pro Gln Val Cys Thr Leu
            340                 345                 350

Pro Pro Ser Arg Asp Glu Leu Thr Lys Asn Gln Val Ser Leu Ser Cys
        355                 360                 365

Ala Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Gly
        435                 440                 445
```

-continued

```
Gly Gly Gly Ser Gly Gly Gly Gly Ser Arg Glu Gly Pro Glu Leu Ser
    450                 455                 460

Pro Asp Asp Pro Ala Gly Leu Leu Asp Leu Arg Gln Gly Met Phe Ala
465                 470                 475                 480

Gln Leu Val Ala Gln Asn Val Leu Leu Ile Asp Gly Pro Leu Ser Trp
                485                 490                 495

Tyr Ser Asp Pro Gly Leu Ala Gly Val Ser Leu Thr Gly Gly Leu Ser
            500                 505                 510

Tyr Lys Glu Asp Thr Lys Glu Leu Val Val Ala Lys Ala Gly Val Tyr
        515                 520                 525

Tyr Val Phe Phe Gln Leu Glu Leu Arg Arg Val Val Ala Gly Glu Gly
    530                 535                 540

Ser Gly Ser Val Ser Leu Ala Leu His Leu Gln Pro Leu Arg Ser Ala
545                 550                 555                 560

Ala Gly Ala Ala Ala Leu Ala Leu Thr Val Asp Leu Pro Pro Ala Ser
                565                 570                 575

Ser Glu Ala Arg Asn Ser Ala Phe Gly Phe Gln Gly Arg Leu Leu His
            580                 585                 590

Leu Ser Ala Gly Gln Arg Leu Gly Val His Leu His Thr Glu Ala Arg
        595                 600                 605

Ala Arg His Ala Trp Gln Leu Thr Gln Gly Ala Thr Val Leu Gly Leu
    610                 615                 620

Phe Arg Val Thr Pro Glu Ile Pro Ala Gly Leu
625                 630                 635


<210> SEQ ID NO 137
<211> LENGTH: 602
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Fc knob dimeric ligand (71-248) chain

<400> SEQUENCE: 137

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160
```

```
Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Gly Ser Gly Gly Gly Gly Ser Arg Glu Gly Pro
225                 230                 235                 240

Glu Leu Ser Pro Asp Asp Pro Ala Gly Leu Leu Asp Leu Arg Gln Gly
                245                 250                 255

Met Phe Ala Gln Leu Val Ala Gln Asn Val Leu Leu Ile Asp Gly Pro
            260                 265                 270

Leu Ser Trp Tyr Ser Asp Pro Gly Leu Ala Gly Val Ser Leu Thr Gly
        275                 280                 285

Gly Leu Ser Tyr Lys Glu Asp Thr Lys Glu Leu Val Val Ala Lys Ala
    290                 295                 300

Gly Val Tyr Tyr Val Phe Phe Gln Leu Glu Leu Arg Arg Val Val Ala
305                 310                 315                 320

Gly Glu Gly Ser Gly Ser Val Ser Leu Ala Leu His Leu Gln Pro Leu
                325                 330                 335

Arg Ser Ala Ala Gly Ala Ala Ala Leu Ala Leu Thr Val Asp Leu Pro
            340                 345                 350

Pro Ala Ser Ser Glu Ala Arg Asn Ser Ala Phe Gly Phe Gln Gly Arg
        355                 360                 365

Leu Leu His Leu Ser Ala Gly Gln Arg Leu Gly Val His Leu His Thr
    370                 375                 380

Glu Ala Arg Ala Arg His Ala Trp Gln Leu Thr Gln Gly Ala Thr Val
385                 390                 395                 400

Leu Gly Leu Phe Arg Val Thr Pro Glu Ile Pro Ala Gly Leu Gly Gly
                405                 410                 415

Gly Gly Ser Gly Gly Gly Gly Ser Arg Glu Gly Pro Glu Leu Ser Pro
            420                 425                 430

Asp Asp Pro Ala Gly Leu Leu Asp Leu Arg Gln Gly Met Phe Ala Gln
        435                 440                 445

Leu Val Ala Gln Asn Val Leu Leu Ile Asp Gly Pro Leu Ser Trp Tyr
    450                 455                 460

Ser Asp Pro Gly Leu Ala Gly Val Ser Leu Thr Gly Gly Leu Ser Tyr
465                 470                 475                 480

Lys Glu Asp Thr Lys Glu Leu Val Val Ala Lys Ala Gly Val Tyr Tyr
                485                 490                 495

Val Phe Phe Gln Leu Glu Leu Arg Arg Val Val Ala Gly Glu Gly Ser
            500                 505                 510

Gly Ser Val Ser Leu Ala Leu His Leu Gln Pro Leu Arg Ser Ala Ala
        515                 520                 525

Gly Ala Ala Ala Leu Ala Leu Thr Val Asp Leu Pro Pro Ala Ser Ser
    530                 535                 540

Glu Ala Arg Asn Ser Ala Phe Gly Phe Gln Gly Arg Leu Leu His Leu
545                 550                 555                 560

Ser Ala Gly Gln Arg Leu Gly Val His Leu His Thr Glu Ala Arg Ala
                565                 570                 575

Arg His Ala Trp Gln Leu Thr Gln Gly Ala Thr Val Leu Gly Leu Phe
```

580 585 590

Arg Val Thr Pro Glu Ile Pro Ala Gly Leu
595 600

<210> SEQ ID NO 138
<211> LENGTH: 1335
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: DP47 Fc hole chain

<400> SEQUENCE: 138
gaggtgcaat tgttggagtc tgggggaggc ttggtacagc ctgggggtc cctgagactc 60 tcctgtgcag cctccggatt cacctttagc agttatgcca tgagctgggt ccgccaggct 120
ccagggaagg ggctggagtg ggtctcagct attagtggta gtggtggtag cacatactac 180
gcagactccg tgaagggccg gttcaccatc tccagagaca attccaagaa cacgctgtat 240
ctgcagatga acagcctgag agccgaggac acggccgtat attactgtgc gaaaggcagc 300
ggatttgact actggggcca aggaaccctg gtcaccgtct cgagtgctag caccaagggc 360
ccatcggtct tccccctggc accctcctcc aagagcacct ctgggggcac agcggccctg 420
ggctgcctgg tcaaggacta cttccccgaa ccggtgacgg tgtcgtggaa ctcaggcgcc 480
ctgaccagcg gcgtgcacac cttcccggct gtcctacagt cctcaggact ctactccctc 540
agcagcgtgg tgaccgtgcc ctccagcagc ttgggcaccc agacctacat ctgcaacgtg 600
aatcacaagc ccagcaacac caaggtggac aagaaagttg agcccaaatc ttgtgacaaa 660
actcacacat gcccaccgtg cccagcacct gaagctgcag gggaccgtc agtcttcctc 720 ttccccccaa aacccaagga caccctcatg atctcccgga cccctgaggt cacatgcgtg 780
gtggtggacg tgagccacga agaccctgag gtcaagttca actggtacgt ggacggcgtg 840
gaggtgcata atgccaagac aaagccgcgg gaggagcagt acaacagcac gtaccgtgtg 900
gtcagcgtcc tcaccgtcct gcaccaggac tggctgaatg gcaaggagta caagtgcaag 960
gtctccaaca aagccctcgg cgcccccatc gagaaaacca tctccaaagc caaagggcag 1020
ccccgagaac cacaggtgtg caccctgccc ccatcccggg atgagctgac caagaaccag 1080
gtcagcctct cgtgcgcagt caaaggcttc tatcccagcg acatcgccgt ggagtgggag 1140
agcaatgggc agccggagaa caactacaag accacgcctc ccgtgctgga ctccgacggc 1200
tccttcttcc tcgtgagcaa gctcaccgtg gacaagagca ggtggcagca ggggaacgtc 1260
ttctcatgct ccgtgatgca tgaggctctg cacaaccact acacgcagaa gagcctctcc 1320
ctgtctccgg gtaaa 1335

<210> SEQ ID NO 139
<211> LENGTH: 645
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: DP47 light chain

<400> SEQUENCE: 139
gaaatcgtgt taacgcagtc tccaggcacc ctgtctttgt ctccagggga aagagccacc 60

```
ctctcttgca gggccagtca gagtgttagc agcagctact tagcctggta ccagcagaaa    120

cctggccagg ctcccaggct cctcatctat ggagcatcca gcagggccac tggcatccca    180

gacaggttca gtggcagtgg atccgggaca gacttcactc tcaccatcag cagactggag    240

cctgaagatt ttgcagtgta ttactgtcag cagtatggta gctcaccgct gacgttcggc    300

caggggacca aagtggaaat caaacgtacg gtggctgcac catctgtctt catcttcccg    360

ccatctgatg agcagttgaa atctggaact gcctctgttg tgtgcctgct gaataacttc    420

tatcccagag aggccaaagt acagtggaag gtggataacg ccctccaatc gggtaactcc    480

caggagagtg tcacagagca ggacagcaag gacagcacct acagcctcag cagcaccctg    540

acgctgagca aagcagacta cgagaaacac aaagtctacg cctgcgaagt cacccatcag    600

ggcctgagct cgcccgtcac aaagagcttc aacaggggag agtgt                    645
```

<210> SEQ ID NO 140
<211> LENGTH: 445
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: DP47 Fc hole chain

<400> SEQUENCE: 140

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Gly Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
```

-continued

```
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Gly Ala Pro Ile Glu Lys Thr Ile Ser Lys
                325                 330                 335

Ala Lys Gly Gln Pro Arg Glu Pro Gln Val Cys Thr Leu Pro Pro Ser
            340                 345                 350

Arg Asp Glu Leu Thr Lys Asn Gln Val Ser Leu Ser Cys Ala Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Val Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445


<210> SEQ ID NO 141
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: DP47 light chain

<400> SEQUENCE: 141

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
```

-continued

```
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 142
<211> LENGTH: 2496
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DP47 Fc hole chain fused to dimeric hu 4-1BBL
      (71-254)

<400> SEQUENCE: 142

gaggtgcaat tgttggagtc tggggggaggc ttggtacagc ctggggggtc cctgagactc     60

tcctgtgcag cctccggatt cacctttagc agttatgcca tgagctgggt ccgccaggct    120

ccagggaagg ggctggagtg ggtctcagct attagtggta gtggtggtag cacatactac    180

gcagactccg tgaagggccg gttcaccatc tccagagaca attccaagaa cacgctgtat    240

ctgcagatga acagcctgag agccgaggac acggccgtat attactgtgc gaaaggcagc    300

ggatttgact actggggcca aggaaccctg gtcaccgtct cgagtgctag caccaagggc    360

ccctccgtgt tccccctggc ccccagcagc aagagcacca gcggcggcac agccgctctg    420

ggctgcctgg tcaaggacta cttccccgag cccgtgaccg tgtcctggaa cagcggagcc    480

ctgacctccg gcgtgcacac cttccccgcc gtgctgcaga gttctggcct gtatagcctg    540

agcagcgtgg tcaccgtgcc ttctagcagc ctgggcaccc agacctacat ctgcaacgtg    600

aaccacaagc ccagcaacac caaggtggac aagaaggtgg agcccaagag ctgcgacaaa    660

actcacacat gcccaccgtg cccagcacct gaagctgcag gggaccgtc agtcttcctc    720

ttccccccaa aacccaagga caccctcatg atctcccgga cccctgaggt cacatgcgtg    780

gtggtggacg tgagccacga agaccctgag gtcaagttca actggtacgt ggacggcgtg    840

gaggtgcata atgccaagac aaagccgcgg gaggagcagt acaacagcac gtaccgtgtg    900

gtcagcgtcc tcaccgtcct gcaccaggac tggctgaatg gcaaggagta caagtgcaag    960

gtctccaaca aagccctcgg cgcccccatc gagaaaacca tctccaaagc caaagggcag   1020

ccccgagaac cacaggtgtg caccctgccc ccatcccggg atgagctgac caagaaccag   1080

gtcagcctct cgtgcgcagt caaaggcttc tatcccagcg acatcgccgt ggagtgggag   1140

agcaatgggc agccggagaa caactacaag accacgcctc ccgtgctgga ctccgacggc   1200

tccttcttcc tcgtgagcaa gctcaccgtg gacaagagca ggtggcagca ggggaacgtc   1260

ttctcatgct ccgtgatgca tgaggctctg cacaaccact acacgcagaa gagcctctcc   1320

ctgtctccgg gtggaggcgg cggaagcgga ggaggaggat ccagagaggg ccctgagctg   1380

agccccgatg atcctgctgg actgctggac ctgcggcagg gcatgtttgc tcagctggtg   1440

gcccagaacg tgctgctgat cgatggcccc ctgtcctggt acagcgatcc tggactggct   1500

ggcgtgtcac tgacaggcgg cctgagctac aaagaggaca ccaaagaact ggtggtggcc   1560
```

aaggccggcg tgtactacgt gttctttcag ctggaactgc ggagagtggt ggccggcgaa 1620
ggatctggct ctgtgtctct ggccctgcat ctgcagcctc tgagaagcgc tgctggcgct 1680
gcagctctgg cactgacagt ggatctgcct cctgccagct ccgaggcccg gaatagcgca 1740
tttgggtttc aaggcaggct gctgcacctg tctgccggcc agaggctggg agtgcatctg 1800
cacacagagg ccagggctag acacgcctgg cagctgacac agggcgctac agtgctgggc 1860
ctgttcagag tgacccccga gattccagcc ggcctgcctt ctccaagaag cgaaggcgga 1920
ggcggatctg gcggcggagg atctagagag ggacccgaac tgtcccctga cgatccagcc 1980
gggctgctgg atctgagaca gggaatgttc gcccagctgg tggctcagaa tgtgctgctg 2040
attgacggac ctctgagctg gtactccgac ccagggctgg caggggtgtc cctgactggg 2100
ggactgtcct acaaagaaga tacaaaagaa ctggtggtgg ctaaagctgg ggtgtactat 2160 gtgtttttc agctggaact gaggcgggtg gtggctgggg agggctcagg atctgtgtcc 2220
ctggctctgc atctgcagcc actgcgctct gctgctggcg cagctgcact ggctctgact 2280
gtggacctgc caccagcctc tagcgaggcc agaaacagcg ccttcgggtt ccaaggacgc 2340
ctgctgcatc tgagcgccgg acagcgcctg ggagtgcatc tgcatactga agccagagcc 2400
cggcatgctt ggcagctgac tcagggggca actgtgctgg gactgtttcg cgtgacacct 2460
gagatccctg ccggactgcc aagccctaga tcagaa 2496

<210> SEQ ID NO 143
<211> LENGTH: 1914
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: DP47 Fc knob chain fused to monomeric hu 4-1BBL
(71-254)

<400> SEQUENCE: 143
gaggtgcaat tgttggagtc tgggggaggc ttggtacagc ctgggggtc cctgagactc 60 tcctgtgcag cctccggatt cacctttagc agttatgcca tgagctgggt ccgccaggct 120
ccagggaagg ggctggagtg ggtctcagct attagtggta gtggtggtag cacatactac 180
gcagactccg tgaagggccg gttcaccatc tccagagaca attccaagaa cacgctgtat 240
ctgcagatga acagcctgag agccgaggac acggccgtat attactgtgc gaaaggcagc 300
ggatttgact actggggcca aggaaccctg gtcaccgtct cgagtgctag caccaagggc 360
ccatcggtct tccccctggc accctcctcc aagagcacct ctgggggcac agcggccctg 420
ggctgcctgg tcaaggacta cttccccgaa ccggtgacgg tgtcgtggaa ctcaggcgcc 480
ctgaccagcg gcgtgcacac cttcccggct gtcctacagt cctcaggact ctactccctc 540
agcagcgtgg tgaccgtgcc ctccagcagc ttgggcaccc agacctacat ctgcaacgtg 600
aatcacaagc ccagcaacac caaggtggac aagaaagttg agcccaaatc ttgtgacaaa 660
actcacacat gcccaccgtg cccagcacct gaagctgcag gggaccgtc agtcttcctc 720 ttcccccaa aacccaagga caccctcatg atctcccgga cccctgaggt cacatgcgtg 780
gtggtggacg tgagccacga agaccctgag gtcaagttca actggtacgt ggacggcgtg 840
gaggtgcata atgccaagac aaagccgcgg gaggagcagt acaacagcac gtaccgtgtg 900
gtcagcgtcc tcaccgtcct gcaccaggac tggctgaatg gcaaggagta caagtgcaag 960

```
gtctccaaca aagccctcgg cgcccccatc gagaaaacca tctccaaagc caaagggcag   1020

ccccgagaac cacaggtgta caccctgccc ccctgcagag atgagctgac caagaaccag   1080

gtgtccctgt ggtgtctggt caagggcttc taccccagcg atatcgccgt ggagtgggag   1140

agcaacggcc agcctgagaa caactacaag accacccccc ctgtgctgga cagcgacggc   1200

agcttcttcc tgtactccaa actgaccgtg gacaagagcc ggtggcagca gggcaacgtg   1260

ttcagctgca gcgtgatgca cgaggccctg cacaaccact acacccagaa gtccctgagc   1320

ctgagccccg gcggaggcgg cggaagcgga ggaggaggat ccagagaggg ccctgagctg   1380

agccccgatg atcctgctgg actgctggac ctgcggcagg gcatgtttgc tcagctggtg   1440

gcccagaacg tgctgctgat cgatggcccc ctgtcctggt acagcgatcc tggactggct   1500

ggcgtgtcac tgacaggcgg cctgagctac aaagaggaca ccaaagaact ggtggtggcc   1560

aaggccggcg tgtactacgt gttctttcag ctggaactgc ggagagtggt ggccggcgaa   1620

ggatctggct ctgtgtctct ggccctgcat ctgcagcctc tgagaagcgc tgctggcgct   1680

gcagctctgg cactgacagt ggatctgcct cctgccagct ccgaggcccg gaatagcgca   1740

tttgggtttc aaggcaggct gctgcacctg tctgccggcc agaggctggg agtgcatctg   1800

cacacagagg ccagggctag acacgcctgg cagctgacac agggcgctac agtgctgggc   1860

ctgttcagag tgacccccga gattccagcc ggcctgcctt ctccaagaag cgaa         1914
```

<210> SEQ ID NO 144
<211> LENGTH: 832
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: DP47 Fc hole chain fused to dimeric hu 4-1BBL (71-254)

<400> SEQUENCE: 144

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Gly Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175
```

```
Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Gly Ala Pro Ile Glu Lys Thr Ile Ser Lys
                325                 330                 335

Ala Lys Gly Gln Pro Arg Glu Pro Gln Val Cys Thr Leu Pro Pro Ser
            340                 345                 350

Arg Asp Glu Leu Thr Lys Asn Gln Val Ser Leu Ser Cys Ala Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Val Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Gly Gly Gly Gly
        435                 440                 445

Ser Gly Gly Gly Gly Ser Arg Glu Gly Pro Glu Leu Ser Pro Asp Asp
    450                 455                 460

Pro Ala Gly Leu Leu Asp Leu Arg Gln Gly Met Phe Ala Gln Leu Val
465                 470                 475                 480

Ala Gln Asn Val Leu Leu Ile Asp Gly Pro Leu Ser Trp Tyr Ser Asp
                485                 490                 495

Pro Gly Leu Ala Gly Val Ser Leu Thr Gly Gly Leu Ser Tyr Lys Glu
            500                 505                 510

Asp Thr Lys Glu Leu Val Val Ala Lys Ala Gly Val Tyr Tyr Val Phe
        515                 520                 525

Phe Gln Leu Glu Leu Arg Arg Val Val Ala Gly Glu Gly Ser Gly Ser
    530                 535                 540

Val Ser Leu Ala Leu His Leu Gln Pro Leu Arg Ser Ala Ala Gly Ala
545                 550                 555                 560

Ala Ala Leu Ala Leu Thr Val Asp Leu Pro Pro Ala Ser Ser Glu Ala
                565                 570                 575

Arg Asn Ser Ala Phe Gly Phe Gln Gly Arg Leu Leu His Leu Ser Ala
            580                 585                 590

Gly Gln Arg Leu Gly Val His Leu His Thr Glu Ala Arg Ala Arg His
```

```
        595                 600                 605

Ala Trp Gln Leu Thr Gln Gly Ala Thr Val Leu Gly Leu Phe Arg Val
    610                 615                 620

Thr Pro Glu Ile Pro Ala Gly Leu Pro Ser Pro Arg Ser Glu Gly Gly
625                 630                 635                 640

Gly Gly Ser Gly Gly Gly Gly Ser Arg Glu Gly Pro Glu Leu Ser Pro
                645                 650                 655

Asp Asp Pro Ala Gly Leu Leu Asp Leu Arg Gln Gly Met Phe Ala Gln
            660                 665                 670

Leu Val Ala Gln Asn Val Leu Leu Ile Asp Gly Pro Leu Ser Trp Tyr
        675                 680                 685

Ser Asp Pro Gly Leu Ala Gly Val Ser Leu Thr Gly Gly Leu Ser Tyr
    690                 695                 700

Lys Glu Asp Thr Lys Glu Leu Val Val Ala Lys Ala Gly Val Tyr Tyr
705                 710                 715                 720

Val Phe Phe Gln Leu Glu Leu Arg Arg Val Val Ala Gly Glu Gly Ser
                725                 730                 735

Gly Ser Val Ser Leu Ala Leu His Leu Gln Pro Leu Arg Ser Ala Ala
            740                 745                 750

Gly Ala Ala Ala Leu Ala Leu Thr Val Asp Leu Pro Pro Ala Ser Ser
        755                 760                 765

Glu Ala Arg Asn Ser Ala Phe Gly Phe Gln Gly Arg Leu Leu His Leu
    770                 775                 780

Ser Ala Gly Gln Arg Leu Gly Val His Leu His Thr Glu Ala Arg Ala
785                 790                 795                 800

Arg His Ala Trp Gln Leu Thr Gln Gly Ala Thr Val Leu Gly Leu Phe
                805                 810                 815

Arg Val Thr Pro Glu Ile Pro Ala Gly Leu Pro Ser Pro Arg Ser Glu
            820                 825                 830


<210> SEQ ID NO 145
<211> LENGTH: 640
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: DP47 Fc knob chain fused to monomeric hu 4-1BBL
      (71-254)

<400> SEQUENCE: 145

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110
```

Val Thr Val Ser Ser Ala Ser Thr Lys Gly Pro Ser Val Phe Pro Leu
115 120 125

Ala Pro Ser Ser Lys Ser Thr Ser Gly Gly Thr Ala Ala Leu Gly Cys
130 135 140

Leu Val Lys Asp Tyr Phe Pro Glu Pro Val Thr Val Ser Trp Asn Ser
145 150 155 160

Gly Ala Leu Thr Ser Gly Val His Thr Phe Pro Ala Val Leu Gln Ser
165 170 175

Ser Gly Leu Tyr Ser Leu Ser Ser Val Val Thr Val Pro Ser Ser Ser
180 185 190

Leu Gly Thr Gln Thr Tyr Ile Cys Asn Val Asn His Lys Pro Ser Asn
195 200 205

Thr Lys Val Asp Lys Lys Val Glu Pro Lys Ser Cys Asp Lys Thr His
210 215 220

Thr Cys Pro Pro Cys Pro Ala Pro Glu Ala Ala Gly Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser His Glu Asp Pro Glu
260 265 270

Val Lys Phe Asn Trp Tyr Val Asp Gly Val Glu Val His Asn Ala Lys
275 280 285

Thr Lys Pro Arg Glu Glu Gln Tyr Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Ala Leu Gly Ala Pro Ile Glu Lys Thr Ile
325 330 335

Ser Lys Ala Lys Gly Gln Pro Arg Glu Pro Gln Val Tyr Thr Leu Pro
340 345 350

Pro Cys Arg Asp Glu Leu Thr Lys Asn Gln Val Ser Leu Trp Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Lys Leu Thr Val Asp Lys Ser Arg
405 410 415

Trp Gln Gln Gly Asn Val Phe Ser Cys Ser Val Met His Glu Ala Leu
420 425 430

His Asn His Tyr Thr Gln Lys Ser Leu Ser Leu Ser Pro Gly Gly Gly
435 440 445

Gly Gly Ser Gly Gly Gly Gly Ser Arg Glu Gly Pro Glu Leu Ser Pro
450 455 460

Asp Asp Pro Ala Gly Leu Leu Asp Leu Arg Gln Gly Met Phe Ala Gln
465 470 475 480

Leu Val Ala Gln Asn Val Leu Leu Ile Asp Gly Pro Leu Ser Trp Tyr
485 490 495

Ser Asp Pro Gly Leu Ala Gly Val Ser Leu Thr Gly Gly Leu Ser Tyr
500 505 510

Lys Glu Asp Thr Lys Glu Leu Val Val Ala Lys Ala Gly Val Tyr Tyr
515 520 525

Val Phe Phe Gln Leu Glu Leu Arg Arg Val Val Ala Gly Glu Gly Ser

Gly Ser Val Ser Leu Ala Leu His Leu Gln Pro Leu Arg Ser Ala Ala
545                 550                 555                 560

Gly Ala Ala Ala Leu Ala Leu Thr Val Asp Leu Pro Pro Ala Ser Ser
                565                 570                 575

Glu Ala Arg Asn Ser Ala Phe Gly Phe Gln Gly Arg Leu Leu His Leu
            580                 585                 590

Ser Ala Gly Gln Arg Leu Gly Val His Leu His Thr Glu Ala Arg Ala
        595                 600                 605

Arg His Ala Trp Gln Leu Thr Gln Gly Ala Thr Val Leu Gly Leu Phe
    610                 615                 620

Arg Val Thr Pro Glu Ile Pro Ala Gly Leu Pro Ser Pro Arg Ser Glu
625                 630                 635                 640

<210> SEQ ID NO 146
<211> LENGTH: 1335
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: DP47 heavy chain (hu IgG1 PGLALA)

<400> SEQUENCE: 146
gaggtgcaat tgttggagtc tgggggaggc ttggtacagc ctggggggtc cctgagactc        60
tcctgtgcag cctccggatt cacctttagc agttatgcca tgagctgggt ccgccaggct       120
ccagggaagg ggctggagtg ggtctcagct attagtggta gtggtggtag cacatactac       180
gcagactccg tgaagggccg gttcaccatc tccagagaca attccaagaa cacgctgtat       240
ctgcagatga acagcctgag agccgaggac acggccgtat attactgtgc gaaaggcagc       300
ggatttgact actggggcca aggaaccctg gtcaccgtct cgagtgctag caccaagggc       360
ccatcggtct tccccctggc accctcctcc aagagcacct ctgggggcac agcggccctg       420
ggctgcctgg tcaaggacta cttccccgaa ccggtgacgg tgtcgtggaa ctcaggcgcc       480
ctgaccagcg gcgtgcacac cttcccggct gtcctacagt cctcaggact ctactccctc       540
agcagcgtgg tgaccgtgcc ctccagcagc ttgggcaccc agacctacat ctgcaacgtg       600
aatcacaagc ccagcaacac caaggtggac aagaaagttg agcccaaatc ttgtgacaaa       660
actcacacat gcccaccgtg cccagcacct gaagctgcag gggaccgtc agtcttcctc        720 ttccccccaa aacccaagga caccctcatg atctcccgga cccctgaggt cacatgcgtg       780
gtggtggacg tgagccacga agaccctgag gtcaagttca actggtacgt ggacggcgtg       840
gaggtgcata atgccaagac aaagccgcgg gaggagcagt acaacagcac gtaccgtgtg       900
gtcagcgtcc tcaccgtcct gcaccaggac tggctgaatg gcaaggagta caagtgcaag       960
gtctccaaca aagccctcgg cgcccccatc gagaaaacca tctccaaagc caaagggcag      1020
ccccgagaac cacaggtgta caccctgccc ccatcccggg atgagctgac caagaaccag      1080
gtcagcctga cctgcctggt caaaggcttc tatcccagcg acatcgccgt ggagtgggag      1140
agcaatgggc agccggagaa caactacaag accacgcctc ccgtgctgga ctccgacggc      1200
tccttcttcc tctacagcaa gctcaccgtg gacaagagca ggtggcagca ggggaacgtc      1260
ttctcatgct ccgtgatgca tgaggctctg cacaaccact acacgcagaa gagcctctcc      1320
ctgtctccgg gtaaa                                                       1335

<210> SEQ ID NO 147
<211> LENGTH: 445
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: DP47 heavy chain (hu IgG1 PGLALA)

<400> SEQUENCE: 147

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Gly Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Gly Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350
```

-continued

```
Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445


<210> SEQ ID NO 148
<211> LENGTH: 1344
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: anti-TnC(18D4) heavy chain (huIgG1 PGLALA)

<400> SEQUENCE: 148

caggtgcaat tggtgcagtc tggggctgag gtgaagaagc ctgggtcctc ggtgaaggtc     60

tcctgcaagg cctccggagg cacattcagc agctacgcta taagctgggt gcgacaggcc    120

cctggacaag ggctcgagtg gatgggaggg atcatcccta tctttggtac agcaaactac    180

gcacagaagt tccagggcag ggtcaccatt actgcagaca aatccacgag cacagcctac    240

atggagctga gcagcctgag atctgaggac accgccgtgt attactgtgc gaaaggtaac    300

ttctacggtg gtctggacta ctggggccaa gggaccaccg tgaccgtctc ctcagctagc    360

accaagggcc catcggtctt ccccctggca ccctcctcca agagcacctc tgggggcaca    420

gcggccctgg gctgcctggt caaggactac ttccccgaac cggtgacggt gtcgtggaac    480

tcaggcgccc tgaccagcgg cgtgcacacc ttcccggctg tcctacagtc ctcaggactc    540

tactccctca gcagcgtggt gaccgtgccc tccagcagct tgggcaccca gacctacatc    600

tgcaacgtga atcacaagcc cagcaacacc aaggtggaca agaaagttga gcccaaatct    660

tgtgacaaaa ctcacacatg cccaccgtgc ccagcacctg aagctgcagg gggaccgtca    720

gtcttcctct tccccccaaa acccaaggac accctcatga tctcccggac ccctgaggtc    780

acatgcgtgg tggtggacgt gagccacgaa gaccctgagg tcaagttcaa ctggtacgtg    840

gacggcgtgg aggtgcataa tgccaagaca aagccgcggg aggagcagta caacagcacg    900

taccgtgtgg tcagcgtcct caccgtcctg caccaggact ggctgaatgg caaggagtac    960

aagtgcaagg tctccaacaa agccctcggc gcccccatcg agaaaaccat ctccaaagcc   1020

aaagggcagc cccgagaacc acaggtgtac accctgcccc catcccggga tgagctgacc   1080

aagaaccagg tcagcctgac ctgcctggtc aaaggcttct atcccagcga catcgccgtg   1140

gagtgggaga gcaatgggca gccggagaac aactacaaga ccacgcctcc cgtgctggac   1200

tccgacggct ccttcttcct ctacagcaag ctcaccgtgg acaagagcag gtggcagcag   1260

gggaacgtct tctcatgctc cgtgatgcat gaggctctgc acaaccacta cacgcagaag   1320

agcctctccc tgtctccggg taaa                                          1344


<210> SEQ ID NO 149
```

```
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: anti-TnC(18D4) heavy chain (huIgG1 PGLALA)

<400> SEQUENCE: 149

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Gly Asn Phe Tyr Gly Gly Leu Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Gly Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365
```

```
Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 150
<211> LENGTH: 10
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: Peptide linker (G4S)2

<400> SEQUENCE: 150

```
Gly Gly Gly Gly Ser Gly Gly Gly Gly Ser
1               5                   10
```

<210> SEQ ID NO 151
<211> LENGTH: 10
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: Peptide linker (SG4)2

<400> SEQUENCE: 151

```
Ser Gly Gly Gly Gly Ser Gly Gly Gly Gly
1               5                   10
```

<210> SEQ ID NO 152
<211> LENGTH: 14
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: Peptide linker G4(SG4)2

<400> SEQUENCE: 152

```
Gly Gly Gly Gly Ser Gly Gly Gly Gly Ser Gly Gly Gly Gly
1               5                   10
```

<210> SEQ ID NO 153
<211> LENGTH: 10
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: Peptide linker

<400> SEQUENCE: 153

```
Gly Ser Pro Gly Ser Ser Ser Ser Gly Ser
1               5                   10
```

<210> SEQ ID NO 154
<211> LENGTH: 20
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Peptide linker (G4S)4

<400> SEQUENCE: 154

Gly Gly Gly Gly Ser Gly Gly Gly Gly Ser Gly Gly Gly Gly Ser Gly
1 5 10 15

Gly Gly Gly Ser
20

<210> SEQ ID NO 155
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Peptide linker

<400> SEQUENCE: 155

Gly Ser Gly Ser Gly Asn Gly Ser
1 5

<210> SEQ ID NO 156
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Peptide linker

<400> SEQUENCE: 156

Gly Gly Ser Gly Ser Gly Ser Gly
1 5

<210> SEQ ID NO 157
<211> LENGTH: 6
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Peptide linker

<400> SEQUENCE: 157

Gly Gly Ser Gly Ser Gly
1 5

<210> SEQ ID NO 158
<211> LENGTH: 4
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Peptide linker

<400> SEQUENCE: 158

Gly Gly Ser Gly
1

<210> SEQ ID NO 159
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Peptide linker

<400> SEQUENCE: 159

Gly Gly Ser Gly Asn Gly Ser Gly
1 5

<210> SEQ ID NO 160
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Peptide linker

<400> SEQUENCE: 160

Gly Gly Asn Gly Ser Gly Ser Gly
1 5

<210> SEQ ID NO 161
<211> LENGTH: 6
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Peptide linker

<400> SEQUENCE: 161

Gly Gly Asn Gly Ser Gly
1 5

<210> SEQ ID NO 162
<211> LENGTH: 5
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Peptide linker

<400> SEQUENCE: 162

Gly Gly Gly Gly Ser
1 5

<210> SEQ ID NO 163
<211> LENGTH: 19
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Leader Sequence 1

<400> SEQUENCE: 163

Met Asp Trp Thr Trp Arg Ile Leu Phe Leu Val Ala Ala Ala Thr Gly
1 5 10 15

Ala His Ser

<210> SEQ ID NO 164
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Leader Sequence 1 (DNA1)

<400> SEQUENCE: 164
atggactgga cctggagaat cctcttcttg gtggcagcag ccacaggagc ccactcc 57

<210> SEQ ID NO 165
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Leader Sequence 1 (DNA 2)

<400> SEQUENCE: 165
atggactgga cctggaggat cctcttcttg gtggcagcag ccacaggagc ccactcc 57

<210> SEQ ID NO 166
<211> LENGTH: 20
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: Leader Sequence 2

<400> SEQUENCE: 166

Met Asp Met Arg Val Pro Ala Gln Leu Leu Gly Leu Leu Leu Leu Trp
1 5 10 15

Phe Pro Gly Ala
20

<210> SEQ ID NO 167
<211> LENGTH: 66
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Leader Sequence 2 (DNA)

<400> SEQUENCE: 167
atggacatga gggtccccgc tcagctcctg ggcctcctgc tgctctggtt cccaggtgcc 60
aggtgt 66

<210> SEQ ID NO 168
<211> LENGTH: 19
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Leader Sequence 3

<400> SEQUENCE: 168

Met Gly Trp Ser Cys Ile Ile Leu Phe Leu Val Ala Thr Ala Thr Gly
1               5                   10                  15

Val His Ser

<210> SEQ ID NO 169
<211> LENGTH: 57
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Leader Sequence 3 (DNA 1)

<400> SEQUENCE: 169
atgggatgga gctgtatcat cctcttcttg gtagcaacag ctaccggtgt gcattcg        57

<210> SEQ ID NO 170
<211> LENGTH: 57
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Leader Sequence 3 (DNA 2)

<400> SEQUENCE: 170
atgggctggt cctgcatcat cctgtttctg gtggctaccg ccactggagt gcattcc        57

<210> SEQ ID NO 171
<211> LENGTH: 57
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Leader Sequence 3 (DNA 3)

<400> SEQUENCE: 171
atgggctggt cctgcatcat cctgtttctg gtcgccacag ccaccggcgt gcactct        57

<210> SEQ ID NO 172
<211> LENGTH: 184
<212> TYPE: PRT
<213> ORGANISM: Homo sapiens

<400> SEQUENCE: 172

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
    50                  55                  60

Val Ala Lys Ala Gly Val Tyr Tyr Val Phe Phe Gln Leu Glu Leu Arg

```
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
    130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Pro Ser Pro Arg Ser Glu
            180
```

```
<210> SEQ ID NO 173
<211> LENGTH: 170
<212> TYPE: PRT
<213> ORGANISM: Homo sapiens

<400> SEQUENCE: 173

Leu Asp Leu Arg Gln Gly Met Phe Ala Gln Leu Val Ala Gln Asn Val
1               5                   10                  15

Leu Leu Ile Asp Gly Pro Leu Ser Trp Tyr Ser Asp Pro Gly Leu Ala
            20                  25                  30

Gly Val Ser Leu Thr Gly Gly Leu Ser Tyr Lys Glu Asp Thr Lys Glu
        35                  40                  45

Leu Val Val Ala Lys Ala Gly Val Tyr Tyr Val Phe Phe Gln Leu Glu
    50                  55                  60

Leu Arg Arg Val Val Ala Gly Glu Gly Ser Gly Ser Val Ser Leu Ala
65                  70                  75                  80

Leu His Leu Gln Pro Leu Arg Ser Ala Ala Gly Ala Ala Ala Leu Ala
                85                  90                  95

Leu Thr Val Asp Leu Pro Pro Ala Ser Ser Glu Ala Arg Asn Ser Ala
            100                 105                 110

Phe Gly Phe Gln Gly Arg Leu Leu His Leu Ser Ala Gly Gln Arg Leu
        115                 120                 125

Gly Val His Leu His Thr Glu Ala Arg Ala Arg His Ala Trp Gln Leu
    130                 135                 140

Thr Gln Gly Ala Thr Val Leu Gly Leu Phe Arg Val Thr Pro Glu Ile
145                 150                 155                 160

Pro Ala Gly Leu Pro Ser Pro Arg Ser Glu
                165                 170
```

```
<210> SEQ ID NO 174
<211> LENGTH: 175
<212> TYPE: PRT
<213> ORGANISM: Homo sapiens

<400> SEQUENCE: 174

Asp Pro Ala Gly Leu Leu Asp Leu Arg Gln Gly Met Phe Ala Gln Leu
1               5                   10                  15

Val Ala Gln Asn Val Leu Leu Ile Asp Gly Pro Leu Ser Trp Tyr Ser
            20                  25                  30

Asp Pro Gly Leu Ala Gly Val Ser Leu Thr Gly Gly Leu Ser Tyr Lys
```

```
        35                  40                  45

Glu Asp Thr Lys Glu Leu Val Val Ala Lys Ala Gly Val Tyr Tyr Val
    50                  55                  60

Phe Phe Gln Leu Glu Leu Arg Arg Val Val Ala Gly Glu Gly Ser Gly
65                  70                  75                  80

Ser Val Ser Leu Ala Leu His Leu Gln Pro Leu Arg Ser Ala Ala Gly
                85                  90                  95

Ala Ala Ala Leu Ala Leu Thr Val Asp Leu Pro Pro Ala Ser Ser Glu
            100                 105                 110

Ala Arg Asn Ser Ala Phe Gly Phe Gln Gly Arg Leu Leu His Leu Ser
        115                 120                 125

Ala Gly Gln Arg Leu Gly Val His Leu His Thr Glu Ala Arg Ala Arg
    130                 135                 140

His Ala Trp Gln Leu Thr Gln Gly Ala Thr Val Leu Gly Leu Phe Arg
145                 150                 155                 160

Val Thr Pro Glu Ile Pro Ala Gly Leu Pro Ser Pro Arg Ser Glu
                165                 170                 175


<210> SEQ ID NO 175
<211> LENGTH: 203
<212> TYPE: PRT
<213> ORGANISM: Homo sapiens

<400> SEQUENCE: 175

Pro Trp Ala Val Ser Gly Ala Arg Ala Ser Pro Gly Ser Ala Ala Ser
1               5                   10                  15

Pro Arg Leu Arg Glu Gly Pro Glu Leu Ser Pro Asp Asp Pro Ala Gly
            20                  25                  30

Leu Leu Asp Leu Arg Gln Gly Met Phe Ala Gln Leu Val Ala Gln Asn
        35                  40                  45

Val Leu Leu Ile Asp Gly Pro Leu Ser Trp Tyr Ser Asp Pro Gly Leu
    50                  55                  60

Ala Gly Val Ser Leu Thr Gly Gly Leu Ser Tyr Lys Glu Asp Thr Lys
65                  70                  75                  80

Glu Leu Val Val Ala Lys Ala Gly Val Tyr Tyr Val Phe Phe Gln Leu
                85                  90                  95

Glu Leu Arg Arg Val Val Ala Gly Glu Gly Ser Gly Ser Val Ser Leu
            100                 105                 110

Ala Leu His Leu Gln Pro Leu Arg Ser Ala Ala Gly Ala Ala Ala Leu
        115                 120                 125

Ala Leu Thr Val Asp Leu Pro Pro Ala Ser Ser Glu Ala Arg Asn Ser
    130                 135                 140

Ala Phe Gly Phe Gln Gly Arg Leu Leu His Leu Ser Ala Gly Gln Arg
145                 150                 155                 160

Leu Gly Val His Leu His Thr Glu Ala Arg Ala Arg His Ala Trp Gln
                165                 170                 175

Leu Thr Gln Gly Ala Thr Val Leu Gly Leu Phe Arg Val Thr Pro Glu
            180                 185                 190

Ile Pro Ala Gly Leu Pro Ser Pro Arg Ser Glu
        195                 200


<210> SEQ ID NO 176
<211> LENGTH: 378
<212> TYPE: PRT
<213> ORGANISM: Artificial Sequence
<220> FEATURE:
```

```
<223> OTHER INFORMATION: Description of Artificial Sequence: Synthetic
      polypeptide
<220> FEATURE:
<223> OTHER INFORMATION: dimeric hu 4-1BBL (71-254) connected by (G4S)2
      linker

<400> SEQUENCE: 176

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
    50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
    130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Pro Ser Pro Arg Ser Glu Gly Gly Gly Gly Ser Gly Gly Gly
            180                 185                 190

Gly Ser Arg Glu Gly Pro Glu Leu Ser Pro Asp Asp Pro Ala Gly Leu
        195                 200                 205

Leu Asp Leu Arg Gln Gly Met Phe Ala Gln Leu Val Ala Gln Asn Val
    210                 215                 220

Leu Leu Ile Asp Gly Pro Leu Ser Trp Tyr Ser Asp Pro Gly Leu Ala
225                 230                 235                 240

Gly Val Ser Leu Thr Gly Gly Leu Ser Tyr Lys Glu Asp Thr Lys Glu
                245                 250                 255

Leu Val Val Ala Lys Ala Gly Val Tyr Tyr Val Phe Phe Gln Leu Glu
            260                 265                 270

Leu Arg Arg Val Val Ala Gly Glu Gly Ser Gly Ser Val Ser Leu Ala
        275                 280                 285

Leu His Leu Gln Pro Leu Arg Ser Ala Ala Gly Ala Ala Ala Leu Ala
    290                 295                 300

Leu Thr Val Asp Leu Pro Pro Ala Ser Ser Glu Ala Arg Asn Ser Ala
305                 310                 315                 320

Phe Gly Phe Gln Gly Arg Leu Leu His Leu Ser Ala Gly Gln Arg Leu
                325                 330                 335

Gly Val His Leu His Thr Glu Ala Arg Ala Arg His Ala Trp Gln Leu
            340                 345                 350

Thr Gln Gly Ala Thr Val Leu Gly Leu Phe Arg Val Thr Pro Glu Ile
        355                 360                 365

Pro Ala Gly Leu Pro Ser Pro Arg Ser Glu
    370                 375
```

```
<210> SEQ ID NO 177
<211> LENGTH: 194
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: monomeric hu 4-1BBL (71-254) plus (G4S)2 linker

<400> SEQUENCE: 177

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
    50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
    130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Pro Ser Pro Arg Ser Glu Gly Gly Gly Gly Ser Gly Gly Gly
            180                 185                 190

Gly Ser


<210> SEQ ID NO 178
<211> LENGTH: 718
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: dimeric hu 4-1BBL (71-254)-CH1 Fc knob chain

<400> SEQUENCE: 178

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
    50                  55                  60

Val Ala Lys Ala Gly Val Tyr Tyr Val Phe Phe Gln Leu Glu Leu Arg
65                  70                  75                  80
```

```
Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
    130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Pro Ser Pro Arg Ser Glu Gly Gly Gly Gly Ser Gly Gly Gly
            180                 185                 190

Gly Ser Arg Glu Gly Pro Glu Leu Ser Pro Asp Asp Pro Ala Gly Leu
        195                 200                 205

Leu Asp Leu Arg Gln Gly Met Phe Ala Gln Leu Val Ala Gln Asn Val
    210                 215                 220

Leu Leu Ile Asp Gly Pro Leu Ser Trp Tyr Ser Asp Pro Gly Leu Ala
225                 230                 235                 240

Gly Val Ser Leu Thr Gly Gly Leu Ser Tyr Lys Glu Asp Thr Lys Glu
                245                 250                 255

Leu Val Val Ala Lys Ala Gly Val Tyr Tyr Val Phe Phe Gln Leu Glu
            260                 265                 270

Leu Arg Arg Val Val Ala Gly Glu Gly Ser Gly Ser Val Ser Leu Ala
        275                 280                 285

Leu His Leu Gln Pro Leu Arg Ser Ala Ala Gly Ala Ala Ala Leu Ala
    290                 295                 300

Leu Thr Val Asp Leu Pro Pro Ala Ser Ser Glu Ala Arg Asn Ser Ala
305                 310                 315                 320

Phe Gly Phe Gln Gly Arg Leu Leu His Leu Ser Ala Gly Gln Arg Leu
                325                 330                 335

Gly Val His Leu His Thr Glu Ala Arg Ala Arg His Ala Trp Gln Leu
            340                 345                 350

Thr Gln Gly Ala Thr Val Leu Gly Leu Phe Arg Val Thr Pro Glu Ile
        355                 360                 365

Pro Ala Gly Leu Pro Ser Pro Arg Ser Glu Gly Gly Gly Gly Ser Gly
    370                 375                 380

Gly Gly Gly Ser Ala Ser Thr Lys Gly Pro Ser Val Phe Pro Leu Ala
385                 390                 395                 400

Pro Ser Ser Lys Ser Thr Ser Gly Gly Thr Ala Ala Leu Gly Cys Leu
                405                 410                 415

Val Lys Asp Tyr Phe Pro Glu Pro Val Thr Val Ser Trp Asn Ser Gly
            420                 425                 430

Ala Leu Thr Ser Gly Val His Thr Phe Pro Ala Val Leu Gln Ser Ser
        435                 440                 445

Gly Leu Tyr Ser Leu Ser Ser Val Val Thr Val Pro Ser Ser Ser Leu
    450                 455                 460

Gly Thr Gln Thr Tyr Ile Cys Asn Val Asn His Lys Pro Ser Asn Thr
465                 470                 475                 480

Lys Val Asp Lys Lys Val Glu Pro Lys Ser Cys Asp Lys Thr His Thr
                485                 490                 495
```

Cys Pro Pro Cys Pro Ala Pro Glu Ala Ala Gly Gly Pro Ser Val Phe
500 505 510

Leu Phe Pro Pro Lys Pro Lys Asp Thr Leu Met Ile Ser Arg Thr Pro
515 520 525

Glu Val Thr Cys Val Val Val Asp Val Ser His Glu Asp Pro Glu Val
530 535 540

Lys Phe Asn Trp Tyr Val Asp Gly Val Glu Val His Asn Ala Lys Thr
545 550 555 560

Lys Pro Arg Glu Glu Gln Tyr Asn Ser Thr Tyr Arg Val Val Ser Val
565 570 575

Leu Thr Val Leu His Gln Asp Trp Leu Asn Gly Lys Glu Tyr Lys Cys
580 585 590

Lys Val Ser Asn Lys Ala Leu Gly Ala Pro Ile Glu Lys Thr Ile Ser
595 600 605

Lys Ala Lys Gly Gln Pro Arg Glu Pro Gln Val Tyr Thr Leu Pro Pro
610 615 620

Cys Arg Asp Glu Leu Thr Lys Asn Gln Val Ser Leu Trp Cys Leu Val
625 630 635 640

Lys Gly Phe Tyr Pro Ser Asp Ile Ala Val Glu Trp Glu Ser Asn Gly
645 650 655

Gln Pro Glu Asn Asn Tyr Lys Thr Thr Pro Pro Val Leu Asp Ser Asp
660 665 670

Gly Ser Phe Phe Leu Tyr Ser Lys Leu Thr Val Asp Lys Ser Arg Trp
675 680 685

Gln Gln Gly Asn Val Phe Ser Cys Ser Val Met His Glu Ala Leu His
690 695 700

Asn His Tyr Thr Gln Lys Ser Leu Ser Leu Ser Pro Gly Lys
705 710 715

<210> SEQ ID NO 179
<211> LENGTH: 301
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: monomeric hu 4-1BBL (71-254)-CL

<400> SEQUENCE: 179

Arg Glu Gly Pro Glu Leu Ser Pro Asp Asp Pro Ala Gly Leu Leu Asp
1 5 10 15

Leu Arg Gln Gly Met Phe Ala Gln Leu Val Ala Gln Asn Val Leu Leu
20 25 30

Ile Asp Gly Pro Leu Ser Trp Tyr Ser Asp Pro Gly Leu Ala Gly Val
35 40 45

Ser Leu Thr Gly Gly Leu Ser Tyr Lys Glu Asp Thr Lys Glu Leu Val
50 55 60

Val Ala Lys Ala Gly Val Tyr Tyr Val Phe Phe Gln Leu Glu Leu Arg
65 70 75 80

Arg Val Val Ala Gly Glu Gly Ser Gly Ser Val Ser Leu Ala Leu His
85 90 95

Leu Gln Pro Leu Arg Ser Ala Ala Gly Ala Ala Ala Leu Ala Leu Thr
100 105 110

Val Asp Leu Pro Pro Ala Ser Ser Glu Ala Arg Asn Ser Ala Phe Gly
115 120 125

Phe Gln Gly Arg Leu Leu His Leu Ser Ala Gly Gln Arg Leu Gly Val
130 135 140

His Leu His Thr Glu Ala Arg Ala Arg His Ala Trp Gln Leu Thr Gln
145 150 155 160

Gly Ala Thr Val Leu Gly Leu Phe Arg Val Thr Pro Glu Ile Pro Ala
165 170 175

Gly Leu Pro Ser Pro Arg Ser Glu Gly Gly Gly Gly Ser Gly Gly Gly
180 185 190

Gly Ser Arg Thr Val Ala Ala Pro Ser Val Phe Ile Phe Pro Pro Ser
195 200 205

Asp Glu Gln Leu Lys Ser Gly Thr Ala Ser Val Val Cys Leu Leu Asn
210 215 220

Asn Phe Tyr Pro Arg Glu Ala Lys Val Gln Trp Lys Val Asp Asn Ala
225 230 235 240

Leu Gln Ser Gly Asn Ser Gln Glu Ser Val Thr Glu Gln Asp Ser Lys
245 250 255

Asp Ser Thr Tyr Ser Leu Ser Ser Thr Leu Thr Leu Ser Lys Ala Asp
260 265 270

Tyr Glu Lys His Lys Val Tyr Ala Cys Glu Val Thr His Gln Gly Leu
275 280 285

Ser Ser Pro Val Thr Lys Ser Phe Asn Arg Gly Glu Cys
290 295 300

<210> SEQ ID NO 180
<211> LENGTH: 205
<212> TYPE: PRT
<213> ORGANISM: Homo sapiens

<400> SEQUENCE: 180

Ala Cys Pro Trp Ala Val Ser Gly Ala Arg Ala Ser Pro Gly Ser Ala
1 5 10 15

Ala Ser Pro Arg Leu Arg Glu Gly Pro Glu Leu Ser Pro Asp Asp Pro
20 25 30

Ala Gly Leu Leu Asp Leu Arg Gln Gly Met Phe Ala Gln Leu Val Ala
35 40 45

Gln Asn Val Leu Leu Ile Asp Gly Pro Leu Ser Trp Tyr Ser Asp Pro
50 55 60

Gly Leu Ala Gly Val Ser Leu Thr Gly Gly Leu Ser Tyr Lys Glu Asp
65 70 75 80

Thr Lys Glu Leu Val Val Ala Lys Ala Gly Val Tyr Tyr Val Phe Phe
85 90 95

Gln Leu Glu Leu Arg Arg Val Val Ala Gly Glu Gly Ser Gly Ser Val
100 105 110

Ser Leu Ala Leu His Leu Gln Pro Leu Arg Ser Ala Ala Gly Ala Ala
115 120 125

Ala Leu Ala Leu Thr Val Asp Leu Pro Pro Ala Ser Ser Glu Ala Arg
130 135 140

Asn Ser Ala Phe Gly Phe Gln Gly Arg Leu Leu His Leu Ser Ala Gly
145 150 155 160

Gln Arg Leu Gly Val His Leu His Thr Glu Ala Arg Ala Arg His Ala
165 170 175

Trp Gln Leu Thr Gln Gly Ala Thr Val Leu Gly Leu Phe Arg Val Thr
180 185 190

Pro Glu Ile Pro Ala Gly Leu Pro Ser Pro Arg Ser Glu
195 200 205

<210> SEQ ID NO 181
<211> LENGTH: 133
<212> TYPE: PRT
<213> ORGANISM: Homo sapiens

<400> SEQUENCE: 181

```
Gln Val Ser His Arg Tyr Pro Arg Ile Gln Ser Ile Lys Val Gln Phe
1               5                   10                  15

Thr Glu Tyr Lys Lys Glu Lys Gly Phe Ile Leu Thr Ser Gln Lys Glu
            20                  25                  30

Asp Glu Ile Met Lys Val Gln Asn Asn Ser Val Ile Ile Asn Cys Asp
        35                  40                  45

Gly Phe Tyr Leu Ile Ser Leu Lys Gly Tyr Phe Ser Gln Glu Val Asn
    50                  55                  60

Ile Ser Leu His Tyr Gln Lys Asp Glu Glu Pro Leu Phe Gln Leu Lys
65                  70                  75                  80

Lys Val Arg Ser Val Asn Ser Leu Met Val Ala Ser Leu Thr Tyr Lys
                85                  90                  95

Asp Lys Val Tyr Leu Asn Val Thr Thr Asp Asn Thr Ser Leu Asp Asp
            100                 105                 110

Phe His Val Asn Gly Gly Glu Leu Ile Leu Ile His Gln Asn Pro Gly
        115                 120                 125

Glu Phe Cys Val Leu
    130
```

<210> SEQ ID NO 182
<211> LENGTH: 132
<212> TYPE: PRT
<213> ORGANISM: Homo sapiens

<400> SEQUENCE: 182

```
Val Ser His Arg Tyr Pro Arg Ile Gln Ser Ile Lys Val Gln Phe Thr
1               5                   10                  15

Glu Tyr Lys Lys Glu Lys Gly Phe Ile Leu Thr Ser Gln Lys Glu Asp
            20                  25                  30

Glu Ile Met Lys Val Gln Asn Asn Ser Val Ile Ile Asn Cys Asp Gly
        35                  40                  45

Phe Tyr Leu Ile Ser Leu Lys Gly Tyr Phe Ser Gln Glu Val Asn Ile
    50                  55                  60

Ser Leu His Tyr Gln Lys Asp Glu Glu Pro Leu Phe Gln Leu Lys Lys
65                  70                  75                  80

Val Arg Ser Val Asn Ser Leu Met Val Ala Ser Leu Thr Tyr Lys Asp
                85                  90                  95

Lys Val Tyr Leu Asn Val Thr Thr Asp Asn Thr Ser Leu Asp Asp Phe
            100                 105                 110

His Val Asn Gly Gly Glu Leu Ile Leu Ile His Gln Asn Pro Gly Glu
        115                 120                 125

Phe Cys Val Leu
    130
```

<210> SEQ ID NO 183
<211> LENGTH: 178
<212> TYPE: PRT
<213> ORGANISM: Homo sapiens

<400> SEQUENCE: 183

```
Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
    50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
    130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu


<210> SEQ ID NO 184
<211> LENGTH: 366
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: dimeric hu 4-1BBL (71-248) connected by (G4S)2
      linker

<400> SEQUENCE: 184

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
    50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
    130                 135                 140

His Leu His Thr Glu Ala Arg Ala Arg His Ala Trp Gln Leu Thr Gln
145                 150                 155                 160
```

Gly Ala Thr Val Leu Gly Leu Phe Arg Val Thr Pro Glu Ile Pro Ala
165 170 175

Gly Leu Gly Gly Gly Gly Ser Gly Gly Gly Gly Ser Arg Glu Gly Pro
180 185 190

Glu Leu Ser Pro Asp Asp Pro Ala Gly Leu Leu Asp Leu Arg Gln Gly
195 200 205

Met Phe Ala Gln Leu Val Ala Gln Asn Val Leu Leu Ile Asp Gly Pro
210 215 220

Leu Ser Trp Tyr Ser Asp Pro Gly Leu Ala Gly Val Ser Leu Thr Gly
225 230 235 240

Gly Leu Ser Tyr Lys Glu Asp Thr Lys Glu Leu Val Val Ala Lys Ala
245 250 255

Gly Val Tyr Tyr Val Phe Phe Gln Leu Glu Leu Arg Arg Val Val Ala
260 265 270

Gly Glu Gly Ser Gly Ser Val Ser Leu Ala Leu His Leu Gln Pro Leu
275 280 285

Arg Ser Ala Ala Gly Ala Ala Ala Leu Ala Leu Thr Val Asp Leu Pro
290 295 300

Pro Ala Ser Ser Glu Ala Arg Asn Ser Ala Phe Gly Phe Gln Gly Arg
305 310 315 320

Leu Leu His Leu Ser Ala Gly Gln Arg Leu Gly Val His Leu His Thr
325 330 335

Glu Ala Arg Ala Arg His Ala Trp Gln Leu Thr Gln Gly Ala Thr Val
340 345 350

Leu Gly Leu Phe Arg Val Thr Pro Glu Ile Pro Ala Gly Leu
355 360 365

<210> SEQ ID NO 185
<211> LENGTH: 360
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: dimeric hu 4-1BBL (80-254) connected by (G4S)2 linker

<400> SEQUENCE: 185

Asp Pro Ala Gly Leu Leu Asp Leu Arg Gln Gly Met Phe Ala Gln Leu
1 5 10 15

Val Ala Gln Asn Val Leu Leu Ile Asp Gly Pro Leu Ser Trp Tyr Ser
20 25 30

Asp Pro Gly Leu Ala Gly Val Ser Leu Thr Gly Gly Leu Ser Tyr Lys
35 40 45

Glu Asp Thr Lys Glu Leu Val Val Ala Lys Ala Gly Val Tyr Tyr Val
50 55 60

Phe Phe Gln Leu Glu Leu Arg Arg Val Val Ala Gly Glu Gly Ser Gly
65 70 75 80

Ser Val Ser Leu Ala Leu His Leu Gln Pro Leu Arg Ser Ala Ala Gly
85 90 95

Ala Ala Ala Leu Ala Leu Thr Val Asp Leu Pro Pro Ala Ser Ser Glu
100 105 110

Ala Arg Asn Ser Ala Phe Gly Phe Gln Gly Arg Leu Leu His Leu Ser
115 120 125

Ala Gly Gln Arg Leu Gly Val His Leu His Thr Glu Ala Arg Ala Arg
130 135 140

```
His Ala Trp Gln Leu Thr Gln Gly Ala Thr Val Leu Gly Leu Phe Arg
145                 150                 155                 160

Val Thr Pro Glu Ile Pro Ala Gly Leu Pro Ser Pro Arg Ser Glu Gly
                165                 170                 175

Gly Gly Gly Ser Gly Gly Gly Gly Ser Asp Pro Ala Gly Leu Leu Asp
            180                 185                 190

Leu Arg Gln Gly Met Phe Ala Gln Leu Val Ala Gln Asn Val Leu Leu
        195                 200                 205

Ile Asp Gly Pro Leu Ser Trp Tyr Ser Asp Pro Gly Leu Ala Gly Val
    210                 215                 220

Ser Leu Thr Gly Gly Leu Ser Tyr Lys Glu Asp Thr Lys Glu Leu Val
225                 230                 235                 240

Val Ala Lys Ala Gly Val Tyr Tyr Val Phe Phe Gln Leu Glu Leu Arg
                245                 250                 255

Arg Val Val Ala Gly Glu Gly Ser Gly Ser Val Ser Leu Ala Leu His
            260                 265                 270

Leu Gln Pro Leu Arg Ser Ala Ala Gly Ala Ala Ala Leu Ala Leu Thr
        275                 280                 285

Val Asp Leu Pro Pro Ala Ser Ser Glu Ala Arg Asn Ser Ala Phe Gly
    290                 295                 300

Phe Gln Gly Arg Leu Leu His Leu Ser Ala Gly Gln Arg Leu Gly Val
305                 310                 315                 320

His Leu His Thr Glu Ala Arg Ala Arg His Ala Trp Gln Leu Thr Gln
                325                 330                 335

Gly Ala Thr Val Leu Gly Leu Phe Arg Val Thr Pro Glu Ile Pro Ala
            340                 345                 350

Gly Leu Pro Ser Pro Arg Ser Glu
        355                 360
```

<210> SEQ ID NO 186
<211> LENGTH: 416
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: dimeric hu 4-1BBL (52-254) connected by (G4S)2 linker

<400> SEQUENCE: 186

```
Pro Trp Ala Val Ser Gly Ala Arg Ala Ser Pro Gly Ser Ala Ala Ser
1               5                   10                  15

Pro Arg Leu Arg Glu Gly Pro Glu Leu Ser Pro Asp Asp Pro Ala Gly
            20                  25                  30

Leu Leu Asp Leu Arg Gln Gly Met Phe Ala Gln Leu Val Ala Gln Asn
        35                  40                  45

Val Leu Leu Ile Asp Gly Pro Leu Ser Trp Tyr Ser Asp Pro Gly Leu
    50                  55                  60

Ala Gly Val Ser Leu Thr Gly Gly Leu Ser Tyr Lys Glu Asp Thr Lys
65                  70                  75                  80

Glu Leu Val Val Ala Lys Ala Gly Val Tyr Tyr Val Phe Phe Gln Leu
                85                  90                  95

Glu Leu Arg Arg Val Val Ala Gly Glu Gly Ser Gly Ser Val Ser Leu
            100                 105                 110

Ala Leu His Leu Gln Pro Leu Arg Ser Ala Ala Gly Ala Ala Ala Leu
```

```
        115                 120                 125

Ala Leu Thr Val Asp Leu Pro Pro Ala Ser Ser Glu Ala Arg Asn Ser
    130                 135                 140

Ala Phe Gly Phe Gln Gly Arg Leu Leu His Leu Ser Ala Gly Gln Arg
145                 150                 155                 160

Leu Gly Val His Leu His Thr Glu Ala Arg Ala Arg His Ala Trp Gln
                165                 170                 175

Leu Thr Gln Gly Ala Thr Val Leu Gly Leu Phe Arg Val Thr Pro Glu
            180                 185                 190

Ile Pro Ala Gly Leu Pro Ser Pro Arg Ser Glu Gly Gly Gly Gly Ser
        195                 200                 205

Gly Gly Gly Gly Ser Pro Trp Ala Val Ser Gly Ala Arg Ala Ser Pro
    210                 215                 220

Gly Ser Ala Ala Ser Pro Arg Leu Arg Glu Gly Pro Glu Leu Ser Pro
225                 230                 235                 240

Asp Asp Pro Ala Gly Leu Leu Asp Leu Arg Gln Gly Met Phe Ala Gln
                245                 250                 255

Leu Val Ala Gln Asn Val Leu Leu Ile Asp Gly Pro Leu Ser Trp Tyr
            260                 265                 270

Ser Asp Pro Gly Leu Ala Gly Val Ser Leu Thr Gly Gly Leu Ser Tyr
        275                 280                 285

Lys Glu Asp Thr Lys Glu Leu Val Val Ala Lys Ala Gly Val Tyr Tyr
    290                 295                 300

Val Phe Phe Gln Leu Glu Leu Arg Arg Val Val Ala Gly Glu Gly Ser
305                 310                 315                 320

Gly Ser Val Ser Leu Ala Leu His Leu Gln Pro Leu Arg Ser Ala Ala
                325                 330                 335

Gly Ala Ala Ala Leu Ala Leu Thr Val Asp Leu Pro Pro Ala Ser Ser
            340                 345                 350

Glu Ala Arg Asn Ser Ala Phe Gly Phe Gln Gly Arg Leu Leu His Leu
        355                 360                 365

Ser Ala Gly Gln Arg Leu Gly Val His Leu His Thr Glu Ala Arg Ala
    370                 375                 380

Arg His Ala Trp Gln Leu Thr Gln Gly Ala Thr Val Leu Gly Leu Phe
385                 390                 395                 400

Arg Val Thr Pro Glu Ile Pro Ala Gly Leu Pro Ser Pro Arg Ser Glu
                405                 410                 415


<210> SEQ ID NO 187
<211> LENGTH: 189
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: monomeric hu 4-1BBL (71-254) plus (G4S)1 linker

<400> SEQUENCE: 187

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
```

```
    50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
    130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Pro Ser Pro Arg Ser Glu Gly Gly Gly Gly Ser
            180                 185


<210> SEQ ID NO 188
<211> LENGTH: 188
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: monomeric hu 4-1BBL (71-248) plus (G4S)2 linker

<400> SEQUENCE: 188

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
    50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
    130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Gly Gly Gly Gly Ser Gly Gly Gly Gly Ser
            180                 185


<210> SEQ ID NO 189
<211> LENGTH: 183
<212> TYPE: PRT
```

```
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: monomeric hu 4-1BBL (71-248) plus (G4S)1 linker

<400> SEQUENCE: 189

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
            20                  25                  30

Ile Asp Gly Pro Leu Ser Trp Tyr Ser Asp Pro Gly Leu Ala Gly Val
        35                  40                  45

Ser Leu Thr Gly Gly Leu Ser Tyr Lys Glu Asp Thr Lys Glu Leu Val
    50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
    130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Gly Gly Gly Gly Ser
            180


<210> SEQ ID NO 190
<211> LENGTH: 276
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: dimeric huOX40L (51-183) connected by (G4S)2
      linker

<400> SEQUENCE: 190

Gln Val Ser His Arg Tyr Pro Arg Ile Gln Ser Ile Lys Val Gln Phe
1               5                   10                  15

Thr Glu Tyr Lys Lys Glu Lys Gly Phe Ile Leu Thr Ser Gln Lys Glu
            20                  25                  30

Asp Glu Ile Met Lys Val Gln Asn Asn Ser Val Ile Ile Asn Cys Asp
        35                  40                  45

Gly Phe Tyr Leu Ile Ser Leu Lys Gly Tyr Phe Ser Gln Glu Val Asn
    50                  55                  60

Ile Ser Leu His Tyr Gln Lys Asp Glu Glu Pro Leu Phe Gln Leu Lys
65                  70                  75                  80

Lys Val Arg Ser Val Asn Ser Leu Met Val Ala Ser Leu Thr Tyr Lys
                85                  90                  95

Asp Lys Val Tyr Leu Asn Val Thr Thr Asp Asn Thr Ser Leu Asp Asp
            100                 105                 110
```

Phe His Val Asn Gly Gly Glu Leu Ile Leu Ile His Gln Asn Pro Gly
115 120 125

Glu Phe Cys Val Leu Gly Gly Gly Gly Ser Gly Gly Gly Gly Ser Gln
130 135 140

Val Ser His Arg Tyr Pro Arg Ile Gln Ser Ile Lys Val Gln Phe Thr
145 150 155 160

Glu Tyr Lys Lys Glu Lys Gly Phe Ile Leu Thr Ser Gln Lys Glu Asp
165 170 175

Glu Ile Met Lys Val Gln Asn Asn Ser Val Ile Ile Asn Cys Asp Gly
180 185 190

Phe Tyr Leu Ile Ser Leu Lys Gly Tyr Phe Ser Gln Glu Val Asn Ile
195 200 205

Ser Leu His Tyr Gln Lys Asp Glu Glu Pro Leu Phe Gln Leu Lys Lys
210 215 220

Val Arg Ser Val Asn Ser Leu Met Val Ala Ser Leu Thr Tyr Lys Asp
225 230 235 240

Lys Val Tyr Leu Asn Val Thr Thr Asp Asn Thr Ser Leu Asp Asp Phe
245 250 255

His Val Asn Gly Gly Glu Leu Ile Leu Ile His Gln Asn Pro Gly Glu
260 265 270

Phe Cys Val Leu
275

<210> SEQ ID NO 191
<211> LENGTH: 274
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: dimeric huOX40L (52-183) connected by (G4S)2 linker

<400> SEQUENCE: 191

Val Ser His Arg Tyr Pro Arg Ile Gln Ser Ile Lys Val Gln Phe Thr
1 5 10 15

Glu Tyr Lys Lys Glu Lys Gly Phe Ile Leu Thr Ser Gln Lys Glu Asp
20 25 30

Glu Ile Met Lys Val Gln Asn Asn Ser Val Ile Ile Asn Cys Asp Gly
35 40 45

Phe Tyr Leu Ile Ser Leu Lys Gly Tyr Phe Ser Gln Glu Val Asn Ile
50 55 60

Ser Leu His Tyr Gln Lys Asp Glu Glu Pro Leu Phe Gln Leu Lys Lys
65 70 75 80

Val Arg Ser Val Asn Ser Leu Met Val Ala Ser Leu Thr Tyr Lys Asp
85 90 95

Lys Val Tyr Leu Asn Val Thr Thr Asp Asn Thr Ser Leu Asp Asp Phe
100 105 110

His Val Asn Gly Gly Glu Leu Ile Leu Ile His Gln Asn Pro Gly Glu
115 120 125

Phe Cys Val Leu Gly Gly Gly Gly Ser Gly Gly Gly Gly Ser Val Ser
130 135 140

His Arg Tyr Pro Arg Ile Gln Ser Ile Lys Val Gln Phe Thr Glu Tyr
145 150 155 160

Lys Lys Glu Lys Gly Phe Ile Leu Thr Ser Gln Lys Glu Asp Glu Ile

```
                165                 170                 175

Met Lys Val Gln Asn Asn Ser Val Ile Ile Asn Cys Asp Gly Phe Tyr
            180                 185                 190

Leu Ile Ser Leu Lys Gly Tyr Phe Ser Gln Glu Val Asn Ile Ser Leu
        195                 200                 205

His Tyr Gln Lys Asp Glu Glu Pro Leu Phe Gln Leu Lys Lys Val Arg
    210                 215                 220

Ser Val Asn Ser Leu Met Val Ala Ser Leu Thr Tyr Lys Asp Lys Val
225                 230                 235                 240

Tyr Leu Asn Val Thr Thr Asp Asn Thr Ser Leu Asp Asp Phe His Val
                245                 250                 255

Asn Gly Gly Glu Leu Ile Leu Ile His Gln Asn Pro Gly Glu Phe Cys
            260                 265                 270

Val Leu


<210> SEQ ID NO 192
<211> LENGTH: 164
<212> TYPE: PRT
<213> ORGANISM: Homo sapiens

<400> SEQUENCE: 192

Leu Asp Leu Arg Gln Gly Met Phe Ala Gln Leu Val Ala Gln Asn Val
1               5                   10                  15

Leu Leu Ile Asp Gly Pro Leu Ser Trp Tyr Ser Asp Pro Gly Leu Ala
            20                  25                  30

Gly Val Ser Leu Thr Gly Gly Leu Ser Tyr Lys Glu Asp Thr Lys Glu
        35                  40                  45

Leu Val Val Ala Lys Ala Gly Val Tyr Tyr Val Phe Phe Gln Leu Glu
    50                  55                  60

Leu Arg Arg Val Val Ala Gly Glu Gly Ser Gly Ser Val Ser Leu Ala
65                  70                  75                  80

Leu His Leu Gln Pro Leu Arg Ser Ala Ala Gly Ala Ala Ala Leu Ala
                85                  90                  95

Leu Thr Val Asp Leu Pro Pro Ala Ser Ser Glu Ala Arg Asn Ser Ala
            100                 105                 110

Phe Gly Phe Gln Gly Arg Leu Leu His Leu Ser Ala Gly Gln Arg Leu
        115                 120                 125

Gly Val His Leu His Thr Glu Ala Arg Ala Arg His Ala Trp Gln Leu
    130                 135                 140

Thr Gln Gly Ala Thr Val Leu Gly Leu Phe Arg Val Thr Pro Glu Ile
145                 150                 155                 160

Pro Ala Gly Leu


<210> SEQ ID NO 193
<211> LENGTH: 169
<212> TYPE: PRT
<213> ORGANISM: Homo sapiens

<400> SEQUENCE: 193

Asp Pro Ala Gly Leu Leu Asp Leu Arg Gln Gly Met Phe Ala Gln Leu
1               5                   10                  15

Val Ala Gln Asn Val Leu Leu Ile Asp Gly Pro Leu Ser Trp Tyr Ser
            20                  25                  30

Asp Pro Gly Leu Ala Gly Val Ser Leu Thr Gly Gly Leu Ser Tyr Lys
        35                  40                  45
```

Glu Asp Thr Lys Glu Leu Val Val Ala Lys Ala Gly Val Tyr Tyr Val
    50                  55                  60

Phe Phe Gln Leu Glu Leu Arg Arg Val Val Ala Gly Glu Gly Ser Gly
65                  70                  75                  80

Ser Val Ser Leu Ala Leu His Leu Gln Pro Leu Arg Ser Ala Ala Gly
                85                  90                  95

Ala Ala Ala Leu Ala Leu Thr Val Asp Leu Pro Pro Ala Ser Ser Glu
            100                 105                 110

Ala Arg Asn Ser Ala Phe Gly Phe Gln Gly Arg Leu Leu His Leu Ser
        115                 120                 125

Ala Gly Gln Arg Leu Gly Val His Leu His Thr Glu Ala Arg Ala Arg
    130                 135                 140

His Ala Trp Gln Leu Thr Gln Gly Ala Thr Val Leu Gly Leu Phe Arg
145                 150                 155                 160

Val Thr Pro Glu Ile Pro Ala Gly Leu
                165

<210> SEQ ID NO 194
<211> LENGTH: 197
<212> TYPE: PRT
<213> ORGANISM: Homo sapiens

<400> SEQUENCE: 194

Pro Trp Ala Val Ser Gly Ala Arg Ala Ser Pro Gly Ser Ala Ala Ser
1               5                   10                  15

Pro Arg Leu Arg Glu Gly Pro Glu Leu Ser Pro Asp Asp Pro Ala Gly
            20                  25                  30

Leu Leu Asp Leu Arg Gln Gly Met Phe Ala Gln Leu Val Ala Gln Asn
        35                  40                  45

Val Leu Leu Ile Asp Gly Pro Leu Ser Trp Tyr Ser Asp Pro Gly Leu
    50                  55                  60

Ala Gly Val Ser Leu Thr Gly Gly Leu Ser Tyr Lys Glu Asp Thr Lys
65                  70                  75                  80

Glu Leu Val Val Ala Lys Ala Gly Val Tyr Tyr Val Phe Phe Gln Leu
                85                  90                  95

Glu Leu Arg Arg Val Val Ala Gly Glu Gly Ser Gly Ser Val Ser Leu
            100                 105                 110

Ala Leu His Leu Gln Pro Leu Arg Ser Ala Ala Gly Ala Ala Ala Leu
        115                 120                 125

Ala Leu Thr Val Asp Leu Pro Pro Ala Ser Ser Glu Ala Arg Asn Ser
    130                 135                 140

Ala Phe Gly Phe Gln Gly Arg Leu Leu His Leu Ser Ala Gly Gln Arg
145                 150                 155                 160

Leu Gly Val His Leu His Thr Glu Ala Arg Ala Arg His Ala Trp Gln
                165                 170                 175

Leu Thr Gln Gly Ala Thr Val Leu Gly Leu Phe Arg Val Thr Pro Glu
            180                 185                 190

Ile Pro Ala Gly Leu
        195

<210> SEQ ID NO 195
<211> LENGTH: 620
<212> TYPE: PRT
<213> ORGANISM: Artificial Sequence
<220> FEATURE:
<223> OTHER INFORMATION: Description of Artificial Sequence: Synthetic
      polypeptide

```
<220> FEATURE:
<223> OTHER INFORMATION: Dimeric hu OX40L (51-183)  - CL* Fc knob chain

<400> SEQUENCE: 195

Gln Val Ser His Arg Tyr Pro Arg Ile Gln Ser Ile Lys Val Gln Phe
1               5                   10                  15

Thr Glu Tyr Lys Lys Glu Lys Gly Phe Ile Leu Thr Ser Gln Lys Glu
            20                  25                  30

Asp Glu Ile Met Lys Val Gln Asp Asn Ser Val Ile Ile Asn Cys Asp
        35                  40                  45

Gly Phe Tyr Leu Ile Ser Leu Lys Gly Tyr Phe Ser Gln Glu Val Asp
    50                  55                  60

Ile Ser Leu His Tyr Gln Lys Asp Glu Glu Pro Leu Phe Gln Leu Lys
65                  70                  75                  80

Lys Val Arg Ser Val Asn Ser Leu Met Val Ala Ser Leu Thr Tyr Lys
                85                  90                  95

Asp Lys Val Tyr Leu Asn Val Thr Thr Asp Asn Thr Ser Leu Asp Asp
            100                 105                 110

Phe His Val Asn Gly Gly Glu Leu Ile Leu Ile His Gln Asn Pro Gly
        115                 120                 125

Glu Phe Cys Val Leu Gly Gly Gly Gly Ser Gly Gly Gly Gly Ser Gln
    130                 135                 140

Val Ser His Arg Tyr Pro Arg Ile Gln Ser Ile Lys Val Gln Phe Thr
145                 150                 155                 160

Glu Tyr Lys Lys Glu Lys Gly Phe Ile Leu Thr Ser Gln Lys Glu Asp
                165                 170                 175

Glu Ile Met Lys Val Gln Asp Asn Ser Val Ile Ile Asn Cys Asp Gly
            180                 185                 190

Phe Tyr Leu Ile Ser Leu Lys Gly Tyr Phe Ser Gln Glu Val Asp Ile
        195                 200                 205

Ser Leu His Tyr Gln Lys Asp Glu Glu Pro Leu Phe Gln Leu Lys Lys
    210                 215                 220

Val Arg Ser Val Asn Ser Leu Met Val Ala Ser Leu Thr Tyr Lys Asp
225                 230                 235                 240

Lys Val Tyr Leu Asn Val Thr Thr Asp Asn Thr Ser Leu Asp Asp Phe
                245                 250                 255

His Val Asn Gly Gly Glu Leu Ile Leu Ile His Gln Asn Pro Gly Glu
            260                 265                 270

Phe Cys Val Leu Gly Gly Gly Gly Ser Gly Gly Gly Gly Ser Arg Thr
        275                 280                 285

Val Ala Ala Pro Ser Val Phe Ile Phe Pro Pro Ser Asp Arg Lys Leu
    290                 295                 300

Lys Ser Gly Thr Ala Ser Val Val Cys Leu Leu Asn Asn Phe Tyr Pro
305                 310                 315                 320

Arg Glu Ala Lys Val Gln Trp Lys Val Asp Asn Ala Leu Gln Ser Gly
                325                 330                 335

Asn Ser Gln Glu Ser Val Thr Glu Gln Asp Ser Lys Asp Ser Thr Tyr
            340                 345                 350

Ser Leu Ser Ser Thr Leu Thr Leu Ser Lys Ala Asp Tyr Glu Lys His
        355                 360                 365

Lys Val Tyr Ala Cys Glu Val Thr His Gln Gly Leu Ser Ser Pro Val
    370                 375                 380

Thr Lys Ser Phe Asn Arg Gly Glu Cys Asp Lys Thr His Thr Cys Pro
385                 390                 395                 400
```

```
Pro Cys Pro Ala Pro Glu Ala Ala Gly Gly Pro Ser Val Phe Leu Phe
                405                 410                 415

Pro Pro Lys Pro Lys Asp Thr Leu Met Ile Ser Arg Thr Pro Glu Val
            420                 425                 430

Thr Cys Val Val Val Asp Val Ser His Glu Asp Pro Glu Val Lys Phe
        435                 440                 445

Asn Trp Tyr Val Asp Gly Val Glu Val His Asn Ala Lys Thr Lys Pro
    450                 455                 460

Arg Glu Glu Gln Tyr Asn Ser Thr Tyr Arg Val Val Ser Val Leu Thr
465                 470                 475                 480

Val Leu His Gln Asp Trp Leu Asn Gly Lys Glu Tyr Lys Cys Lys Val
                485                 490                 495

Ser Asn Lys Ala Leu Gly Ala Pro Ile Glu Lys Thr Ile Ser Lys Ala
            500                 505                 510

Lys Gly Gln Pro Arg Glu Pro Gln Val Tyr Thr Leu Pro Pro Cys Arg
        515                 520                 525

Asp Glu Leu Thr Lys Asn Gln Val Ser Leu Trp Cys Leu Val Lys Gly
    530                 535                 540

Phe Tyr Pro Ser Asp Ile Ala Val Glu Trp Glu Ser Asn Gly Gln Pro
545                 550                 555                 560

Glu Asn Asn Tyr Lys Thr Thr Pro Pro Val Leu Asp Ser Asp Gly Ser
                565                 570                 575

Phe Phe Leu Tyr Ser Lys Leu Thr Val Asp Lys Ser Arg Trp Gln Gln
            580                 585                 590

Gly Asn Val Phe Ser Cys Ser Val Met His Glu Ala Leu His Asn His
        595                 600                 605

Tyr Thr Gln Lys Ser Leu Ser Leu Ser Pro Gly Lys
    610                 615                 620


<210> SEQ ID NO 196
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Monomeric hu OX40L (51-183) - CH1*

<400> SEQUENCE: 196

Gln Val Ser His Arg Tyr Pro Arg Ile Gln Ser Ile Lys Val Gln Phe
1               5                   10                  15

Thr Glu Tyr Lys Lys Glu Lys Gly Phe Ile Leu Thr Ser Gln Lys Glu
            20                  25                  30

Asp Glu Ile Met Lys Val Gln Asp Asn Ser Val Ile Ile Asn Cys Asp
        35                  40                  45

Gly Phe Tyr Leu Ile Ser Leu Lys Gly Tyr Phe Ser Gln Glu Val Asp
    50                  55                  60

Ile Ser Leu His Tyr Gln Lys Asp Glu Glu Pro Leu Phe Gln Leu Lys
65                  70                  75                  80

Lys Val Arg Ser Val Asn Ser Leu Met Val Ala Ser Leu Thr Tyr Lys
                85                  90                  95

Asp Lys Val Tyr Leu Asn Val Thr Thr Asp Asn Thr Ser Leu Asp Asp
            100                 105                 110

Phe His Val Asn Gly Gly Glu Leu Ile Leu Ile His Gln Asn Pro Gly
        115                 120                 125
```

```
Glu Phe Cys Val Leu Gly Gly Gly Gly Ser Gly Gly Gly Gly Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Glu Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Glu Lys
225                 230                 235                 240

Val Glu Pro Lys Ser Cys
                245


<210> SEQ ID NO 197
<211> LENGTH: 2201
<212> TYPE: PRT
<213> ORGANISM: Homo sapiens

<400> SEQUENCE: 197

Met Gly Ala Met Thr Gln Leu Leu Ala Gly Val Phe Leu Ala Phe Leu
1               5                   10                  15

Ala Leu Ala Thr Glu Gly Gly Val Leu Lys Lys Val Ile Arg His Lys
            20                  25                  30

Arg Gln Ser Gly Val Asn Ala Thr Leu Pro Glu Glu Asn Gln Pro Val
        35                  40                  45

Val Phe Asn His Val Tyr Asn Ile Lys Leu Pro Val Gly Ser Gln Cys
    50                  55                  60

Ser Val Asp Leu Glu Ser Ala Ser Gly Glu Lys Asp Leu Ala Pro Pro
65                  70                  75                  80

Ser Glu Pro Ser Glu Ser Phe Gln Glu His Thr Val Asp Gly Glu Asn
                85                  90                  95

Gln Ile Val Phe Thr His Arg Ile Asn Ile Pro Arg Arg Ala Cys Gly
            100                 105                 110

Cys Ala Ala Ala Pro Asp Val Lys Glu Leu Leu Ser Arg Leu Glu Glu
        115                 120                 125

Leu Glu Asn Leu Val Ser Ser Leu Arg Glu Gln Cys Thr Ala Gly Ala
    130                 135                 140

Gly Cys Cys Leu Gln Pro Ala Thr Gly Arg Leu Asp Thr Arg Pro Phe
145                 150                 155                 160

Cys Ser Gly Arg Gly Asn Phe Ser Thr Glu Gly Cys Gly Cys Val Cys
                165                 170                 175

Glu Pro Gly Trp Lys Gly Pro Asn Cys Ser Glu Pro Glu Cys Pro Gly
            180                 185                 190

Asn Cys His Leu Arg Gly Arg Cys Ile Asp Gly Gln Cys Ile Cys Asp
        195                 200                 205

Asp Gly Phe Thr Gly Glu Asp Cys Ser Gln Leu Ala Cys Pro Ser Asp
    210                 215                 220

Cys Asn Asp Gln Gly Lys Cys Val Asn Gly Val Cys Ile Cys Phe Glu
225                 230                 235                 240

Gly Tyr Ala Gly Ala Asp Cys Ser Arg Glu Ile Cys Pro Val Pro Cys
```

```
                245                 250                 255

Ser Glu Glu His Gly Thr Cys Val Asp Gly Leu Cys Val Cys His Asp
            260                 265                 270

Gly Phe Ala Gly Asp Asp Cys Asn Lys Pro Leu Cys Leu Asn Asn Cys
        275                 280                 285

Tyr Asn Arg Gly Arg Cys Val Glu Asn Glu Cys Val Cys Asp Glu Gly
    290                 295                 300

Phe Thr Gly Glu Asp Cys Ser Glu Leu Ile Cys Pro Asn Asp Cys Phe
305                 310                 315                 320

Asp Arg Gly Arg Cys Ile Asn Gly Thr Cys Tyr Cys Glu Glu Gly Phe
                325                 330                 335

Thr Gly Glu Asp Cys Gly Lys Pro Thr Cys Pro His Ala Cys His Thr
            340                 345                 350

Gln Gly Arg Cys Glu Glu Gly Gln Cys Val Cys Asp Glu Gly Phe Ala
        355                 360                 365

Gly Val Asp Cys Ser Glu Lys Arg Cys Pro Ala Asp Cys His Asn Arg
    370                 375                 380

Gly Arg Cys Val Asp Gly Arg Cys Glu Cys Asp Asp Gly Phe Thr Gly
385                 390                 395                 400

Ala Asp Cys Gly Glu Leu Lys Cys Pro Asn Gly Cys Ser Gly His Gly
                405                 410                 415

Arg Cys Val Asn Gly Gln Cys Val Cys Asp Glu Gly Tyr Thr Gly Glu
            420                 425                 430

Asp Cys Ser Gln Leu Arg Cys Pro Asn Asp Cys His Ser Arg Gly Arg
        435                 440                 445

Cys Val Glu Gly Lys Cys Val Cys Glu Gln Gly Phe Lys Gly Tyr Asp
    450                 455                 460

Cys Ser Asp Met Ser Cys Pro Asn Asp Cys His Gln His Gly Arg Cys
465                 470                 475                 480

Val Asn Gly Met Cys Val Cys Asp Asp Gly Tyr Thr Gly Glu Asp Cys
                485                 490                 495

Arg Asp Arg Gln Cys Pro Arg Asp Cys Ser Asn Arg Gly Leu Cys Val
            500                 505                 510

Asp Gly Gln Cys Val Cys Glu Asp Gly Phe Thr Gly Pro Asp Cys Ala
        515                 520                 525

Glu Leu Ser Cys Pro Asn Asp Cys His Gly Gln Gly Arg Cys Val Asn
    530                 535                 540

Gly Gln Cys Val Cys His Glu Gly Phe Met Gly Lys Asp Cys Lys Glu
545                 550                 555                 560

Gln Arg Cys Pro Ser Asp Cys His Gly Gln Gly Arg Cys Val Asp Gly
                565                 570                 575

Gln Cys Ile Cys His Glu Gly Phe Thr Gly Leu Asp Cys Gly Gln His
            580                 585                 590

Ser Cys Pro Ser Asp Cys Asn Asn Leu Gly Gln Cys Val Ser Gly Arg
        595                 600                 605

Cys Ile Cys Asn Glu Gly Tyr Ser Gly Glu Asp Cys Ser Glu Val Ser
    610                 615                 620

Pro Pro Lys Asp Leu Val Val Thr Glu Val Thr Glu Glu Thr Val Asn
625                 630                 635                 640

Leu Ala Trp Asp Asn Glu Met Arg Val Thr Glu Tyr Leu Val Val Tyr
                645                 650                 655

Thr Pro Thr His Glu Gly Gly Leu Glu Met Gln Phe Arg Val Pro Gly
            660                 665                 670
```

```
Asp Gln Thr Ser Thr Ile Ile Gln Glu Leu Glu Pro Gly Val Glu Tyr
      675                 680                 685

Phe Ile Arg Val Phe Ala Ile Leu Glu Asn Lys Lys Ser Ile Pro Val
    690                 695                 700

Ser Ala Arg Val Ala Thr Tyr Leu Pro Ala Pro Glu Gly Leu Lys Phe
705                 710                 715                 720

Lys Ser Ile Lys Glu Thr Ser Val Glu Val Glu Trp Asp Pro Leu Asp
                725                 730                 735

Ile Ala Phe Glu Thr Trp Glu Ile Ile Phe Arg Asn Met Asn Lys Glu
            740                 745                 750

Asp Glu Gly Glu Ile Thr Lys Ser Leu Arg Arg Pro Glu Thr Ser Tyr
        755                 760                 765

Arg Gln Thr Gly Leu Ala Pro Gly Gln Glu Tyr Glu Ile Ser Leu His
    770                 775                 780

Ile Val Lys Asn Asn Thr Arg Gly Pro Gly Leu Lys Arg Val Thr Thr
785                 790                 795                 800

Thr Arg Leu Asp Ala Pro Ser Gln Ile Glu Val Lys Asp Val Thr Asp
                805                 810                 815

Thr Thr Ala Leu Ile Thr Trp Phe Lys Pro Leu Ala Glu Ile Asp Gly
            820                 825                 830

Ile Glu Leu Thr Tyr Gly Ile Lys Asp Val Pro Gly Asp Arg Thr Thr
        835                 840                 845

Ile Asp Leu Thr Glu Asp Glu Asn Gln Tyr Ser Ile Gly Asn Leu Lys
    850                 855                 860

Pro Asp Thr Glu Tyr Glu Val Ser Leu Ile Ser Arg Arg Gly Asp Met
865                 870                 875                 880

Ser Ser Asn Pro Ala Lys Glu Thr Phe Thr Thr Gly Leu Asp Ala Pro
                885                 890                 895

Arg Asn Leu Arg Arg Val Ser Gln Thr Asp Asn Ser Ile Thr Leu Glu
            900                 905                 910

Trp Arg Asn Gly Lys Ala Ala Ile Asp Ser Tyr Arg Ile Lys Tyr Ala
        915                 920                 925

Pro Ile Ser Gly Gly Asp His Ala Glu Val Asp Val Pro Lys Ser Gln
    930                 935                 940

Gln Ala Thr Thr Lys Thr Thr Leu Thr Gly Leu Arg Pro Gly Thr Glu
945                 950                 955                 960

Tyr Gly Ile Gly Val Ser Ala Val Lys Glu Asp Lys Glu Ser Asn Pro
                965                 970                 975

Ala Thr Ile Asn Ala Ala Thr Glu Leu Asp Thr Pro Lys Asp Leu Gln
            980                 985                 990

Val Ser Glu Thr Ala Glu Thr Ser  Leu Thr Leu Leu Trp  Lys Thr Pro
        995                 1000                1005

Leu Ala  Lys Phe Asp Arg Tyr  Arg Leu Asn Tyr Ser  Leu Pro Thr
    1010                1015                1020

Gly Gln  Trp Val Gly Val Gln  Leu Pro Arg Asn Thr  Thr Ser Tyr
    1025                1030                1035

Val Leu  Arg Gly Leu Glu Pro  Gly Gln Glu Tyr Asn  Val Leu Leu
    1040                1045                1050

Thr Ala  Glu Lys Gly Arg His  Lys Ser Lys Pro Ala  Arg Val Lys
    1055                1060                1065

Ala Ser  Thr Glu Gln Ala Pro  Glu Leu Glu Asn Leu  Thr Val Thr
    1070                1075                1080
```

-continued

Glu Val Gly Trp Asp Gly Leu Arg Leu Asn Trp Thr Ala Ala Asp
1085 1090 1095

Gln Ala Tyr Glu His Phe Ile Ile Gln Val Gln Glu Ala Asn Lys
1100 1105 1110

Val Glu Ala Ala Arg Asn Leu Thr Val Pro Gly Ser Leu Arg Ala
1115 1120 1125

Val Asp Ile Pro Gly Leu Lys Ala Ala Thr Pro Tyr Thr Val Ser
1130 1135 1140

Ile Tyr Gly Val Ile Gln Gly Tyr Arg Thr Pro Val Leu Ser Ala
1145 1150 1155

Glu Ala Ser Thr Gly Glu Thr Pro Asn Leu Gly Glu Val Val Val
1160 1165 1170

Ala Glu Val Gly Trp Asp Ala Leu Lys Leu Asn Trp Thr Ala Pro
1175 1180 1185

Glu Gly Ala Tyr Glu Tyr Phe Phe Ile Gln Val Gln Glu Ala Asp
1190 1195 1200

Thr Val Glu Ala Ala Gln Asn Leu Thr Val Pro Gly Gly Leu Arg
1205 1210 1215

Ser Thr Asp Leu Pro Gly Leu Lys Ala Ala Thr His Tyr Thr Ile
1220 1225 1230

Thr Ile Arg Gly Val Thr Gln Asp Phe Ser Thr Thr Pro Leu Ser
1235 1240 1245

Val Glu Val Leu Thr Glu Glu Val Pro Asp Met Gly Asn Leu Thr
1250 1255 1260

Val Thr Glu Val Ser Trp Asp Ala Leu Arg Leu Asn Trp Thr Thr
1265 1270 1275

Pro Asp Gly Thr Tyr Asp Gln Phe Thr Ile Gln Val Gln Glu Ala
1280 1285 1290

Asp Gln Val Glu Glu Ala His Asn Leu Thr Val Pro Gly Ser Leu
1295 1300 1305

Arg Ser Met Glu Ile Pro Gly Leu Arg Ala Gly Thr Pro Tyr Thr
1310 1315 1320

Val Thr Leu His Gly Glu Val Arg Gly His Ser Thr Arg Pro Leu
1325 1330 1335

Ala Val Glu Val Val Thr Glu Asp Leu Pro Gln Leu Gly Asp Leu
1340 1345 1350

Ala Val Ser Glu Val Gly Trp Asp Gly Leu Arg Leu Asn Trp Thr
1355 1360 1365

Ala Ala Asp Asn Ala Tyr Glu His Phe Val Ile Gln Val Gln Glu
1370 1375 1380

Val Asn Lys Val Glu Ala Ala Gln Asn Leu Thr Leu Pro Gly Ser
1385 1390 1395

Leu Arg Ala Val Asp Ile Pro Gly Leu Glu Ala Ala Thr Pro Tyr
1400 1405 1410

Arg Val Ser Ile Tyr Gly Val Ile Arg Gly Tyr Arg Thr Pro Val
1415 1420 1425

Leu Ser Ala Glu Ala Ser Thr Ala Lys Glu Pro Glu Ile Gly Asn
1430 1435 1440

Leu Asn Val Ser Asp Ile Thr Pro Glu Ser Phe Asn Leu Ser Trp
1445 1450 1455

Met Ala Thr Asp Gly Ile Phe Glu Thr Phe Thr Ile Glu Ile Ile
1460 1465 1470

Asp Ser Asn Arg Leu Leu Glu Thr Val Glu Tyr Asn Ile Ser Gly 1475 1480 1485

Ala Glu Arg Thr Ala His Ile Ser Gly Leu Pro Pro Ser Thr Asp
1490 1495 1500

Phe Ile Val Tyr Leu Ser Gly Leu Ala Pro Ser Ile Arg Thr Lys
1505 1510 1515

Thr Ile Ser Ala Thr Ala Thr Thr Glu Ala Leu Pro Leu Leu Glu
1520 1525 1530

Asn Leu Thr Ile Ser Asp Ile Asn Pro Tyr Gly Phe Thr Val Ser
1535 1540 1545

Trp Met Ala Ser Glu Asn Ala Phe Asp Ser Phe Leu Val Thr Val
1550 1555 1560

Val Asp Ser Gly Lys Leu Leu Asp Pro Gln Glu Phe Thr Leu Ser
1565 1570 1575

Gly Thr Gln Arg Lys Leu Glu Leu Arg Gly Leu Ile Thr Gly Ile
1580 1585 1590

Gly Tyr Glu Val Met Val Ser Gly Phe Thr Gln Gly His Gln Thr
1595 1600 1605

Lys Pro Leu Arg Ala Glu Ile Val Thr Glu Ala Glu Pro Glu Val
1610 1615 1620

Asp Asn Leu Leu Val Ser Asp Ala Thr Pro Asp Gly Phe Arg Leu
1625 1630 1635

Ser Trp Thr Ala Asp Glu Gly Val Phe Asp Asn Phe Val Leu Lys
1640 1645 1650

Ile Arg Asp Thr Lys Lys Gln Ser Glu Pro Leu Glu Ile Thr Leu
1655 1660 1665

Leu Ala Pro Glu Arg Thr Arg Asp Ile Thr Gly Leu Arg Glu Ala
1670 1675 1680

Thr Glu Tyr Glu Ile Glu Leu Tyr Gly Ile Ser Lys Gly Arg Arg
1685 1690 1695

Ser Gln Thr Val Ser Ala Ile Ala Thr Thr Ala Met Gly Ser Pro
1700 1705 1710

Lys Glu Val Ile Phe Ser Asp Ile Thr Glu Asn Ser Ala Thr Val
1715 1720 1725

Ser Trp Arg Ala Pro Thr Ala Gln Val Glu Ser Phe Arg Ile Thr
1730 1735 1740

Tyr Val Pro Ile Thr Gly Gly Thr Pro Ser Met Val Thr Val Asp
1745 1750 1755

Gly Thr Lys Thr Gln Thr Arg Leu Val Lys Leu Ile Pro Gly Val
1760 1765 1770

Glu Tyr Leu Val Ser Ile Ile Ala Met Lys Gly Phe Glu Glu Ser
1775 1780 1785

Glu Pro Val Ser Gly Ser Phe Thr Thr Ala Leu Asp Gly Pro Ser
1790 1795 1800

Gly Leu Val Thr Ala Asn Ile Thr Asp Ser Glu Ala Leu Ala Arg
1805 1810 1815

Trp Gln Pro Ala Ile Ala Thr Val Asp Ser Tyr Val Ile Ser Tyr
1820 1825 1830

Thr Gly Glu Lys Val Pro Glu Ile Thr Arg Thr Val Ser Gly Asn
1835 1840 1845

Thr Val Glu Tyr Ala Leu Thr Asp Leu Glu Pro Ala Thr Glu Tyr
1850 1855 1860

Thr Leu Arg Ile Phe Ala Glu Lys Gly Pro Gln Lys Ser Ser Thr
1865 1870 1875

Ile Thr Ala Lys Phe Thr Thr Asp Leu Asp Ser Pro Arg Asp Leu
1880 1885 1890

Thr Ala Thr Glu Val Gln Ser Glu Thr Ala Leu Leu Thr Trp Arg
1895 1900 1905

Pro Pro Arg Ala Ser Val Thr Gly Tyr Leu Leu Val Tyr Glu Ser
1910 1915 1920

Val Asp Gly Thr Val Lys Glu Val Ile Val Gly Pro Asp Thr Thr
1925 1930 1935

Ser Tyr Ser Leu Ala Asp Leu Ser Pro Ser Thr His Tyr Thr Ala
1940 1945 1950

Lys Ile Gln Ala Leu Asn Gly Pro Leu Arg Ser Asn Met Ile Gln
1955 1960 1965

Thr Ile Phe Thr Thr Ile Gly Leu Leu Tyr Pro Phe Pro Lys Asp
1970 1975 1980

Cys Ser Gln Ala Met Leu Asn Gly Asp Thr Thr Ser Gly Leu Tyr
1985 1990 1995

Thr Ile Tyr Leu Asn Gly Asp Lys Ala Glu Ala Leu Glu Val Phe
2000 2005 2010

Cys Asp Met Thr Ser Asp Gly Gly Gly Trp Ile Val Phe Leu Arg
2015 2020 2025

Arg Lys Asn Gly Arg Glu Asn Phe Tyr Gln Asn Trp Lys Ala Tyr
2030 2035 2040

Ala Ala Gly Phe Gly Asp Arg Arg Glu Glu Phe Trp Leu Gly Leu
2045 2050 2055

Asp Asn Leu Asn Lys Ile Thr Ala Gln Gly Gln Tyr Glu Leu Arg
2060 2065 2070

Val Asp Leu Arg Asp His Gly Glu Thr Ala Phe Ala Val Tyr Asp
2075 2080 2085

Lys Phe Ser Val Gly Asp Ala Lys Thr Arg Tyr Lys Leu Lys Val
2090 2095 2100

Glu Gly Tyr Ser Gly Thr Ala Gly Asp Ser Met Ala Tyr His Asn
2105 2110 2115

Gly Arg Ser Phe Ser Thr Phe Asp Lys Asp Thr Asp Ser Ala Ile
2120 2125 2130

Thr Asn Cys Ala Leu Ser Tyr Lys Gly Ala Phe Trp Tyr Arg Asn
2135 2140 2145

Cys His Arg Val Asn Leu Met Gly Arg Tyr Gly Asp Asn Asn His
2150 2155 2160

Ser Gln Gly Val Asn Trp Phe His Trp Lys Gly His Glu His Ser
2165 2170 2175

Ile Gln Phe Ala Glu Met Lys Leu Arg Pro Ser Asn Phe Arg Asn
2180 2185 2190

Leu Glu Gly Arg Arg Lys Arg Ala
2195 2200

<210> SEQ ID NO 198
<211> LENGTH: 2322
<212> TYPE: PRT
<213> ORGANISM: Homo sapiens

<400> SEQUENCE: 198

Met Gln Ser Gly Pro Arg Pro Pro Leu Pro Ala Pro Gly Leu Ala Leu
1 5 10 15

Ala Leu Thr Leu Thr Met Leu Ala Arg Leu Ala Ser Ala Ala Ser Phe

-continued

```
            20                  25                  30

Phe Gly Glu Asn His Leu Glu Val Pro Val Ala Thr Ala Leu Thr Asp
        35                  40                  45

Ile Asp Leu Gln Leu Gln Phe Ser Thr Ser Gln Pro Glu Ala Leu Leu
    50                  55                  60

Leu Leu Ala Ala Gly Pro Ala Asp His Leu Leu Leu Gln Leu Tyr Ser
65                  70                  75                  80

Gly Arg Leu Gln Val Arg Leu Val Leu Gly Gln Glu Glu Leu Arg Leu
                85                  90                  95

Gln Thr Pro Ala Glu Thr Leu Leu Ser Asp Ser Ile Pro His Thr Val
            100                 105                 110

Val Leu Thr Val Val Glu Gly Trp Ala Thr Leu Ser Val Asp Gly Phe
        115                 120                 125

Leu Asn Ala Ser Ser Ala Val Pro Gly Ala Pro Leu Glu Val Pro Tyr
    130                 135                 140

Gly Leu Phe Val Gly Gly Thr Gly Thr Leu Gly Leu Pro Tyr Leu Arg
145                 150                 155                 160

Gly Thr Ser Arg Pro Leu Arg Gly Cys Leu His Ala Ala Thr Leu Asn
                165                 170                 175

Gly Arg Ser Leu Leu Arg Pro Leu Thr Pro Asp Val His Glu Gly Cys
            180                 185                 190

Ala Glu Glu Phe Ser Ala Ser Asp Asp Val Ala Leu Gly Phe Ser Gly
        195                 200                 205

Pro His Ser Leu Ala Ala Phe Pro Ala Trp Gly Thr Gln Asp Glu Gly
    210                 215                 220

Thr Leu Glu Phe Thr Leu Thr Thr Gln Ser Arg Gln Ala Pro Leu Ala
225                 230                 235                 240

Phe Gln Ala Gly Gly Arg Arg Gly Asp Phe Ile Tyr Val Asp Ile Phe
                245                 250                 255

Glu Gly His Leu Arg Ala Val Val Glu Lys Gly Gln Gly Thr Val Leu
            260                 265                 270

Leu His Asn Ser Val Pro Val Ala Asp Gly Gln Pro His Glu Val Ser
        275                 280                 285

Val His Ile Asn Ala His Arg Leu Glu Ile Ser Val Asp Gln Tyr Pro
    290                 295                 300

Thr His Thr Ser Asn Arg Gly Val Leu Ser Tyr Leu Glu Pro Arg Gly
305                 310                 315                 320

Ser Leu Leu Leu Gly Gly Leu Asp Ala Glu Ala Ser Arg His Leu Gln
                325                 330                 335

Glu His Arg Leu Gly Leu Thr Pro Glu Ala Thr Asn Ala Ser Leu Leu
            340                 345                 350

Gly Cys Met Glu Asp Leu Ser Val Asn Gly Gln Arg Arg Gly Leu Arg
        355                 360                 365

Glu Ala Leu Leu Thr Arg Asn Met Ala Ala Gly Cys Arg Leu Glu Glu
    370                 375                 380

Glu Glu Tyr Glu Asp Asp Ala Tyr Gly His Tyr Glu Ala Phe Ser Thr
385                 390                 395                 400

Leu Ala Pro Glu Ala Trp Pro Ala Met Glu Leu Pro Glu Pro Cys Val
                405                 410                 415

Pro Glu Pro Gly Leu Pro Pro Val Phe Ala Asn Phe Thr Gln Leu Leu
            420                 425                 430

Thr Ile Ser Pro Leu Val Val Ala Glu Gly Gly Thr Ala Trp Leu Glu
        435                 440                 445
```

```
Trp Arg His Val Gln Pro Thr Leu Asp Leu Met Glu Ala Glu Leu Arg
    450                 455                 460

Lys Ser Gln Val Leu Phe Ser Val Thr Arg Gly Ala Arg His Gly Glu
465                 470                 475                 480

Leu Glu Leu Asp Ile Pro Gly Ala Gln Ala Arg Lys Met Phe Thr Leu
                485                 490                 495

Leu Asp Val Val Asn Arg Lys Ala Arg Phe Ile His Asp Gly Ser Glu
            500                 505                 510

Asp Thr Ser Asp Gln Leu Val Leu Glu Val Ser Val Thr Ala Arg Val
        515                 520                 525

Pro Met Pro Ser Cys Leu Arg Arg Gly Gln Thr Tyr Leu Leu Pro Ile
    530                 535                 540

Gln Val Asn Pro Val Asn Asp Pro Pro His Ile Ile Phe Pro His Gly
545                 550                 555                 560

Ser Leu Met Val Ile Leu Glu His Thr Gln Lys Pro Leu Gly Pro Glu
                565                 570                 575

Val Phe Gln Ala Tyr Asp Pro Asp Ser Ala Cys Glu Gly Leu Thr Phe
            580                 585                 590

Gln Val Leu Gly Thr Ser Ser Gly Leu Pro Val Glu Arg Arg Asp Gln
        595                 600                 605

Pro Gly Glu Pro Ala Thr Glu Phe Ser Cys Arg Glu Leu Glu Ala Gly
    610                 615                 620

Ser Leu Val Tyr Val His Arg Gly Gly Pro Ala Gln Asp Leu Thr Phe
625                 630                 635                 640

Arg Val Ser Asp Gly Leu Gln Ala Ser Pro Pro Ala Thr Leu Lys Val
                645                 650                 655

Val Ala Ile Arg Pro Ala Ile Gln Ile His Arg Ser Thr Gly Leu Arg
            660                 665                 670

Leu Ala Gln Gly Ser Ala Met Pro Ile Leu Pro Ala Asn Leu Ser Val
        675                 680                 685

Glu Thr Asn Ala Val Gly Gln Asp Val Ser Val Leu Phe Arg Val Thr
    690                 695                 700

Gly Ala Leu Gln Phe Gly Glu Leu Gln Lys Gln Gly Ala Gly Gly Val
705                 710                 715                 720

Glu Gly Ala Glu Trp Trp Ala Thr Gln Ala Phe His Gln Arg Asp Val
                725                 730                 735

Glu Gln Gly Arg Val Arg Tyr Leu Ser Thr Asp Pro Gln His His Ala
            740                 745                 750

Tyr Asp Thr Val Glu Asn Leu Ala Leu Glu Val Gln Val Gly Gln Glu
        755                 760                 765

Ile Leu Ser Asn Leu Ser Phe Pro Val Thr Ile Gln Arg Ala Thr Val
    770                 775                 780

Trp Met Leu Arg Leu Glu Pro Leu His Thr Gln Asn Thr Gln Gln Glu
785                 790                 795                 800

Thr Leu Thr Thr Ala His Leu Glu Ala Thr Leu Glu Glu Ala Gly Pro
                805                 810                 815

Ser Pro Pro Thr Phe His Tyr Glu Val Val Gln Ala Pro Arg Lys Gly
            820                 825                 830

Asn Leu Gln Leu Gln Gly Thr Arg Leu Ser Asp Gly Gln Gly Phe Thr
        835                 840                 845

Gln Asp Asp Ile Gln Ala Gly Arg Val Thr Tyr Gly Ala Thr Ala Arg
    850                 855                 860
```

-continued

```
Ala Ser Glu Ala Val Glu Asp Thr Phe Arg Phe Arg Val Thr Ala Pro
865                 870                 875                 880

Pro Tyr Phe Ser Pro Leu Tyr Thr Phe Pro Ile His Ile Gly Gly Asp
                885                 890                 895

Pro Asp Ala Pro Val Leu Thr Asn Val Leu Leu Val Val Pro Glu Gly
            900                 905                 910

Gly Glu Gly Val Leu Ser Ala Asp His Leu Phe Val Lys Ser Leu Asn
        915                 920                 925

Ser Ala Ser Tyr Leu Tyr Glu Val Met Glu Arg Pro Arg His Gly Arg
    930                 935                 940

Leu Ala Trp Arg Gly Thr Gln Asp Lys Thr Thr Met Val Thr Ser Phe
945                 950                 955                 960

Thr Asn Glu Asp Leu Leu Arg Gly Arg Leu Val Tyr Gln His Asp Asp
                965                 970                 975

Ser Glu Thr Thr Glu Asp Asp Ile Pro Phe Val Ala Thr Arg Gln Gly
            980                 985                 990

Glu Ser Ser Gly Asp Met Ala Trp  Glu Glu Val Arg Gly  Val Phe Arg
        995                 1000                1005

Val Ala  Ile Gln Pro Val Asn  Asp His Ala Pro Val  Gln Thr Ile
    1010                1015                1020

Ser Arg  Ile Phe His Val Ala  Arg Gly Gly Arg Arg  Leu Leu Thr
    1025                1030                1035

Thr Asp  Asp Val Ala Phe Ser  Asp Ala Asp Ser Gly  Phe Ala Asp
    1040                1045                1050

Ala Gln  Leu Val Leu Thr Arg  Lys Asp Leu Leu Phe  Gly Ser Ile
    1055                1060                1065

Val Ala  Val Asp Glu Pro Thr  Arg Pro Ile Tyr Arg  Phe Thr Gln
    1070                1075                1080

Glu Asp  Leu Arg Lys Arg Arg  Val Leu Phe Val His  Ser Gly Ala
    1085                1090                1095

Asp Arg  Gly Trp Ile Gln Leu  Gln Val Ser Asp Gly  Gln His Gln
    1100                1105                1110

Ala Thr  Ala Leu Leu Glu Val  Gln Ala Ser Glu Pro  Tyr Leu Arg
    1115                1120                1125

Val Ala  Asn Gly Ser Ser Leu  Val Val Pro Gln Gly  Gly Gln Gly
    1130                1135                1140

Thr Ile  Asp Thr Ala Val Leu  His Leu Asp Thr Asn  Leu Asp Ile
    1145                1150                1155

Arg Ser  Gly Asp Glu Val His  Tyr His Val Thr Ala  Gly Pro Arg
    1160                1165                1170

Trp Gly  Gln Leu Val Arg Ala  Gly Gln Pro Ala Thr  Ala Phe Ser
    1175                1180                1185

Gln Gln  Asp Leu Leu Asp Gly  Ala Val Leu Tyr Ser  His Asn Gly
    1190                1195                1200

Ser Leu  Ser Pro Arg Asp Thr  Met Ala Phe Ser Val  Glu Ala Gly
    1205                1210                1215

Pro Val  His Thr Asp Ala Thr  Leu Gln Val Thr Ile  Ala Leu Glu
    1220                1225                1230

Gly Pro  Leu Ala Pro Leu Lys  Leu Val Arg His Lys  Lys Ile Tyr
    1235                1240                1245

Val Phe  Gln Gly Glu Ala Ala  Glu Ile Arg Arg Asp  Gln Leu Glu
    1250                1255                1260

Ala Ala  Gln Glu Ala Val Pro  Pro Ala Asp Ile Val  Phe Ser Val
```

```
    1265                1270                1275

Lys Ser  Pro Pro Ser Ala Gly  Tyr Leu Val Met Val  Ser Arg Gly
    1280                1285                1290

Ala Leu  Ala Asp Glu Pro Pro  Ser Leu Asp Pro Val  Gln Ser Phe
    1295                1300                1305

Ser Gln  Glu Ala Val Asp Thr  Gly Arg Val Leu Tyr  Leu His Ser
    1310                1315                1320

Arg Pro  Glu Ala Trp Ser Asp  Ala Phe Ser Leu Asp  Val Ala Ser
    1325                1330                1335

Gly Leu  Gly Ala Pro Leu Glu  Gly Val Leu Val Glu  Leu Glu Val
    1340                1345                1350

Leu Pro  Ala Ala Ile Pro Leu  Glu Ala Gln Asn Phe  Ser Val Pro
    1355                1360                1365

Glu Gly  Gly Ser Leu Thr Leu  Ala Pro Pro Leu Leu  Arg Val Ser
    1370                1375                1380

Gly Pro  Tyr Phe Pro Thr Leu  Leu Gly Leu Ser Leu  Gln Val Leu
    1385                1390                1395

Glu Pro  Pro Gln His Gly Ala  Leu Gln Lys Glu Asp  Gly Pro Gln
    1400                1405                1410

Ala Arg  Thr Leu Ser Ala Phe  Ser Trp Arg Met Val  Glu Glu Gln
    1415                1420                1425

Leu Ile  Arg Tyr Val His Asp  Gly Ser Glu Thr Leu  Thr Asp Ser
    1430                1435                1440

Phe Val  Leu Met Ala Asn Ala  Ser Glu Met Asp Arg  Gln Ser His
    1445                1450                1455

Pro Val  Ala Phe Thr Val Thr  Val Leu Pro Val Asn  Asp Gln Pro
    1460                1465                1470

Pro Ile  Leu Thr Thr Asn Thr  Gly Leu Gln Met Trp  Glu Gly Ala
    1475                1480                1485

Thr Ala  Pro Ile Pro Ala Glu  Ala Leu Arg Ser Thr  Asp Gly Asp
    1490                1495                1500

Ser Gly  Ser Glu Asp Leu Val  Tyr Thr Ile Glu Gln  Pro Ser Asn
    1505                1510                1515

Gly Arg  Val Val Leu Arg Gly  Ala Pro Gly Thr Glu  Val Arg Ser
    1520                1525                1530

Phe Thr  Gln Ala Gln Leu Asp  Gly Gly Leu Val Leu  Phe Ser His
    1535                1540                1545

Arg Gly  Thr Leu Asp Gly Gly  Phe Arg Phe Arg Leu  Ser Asp Gly
    1550                1555                1560

Glu His  Thr Ser Pro Gly His  Phe Phe Arg Val Thr  Ala Gln Lys
    1565                1570                1575

Gln Val  Leu Leu Ser Leu Lys  Gly Ser Gln Thr Leu  Thr Val Cys
    1580                1585                1590

Pro Gly  Ser Val Gln Pro Leu  Ser Ser Gln Thr Leu  Arg Ala Ser
    1595                1600                1605

Ser Ser  Ala Gly Thr Asp Pro  Gln Leu Leu Leu Tyr  Arg Val Val
    1610                1615                1620

Arg Gly  Pro Gln Leu Gly Arg  Leu Phe His Ala Gln  Gln Asp Ser
    1625                1630                1635

Thr Gly  Glu Ala Leu Val Asn  Phe Thr Gln Ala Glu  Val Tyr Ala
    1640                1645                1650

Gly Asn  Ile Leu Tyr Glu His  Glu Met Pro Pro Glu  Pro Phe Trp
    1655                1660                1665
```

Glu Ala His Asp Thr Leu Glu Leu Gln Leu Ser Ser Pro Pro Ala
1670 1675 1680

Arg Asp Val Ala Ala Thr Leu Ala Val Ala Val Ser Phe Glu Ala
1685 1690 1695

Ala Cys Pro Gln Arg Pro Ser His Leu Trp Lys Asn Lys Gly Leu
1700 1705 1710

Trp Val Pro Glu Gly Gln Arg Ala Arg Ile Thr Val Ala Ala Leu
1715 1720 1725

Asp Ala Ser Asn Leu Leu Ala Ser Val Pro Ser Pro Gln Arg Ser
1730 1735 1740

Glu His Asp Val Leu Phe Gln Val Thr Gln Phe Pro Ser Arg Gly
1745 1750 1755

Gln Leu Leu Val Ser Glu Glu Pro Leu His Ala Gly Gln Pro His
1760 1765 1770

Phe Leu Gln Ser Gln Leu Ala Ala Gly Gln Leu Val Tyr Ala His
1775 1780 1785

Gly Gly Gly Gly Thr Gln Gln Asp Gly Phe His Phe Arg Ala His
1790 1795 1800

Leu Gln Gly Pro Ala Gly Ala Ser Val Ala Gly Pro Gln Thr Ser
1805 1810 1815

Glu Ala Phe Ala Ile Thr Val Arg Asp Val Asn Glu Arg Pro Pro
1820 1825 1830

Gln Pro Gln Ala Ser Val Pro Leu Arg Leu Thr Arg Gly Ser Arg
1835 1840 1845

Ala Pro Ile Ser Arg Ala Gln Leu Ser Val Val Asp Pro Asp Ser
1850 1855 1860

Ala Pro Gly Glu Ile Glu Tyr Glu Val Gln Arg Ala Pro His Asn
1865 1870 1875

Gly Phe Leu Ser Leu Val Gly Gly Gly Leu Gly Pro Val Thr Arg
1880 1885 1890

Phe Thr Gln Ala Asp Val Asp Ser Gly Arg Leu Ala Phe Val Ala
1895 1900 1905

Asn Gly Ser Ser Val Ala Gly Ile Phe Gln Leu Ser Met Ser Asp
1910 1915 1920

Gly Ala Ser Pro Pro Leu Pro Met Ser Leu Ala Val Asp Ile Leu
1925 1930 1935

Pro Ser Ala Ile Glu Val Gln Leu Arg Ala Pro Leu Glu Val Pro
1940 1945 1950

Gln Ala Leu Gly Arg Ser Ser Leu Ser Gln Gln Gln Leu Arg Val
1955 1960 1965

Val Ser Asp Arg Glu Glu Pro Glu Ala Ala Tyr Arg Leu Ile Gln
1970 1975 1980

Gly Pro Gln Tyr Gly His Leu Leu Val Gly Gly Arg Pro Thr Ser
1985 1990 1995

Ala Phe Ser Gln Phe Gln Ile Asp Gln Gly Glu Val Val Phe Ala
2000 2005 2010

Phe Thr Asn Phe Ser Ser Ser His Asp His Phe Arg Val Leu Ala
2015 2020 2025

Leu Ala Arg Gly Val Asn Ala Ser Ala Val Val Asn Val Thr Val
2030 2035 2040

Arg Ala Leu Leu His Val Trp Ala Gly Gly Pro Trp Pro Gln Gly
2045 2050 2055

-continued

Ala Thr Leu Arg Leu Asp Pro Thr Val Leu Asp Ala Gly Glu Leu
2060 2065 2070

Ala Asn Arg Thr Gly Ser Val Pro Arg Phe Arg Leu Leu Glu Gly
2075 2080 2085

Pro Arg His Gly Arg Val Val Arg Val Pro Arg Ala Arg Thr Glu
2090 2095 2100

Pro Gly Gly Ser Gln Leu Val Glu Gln Phe Thr Gln Gln Asp Leu
2105 2110 2115

Glu Asp Gly Arg Leu Gly Leu Glu Val Gly Arg Pro Glu Gly Arg
2120 2125 2130

Ala Pro Gly Pro Ala Gly Asp Ser Leu Thr Leu Glu Leu Trp Ala
2135 2140 2145

Gln Gly Val Pro Pro Ala Val Ala Ser Leu Asp Phe Ala Thr Glu
2150 2155 2160

Pro Tyr Asn Ala Ala Arg Pro Tyr Ser Val Ala Leu Leu Ser Val
2165 2170 2175

Pro Glu Ala Ala Arg Thr Glu Ala Gly Lys Pro Glu Ser Ser Thr
2180 2185 2190

Pro Thr Gly Glu Pro Gly Pro Met Ala Ser Ser Pro Glu Pro Ala
2195 2200 2205

Val Ala Lys Gly Gly Phe Leu Ser Phe Leu Glu Ala Asn Met Phe
2210 2215 2220

Ser Val Ile Ile Pro Met Cys Leu Val Leu Leu Leu Leu Ala Leu
2225 2230 2235

Ile Leu Pro Leu Leu Phe Tyr Leu Arg Lys Arg Asn Lys Thr Gly
2240 2245 2250

Lys His Asp Val Gln Val Leu Thr Ala Lys Pro Arg Asn Gly Leu
2255 2260 2265

Ala Gly Asp Thr Glu Thr Phe Arg Lys Val Glu Pro Gly Gln Ala
2270 2275 2280

Ile Pro Leu Thr Ala Val Pro Gly Gln Gly Pro Pro Pro Gly Gly
2285 2290 2295

Gln Pro Asp Pro Glu Leu Leu Gln Phe Cys Arg Thr Pro Asn Pro
2300 2305 2310

Ala Leu Lys Asn Gly Gln Tyr Trp Val
2315 2320

<210> SEQ ID NO 199
<211> LENGTH: 1210
<212> TYPE: PRT
<213> ORGANISM: Homo sapiens

<400> SEQUENCE: 199

Met Arg Pro Ser Gly Thr Ala Gly Ala Ala Leu Leu Ala Leu Leu Ala
1 5 10 15

Ala Leu Cys Pro Ala Ser Arg Ala Leu Glu Glu Lys Lys Val Cys Gln
20 25 30

Gly Thr Ser Asn Lys Leu Thr Gln Leu Gly Thr Phe Glu Asp His Phe
35 40 45

Leu Ser Leu Gln Arg Met Phe Asn Asn Cys Glu Val Val Leu Gly Asn
50 55 60

Leu Glu Ile Thr Tyr Val Gln Arg Asn Tyr Asp Leu Ser Phe Leu Lys
65 70 75 80

Thr Ile Gln Glu Val Ala Gly Tyr Val Leu Ile Ala Leu Asn Thr Val
85 90 95

-continued

```
Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510
```

-continued

```
Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
    770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
```

```
    930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala  Leu Met Asp Glu Glu  Asp Met Asp
        995                 1000                 1005

Asp Val  Val Asp Ala Asp Glu  Tyr Leu Ile Pro Gln  Gln Gly Phe
    1010                 1015                 1020

Phe Ser  Ser Pro Ser Thr Ser  Arg Thr Pro Leu Leu  Ser Ser Leu
    1025                 1030                 1035

Ser Ala  Thr Ser Asn Asn Ser  Thr Val Ala Cys Ile  Asp Arg Asn
    1040                 1045                 1050

Gly Leu  Gln Ser Cys Pro Ile  Lys Glu Asp Ser Phe  Leu Gln Arg
    1055                 1060                 1065

Tyr Ser  Ser Asp Pro Thr Gly  Ala Leu Thr Glu Asp  Ser Ile Asp
    1070                 1075                 1080

Asp Thr  Phe Leu Pro Val Pro  Glu Tyr Ile Asn Gln  Ser Val Pro
    1085                 1090                 1095

Lys Arg  Pro Ala Gly Ser Val  Gln Asn Pro Val Tyr  His Asn Gln
    1100                 1105                 1110

Pro Leu  Asn Pro Ala Pro Ser  Arg Asp Pro His Tyr  Gln Asp Pro
    1115                 1120                 1125

His Ser  Thr Ala Val Gly Asn  Pro Glu Tyr Leu Asn  Thr Val Gln
    1130                 1135                 1140

Pro Thr  Cys Val Asn Ser Thr  Phe Asp Ser Pro Ala  His Trp Ala
    1145                 1150                 1155

Gln Lys  Gly Ser His Gln Ile  Ser Leu Asp Asn Pro  Asp Tyr Gln
    1160                 1165                 1170

Gln Asp  Phe Phe Pro Lys Glu  Ala Lys Pro Asn Gly  Ile Phe Lys
    1175                 1180                 1185

Gly Ser  Thr Ala Glu Asn Ala  Glu Tyr Leu Arg Val  Ala Pro Gln
    1190                 1195                 1200

Ser Ser  Glu Phe Ile Gly Ala
    1205                 1210


<210> SEQ ID NO 200
<211> LENGTH: 556
<212> TYPE: PRT
<213> ORGANISM: Homo sapiens

<400> SEQUENCE: 200

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80
```

-continued

```
Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Phe Lys Val
                325                 330                 335

Thr Pro Pro Pro Gly Ser Gly Pro Gln Asn Gln Tyr Gly Asn Val Leu
            340                 345                 350

Ser Leu Pro Thr Pro Thr Ser Gly Leu Gly Arg Ala Gln Arg Trp Ala
        355                 360                 365

Ala Gly Leu Gly Gly Thr Ala Pro Ser Tyr Gly Asn Pro Ser Ser Asp
    370                 375                 380

Val Gln Ala Asp Gly Ala Leu Gly Ser Arg Ser Pro Pro Gly Val Gly
385                 390                 395                 400

Pro Glu Glu Glu Glu Gly Glu Gly Tyr Glu Glu Pro Asp Ser Glu Glu
                405                 410                 415

Asp Ser Glu Phe Tyr Glu Asn Asp Ser Asn Leu Gly Gln Asp Gln Leu
            420                 425                 430

Ser Gln Asp Gly Ser Gly Tyr Glu Asn Pro Glu Asp Glu Pro Leu Gly
        435                 440                 445

Pro Glu Asp Glu Asp Ser Phe Ser Asn Ala Glu Ser Tyr Glu Asn Glu
    450                 455                 460

Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Gly
                485                 490                 495

Ser Gln Ser Tyr Glu Asp Met Arg Gly Ile Leu Tyr Ala Ala Pro Gln
```

```
            500                 505                 510

Leu Arg Ser Ile Arg Gly Gln Pro Gly Pro Asn His Glu Glu Asp Ala
        515                 520                 525

Asp Ser Tyr Glu Asn Met Asp Asn Pro Asp Gly Pro Asp Pro Ala Trp
    530                 535                 540

Gly Gly Gly Gly Arg Met Gly Thr Trp Ser Thr Arg
545                 550                 555


<210> SEQ ID NO 201
<211> LENGTH: 297
<212> TYPE: PRT
<213> ORGANISM: Homo sapiens

<400> SEQUENCE: 201

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
    290                 295


<210> SEQ ID NO 202
<211> LENGTH: 364
```

<212> TYPE: PRT
<213> ORGANISM: Homo sapiens

<400> SEQUENCE: 202

Met Pro Leu Leu Leu Leu Leu Pro Leu Leu Trp Ala Gly Ala Leu Ala
1               5                   10                  15

Met Asp Pro Asn Phe Trp Leu Gln Val Gln Glu Ser Val Thr Val Gln
            20                  25                  30

Glu Gly Leu Cys Val Leu Val Pro Cys Thr Phe Phe His Pro Ile Pro
        35                  40                  45

Tyr Tyr Asp Lys Asn Ser Pro Val His Gly Tyr Trp Phe Arg Glu Gly
    50                  55                  60

Ala Ile Ile Ser Arg Asp Ser Pro Val Ala Thr Asn Lys Leu Asp Gln
65                  70                  75                  80

Glu Val Gln Glu Glu Thr Gln Gly Arg Phe Arg Leu Leu Gly Asp Pro
                85                  90                  95

Ser Arg Asn Asn Cys Ser Leu Ser Ile Val Asp Ala Arg Arg Arg Asp
            100                 105                 110

Asn Gly Ser Tyr Phe Phe Arg Met Glu Arg Gly Ser Thr Lys Tyr Ser
        115                 120                 125

Tyr Lys Ser Pro Gln Leu Ser Val His Val Thr Asp Leu Thr His Arg
    130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
            180                 185                 190

His Ser Ser Val Leu Ile Ile Thr Pro Arg Pro Gln Asp His Gly Thr
        195                 200                 205

Asn Leu Thr Cys Gln Val Lys Phe Ala Gly Ala Gly Val Thr Thr Glu
    210                 215                 220

Arg Thr Ile Gln Leu Asn Val Thr Tyr Val Pro Gln Asn Pro Thr Thr
225                 230                 235                 240

Gly Ile Phe Pro Gly Asp Gly Ser Gly Lys Gln Glu Thr Arg Ala Gly
                245                 250                 255

Val Val His Gly Ala Ile Gly Gly Ala Gly Val Thr Ala Leu Leu Ala
            260                 265                 270

Leu Cys Leu Cys Leu Ile Phe Phe Ile Val Lys Thr His Arg Arg Lys
        275                 280                 285

Ala Ala Arg Thr Ala Val Gly Arg Asn Asp Thr His Pro Thr Thr Gly
    290                 295                 300

Ser Ala Ser Pro Lys His Gln Lys Lys Ser Lys Leu His Gly Pro Thr
305                 310                 315                 320

Glu Thr Ser Ser Cys Ser Gly Ala Ala Pro Thr Val Glu Met Asp Glu
                325                 330                 335

Glu Leu His Tyr Ala Ser Leu Asn Phe His Gly Met Asn Pro Ser Lys
            340                 345                 350

Asp Thr Ser Thr Glu Tyr Ser Glu Val Arg Thr Gln
        355                 360

<210> SEQ ID NO 203
<211> LENGTH: 205
<212> TYPE: PRT
<213> ORGANISM: Homo sapiens

<400> SEQUENCE: 203

Met Thr Pro Pro Glu Arg Leu Phe Leu Pro Arg Val Cys Gly Thr Thr
1               5                   10                  15

Leu His Leu Leu Leu Leu Gly Leu Leu Leu Val Leu Leu Pro Gly Ala
            20                  25                  30

Gln Gly Leu Pro Gly Val Gly Leu Thr Pro Ser Ala Ala Gln Thr Ala
        35                  40                  45

Arg Gln His Pro Lys Met His Leu Ala His Ser Thr Leu Lys Pro Ala
    50                  55                  60

Ala His Leu Ile Gly Asp Pro Ser Lys Gln Asn Ser Leu Leu Trp Arg
65                  70                  75                  80

Ala Asn Thr Asp Arg Ala Phe Leu Gln Asp Gly Phe Ser Leu Ser Asn
                85                  90                  95

Asn Ser Leu Leu Val Pro Thr Ser Gly Ile Tyr Phe Val Tyr Ser Gln
            100                 105                 110

Val Val Phe Ser Gly Lys Ala Tyr Ser Pro Lys Ala Thr Ser Ser Pro
        115                 120                 125

Leu Tyr Leu Ala His Glu Val Gln Leu Phe Ser Ser Gln Tyr Pro Phe
    130                 135                 140

His Val Pro Leu Leu Ser Ser Gln Lys Met Val Tyr Pro Gly Leu Gln
145                 150                 155                 160

Glu Pro Trp Leu His Ser Met Tyr His Gly Ala Ala Phe Gln Leu Thr
                165                 170                 175

Gln Gly Asp Gln Leu Ser Thr His Thr Asp Gly Ile Pro His Leu Val
            180                 185                 190

Leu Ser Pro Ser Thr Val Phe Phe Gly Ala Phe Ala Leu
        195                 200                 205

<210> SEQ ID NO 204
<211> LENGTH: 233
<212> TYPE: PRT
<213> ORGANISM: Homo sapiens

<400> SEQUENCE: 204

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

```
Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230


<210> SEQ ID NO 205
<211> LENGTH: 244
<212> TYPE: PRT
<213> ORGANISM: Homo sapiens

<400> SEQUENCE: 205

Met Gly Ala Leu Gly Leu Glu Gly Arg Gly Gly Arg Leu Gln Gly Arg
1               5                   10                  15

Gly Ser Leu Leu Leu Ala Val Ala Gly Ala Thr Ser Leu Val Thr Leu
            20                  25                  30

Leu Leu Ala Val Pro Ile Thr Val Leu Ala Val Leu Ala Leu Val Pro
        35                  40                  45

Gln Asp Gln Gly Gly Leu Val Thr Glu Thr Ala Asp Pro Gly Ala Gln
    50                  55                  60

Ala Gln Gln Gly Leu Gly Phe Gln Lys Leu Pro Glu Glu Glu Pro Glu
65                  70                  75                  80

Thr Asp Leu Ser Pro Gly Leu Pro Ala Ala His Leu Ile Gly Ala Pro
                85                  90                  95

Leu Lys Gly Gln Gly Leu Gly Trp Glu Thr Thr Lys Glu Gln Ala Phe
            100                 105                 110

Leu Thr Ser Gly Thr Gln Phe Ser Asp Ala Glu Gly Leu Ala Leu Pro
        115                 120                 125

Gln Asp Gly Leu Tyr Tyr Leu Tyr Cys Leu Val Gly Tyr Arg Gly Arg
    130                 135                 140

Ala Pro Pro Gly Gly Gly Asp Pro Gln Gly Arg Ser Val Thr Leu Arg
145                 150                 155                 160

Ser Ser Leu Tyr Arg Ala Gly Gly Ala Tyr Gly Pro Gly Thr Pro Glu
                165                 170                 175

Leu Leu Leu Glu Gly Ala Glu Thr Val Thr Pro Val Leu Asp Pro Ala
            180                 185                 190

Arg Arg Gln Gly Tyr Gly Pro Leu Trp Tyr Thr Ser Val Gly Phe Gly
        195                 200                 205

Gly Leu Val Gln Leu Arg Arg Gly Glu Arg Val Tyr Val Asn Ile Ser
    210                 215                 220

His Pro Asp Met Val Asp Phe Ala Arg Gly Lys Thr Phe Phe Gly Ala
225                 230                 235                 240

Val Met Val Gly


<210> SEQ ID NO 206
<211> LENGTH: 183
<212> TYPE: PRT
<213> ORGANISM: Homo sapiens

<400> SEQUENCE: 206
```

```
Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
        35                  40                  45

Ala Leu Gln Val Ser His Arg Tyr Pro Arg Ile Gln Ser Ile Lys Val
    50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
        115                 120                 125

Leu Lys Lys Val Arg Ser Val Asn Ser Leu Met Val Ala Ser Leu Thr
    130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180


<210> SEQ ID NO 207
<211> LENGTH: 261
<212> TYPE: PRT
<213> ORGANISM: Homo sapiens

<400> SEQUENCE: 207

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190
```

```
Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260


<210> SEQ ID NO 208
<211> LENGTH: 281
<212> TYPE: PRT
<213> ORGANISM: Homo sapiens

<400> SEQUENCE: 208

Met Gln Gln Pro Phe Asn Tyr Pro Tyr Pro Gln Ile Tyr Trp Val Asp
1               5                   10                  15

Ser Ser Ala Ser Ser Pro Trp Ala Pro Pro Gly Thr Val Leu Pro Cys
            20                  25                  30

Pro Thr Ser Val Pro Arg Arg Pro Gly Gln Arg Arg Pro Pro Pro Pro
        35                  40                  45

Pro Pro Pro Pro Pro Leu Pro Pro Pro Pro Pro Pro Pro Pro Leu Pro
    50                  55                  60

Pro Leu Pro Leu Pro Pro Leu Lys Lys Arg Gly Asn His Ser Thr Gly
65                  70                  75                  80

Leu Cys Leu Leu Val Met Phe Phe Met Val Leu Val Ala Leu Val Gly
                85                  90                  95

Leu Gly Leu Gly Met Phe Gln Leu Phe His Leu Gln Lys Glu Leu Ala
            100                 105                 110

Glu Leu Arg Glu Ser Thr Ser Gln Met His Thr Ala Ser Ser Leu Glu
        115                 120                 125

Lys Gln Ile Gly His Pro Ser Pro Pro Pro Glu Lys Lys Glu Leu Arg
    130                 135                 140

Lys Val Ala His Leu Thr Gly Lys Ser Asn Ser Arg Ser Met Pro Leu
145                 150                 155                 160

Glu Trp Glu Asp Thr Tyr Gly Ile Val Leu Leu Ser Gly Val Lys Tyr
                165                 170                 175

Lys Lys Gly Gly Leu Val Ile Asn Glu Thr Gly Leu Tyr Phe Val Tyr
            180                 185                 190

Ser Lys Val Tyr Phe Arg Gly Gln Ser Cys Asn Asn Leu Pro Leu Ser
        195                 200                 205

His Lys Val Tyr Met Arg Asn Ser Lys Tyr Pro Gln Asp Leu Val Met
    210                 215                 220

Met Glu Gly Lys Met Met Ser Tyr Cys Thr Thr Gly Gln Met Trp Ala
225                 230                 235                 240

Arg Ser Ser Tyr Leu Gly Ala Val Phe Asn Leu Thr Ser Ala Asp His
                245                 250                 255

Leu Tyr Val Asn Val Ser Glu Leu Ser Leu Val Asn Phe Glu Glu Ser
            260                 265                 270

Gln Thr Phe Phe Gly Leu Tyr Lys Leu
        275                 280
```

```
<210> SEQ ID NO 209
<211> LENGTH: 193
<212> TYPE: PRT
<213> ORGANISM: Homo sapiens

<400> SEQUENCE: 209

Met Pro Glu Glu Gly Ser Gly Cys Ser Val Arg Arg Arg Pro Tyr Gly
1               5                   10                  15

Cys Val Leu Arg Ala Ala Leu Val Pro Leu Val Ala Gly Leu Val Ile
            20                  25                  30

Cys Leu Val Val Cys Ile Gln Arg Phe Ala Gln Ala Gln Gln Gln Leu
        35                  40                  45

Pro Leu Glu Ser Leu Gly Trp Asp Val Ala Glu Leu Gln Leu Asn His
    50                  55                  60

Thr Gly Pro Gln Gln Asp Pro Arg Leu Tyr Trp Gln Gly Gly Pro Ala
65                  70                  75                  80

Leu Gly Arg Ser Phe Leu His Gly Pro Glu Leu Asp Lys Gly Gln Leu
                85                  90                  95

Arg Ile His Arg Asp Gly Ile Tyr Met Val His Ile Gln Val Thr Leu
            100                 105                 110

Ala Ile Cys Ser Ser Thr Thr Ala Ser Arg His His Pro Thr Thr Leu
        115                 120                 125

Ala Val Gly Ile Cys Ser Pro Ala Ser Arg Ser Ile Ser Leu Leu Arg
    130                 135                 140

Leu Ser Phe His Gln Gly Cys Thr Ile Ala Ser Gln Arg Leu Thr Pro
145                 150                 155                 160

Leu Ala Arg Gly Asp Thr Leu Cys Thr Asn Leu Thr Gly Thr Leu Leu
                165                 170                 175

Pro Ser Arg Asn Thr Asp Glu Thr Phe Phe Gly Val Gln Trp Val Arg
            180                 185                 190

Pro


<210> SEQ ID NO 210
<211> LENGTH: 234
<212> TYPE: PRT
<213> ORGANISM: Homo sapiens

<400> SEQUENCE: 210

Met Asp Pro Gly Leu Gln Gln Ala Leu Asn Gly Met Ala Pro Pro Gly
1               5                   10                  15

Asp Thr Ala Met His Val Pro Ala Gly Ser Val Ala Ser His Leu Gly
            20                  25                  30

Thr Thr Ser Arg Ser Tyr Phe Tyr Leu Thr Thr Ala Thr Leu Ala Leu
        35                  40                  45

Cys Leu Val Phe Thr Val Ala Thr Ile Met Val Leu Val Val Gln Arg
    50                  55                  60

Thr Asp Ser Ile Pro Asn Ser Pro Asp Asn Val Pro Leu Lys Gly Gly
65                  70                  75                  80

Asn Cys Ser Glu Asp Leu Leu Cys Ile Leu Lys Arg Ala Pro Phe Lys
                85                  90                  95

Lys Ser Trp Ala Tyr Leu Gln Val Ala Lys His Leu Asn Lys Thr Lys
            100                 105                 110

Leu Ser Trp Asn Lys Asp Gly Ile Leu His Gly Val Arg Tyr Gln Asp
        115                 120                 125

Gly Asn Leu Val Ile Gln Phe Pro Gly Leu Tyr Phe Ile Ile Cys Gln
    130                 135                 140
```

```
Leu Gln Phe Leu Val Gln Cys Pro Asn Asn Ser Val Asp Leu Lys Leu
145                 150                 155                 160

Glu Leu Leu Ile Asn Lys His Ile Lys Lys Gln Ala Leu Val Thr Val
                165                 170                 175

Cys Glu Ser Gly Met Gln Thr Lys His Val Tyr Gln Asn Leu Ser Gln
            180                 185                 190

Phe Leu Leu Asp Tyr Leu Gln Val Asn Thr Thr Ile Ser Val Asn Val
        195                 200                 205

Asp Thr Phe Gln Tyr Ile Asp Thr Ser Thr Phe Pro Leu Glu Asn Val
    210                 215                 220

Leu Ser Ile Phe Leu Tyr Ser Asn Ser Asp
225                 230


<210> SEQ ID NO 211
<211> LENGTH: 254
<212> TYPE: PRT
<213> ORGANISM: Homo sapiens

<400> SEQUENCE: 211

Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
            20                  25                  30

Ala Gly Leu Leu Leu Leu Leu Leu Leu Ala Ala Ala Cys Ala Val Phe
        35                  40                  45

Leu Ala Cys Pro Trp Ala Val Ser Gly Ala Arg Ala Ser Pro Gly Ser
    50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
                85                  90                  95

Ala Gln Asn Val Leu Leu Ile Asp Gly Pro Leu Ser Trp Tyr Ser Asp
            100                 105                 110

Pro Gly Leu Ala Gly Val Ser Leu Thr Gly Gly Leu Ser Tyr Lys Glu
        115                 120                 125

Asp Thr Lys Glu Leu Val Val Ala Lys Ala Gly Val Tyr Tyr Val Phe
    130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
            180                 185                 190

Arg Asn Ser Ala Phe Gly Phe Gln Gly Arg Leu Leu His Leu Ser Ala
        195                 200                 205

Gly Gln Arg Leu Gly Val His Leu His Thr Glu Ala Arg Ala Arg His
    210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250


<210> SEQ ID NO 212
<211> LENGTH: 281
<212> TYPE: PRT
```

<213> ORGANISM: Homo sapiens

<400> SEQUENCE: 212

Met Ala Met Met Glu Val Gln Gly Gly Pro Ser Leu Gly Gln Thr Cys
1 5 10 15

Val Leu Ile Val Ile Phe Thr Val Leu Leu Gln Ser Leu Cys Val Ala
20 25 30

Val Thr Tyr Val Tyr Phe Thr Asn Glu Leu Lys Gln Met Gln Asp Lys
35 40 45

Tyr Ser Lys Ser Gly Ile Ala Cys Phe Leu Lys Glu Asp Asp Ser Tyr
50 55 60

Trp Asp Pro Asn Asp Glu Glu Ser Met Asn Ser Pro Cys Trp Gln Val
65 70 75 80

Lys Trp Gln Leu Arg Gln Leu Val Arg Lys Met Ile Leu Arg Thr Ser
85 90 95

Glu Glu Thr Ile Ser Thr Val Gln Glu Lys Gln Gln Asn Ile Ser Pro
100 105 110

Leu Val Arg Glu Arg Gly Pro Gln Arg Val Ala Ala His Ile Thr Gly
115 120 125

Thr Arg Gly Arg Ser Asn Thr Leu Ser Ser Pro Asn Ser Lys Asn Glu
130 135 140

Lys Ala Leu Gly Arg Lys Ile Asn Ser Trp Glu Ser Ser Arg Ser Gly
145 150 155 160

His Ser Phe Leu Ser Asn Leu His Leu Arg Asn Gly Glu Leu Val Ile
165 170 175

His Glu Lys Gly Phe Tyr Tyr Ile Tyr Ser Gln Thr Tyr Phe Arg Phe
180 185 190

Gln Glu Glu Ile Lys Glu Asn Thr Lys Asn Asp Lys Gln Met Val Gln
195 200 205

Tyr Ile Tyr Lys Tyr Thr Ser Tyr Pro Asp Pro Ile Leu Leu Met Lys
210 215 220

Ser Ala Arg Asn Ser Cys Trp Ser Lys Asp Ala Glu Tyr Gly Leu Tyr
225 230 235 240

Ser Ile Tyr Gln Gly Gly Ile Phe Glu Leu Lys Glu Asn Asp Arg Ile
245 250 255

Phe Val Ser Val Thr Asn Glu His Leu Ile Asp Met Asp His Glu Ala
260 265 270

Ser Phe Phe Gly Ala Phe Leu Val Gly
275 280

<210> SEQ ID NO 213
<211> LENGTH: 317
<212> TYPE: PRT
<213> ORGANISM: Homo sapiens

<400> SEQUENCE: 213

Met Arg Arg Ala Ser Arg Asp Tyr Thr Lys Tyr Leu Arg Gly Ser Glu
1 5 10 15

Glu Met Gly Gly Gly Pro Gly Ala Pro His Glu Gly Pro Leu His Ala
20 25 30

Pro Pro Pro Pro Ala Pro His Gln Pro Pro Ala Ala Ser Arg Ser Met
35 40 45

Phe Val Ala Leu Leu Gly Leu Gly Leu Gly Gln Val Val Cys Ser Val
50 55 60

Ala Leu Phe Phe Tyr Phe Arg Ala Gln Met Asp Pro Asn Arg Ile Ser

```
65                  70                  75                  80

Glu Asp Gly Thr His Cys Ile Tyr Arg Ile Leu Arg Leu His Glu Asn
                85                  90                  95

Ala Asp Phe Gln Asp Thr Thr Leu Glu Ser Gln Asp Thr Lys Leu Ile
            100                 105                 110

Pro Asp Ser Cys Arg Arg Ile Lys Gln Ala Phe Gln Gly Ala Val Gln
        115                 120                 125

Lys Glu Leu Gln His Ile Val Gly Ser Gln His Ile Arg Ala Glu Lys
    130                 135                 140

Ala Met Val Asp Gly Ser Trp Leu Asp Leu Ala Lys Arg Ser Lys Leu
145                 150                 155                 160

Glu Ala Gln Pro Phe Ala His Leu Thr Ile Asn Ala Thr Asp Ile Pro
                165                 170                 175

Ser Gly Ser His Lys Val Ser Leu Ser Ser Trp Tyr His Asp Arg Gly
            180                 185                 190

Trp Ala Lys Ile Ser Asn Met Thr Phe Ser Asn Gly Lys Leu Ile Val
        195                 200                 205

Asn Gln Asp Gly Phe Tyr Tyr Leu Tyr Ala Asn Ile Cys Phe Arg His
    210                 215                 220

His Glu Thr Ser Gly Asp Leu Ala Thr Glu Tyr Leu Gln Leu Met Val
225                 230                 235                 240

Tyr Val Thr Lys Thr Ser Ile Lys Ile Pro Ser Ser His Thr Leu Met
                245                 250                 255

Lys Gly Gly Ser Thr Lys Tyr Trp Ser Gly Asn Ser Glu Phe His Phe
            260                 265                 270

Tyr Ser Ile Asn Val Gly Gly Phe Phe Lys Leu Arg Ser Gly Glu Glu
        275                 280                 285

Ile Ser Ile Glu Val Ser Asn Pro Ser Leu Leu Asp Pro Asp Gln Asp
    290                 295                 300

Ala Thr Tyr Phe Gly Ala Phe Lys Val Arg Asp Ile Asp
305                 310                 315


<210> SEQ ID NO 214
<211> LENGTH: 249
<212> TYPE: PRT
<213> ORGANISM: Homo sapiens

<400> SEQUENCE: 214

Met Ala Ala Arg Arg Ser Gln Arg Arg Arg Gly Arg Arg Gly Glu Pro
1               5                   10                  15

Gly Thr Ala Leu Leu Val Pro Leu Ala Leu Gly Leu Gly Leu Ala Leu
            20                  25                  30

Ala Cys Leu Gly Leu Leu Leu Ala Val Val Ser Leu Gly Ser Arg Ala
        35                  40                  45

Ser Leu Ser Ala Gln Glu Pro Ala Gln Glu Glu Leu Val Ala Glu Glu
    50                  55                  60

Asp Gln Asp Pro Ser Glu Leu Asn Pro Gln Thr Glu Glu Ser Gln Asp
65                  70                  75                  80

Pro Ala Pro Phe Leu Asn Arg Leu Val Arg Pro Arg Arg Ser Ala Pro
                85                  90                  95

Lys Gly Arg Lys Thr Arg Ala Arg Arg Ala Ile Ala Ala His Tyr Glu
            100                 105                 110

Val His Pro Arg Pro Gly Gln Asp Gly Ala Gln Ala Gly Val Asp Gly
        115                 120                 125
```

-continued

```
Thr Val Ser Gly Trp Glu Glu Ala Arg Ile Asn Ser Ser Ser Pro Leu
    130                 135                 140

Arg Tyr Asn Arg Gln Ile Gly Glu Phe Ile Val Thr Arg Ala Gly Leu
145                 150                 155                 160

Tyr Tyr Leu Tyr Cys Gln Val His Phe Asp Glu Gly Lys Ala Val Tyr
                165                 170                 175

Leu Lys Leu Asp Leu Leu Val Asp Gly Val Leu Ala Leu Arg Cys Leu
            180                 185                 190

Glu Glu Phe Ser Ala Thr Ala Ala Ser Ser Leu Gly Pro Gln Leu Arg
        195                 200                 205

Leu Cys Gln Val Ser Gly Leu Leu Ala Leu Arg Pro Gly Ser Ser Leu
    210                 215                 220

Arg Ile Arg Thr Leu Pro Trp Ala His Leu Lys Ala Ala Pro Phe Leu
225                 230                 235                 240

Thr Tyr Phe Gly Leu Phe Gln Val His
                245


<210> SEQ ID NO 215
<211> LENGTH: 250
<212> TYPE: PRT
<213> ORGANISM: Homo sapiens

<400> SEQUENCE: 215

Met Pro Ala Ser Ser Pro Phe Leu Leu Ala Pro Lys Gly Pro Pro Gly
1               5                   10                  15

Asn Met Gly Gly Pro Val Arg Glu Pro Ala Leu Ser Val Ala Leu Trp
            20                  25                  30

Leu Ser Trp Gly Ala Ala Leu Gly Ala Val Ala Cys Ala Met Ala Leu
        35                  40                  45

Leu Thr Gln Gln Thr Glu Leu Gln Ser Leu Arg Arg Glu Val Ser Arg
    50                  55                  60

Leu Gln Gly Thr Gly Gly Pro Ser Gln Asn Gly Glu Gly Tyr Pro Trp
65                  70                  75                  80

Gln Ser Leu Pro Glu Gln Ser Ser Asp Ala Leu Glu Ala Trp Glu Asn
                85                  90                  95

Gly Glu Arg Ser Arg Lys Arg Arg Ala Val Leu Thr Gln Lys Gln Lys
            100                 105                 110

Lys Gln His Ser Val Leu His Leu Val Pro Ile Asn Ala Thr Ser Lys
        115                 120                 125

Asp Asp Ser Asp Val Thr Glu Val Met Trp Gln Pro Ala Leu Arg Arg
    130                 135                 140

Gly Arg Gly Leu Gln Ala Gln Gly Tyr Gly Val Arg Ile Gln Asp Ala
145                 150                 155                 160

Gly Val Tyr Leu Leu Tyr Ser Gln Val Leu Phe Gln Asp Val Thr Phe
                165                 170                 175

Thr Met Gly Gln Val Val Ser Arg Glu Gly Gln Gly Arg Gln Glu Thr
            180                 185                 190

Leu Phe Arg Cys Ile Arg Ser Met Pro Ser His Pro Asp Arg Ala Tyr
        195                 200                 205

Asn Ser Cys Tyr Ser Ala Gly Val Phe His Leu His Gln Gly Asp Ile
    210                 215                 220

Leu Ser Val Ile Ile Pro Arg Ala Arg Ala Lys Leu Asn Leu Ser Pro
225                 230                 235                 240

His Gly Thr Phe Leu Gly Phe Val Lys Leu
                245                 250
```

<210> SEQ ID NO 216
<211> LENGTH: 285
<212> TYPE: PRT
<213> ORGANISM: Homo sapiens

<400> SEQUENCE: 216

```
Met Asp Asp Ser Thr Glu Arg Glu Gln Ser Arg Leu Thr Ser Cys Leu
1               5                   10                  15

Lys Lys Arg Glu Glu Met Lys Leu Lys Glu Cys Val Ser Ile Leu Pro
            20                  25                  30

Arg Lys Glu Ser Pro Ser Val Arg Ser Ser Lys Asp Gly Lys Leu Leu
        35                  40                  45

Ala Ala Thr Leu Leu Leu Ala Leu Leu Ser Cys Cys Leu Thr Val Val
    50                  55                  60

Ser Phe Tyr Gln Val Ala Ala Leu Gln Gly Asp Leu Ala Ser Leu Arg
65                  70                  75                  80

Ala Glu Leu Gln Gly His His Ala Glu Lys Leu Pro Ala Gly Ala Gly
                85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Glu Gly Asn Ser Ser Gln Asn
        115                 120                 125

Ser Arg Asn Lys Arg Ala Val Gln Gly Pro Glu Glu Thr Val Thr Gln
    130                 135                 140

Asp Cys Leu Gln Leu Ile Ala Asp Ser Glu Thr Pro Thr Ile Gln Lys
145                 150                 155                 160

Gly Ser Tyr Thr Phe Val Pro Trp Leu Leu Ser Phe Lys Arg Gly Ser
                165                 170                 175

Ala Leu Glu Glu Lys Glu Asn Lys Ile Leu Val Lys Glu Thr Gly Tyr
            180                 185                 190

Phe Phe Ile Tyr Gly Gln Val Leu Tyr Thr Asp Lys Thr Tyr Ala Met
        195                 200                 205

Gly His Leu Ile Gln Arg Lys Lys Val His Val Phe Gly Asp Glu Leu
    210                 215                 220

Ser Leu Val Thr Leu Phe Arg Cys Ile Gln Asn Met Pro Glu Thr Leu
225                 230                 235                 240

Pro Asn Asn Ser Cys Tyr Ser Ala Gly Ile Ala Lys Leu Glu Glu Gly
                245                 250                 255

Asp Glu Leu Gln Leu Ala Ile Pro Arg Glu Asn Ala Gln Ile Ser Leu
            260                 265                 270

Asp Gly Asp Val Thr Phe Phe Gly Ala Leu Lys Leu Leu
        275                 280                 285
```

<210> SEQ ID NO 217
<211> LENGTH: 240
<212> TYPE: PRT
<213> ORGANISM: Homo sapiens

<400> SEQUENCE: 217

```
Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser
            20                  25                  30

Cys Ser Val Ala Arg Val Gly Leu Gly Leu Leu Leu Leu Leu Met Gly
        35                  40                  45
```

```
Ala Gly Leu Ala Val Gln Gly Trp Phe Leu Leu Gln Leu His Trp Arg
    50                  55                  60

Leu Gly Glu Met Val Thr Arg Leu Pro Asp Gly Pro Ala Gly Ser Trp
65                  70                  75                  80

Glu Gln Leu Ile Gln Glu Arg Arg Ser His Glu Val Asn Pro Ala Ala
                85                  90                  95

His Leu Thr Gly Ala Asn Ser Ser Leu Thr Gly Ser Gly Gly Pro Leu
            100                 105                 110

Leu Trp Glu Thr Gln Leu Gly Leu Ala Phe Leu Arg Gly Leu Ser Tyr
        115                 120                 125

His Asp Gly Ala Leu Val Val Thr Lys Ala Gly Tyr Tyr Tyr Ile Tyr
    130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
            180                 185                 190

Ser Ser Arg Val Trp Trp Asp Ser Ser Phe Leu Gly Gly Val Val His
        195                 200                 205

Leu Glu Ala Gly Glu Lys Val Val Val Arg Val Leu Asp Glu Arg Leu
    210                 215                 220

Val Arg Leu Arg Asp Gly Thr Arg Ser Tyr Phe Gly Ala Phe Met Val
225                 230                 235                 240


<210> SEQ ID NO 218
<211> LENGTH: 251
<212> TYPE: PRT
<213> ORGANISM: Homo sapiens

<400> SEQUENCE: 218

Met Ala Glu Asp Leu Gly Leu Ser Phe Gly Glu Thr Ala Ser Val Glu
1               5                   10                  15

Met Leu Pro Glu His Gly Ser Cys Arg Pro Lys Ala Arg Ser Ser Ser
            20                  25                  30

Ala Arg Trp Ala Leu Thr Cys Cys Leu Val Leu Leu Pro Phe Leu Ala
        35                  40                  45

Gly Leu Thr Thr Tyr Leu Leu Val Ser Gln Leu Arg Ala Gln Gly Glu
    50                  55                  60

Ala Cys Val Gln Phe Gln Ala Leu Lys Gly Gln Glu Phe Ala Pro Ser
65                  70                  75                  80

His Gln Gln Val Tyr Ala Pro Leu Arg Ala Asp Gly Asp Lys Pro Arg
                85                  90                  95

Ala His Leu Thr Val Val Arg Gln Thr Pro Thr Gln His Phe Lys Asn
            100                 105                 110

Gln Phe Pro Ala Leu His Trp Glu His Glu Leu Gly Leu Ala Phe Thr
        115                 120                 125

Lys Asn Arg Met Asn Tyr Thr Asn Lys Phe Leu Leu Ile Pro Glu Ser
    130                 135                 140

Gly Asp Tyr Phe Ile Tyr Ser Gln Val Thr Phe Arg Gly Met Thr Ser
145                 150                 155                 160

Glu Cys Ser Glu Ile Arg Gln Ala Gly Arg Pro Asn Lys Pro Asp Ser
                165                 170                 175

Ile Thr Val Val Ile Thr Lys Val Thr Asp Ser Tyr Pro Glu Pro Thr
```

180 185 190

Gln Leu Leu Met Gly Thr Lys Ser Val Cys Glu Val Gly Ser Asn Trp
195 200 205

Phe Gln Pro Ile Tyr Leu Gly Ala Met Phe Ser Leu Gln Glu Gly Asp
210 215 220

Lys Leu Met Val Asn Val Ser Asp Ile Ser Leu Val Asp Tyr Thr Lys
225 230 235 240

Glu Asp Lys Thr Phe Phe Gly Ala Phe Leu Leu
245 250

<210> SEQ ID NO 219
<211> LENGTH: 199
<212> TYPE: PRT
<213> ORGANISM: Homo sapiens

<400> SEQUENCE: 219

Met Thr Leu His Pro Ser Pro Ile Thr Cys Glu Phe Leu Phe Ser Thr
1 5 10 15

Ala Leu Ile Ser Pro Lys Met Cys Leu Ser His Leu Glu Asn Met Pro
20 25 30

Leu Ser His Ser Arg Thr Gln Gly Ala Gln Arg Ser Ser Trp Lys Leu
35 40 45

Trp Leu Phe Cys Ser Ile Val Met Leu Leu Phe Leu Cys Ser Phe Ser
50 55 60

Trp Leu Ile Phe Ile Phe Leu Gln Leu Glu Thr Ala Lys Glu Pro Cys
65 70 75 80

Met Ala Lys Phe Gly Pro Leu Pro Ser Lys Trp Gln Met Ala Ser Ser
85 90 95

Glu Pro Pro Cys Val Asn Lys Val Ser Asp Trp Lys Leu Glu Ile Leu
100 105 110

Gln Asn Gly Leu Tyr Leu Ile Tyr Gly Gln Val Ala Pro Asn Ala Asn
115 120 125

Tyr Asn Asp Val Ala Pro Phe Glu Val Arg Leu Tyr Lys Asn Lys Asp
130 135 140

Met Ile Gln Thr Leu Thr Asn Lys Ser Lys Ile Gln Asn Val Gly Gly
145 150 155 160

Thr Tyr Glu Leu His Val Gly Asp Thr Ile Asp Leu Ile Phe Asn Ser
165 170 175

Glu His Gln Val Leu Lys Asn Asn Thr Tyr Trp Gly Ile Ile Leu Leu
180 185 190

Ala Asn Pro Gln Phe Ile Ser
195

<210> SEQ ID NO 220
<211> LENGTH: 391
<212> TYPE: PRT
<213> ORGANISM: Homo sapiens

<400> SEQUENCE: 220

Met Gly Tyr Pro Glu Val Glu Arg Arg Glu Leu Leu Pro Ala Ala Ala
1 5 10 15

Pro Arg Glu Arg Gly Ser Gln Gly Cys Gly Cys Gly Gly Ala Pro Ala
20 25 30

Arg Ala Gly Glu Gly Asn Ser Cys Leu Leu Phe Leu Gly Phe Phe Gly
35 40 45

Leu Ser Leu Ala Leu His Leu Leu Thr Leu Cys Cys Tyr Leu Glu Leu

-continued

```
    50                  55                  60

Arg Ser Glu Leu Arg Arg Glu Arg Gly Ala Glu Ser Arg Leu Gly Gly
65                  70                  75                  80

Ser Gly Thr Pro Gly Thr Ser Gly Thr Leu Ser Ser Leu Gly Gly Leu
                85                  90                  95

Asp Pro Asp Ser Pro Ile Thr Ser His Leu Gly Gln Pro Ser Pro Lys
            100                 105                 110

Gln Gln Pro Leu Glu Pro Gly Glu Ala Ala Leu His Ser Asp Ser Gln
        115                 120                 125

Asp Gly His Gln Met Ala Leu Leu Asn Phe Phe Phe Pro Asp Glu Lys
    130                 135                 140

Pro Tyr Ser Glu Glu Glu Ser Arg Arg Val Arg Arg Asn Lys Arg Ser
145                 150                 155                 160

Lys Ser Asn Glu Gly Ala Asp Gly Pro Val Lys Asn Lys Lys Lys Gly
                165                 170                 175

Lys Lys Ala Gly Pro Pro Gly Pro Asn Gly Pro Pro Gly Pro Pro Gly
            180                 185                 190

Pro Pro Gly Pro Gln Gly Pro Pro Gly Ile Pro Gly Ile Pro Gly Ile
        195                 200                 205

Pro Gly Thr Thr Val Met Gly Pro Pro Gly Pro Pro Gly Pro Pro Gly
    210                 215                 220

Pro Gln Gly Pro Pro Gly Leu Gln Gly Pro Ser Gly Ala Ala Asp Lys
225                 230                 235                 240

Ala Gly Thr Arg Glu Asn Gln Pro Ala Val Val His Leu Gln Gly Gln
                245                 250                 255

Gly Ser Ala Ile Gln Val Lys Asn Asp Leu Ser Gly Gly Val Leu Asn
            260                 265                 270

Asp Trp Ser Arg Ile Thr Met Asn Pro Lys Val Phe Lys Leu His Pro
        275                 280                 285

Arg Ser Gly Glu Leu Glu Val Leu Val Asp Gly Thr Tyr Phe Ile Tyr
    290                 295                 300

Ser Gln Val Glu Val Tyr Tyr Ile Asn Phe Thr Asp Phe Ala Ser Tyr
305                 310                 315                 320

Glu Val Val Val Asp Glu Lys Pro Phe Leu Gln Cys Thr Arg Ser Ile
                325                 330                 335

Glu Thr Gly Lys Thr Asn Tyr Asn Thr Cys Tyr Thr Ala Gly Val Cys
            340                 345                 350

Leu Leu Lys Ala Arg Gln Lys Ile Ala Val Lys Met Val His Ala Asp
        355                 360                 365

Ile Ser Ile Asn Met Ser Lys His Thr Thr Phe Phe Gly Ala Ile Arg
    370                 375                 380

Leu Gly Glu Ala Pro Ala Ser
385                 390


<210> SEQ ID NO 221
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 221

His His His His His His
1               5
```

<210> SEQ ID NO 222
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(50)
<223> OTHER INFORMATION: This sequence may encompass 1-10 "Gly Gly Gly
      Gly Ser" repeating units
<220> FEATURE:
<223> OTHER INFORMATION: See specification as filed for detailed
      description of substitutions and preferred embodiments

<400> SEQUENCE: 222

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50

<210> SEQ ID NO 223
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(50)
<223> OTHER INFORMATION: This sequence may encompass 1-10 "Ser Gly Gly
      Gly Gly" repeating units
<220> FEATURE:
<223> OTHER INFORMATION: See specification as filed for detailed
      description of substitutions and preferred embodiments

<400> SEQUENCE: 223

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser Gly Gly Gly Gly Ser Gly
            20                  25                  30

Gly Gly Gly Ser Gly Gly Gly Gly Ser Gly Gly Gly Gly Ser Gly Gly
        35                  40                  45

Gly Gly
    50

<210> SEQ ID NO 224
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (5)..(54)
<223> OTHER INFORMATION: This region may encompass 1-10 "Ser Gly Gly Gly
      Gly" repeating units
<220> FEATURE:
<223> OTHER INFORMATION: See specification as filed for detailed
      description of substitutions and preferred embodiments -continued

```
<400> SEQUENCE: 224

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly
    50


<210> SEQ ID NO 225
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Gly Leu Asn Asp Ile Phe Glu Ala Gln Lys Ile Glu Trp His Glu
1               5                   10                  15
```

ANTIGEN BINDING MOLECULES COMPRISING A TNF FAMILY LIGAND TRIMER AND A TENASCIN BINDING MOIETY

CROSS REFERENCE TO RELATED APPLICATIONS

This application is a continuation of International Application No. PCT/EP2017/060870, filed May 8, 2017, which claims priority from European Patent Application No. 16169244.7, filed May 11, 2016. The contents of each of the foregoing applications are incorporated herein by reference in their entireties.

SEQUENCE LISTING

This application contains a Sequence Listing submitted via EFS-Web and hereby incorporated by reference in its entirety. Said ASCII copy, created on Dec. 20, 2018, is named P33586-US_SL.txt and is 538,620 bytes in size.

FIELD OF THE INVENTION

The invention relates to novel TNF family ligand trimer-containing antigen binding molecules comprising (a) at least one antigen binding moiety capable of specific binding to Tenascin-C (TnC) and (b) a first and a second polypeptide that are linked to each other by a disulfide bond, wherein the antigen binding molecules are characterized in that the first polypeptide comprises two ectodomains of a TNF ligand family member or two fragments thereof that are connected to each other by a peptide linker and in that the second polypeptide comprises only one ectodomain of said TNF ligand family member or a fragment thereof. The invention further relates to methods of producing these molecules and to methods of using the same.

BACKGROUND

Ligands interacting with molecules of the TNF (tumor necrosis factor) receptor superfamily have pivotal roles in the organization and function of the immune system. While regulating normal functions such as immune responses, hematopoiesis and morphogenesis, the TNF family ligands (also called cytokines) play a role in tumorgenesis, transplant rejection, septic shock, viral replication, bone resorption, rheumatoid arthritis and diabetes (Aggarwal, 2003). The TNF ligand family comprises 18 genes encoding 19 type II (i.e. intracellular N terminus and extracellular C-terminus) transmembrane proteins, characterized by the presence of a conserved C-terminal domain coined the 'TNF homology domain' (THD). This domain is responsible for receptor binding and is thus critical for the biological activity of the TNF ligand family members. The sequence identity between family members is about 20-30% (Bodmer, 2002). Members of the TNF ligand family exert their biological function as self-assembling, noncovalent trimers (Banner et al, Cell 1993, 73, 431-445). Thus, the TNF family ligands form a trimer that is able to bind to and to activate the corresponding receptors of TNFR superfamily.

4-1BB (CD137), a member of the TNF receptor superfamily, has been first identified as a molecule whose expression is induced by T-cell activation (Kwon and Weissman, 1989). Subsequent studies demonstrated expression of 4-1BB in T- and B-lymphocytes (Snell et al., 2011; Zhang et al., 2010), NK-cells (Lin et al., 2008), NKT-cells (Kim et al., 2008), monocytes (Kienzle and von Kempis, 2000; Schwarz et al., 1995), neutrophils (Heinisch et al., 2000), mast (Nishimoto et al., 2005) and dendritic cells as well as cells of non-hematopoietic origin such as endothelial and smooth muscle cells (Broil et al., 2001; Olofsson et al., 2008). Expression of 4-1BB in different cell types is mostly inducible and driven by various stimulatory signals, such as T-cell receptor (TCR) or B-cell receptor triggering, as well as signaling induced through co-stimulatory molecules or receptors of pro-inflammatory cytokines (Diehl et al., 2002; von Kempis et al., 1997; Zhang et al., 2010).

Expression of 4-1BB ligand (4-1BBL or CD137L) is more restricted and is observed on professional antigen presenting cells (APC) such as B-cells, dendritic cells (DCs) and macrophages. Inducible expression of 4-1BBL is characteristic for T-cells, including both αβ and γδT-cell subsets, and endothelial cells (reviewed in Shao and Schwarz, 2011).

CD137 signaling is known to stimulate IFNγ secretion and proliferation of NK cells (Buechele et al., 2012; Lin et al., 2008; Melero et al., 1998) as well as to promote DC activation as indicated by their increased survival and capacity to secret cytokines and upregulate co-stimulatory molecules (Choi et al., 2009; Futagawa et al., 2002; Wilcox et al., 2002). However, CD137 is best characterized as a co-stimulatory molecule which modulates TCR-induced activation in both the CD4+ and CD8+ subsets of T-cells. In combination with TCR triggering, agonistic 4-1BB-specific antibodies enhance proliferation of T-cells, stimulate lymphokine secretion and decrease sensitivity of T-lymphocytes to activation-induced cells death (reviewed in Snell et al., 2011).

In line with these co-stimulatory effects of 4-1BB antibodies on T-cells in vitro, their administration to tumor bearing mice leads to potent anti-tumor effects in many experimental tumor models (Melero et al., 1997; Narazaki et al., 2010). However, 4-1BB usually exhibits its potency as an anti-tumor agent only when administered in combination with other immunomodulatory compounds (Curran et al., 2011; Guo et al., 2013; Morales-Kastresana et al., 2013; Teng et al., 2009; Wei et al., 2013), chemotherapeutic reagents (Ju et al., 2008; Kim et al., 2009), tumor-specific vaccination (Cuadros et al., 2005; Lee et al., 2011) or radiotherapy (Shi and Siemann, 2006). In vivo depletion experiments demonstrated that CD8+ T-cells play the most critical role in anti-tumoral effect of 4-1BB-specific antibodies. However, depending on the tumor model or combination therapy, which includes anti-4-1BB, contributions of other types of cells such as DCs, NK-cells or CD4+ T-cells have been reported (Melero et al., 1997; Murillo et al., 2009; Narazaki et al., 2010; Stagg et al., 2011).

In addition to their direct effects on different lymphocyte subsets, 4-1BB agonists can also induce infiltration and retention of activated T-cells in the tumor through 4-1BB-mediated upregulation of intercellular adhesion molecule 1 (ICAM1) and vascular cell adhesion molecule 1 (VCAM1) on tumor vascular endothelium (Palazon et al., 2011).

4-1BB triggering may also reverse the state of T-cell anergy induced by exposure to soluble antigen that may contribute to disruption of immunological tolerance in the tumor microenvironment or during chronic infections (Wilcox et al., 2004).

It appears that the immunomodulatory properties of 4-1BB agonistic antibodies in vivo require the presence of the wild type Fc-portion on the antibody molecule thereby implicating Fc-receptor binding as an important event required for the pharmacological activity of such reagents as has been described for agonistic antibodies specific to other apoptosis-inducing or immunomodulatory members of the TNFR-superfamily (Li and Ravetch, 2011; Teng et al., 2009). However, systemic administration of 4-1BB-specific agonistic antibodies with the functionally active Fc domain also induces expansion of CD8+ T-cells associated with liver toxicity (Dubrot et al., 2010) that is diminished or significantly ameliorated in the absence of functional Fc-receptors in mice. In human clinical trials (ClinicalTrials.gov, NCT00309023), Fc-competent 4-1BB agonistic antibodies (BMS-663513) administered once every three weeks for 12 weeks induced stabilization of the disease in patients with melanoma, ovarian or renal cell carcinoma. However, the same antibody given in another trial (NCT00612664) caused grade 4 hepatitis leading to termination of the trial (Simeone and Ascierto, 2012).

Collectively, the available pre-clinical and clinical data clearly demonstrate that there is a high clinical need for effective 4-1BB agonists. However, new generation drug candidates should not only effectively engage 4-1BB on the surface of hematopoietic and endothelial cells but also be capable of achieving that through mechanisms other than binding to Fc-receptors in order to avoid uncontrollable side effects. The latter may be accomplished through preferential binding to tumor-specific or tumor-associated moieties.

Tenascins are a highly conserved family of large multimeric extracellular matrix (ECM) glycoproteins, which is found in vertebrates. Four Tenascin paralogues have been identified in mammals, termed Tenascin-C, Tenascin-R, Tenascin-X and Tenascin-W. Tenascin family proteins have a common primary structure, comprising N-terminal heptad repeats, epidermal growth factor (EGF)-like repeats, fibronectin type III domain repeats and a C-terminal fibrinogen-like globular domain. Via an N-terminal oligomerization domain, individual subunits assemble into trimers or, as is the case for TnC, even hexamers. Indeed, the oligomerization domain of TnC was reported to improve trimerzation of CD27L, CD40L, 41BBL, and glucocorticoid-induced TNF receptor ligand when fused to the respective TNF receptor ligand (see Wyzgol et al., J Immunol. 183(3), 1851-61 (2009) and Berg et al., Cell Deatch and Differentiation 14(12, 2021-2034 (2007)). These studies used fragments of the TnC polypeptide chain to stabilice the active trimeric form of the TNF ligands in TnC-TNF-ligand fusion polypetides.

Mammalian Tenascin-C (TnC) monomers typically have 14.5 EGF-like repeats and 8 fibronectin type III domain repeats that are shared by all Tenascin-C isoforms. However, up to 9 additional fibronectin type III domain repeats (domains A1 to D) can be independently included or excluded by alternative splicing, giving rise to a large number of Tenascin-C isoforms (see e.g. Hsia and Schwarzbauer, J Biol Chem 280, 26641-26644 (2005)).

Tenascin-C is transiently expressed in the developing embryo, but virtually absent from adult tissues. It reappears, however, in tissues undergoing remodeling processes, including certain pathological conditions such as wound healing, inflammation and cancer (reviewed in Chiquet-Ehrismann & Chiquet, J Pathol 200, 488-499 (2003)).

Importantly, Tenascin-C is highly expressed in the majority of malignant solid tumors, including tumors of the brain, breast, colon, lung, skin and other organs (reviewed in Orend and Chiquet-Ehrismann, Cancer Letters 244, 143-163 (2006)), where it may be expressed by transformed epithelial cells as well as stromal cells in the tumor microenvironment (Yoshida et al., J Pathol 182, 421-428 (1997), Hanamura et al., Int J Cancer 73, 10-15 (1997)). In particular, the "large isoform" of Tenascin-C, containing the alternatively spliced domains A1 to D, is expressed in invasive carcinomas while being nearly undetectable in healthy adult tissues (Borsi et al., Int J Cancer 52, 688-692 (1992), Carnemolla et al., Eur J Biochem 205, 561-567 (1992)).

SUMMARY OF THE INVENTION

There remains a need for active and safe 4-1BB agonists. The bispecific molecules of the invention with at least one TnC antigen binding moiety targeting the molecules of the invention to tumor cells of a broad range of malignancies, and a trimeric and thus biologically active TNF ligand, provide a unique targeting tool to address tumor cells. The antigen binding molecules of the invention have sufficient stability to be pharmaceutically useful and can be used to treat different cancer with increased efficiency and safety.

In one aspect, the invention provides a TNF family ligand trimer-containing antigen binding molecule comprising (a) at least one moiety capable of specific binding to Tenascin-C (TnC) and (b) a first and a second polypeptide that are linked to each other by a disulfide bond, wherein the antigen binding molecule is characterized in that the first polypeptide comprises two ectodomains of a TNF ligand family member or two fragments thereof that are connected to each other by a peptide linker and in that the second polypeptide comprises only one ectodomain of said TNF ligand family member or a fragment thereof.

In a particular aspect, the invention provides a TNF family ligand trimer-containing antigen binding molecule comprising (a) at least one moiety capable of specific binding to TnC, (b) a first and a second polypeptide that are linked to each other by a disulfide bond, wherein the antigen binding molecule is characterized in that the first polypeptide comprises two ectodomains of a TNF ligand family member or two fragments thereof that are connected to each other by a peptide linker and in that the second polypeptide comprises only one ectodomain of said TNF ligand family member or a fragment thereof, and (c) an Fc domain composed of a first and a second subunit capable of stable association.

In a further aspect, the invention provides a TNF family ligand trimer-containing antigen binding molecule, comprising (a) at least one moiety capable of specific binding to TnC and (b) a first and a second polypeptide that are linked to each other by a disulfide bond, wherein the antigen binding molecule is characterized in that (i) the first polypeptide contains a CH1 or CL domain and the second polypeptide contains a CL or CH1 domain, respectively, wherein the second polypeptide is linked to the first polypeptide by a disulfide bond between the CH1 and CL domain, and wherein the first polypeptide comprises two ectodomains of a TNF ligand family member or fragments thereof that are connected to each other and to the CH1 or CL domain by a peptide linker and wherein the second polypeptide comprises one ectodomain of said TNF ligand family member or a fragment thereof connected via a peptide linker to the CL or CH1 domain of said polypeptide, or (ii) the first polypeptide contains a CH3 domain and the second polypeptide contains a CH3 domain, respectively, and wherein the first polypeptide comprises two ectodomains of a TNF ligand family member or fragments thereof that are connected to each other and to the C-terminus of the CH3 domain by a peptide linker and wherein the second polypeptide comprises only one ectodomain of said TNF ligand family member or a fragment thereof connected via a peptide linker to C-terminus of the CH3 domain of said polypeptide, or (iii) the first polypeptide contains a VH-CL or a VL-CH1 domain and the second polypeptide contains a VL-CH1 domain or a VH-CL domain, respectively, wherein the second polypeptide is linked to the first polypeptide by a disulfide bond between the CH1 and CL domain, and wherein the first polypeptide comprises two ectodomains of a TNF ligand family member or fragments thereof that are connected to each other and to to VH or VL by a peptide linker and wherein the second polypeptide comprises one ectodomain of said TNF ligand family member or a fragment thereof connected via a peptide linker to VL or VH of said polypeptide.

In a particular aspect, the TNF ligand family member is one that costimulates human T-cell activation. Thus, the TNF family ligand trimer-containing antigen binding molecule comprises (a) at least one moiety capable of specific binding to TnC and (b) a first and a second polypeptide that are linked to each other by a disulfide bond, wherein the antigen binding molecule is characterized in that the first polypeptide comprises two ectodomains of a TNF ligand family member or two fragments thereof that are connected to each other by a peptide linker and in that the second polypeptide comprises only one ectodomain of said TNF ligand family member or a fragment thereof, wherein the TNF ligand family member costimulates human T-cell activation. More particularly, the TNF ligand family member is selected from 4-1BBL and OX40L.

In one aspect, the TNF ligand family member is 4-1BBL.

In a further aspect, the ectodomain of a TNF ligand family member comprises the amino acid sequence selected from the group consisting of SEQ ID NO: 172, SEQ ID NO: 173, SEQ ID NO: 174, SEQ ID NO: 175, SEQ ID NO: 183, SEQ ID NO: 192, SEQ ID NO: 193 and SEQ ID NO: 194, particularly the amino acid sequence of SEQ ID NO: 172 or SEQ ID NO: 183.

In another aspect, the ectodomain of a TNF ligand family member or fragment thereof comprises the amino acid sequence selected from the group consisting of SEQ ID NO: 172, SEQ ID NO: 173, SEQ ID NO: 174, SEQ ID NO: 175 and SEQ ID NO: 183, particularly the amino acid sequence of SEQ ID NO: 172 or SEQ ID NO: 183. More particularly, the ectodomain of a TNF ligand family member comprises the amino acid sequence of SEQ ID NO: 183.

In a further aspect, the TNF family ligand trimer-containing antigen binding molecule of the invention comprises (a) at least one moiety capable of specific binding to TnC and (b) a first and a second polypeptide that are linked to each other by a disulfide bond, wherein the antigen binding molecule is characterized in that the first polypeptide comprises the amino acid sequence selected from the group consisting of SEQ ID NO: 176, SEQ ID NO: 184, SEQ ID NO: 185 and SEQ ID NO: 186 and in that the second polypeptide comprises the amino acid sequence selected from the group consisting of SEQ ID NO: 172, SEQ ID NO: 174 and SEQ ID NO: 175 and SEQ ID NO: 183.

In one aspect, the TNF family ligand trimer-containing antigen binding molecule of the invention comprises (a) at least one moiety capable of specific binding to TnC and (b) a first and a second polypeptide that are linked to each other by a disulfide bond, wherein the antigen binding molecule is characterized in that the first polypeptide comprises the amino acid sequence of SEQ ID NO: 176 and in that the second polypeptide comprises the amino acid sequence of SEQ ID NO: 177.

In a further aspect, the TNF family ligand trimer-containing antigen binding molecule of the invention comprises (a) at least one moiety capable of specific binding to TnC and (b) a first and a second polypeptide that are linked to each other by a disulfide bond, wherein the antigen binding molecule is characterized in that the first polypeptide comprises the amino acid sequence of SEQ ID NO: 176 and in that the second polypeptide comprises the amino acid sequence of SEQ ID NO: 187.

In yet a further aspect, the TNF family ligand trimer-containing antigen binding molecule of the invention comprises (a) at least one moiety capable of specific binding to TnC and (b) a first and a second polypeptide that are linked to each other by a disulfide bond, wherein the antigen binding molecule is characterized in that the first polypeptide comprises the amino acid sequence of SEQ ID NO: 184 and in that the second polypeptide comprises the amino acid sequence of SEQ ID NO: 188 or SEQ ID NO: 189.

In another aspect, the TNF family ligand trimer-containing antigen binding molecule of the invention comprises (a) at least one moiety capable of specific binding to TnC, (b) a first polypeptide containing a CH1 or CL domain and a second polypeptide containing a CL or CH1 domain, respectively, wherein the second polypeptide is linked to the first polypeptide by a disulfide bond between the CH1 and CL domain, and wherein the antigen binding molecule is characterized in that the first polypeptide comprises two ectodomains of a TNF ligand family member or two fragments thereof that are connected to each other and to the CH1 or CL domain by a peptide linker and in that the second polypeptide comprises only one ectodomain of said TNF ligand family member or a fragment thereof connected by a peptide linker to the CL or CH1 domain of said polypeptide.

In one aspect, provided is a TNF family ligand trimer-containing antigen binding molecule comprising (a) at least one moiety capable of specific binding to TnC, (b) a first polypeptide containing a CH1 domain and a second polypeptide containing a CL domain, wherein the second polypeptide is linked to the first polypeptide by a disulfide bond between the CH1 and CL domain, and wherein the antigen binding molecule is characterized in that the first polypeptide comprises two ectodomains of a TNF ligand family member or fragments thereof that are connected to each other and to the CH1 domain by a peptide linker and in that the second polypeptide comprises one ectodomain of said TNF ligand family member or a fragment thereof connected via a peptide linker to the CL domain of said polypeptide.

In another aspect, provided is a TNF family ligand trimer-containing antigen binding molecule comprising (a) at least one moiety capable of specific binding to TnC, (b) a first polypeptide containing a CL domain and a second polypeptide containing a CH1 domain, wherein the second polypeptide is linked to the first polypeptide by a disulfide bond between the CH1 and CL domain, and wherein the antigen binding molecule is characterized in that the first polypeptide comprises two ectodomains of a TNF ligand family member or fragments thereof that are connected to each other and to the CL domain by a peptide linker and in that the second polypeptide comprises one ectodomain of said TNF ligand family member or a fragment thereof connected via a peptide linker to the CH1 domain of said polypeptide.

In one aspect, the invention provides a TNF family ligand trimer-containing antigen binding molecule as defined herein before, wherein the moiety capable of specific binding to TnC is an antibody fragment.

In particular, the moiety capable of specific binding to TnC is an antigen binding moiety.

In particular, the moiety capable of specific binding to TnC is selected from the group consisting of an antibody fragment, a Fab molecule, a crossover Fab molecule, a single chain Fab molecule, a Fv molecule, a scFv molecule, a single domain antibody, and aVH and a scaffold antigen binding protein.

In particular, the TNF family ligand trimer-containing antigen binding molecule comprises one or two moieties capable of specific binding to TnC.

In a particular aspect, the invention is concerned with a TNF family ligand trimer-containing antigen binding molecule as defined above, wherein the moiety capable of specific binding to TnC is a Fab molecule.

In one aspect, the invention provides a TNF family ligand trimer-containing antigen binding molecule as defined herein before, wherein the moiety capable of specific binding to TnC antigen is a scaffold antigen binding protein.

The invention provides a TNF family ligand trimer-containing antigen binding molecule that comprises at least one moiety capable of specific binding to TnC. In a particular aspect, the TNF family ligand trimer-containing antigen binding molecule comprises one moiety capable of specific binding to TnC. In another aspect, the invention provides a TNF family ligand trimer-containing antigen binding molecule comprising two moieties capable of specific binding TnC.

In one aspect, the invention provides a TNF family ligand trimer-containing antigen binding molecule, wherein the moiety capable of specific binding to TnC comprises a VH domain comprising (i) CDR-H1 comprising the amino acid sequence of SEQ ID NO: 67 or SEQ ID NO: 70, (ii) CDR-H2 comprising the amino acid sequence of SEQ ID NO: 68 or SEQ ID NO: 71, and (iii) CDR-H3 comprising the amino acid sequence of SEQ ID NO: 69 or SEQ ID NO: 72, and a VL domain comprising (iv) CDR-L1 comprising the amino acid sequence of SEQ ID NO: 55 or SEQ ID NO: 58, (v) CDR-L2 comprising the amino acid sequence of SEQ ID NO: 56 or SEQ ID NO: 59, and (vi) CDR-L3 comprising the amino acid sequence of SEQ ID NO: 57 or SEQ ID NO: 60.

In one aspect, the invention provides a TNF family ligand trimer-containing antigen binding molecule, wherein the moiety capable of specific binding to TnC comprises a VH domain comprising (i) CDR-H1 comprising the amino acid sequence of SEQ ID NO: 67, (ii) CDR-H2 comprising the amino acid sequence of SEQ ID NO: 68 and (iii) CDR-H3 comprising the amino acid sequence of SEQ ID NO: 69, and a VL domain comprising (iv) CDR-L1 comprising the amino acid sequence of SEQ ID NO: 55, (v) CDR-L2 comprising the amino acid sequence of SEQ ID NO: 56 and (vi) CDR-L3 comprising the amino acid sequence of SEQ ID NO: 57.

In another aspect, the invention provides a TNF family ligand trimer-containing antigen binding molecule, wherein the moiety capable of specific binding to TnC comprises a VH domain comprising (i) CDR-H1 comprising the amino acid sequence of SEQ ID NO: 70, (ii) CDR-H2 comprising the amino acid sequence SEQ ID NO: 71, and (iii) CDR-H3 comprising the amino acid sequence of SEQ ID NO: 72, and a VL domain comprising (iv) CDR-L1 comprising the amino acid sequence of SEQ ID NO: 58, (v) CDR-L2 comprising the amino acid sequence of SEQ ID NO: 59, and (vi) CDR-L3 comprising the amino acid sequence of SEQ ID NO: 60.

In one aspect, provided is a TNF family ligand trimer-containing antigen binding molecule as defined herein before, wherein the moiety capable of specific binding to TnC comprises a variable heavy chain comprising an amino acid sequence of SEQ ID NO: 46 and a variable light chain comprising an amino acid sequence of SEQ ID NO: 45 or wherein the moiety capable of specific binding to TnC comprises a variable heavy chain comprising an amino acid sequence of SEQ ID NO: 48 and a variable light chain comprising an amino acid sequence of SEQ ID NO: 47.

In a further aspect, provided is a TNF family ligand trimer-containing antigen binding molecule according to the invention, wherein a peptide comprising two ectodomains of a TNF ligand family member or fragments thereof connected to each other by a first peptide linker is fused at its C-terminus to the CH1 or CL domain of a heavy chain by a second peptide linker and wherein one ectodomain of said TNF ligand family member or a fragment thereof is fused at the its C-terminus the CL or CH1 domain on a light chain by a third peptide linker.

In a particular aspect, the invention relates to a TNF family ligand trimer-containing antigen binding molecule as defined above, wherein the peptide linker is $(G4S)_2$, i.e. a peptide linker of SEQ ID NO: 150. In one aspect, the first peptide linker is $(G4S)_2$, the second peptide linker is GSPGSSSSGS (SEQ ID NO: 153) and the third peptide linker is $(G4S)_2$. In another aspect, the first, the second and the third peptide linker is $(G4S)_2$.

The invention is further concerned with a TNF family ligand trimer-containing antigen binding molecule as defined herein before, comprising an Fc domain composed of a first and a second subunit capable of stable association.

In particular, the TNF family ligand trimer-containing antigen binding molecule of the invention comprising (c) an Fc domain composed of a first and a second subunit capable of stable association further comprises (a) a Fab molecule capable of specific binding to a target cell antigen, wherein the Fab heavy chain is fused at the C-terminus to the N-terminus of a CH2 domain in the Fc domain.

In a further aspect, the Fc domain is an IgG, particularly an IgG1 Fc domain or an IgG4 Fc domain. More particularly, the Fc domain is an IgG1 Fc domain. In a particular aspect, the Fc domain comprises a modification promoting the association of the first and second subunit of the Fc domain.

In another aspect, the invention is concerned with a TNF family ligand trimer-containing antigen binding molecule as defined herein before, comprising (c) an Fc domain composed of a first and a second subunit capable of stable association, wherein the Fc domain comprises one or more amino acid substitution that reduces binding to an Fc receptor, in particular towards Fcγ receptor.

In particular, the Fc domain comprises amino acid substitutions at positions 234 and 235 (EU numbering) and/or 329 (EU numbering) of the IgG heavy chains. More particularly, provided is a trimeric TNF family ligand-containing antigen binding molecule according to the invention which comprises an IgG1 Fc domain with the amino acid substitutions L234A, L235A and P329G (EU numbering).

In a further aspect, the invention provides a TNF family ligand trimer-containing antigen binding molecule, wherein the antigen binding molecule comprises a first heavy chain and a first light chain, both comprising a Fab molecule capable of specific binding to TnC, a first peptide comprising two ectodomains of a TNF ligand family member or fragments thereof connected to each other by a first peptide linker fused at its C-terminus by a second peptide linker to a second heavy or light chain, and a second peptide comprising one ectodomain of said TNF ligand family member fused at its C-terminus by a third peptide linker to a second light or heavy chain, respectively.

In another aspect, provided is a TNF family ligand trimer-containing antigen binding molecule, wherein the first peptide comprising two ectodomains of a TNF ligand family member or fragments thereof connected to each other by a first peptide linker is fused at its C-terminus by a second peptide linker to a CH1 domain that is part of a heavy chain, and the second peptide comprising one ectodomain of said TNF ligand family member or a fragment thereof is fused at its C-terminus by a third peptide linker to a CL domain that is part of a light chain.

In yet another aspect, provided is a TNF family ligand trimer-containing antigen binding molecule, wherein the first peptide comprising two ectodomains of a TNF ligand family member or fragments thereof connected to each other by a first peptide linker is fused at its C-terminus by a second peptide linker to a CL domain that is part of a heavy chain, and the second peptide comprising one ectodomain of said TNF ligand family member or a fragment thereof is fused at its C-terminus by a third peptide linker to a CH1 domain that is part of a light chain.

In a further aspect, the invention provides a TNF family ligand trimer-containing antigen binding molecule, wherein the first peptide comprising two ectodomains of a TNF ligand family member or fragments thereof connected to each other by a first peptide linker is fused at its C-terminus by a second peptide linker to a VH domain that is part of a heavy chain, and the second peptide comprising one ectodomain of said TNF ligand family member or a fragment thereof is fused at its C-terminus by a third peptide linker to a VL domain that is part of a light chain.

Provided is further a TNF family ligand trimer-containing antigen binding molecule, wherein in the CL domain adjacent to the TNF ligand family member the amino acid at position 123 (EU numbering) has been replaced by arginine (R) and the amino acid at position 124 (EU numbering) has been substituted by lysine (K), and wherein in the CH1 domain adjacent to the TNF ligand family member the amino acids at position 147 (EU numbering) and at position 213 (EU numbering) have been substituted by glutamic acid (E).

In a further aspect, provided is a TNF family ligand trimer-containing antigen binding molecule as described herein before, wherein the antigen binding molecule comprises (a) a first heavy chain and a first light chain, both comprising a Fab molecule capable of specific binding to TnC, (b) a second heavy chain comprising an amino acid sequence selected from the group consisting of SEQ ID NO: 176, SEQ ID NO: 184, SEQ ID NO: 185 and SEQ ID NO: 186, and a second light chain comprising an amino acid sequence selected from the group consisting of SEQ ID NO: 172, SEQ ID NO: 174, SEQ ID NO: 175 and SEQ ID NO: 183.

In one aspect, provided is a TNF family ligand trimer-containing antigen binding molecule, wherein the antigen binding molecule comprises (i) a first heavy chain comprising the VH domain comprising the amino acid sequence of SEQ ID NO: 46 and a first light chain comprising the VL domain comprising the amino acid sequence of SEQ ID NO: 45 or a first heavy chain comprising the VH domain comprising the amino acid sequence of SEQ ID NO: 48 and a first light chain comprising the VL domain comprising the amino acid sequence of SEQ ID NO: 47, (ii) a second heavy chain comprising the amino acid sequence of SEQ ID NO: 178, and (iii) a second light chain comprising the amino acid sequence of SEQ ID NO: 179.

In another aspect, the invention provides a TNF family ligand trimer-containing antigen binding molecule, wherein the antigen binding molecule comprises (i) a first heavy chain comprising the VH domain comprising the amino acid sequence of SEQ ID NO: 46 and a first light chain comprising the VL domain comprising the amino acid sequence of SEQ ID NO: 45 or a first heavy chain comprising the VH domain comprising the amino acid sequence of SEQ ID NO: 48 and a first light chain comprising the VL domain comprising the amino acid sequence of SEQ ID NO: 47, (ii) a second heavy chain comprising the amino acid sequence selected from the group consisting of SEQ ID NO: 102, SEQ ID NO: 108, SEQ ID NO: 116 and SEQ ID NO: 120, and (iii) a second light chain comprising the amino acid sequence selected from the group consisting of SEQ ID NO: 103, SEQ ID NO: 109, SEQ ID NO: 117 and SEQ ID NO: 121.

In yet another aspect, the invention provides a TNF family ligand trimer-containing antigen binding molecule, comprising (a) at least one moiety capable of specific binding to TnC, and (b) a first and a second polypeptide that are linked to each other by a disulfide bond, wherein the antigen binding molecule is characterized in that the first polypeptide contains a CH3 domain and the second polypeptide contains a CH3 domain, respectively, and wherein the first polypeptide comprises two ectodomains of a TNF ligand family member or fragments thereof that are connected to each other and to the C-terminus of the CH3 domain by a peptide linker and wherein the second polypeptide comprises one ectodomain of said TNF ligand family member or a fragment thereof connected via a peptide linker to C-terminus of the CH3 domain of said polypeptide.

In a further aspect, the TNF family ligand trimer-containing antigen binding molecule of the invention comprises (a) a Fab domain capable of specific binding to TnC, (b) a Fc domain composed of a first and a second subunit capable of stable association, and (c) a first polypeptide comprising two ectodomains of a TNF ligand family member or fragments thereof that are connected to each other by a peptide linker and a second polypeptide comprising one ectodomain of said TNF ligand family member or a fragment thereof, wherein the first polypeptide is fused at its N-terminus to the C-terminus to one of the subunits of the Fc domain and wherein the second polypeptide is fused at its N-terminus to the C-terminus of the other subunit of the Fc domain and wherein the first polypeptide comprising two ectodomains of a TNF ligand family member or fragments thereof comprises an amino acid sequence selected from the group consisting of SEQ ID NO: 176 and SEQ ID NO: 184 and the second polypeptide comprising one ectodomain of said TNF ligand family member or a fragment thereof comprises the amino acid sequence selected from the group consisting of SEQ ID NO: 172 and SEQ ID NO: 183. In one aspect, the first polypeptide comprising two ectodomains of a TNF ligand family member or fragments thereof comprises an amino acid sequence SEQ ID NO: 176 and the second polypeptide comprising one ectodomain of said TNF ligand family member or a fragment thereof comprises the amino acid sequence of SEQ ID NO: 172. In a particular aspect, the first polypeptide comprising two ectodomains of a TNF ligand family member or fragments thereof comprises an amino acid sequence of SEQ ID NO: 184 and the second polypeptide comprising one ectodomain of said TNF ligand family member or a fragment thereof comprises the amino acid sequence of SEQ ID NO: 183.

In one aspect, the invention provides a TNF family ligand trimer-containing antigen binding molecule comprising (a) one Fab domain capable of specific binding to TnC, (b) a Fc domain composed of a first and a second subunit capable of stable association, and (c) a first polypeptide comprising two ectodomains of a TNF ligand family member or fragments thereof that are connected to each other by a peptide linker and a second polypeptide comprising one ectodomain of said TNF ligand family member or a fragment thereof, wherein the first polypeptide is fused at its N-terminus to the C-terminus to one of the subunits of the Fc domain and wherein the second polypeptide is fused at its N-terminus to the C-terminus of the other subunit of the Fc domain. The invention thus relates to a TNF family ligand trimer-containing antigen binding molecule, wherein TNF family ligand trimer-containing antigen binding molecule is monovalent for the binding to the target cell antigen.

In a further aspect, the invention provides a TNF family ligand trimer-containing antigen binding molecule as defined before further comprising (d) a Fab domain that is not capable of specific binding to TnC. Thus, the invention provides a TNF family ligand trimer-containing antigen binding molecule comprising (a) a Fab domain capable of specific binding to TnC, (b) a Fc domain composed of a first and a second subunit capable of stable association, (c) a first polypeptide comprising two ectodomains of a TNF ligand family member or fragments thereof that are connected to each other by a peptide linker and a second polypeptide comprising one ectodomain of said TNF ligand family member or a fragment thereof, wherein the first polypeptide is fused at its N-terminus to the C-terminus to one of the subunits of the Fc domain and wherein the second polypeptide is fused at its N-terminus to the C-terminus of the other subunit of the Fc domain, and (d) a Fab domain that is not capable of specific binding to a target cell antigen.

In particular, provided is a TNF family ligand trimer-containing antigen binding molecule as described herein before comprising (i) a first heavy chain comprising the amino acid sequence of SEQ ID NO: 127, a second heavy chain comprising the amino acid sequence of SEQ ID NO: 125, and one light chain comprising the amino acid sequence of SEQ ID NO: 77, or (ii) a first heavy chain comprising the amino acid sequence of SEQ ID NO:130, a second heavy chain comprising the amino acid sequence of SEQ ID NO:131, and one light chain comprising the amino acid sequence of SEQ ID NO: 77, or (ii) a first heavy chain comprising the amino acid sequence of SEQ ID NO: 124, a second heavy chain comprising the amino acid sequence of SEQ ID NO: 133, and one light chain comprising the amino acid sequence of SEQ ID NO: 77, or (ii) a first heavy chain comprising the amino acid sequence of SEQ ID NO: 136, a second heavy chain comprising the amino acid sequence of SEQ ID NO: 137, and one light chain comprising the amino acid sequence of SEQ ID NO: 77.

In particular, such a TNF family ligand trimer-containing antigen binding molecule comprises two moieties capable of specific binding to TnC. In one aspect, the invention provides a TNF family ligand trimer-containing antigen binding molecule comprising two moieties capable of specific binding to TnC. In particular, provided is a TNF family ligand trimer-containing antigen binding molecule as described herein before comprising (i) a first heavy chain comprising the amino acid sequence of SEQ ID NO: 112, a second heavy chain comprising the amino acid sequence of SEQ ID NO: 113, and two light chains comprising the amino acid sequence of SEQ ID NO: 77, or (ii) a first heavy chain comprising the amino acid sequence of SEQ ID NO: 124, a second heavy chain comprising the amino acid sequence of SEQ ID NO: 125, and two light chains comprising the amino acid sequence of SEQ ID NO: 77.

In one aspect, the TNF ligand family member is OX40L. In a further aspect, the ectodomain of a TNF ligand family member comprises the amino acid sequence selected from the group consisting of SEQ ID NO: 181 or SEQ ID NO: 182, particularly the amino acid sequence SEQ ID NO: 181.

In a further aspect, provided is a TNF family ligand trimer-containing antigen binding molecule as described herein before, comprising (a) at least one moiety capable of specific binding to TnC and (b) a first and a second polypeptide that are linked to each other by a disulfide bond, wherein the antigen binding molecule is characterized in that the first polypeptide comprises the amino acid sequence of SEQ ID NO: 190 or SEQ ID: 191 and in that the second polypeptide comprises the amino acid sequence of SEQ ID NO: 181 or SEQ ID NO: 182.

In another aspect, provided is a TNF family ligand trimer-containing antigen binding molecule as describe herein, wherein the target cell antigen is Tenascin-C (TnC) and the moiety capable of specific binding to TnC comprises a VH domain comprising (i) CDR-H1 comprising the amino acid sequence of SEQ ID NO: 67 or SEQ ID NO: 70, (ii) CDR-H2 comprising the amino acid sequence of SEQ ID NO: 68 or SEQ ID NO: 71, and (iii) CDR-H3 comprising the amino acid sequence of SEQ ID NO: 69 or SEQ ID NO: 72, and a VL domain comprising (iv) CDR-L1 comprising the amino acid sequence of SEQ ID NO: 55 or SEQ ID NO: 58, (v) CDR-L2 comprising the amino acid sequence of SEQ ID NO: 56 or SEQ ID NO: 59, and (vi) CDR-L3 comprising the amino acid sequence of SEQ ID NO: 57 or SEQ ID NO: 60.

Particularly, provided is a TNF family ligand trimer-containing antigen binding molecule as described herein, wherein the antigen binding molecule comprises (i) a first heavy chain comprising the VH domain comprising the amino acid sequence of SEQ ID NO: 46 and a first light chain comprising the VL domain comprising the amino acid sequence of SEQ ID NO:45 or a first heavy chain comprising the VH domain comprising the amino acid sequence of SEQ ID NO: 48 and a first light chain comprising the VL domain comprising the amino acid sequence of SEQ ID NO: 47, (ii) a second heavy chain comprising the amino acid sequence selected from the group consisting of SEQ ID NO: 195, and (iii) a second light chain comprising the amino acid sequence of SEQ ID NO: 196.

According to another aspect of the invention, there is provided an isolated polynucleotide encoding an antigen binding molecule as defined herein before. The invention further provides a vector, particularly an expression vector, comprising the isolated polynucleotide of the invention and a host cell comprising the isolated polynucleotide or the vector of the invention. In some embodiments the host cell is a eukaryotic cell, particularly a mammalian cell.

In another aspect, provided is a method for producing the antigen binding molecule of the invention, comprising the steps of (i) culturing the host cell of the invention under conditions suitable for expression of the antigen binding molecule, and (ii) recovering the antigen binding molecule. The invention also encompasses an antigen binding molecule produced by the method of the invention.

The invention further provides a pharmaceutical composition comprising the antigen binding molecule of the invention and at least one pharmaceutically acceptable excipient.

Also encompassed by the invention is the antigen binding molecule of the invention, or the pharmaceutical composition of the invention, for use as a medicament. In one aspect is provided the antigen binding molecule of the invention, or the pharmaceutical composition of the invention, for use in the treatment of a disease in an individual in need thereof. In a specific embodiment, provided is the antigen binding molecule of the invention, or the pharmaceutical composition of the invention, for use in the treatment of cancer.

Also provided is the use of the antigen binding molecule of the invention for the manufacture of a medicament for the treatment of a disease in an individual in need thereof, in particular for the manufacture of a medicament for the treatment of cancer, as well as a method of treating a disease in an individual, comprising administering to said individual a therapeutically effective amount of a composition comprising the antigen binding molecule of the invention in a pharmaceutically acceptable form. In a specific embodiment, the disease is cancer. In any of the above embodiments the individual is preferably a mammal, particularly a human.

BRIEF DESCRIPTION OF THE DRAWINGS

FIG. 2 shows the results of the immunohistological staining in human tumor array with a rabbit isotype control. Negative isotype control signal in all tissues tested validates the specificity of the technique.

FIG. 3 shows the results of the immunohistological staining in human tumor array with anti-TnC clone 18D4. The pattern of staining corresponds to specific TnC stroma fibers. The TnC staining is expressed at higher levels in most tumor tissues compared to control normal pair tissue.

FIG. 4 shows the results of the immunohistological staining in human tumor array with anti-TnC clone 11C7. The pattern of staining corresponds to specific TnC stroma fibers. The TnC staining is expressed at higher levels in most tumor tissues compared to control normal pair tissue.

FIG. 5A shows a dimeric ligand fused to human IgG1-CL domain. FIG. 5B shows a monomeric ligand fused to human IgG1-CH1 domain. "GGGGSGGGGS" is disclosed as SEQ ID NO: 150.

FIG. 7A shows dimeric ligand fused to human IgG1-CL domain. FIG. 7B shows monomeric ligand fused to human IgG1-CH1 domain. "GGGGSGGGGS" is disclosed as SEQ ID NO: 150.

FIG. 9A shows dimeric ligand fused to human IgG1 Fc hole chain. FIG. 9B shows monomeric ligand fused to human IgG1 Fc knob chain. "GGGGSGGGGS" is disclosed as SEQ ID NO: 150.

FIG. 11A shows dimeric ligand fused to human IgG1-CL domain. FIG. 11B shows monomeric ligand fused to human IgG1-CH1 domain. "GGGGSGGGGS" is disclosed as SEQ ID NO: 150.

FIG. 13A shows dimeric ligand fused to human IgG1-CL domain. FIG. 13B shows monomeric ligand fused to human IgG1-CH1 domain. "GGGGSGGGGS" is disclosed as SEQ ID NO: 150.

FIG. 15A shows dimeric ligand fused to human IgG1 Fc hole chain. FIG. 15B shows monomeric ligand fused to human IgG1 Fc knob chain. "GGGGSGGGGS" is disclosed as SEQ ID NO: 150.

FIG. 17A shows dimeric ligand fused to human IgG1 Fc hole or knob chain. FIG. 17B shows monomeric ligand fused to human IgG1 Fc knob or hole chain. "GGGGSGGGGS" is disclosed as SEQ ID NO: 150.

FIG. 18A shows construct 6.11, dimeric 4-1BBL fused to hole Fc chain and monomeric 4-1BBL fused to knob Fc chain. FIG. 18B shows construct 6.12, dimeric 4-1BBL fused to knob Fc chain and monomeric 4-1BBL fused to hole Fc chain. The preparation and production of these constructs is described in Example 1.7. The VH and VL domains are those of anti-TnC antibody 18D4, the thick black point stands for the knob-into-hole modification.

FIG. 19A shows construct 6.13, dimeric 4-1BBL fused to hole Fc chain and monomeric 4-1BBL fused to knob Fc chain. FIG. 19B shows construct 6.14, dimeric 4-1BBL fused to knob Fc chain and monomeric 4-1BBL fused to hole Fc chain. The preparation and production of these constructs is described in Example 1.8. The VH and VL domains are those of anti-TnC antibody 18D4, the thick black point stands for the knob-into-hole modification.

FIG. 20A shows setup of the SPR experiments. FIG. 20B shows simultaneous binding of human 4-1BB and human TnC for construct 6.5. FIG. 20C shows simultaneous binding of human 4-1BB and human TnC for construct 6.6.

FIG. 27A shows expression levels of CD25 as frequency of total CD8+ T cells are plotted against the used concentration of construct 6.5 and 6.6 or controls (control F, control L and control E). FIG. 27B shows levels of CD137 (4-1BB) as frequency of total CD8+ T cells are plotted against the used concentration of construct 6.5 and 6.6 or controls (control F, control L and control E).

DETAILED DESCRIPTION OF THE INVENTION

Definitions

Figure 1A:
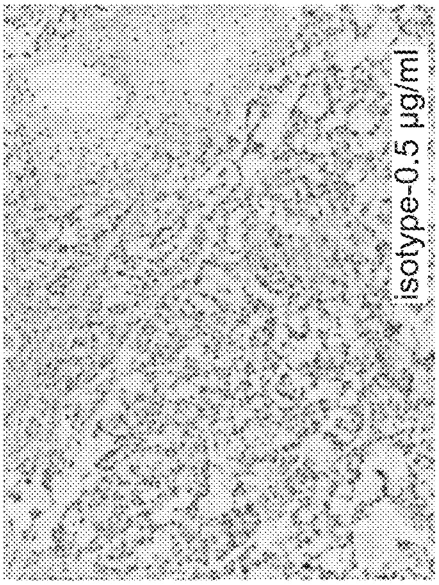
FIGS. 1A, 1B, and 1C shows immunohistological staining in LS174T xenografts tumors at 100× magnification as stained with anti-TnC clone 18D4 (FIG. 1B) and anti-TnC clone 11C7 (FIG. 1C). The pattern of staining corresponds to specific TnC stroma fibers. The TnC staining, for both clones 18D4 and 11C7, is overall expressed with moderate intensity. Negative isotype control signal validates the specificity of the technique (FIG. 1A).

Unless defined otherwise, technical and scientific terms used herein have the same meaning as generally used in the art to which this invention belongs. For purposes of interpreting this specification, the following definitions will apply and whenever appropriate, terms used in the singular will also include the plural and vice versa.

As used herein, the term "antigen binding molecule" refers in its broadest sense to a molecule that specifically binds an antigenic determinant Examples of antigen binding molecules are antibodies, antibody fragments and scaffold antigen binding proteins.

As used herein, the term "moiety capable of specific binding" refers to a polypeptide molecule that specifically binds to an antigenic determinant. In one aspect, the antigen binding moiety is able to activate signaling through its target cell antigen. In a particular aspect, the antigen binding moiety is able to direct the entity to which it is attached (e.g., the TNF family ligand trimer) to a target site, for example to a specific type of tumor cell or tumor stroma bearing the antigenic determinant Moieties capable of specific binding to a target cell antigen include antibodies and fragments thereof as further defined herein. In addition, moieties capable of specific binding to a target cell antigen include scaffold antigen binding proteins as further defined herein, e.g., binding domains which are based on designed repeat proteins or designed repeat domains (see e.g., WO 2002/020565).

In relation to an antibody or fragment thereof, the term "moiety capable of specific binding" refers to the part of the molecule that comprises the area which specifically binds to and is complementary to part or all of an antigen. A moiety capable of specific antigen binding may be provided, for example, by one or more antibody variable domains (also called antibody variable regions). Particularly, a moiety capable of specific antigen binding comprises an antibody light chain variable region (VL) and an antibody heavy chain variable region (VH).

The term "antibody" herein is used in the broadest sense and encompasses various antibody structures, including but not limited to monoclonal antibodies, polyclonal antibodies, monospecific and multispecific antibodies (e.g., bispecific antibodies), and antibody fragments so long as they exhibit the desired antigen-binding activity.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen.

The term "monospecific" antibody as used herein denotes an antibody that has one or more binding sites each of which bind to the same epitope of the same antigen. The term "bispecific" means that the antigen binding molecule is able to specifically bind to at least two distinct antigenic determinants Typically, a bispecific antigen binding molecule comprises two antigen binding sites, each of which is specific for a different antigenic determinant. In certain embodiments the bispecific antigen binding molecule is capable of simultaneously binding two antigenic determinants, particularly two antigenic determinants expressed on two distinct cells.

The term "valent" as used within the current application denotes the presence of a specified number of binding sites in an antigen binding molecule. As such, the terms "bivalent", "tetravalent", and "hexavalent" denote the presence of two binding sites, four binding sites, and six binding sites, respectively, in an antigen binding molecule.

The terms "full length antibody", "intact antibody", and "whole antibody" are used herein interchangeably to refer to an antibody having a structure substantially similar to a native antibody structure. "Native antibodies" refer to naturally occurring immunoglobulin molecules with varying structures. For example, native IgG-class antibodies are heterotetrameric glycoproteins of about 150,000 daltons, composed of two light chains and two heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a light chain constant domain (CL), also called a light chain constant region. The heavy chain of an antibody may be assigned to one of five types, called α (IgA), δ (IgD), ε (IgE), γ (IgG), or μ (IgM), some of which may be further divided into subtypes, e.g., γ1 (IgG1), γ2 (IgG2), γ3 (IgG3), γ4 (IgG4), α1 (IgA1) and α2 (IgA2). The light chain of an antibody may be assigned to one of two types, called kappa (κ) and lambda (λ), based on the amino acid sequence of its constant domain.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, $F(ab')_2$; diabodies, triabodies, tetrabodies, cross-Fab fragments; linear antibodies; single-chain antibody molecules (e.g., scFv); and single domain antibodies. For a review of certain antibody fragments, see Hudson et al., Nat Med 9, 129-134 (2003). For a review of scFv fragments, see e.g., Plückthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046. Diabodies are antibody fragments with two antigen-binding sites that may be bivalent or bispecific, see, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see e.g., U.S. Pat. No. 6,248,516 B1). Antibody fragments can be made by various techniques, including but not limited to proteolytic digestion of an intact antibody as well as production by recombinant host cells (e.g., *E. coli* or phage), as described herein.

Papain digestion of intact antibodies produces two identical antigen-binding fragments, called "Fab" fragments containing each the heavy- and light-chain variable domains and also the constant domain of the light chain and the first constant domain (CH1) of the heavy chain. As used herein, thus, the term "Fab fragment" refers to an antibody fragment comprising a light chain fragment comprising a VL domain and a constant domain of a light chain (CL), and a VH domain and a first constant domain (CH1) of a heavy chain. Fab' fragments differ from Fab fragments by the addition of a few residues at the carboxy terminus of the heavy chain CH1 domain including one or more cysteins from the antibody hinge region. Fab'-SH are Fab' fragments in which the cysteine residue(s) of the constant domains bear a free thiol group. Pepsin treatment yields an $F(ab')_2$ fragment that has two antigen-combining sites (two Fab fragments) and a part of the Fc region.

The term "cross-Fab fragment" or "xFab fragment" or "crossover Fab fragment" refers to a Fab fragment, wherein either the variable regions or the constant regions of the heavy and light chain are exchanged. Two different chain compositions of a crossover Fab molecule are possible and comprised in the bispecific antibodies of the invention: On the one hand, the variable regions of the Fab heavy and light chain are exchanged, i.e., the crossover Fab molecule comprises a peptide chain composed of the light chain variable region (VL) and the heavy chain constant region (CH1), and a peptide chain composed of the heavy chain variable region (VH) and the light chain constant region (CL). This crossover Fab molecule is also referred to as $CrossFab_{(VLVH)}$. On the other hand, when the constant regions of the Fab heavy and light chain are exchanged, the crossover Fab molecule comprises a peptide chain composed of the heavy chain variable region (VH) and the light chain constant region (CL), and a peptide chain composed of the light chain variable region (VL) and the heavy chain constant region (CH1). This crossover Fab molecule is also referred to as $CrossFab_{(CLCH)}$.

A "single chain Fab fragment" or "scFab" is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CH1-linker-VL-CL, b) VL-CL-linker-VH-CH1, c) VH-CL-linker-VL-CH1 or d) VL-CH1-linker-VH-CL; and wherein said linker is a polypeptide of at least 30 amino acids, preferably between 32 and 50 amino acids. Said single chain Fab fragments are stabilized via the natural disulfide bond between the CL domain and the CH1 domain. In addition, these single chain Fab molecules might be further stabilized by generation of interchain disulfide bonds via insertion of cysteine residues (e.g., position 44 in the variable heavy chain and position 100 in the variable light chain according to Kabat numbering).

A "crossover single chain Fab fragment" or "x-scFab" is a is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CL-linker-VL-CH1 and b) VL-CH1-linker-VH-CL; wherein VH and VL form together an antigen-binding site which binds specifically to an antigen and wherein said linker is a polypeptide of at least 30 amino acids. In addition, these x-scFab molecules might be further stabilized by generation of interchain disulfide bonds via insertion of cysteine residues (e.g., position 44 in the variable heavy chain and position 100 in the variable light chain according to Kabat numbering).

A "single-chain variable fragment (scFv)" is a fusion protein of the variable regions of the heavy ($V_H$) and light chains ($V_L$) of an antibody, connected with a short linker peptide of ten to about 25 amino acids. The linker is usually rich in glycine for flexibility, as well as serine or threonine for solubility, and can either connect the N-terminus of the $V_H$ with the C-terminus of the $V_L$, or vice versa. This protein retains the specificity of the original antibody, despite removal of the constant regions and the introduction of the linker. scFv antibodies are, e.g. described in Houston, J. S., Methods in Enzymol. 203 (1991) 46-96). In addition, antibody fragments comprise single chain polypeptides having the characteristics of a VH domain, namely being able to assemble together with a VL domain, or of a VL domain, namely being able to assemble together with a VH domain to a functional antigen binding site and thereby providing the antigen binding property of full length antibodies.

"Scaffold antigen binding proteins" are known in the art, for example, fibronectin and designed ankyrin repeat proteins (DARPins) have been used as alternative scaffolds for antigen-binding domains, see, e.g., Gebauer and Skerra, Engineered protein scaffolds as next-generation antibody therapeutics. Curr Opin Chem Biol 13:245-255 (2009) and Stumpp et al., Darpins: A new generation of protein therapeutics. Drug Discovery Today 13: 695-701 (2008). In one aspect of the invention, a scaffold antigen binding protein is selected from the group consisting of CTLA-4 (Evibody), Lipocalins (Anticalin), a Protein A-derived molecule such as Z-domain of Protein A (Affibody), an A-domain (Avimer/Maxibody), a serum transferrin (trans-body); a designed ankyrin repeat protein (DARPin), a variable domain of antibody light chain or heavy chain (single-domain antibody, sdAb), a variable domain of antibody heavy chain (nanobody, aVH), $V_{NAR}$ fragments, a fibronectin (AdNectin), a C-type lectin domain (Tetranectin); a variable domain of a new antigen receptor beta-lactamase ($V_{NAR}$ fragments), a human gamma-crystallin or ubiquitin (Affilin molecules); a kunitz type domain of human protease inhibitors, microbodies such as the proteins from the knottin family, peptide aptamers and fibronectin (adnectin).

CTLA-4 (Cytotoxic T Lymphocyte-associated Antigen 4) is a CD28-family receptor expressed on mainly CD4+ T-cells. Its extracellular domain has a variable domain-like Ig fold. Loops corresponding to CDRs of antibodies can be substituted with heterologous sequence to confer different binding properties. CTLA-4 molecules engineered to have different binding specificities are also known as Evibodies (e.g. U.S. Pat. No. 7,166,697B1). Evibodies are around the same size as the isolated variable region of an antibody (e.g., a domain antibody). For further details see Journal of Immunological Methods 248 (1-2), 31-45 (2001).

Lipocalins are a family of extracellular proteins which transport small hydrophobic molecules such as steroids, bilins, retinoids and lipids. They have a rigid beta-sheet secondary structure with a number of loops at the open end of the conical structure which can be engineered to bind to different target antigens. Anticalins are between 160-180 amino acids in size, and are derived from lipocalins. For further details see Biochim Biophys Acta 1482: 337-350 (2000), U.S. Pat. No. 7,250,297B1 and US20070224633.

An affibody is a scaffold derived from Protein A of *Staphylococcus aureus* which can be engineered to bind to antigen. The domain consists of a three-helical bundle of approximately 58 amino acids. Libraries have been generated by randomization of surface residues. For further details see Protein Eng. Des. Sel. 17, 455-462 (2004) and EP 1641818A1.

Avimers are multidomain proteins derived from the A-domain scaffold family. The native domains of approximately 35 amino acids adopt a defined disulfide bonded structure.

Diversity is generated by shuffling of the natural variation exhibited by the family of A-domains. For further details see Nature Biotechnology 23(12), 1556-1561 (2005) and Expert Opinion on Investigational Drugs 16(6), 909-917 (June 2007).

A transferrin is a monomeric serum transport glycoprotein. Transferrins can be engineered to bind different target antigens by insertion of peptide sequences in a permissive surface loop. Examples of engineered transferrin scaffolds include the Trans-body. For further details see J. Biol. Chem 274, 24066-24073 (1999).

Designed Ankyrin Repeat Proteins (DARPins) are derived from Ankyrin which is a family of proteins that mediate attachment of integral membrane proteins to the cytoskeleton. A single ankyrin repeat is a 33 residue motif consisting of two alpha-helices and a beta-turn. They can be engineered to bind different target antigens by randomizing residues in the first alpha-helix and a beta-turn of each repeat. Their binding interface can be increased by increasing the number of modules (a method of affinity maturation). For further details see J. Mol. Biol. 332, 489-503 (2003), PNAS 100(4), 1700-1705 (2003) and J. Mol. Biol. 369, 1015-1028 (2007) and US20040132028A1.

A single-domain antibody is an antibody fragment consisting of a single monomeric variable antibody domain. The first single domain antibodies were derived from the variable domain of the antibody heavy chain from camelids (nanobodies or $V_H$H fragments). Furthermore, the term single-domain antibody includes an autonomous human heavy chain variable domain (aVH) or $V_{NAR}$ fragments derived from sharks.

Fibronectin is a scaffold which can be engineered to bind to antigen. Adnectins consists of a backbone of the natural amino acid sequence of the 10th domain of the 15 repeating units of human fibronectin type III (FN3). Three loops at one end of the .beta.-sandwich can be engineered to enable an Adnectin to specifically recognize a therapeutic target of interest. For further details see Protein Eng. Des. Sel. 18, 435-444 (2005), US20080139791, WO2005056764 and U.S. Pat. No. 6,818,418B1.

Peptide aptamers are combinatorial recognition molecules that consist of a constant scaffold protein, typically thioredoxin (TrxA) which contains a constrained variable peptide loop inserted at the active site. For further details see Expert Opin. Biol. Ther. 5, 783-797 (2005).

Microbodies are derived from naturally occurring microproteins of 25-50 amino acids in length which contain 3-4 cysteine bridges—examples of microproteins include KalataBl and conotoxin and knottins. The microproteins have a loop which can be engineered to include up to 25 amino acids without affecting the overall fold of the microprotein. For further details of engineered knottin domains, see WO2008098796.

An “antigen binding molecule that binds to the same epitope” as a reference molecule refers to an antigen binding molecule that blocks binding of the reference molecule to its antigen in a competition assay by 50% or more, and conversely, the reference molecule blocks binding of the antigen binding molecule to its antigen in a competition assay by 50% or more.

The term “antigen binding domain” refers to the part of an antigen binding molecule that comprises the area which specifically binds to and is complementary to part or all of an antigen. Where an antigen is large, an antigen binding molecule may only bind to a particular part of the antigen, which part is termed an epitope. An antigen binding domain may be provided by, for example, one or more variable domains (also called variable regions). Preferably, an antigen binding domain comprises an antibody light chain variable region (VL) and an antibody heavy chain variable region (VH).

As used herein, the term “antigenic determinant” is synonymous with “antigen” and “epitope”, and refers to a site (e.g., a contiguous stretch of amino acids or a conformational configuration made up of different regions of non-contiguous amino acids) on a polypeptide macromolecule to which an antigen binding moiety binds, forming an antigen binding moiety-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM). The proteins useful as antigens herein can be any native form the proteins from any vertebrate source, including mammals such as primates (e.g. humans) and rodents (e.g. mice and rats), unless otherwise indicated. In a particular embodiment the antigen is a human protein. Where reference is made to a specific protein herein, the term encompasses the “full-length”, unprocessed protein as well as any form of the protein that results from processing in the cell. The term also encompasses naturally occurring variants of the protein, e.g., splice variants or allelic variants.

The terms “capable of specific binding to TnC” refer to an antigen binding molecule or antigen binding moiety that is capable of binding Tenascin-C (TnC) with sufficient affinity such that the antigen binding molecule is useful as a diagnostic and/or therapeutic agent in targeting TnC. The antigen binding molecules include but are not limited to, antibodies, Fab molecules, crossover Fab molecules, single chain Fab molecules, Fv molecules, scFv molecules, single domain antibodies, and VH and scaffold antigen binding protein. In one embodiment, the extent of binding of an anti-TnC antigen binding molecule to an unrelated, non-TnC protein is less than about 10% of the binding of the antigen binding molecule to TnC as measured, e.g., by a radioimmunoassay (RIA). In certain embodiments, an antigen binding molecule that binds to TnC has a dissociation constant ($K_D$) of ≤1 μM, ≤100 nM, ≤10 nM, ≤5 nM, ≤2 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$M to $10^{-13}$ M, e.g., from 10 nM to 0.1 nM, e.g., from 5 nM to 0.1 nM, e.g., from 2 nM to 0.1 nM). In certain embodiments, an anti-TnC antigen binding molecule binds to an epitope of TnC that is conserved among TnC from different species. In certain embodiments, an antigen binding molecule that binds to an epitope of TnC is specific for at least one of the domains selected from the group consisting of A1, A2, A3, A4, B, AD1, AD2, C and D. In certain embodiments an antigen binding molecule specific for the TnC A1 and TnC A4 domains is provided. In certain embodiments an antigen binding molecule specific for the TnC C domain is provided. By “specific binding” is meant that the binding is selective for the antigen and can be discriminated from unwanted or non-specific interactions. The ability of an antigen binding molecule to bind to a specific antigen can be measured either through an enzyme-linked immunosorbent assay (ELISA) or other techniques familiar to one of skill in the art, e.g., Surface Plasmon Resonance (SPR) technique (analyzed on a BIAcore instrument) (Liljeblad et al., Glyco J 17, 323-329 (2000)), and traditional binding assays (Heeley, Endocr Res 28, 217-229 (2002)). In one embodiment, the extent of binding of an antigen binding molecule to an unrelated protein is less than about 10% of the binding of the antigen binding molecule to the antigen as measured, e.g., by SPR.

In certain embodiments, a molecule that binds to the antigen has a dissociation constant (Kd) of ≤1 μM, ≤100 nM, ≤10 nM, ≤5 nM, ≤2 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g. from $10^{-9}$ M to $10^{-13}$ M).

"Affinity" or "binding affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd), which is the ratio of dissociation and association rate constants ($k_{off}$ and $k_{on}$, respectively). Thus, equivalent affinities may comprise different rate constants, as long as the ratio of the rate constants remains the same. Affinity can be measured by common methods known in the art, including those described herein. A particular method for measuring affinity is Surface Plasmon Resonance (SPR).

A "target cell antigen" as used herein refers to an antigenic determinant presented on the surface of a target cell or in the environment of a target cell, for example a cell in a tumor such as a cancer cell or a cell of the tumor stroma. In certain embodiments, the target cell antigen is expressed in the extracellular matrix in or around tumor tissue. In particular, the target cell antigen is Tenascin-C (TnC). The term "Tenascin-C" or "TnC" as used herein, refers to any native TnC from any vertebrate source, including mammals such as primates (e.g., humans and cynomolgus monkey) and rodents (e.g., mice and rats), unless otherwise indicated. The term encompasses "full-length," unprocessed TnC as well as any form of TnC that results from processing in the cell. The term also encompasses naturally occurring variants of TnC, e.g., splice variants or allelic variants. The amino acid sequence of an exemplary human TnC antigen sequence (with N-terminal GST and 6×His-tag; and C-terminal avi-tag and 6×His-tag) is shown in SEQ ID NO: 4. The amino acid sequence of an exemplary mouse TnC antigen sequence (with N-terminal GST and 6×His-tag; and C-terminal avi-tag and 6×His-tag) is shown in SEQ ID NO: 5. The amino acid sequence of an exemplary cynomolgus TnC antigen sequence (with N-terminal GST and 6×His-tag (SEQ ID NO: 221); and C-terminal avi-tag and 6×His-tag) is shown in SEQ ID NO: 6. In the human TnC molecule, up to nine alternatively spliced fibronectin-type III domains, which may be inserted between the fifth and the sixth of the constant fibronectin-type III domains are known (for a schematic representation of the domain structure of TnC, see e.g., Orend and Chiquet-Ehrismann, Cancer Letters 244, 143-163 (2006). Similarly, in the mouse TnC molecule, six alternatively spliced fibronectin-type III domains are described (e.g., in Joestner and Faissner, J Biol Chem 274, 17144-17151 (1999)).

The term "variable region" or "variable domain" refers to the domain of an antibody heavy or light chain that is involved in binding the antigen binding molecule to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, 6th ed., W.H. Freeman and Co., page 91 (2007). A single VH or VL domain may be sufficient to confer antigen-binding specificity.

The term "hypervariable region" or "HVR," as used herein refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest,* 5th Ed. Public Health Service, National Institutes of Health, Bethesda, Md. (1991).) Hypervariable regions (HVRs) are also referred to as complementarity determining regions (CDRs), and these terms are used herein interchangeably in reference to portions of the variable region that form the antigen binding regions. This particular region has been described by Kabat et al., U.S. Dept. of Health and Human Services, "Sequences of Proteins of Immunological Interest" (1983) and by Chothia et al., *J. Mol. Biol.* 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table A as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE A

| CDR Definitions[1] | | | |
|---|---|---|---|
| CDR | Kabat | Chothia | AbM[2] |
| $V_H$ CDR1 | 31-35 | 26-32 | 26-35 |
| $V_H$ CDR2 | 50-65 | 52-58 | 50-58 |
| $V_H$ CDR3 | 95-102 | 95-102 | 95-102 |
| $V_L$ CDR1 | 24-34 | 26-32 | 24-34 |
| $V_L$ CDR2 | 50-56 | 50-52 | 50-56 |
| $V_L$ CDR3 | 89-97 | 91-96 | 89-97 |

[1]Numbering of all CDR definitions in Table A is according to the numbering conventions set forth by Kabat et al. (see below).
[2]"AbM" with a lowercase "b" as used in Table A refers to the CDRs as defined by Oxford Molecular's "AbM" antibody modeling software.

Kabat et al. also defined a numbering system for variable region sequences that is applicable to any antibody. One of ordinary skill in the art can unambiguously assign this system of "Kabat numbering" to any variable region sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody variable region are according to the Kabat numbering system.

With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

As used herein, the term "affinity matured" in the context of antigen binding molecules (e.g., antibodies) refers to an antigen binding molecule that is derived from a parent antigen binding molecule, e.g., by mutation, binds to the same antigen, preferably binds to the same epitope, as the parent antibody; and has a higher affinity for the antigen than that of the reference antigen binding molecule. Affinity maturation generally involves modification of one or more amino acid residues in one or more CDRs of the antigen binding molecule. Typically, the affinity matured antigen binding molecule binds to the same epitope as the initial parent antigen binding molecule.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called $\alpha$, $\delta$, $\varepsilon$, $\gamma$, and $\mu$ respectively.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

A "human" antibody is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

The term "Fc domain" or "Fc region" herein is used to define a C-terminal region of an antibody heavy chain that contains at least a portion of the constant region. The term includes native sequence Fc regions and variant Fc regions. An IgG Fc region comprises an IgG CH2 and an IgG CH3 domain. The "CH2 domain" of a human IgG Fc region usually extends from an amino acid residue at about position 231 to an amino acid residue at about position 340. In one embodiment, a carbohydrate chain is attached to the CH2 domain. The CH2 domain herein may be a native sequence CH2 domain or variant CH2 domain. The "CH3 domain" comprises the stretch of residues C-terminal to a CH2 domain in an Fc region (i.e., from an amino acid residue at about position 341 to an amino acid residue at about position 447 of an IgG). The CH3 region herein may be a native sequence CH3 domain or a variant CH3 domain (e.g., a CH3 domain with an introduced "protuberance" ("knob") in one chain thereof and a corresponding introduced "cavity" ("hole") in the other chain thereof; see U.S. Pat. No. 5,821,333, expressly incorporated herein by reference). Such variant CH3 domains may be used to promote heterodimerization of two non-identical antibody heavy chains as herein described. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

The "knob-into-hole" (kih) technology is described e.g., in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g., tyrosine or tryptophan). Compensatory cavities of identical or similar size to the protuberances are created in the interface of the second polypeptide by replacing large amino acid side chains with smaller ones (e.g., alanine or threonine). The protuberance and cavity can be made by altering the nucleic acid encoding the polypeptides, e.g., by site-specific mutagenesis, or by peptide synthesis. In a specific embodiment a knob modification comprises the amino acid substitution T366W in one of the two subunits of the Fc domain, and the hole modification comprises the amino acid substitutions T366S, L368A and Y407V in the other one of the two subunits of the Fc domain. In a further specific embodiment, the subunit of the Fc domain comprising the knob modification additionally comprises the amino acid substitution S354C, and the subunit of the Fc domain comprising the hole modification additionally comprises the amino acid substitution Y349C. Introduction of these two cysteine residues results in the formation of a disulfide bridge between the two subunits of the Fc region, thus further stabilizing the dimer (Carter, J Immunol Methods 248, 7-15 (2001)). The numbering is according to EU index of Kabat et al, Sequences of Proteins of Immunological Interest, 5th Ed. Public Health Service, National Institutes of Health, Bethesda, Md., 1991.

A "region equivalent to the Fc region of an immunoglobulin" is intended to include naturally occurring allelic variants of the Fc region of an immunoglobulin as well as variants having alterations which produce substitutions, additions, or deletions but which do not decrease substantially the ability of the immunoglobulin to mediate effector functions (such as antibody-dependent cellular cytotoxicity). For example, one or more amino acids can be deleted from the N-terminus or C-terminus of the Fc region of an immunoglobulin without substantial loss of biological function. Such variants can be selected according to general rules known in the art so as to have minimal effect on activity (see, e.g., Bowie, J. U. et al., Science 247:1306-10 (1990)). The term "effector functions" refers to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g., B cell receptor), and B cell activation.

An "activating Fc receptor" is an Fc receptor that following engagement by an Fc region of an antibody elicits signaling events that stimulate the receptor-bearing cell to perform effector functions. Activating Fc receptors include FcγRIIIa (CD16a), FcγRI (CD64), FcγRIIa (CD32), and FcαRI (CD89). A particular activating Fc receptor is human FcγRIIIa (see UniProt accession no. P08637, version 141).

The term "TNF ligand family member" or "TNF family ligand" refers to a proinflammatory cytokine. Cytokines in general, and in particular the members of the TNF ligand family, play a crucial role in the stimulation and coordination of the immune system. At present, nineteen cytokines have been identified as members of the TNF (tumor necrosis factor) ligand superfamily on the basis of sequence, functional, and structural similarities. All these ligands are type II transmembrane proteins with a C-terminal extracellular domain (ectodomain), N-terminal intracellular domain and a single transmembrane domain. The C-terminal extracellular domain, known as TNF homology domain (THD), has 20-30% amino acid identity between the superfamily members and is responsible for binding to the receptor. The TNF ectodomain is also responsible for the TNF ligands to form trimeric complexes that are recognized by their specific receptors.

Members of the TNF ligand family are selected from the group consisting of Lymphotoxin α (also known as LTA or TNFSF1), TNF (also known as TNFSF2), LTβ (also known as TNFSF3), OX40L (also known as TNFSF4), CD40L (also known as CD154 or TNFSF5), FasL (also known as CD95L, CD178 or TNFSF6), CD27L (also known as CD70 or TNFSF7), CD30L (also known as CD153 or TNFSF8), 4-1BBL (also known as TNFSF9), TRAIL (also known as APO2L, CD253 or TNFSF10), RANKL (also known as CD254 or TNFSF11), TWEAK (also known as TNFSF12), APRIL (also known as CD256 or TNFSF13), BAFF (also known as CD257 or TNFSF13B), LIGHT (also known as CD258 or TNFSF14), TL1A (also known as VEGI or TNFSF15), GITRL (also known as TNFSF18), EDA-A1 (also known as ectodysplasin A1) and EDA-A2 (also known as ectodysplasin A2). The term refers to any native TNF family ligand from any vertebrate source, including mammals such as primates (e.g., humans), non-human primates (e.g., cynomolgus monkeys) and rodents (e.g., mice and rats), unless otherwise indicated. In specific embodiments of the invention, the TNF ligand family member is selected from the group consisting of OX40L, FasL, CD27L, TRAIL, 4-1BBL, CD40L and GITRL. In a particular embodiment, the TNF ligand family member is selected from 4-1BBL and OX40L.

Further information, in particular sequences, of the TNF ligand family members may be obtained from publically accessible databases such as Uniprot (www.uniprot.org). For instance, the human TNF ligands have the following amino acid sequences: human Lymphotoxin α (UniProt accession no. P01374, SEQ ID NO: 203), human TNF (UniProt accession no. P01375, SEQ ID NO: 204), human Lymphotoxin β (UniProt accession no. Q06643, SEQ ID NO: 205), human OX40L (UniProt accession no. P23510, SEQ ID NO: 206), human CD40L (UniProt accession no. P29965, SEQ ID NO: 207), human FasL (UniProt accession no. P48023, SEQ ID NO: 208), human CD27L (UniProt accession no. P32970, SEQ ID NO: 209), human CD30L (UniProt accession no. P32971, SEQ ID NO: 210), 4-1BBL (UniProt accession no. P41273, SEQ ID NO: 211), TRAIL (UniProt accession no. P50591, SEQ ID NO: 212), RANKL (UniProt accession no. 014788, SEQ ID NO: 213), TWEAK (UniProt accession no. 043508, SEQ ID NO: 214), APRIL (UniProt accession no. 075888, SEQ ID NO: 215), BAH- (UniProt accession no. Q9Y275, SEQ ID NO: 216), LIGHT (UniProt accession no. 043557, SEQ ID NO: 217), TL1A (UniProt accession no. 095150, SEQ ID NO: 218), GITRL (UniProt accession no. Q9UNG2, SEQ ID NO: 219) and ectodysplasin A (UniProt accession no. Q92838, SEQ ID NO: 220).

An "ectodomain" is the domain of a membrane protein that extends into the extracellular space (i.e., the space outside the target cell). Ectodomains are usually the parts of proteins that initiate contact with surfaces, which leads to signal transduction. The ectodomain of TNF ligand family member as defined herein thus refers to the part of the TNF ligand protein that extends into the extracellular space (the extracellular domain), but also includes shorter parts or fragments thereof that are responsible for the trimerization and for the binding to the corresponding TNF receptor. The term "ectodomain of a TNF ligand family member or a fragment thereof" thus refers to the extracellular domain of the TNF ligand family member that forms the extracellular domain or to parts thereof that are still able to bind to the receptor (receptor binding domain).

The term "costimulatory TNF ligand family member" or "costimulatory TNF family ligand" refers to a subgroup of TNF ligand family members, which are able to costimulate proliferation and cytokine production of T-cells. These TNF family ligands can costimulate TCR signals upon interaction with their corresponding TNF receptors and the interaction with their receptors leads to recruitment of TNFR-associated factors (TRAF), which initiate signalling cascades that result in T-cell activation. Costimulatory TNF family ligands are selected from the group consisting of 4-1BBL, OX40L, GITRL, CD70, CD30L and LIGHT, more particularly the costimulatory TNF ligand family member is selected from 4-1BBL and OX40L.

As described herein before, 4-1BBL is a type II transmembrane protein and one member of the TNF ligand family Complete or full length 4-1BBL having the amino acid sequence of SEQ ID NO: 212 has been described to form trimers on the surface of cells. The formation of trimers is enabled by specific motives of the ectodomain of 4-1BBL. Said motives are designated herein as "trimerization region". The amino acids 50-254 of the human 4-1BBL sequence (SEQ ID NO: 180) form the extracellular domain of 4-1BBL, but even fragments thereof are able to form the trimers. In specific embodiments of the invention, the term "ectodomain of 4-1BBL or a fragment thereof" refers to a polypeptide having an amino acid sequence selected from SEQ ID NO: 175 (amino acids 52-254 of human 4-1BBL), SEQ ID NO: 172 (amino acids 71-254 of human 4-1BBL), SEQ ID NO: 174 (amino acids 80-254 of human 4-1BBL) and SEQ ID NO: 173 (amino acids 85-254 of human 4-1BBL) or a polypeptide having an amino acid sequence selected from SEQ ID NO: 183 (amino acids 71-248 of human 4-1BBL), SEQ ID NO: 194 (amino acids 52-248 of human 4-1BBL), SEQ ID NO: 193 (amino acids 80-248 of human 4-1BBL) and SEQ ID NO: 192 (amino acids 85-248 of human 4-1BBL), but also other fragments of the ectodomain capable of trimerization are included herein.

As described herein before, OX40L is another type II transmembrane protein and a further member of the TNF ligand family Complete or full length human OX40L has the amino acid sequence of SEQ ID NO: 206. The amino acids 51-183 of the human OX40L sequence (SEQ ID NO: 181) form the extracellular domain of OX40L, but even fragments thereof that are able to form the trimers. In specific embodiments of the invention, the term "ectodomain of OX40L or a fragment thereof" refers to a polypeptide having an amino acid sequence selected from SEQ ID NO: 181 (amino acids 51-183 of human OX40L) or SEQ ID NO: 182 (amino acids 52-183 of human OX40L), but also other fragments of the ectodomain capable of trimerization are included herein.

The term "peptide linker" refers to a peptide comprising one or more amino acids, typically about 2 to 20 amino acids. Peptide linkers are known in the art or are described herein. Suitable, non-immunogenic linker peptides are, for example, $(G_4S)_n$ (SEQ ID NO: 222), $(SG_4)_n$ (SEQ ID NO: 223) or $G_4(SG_4)_n$ (SEQ ID NO: 224) peptide linkers, wherein "n" is generally a number between 1 and 10, typically between 1 and 4, in particular 2, i.e., the peptides selected from the group consisting of GGGGS (SEQ ID NO: 162), GGGGSGGGGS (SEQ ID NO: 150), SGGGGSGGGG (SEQ ID NO: 151) and GGGGSGGGGSGGGG (SEQ ID NO: 152), but also include the sequences GSPGSSSSGS (SEQ ID NO: 153), GGGGSGGGGSGGGGSGGGGS (SEQ ID NO: 154), GSGSGNGS (SEQ ID NO: 155), GGSGSGSG (SEQ ID NO: 156), GGSGSG (SEQ ID NO: 157), GGSG (SEQ ID NO: 158), GGSGNGSG (SEQ ID NO: 159), GGNGSGSG (SEQ ID NO: 160) and GGNGSG (SEQ ID NO: 161). Peptide linkers of particular interest are $(G4S)_1$ (SEQ ID NO: 162) or GGGGS (SEQ ID NO: 162), $(G_4S)_2$ (SEQ ID NO: 150) or GGGGSGGGGS (SEQ ID NO: 150) and GSPGSSSSGS (SEQ ID NO: 153), more particularly $(G_4S)_2$ (SEQ ID NO: 150) or GGGGSGGGGS (SEQ ID NO: 150) and GSPGSSSSGS (SEQ ID NO: 153).

The term "amino acid" as used within this application denotes the group of naturally occurring carboxy α-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

A "single chain fusion protein" as used herein refers to a single chain polypeptide composed of one or two ectodomains of said TNF ligand family member fused to a part of antigen binding moiety or Fc part. The fusion may occur by directly linking the N or C-terminal amino acid of the antigen binding moiety via a peptide linker to the C- or N-terminal amino acid of the ectodomain of said TNF ligand family member.

By "fused" or "connected" is meant that the components (e.g., a polypeptide and an ectodomain of said TNF ligand family member) are linked by peptide bonds, either directly or via one or more peptide linkers.

"Percent (%) amino acid sequence identity" with respect to a reference polypeptide (protein) sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN. SAWI or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction $X/Y$ where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

In certain embodiments, "amino acid sequence variants" of the TNF ligand trimer-containing antigen binding molecules provided herein are contemplated. For example, it may be desirable to improve the binding affinity and/or other biological properties of the TNF ligand trimer-containing antigen binding molecules Amino acid sequence variants of the TNF ligand trimer-containing antigen binding molecules may be prepared by introducing appropriate modifications into the nucleotide sequence encoding the molecules, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding. Sites of interest for substitutional mutagenesis include the HVRs and Framework (FRs). Conservative substitutions are provided in Table B under the heading "Preferred Substitutions" and further described below in reference to amino acid side chain classes (1) to (6) Amino acid substitutions may be introduced into the molecule of interest and the products screened for a desired activity, e.g., retained/improved antigen binding, decreased immunogenicity, or improved ADCC or CDC.

TABLE B

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

The term "amino acid sequence variants" includes substantial variants wherein there are amino acid substitutions in one or more hypervariable region residues of a parent antigen binding molecule (e.g., a humanized or human antibody). Generally, the resulting variant(s) selected for further study will have modifications (e.g., improvements) in certain biological properties (e.g., increased affinity, reduced immunogenicity) relative to the parent antigen binding molecule and/or will have substantially retained certain biological properties of the parent antigen binding molecule. An exemplary substitutional variant is an affinity matured antibody, which may be generated, e.g., using phage display-based affinity maturation techniques such as those described herein. Briefly, one or more HVR residues are mutated and the variant antigen binding molecules displayed on phage and screened for a particular biological activity (e.g., binding affinity). In certain embodiments, substitutions, insertions, or deletions may occur within one or more HVRs so long as such alterations do not substantially reduce the ability of the antigen binding molecule to bind antigen. For example, conservative alterations (e.g., conservative substitutions as provided herein) that do not substantially reduce binding affinity may be made in HVRs. A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antigen binding molecule complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include TNF family ligand trimer-containing antigen binding molecule with an N-terminal methionyl residue. Other insertional variants of the molecule include the fusion of the N- or C-terminus to a polypeptide which increases the serum half-life of the TNF ligand trimer-containing antigen binding molecules.

In certain embodiments, the TNF family ligand trimer-containing antigen binding molecules provided herein are altered to increase or decrease the extent to which the antibody is glycosylated. Glycosylation variants of the molecules may be obtained by altering the amino acid sequence such that one or more glycosylation sites is created or removed. Where the TNF ligand trimer-containing antigen binding molecule comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in TNF family ligand trimer-containing antigen binding molecule may be made in order to create variants with certain improved properties. In one aspect, variants of TNF family ligand trimer-containing antigen binding molecules are provided having a carbohydrate structure that lacks fucose attached (directly or indirectly) to an Fc region. Such fucosylation variants may have improved ADCC function, see e.g., US Patent Publication Nos. US 2003/0157108 (Presta, L.) or US 2004/0093621 (Kyowa Hakko Kogyo Co., Ltd). Further variants of the TNF family ligand trimer-containing antigen binding molecules of the invention include those with bisected oligosaccharides, e.g., in which a biantennary oligosaccharide attached to the Fc region is bisected by GlcNAc. Such variants may have reduced fucosylation and/or improved ADCC function, see for example WO 2003/011878 (Jean-Mairet et al.); U.S. Pat. No. 6,602,684 (Umana et al.); and US 2005/0123546 (Umana et al.). Variants with at least one galactose residue in the oligosaccharide attached to the Fc region are also provided. Such antibody variants may have improved CDC function and are described, e.g., in WO 1997/30087 (Patel et al.); WO 1998/58964 (Raju, S.); and WO 1999/22764 (Raju, S.).

In certain embodiments, it may be desirable to create cysteine engineered variants of the TNF family ligand trimer-containing antigen binding molecule of the invention, e.g., "thioMAbs," in which one or more residues of the molecule are substituted with cysteine residues. In particular embodiments, the substituted residues occur at accessible sites of the molecule. By substituting those residues with cysteine, reactive thiol groups are thereby positioned at accessible sites of the antibody and may be used to conjugate the antibody to other moieties, such as drug moieties or linker-drug moieties, to create an immunoconjugate. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antigen binding molecules may be generated as described, e.g., in U.S. Pat. No. 7,521,541.

In certain aspects, the TNF family ligand trimer-containing antigen binding molecules provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc. In another aspect, conjugates of an antibody and non-proteinaceous moiety that may be selectively heated by exposure to radiation are provided. In one embodiment, the non-proteinaceous moiety is a carbon nanotube (Kam, N. W. et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed.

In another aspect, immunoconjugates of the TNF family ligand trimer-containing antigen binding molecules provided herein may be obtained. An "immunoconjugate" is an antibody conjugated to one or more heterologous molecule(s), including but not limited to a cytotoxic agent.

"Cross-species reactivity" refers to the ability of certain antibodies to specifically bind to their respective target antigen wherein said target antigen may derive from different species (e.g., human, mouse, cynomolgus, etc.). A cross-species reactive antibody binds to its respective target antigen derived from at least two different species with a $K_D$ value lower than about 1 μM, preferably lower than about 100 nM, more preferably lower than about 10 nM, more preferably lower than about 5 nM, most preferably lower than about 2 nM. The term "binds to its respective target antigen derived from at least two different species with a $K_D$ value lower than" means that the respective antibody binds to the target antigen deriving from each of the indicated species with a dissociation constant $K_D$ lower than the indicated $K_D$ value. In preferred embodiments a cross-species reactive antibody binds to the target antigen from all indicated species with similar affinity, preferably within a $K_D$ range of 10 nM to 0.1 nM, more preferably 5 nM to 0.1 nM, most preferably 2 nM to 0.1 nM. In some embodiment, similar affinity for the antigen derived from several species, which means binding of the target antigen within a narrow $K_D$ range (e.g., within a range of 10 nM to 0.1 nM or narrower) for all species of interest, is advantageous, e.g., for diagnostic assays or animal models of human diseases. In further preferred embodiment, a cross-species reactive antibody binds to the target antigen from all indicated species (e.g., human, mouse and cynomolgus monkey) with similar affinity, in particular within a $K_D$ range of a factor of 100, within a $K_D$ range of a factor of 50, within a $K_D$ range of a factor of 20, within a $K_D$ range of a factor of 10, within a $K_D$ range of a factor of 5. In a preferred embodiment, a cross-species reactive antibody binds to the target antigen from human, mouse and cynomolgus monkey with similar affinity, in particular within a $K_D$ range of a factor of 10. For clarity, the cross-species reactive antibody binds to one of the indicated species with highest affinity compared to the other indicated species. Accordingly, the cross-species reactive antibody binds to one of the indicated species with lowest affinity compared to the other indicated species. Within a $K_D$ range of a defined factor X means that the affinity for the indicated species with hightest affinity is not more than X-times higher than the affinity for the indicated species with lowest affinity. In other words, the $K_D$ value for the indicated species with lowest affinity is not more than X-times the $K_D$ value for the indicated species with highest affinity. It is clear to the field that any method for measuring affinity or avidity can be used to verify that a cross-species reactive antibody binds to the target antigen from all indicated species within a given $K_D$ factor range as described herein as long as the same conditions are applied to the $K_D$ measurement for all indicated species. Preferably, the $K_D$ values are measured using SPR, in particular at 25° C. Preferably, the affinities are measured using the cross-species reactive antibody as Fab fragment.

The term "polynucleotide" refers to an isolated nucleic acid molecule or construct, e.g., messenger RNA (mRNA), virally-derived RNA, or plasmid DNA (pDNA). A polynucleotide may comprise a conventional phosphodiester bond or a non-conventional bond (e.g., an amide bond, such as found in peptide nucleic acids (PNA). The term "nucleic acid molecule" refers to any one or more nucleic acid segments, e.g. DNA or RNA fragments, present in a polynucleotide.

By "isolated" nucleic acid molecule or polynucleotide is intended a nucleic acid molecule, DNA or RNA, which has been removed from its native environment. For example, a recombinant polynucleotide encoding a polypeptide contained in a vector is considered isolated for the purposes of the present invention. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extrachromosomally or at a chromosomal location that is different from its natural chromosomal location. Isolated RNA molecules include in vivo or in vitro RNA transcripts of the present invention, as well as positive and negative strand forms, and double-stranded forms. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98% or 99% identical to a nucleotide sequence of the present invention can be determined conventionally using known computer programs, such as the ones discussed above for polypeptides (e.g., ALIGN-2).

The term "expression cassette" refers to a polynucleotide generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In certain embodiments, the expression cassette of the invention comprises polynucleotide sequences that encode bispecific antigen binding molecules of the invention or fragments thereof.

The term "vector" or "expression vector" is synonymous with "expression construct" and refers to a DNA molecule that is used to introduce and direct the expression of a specific gene to which it is operably associated in a target cell. The term includes the vector as a self-replicating nucleic acid structure as well as the vector incorporated into the genome of a host cell into which it has been introduced. The expression vector of the present invention comprises an expression cassette. Expression vectors allow transcription of large amounts of stable mRNA. Once the expression vector is inside the target cell, the ribonucleic acid molecule or protein that is encoded by the gene is produced by the cellular transcription and/or translation machinery. In one embodiment, the expression vector of the invention comprises an expression cassette that comprises polynucleotide sequences that encode bispecific antigen binding molecules of the invention or fragments thereof.

The terms "host cell", "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the bispecific antigen binding molecules of the present invention. Host cells include cultured cells, e.g., mammalian cultured cells, such as CHO cells, BHK cells, NS0 cells, SP2/0 cells, YO myeloma cells, P3X63 mouse myeloma cells, PER cells, PER. C6 cells or hybridoma cells, yeast cells, insect cells, and plant cells, to name only a few, but also cells comprised within a transgenic animal, transgenic plant or cultured plant or animal tissue.

An "effective amount" of an agent refers to the amount that is necessary to result in a physiological change in the cell or tissue to which it is administered.

A "therapeutically effective amount" of an agent, e.g., a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). Particularly, the individual or subject is a human.

The term "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable excipient" refers to an ingredient in a pharmaceutical composition, other than an active ingredient, which is nontoxic to a subject. A pharmaceutically acceptable excipient includes, but is not limited to, a buffer, a stabilizer, or a preservative.

The term "package insert" is used to refer to instructions customarily included in commercial packages of therapeutic products, that contain information about the indications, usage, dosage, administration, combination therapy, contraindications and/or warnings concerning the use of such therapeutic products.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, the molecules of the invention are used to delay development of a disease or to slow the progression of a disease.

The term "cancer" as used herein refers to proliferative diseases, such as lymphomas, carcinoma, lymphoma, blastoma, sarcoma, leukemia, lymphocytic leukemias, lung cancer, non-small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colorectal cancer (CRC), pancreatic cancer, breast cancer, triple-negative breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma and Ewings sarcoma, melanoma, multiple myeloma, B-cell cancer (lymphoma), chronic lymphocytic leukemia (CLL), acute lymphoblastic leukemia (ALL), hairy cell leukemia, chronic myeloblastic leukemia, including refractory versions of any of the above cancers, or a combination of one or more of the above cancers.

Compositions and Methods

Distinct alternatively spliced isoforms of Tenascin-C (TnC), are specifically expressed in certain pathological conditions but essentially absent from healthy adult tissues, thus antigen binding molecules targeting TnC have great therapeutic potential. The present invention provides novel TNF family ligand trimer-containing antigen binding molecules with particularly advantageous properties such as producibility, stability, binding affinity, biological activity, targeting efficiency and reduced toxicity. The invention further provides antigen binding molecules that bind to TnC, in particular antigen binding molecules with improved affinity and cross-species reactivity. Antigen binding molecules of the invention are useful, e.g., for the diagnosis or treatment of diseases characterized by expression of TnC, such as cancer.

In a one aspect, provided is a TNF family ligand trimer-containing antigen binding molecule, wherein the target cell antigen is Tenascin-C (TnC). In a further aspect, the invention provides a TNF family ligand trimer-containing antigen binding molecule comprising (a) at least one moiety capable of specific binding to Tenascin-C (TnC) and (b) a first and a second polypeptide that are linked to each other by a disulfide bond, wherein the antigen binding molecule is characterized in that the first polypeptide comprises two ectodomains of a TNF ligand family member or two fragments thereof that are connected to each other by a peptide linker and in that the second polypeptide comprises only one ectodomain of said TNF ligand family member or a fragment thereof.

In a particular aspect, the invention provides a TNF family ligand trimer-containing antigen binding molecule comprising (a) at least one moiety capable of specific binding to TnC, (b) a first and a second polypeptide that are linked to each other by a disulfide bond, wherein the antigen binding molecule is characterized in that the first polypeptide comprises two ectodomains of a TNF ligand family member or two fragments thereof that are connected to each other by a peptide linker and in that the second polypeptide comprises only one ectodomain of said TNF ligand family member or a fragment thereof, and (c) an Fc domain composed of a first and a second subunit capable of stable association.

In a particular aspect, the TNF family ligand trimer-containing antigen binding molecule comprises (a) at least one moiety capable of specific binding to TnC and (b) a first and a second polypeptide that are linked to each other by a disulfide bond, wherein the antigen binding molecule is characterized in that the first polypeptide comprises two ectodomains of a TNF ligand family member or two fragments thereof that are connected to each other by a peptide linker and in that the second polypeptide comprises only one ectodomain of said TNF ligand family member or a fragment thereof, wherein the TNF ligand family member costimulates human T-cell activation.

In another particular aspect, the TNF family ligand trimer-containing antigen binding molecule comprises (a) at least one moiety capable of specific binding to TnC and (b) a first and a second polypeptide that are linked to each other by a disulfide bond, wherein the antigen binding molecule is characterized in that the first polypeptide comprises two ectodomains of a TNF ligand family member or two fragments thereof that are connected to each other by a peptide linker and in that the second polypeptide comprises only one ectodomain of said TNF ligand family member or a fragment thereof, wherein the ectodomains of a TNF ligand family member are identical in all instances.

In a further aspect, provided is a TNF family ligand trimer-containing antigen binding molecule as described herein, comprising (a) at least one moiety capable of specific binding to TnC and (b) a first and a second polypeptide that are linked to each other by a disulfide bond, wherein the antigen binding molecule is characterized in that (i) the first polypeptide contains a CH1 or CL domain and the second polypeptide contains a CL or CH1 domain, respectively, wherein the second polypeptide is linked to the first polypeptide by a disulfide bond between the CH1 and CL domain, and wherein the first polypeptide comprises two ectodomains of a TNF ligand family member or fragments thereof that are connected to each other and to the CH1 or CL domain by a peptide linker and wherein the second polypeptide comprises one ectodomain of said TNF ligand family member or a fragment thereof connected via a peptide linker to the CL or CH1 domain of said polypeptide, or (ii) the first polypeptide contains a CH3 domain and the second polypeptide contains a CH3 domain, respectively, and wherein the first polypeptide comprises two ectodomains of a TNF ligand family member or fragments thereof that are connected to each other and to the C-terminus of the CH3 domain by a peptide linker and wherein the second polypeptide comprises only one ectodomain of said TNF ligand family member or a fragment thereof connected via a peptide linker to C-terminus of the CH3 domain of said polypeptide, or (iii) the first polypeptide contains a VH-CL or a VL-CH1 domain and the second polypeptide contains a VL-CH1 domain or a VH-CL domain, respectively, wherein the second polypeptide is linked to the first polypeptide by a disulfide bond between the CH1 and CL domain, and wherein the first polypeptide comprises two ectodomains of a TNF ligand family member or fragments thereof that are connected to each other and to VH or VL by a peptide linker and wherein the second polypeptide comprises one ectodomain of said TNF ligand family member or a fragment thereof connected via a peptide linker to VL or VH of said polypeptide.

In a further aspect, provided is a TNF family ligand trimer-containing antigen binding molecule of claim 1, comprising (a) at least one moiety capable of specific binding to TnC and (b) a first and a second polypeptide that are linked to each other by a disulfide bond, wherein the antigen binding molecule is characterized in that (i) the first polypeptide contains a CH1 or CL domain and the second polypeptide contains a CL or CH1 domain, respectively, wherein the second polypeptide is linked to the first polypeptide by a disulfide bond between the CH1 and CL domain, and wherein the first polypeptide comprises two ectodomains of a TNF ligand family member or fragments thereof that are connected to each other and to the CH1 or CL domain by a peptide linker and wherein the second polypeptide comprises one ectodomain of said TNF ligand family member or a fragment thereof connected via a peptide linker to the CL or CH1 domain of said polypeptide, or (ii) the first polypeptide contains a CH3 domain and the second polypeptide contains a CH3 domain, respectively, and wherein the first polypeptide comprises two ectodomains of a TNF ligand family member or fragments thereof that are connected to each other and to the C-terminus of the CH3 domain by a peptide linker and wherein the second polypeptide comprises only one ectodomain of said TNF ligand family member or a fragment thereof connected via a peptide linker to C-terminus of the CH3 domain of said polypeptide.

In a particular aspect, the TNF family ligand trimer-containing antigen binding molecule comprises a TNF ligand family member that costimulates human T-cell activation which is selected from 4-1BBL and OX40L. More particularly, the TNF ligand family member is 4-1BBL.

In another aspect, wherein the ectodomain of a TNF ligand family member comprises the amino acid sequence selected from the group consisting of SEQ ID NO: 172, SEQ ID NO: 173, SEQ ID NO: 174, SEQ ID NO: 175, SEQ ID NO: 183, SEQ ID NO: 192, SEQ ID NO: 193 and SEQ ID NO: 194, particularly the amino acid sequence of SEQ ID NO: 172 or SEQ ID NO: 183. In one aspect, the ectodomain of a TNF ligand family member or fragment thereof comprises the amino acid sequence selected from the group consisting of SEQ ID NO: 172, SEQ ID NO: 173, SEQ ID NO: 174, SEQ ID NO: 175 and SEQ ID NO: 183, particularly the amino acid sequence of SEQ ID NO: 172 or SEQ ID NO: 183. In a particular aspect, the ectodomain of a TNF ligand family member or fragment thereof comprises the amino acid sequence of SEQ ID NO: 183.

In a further aspect, the TNF family ligand trimer-containing antigen binding molecule of the invention comprises (a) at least one moiety capable of specific binding to TnC and (b) a first and a second polypeptide that are linked to each other by a disulfide bond, wherein the antigen binding molecule is characterized in that the first polypeptide comprises the amino acid sequence selected from the group consisting of SEQ ID NO: 176, SEQ ID NO: 184, SEQ ID NO: 185 and SEQ ID NO: 186 and in that the second polypeptide comprises the amino acid sequence selected from the group consisting of SEQ ID NO: 172, SEQ ID NO: 174, SEQ ID NO: 175 and SEQ ID NO: 183. In a particular aspect, the first polypeptide comprises the amino acid sequence of SEQ ID NO: 184 and the second polypeptide comprises the amino acid sequence of SEQ ID NO: 183.

In one aspect, the TNF family ligand trimer-containing antigen binding molecule of the invention comprises (a) at least one moiety capable of specific binding to TnC and (b) a first and a second polypeptide that are linked to each other by a disulfide bond, wherein the antigen binding molecule is characterized in that the first polypeptide comprises the amino acid sequence of SEQ ID NO: 176 and in that the second polypeptide comprises the amino acid sequence of SEQ ID NO: 177.

In a further aspect, the TNF family ligand trimer-containing antigen binding molecule of the invention comprises (a) at least one moiety capable of specific binding to TnC and (b) a first and a second polypeptide that are linked to each other by a disulfide bond, wherein the antigen binding molecule is characterized in that the first polypeptide comprises the amino acid sequence of SEQ ID NO: 176 and in that the second polypeptide comprises the amino acid sequence of SEQ ID NO: 187.

In yet a further aspect, the TNF family ligand trimer-containing antigen binding molecule of the invention comprises (a) at least one moiety capable of specific binding to TnC and (b) a first and a second polypeptide that are linked to each other by a disulfide bond, wherein the antigen binding molecule is characterized in that the first polypeptide comprises the amino acid sequence of SEQ ID NO: 184 and in that the second polypeptide comprises the amino acid sequence of SEQ ID NO: 188 or SEQ ID NO: 189.

In another aspect, the TNF ligand family member is OX40L. In a particular aspect, provided is TNF family ligand trimer-containing antigen binding molecule, wherein the ectodomain of a TNF ligand family member comprises the amino acid sequence of SEQ ID NO: 181 or SEQ ID NO: 182, particularly the amino acid sequence of SEQ ID NO: 181.

In one aspect, the invention relates to a TNF family ligand trimer-containing antigen binding molecule comprising (a) at least one moiety capable of specific binding to TnC and (b) a first and a second polypeptide that are linked to each other by a disulfide bond, wherein the antigen binding molecule is characterized in that the first polypeptide comprises the amino acid sequence of SEQ ID NO: 190 or SEQ ID: 191 and in that the second polypeptide comprises the amino acid sequence of SEQ ID NO: 181 or SEQ ID NO: 182, respectively.

In one aspect, the TNF family ligand trimer-containing antigen binding molecule of the invention comprises (a) at least one moiety capable of specific binding to TnC, (b) a first polypeptide containing a CH1 or CL domain and a second polypeptide containing a CL or CH1 domain, respectively, wherein the second polypeptide is linked to the first polypeptide by a disulfide bond between the CH1 and CL domain, and wherein the antigen binding molecule is characterized in that the first polypeptide comprises two ectodomains of a TNF ligand family member or fragments thereof that are connected to each other and to the CH1 or CL domain by a peptide linker and in that the second polypeptide comprises only one ectodomain of said TNF ligand family member or a fragment thereof connected via a peptide linker to the CL or CH1 domain of said polypeptide.

In one aspect, provided is a TNF family ligand trimer-containing antigen binding molecule comprising (a) at least one moiety capable of specific binding to TnC, (b) a first polypeptide containing a CH1 domain and a second polypeptide containing a CL domain, wherein the second polypeptide is linked to the first polypeptide by a disulfide bond between the CH1 and CL domain, and wherein the antigen binding molecule is characterized in that the first polypeptide comprises two ectodomains of a TNF ligand family member or fragments thereof that are connected to each other and to the CH1 domain by a peptide linker and in that the second polypeptide comprises one ectodomain of said TNF ligand family member or a fragment thereof connected via a peptide linker to the CL domain of said polypeptide.

In another aspect, provided is a TNF family ligand trimer-containing antigen binding molecule comprising (a) at least one moiety capable of specific binding to TnC, (b) a first polypeptide containing a CL domain and a second polypeptide containing a CH1 domain, wherein the second polypeptide is linked to the first polypeptide by a disulfide bond between the CH1 and CL domain, and wherein the antigen binding molecule is characterized in that the first polypeptide comprises two ectodomains of a TNF ligand family member or fragments thereof that are connected to each other and to the CL domain by a peptide linker and in that the second polypeptide comprises one ectodomain of said TNF ligand family member or a fragment thereof connected via a peptide linker to the CH1 domain of said polypeptide.

In another aspect, the invention provides a TNF family ligand trimer-containing antigen binding molecule comprising (a) one moiety capable of specific binding to TnC and (b) a first and a second polypeptide that are linked to each other by a disulfide bond, wherein the antigen binding molecule is characterized in that the first polypeptide comprises two ectodomains of a TNF ligand family member or two fragments thereof that are connected to each other by a peptide linker and in that the second polypeptide comprises only one ectodomain of said TNF ligand family member or a fragment thereof.

In yet another aspect, the invention provides a TNF family ligand trimer-containing antigen binding molecule comprising (a) more than one moiety capable of specific binding to TnC and (b) a first and a second polypeptide that are linked to each other by a disulfide bond, wherein the antigen binding molecule is characterized in that the first polypeptide comprises two ectodomains of a TNF ligand family member or two fragments thereof that are connected to each other by a peptide linker and in that the second polypeptide comprises only one ectodomain of said TNF ligand family member or a fragment thereof connected via a peptide linker to said polypeptide.

In one aspect, the invention provides a TNF family ligand trimer-containing antigen binding molecule comprising (a) two moities capable of specific binding to TnC and (b) a first and a second polypeptide that are linked to each other by a disulfide bond, wherein the antigen binding molecule is characterized in that the first polypeptide comprises two ectodomains of a TNF ligand family member or two fragments thereof that are connected to each other by a peptide linker and in that the second polypeptide comprises only one ectodomain of said TNF ligand family member or a fragment thereof.

In a particular aspect, provided is a TNF family ligand trimer-containing antigen binding molecule, comprising (a) at least one moiety capable of specific binding to TnC, and (b) a first and a second polypeptide that are linked to each other by a disulfide bond, wherein the antigen binding molecule is characterized in that the first polypeptide contains a CH3 domain and the second polypeptide contains a CH3 domain, respectively, and wherein the first polypeptide comprises two ectodomains of a TNF ligand family member or fragments thereof that are connected to each other and to the C-terminus of the CH3 domain by a peptide linker and wherein the second polypeptide comprises one ectodomain of said TNF ligand family member or a fragment thereof connected via a peptide linker to C-terminus of the CH3 domain of said polypeptide. Particularly, such TNF family ligand trimer-containing antigen binding molecule comprises two moieties capable of specific binding to TnC.

In a further aspect, the invention provides a TNF family ligand trimer-containing antigen binding molecule as defined herein before, wherein the moiety capable of specific binding to TnC is selected from the group consisting of an antibody, an antibody fragment and a scaffold antigen binding protein.

In one aspect, provided is a TNF family ligand trimer-containing antigen binding molecule as described herein before, wherein the moiety capable of specific binding to TnC is selected from the group consisting of an antibody fragment, a Fab molecule, a crossover Fab molecule, a single chain Fab molecule, a Fv molecule, a scFv molecule, a single domain antibody, an aVH and a scaffold antigen binding protein. In one aspect, the moiety capable of specific binding to TnC is an aVH or a scaffold antigen binding protein. In one aspect, the moiety capable of specific binding to a target cell antigen is a scaffold antigen binding protein capable of specific binding to a target cell antigen.

In particular, the TNF family ligand trimer-containing antigen binding molecule comprises one or two moieties capable of specific binding to TnC.

In a particular aspect, provided is a TNF family ligand trimer-containing antigen binding molecule, wherein the moiety capable of specific binding to TnC is a Fab molecule or a crossover Fab molecule capable of specific binding to a target cell antigen. In particular, the moiety capable of specific binding to TnC is a Fab molecule.

In a further aspect, provided is a TNF family ligand trimer-containing antigen binding molecule according to the invention, wherein the antigen binding molecule comprises a first heavy chain and a first light chain, both comprising a Fab molecule capable of specific binding to TnC, a first peptide comprising two ectodomains of a TNF ligand family member or fragments thereof connected to each other by a first peptide linker fused at its C-terminus by a second peptide linker to a second heavy or light chain, and a second peptide comprising one ectodomain of said TNF ligand family member fused at its C-terminus by a third peptide linker to a second light or heavy chain, respectively.

In a further aspect, provided is a TNF family ligand trimer-containing antigen binding molecule according to the invention, wherein a peptide comprising two ectodomains of a TNF ligand family member or fragments thereof connected to each other by a first peptide linker is fused at its C-terminus to the CH1 domain of a heavy chain by a second peptide linker and wherein one ectodomain of said TNF ligand family member or a fragment thereof is fused at the its C-terminus to the CL domain on a light chain by a third peptide linker.

In a further aspect, provided is a TNF family ligand trimer-containing antigen binding molecule according to the invention, wherein the first peptide comprising two ectodomains of a TNF ligand family member or fragments thereof connected to each other by a first peptide linker is fused at its C-terminus by a second peptide linker to a CH1 domain that is part of a heavy chain, and the second peptide comprising one ectodomain of said TNF ligand family member or a fragment thereof is fused at its C-terminus by a third peptide linker to a CL domain that is part of a light chain.

In another aspect, provided is a TNF family ligand trimer-containing antigen binding molecule according to the invention, wherein a peptide comprising two ectodomains of a TNF ligand family member or fragments thereof connected to each other by a first peptide linker is fused at its C-terminus to the CL domain of a heavy chain by a second peptide linker and wherein one ectodomain of said TNF ligand family member or a fragment thereof is fused at the its C-terminus to the CH1 domain on a light chain by a third peptide linker.

In another aspect, provided is a TNF family ligand trimer-containing antigen binding molecule according to the invention, wherein the first peptide comprising two ectodomains of a TNF ligand family member or fragments thereof connected to each other by a first peptide linker is fused at its C-terminus by a second peptide linker to a CL domain that is part of a heavy chain, and the second peptide comprising one ectodomain of said TNF ligand family member or a fragment thereof is fused at its C-terminus by a third peptide linker to a CH1 domain that is part of a light chain.

In a further aspect, the invention is concerned with a TNF family ligand trimer-containing antigen binding molecule according to the invention, wherein a peptide comprising two ectodomains of a TNF ligand family member or fragments thereof connected to each other by a first peptide linker is fused at its C-terminus to the CL domain of a light chain by a second peptide linker and wherein one ectodomain of said TNF ligand family member or a fragment thereof is fused at the its C-terminus to the CH1 domain of the heavy chain by a third peptide linker.

In another aspect, provided is a TNF family ligand trimer-containing antigen binding molecule according to the invention, wherein the first peptide comprising two ectodomains of a TNF ligand family member or fragments thereof connected to each other by a first peptide linker is fused at its C-terminus by a second peptide linker to a VH domain that is part of a heavy chain, and the second peptide comprising one ectodomain of said TNF ligand family member or a fragment thereof is fused at its C-terminus by a third peptide linker to a VL domain that is part of a light chain.

In a particular aspect, the invention relates to a TNF family ligand trimer-containing antigen binding molecule as defined above, wherein the peptide linker is $(G4S)_2$ (SEQ ID NO: 150). In one aspect, the first peptide linker is $(G4S)_2$ (SEQ ID NO: 150), the second peptide linker is GSPGSSSSGS (SEQ ID NO: 153) and the third peptide linker is $(G4S)_2$ (SEQ ID NO: 150). In particular, the invention relates to a TNF ligand trimer-containing antigen binding molecule as defined above, wherein the first peptide linker is $(G4S)_2$ (SEQ ID NO: 150), the second peptide linker is $(G4S)_2$ (SEQ ID NO: 150), and the third peptide linker is $(G4S)_2$ (SEQ ID NO: 150).

In another aspect, the TNF family ligand trimer-containing antigen binding molecule as defined herein before comprises an Fc domain composed of a first and a second subunit capable of stable association.

In particular, the TNF family ligand trimer-containing antigen binding molecule of the invention comprises (a) a Fab molecule capable of specific binding to TnC, wherein the Fab heavy chain is fused at the C-terminus to the N-terminus of a CH2 domain in the Fc domain and (c) an Fc domain composed of a first and a second subunit capable of stable association.

In a further aspect, the Fc domain is an IgG, particularly an IgG1 Fc domain or an IgG4 Fc domain. More particularly, the Fc domain is an IgG1 Fc domain. In a particular aspect, the Fc domain comprises a modification promoting the association of the first and second subunit of the Fc domain.

Fc Domain Modifications Reducing Fc Receptor Binding and/or Effector Function

The Fc domain of the TNF family ligand trimer-containing antigen binding molecules of the invention consists of a pair of polypeptide chains comprising heavy chain domains of an immunoglobulin molecule. For example, the Fc domain of an immunoglobulin G (IgG) molecule is a dimer, each subunit of which comprises the CH2 and CH3 IgG heavy chain constant domains. The two subunits of the Fc domain are capable of stable association with each other.

The Fc domain confers favorable pharmacokinetic properties to the antigen binding molecules of the invention, including a long serum half-life which contributes to good accumulation in the target tissue and a favorable tissue-blood distribution ratio. At the same time it may, however, lead to undesirable targeting of the bispecific antibodies of the invention to cells expressing Fc receptors rather than to the preferred antigen-bearing cells. Accordingly, in particular aspects, the Fc domain of the TNF family ligand trimer-containing antigen binding molecule of the invention exhibits reduced binding affinity to an Fc receptor and/or reduced effector function, as compared to a native IgG1 Fc domain. In one aspect, the Fc does not substantially bind to an Fc receptor and/or does not induce effector function. In a particular aspect the Fc receptor is an Fcγ receptor. In one aspect, the Fc receptor is a human Fc receptor. In a specific aspect, the Fc receptor is an activating human Fcγ receptor, more specifically human FcγRIIIa, FcγRI or FcγRIIa, most specifically human FcγRIIIa. In one aspect, the Fc domain does not induce effector function. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced dendritic cell maturation, or reduced T cell priming.

In certain aspects, one or more amino acid modifications may be introduced into the Fc region of a antigen binding molecule provided herein, thereby generating an Fc region variant. The Fc region variant may comprise a human Fc region sequence (e.g., a human IgG1, IgG2, IgG3 or IgG4 Fc region) comprising an amino acid modification (e.g., a substitution) at one or more amino acid positions.

In a particular aspect, the invention provides a TNF family ligand trimer-containing antigen binding molecule comprising (a) at least one moiety capable of specific binding to TnC, (b) a first and a second polypeptide that are linked to each other by a disulfide bond, wherein the antigen binding molecule is characterized in that the first polypeptide comprises two ectodomains of a TNF ligand family member or two fragments thereof that are connected to each other by a peptide linker and in that the second polypeptide comprises only one ectodomain of said TNF ligand family member or a fragment thereof, and (c) an Fc domain composed of a first and a second subunit capable of stable association, wherein the Fc domain comprises one or more amino acid substitution that reduces binding to an Fc receptor, in particular towards Fcγ receptor.

In one aspect, the Fc domain of the antigen binding molecule of the invention comprises one or more amino acid mutation that reduces the binding affinity of the Fc domain to an Fc receptor and/or effector function. Typically, the same one or more amino acid mutation is present in each of the two subunits of the Fc domain. In particular, the Fc domain comprises an amino acid substitution at a position of E233, L234, L235, N297, P331 and P329 (EU numbering). In particular, the Fc domain comprises amino acid substitutions at positions 234 and 235 (EU numbering) and/or 329 (EU numbering) of the IgG heavy chains. More particularly, provided is an antigen binding molecule according to the invention which comprises an Fc domain with the amino acid substitutions L234A, L235A and P329G ("PGLALA", EU numbering) in the IgG heavy chains. The amino acid substitutions L234A and L235A refer to the so-called LALA mutation. The "PGLALA" combination of amino acid substitutions almost completely abolishes Fcγ receptor binding of a human IgG1 Fc domain and is described in International Patent Appl. Publ. No. WO 2012/130831 A1 which also describes methods of preparing such mutant Fc domains and methods for determining its properties such as Fc receptor binding or effector functions. "EU numbering" refers to the numbering according to EU index of Kabat et al, Sequences of Proteins of Immunological Interest, 5th Ed. Public Health Service, National Institutes of Health, Bethesda, Md., 1991.

Fc domains with reduced Fc receptor binding and/or effector function also include those with substitution of one or more of Fc domain residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

In another aspect, the Fc domain is an IgG4 Fc domain. IgG4 antibodies exhibit reduced binding affinity to Fc receptors and reduced effector functions as compared to IgG1 antibodies. In a more specific aspect, the Fc domain is an IgG4 Fc domain comprising an amino acid substitution at position 5228 (Kabat numbering), particularly the amino acid substitution S228P. In a more specific aspect, the Fc domain is an IgG4 Fc domain comprising amino acid substitutions L235E and S228P and P329G (EU numbering). Such IgG4 Fc domain mutants and their Fcγ receptor binding properties are also described in WO 2012/130831.

Mutant Fc domains can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing.

Binding to Fc receptors can be easily determined e.g., by ELISA, or by Surface Plasmon Resonance (SPR) using standard instrumentation such as a BIAcore instrument (GE Healthcare), and Fc receptors such as may be obtained by recombinant expression. A suitable such binding assay is described herein. Alternatively, binding affinity of Fc domains or cell activating bispecific antigen binding molecules comprising an Fc domain for Fc receptors may be evaluated using cell lines known to express particular Fc receptors, such as human NK cells expressing FcγIIIa receptor.

Effector function of an Fc domain, or antigen binding molecule of the invention comprising an Fc domain, can be measured by methods known in the art. A suitable assay for measuring ADCC is described herein. Other examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays methods may be employed (see, for example, ACTI™ non-radioactive cytotoxicity assay for flow cytometry (CellTechnology, Inc. Mountain View, Calif.); and CytoTox 96® non-radioactive cytotoxicity assay (Promega, Madison, Wis.)). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al., Proc Natl Acad Sci USA 95, 652-656 (1998).

In some embodiments, binding of the Fc domain to a complement component, specifically to C1q, is reduced. Accordingly, in some embodiments wherein the Fc domain is engineered to have reduced effector function, said reduced effector function includes reduced CDC. C1q binding assays may be carried out to determine whether the antigen binding molecule of the invention is able to bind C1q and hence has CDC activity. See e.g., C1q and C3c binding ELISA in WO 2006/029879 and WO 2005/100402. To assess complement activation, a CDC assay may be performed (see, for example, Gazzano-Santoro et al., J Immunol Methods 202, 163 (1996); Cragg et al., Blood 101, 1045-1052 (2003); and Cragg and Glennie, Blood 103, 2738-2743 (2004)).

In a particular aspect, the Fc domain comprises a modification promoting the association of the first and second subunit of the Fc domain.

Fc Domain Modifications Promoting Heterodimerization

In one aspect, the TNF family ligand trimer-containing antigen binding molecules of the invention comprise (a) at least one moiety capable of specific binding to TnC, (b) a first and a second polypeptide that are linked to each other by a disulfide bond, wherein the antigen binding molecule is characterized in that the first polypeptide comprises two ectodomains of a TNF ligand family member or two fragments thereof that are connected to each other by a peptide linker and in that the second polypeptide comprises only one ectodomain of said TNF ligand family member or a fragment thereof, and (c) an Fc domain composed of a first and a second subunit capable of stable association, wherein the Fc domain comprises one or more amino acid substitution that reduces binding to an Fc receptor, in particular to Fcγ receptor. Thus, they comprise different moieties, fused to one or the other of the two subunits of the Fc domain that are typically comprised in two non-identical polypetide chains ("heavy chains"). Recombinant co-expression of these polypeptides and subsequent dimerization leads to several possible combinations of the two polypeptides. To improve the yield and purity of the TNF family ligand trimer-containing antigen binding molecules in recombinant production, it will thus be advantageous to introduce in the Fc domain of the TNF family ligand trimer-containing antigen binding molecules of the invention a modification promoting the association of the desired polypeptides.

Accordingly, the Fc domain of the TNF family ligand trimer-containing antigen binding molecules of the invention comprises a modification promoting the association of the first and the second subunit of the Fc domain. The site of most extensive protein-protein interaction between the two subunits of a human IgG Fc domain is in the CH3 domain of the Fc domain. Thus, said modification is particularly in the CH3 domain of the Fc domain In a specific aspect, said modification is a so-called "knob-into-hole" modification, comprising a "knob" modification in one of the two subunits of the Fc domain and a "hole" modification in the other one of the two subunits of the Fc domain. Thus, in a particular aspect, the invention relates to a TNF family ligand trimer-containing antigen binding molecule as described herein before which comprises an IgG molecule, wherein the Fc part of the first heavy chain comprises a first dimerization module and the Fc part of the second heavy chain comprises a second dimerization module allowing a heterodimerization of the two heavy chains of the IgG molecule and the first dimerization module comprises knobs and the second dimerization module comprises holes according to the knob into hole technology.

The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g., tyrosine or tryptophan). Compensatory cavities of identical or similar size to the protuberances are created in the interface of the second polypeptide by replacing large amino acid side chains with smaller ones (e.g., alanine or threonine).

Accordingly, in a particular aspect, in the CH3 domain of the first subunit of the Fc domain of the TNF family ligand trimer-containing antigen binding molecules of the invention an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable.

The protuberance and cavity can be made by altering the nucleic acid encoding the polypeptides, e.g., by site-specific mutagenesis, or by peptide synthesis.

In a specific aspect, in the CH3 domain of the first subunit of the Fc domain the threonine residue at position 366 is replaced with a tryptophan residue (T366W), and in the CH3 domain of the second subunit of the Fc domain the tyrosine residue at position 407 is replaced with a valine residue (Y407V). More particularly, in the second subunit of the Fc domain additionally the threonine residue at position 366 is replaced with a serine residue (T366S) and the leucine residue at position 368 is replaced with an alanine residue (L368A). More particularly, in the first subunit of the Fc domain additionally the serine residue at position 354 is replaced with a cysteine residue (S354C), and in the second subunit of the Fc domain additionally the tyrosine residue at position 349 is replaced by a cysteine residue (Y349C). The introduction of these two cysteine residues results in the formation of a disulfide bridge between the two subunits of the Fc domain. The disulfide bridge further stabilizes the dimer (Carter, J Immunol Methods 248, 7-15 (2001)).

In an alternative aspect, a modification promoting association of the first and the second subunit of the Fc domain comprises a modification mediating electrostatic steering effects, e.g., as described in PCT publication WO 2009/089004. Generally, this method involves replacement of one or more amino acid residues at the interface of the two Fc domain subunits by charged amino acid residues so that homodimer formation becomes electrostatically unfavorable but heterodimerization electrostatically favorable.

Modifications in the CH1/CL Domains

To further improve correct pairing, the TNF family ligand trimer-containing antigen binding molecules can contain different charged amino acid substitutions (so-called "charged residues"). These modifications are introduced in the crossed or non-crossed CH1 and CL domains. In a particular aspect, the invention relates to a TNF family ligand trimer-containing antigen binding molecule, wherein in one of CL domains the amino acid at position 123 (EU numbering) has been replaced by arginine (R) and the amino acid at position 124 (EU numbering) has been substituted by lysine (K) and wherein in one of the CH1 domains the amino acids at position 147 (EU numbering) and at position 213 (EU numbering) have been substituted by glutamic acid (E).

More particularly, the invention relates to a TNF family ligand trimer-containing antigen binding molecule, wherein in the CL domain adjacent to the TNF ligand family member the amino acid at position 123 (EU numbering) has been replaced by arginine (R) and the amino acid at position 124 (EU numbering) has been substituted by lysine (K), and wherein in the CH1 domain adjacent to the TNF ligand family member the amino acids at position 147 (EU numbering) and at position 213 (EU numbering) have been substituted by glutamic acid (E).

Particular TNF Family Ligand Trimer-Containing Antigen Binding Molecules

In another aspect, the invention provides a TNF family ligand trimer-containing antigen binding molecule, wherein the antigen binding molecule comprises a first heavy chain and a first light chain, both comprising a Fab molecule capable of specific binding to TnC, a first peptide comprising two ectodomains of a TNF ligand family member or fragments thereof connected to each other by a first peptide linker fused at its C-terminus by a second peptide linker to a second heavy or light chain, and a second peptide comprising one ectodomain of said TNF ligand family member fused at its C-terminus by a third peptide linker to a second light or heavy chain, respectively.

In a further aspect, provided is a TNF family ligand trimer-containing antigen binding molecule, wherein the first peptide comprising two ectodomains of a TNF ligand family member or fragments thereof connected to each other by a first peptide linker is fused at its C-terminus by a second peptide linker to a CH1 domain that is part of a heavy chain, and the second peptide comprising one ectodomain of said TNF ligand family member or a fragment thereof is fused at its C-terminus by a third peptide linker to a CL domain that is part of a light chain.

In yet another aspect, provided is a TNF family ligand trimer-containing antigen binding molecule, wherein the first peptide comprising two ectodomains of a TNF ligand family member or fragments thereof connected to each other by a first peptide linker is fused at its C-terminus by a second peptide linker to a CL domain that is part of a heavy chain, and the second peptide comprising one ectodomain of said TNF ligand family member or a fragment thereof that is fused at its C-terminus by a third peptide linker to a CH1 domain that is part of a light chain.

In a further aspect, provided is a TNF family ligand trimer-containing antigen binding molecule, wherein the first peptide comprising two ectodomains of a TNF ligand family member or fragments thereof connected to each other by a first peptide linker is fused at its C-terminus by a second peptide linker to a VH domain that is part of a heavy chain, and the second peptide comprising one ectodomain of said TNF ligand family member or a fragment thereof is fused at its C-terminus by a third peptide linker to a VL domain that is part of a light chain.

In one aspect, the invention provides a TNF family ligand trimer-containing antigen binding molecule as described herein, wherein in the CL domain adjacent to the TNF ligand family member the amino acid at position 123 (EU numbering) has been replaced by arginine (R) and the amino acid at position 124 (EU numbering) has been substituted by lysine (K), and wherein in the CH1 domain adjacent to the TNF ligand family member the amino acids at position 147 (EU numbering) and at position 213 (EU numbering) have been substituted by glutamic acid (E). These modifications lead to so-called charged residues with advantageous properties that avoid undesired effects such as for example mispairing.

In one aspect, provided is a TNF family ligand trimer-containing antigen binding molecule comprising (a) a Fab domain capable of specific binding to TnC, (b) a Fc domain composed of a first and a second subunit capable of stable association, and (c) a first polypeptide comprising two ectodomains of a TNF ligand family member or fragments thereof that are connected to each other by a peptide linker and a second polypeptide comprising one ectodomain of said TNF ligand family member or a fragment thereof, wherein the first polypeptide is fused at its N-terminus to the C-terminus to the second subunit of the Fc domain comprising the knob mutations and wherein the second polypeptide is fused at its N-terminus to the C-terminus of the first subunit of the Fc domain comprising the hole mutations.

In a particular aspect, the invention provides a TNF family ligand trimer-containing antigen binding molecule comprising (a) a Fab domain capable of specific binding to TnC, (b) a Fc domain composed of a first and a second subunit capable of stable association, and (c) a first polypeptide comprising two ectodomains of a TNF ligand family member or fragments thereof that are connected to each other by a peptide linker and a second polypeptide comprising one ectodomain of said TNF ligand family member or a fragment thereof, wherein the first polypeptide is fused at its N-terminus to the C-terminus to the second subunit of the Fc domain comprising the knob mutations and wherein the second polypeptide is fused at its N-terminus to the C-terminus of the first subunit of the Fc domain comprising the hole mutations and wherein the Fab heavy chain is fused at the C-terminus to the N-terminus of the second subunit of the Fc domain comprising the knob mutations.

In another aspect, the invention provides a TNF family ligand trimer-containing antigen binding molecule comprising (a) a Fab domain capable of specific binding to TnC, (b) a Fc domain composed of a first and a second subunit capable of stable association, and (c) a first polypeptide comprising two ectodomains of a TNF ligand family member or fragments thereof that are connected to each other by a peptide linker and a second polypeptide comprising one ectodomain of said TNF ligand family member or a fragment thereof, wherein the first polypeptide is fused at its N-terminus to the C-terminus to the second subunit of the Fc domain comprising the knob mutations and wherein the second polypeptide is fused at its N-terminus to the C-terminus of the first subunit of the Fc domain comprising the hole mutations and wherein the Fab heavy chain is fused at the C-terminus to the N-terminus of the first subunit of the Fc domain comprising the hole mutations.

In a further aspect, provided is a TNF family ligand trimer-containing antigen binding molecule comprising (a) a Fab domain capable of specific binding to TnC, (b) a Fc domain composed of a first and a second subunit capable of stable association, and (c) a first polypeptide comprising two ectodomains of a TNF ligand family member or fragments thereof that are connected to each other by a peptide linker and a second polypeptide comprising one ectodomain of said TNF ligand family member or a fragment thereof, wherein the first polypeptide is fused at its N-terminus to the C-terminus to the first subunit of the Fc domain comprising the hole mutations and wherein the second polypeptide is fused at its N-terminus to the C-terminus of the second subunit of the Fc domain comprising the knob mutations.

In a particular aspect, the invention provides a TNF family ligand trimer-containing antigen binding molecule comprising (a) a Fab domain capable of specific binding to TnC, (b) a Fc domain composed of a first and a second subunit capable of stable association, and (c) a first polypeptide comprising two ectodomains of a TNF ligand family member or fragments thereof that are connected to each other by a peptide linker and a second polypeptide comprising one ectodomain of said TNF ligand family member or a fragment thereof, wherein the first polypeptide is fused at its N-terminus to the C-terminus to the first subunit of the Fc domain comprising the hole mutations and wherein the second polypeptide is fused at its N-terminus to the C-terminus of the second subunit of the Fc domain comprising the knob mutations and wherein the Fab heavy chain is fused at the C-terminus to the N-terminus of the second subunit of the Fc domain comprising the knob mutations.

In another aspect, the invention provides a TNF family ligand trimer-containing antigen binding molecule comprising (a) a Fab domain capable of specific binding to TnC, (b) a Fc domain composed of a first and a second subunit capable of stable association, and (c) a first polypeptide comprising two ectodomains of a TNF ligand family member or fragments thereof that are connected to each other by a peptide linker and a second polypeptide comprising one ectodomain of said TNF ligand family member or a fragment thereof, wherein the first polypeptide is fused at its N-terminus to the C-terminus to the first subunit of the Fc domain comprising the hole mutations and wherein the second polypeptide is fused at its N-terminus to the C-terminus of the second subunit of the Fc domain comprising the knob mutations and wherein the Fab heavy chain is fused at the C-terminus to the N-terminus of the first subunit of the Fc domain comprising the hole mutations.

Particular TnC Binding Moieties

In one aspect, the present invention provides for TnC binding moieties. In another aspect, TNC binding moieties of the present invention can be included in bivalent or multivalent binding molecules as described herein. In one embodiment the moiety capable of specific binding to TnC is selected from the group consisting of an antibody fragment, a Fab molecule, a crossover Fab molecule, a single chain Fab molecule, a Fv molecule, a scFv molecule, a single domain antibody, and aVH and a scaffold antigen binding protein. In another aspect, the present invention provides for antigen binding molecules comprising one or more moiety capable of specific binding to TnC. The molecules of the invention comprising a TnC binding moiety as described herein have a high affinity for one ore more TnC domains and/or cross-species reactivity.

In one embodiment, an anti-TnC antigen binding molecule of the invention comprises at least one (e.g., one, two, three, four, five, or six) heavy or light chain complementarity determining region (CDR) selected from the group consisting of SEQ ID NO: 55, SEQ ID NO: 56, SEQ ID NO: 57, SEQ ID NO: 58, SEQ ID NO: 59, SEQ ID NO: 60, SEQ ID NO: 67, SEQ ID NO: 68, SEQ ID NO: 69, SEQ ID NO: 70, SEQ ID NO: 71 and SEQ ID NO: 72, or a variant or truncated form thereof containing at least the specificity-determining residues (SDRs) for said CDR.

In one embodiment, an antigen binding molecule of the invention comprises at least one, at least two, or all three heavy chain CDR (HCDR) sequences selected from (a) HCDR1 comprising an amino acid sequence selected from the group consisting of SEQ ID NO: 67 and SEQ ID NO: 70; (b) HCDR2 comprising an amino acid sequence selected from the group consisting of SEQ ID NO: 68 and SEQ ID NO: 71; and (c) HCDR3 comprising an amino acid sequence selected from the group consisting of SEQ ID NO: 69 and SEQ ID NO: 72. In a further embodiment, the antigen binding molecule comprises a heavy chain variable region comprising (a) a heavy chain CDR1 selected from the group consisting of SEQ ID NO: 67 and SEQ ID NO: 70; (b) a heavy chain CDR2 selected from the group consisting of SEQ ID NO: 68 and SEQ ID NO: 71; and (c) a heavy chain CDR3 selected from the group consisting of SEQ ID NO: 69 and SEQ ID NO: 72, or variants or truncated forms thereof containing at least the SDRs for said CDRs.

In one embodiment, an antigen binding molecule of the invention comprises at least one, at least two, or all three light chain CDR (LCDR) sequences selected from (a) LCDR1 comprising an amino acid sequence selected from the group consisting of SEQ ID NO: 55 and SEQ ID NO: 58; (b) LCDR2 comprising an amino acid sequence selected from the group consisting of SEQ ID NO: 56 and SEQ ID NO: 59; and (c) LCDR3 comprising an amino acid sequence selected from the group consisting of SEQ ID NO: 57 and SEQ ID NO: 60. In a further embodiment, the antigen binding molecule comprises a light chain variable region comprising (a) a light chain CDR1 selected from the group consisting of SEQ ID NO: 55 and SEQ ID NO: 58 (b) a light chain CDR2 selected from the group consisting of SEQ ID NO: 56 and SEQ ID NO: 59; and (c) a light chain CDR3 selected from the group consisting of SEQ ID NO: 57 and SEQ ID NO: 60, or variants or truncated forms thereof containing at least the SDRs for said CDRs.

In one embodiment, an antigen binding molecule of the invention comprises a heavy chain variable region comprising a heavy chain CDR1 selected from the group consisting of SEQ ID NO: 67 and SEQ ID NO: 70; a heavy chain CDR2 selected from the group consisting of SEQ ID NO: 68 and SEQ ID NO: 71; and a heavy chain CDR3 selected from the group consisting of SEQ ID NO: 69 and SEQ ID NO: 72, and a light chain variable region comprising a light chain CDR1 selected from the group consisting of SEQ ID NO: 55 and SEQ ID NO: 58; a light chain CDR2 selected from the group consisting of SEQ ID NO: 56 and SEQ ID NO: 59; and a light chain CDR3 selected from the group consisting of SEQ ID NO: 57 and SEQ ID NO: 60, or variants or truncated forms thereof containing at least the SDRs for said CDRs.

In yet another specific embodiment, an antigen binding molecule of the invention comprises a heavy chain variable region comprising the heavy chain CDR1 of SEQ ID NO: 67; the heavy chain CDR2 of SEQ ID NO: 68; and the heavy chain CDR3 of SEQ ID NO: 69, and a light chain variable region comprising the light chain CDR1 of SEQ ID NO: 55; the light chain CDR2 of SEQ ID NO: 56; and the light chain CDR3 of SEQ ID NO: 57.

In yet another specific embodiment, an antigen binding molecule of the invention comprises a heavy chain variable region comprising the heavy chain CDR1 of SEQ ID NO:

70; the heavy chain CDR2 of SEQ ID NO: 71; and the heavy chain CDR3 of SEQ ID NO: 72, and a light chain variable region comprising the light chain CDR1 of SEQ ID NO: 58, the light chain CDR2 of SEQ ID NO: 59; and the light chain CDR3 of SEQ ID NO: 60.

In one embodiment, an antigen binding molecule of the invention comprises a heavy chain variable region (VH) comprising an amino acid sequence having at least about 90%, 91%, 92%, 93%, 94%, 95%, 96%, 97%, 98% or 99% identity to a sequence selected from the group consisting of SEQ ID NO: 46 and SEQ ID NO: 48. In one embodiment, the antigen binding molecule comprises a heavy chain variable region comprising an amino acid sequence selected from the group consisting of: SEQ ID NO: 46 and SEQ ID NO: 48.

In certain embodiments, a VH sequence having at least 90%, 91%, 92%, 93%, 94%, 95%, 96%, 97%, 98% or 99% identity contains substitutions (e.g., conservative substitutions), insertions, or deletions relative to the reference sequence, but an anti-TnC antigen binding molecule comprising that sequence retains the ability to bind to TnC. In certain embodiments, a total of 1 to 10 amino acids have been substituted, inserted and/or deleted in SEQ ID NO: 46 or SEQ ID NO: 48. In certain embodiments, substitutions, insertions, or deletions occur in regions outside the HVRs or CDRs (i.e., in the FRs). Optionally, an anti-TnC antigen binding molecule according to the invention comprises the VH sequence in SEQ ID NO: 46 or SEQ ID NO: 48, including post-translational modifications of that sequence. In a particular embodiment, the VH comprises one, two or three heavy chain CDRs selected from the sequences set forth in SEQ ID NO: 67, SEQ ID NO: 68, SEQ ID NO: 69, SEQ ID NO: 70, SEQ ID NO: 71 and SEQ ID NO: 72 for the HCDR1, HCDR2 and HCDR3.

In another embodiment, an antigen binding molecule of the invention comprises a light chain variable region comprising an amino acid sequence having at least about 90%, 91%, 92%, 93%, 94%, 95%, 96%, 97%, 98% or 99% identity to a sequence selected from the group consisting of SEQ ID NO: 45 and SEQ ID NO: 47. In yet another embodiment, the antigen binding molecule comprises a light chain variable region comprising an amino acid sequence selected from the group consisting of: SEQ ID NO: 45 and SEQ ID NO: 47.

In certain embodiments, a VL sequence having at least 90%, 91%, 92%, 93%, 94%, 95%, 96%, 97%, 98% or 99% identity contains substitutions (e.g., conservative substitutions), insertions, or deletions relative to the reference sequence, but an anti-TnC antigen binding molecule comprising that sequence retains the ability to bind to TnC. In certain embodiments, a total of 1 to 10 amino acids have been substituted, inserted and/or deleted in SEQ ID NO: 45 or SEQ ID NO: 47. In certain embodiments, the substitutions, insertions, or deletions occur in regions outside the HVRs or CDRs (i.e., in the FRs). Optionally, an anti-TnC antigen binding molecule of the invention comprises the VL sequence in SEQ ID NO: 45 or SEQ ID NO: 47, including post-translational modifications of that sequence. In a particular embodiment, the VL comprises one, two or three light chain CDRs selected from sequences set forth in SEQ ID NO: 55, SEQ ID NO: 56, SEQ ID NO: 57, SEQ ID NO: 58, SEQ ID NO: 59 and SEQ ID NO: 60 for the LCDR1, LCDR2 and LCDR3.

In another aspect, an anti-TnC antigen binding molecule is provided, wherein the antigen binding molecule comprises a VH as in any of the embodiments provided above, and a VL as in any of the embodiments provided above. In one embodiment, the antigen binding molecule comprises a heavy chain variable region comprising an amino acid sequence that is at least about 90%, 91%, 92%, 93%, 94%, 95%, 96%, 97%, 98%, 99% or 100% identical to a sequence selected from the group of: SEQ ID NO: 46 and SEQ ID NO: 48, and a light chain variable region comprising an amino acid sequence that is at least about 90%, 91%, 92%, 93%, 94%, 95%, 96%, 97%, 98%, 99% or 100% identical to a sequence selected from the group of: SEQ ID NO: 45 and SEQ ID NO: 47. In one embodiment, the antigen binding molecule comprises the VH and VL sequences in SEQ ID NO: 46 or SEQ ID NO: 48 and SEQ ID NO: 45 or SEQ ID NO: 47, respectively, including post-translational modifications of those sequences.

In a specific embodiment, an antigen binding molecule of the invention comprises a heavy chain variable region comprising the amino acid sequence of SEQ ID NO: 46 and a light chain variable region comprising the amino acid sequence of SEQ ID NO: 45. In a specific embodiment, an antigen binding molecule of the invention comprises a heavy chain variable region comprising the amino acid sequence of SEQ ID NO: 48 and a light chain variable region comprising the amino acid sequence of SEQ ID NO: 47. In a particular embodiment, the antigen binding molecule according to any of the above embodiments additionally comprises an Fc region or a region equivalent to the Fc region of an immunoglobulin. In one embodiment an antigen binding molecule of the invention comprises an Fc region, particularly a IgG Fc region, most particularly a IgG1 Fc region. In a particular embodiment, the antigen binding molecule of the invention is a full length antibody, particularly an IgG class antibody, most particularly an IgG1 isotype antibody. In another embodiment, the TnC binding moiety of the antigen binding molecule of the invention is an antibody fragment, selected from the group of: an scFv fragment, an Fv fragment, a Fab fragment, and a F(ab')2 fragment. In a further embodiment, the antigen binding molecule of the invention is an antibody fragment having an Fc region, or a fusion protein that comprises a region equivalent to the Fc region of an immunoglobulin. In one embodiment, the antigen binding molecule of the invention is a monoclonal antibody. In one embodiment, an antigen binding molecule of the invention is chimeric, more specifically humanized. In a particular embodiment, an antigen binding molecule of the invention is human. In another embodiment, an antigen binding molecule of the invention comprises a human constant region. In one embodiment the antigen binding molecule of the invention comprises a human Fc region, preferably a human IgG Fc region, most particularly a human IgG1 Fc region.

In one embodiment, an antigen binding molecule of the invention comprises a heavy chain constant region, wherein said heavy chain constant region is a human IgG constant region, particularly a human IgG1 constant region, comprising an Fc region. In one embodiment, an antigen binding molecule of the invention comprises a heavy chain region, wherein said heavy chain region is a human IgG heavy chain region, particularly a human IgG1 heavy chain region, comprising an Fc region. In a specific embodiment, the antigen binding molecule comprises a heavy chain region comprising an amino acid sequence selected from the group consisting of: SEQ ID NO: 78, SEQ ID NO: 80, SEQ ID NO: 83, and SEQ ID NO: 84. In another specific embodiment an antigen binding molecule of the invention comprises a light chain region comprising an amino acid sequence selected from the group consisting of: SEQ ID NO: 77 and SEQ ID NO: 79. In yet another specific embodiment, an antigen binding molecule of the invention comprises a heavy chain region comprising the amino acid sequence of SEQ ID NO: 78, and a light chain region comprising the amino acid sequence of SEQ ID NO: 77. In yet another specific embodiment, an antigen binding molecule of the invention comprises a heavy chain region comprising the amino acid sequence of SEQ ID NO: 80, and a light chain region comprising the amino acid sequence of SEQ ID NO: 79.

In a particular embodiment, the invention provides an antigen binding molecule that specifically binds to TnC, wherein said antigen binding molecule comprises a) a heavy chain region comprising an amino acid sequence that is at least about 90%, 91%, 92%, 93%, 94%, 95%, 96%, 97%, 98%, 99% or 100% identical to a sequence selected from the group consisting of: SEQ ID NO: 78 and SEQ ID NO: 80, or a light chain region comprising an amino acid sequence that is at least about 90%, 91%, 92%, 93%, 94%, 95%, 96%, 97%, 98%, 99% or 100% identical to a sequence selected from the group consisting of SEQ ID NO: 77 and SEQ ID NO: 79, or a combination thereof, comprising an Fc region or a region equivalent to the Fc region of an immunoglobulin.

In one embodiment, an antigen binding molecule of the invention binds to Tenascin-C (TnC) with a dissociation constant ($K_D$) value lower than about 1 μM to about 0.001 nM, particularly a $K_D$ value lower than about 100 nM, lower than about 10 nM, or lower than about 1 nM. In a specific embodiment, an antigen binding molecule of the invention binds to human Tenascin-C (TnC) with a dissociation constant ($K_D$) value lower than about 1 nM. In one embodiment, an antigen binding molecule of the invention binds to human, mouse, and cynomolgus TnC. In one embodiment, an antigen binding molecule of the invention has cross-species reactivity. In another specific embodiment, an antigen binding molecule of the invention binds to the C domain of human, mouse, and cynomolgus TnC. In one embodiment the antigen binding molecule of the invention has cross-species reactivity. In one embodiment the antigen binding molecule of the present invention binds to at least one of human, mouse and cynomolgus TnC with a $K_D$ value lower than about 100 nM, lower than 10 nM, lower than 5 nM or lower than 2 nM. In a specific embodiment the antigen binding molecule of the present invention binds to at least one of human, mouse and cynomolgus TnC with a $K_D$ value lower than about 2 nM. In further embodiments, the antigen binding molecule of the present invention binds to human TnC with a first $K_D$ value $K_D1$, wherein said antigen binding molecule binds to mouse TnC with a second $K_D$ value $K_D2$, and wherein said antigen binding molecule binds to cynomolgus TnC with a third $K_D$ value $K_D3$, wherein all of the $K_D$ values selected from the group consisting of $K_D1$, $K_D2$ and $K_D3$ are lower than about 10 nM, lower than about 5 nM or lower than about 2 nM. In yet further embodiments, the antigen binding molecule of the present invention binds to human TnC with a first $K_D$ value $K_D1$, wherein said antigen binding molecule binds to mouse TnC with a second $K_D$ value $K_D2$, and wherein said antigen binding molecule binds to cynomolgus TnC with a third $K_D$ value $K_D3$, wherein all of the $K_D$ values selected from the group consisting of $K_D1$, $K_D2$ and $K_D3$ are in the range of 10 nM to 0.1 nM, in the range of 5 nM to 0.1 nM or in the range of 2 nM to 0.1 nM. In a further embodiment, the antibody of the present invention binds to human TnC with a first $K_D$ value $K_D1$, wherein said antibody binds to mouse TnC with a second $K_D$ value $K_D2$, and wherein said antibody binds to cynomolgus TnC with a third $K_D$ value $K_D3$, wherein all of the $K_D$ values selected from the group consisting of $K_D1$, $K_D2$ and $K_D3$ are within a $K_D$ range of a factor of 20. In a further embodiment, the antibody of the present invention binds to human TnC with a first $K_D$ value $K_D1$, wherein said antibody binds to mouse TnC with a second $K_D$ value $K_D2$, and wherein said antibody binds to cynomolgus TnC with a third $K_D$ value $K_D3$, wherein all of the $K_D$ values selected from the group consisting of $K_D1$, $K_D2$ and $K_D3$ are within a $K_D$ range of a factor of 10. In one embodiment an antigen binding molecule of the invention is specific for at least one of the TnC domain selected from the group consisting of A1, A2, A3, A4, B, AD1, AD2, C and D. In one embodiment, an antigen binding molecule is provided, wherein said antigen binding molecule is able to bind to at least one of the TnC domain selected from the group consisting of A1, A4 and C. In one embodiment, an antigen binding molecule of the invention is specific for the TnC domains A1 and A4. In one embodiment, an antigen binding molecule of the invention is specific for the TnC domain C. In a specific embodiment, an antigen binding molecule of the invention binds to the A1 and to the A4 domain of human, mouse, and cynomolgus TnC. In another specific embodiment, an antigen binding molecule of the invention binds to the C domain of human, mouse, and cynomolgus TnC. In one embodiment the antigen binding molecule of the invention has cross-species reactivity. In a more specific embodiment, an antigen binding molecule of the invention binds to the A1 domain of human, mouse and cynomolgus TnC A1 and to the A4 domain of human, mouse and cynomolgus TnC A4 with a $K_D$ value lower than about 100 nM, lower than about 10 nM, lower than about 5 nM or lower than about 2 nM. $K_D$ values are determined by Surface Plasmon Resonance, using the antibodies as Fab or IgG. In one embodiment, an anti-TnC antigen binding molecule of the invention binds TnC in human tissues.

In one embodiment, an antigen binding molecule of the invention comprises an Fc region, wherein said antigen binding molecule comprises at least one amino acid substitution in the Fc region. In one embodiment, an antigen binding molecule of the invention comprising at least one amino acid substitution in the Fc region has decreased effector function and/or decreased Fc receptor binding affinity compared to an antigen binding molecule comprising the parent non-substituted Fc region. In a specific embodiment said parent non-substituted Fc region comprises the amino acid residues Leu234, Leu235 and Pro329, wherein the substituted Fc region comprises at least one of the amino acid substitutions selected from the group consisting of Leu234Ala, Leu235Ala and Pro329Gly relative to the parent non-substituted Fc region. In a particular embodiment, the invention provides an antigen binding molecule that specifically binds to TnC, wherein said antigen binding molecule comprises a) a heavy chain region comprising an amino acid sequence that is at least about 90%, 91%, 92%, 93%, 94%, 95%, 96%, 97%, 98%, 99% or 100% identical to a sequence selected from the group consisting of SEQ ID NO: 83 and SEQ ID NO: 84, and a light chain region comprising an amino acid sequence that is at least about 90%, 91%, 92%, 93%, 94%, 95%, 96%, 97%, 98%, 99% or 100% identical to a sequence selected from the group consisting of SEQ ID NO: 77 and SEQ ID NO: 79. In a specific embodiment, antibodies of the invention comprise a heavy chain region comprising an amino acid sequence selected from the group of: SEQ ID NO: 83, and SEQ ID NO: 84. In a further embodiment antigen binding molecule comprising the substituted Fc region has decreased effector function and/or decreased Fc receptor binding affinity compared to the antigen binding molecule comprising the parent non-substituted heavy chain region. In a further specific embodiment, the antigen binding molecule of the invention, comprising said substituted Fc region, comprises the amino acid substitutions Leu234Ala, Leu235Ala and Pro329Gly relative to the parent non-substituted Fc region, wherein binding to FcγR and C1q is abolished and/or wherein Fc-mediated effector function is abolished. In a particular embodiment, the decreased effector function is decreased ADCC. In another particular embodiment, the decreased effector function is abolished ADCC. The decreased Fc receptor binding preferably is decreased binding to an activating Fc receptor, most preferably FcγRIIIa. In one embodiment, an antigen binding molecule of the invention does not cause a clinically significant level of toxicity when administered to an individual in a therapeutically effective amount.

In a particular embodiment, the invention provides an antigen binding molecule that specifically binds to TnC, wherein said antigen binding molecule comprises a) a heavy chain variable region comprising an amino acid sequence that is at least about 90%, 91%, 92%, 93%, 94%, 95%, 96%, 97%, 98%, 99% or 100% identical to a sequence selected from the group consisting of SEQ ID NO: 46 and SEQ ID NO: 48, or a light chain variable region comprising an amino acid sequence that is at least about 90%, 91%, 92%, 93%, 94%, 95%, 96%, 97%, 98%, 99% or 100% identical to a sequence selected from the group consisting of SEQ ID NO: 45 and SEQ ID NO: 47, or a combination thereof, and b) an Fc region or a region equivalent to the Fc region of an immunoglobulin. In one embodiment, an antigen binding molecule of the invention comprises an Fc region, wherein said Fc region is a glycoengineered Fc region. In a further embodiment, an antigen binding molecule of the invention is glycoengineered to have modified oligosaccharides in the Fc region. In a specific embodiment, the antigen binding molecule has an increased proportion of bisected oligosaccharides in the Fc region, compared to a non-glycoengineered antigen binding molecule. In a more specific embodiment, at least about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, preferably at least about 50%, more preferably at least about 70%, of the N-linked oligosaccharides in the Fc region of the antigen binding molecule are bisected. The bisected oligosaccharides may be of the hybrid or complex type. In another specific embodiment, an antigen binding molecule of the invention has an increased proportion of non-fucosylated oligosaccharides in the Fc region, compared to a non-glycoengineered antigen binding molecule. In a more specific embodiment, at least about 20%, about 25%, about 30%, about 35%, about 40%, about 45%, about 50%, about 55%, about 60%, about 65%, about 70%, about 75%, about 80%, about 85%, about 90%, about 95%, or about 100%, preferably at least about 50%, more preferably at least about 70%, of the N-linked oligosaccharides in the Fc region of the antigen binding molecule are non-fucosylated. The non-fucosylated oligosaccharides may be of the hybrid or complex type. In a particular embodiment, an antigen binding molecule of the invention has an increased proportion of bisected, non-fucosylated oligosaccharides in the Fc region, compared to a non-glycoengineered antigen binding molecule. Specifically, the antigen binding molecule comprises an Fc region in which at least about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, preferably at least about 15%, more preferably at least about 25%, at least about 35% or at least about 50%, of the N-linked oligosaccharides are bisected, non-fucosylated. The bisected, non-fucosylated oligosaccharides may be of the hybrid or complex type. In one embodiment, an antigen binding molecule of the invention has increased effector function and/or increased Fc receptor binding affinity. Increased effector function and/or increased Fc receptor binding can result e.g., from glycoengineering and/or affinity maturation of antibodies. In one embodiment, the increased effector function and/or increased Fc receptor binding is a result of glycoengineering of the Fc region of the antigen binding molecule. In another embodiment, the increased effector function and/or increased Fc receptor binding is a result of a combination of increased affinity and glycoengineering. The increased effector function can include, but is not limited to, one or more of the following: increased Fc-mediated cellular cytotoxicity (including increased antibody-dependent cell-mediated cytotoxicity (ADCC)), increased antibody-dependent cellular phagocytosis (ADCP), increased cytokine secretion, increased immune-complex-mediated antigen uptake by antigen-presenting cells, increased binding to NK cells, increased binding to macrophages, increased binding to monocytes, increased binding to polymorphonuclear cells, increased direct signaling inducing apoptosis, increased crosslinking of target-bound antibodies, increased dendritic cell maturation, or increased T cell priming. In a particular embodiment, the increased effector function is increased ADCC. The increased Fc receptor binding preferably is increased binding to an activating Fc receptor, most preferably FcγRIIIa. In one embodiment, an antigen binding molecule of the invention does not cause a clinically significant level of toxicity when administered to an individual in a therapeutically effective amount.

In a particular embodiment, the invention provides an antigen binding molecule that specifically binds to the A1 and A4 domain of TnC, wherein said antigen binding molecule comprises a heavy chain variable region comprising the amino acid sequence SEQ ID NO: 46, a light chain variable region comprising the amino acid sequence SEQ ID NO: 45, and a human IgG Fc region.

In a particular embodiment, the invention provides an antigen binding molecule that specifically binds to the C domain of TnC, wherein said antigen binding molecule comprises a heavy chain variable region comprising the amino acid sequence SEQ ID NO: 48, a light chain variable region comprising the amino acid sequence SEQ ID NO: 47, and a human IgG Fc region.

In a particular embodiment, the invention provides an antigen binding molecule that specifically binds to the A1 and A4 domain of TnC, wherein said antigen binding molecule comprises a heavy chain variable region comprising the amino acid sequence SEQ ID NO: 46, a light chain variable region comprising the amino acid sequence SEQ ID NO: 45, and a human IgG Fc region, and wherein said antigen binding molecule is glycoengineered to have increased effector function and/or Fc receptor binding affinity.

In a particular embodiment, the invention provides an antigen binding molecule that specifically binds to the C domain of TnC, wherein said antigen binding molecule comprises a heavy chain variable region comprising the amino acid sequence SEQ ID NO: 48, a light chain variable region comprising the amino acid sequence SEQ ID NO: 47, and a human IgG Fc region, and wherein said antigen binding molecule is glycoengineered to have increased effector function and/or Fc receptor binding affinity.

In a particular embodiment, the invention provides an antigen binding molecule that specifically binds to the A1 and A4 domain of TnC, wherein said antigen binding molecule comprises a heavy chain variable region comprising the amino acid sequence SEQ ID NO: 46, a light chain variable region comprising the amino acid sequence SEQ ID NO: 45, and a human IgG Fc region, wherein said antigen binding molecule comprises at least one amino acid substitution in the Fc region, wherein the parent non-substituted Fc region comprises the amino acid residues Leu234, Leu235 and Pro329, wherein the substituted Fc region comprises at least one of the amino acid substitutions selected from the group consisting of Leu234Ala, Leu235Ala and Pro329Gly relative to the parent non-substituted Fc region, wherein the antigen binding molecule comprising the substituted Fc region has decreased effector function and/or decreased Fc receptor binding affinity compared to the antigen binding molecule comprising the parent non-substituted Fc region.

In a particular embodiment, the invention provides an antigen binding molecule that specifically binds to the C domain of TnC, wherein said antigen binding molecule comprises a heavy chain variable region comprising the amino acid sequence SEQ ID NO: 48, a light chain variable region comprising the amino acid sequence SEQ ID NO: 47, and a human IgG Fc region, wherein said antigen binding molecule comprises at least one amino acid substitution in the Fc region, wherein the parent non-substituted Fc region comprises the amino acid residues Leu234, Leu235 and Pro329, wherein the substituted Fc region comprises at least one of the amino acid substitutions selected from the group consisting of Leu234Ala, Leu235Ala and Pro329Gly relative to the parent non-substituted Fc region, wherein the antigen binding molecule comprising the substituted Fc region has decreased effector function and/or decreased Fc receptor binding affinity compared to the antigen binding molecule comprising the parent non-substituted Fc region.

In a particular embodiment, the invention provides an antigen binding molecule that specifically binds to the A1 and A4 domain of TnC, wherein said antigen binding molecule comprises a heavy chain variable region comprising (a) the heavy chain CDR1 of SEQ ID NO: 67;
(b) the heavy chain CDR2 of SEQ ID NO: 68;
(c) the heavy chain CDR3 of SEQ ID NO: 69,
and a light chain variable region comprising
(a) the light chain CDR1 of SEQ ID NO: 55;
(b) the light chain CDR2 of SEQ ID NO: 56, and
(c) the light chain CDR3 of SEQ ID NO: 57.

In a particular embodiment, the invention provides an antigen binding molecule that specifically binds to the C domain of TnC, wherein said antigen binding molecule comprises a heavy chain variable region comprising (a) the heavy chain CDR1 of SEQ ID NO: 70;
(b) the heavy chain CDR2 of SEQ ID NO: 71;
(c) the heavy chain CDR3 of SEQ ID NO: 72,
and a light chain variable region comprising
(a) the light chain CDR1 of SEQ ID NO: 58;
(b) the light chain CDR2 of SEQ ID NO: 59, and
(c) the light chain CDR3 of SEQ ID NO: 60.

In a particular embodiment, the invention provides an antigen binding molecule that specifically binds to the A1 and A4 domain of TnC, wherein said antigen binding molecule comprises a heavy chain region comprising the amino acid sequence SEQ ID NO: 78, and a light chain region comprising the amino acid sequence SEQ ID NO: 77.

In a particular embodiment, the invention provides an antigen binding molecule that specifically binds to the A1 and A4 domain of human, mouse and cynomolgus TnC, wherein said antigen binding molecule comprises a heavy chain variable region comprising the amino acid sequence SEQ ID NO: 46, a light chain variable region comprising the amino acid sequence SEQ ID NO: 45, and a human IgG Fc region.

In a particular embodiment, the invention provides an antigen binding molecule that specifically binds to the C domain of TnC, wherein said antigen binding molecule comprises a heavy chain region comprising the amino acid sequence SEQ ID NO: 80, and a light chain region comprising an amino acid sequence selected from the group of SEQ ID NO: 79.

In a particular embodiment, the invention provides an antigen binding molecule that specifically binds to the C domain of human, mouse and cynomolgus TnC, wherein said antigen binding molecule comprises a heavy chain variable region comprising the amino acid sequence SEQ ID NO: 48, a light chain variable region comprising the amino acid sequence SEQ ID NO: 47, and a human IgG Fc region.

In another particular embodiment, the invention provides an antigen binding molecule that specifically binds to the A1 and A4 domain of TnC, wherein said antigen binding molecule comprises a heavy chain variable region comprising the amino acid sequence SEQ ID NO: 46, a light chain variable region comprising the amino acid sequence SEQ ID NO: 45, and a human IgG Fc region, and wherein said antigen binding molecule has an increased proportion of non-fucosylated oligosaccharides and/or an increased proportion of bisected oligosaccharides in said Fc region. In another particular embodiment, the invention provides an antigen binding molecule that specifically binds to the C domain of TnC, wherein said antigen binding molecule comprises a heavy chain variable region comprising the amino acid sequence SEQ ID NO: 48, a light chain variable region comprising the amino acid sequence SEQ ID NO: 47, and a human IgG Fc region, and wherein said antigen binding molecule has an increased proportion of non-fucosylated oligosaccharides and/or an increased proportion of bisected oligosaccharides in said Fc region.

In one aspect, the invention provides for an antigen binding molecule that specifically binds to TnC, wherein said antigen binding molecule comprises at least one amino acid substitution in at least one heavy or light chain CDR of the parent antigen binding molecule. For example, the antigen binding molecule may comprise at least one, e.g., from about one to about ten (i.e., about 1, 2, 3, 4, 5, 6, 7, 8, 9, or 10), and particularly from about two to about five, substitutions in one or more hypervariable regions or CDRs (i.e., 1, 2, 3, 4, 5, or 6 hypervariable regions or CDRs) of the parent antigen binding molecule.

Additionally, the antigen binding molecule may also comprise one or more additions, deletions and/or substitutions in one or more framework regions of either the heavy or the light chain, compared to the parent antigen binding molecule. In one embodiment, said at least one amino acid substitution in at least one CDR contributes to increased binding affinity of the antigen binding molecule compared to its parent antigen binding molecule. In another embodiment said antigen binding molecule has at least about 2-fold to about 10-fold greater affinity for TnC than the parent antigen binding molecule (when comparing the antigen binding molecule of the invention and the parent antigen binding molecule in the same format, e.g., the Fab format). Further, the antigen binding molecule derived from a parent antigen binding molecule may incorporate any of the features, singly or in combination, described in the preceding paragraphs in relation to the antibodies of the invention.

TNF Family Ligand Trimer-Containing Antigen Binding Molecules which Particular TnC Binding Moieties In one aspect, the invention provides a TNF family ligand trimer-containing antigen binding molecule, wherein the moiety capable of specific binding to TnC comprises a VH domain comprising (i) CDR-H1 comprising the amino acid sequence of SEQ ID NO: 67 or SEQ ID NO: 70, (ii) CDR-H2 comprising the amino acid sequence of SEQ ID NO: 68 or SEQ ID NO: 71, and (iii) CDR-H3 comprising the amino acid sequence of SEQ ID NO: 69 or SEQ ID NO: 72, and a VL domain comprising (iv) CDR-L1 comprising the amino acid sequence of SEQ ID NO: 55 or SEQ ID NO: 58, (v) CDR-L2 comprising the amino acid sequence of SEQ ID NO: 56 or SEQ ID NO: 59, and (vi) CDR-L3 comprising the amino acid sequence of SEQ ID NO: 57 or SEQ ID NO: 60.

In a particular aspect, provided is a TNF family ligand trimer-containing antigen binding molecule of the invention, wherein the moiety capable of specific binding to TnC is a Fab molecule capable of specific binding to TnC and comprises a VH domain comprising (i) CDR-H1 comprising the amino acid sequence of SEQ ID NO: 67, (ii) CDR-H2 comprising the amino acid sequence of SEQ ID NO: 68 and (iii) CDR-H3 comprising the amino acid sequence of SEQ ID NO: 69, and a VL domain comprising (iv) CDR-L1 comprising the amino acid sequence of SEQ ID NO: 55, (v) CDR-L2 comprising the amino acid sequence of SEQ ID NO: 56 and (vi) CDR-L3 comprising the amino acid sequence of SEQ ID NO: 57.

In another aspect, provided is a TNF family ligand trimer-containing antigen binding molecule of the invention, wherein the moiety capable of specific binding to TnC is a Fab molecule capable of specific binding to TnC and comprises a VH domain comprising (i) CDR-H1 comprising the amino acid sequence of SEQ ID NO: 70, (ii) CDR-H2 comprising the amino acid sequence of SEQ ID NO: 71 and (iii) CDR-H3 comprising the amino acid sequence of SEQ ID NO: 72, and a VL domain comprising (iv) CDR-L1 comprising the amino acid sequence of SEQ ID NO: 58, (v) CDR-L2 comprising the amino acid sequence of SEQ ID NO: 59 and (vi) CDR-L3 comprising the amino acid sequence of SEQ ID NO: 60.

In one aspect, the moiety capable of specific binding to TnC comprises a variable heavy chain comprising an amino acid sequence of SEQ ID NO: 46 and a variable light chain comprising an amino acid sequence of SEQ ID NO: 45 or a variable heavy chain comprising an amino acid sequence of SEQ ID NO: 48 and a variable light chain comprising an amino acid sequence of SEQ ID NO: 47.

In a further aspect, the moiety capable of specific binding to TnC comprises a heavy chain variable region comprising an amino acid sequence that is at least about 95%, 96%, 97%, 98%, 99% or 100% identical to the amino acid sequence of SEQ ID NO: 46 and a light chain variable region comprising an amino acid sequence that is at least about 95%, 96%, 97%, 98%, 99% or 100% identical to the amino acid sequence of SEQ ID NO: 45.

In another aspect, the moiety capable of specific binding to TnC comprises a heavy chain variable region comprising an amino acid sequence that is at least about 95%, 96%, 97%, 98%, 99% or 100% identical to the amino acid sequence of SEQ ID NO: 48 and a light chain variable region comprising an amino acid sequence that is at least about 95%, 96%, 97%, 98%, 99% or 100% identical to the amino acid sequence of SEQ ID NO: 47.

In a particular aspect, the moiety capable of specific binding to TnC comprises a heavy chain variable region comprising the amino acid sequence of SEQ ID NO: 46 and a light chain variable region comprising the amino acid sequence of SEQ ID NO: 45. In another particular aspect, the moiety capable of specific binding to TnC comprises a heavy chain variable region comprising the amino acid sequence of SEQ ID NO: 48 and a light chain variable region comprising the amino acid sequence of SEQ ID NO: 47. In a specific aspect, the moiety capable of specific binding to TnC comprises a VH domain consisting of amino acid sequence of SEQ ID NO: 46 and a VL domain consisting of the amino acid sequence of SEQ ID NO: 45.

In a further aspect, the TNF family ligand trimer-containing antigen binding molecule of the invention comprises (a) a first heavy chain and a first light chain, both comprising a Fab molecule capable of specific binding to TnC, (b) a second heavy chain comprising an amino acid sequence selected from the group consisting of SEQ ID NO: 176, SEQ ID NO: 184, SEQ ID NO: 185 and SEQ ID NO: 186, and a second light chain comprising an amino acid sequence selected from the group consisting of SEQ ID NO: 172, SEQ ID NO: 174, SEQ ID NO: 175 and SEQ ID NO: 183.

In a further aspect, the TNF family ligand trimer-containing antigen binding molecule of the invention comprises (a) at least one moiety capable of specific binding to TnC comprising a heavy chain variable region comprising the amino acid sequence of SEQ ID NO: 46 and a light chain variable region comprising the amino acid sequence of SEQ ID NO: 45, and (b) a first and a second polypeptide that are linked to each other by a disulfide bond, wherein the antigen binding molecule is characterized in that the first polypeptide comprises the amino acid sequence selected from the group consisting of SEQ ID NO: 176, SEQ ID NO: 184, SEQ ID NO: 185 and SEQ ID NO: 186 and in that the second polypeptide comprises the amino acid sequence selected from the group consisting of SEQ ID NO: 172, SEQ ID NO: 174, SEQ ID NO: 175 and SEQ ID NO: 183.

In a particular aspect, the TNF family ligand trimer-containing antigen binding molecule of the invention comprises (a) at least one moiety capable of specific binding TnC comprising a heavy chain variable region comprising the amino acid sequence of SEQ ID NO: 46 and a light chain variable region comprising the amino acid sequence of SEQ ID NO: 45, and (b) a first and a second polypeptide that are linked to each other by a disulfide bond, wherein the antigen binding molecule is characterized in that the first polypeptide comprises the the amino acid sequence of SEQ ID NO: 176 and the second polypeptide comprises the amino acid sequence of SEQ ID NO: 172.

In a particular aspect, the TNF family ligand trimer-containing antigen binding molecule of the invention comprises (a) at least one moiety capable of specific binding TnC comprising a heavy chain variable region comprising the amino acid sequence of SEQ ID NO: 46 and a light chain variable region comprising the amino acid sequence of SEQ ID NO: 45, and (b) a first and a second polypeptide that are linked to each other by a disulfide bond, wherein the antigen binding molecule is characterized in that the first polypeptide comprises the the amino acid sequence of SEQ ID NO: 184 and the second polypeptide comprises the amino acid sequence of SEQ ID NO: 183.

In another aspect, the TNF family ligand trimer-containing antigen binding molecule of the invention comprises (a) at least one moiety capable of specific binding to TnC comprising a heavy chain variable region comprising the amino acid sequence of SEQ ID NO: 48 and a light chain variable region comprising the amino acid sequence of SEQ ID NO: 47, and a first and a second polypeptide that are linked to each other by a disulfide bond, wherein the antigen binding molecule is characterized in that the first polypeptide comprises the amino acid sequence selected from the group consisting of SEQ ID NO: 176, SEQ ID NO: 184, SEQ ID NO: 185 and SEQ ID NO: 186 and in that the second polypeptide comprises the amino acid sequence selected from the group consisting of SEQ ID NO: 172, SEQ ID NO: 174, SEQ ID NO: 175 and SEQ ID NO: 183.

In a particular aspect, the TNF family ligand trimer-containing antigen binding molecule of the invention comprises (a) at least one moiety capable of specific binding to TnC comprising a heavy chain variable region comprising the amino acid sequence of SEQ ID NO: 48 and a light chain variable region comprising the amino acid sequence of SEQ ID NO: 47, and (b) a first and a second polypeptide that are linked to each other by a disulfide bond, wherein the antigen binding molecule is characterized in that the first polypeptide comprises the the amino acid sequence of SEQ ID NO: 176 and the second polypeptide comprises the amino acid sequence of SEQ ID NO: 172.

In a particular aspect, the TNF family ligand trimer-containing antigen binding molecule of the invention comprises (a) at least one moiety capable of specific binding TnC comprising a heavy chain variable region comprising the amino acid sequence of SEQ ID NO: 48 and a light chain variable region comprising the amino acid sequence of SEQ ID NO: 47, and (b) a first and a second polypeptide that are linked to each other by a disulfide bond, wherein the antigen binding molecule is characterized in that the first polypeptide comprises the the amino acid sequence of SEQ ID NO: 184 and the second polypeptide comprises the amino acid sequence of SEQ ID NO: 183.

In one aspect, provided is a TNF family ligand trimer-containing antigen binding molecule, wherein the antigen binding molecule comprises (i) a first heavy chain comprising the VH domain comprising the amino acid sequence of SEQ ID NO: 46 and a first light chain comprising the VL domain comprising the amino acid sequence of SEQ ID NO: 45 or a first heavy chain comprising the VH domain comprising the amino acid sequence of SEQ ID NO: 48 and a first light chain comprising the VL domain comprising the amino acid sequence of SEQ ID NO: 47, (ii) a second heavy chain comprising the amino acid sequence of SEQ ID NO: 178, and (iii) a second light chain comprising the amino acid sequence of SEQ ID NO: 179.

In another aspect, provided is a TNF family ligand trimer-containing antigen binding molecule, wherein the antigen binding molecule comprises a first heavy chain and a first light chain, both comprising a Fab molecule capable of specific binding to TnC, a second heavy chain comprising two ectodomains of a TNF ligand family member or fragments thereof connected to each other by a first peptide linker that is fused at its C-terminus by a second peptide linker to a CH1 domain, and a second light chain comprising one ectodomain of said TNF ligand family member or a fragment thereof is fused at its C-terminus by a third peptide linker to a CL domain, and wherein the antigen binding molecule comprises (i) a first heavy chain comprising the VH domain comprising the amino acid sequence of SEQ ID NO: 46 and a first light chain comprising the VL domain comprising the amino acid sequence of SEQ ID NO: 45 or a first heavy chain comprising the VH domain comprising the amino acid sequence of SEQ ID NO: 48 and a first light chain comprising the VL domain comprising the amino acid sequence of SEQ ID NO: 47, (ii) a second heavy chain comprising the amino acid sequence of SEQ ID NO: 178, and (iii) a second light chain comprising the amino acid sequence of SEQ ID NO: 179.

In a further particular aspect, provided is a TNF family ligand trimer-containing antigen binding molecule, wherein the antigen binding molecule comprises a first heavy chain and a first light chain, both comprising a Fab molecule capable of specific binding to TnC, a second heavy chain comprising two ectodomains of a TNF ligand family member or fragments thereof connected to each other by a first peptide linker and fused at its C-terminus by a second peptide linker to a CL domain, and a second light chain comprising one ectodomain of said TNF ligand family member or a fragment thereof that is fused at its C-terminus by a third peptide linker to a CH1 domain, and wherein the molecule comprises (i) a first heavy chain comprising the VH domain comprising the amino acid sequence of SEQ ID NO: 46 and a first light chain comprising the VL domain comprising the amino acid sequence of SEQ ID NO: 45 or a first heavy chain comprising the VH domain comprising the amino acid sequence of SEQ ID NO: 48 and a first light chain comprising the VL domain comprising the amino acid sequence of SEQ ID NO: 47, (ii) a second heavy chain comprising the amino acid sequence selected from the group consisting of SEQ ID NO: 102, SEQ ID NO: 108, SEQ ID NO: 116 and SEQ ID NO: 120, and (iii) a second light chain comprising the amino acid sequence selected from the group consisting of SEQ ID NO: 103, SEQ ID NO: 109, SEQ ID NO: 117 and SEQ ID NO: 121.

In another aspect, the invention provides a TNF family ligand trimer-containing antigen binding molecule, wherein the antigen binding molecule comprises (i) a first heavy chain comprising the VH domain comprising the amino acid sequence of SEQ ID NO: 46 and a first light chain comprising the VL domain comprising the amino acid sequence of SEQ ID NO: 45 or a first heavy chain comprising the VH domain comprising the amino acid sequence of SEQ ID NO: 48 and a first light chain comprising the VL domain comprising the amino acid sequence of SEQ ID NO: 47, (ii) a second heavy chain comprising the amino acid sequence selected from the group consisting of SEQ ID NO: 102, SEQ ID NO: 108, SEQ ID NO: 116 and SEQ ID NO: 120, and (iii) a second light chain comprising the amino acid sequence selected from the group consisting of SEQ ID NO: 103, SEQ ID NO: 109, SEQ ID NO: 117 and SEQ ID NO: 121.

In yet another aspect, the invention provides a TNF family ligand trimer-containing antigen binding molecule, comprising (a) at least one moiety capable of specific binding to TnC, and (b) a first and a second polypeptide that are linked to each other by a disulfide bond, wherein the antigen binding molecule is characterized in that the first polypeptide contains a CH3 domain and the second polypeptide contains a CH3 domain, respectively, and wherein the first polypeptide comprises two ectodomains of a TNF ligand family member or fragments thereof that are connected to each other and to the C-terminus of the CH3 domain by a peptide linker and wherein the second polypeptide comprises one ectodomain of said TNF ligand family member or a fragment thereof connected via a peptide linker to C-terminus of the CH3 domain of said polypeptide.

In a further aspect, the TNF family ligand trimer-containing antigen binding molecule of the invention comprises (a) a Fab domain capable of specific binding to TnC, (b) a Fc domain composed of a first and a second subunit capable of stable association, and (c) a first polypeptide comprising two ectodomains of a TNF ligand family member or fragments thereof that are connected to each other by a peptide linker and a second polypeptide comprising one ectodomain of said TNF ligand family member or a fragment thereof, wherein the first polypeptide is fused at its N-terminus to the C-terminus to one of the subunits of the Fc domain and wherein the second polypeptide is fused at its N-terminus to the C-terminus of the other subunit of the Fc domain and wherein the first polypeptide comprising two ectodomains of a TNF ligand family member or fragments thereof comprises an amino acid sequence selected from the group consisting of SEQ ID NO: 176 and SEQ ID NO: 184 and the second polypeptide comprising one ectodomain of said TNF ligand family member or a fragment thereof comprises the amino acid sequence selected from the group consisting of SEQ ID NO: 172 and SEQ ID NO: 183. In one aspect, the first polypeptide comprising two ectodomains of a TNF ligand family member or fragments thereof comprises an amino acid sequence SEQ ID NO: 176 and the second polypeptide comprising one ectodomain of said TNF ligand family member or a fragment thereof comprises the amino acid sequence of SEQ ID NO: 172. In a particular aspect, the first polypeptide comprising two ectodomains of a TNF ligand family member or fragments thereof comprises an amino acid sequence of SEQ ID NO: 184 and the second polypeptide comprising one ectodomain of said TNF ligand family member or a fragment thereof comprises the amino acid sequence of SEQ ID NO: 183.

In one aspect, the invention provides a TNF family ligand trimer-containing antigen binding molecule comprising (a) one Fab domain capable of specific binding to TnC, (b) a Fc domain composed of a first and a second subunit capable of stable association, and (c) a first polypeptide comprising two ectodomains of a TNF ligand family member or fragments thereof that are connected to each other by a peptide linker and a second polypeptide comprising one ectodomain of said TNF ligand family member or a fragment thereof, wherein the first polypeptide is fused at its N-terminus to the C-terminus to one of the subunits of the Fc domain and wherein the second polypeptide is fused at its N-terminus to the C-terminus of the other subunit of the Fc domain. The invention thus relates to a TNF family ligand trimer-containing antigen binding molecule, wherein TNF family ligand trimer-containing antigen binding molecule is monovalent for the binding to the target cell antigen.

In a further aspect, the invention provides a TNF family ligand trimer-containing antigen binding molecule comprising (a) a Fab domain capable of specific binding to TnC comprising a VH domain comprising an amino acid sequence of SEQ ID NO: 46 and a VL domain comprising an amino acid sequence of SEQ ID NO: 45, or a VH domain comprising an amino acid sequence of SEQ ID NO: 48 and a VL domain comprising an amino acid sequence of SEQ ID NO: 47, (b) a Fc domain composed of a first and a second subunit capable of stable association, and (c) a first polypeptide comprising two ectodomains of a TNF ligand family member or fragments thereof that are connected to each other by a peptide linker and a second polypeptide comprising one ectodomain of said TNF ligand family member or a fragment thereof, wherein the first polypeptide is fused at its N-terminus to the C-terminus to one of the subunits of the Fc domain and wherein the second polypeptide is fused at its N-terminus to the C-terminus of the other subunit of the Fc domain.

In another aspect, the invention provides a TNF family ligand trimer-containing antigen binding molecule comprising (a) a Fab domain capable of specific binding to TnC comprising a VH domain comprising an amino acid sequence of SEQ ID NO: 46 and a VL domain comprising an amino acid sequence of SEQ ID NO: 45, or a VH domain comprising an amino acid sequence of SEQ ID NO: 48 and a VL domain comprising an amino acid sequence of SEQ ID NO: 47, (b) a Fc domain composed of a first and a second subunit capable of stable association, and (c) a first polypeptide comprising two ectodomains of a TNF ligand family member or fragments thereof that are connected to each other by a peptide linker and a second polypeptide comprising one ectodomain of said TNF ligand family member or a fragment thereof, wherein the first polypeptide is fused at its N-terminus to the C-terminus to one of the subunits of the Fc domain and wherein the second polypeptide is fused at its N-terminus to the C-terminus of the other subunit of the Fc domain and wherein the first polypeptide comprising two ectodomains of a TNF ligand family member or fragments thereof comprises an amino acid sequence selected from the group consisting of SEQ ID NO: 176 and SEQ ID NO: 184 and the second polypeptide comprising one ectodomain of said TNF ligand family member or a fragment thereof comprises the amino acid sequence selected from the group consisting of SEQ ID NO: 172 and SEQ ID NO: 183.

In a particular aspect, provided is a TNF family ligand trimer-containing antigen binding molecule comprising (a) a Fab domain capable of specific binding to TnC comprising a VH domain comprising an amino acid sequence of SEQ ID NO: 46 and a VL domain comprising an amino acid sequence of SEQ ID NO: 45, (b) a Fc domain composed of a first and a second subunit capable of stable association, and (c) a first polypeptide comprising two ectodomains of a TNF ligand family member or fragments thereof that are connected to each other by a peptide linker and a second polypeptide comprising one ectodomain of said TNF ligand family member or a fragment thereof, wherein the first polypeptide is fused at its N-terminus to the C-terminus to one of the subunits of the Fc domain and wherein the second polypeptide is fused at its N-terminus to the C-terminus of the other subunit of the Fc domain and wherein the first polypeptide comprising two ectodomains of a TNF ligand family member comprising an amino acid sequence of SEQ ID NO: 184 and the second polypeptide comprising one ectodomain of said TNF ligand family member comprising the amino acid sequence of SEQ ID NO: 183.

In another aspect, provided is a TNF family ligand trimer-containing antigen binding molecule, wherein the antigen binding molecule comprises (i) a light chain comprising the VL domain of the Fab domain capable of specific binding to TnC, (ii) a fusion polypeptide comprising a first subunit of a Fc domain and a first polypeptide comprising two ectodomains of a TNF ligand family member or fragments thereof that are connected to each other by a peptide linker, wherein the first polypeptide is fused at its N-terminus to the C-terminus of the first subunit of the Fc domain, and (iii) a heavy chain comprising the VH domain of the Fab domain capable of specific binding to TnC, a second subunit of the Fc domain and a second polypeptide comprising one ectodomain of said TNF ligand family member or a fragment thereof, wherein the variable heavy chain of the Fab domain capable of specific binding to TnC is fused at its C-terminus to the N-terminus of the second subunit of the Fc domain and wherein the second polypeptide comprising one ectodomain of said TNF ligand family member or a fragment thereof is fused at its N-terminus to the C-terminus of the second subunit of the Fc domain.

In a further aspect, the invention provides a TNF family ligand trimer-containing antigen binding molecule as defined before further comprising (d) a Fab domain that is not capable of specific binding to TnC. Thus, the invention provides a TNF family ligand trimer-containing antigen binding molecule comprising (a) a Fab domain capable of specific binding to TnC, (b) a Fc domain composed of a first and a second subunit capable of stable association, (c) a first polypeptide comprising two ectodomains of a TNF ligand family member or fragments thereof that are connected to each other by a peptide linker and a second polypeptide comprising one ectodomain of said TNF ligand family member or a fragment thereof, wherein the first polypeptide is fused at its N-terminus to the C-terminus to one of the subunits of the Fc domain and wherein the second polypeptide is fused at its N-terminus to the C-terminus of the other subunit of the Fc domain, and (d) a Fab domain that is not capable of specific binding to a target cell antigen.

In a further particular aspect of the invention, provided is a TNF family ligand trimer-containing antigen binding molecule comprising (a) a first heavy chain and a first light chain, both comprising a Fab molecule capable of specific binding to TnC, wherein the first heavy chain comprises the VH domain comprising the amino acid sequence of SEQ ID NO: 46 and the first light chain comprises the VL domain comprising the amino acid sequence of SEQ ID NO: 45, and (b) a second heavy chain comprising two ectodomains of a TNF ligand family member or fragments thereof connected to each other by a first peptide linker that is fused at its C-terminus by a second peptide linker to a CL domain, and a second light chain comprising one ectodomain of said TNF ligand family member or a fragment thereof that is fused at its C-terminus by a third peptide linker to a CH1 domain, wherein the second heavy chain comprises the amino acid sequence of SEQ ID NO: 116 or SEQ ID NO: 120, and the second light chain comprises the amino acid sequence of SEQ ID NO: 117 or SEQ ID NO: 121. In particular, the second heavy chain comprises the amino acid sequence of SEQ ID NO: 116 and the second light chain comprises the amino acid sequence of SEQ ID NO: 117.

Furthermore, the invention provides a TNF family ligand trimer-containing antigen binding molecule, comprising (a) at least one moiety capable of specific binding to TnC, and (b) a first and a second polypeptide that are linked to each other by a disulfide bond, wherein the antigen binding molecule is characterized in that the first polypeptide contains a CH3 domain and the second polypeptide contains a CH3 domain, respectively, and wherein the first polypeptide comprises two ectodomains of a TNF ligand family member or fragments thereof that are connected to each other and to the C-terminus of the CH3 domain by a peptide linker and wherein the second polypeptide comprises one ectodomain of said TNF ligand family member or a fragment thereof connected via a peptide linker to C-terminus of the CH3 domain of said polypeptide.

In particular, provided is a TNF family ligand trimer-containing antigen binding molecule as described herein before comprising (i) a first heavy chain comprising the amino acid sequence of SEQ ID NO: 127, a second heavy chain comprising the amino acid sequence of SEQ ID NO: 125, and one light chain comprising the amino acid sequence of SEQ ID NO: 77, or (ii) a first heavy chain comprising the amino acid sequence of SEQ ID NO: 130, a second heavy chain comprising the amino acid sequence of SEQ ID NO:131, and one light chain comprising the amino acid sequence of SEQ ID NO: 77, or (ii) a first heavy chain comprising the amino acid sequence of SEQ ID NO:124, a second heavy chain comprising the amino acid sequence of SEQ ID NO:133, and one light chain comprising the amino acid sequence of SEQ ID NO: 77, or (ii) a first heavy chain comprising the amino acid sequence of SEQ ID NO: 136, a second heavy chain comprising the amino acid sequence of SEQ ID NO:137, and one light chain comprising the amino acid sequence of SEQ ID NO: 77.

In a particular aspect, such a TNF family ligand trimer-containing antigen binding molecule comprises two moieties capable of specific binding to TnC.

In one aspect, the invention provides a TNF family ligand trimer-containing antigen binding molecule comprising two moieties capable of specific binding to TnC. In particular, provided is a TNF family ligand trimer-containing antigen binding molecule as described herein before comprising (i) a first heavy chain comprising the amino acid sequence of SEQ ID NO: 112, a second heavy chain comprising the amino acid sequence of SEQ ID NO: 113, and two light chains comprising the amino acid sequence of SEQ ID NO: 77, or (ii) a first heavy chain comprising the amino acid sequence of SEQ ID NO: 124, a second heavy chain comprising the amino acid sequence of SEQ ID NO: 125, and two light chains comprising the amino acid sequence of SEQ ID NO: 77.

In another aspect, provided is a TNF family ligand trimer-containing antigen binding molecule, wherein the antigen binding molecule comprises (i) a light chain comprising the VL domain of the Fab domain capable of specific binding to TNC, (ii) a fusion polypeptide comprising a first subunit of a Fc domain and a second polypeptide comprising one ectodomain of said TNF ligand family member or a fragment thereof, wherein the second polypeptide is fused at its N-terminus to the C-terminus of the first subunit of the Fc domain, and (iii) a heavy chain comprising the VH domain of the Fab domain capable of specific binding to TNC, a second subunit of the Fc domain and a first polypeptide comprising two ectodomains of a TNF ligand family member or fragments thereof that are connected to each other by a peptide linker, wherein the variable heavy chain of the Fab domain capable of specific binding to TNC is fused at its C-terminus to the N-terminus of the second subunit of the Fc domain and wherein the first polypeptide comprising two ectodomains of a TNF ligand family member or fragments thereof is fused at its N-terminus to the C-terminus of the second subunit of the Fc domain.

In a further aspect, provided is a TNF family ligand trimer-containing antigen binding molecule, wherein the antigen binding molecule comprises (i) a first light chain comprising the VL domain of the Fab domain capable of specific binding to TnC, (ii) a first heavy chain comprising the VH domain of the Fab domain capable of specific binding to TnC, a first subunit of a Fc domain and a second polypeptide comprising one ectodomain of said TNF ligand family member or a fragment thereof, wherein the variable heavy chain of the Fab domain capable of specific binding to TnC is fused at its C-terminus to the N-terminus of the second subunit of the Fc domain and wherein the second polypeptide is fused at its N-terminus to the C-terminus of the first subunit of the Fc domain, (iii) a second heavy chain comprising the VH domain of a Fab domain that is not capable of specific binding to a target cell antigen, a second subunit of the Fc domain and a first polypeptide comprising two ectodomains of a TNF ligand family member or fragments thereof that are connected to each other by a peptide linker, wherein the variable heavy chain of the Fab domain not capable of specific binding to a target cell antigen is fused at its C-terminus to the N-terminus of the second subunit of the Fc domain and wherein the first polypeptide comprising two ectodomains of a TNF ligand family member or fragments thereof is fused at its N-terminus to the C-terminus of the second subunit of the Fc domain, and (iv) a second light chain comprising the VL domain of the Fab domain that is not capable of specific binding to a target cell antigen.

In another aspect, provided is a TNF family ligand trimer-containing antigen binding molecule, wherein the antigen binding molecule comprises (i) a first light chain comprising the VL domain of the Fab domain capable of specific binding to TnC, (ii) a first heavy chain comprising the VH domain of the Fab domain capable of specific binding to TnC, a first subunit of a Fc domain and a first polypeptide comprising two ectodomains of a TNF ligand family member or fragments thereof that are connected to each other by a peptide linker, wherein the variable heavy chain of the Fab domain capable of specific binding to TnC is fused at its C-terminus to the N-terminus of the second subunit of the Fc domain and wherein the first polypeptide comprising ectodomains of a TNF ligand family member or fragments thereof is fused at its N-terminus to the C-terminus of the first subunit of the Fc domain, (iii) a second heavy chain comprising the VH domain of a Fab domain that is not capable of specific binding to a target cell antigen, a second subunit of the Fc domain and a second polypeptide comprising one ectodomain of said TNF ligand family member or a fragment thereof, wherein the variable heavy chain of the Fab domain not capable of specific binding to a target cell antigen is fused at its C-terminus to the N-terminus of the second subunit of the Fc domain and wherein the second polypeptide comprising one ectodomain of a TNF ligand family member or fragments thereof is fused at its N-terminus to the C-terminus of the second subunit of the Fc domain, and (iv) a second light chain comprising the VL domain of the Fab domain that is not capable of specific binding to a target cell antigen.

In further particular aspects, provided is a TNF family ligand trimer-containing antigen binding molecule, wherein the antigen binding molecule comprises a) a first heavy chain comprising an amino acid sequence that is at least about 95%, 96%, 97%, 98%, 99% or 100% identical to the amino acid sequence of SEQ ID NO: 104, a first light chain comprising an amino acid sequence that is at least about 95%, 96%, 97%, 98%, 99% or 100% identical to the amino acid sequence of SEQ ID NO: 77, a second heavy chain comprising an amino acid sequence that is at least about 95%, 96%, 97%, 98%, 99% or 100% identical to the amino acid sequence of SEQ ID NO: 102 and a second light chain comprising an amino acid sequence that is at least about 95%, 96%, 97%, 98%, 99% or 100% identical to the amino acid sequence of SEQ ID NO: 103; or b) a first heavy chain comprising an amino acid sequence that is at least about 95%, 96%, 97%, 98%, 99% or 100% identical to the amino acid sequence of SEQ ID NO: 104, a first light chain comprising an amino acid sequence that is at least about 95%, 96%, 97%, 98%, 99% or 100% identical to the amino acid sequence of SEQ ID NO: 77, a second heavy chain comprising an amino acid sequence that is at least about 95%, 96%, 97%, 98%, 99% or 100% identical to the amino acid sequence of SEQ ID NO: 108 and a second light chain comprising an amino acid sequence that is at least about 95%, 96%, 97%, 98%, 99% or 100% identical to the amino acid sequence of SEQ ID NO: 109; or (c) a first heavy chain comprising an amino acid sequence that is at least about 95%, 96%, 97%, 98%, 99% or 100% identical to the amino acid sequence of SEQ ID NO: 112, a second heavy chain comprising an amino acid sequence that is at least about 95%, 96%, 97%, 98%, 99% or 100% identical to the amino acid sequence of SEQ ID NO: 113 and two light chains comprising an amino acid sequence that is at least about 95%, 96%, 97%, 98%, 99% or 100% identical to the amino acid sequence of SEQ ID NO: 77; or d) a first heavy chain comprising an amino acid sequence that is at least about 95%, 96%, 97%, 98%, 99% or 100% identical to the amino acid sequence of SEQ ID NO: 104, a first light chain comprising an amino acid sequence that is at least about 95%, 96%, 97%, 98%, 99% or 100% identical to the amino acid sequence of SEQ ID NO: 77, a second heavy chain comprising an amino acid sequence that is at least about 95%, 96%, 97%, 98%, 99% or 100% identical to the amino acid sequence of SEQ ID NO: 116 and a second light chain comprising an amino acid sequence that is at least about 95%, 96%, 97%, 98%, 99% or 100% identical to the amino acid sequence of SEQ ID NO: 117; or e) a first heavy chain comprising an amino acid sequence that is at least about 95%, 96%, 97%, 98%, 99% or 100% identical to the amino acid sequence of SEQ ID NO: 104, a first light chain comprising an amino acid sequence that is at least about 95%, 96%, 97%, 98%, 99% or 100% identical to the amino acid sequence of SEQ ID NO: 77, a second heavy chain comprising an amino acid sequence that is at least about 95%, 96%, 97%, 98%, 99% or 100% identical to the amino acid sequence of SEQ ID NO: 120 and a second light chain comprising an amino acid sequence that is at least about 95%, 96%, 97%, 98%, 99% or 100% identical to the amino acid sequence of SEQ ID NO: 121; or (f) a first heavy chain comprising an amino acid sequence that is at least about 95%, 96%, 97%, 98%, 99% or 100% identical to the amino acid sequence of SEQ ID NO: 124, a second heavy chain comprising an amino acid sequence that is at least about 95%, 96%, 97%, 98%, 99% or 100% identical to the amino acid sequence of SEQ ID NO: 125, and two light chains comprising an amino acid sequence that is at least about 95%, 96%, 97%, 98%, 99% or 100% identical to the amino acid sequence of SEQ ID NO: 77; or (g) a first heavy chain comprising an amino acid sequence that is at least about 95%, 96%, 97%, 98%, 99% or 100% identical to the amino acid sequence of SEQ ID NO: 127, a second heavy chain comprising an amino acid sequence that is at least about 95%, 96%, 97%, 98%, 99% or 100% identical to the amino acid sequence of SEQ ID NO: 128, and one light chains comprising an amino acid sequence that is at least about 95%, 96%, 97%, 98%, 99% or 100% identical to the amino acid sequence of SEQ ID NO: 77; or (h) a first heavy chain comprising an amino acid sequence that is at least about 95%, 96%, 97%, 98%, 99% or 100% identical to the amino acid sequence of SEQ ID NO: 130, a second heavy chain comprising an amino acid sequence that is at least about 95%, 96%, 97%, 98%, 99% or 100% identical to the amino acid sequence of SEQ ID NO: 131, and one light chains comprising an amino acid sequence that is at least about 95%, 96%, 97%, 98%, 99% or 100% identical to the amino acid sequence of SEQ ID NO: 77; or (i) a first heavy chain comprising an amino acid sequence that is at least about 95%, 96%, 97%, 98%, 99% or 100% identical to the amino acid sequence of SEQ ID NO: 124, a second heavy chain comprising an amino acid sequence that is at least about 95%, 96%, 97%, 98%, 99% or 100% identical to the amino acid sequence of SEQ ID NO: 133, and one light chains comprising an amino acid sequence that is at least about 95%, 96%, 97%, 98%, 99% or 100% identical to the amino acid sequence of SEQ ID NO: 77; or (j) a first heavy chain comprising an amino acid sequence that is at least about 95%, 96%, 97%, 98%, 99% or 100% identical to the amino acid sequence of SEQ ID NO: 136, a second heavy chain comprising an amino acid sequence that is at least about 95%, 96%, 97%, 98%, 99% or 100% identical to the amino acid sequence of SEQ ID NO: 137, and one light chains comprising an amino acid sequence that is at least about 95%, 96%, 97%, 98%, 99% or 100% identical to the amino acid sequence of SEQ ID NO: 77.

In further particular aspects, the invention relates to a TNF family ligand trimer-containing antigen binding molecule, selected from the group consisting of:

a) a molecule comprising a first heavy chain comprising the amino acid sequence of SEQ ID NO: 104, a first light chain comprising the amino acid sequence of SEQ ID NO: 77, a second heavy chain comprising the amino acid sequence of SEQ ID NO: 102 and a second light chain comprising the amino acid sequence of SEQ ID NO: 103;

b) a molecule comprising a first heavy chain comprising the amino acid sequence of SEQ ID NO: 104, a first light chain comprising the amino acid sequence of SEQ ID NO: 77, a second heavy chain comprising the amino acid sequence of SEQ ID NO: 108 and a second light chain comprising the amino acid sequence of SEQ ID NO: 109;

(c) a molecule comprising a first heavy chain comprising the amino acid sequence of SEQ ID NO: 112, a second heavy chain comprising the amino acid sequence of SEQ ID NO: 113 and two light chains comprising the amino acid sequence of SEQ ID NO: 77;

d) a molecule comprising a first heavy chain comprising the amino acid sequence of SEQ ID NO: 104, a first light chain comprising the amino acid sequence of SEQ ID NO: 77, a second heavy chain comprising the amino acid sequence of SEQ ID NO: 116 and a second light chain comprising the amino acid sequence of SEQ ID NO: 117;

e) a molecule comprising a first heavy chain comprising the amino acid sequence of SEQ ID NO: 104, a first light chain comprising the amino acid sequence of SEQ ID NO: 77, a second heavy chain comprising the amino acid sequence of SEQ ID NO: 120 and a second light chain comprising the amino acid sequence of SEQ ID NO: 121;

(f) a molecule comprising a first heavy chain comprising the amino acid sequence of SEQ ID NO: 124, a second heavy chain comprising the amino acid sequence of SEQ ID NO: 125, and two light chains comprising the amino acid sequence of SEQ ID NO: 77;

(g) a molecule comprising a first heavy chain comprising the amino acid sequence of SEQ ID NO: 127, a second heavy chain comprising the amino acid sequence of SEQ ID NO: 128, and one light chains comprising the amino acid sequence of SEQ ID NO: 77.

(h) a molecule comprising a first heavy chain comprising the amino acid sequence of SEQ ID NO: 130, a second heavy chain comprising the amino acid sequence of SEQ ID NO: 131, and one light chains comprising the amino acid sequence of SEQ ID NO: 77.

(i) a molecule comprising a first heavy chain comprising the amino acid sequence of SEQ ID NO: 124, a second heavy chain comprising the amino acid sequence of SEQ ID NO: 133, and one light chains comprising the amino acid sequence of SEQ ID NO: 77.

(j) a molecule comprising a first heavy chain comprising the amino acid sequence of SEQ ID NO: 136, a second heavy chain comprising the amino acid sequence of SEQ ID NO: 137, and one light chains comprising the amino acid sequence of SEQ ID NO: 77.

In another aspect, provided is a TNF family ligand trimer-containing antigen binding molecule, wherein the TNF ligand family member is OX40L and wherein the target cell antigen is Tenascin-C (TnC) and the moiety capable of specific binding to TnC comprises a VH domain comprising (i) CDR-H1 comprising the amino acid sequence of SEQ ID NO: 67 or SEQ ID NO: 70, (ii) CDR-H2 comprising the amino acid sequence of SEQ ID NO: 68 or SEQ ID NO: 71, and (iii) CDR-H3 comprising the amino acid sequence of SEQ ID NO: 69 or SEQ ID NO: 72, and a VL domain comprising (iv) CDR-L1 comprising the amino acid sequence of SEQ ID NO: 55 or SEQ ID NO: 58, (v) CDR-L2 comprising the amino acid sequence of SEQ ID NO: 56 or SEQ ID NO: 59, and (vi) CDR-L3 comprising the amino acid sequence of SEQ ID NO: 57 or SEQ ID NO: 60.

In a particular aspect, the TNF family ligand trimer-containing antigen binding molecule of comprises (i) a first heavy chain comprising the VH domain comprising the amino acid sequence of SEQ ID NO: 46 and a first light chain comprising the VL domain comprising the amino acid sequence of SEQ ID NO: 45 or a first heavy chain comprising the VH domain comprising the amino acid sequence of SEQ ID NO: 48 and a first light chain comprising the VL domain comprising the amino acid sequence of SEQ ID NO: 47, (ii) a second heavy chain comprising the amino acid sequence selected from the group consisting of SEQ ID NO: 195, and (iii) a second light chain comprising the amino acid sequence of SEQ ID NO: 196.

Polynucleotides

The invention further provides isolated polynucleotides encoding an antigen binding molecule as described herein or a fragment thereof.

The isolated polynucleotides antigen binding molecules of the invention may be expressed as a single polynucleotide that encodes the entire antigen binding molecule or as multiple (e.g., two or more) polynucleotides that are co-expressed. Polypeptides encoded by polynucleotides that are co-expressed may associate through, e.g., disulfide bonds or other means to form a functional antigen binding molecule. For example, the light chain portion of an immunoglobulin may be encoded by a separate polynucleotide from the heavy chain portion of the immunoglobulin. When co-expressed, the heavy chain polypeptides will associate with the light chain polypeptides to form the immunoglobulin.

In some aspects, the isolated polynucleotide encodes the entire antigen binding molecule according to the invention as described herein. In particular, the isolated polynucleotide encodes a polypeptide comprised in the TNF family ligand trimer-containing antigen binding molecule according to the invention as described herein.

In one aspect, the present invention is directed to an isolated polynucleotide encoding a TNF family ligand trimer-containing antigen binding molecule, wherein the polynucleotide comprises (a) a sequence that encodes a moiety capable of specific binding to TnC, (b) a sequence that encodes a polypeptide comprising two ectodomains of a TNF ligand family member or two fragments thereof that are connected to each other by a peptide linker and (c) a sequence that encodes a polypeptide comprising one ectodomain of said TNF ligand family member or a fragment thereof.

In another aspect, provided is an isolated polynucleotide encoding a 4-1BB ligand trimer-containing antigen binding molecule, wherein the polynucleotide comprises (a) a sequence that encodes a moiety capable of specific binding to TnC, (b) a sequence that encodes a polypeptide comprising two ectodomains of 4-1BBL or two fragments thereof that are connected to each other by a peptide linker and (c) a sequence that encodes a polypeptide comprising one ectodomain of 4-1BBL or a fragment thereof.

In one embodiment, the invention is directed to an isolated polynucleotide comprising a sequence encoding one or more (e.g., one, two, three, four, five, or six) of the heavy or light chain complementarity determining regions (CDRs) set forth in SEQ ID NO: 55, SEQ ID NO: 56, SEQ ID NO: 57, SEQ ID NO: 58, SEQ ID NO: 59, SEQ ID NO: 60, SEQ ID NO: 67, SEQ ID NO: 68, SEQ ID NO: 69, SEQ ID NO: 70, SEQ ID NO: 71 and SEQ ID NO: 72, or a variant or truncated form thereof containing at least the specificity-determining residues (SDRs) for said CDR.

In another embodiment, the polynucleotide comprises a sequence that encodes three heavy chain CDRs (e.g., HCDR1, HCDR2, and HCDR3) or three light chain CDRs (e.g., LCDR1, LCDR2, and LCDR3) selected from SEQ ID NO: 55, SEQ ID NO: 56, SEQ ID NO: 57, SEQ ID NO: 58, SEQ ID NO: 59, SEQ ID NO: 60, SEQ ID NO: 67, SEQ ID NO: 68, SEQ ID NO: 69, SEQ ID NO: 70, SEQ ID NO: 71 and SEQ ID NO: 72, or variants or truncated forms thereof containing at least the SDRs for each of said three complementarity determining regions. In yet another embodiment, the polynucleotide comprises a sequence encoding three heavy chain CDRs (e.g., HCDR1, HCDR2, and HCDR3) and three light chain CDRs (e.g., LCDR1, LCDR2, and LCDR3) selected from SEQ ID NO: 55, SEQ ID NO: 56, SEQ ID NO: 57, SEQ ID NO: 58, SEQ ID NO: 59, SEQ ID NO: 60, SEQ ID NO: 67, SEQ ID NO: 68, SEQ ID NO: 69, SEQ ID NO: 70, SEQ ID NO: 71 and SEQ ID NO: 72.

In a particular embodiment the polynucleotide encoding one or more CDRs comprises a sequence that is at least about 90%, 95%, 96%, 97%, 98%, 99%, or 100% identical to one or more of the CDR nucleotide sequences of SEQ ID NO: 49, SEQ ID NO: 50, SEQ ID NO: 51, SEQ ID NO: 52, SEQ ID NO: 53, SEQ ID NO: 54, SEQ ID NO: 61, SEQ ID NO: 62, SEQ ID NO: 63, SEQ ID NO: 64, SEQ ID NO: 65 and SEQ ID NO: 66.

In a further embodiment, the polynucleotide comprises a sequence encoding a heavy chain variable region selected from the group of SEQ ID NO: 46 and SEQ ID NO: 48, and/or a sequence encoding a light chain variable region selected from the group of SEQ ID NO: 45 and SEQ ID NO: 47. In a particular embodiment, the polynucleotide encoding a heavy chain and/or light chain variable region comprises a sequence selected from the group of variable region nucleotide sequences consisting of SEQ ID NO: 41, SEQ ID NO: 42, SEQ ID NO: 43 and SEQ ID NO: 44, or a combination thereof.

In a specific embodiment, the polynucleotide comprises a sequence encoding a heavy chain variable region selected from the group of SEQ ID NO: 46 and SEQ ID NO: 48, and a sequence encoding a heavy chain constant region, particularly a human heavy chain constant region. In a particular embodiment, said heavy chain constant region is a human IgG heavy chain constant region, specifically a human IgG1 heavy chain constant region, comprising an Fc region. In another specific embodiment, the polynucleotide comprises a sequence encoding a light chain variable region selected from the group of SEQ ID NO: 45 and SEQ ID NO: 47, and a sequence encoding a light chain constant region, particularly a human light chain constant region.

In one embodiment, the invention is directed to a composition that comprises a first isolated polynucleotide encoding a polypeptide comprising an amino acid sequence that is at least about 90%, 95%, 96%, 97%, 98%, 99%, or 100% identical to a sequence selected from the group consisting of SEQ ID NO: 77 and SEQ ID NO: 79, and a second isolated polynucleotide encoding a polypeptide comprising an amino acid sequence that is at least about 90%, 95%, 96%, 97%, 98%, 99%, or 100% identical to a sequence selected from the group consisting of SEQ ID NO: 78, and SEQ ID NO: 80.

In one embodiment, the invention is directed to a composition that comprises a first isolated polynucleotide comprising a sequence that is at least about 90%, 95%, 96%, 97%, 98%, 99%, or 100% identical to a sequence selected from the group consisting of SEQ ID NO: 77 and SEQ ID NO: 79, and a second isolated polynucleotide comprising a sequence that is at least about 90%, 95%, 96%, 97%, 98%, 99%, or 100% identical to a sequence selected from the group consisting of SEQ ID NO: 83, and SEQ ID NO: 84.

In a further aspect, the invention is directed to an isolated polynucleotide comprising a sequence that encodes a polypeptide comprising two 4-1BBL fragments comprising an amino acid sequence that is at least about 90%, 95%, 98% or 100% identical to an amino acid sequence shown in SEQ ID NO: 172, SEQ ID NO: 173, SEQ ID NO: 174, SEQ ID NO: 175 or SEQ ID NO: 183, and to a polynucleotide comprising a sequence that encodes a polypeptide comprising one 4-1BBL fragment comprising an amino acid sequence that is at least about 90%, 95%, 98% or 100% identical to an amino acid sequence shown in SEQ ID NO: 172, SEQ ID NO: 173, SEQ ID NO: 174, SEQ ID NO: 175 or SEQ ID NO: 183.

Furthermore, provided is an isolated polynucleotide encoding a OX40 ligand trimer-containing antigen binding molecule, wherein the polynucleotide comprises (a) a sequence that encodes a moiety capable of specific binding to TnC, (b) a sequence that encodes a polypeptide comprising two ectodomains of OX40L or two fragments thereof that are connected to each other by a peptide linker and (c) a sequence that encodes a polypeptide comprising one ectodomain of OX40L or a fragment thereof.

In another aspect, the invention is directed to an isolated polynucleotide comprising a sequence that encodes a polypeptide comprising two 4-1BBL fragments comprising an amino acid sequence that is at least about 90%, 95%, 98% or 100% identical to an amino acid sequence shown in SEQ ID NO: 181 or SEQ ID NO: 182, and to a polynucleotide comprising a sequence that encodes a polypeptide comprising one 4-1BBL fragment comprising an amino acid sequence that is at least about 90%, 95%, 98% or 100% identical to an amino acid sequence shown in SEQ ID NO: 181 or SEQ ID NO: 182.

In further aspects, the invention relates to the polynucleotides comprising a sequence that is at least about 90%, 95%, 98% or 100% identical to the specific cDNA sequences disclosed herein. In a particular aspect, the invention relates to a polynucleotide comprising a sequence that is identical to one of the specific cDNA sequences disclosed herein.

In other aspects, the nucleic acid molecule comprises or consists of a nucleotide sequence that encodes an amino acid sequence as set forth in any one of SEQ ID NOs: 176, 177, 184, 185, 186, 187, 188 or 189. In a further aspect, the nucleic acid molecule comprises or consists of a nucleotide sequence that encodes an amino acid sequence as set forth in any one of SEQ ID NOs: 102, 103, 104, 108, 109, 112, 113, 116, 117, 120, 121, 124, 125, 127, 130, 131, 133, 136, 137, 178 and 179.

In still other aspects, the nucleic acid molecule comprises or consists of a nucleotide sequence selected from the group consisting of SEQ ID NOs: 41, 42, 43, 44, 49, 50, 51, 52, 53, 54, 61, 62, 63, 64, 65, 66, 73, 74, 75, 76, 81, 82, 88, 89, 90, 91, 96, 98, 99, 100, 106, 107, 110, 111, 114, 115, 118, 119, 122, 123, 126, 128, 129, 132, 134 or 135.

In certain aspects, the polynucleotide or nucleic acid is DNA. In other embodiments, a polynucleotide of the present invention is RNA, for example, in the form of messenger RNA (mRNA). RNA of the present invention may be single stranded or double stranded.

Recombinant Methods

Antigen binding molecules of the invention may be obtained, for example, by solid-state peptide synthesis (e.g. Merrifield solid phase synthesis) or recombinant production. For recombinant production one or more polynucleotide encoding the antigen binding molecule or polypeptide fragments thereof, e.g., as described above, is isolated and inserted into one or more vectors for further cloning and/or expression in a host cell. Such polynucleotide may be readily isolated and sequenced using conventional procedures. In one aspect of the invention, a vector, preferably an expression vector, comprising one or more of the polynucleotides of the invention is provided. Methods which are well known to those skilled in the art can be used to construct expression vectors containing the coding sequence of the antigen binding molecule (fragment) along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989); and Ausubel et al., CURRENT PROTOCOLS IN MOLECULAR BIOLOGY, Greene Publishing Associates and Wiley Interscience, N.Y. (1989). The expression vector can be part of a plasmid, virus, or may be a nucleic acid fragment. The expression vector includes an expression cassette into which the polynucleotide encoding the antigen binding molecule or polypeptide fragments thereof (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g. on a single vector, or in separate polynucleotide constructs, e.g. on separate (different) vectors. Furthermore, any vector may contain a single coding region, or may comprise two or more coding regions, e.g. a vector of the present invention may encode one or more polypeptides, which are post- or co-translationally separated into the final proteins via proteolytic cleavage. In addition, a vector, polynucleotide, or nucleic acid of the invention may encode heterologous coding regions, either fused or unfused to a polynucleotide encoding the antigen binding molecule of the invention or polypeptide fragments thereof, or variants or derivatives thereof. Heterologous coding regions include without limitation specialized elements or motifs, such as a secretory signal peptide or a heterologous functional domain. An operable association is when a coding region for a gene product, e.g. a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription.

Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus 40 (e.g. the early promoter), and retroviruses (such as, e.g. Rous sarcoma virus). Other transcription control regions include those derived from vertebrate genes such as actin, heat shock protein, bovine growth hormone and rabbit â-globin, as well as other sequences capable of controlling gene expression in eukaryotic cells. Additional suitable transcription control regions include tissue-specific promoters and enhancers as well as inducible promoters (e.g. promoters inducible tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Polynucleotide and nucleic acid coding regions of the present invention may be associated with additional coding regions which encode secretory or signal peptides, which direct the secretion of a polypeptide encoded by a polynucleotide of the present invention. For example, if secretion of the antigen binding molecule or polypeptide fragments thereof is desired, DNA encoding a signal sequence may be placed upstream of the nucleic acid encoding an antigen binding molecule of the invention or polypeptide fragments thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the translated polypeptide to produce a secreted or "mature" form of the polypeptide. In certain embodiments, the native signal peptide, e.g. an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

DNA encoding a short protein sequence that could be used to facilitate later purification (e.g. a histidine tag) or assist in labeling the fusion protein may be included within or at the ends of the polynucleotide encoding an antigen binding molecule of the invention or polypeptide fragments thereof.

In a further aspect of the invention, a host cell comprising one or more polynucleotides of the invention is provided. In certain embodiments a host cell comprising one or more vectors of the invention is provided. The polynucleotides and vectors may incorporate any of the features, singly or in combination, described herein in relation to polynucleotides and vectors, respectively. In one aspect, a host cell comprises (e.g. has been transformed or transfected with) a vector comprising a polynucleotide that encodes (part of) an antigen binding molecule of the invention of the invention.

As used herein, the term "host cell" refers to any kind of cellular system which can be engineered to generate the fusion proteins of the invention or fragments thereof. Host cells suitable for replicating and for supporting expression of antigen binding molecules are well known in the art. Such cells may be transfected or transduced as appropriate with the particular expression vector and large quantities of vector containing cells can be grown for seeding large scale fermenters to obtain sufficient quantities of the antigen binding molecule for clinical applications. Suitable host cells include prokaryotic microorganisms, such as *E. coli*, or various eukaryotic cells, such as Chinese hamster ovary cells (CHO), insect cells, or the like. For example, polypeptides may be produced in bacteria in particular when glycosylation is not needed. After expression, the polypeptide may be isolated from the bacterial cell paste in a soluble fraction and can be further purified. In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of a polypeptide with a partially or fully human glycosylation pattern. See Gerngross, Nat Biotech 22, 1409-1414 (2004), and Li et al., Nat Biotech 24, 210-215 (2006).

Suitable host cells for the expression of (glycosylated) polypeptides are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts. See e.g. U.S. Pat. Nos. 5,959,177, 6,040,498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells (as described, e.g., in Mather et al., Annals N.Y. Acad Sci 383, 44-68 (1982)), MRC 5 cells, and FS4 cells. Other useful mammalian host cell lines include Chinese hamster ovary (CHO) cells, including dhfr-CHO cells (Urlaub et al., Proc Natl Acad Sci USA 77, 4216 (1980)); and myeloma cell lines such as YO, NS0, P3X63 and Sp2/0. For a review of certain mammalian host cell lines suitable for protein production, see, e.g., Yazaki and Wu, Methods in Molecular Biology, Vol. 248 (B. K. C. Lo, ed., Humana Press, Totowa, N.J.), pp. 255-268 (2003). Host cells include cultured cells, e g, mammalian cultured cells, yeast cells, insect cells, bacterial cells and plant cells, to name only a few, but also cells comprised within a transgenic animal, transgenic plant or cultured plant or animal tissue. In one embodiment, the host cell is a eukaryotic cell, preferably a mammalian cell, such as a Chinese Hamster Ovary (CHO) cell, a human embryonic kidney (HEK) cell or a lymphoid cell (e.g., Y0, NS0, Sp20 cell). Standard technologies are known in the art to express foreign genes in these systems. Cells expressing a polypeptide comprising either the heavy or the light chain of an immunoglobulin, may be engineered so as to also express the other of the immunoglobulin chains such that the expressed product is an immunoglobulin that has both a heavy and a light chain.

In one aspect, a method of producing an antigen binding molecule of the invention or polypeptide fragments thereof is provided, wherein the method comprises culturing a host cell comprising polynucleotides encoding the antigen binding molecule of the invention or polypeptide fragments thereof, as provided herein, under conditions suitable for expression of the antigen binding molecule of the invention or polypeptide fragments thereof, and recovering the antigen binding molecule of the invention or polypeptide fragments thereof from the host cell (or host cell culture medium).

In the TNF family ligand trimer-containing antigen binding molecule of the invention, the components (at least one moiety capable of specific binding to TnC, one polypeptide comprising two ectodomains of a TNF ligand family member or fragments thereof and a polypeptide comprising one ectodomain of said TNF family ligand family member or a fragment thereof) are not genetically fused to each other. The polypeptides are designed such that its components (two ectodomains of a TNF ligand family member or fragments thereof and other components such as CH or CL) are fused to each other directly or through a linker sequence. The composition and length of the linker may be determined in accordance with methods well known in the art and may be tested for efficacy. Examples of linker sequences between different components of the antigen binding molecules of the invention are found in the sequences provided herein. Additional sequences may also be included to incorporate a cleavage site to separate the individual components of the fusion protein if desired, for example an endopeptidase recognition sequence.

In certain embodiments the moieties capable of specific binding to TnC (e.g. Fab fragments) forming part of the antigen binding molecule comprise at least an immunoglobulin variable region capable of binding to an antigen. Variable regions can form part of and be derived from naturally or non-naturally occurring antibodies and fragments thereof. Methods to produce polyclonal antibodies and monoclonal antibodies are well known in the art (see e.g. Harlow and Lane, “Antibodies, a laboratory manual”, Cold Spring Harbor Laboratory, 1988). Non-naturally occurring antibodies can be constructed using solid phase-peptide synthesis, can be produced recombinantly (e.g. as described in U.S. Pat. No. 4,186,567) or can be obtained, for example, by screening combinatorial libraries comprising variable heavy chains and variable light chains (see e.g., U.S. Pat. No. 5,969,108 to McCafferty).

Any animal species of immunoglobulin can be used in the invention. Non-limiting immunoglobulins useful in the present invention can be of murine, primate, or human origin. If the fusion protein is intended for human use, a chimeric form of immunoglobulin may be used wherein the constant regions of the immunoglobulin are from a human. A humanized or fully human form of the immunoglobulin can also be prepared in accordance with methods well known in the art (see e.g., U.S. Pat. No. 5,565,332 to Winter). Humanization may be achieved by various methods including, but not limited to (a) grafting the non-human (e.g., donor antibody) CDRs onto human (e.g., recipient antibody) framework and constant regions with or without retention of critical framework residues (e.g., those that are important for retaining good antigen binding affinity or antibody functions), (b) grafting only the non-human specificity-determining regions (SDRs or a-CDRs; the residues critical for the antibody-antigen interaction) onto human framework and constant regions, or (c) transplanting the entire non-human variable domains, but “cloaking” them with a human-like section by replacement of surface residues. Humanized antibodies and methods of making them are reviewed, e.g., in Almagro and Fransson, Front Biosci 13, 1619-1633 (2008), and are further described, e.g., in Riechmann et al., Nature 332, 323-329 (1988); Queen et al., Proc Natl Acad Sci USA 86, 10029-10033 (1989); U.S. Pat. Nos. 5,821,337, 7,527,791, 6,982,321, and 7,087,409; Jones et al., Nature 321, 522-525 (1986); Morrison et al., Proc Natl Acad Sci 81, 6851-6855 (1984); Morrison and Oi, Adv Immunol 44, 65-92 (1988); Verhoeyen et al., Science 239, 1534-1536 (1988); Padlan, Molec Immun 31(3), 169-217 (1994); Kashmiri et al., Methods 36, 25-34 (2005) (describing SDR (a-CDR) grafting); Padlan, Mol Immunol 28, 489-498 (1991) (describing “resurfacing”); Dall’Acqua et al., Methods 36, 43-60 (2005) (describing “FR shuffling”); and Osbourn et al., Methods 36, 61-68 (2005) and Klimka et al., Br J Cancer 83, 252-260 (2000) (describing the “guided selection” approach to FR shuffling). Particular immunoglobulins according to the invention are human immunoglobulins. Human antibodies and human variable regions can be produced using various techniques known in the art. Human antibodies are described generally in van Dijk and van de Winkel, Curr Opin Pharmacol 5, 368-74 (2001) and Lonberg, Curr Opin Immunol 20, 450-459 (2008). Human variable regions can form part of and be derived from human monoclonal antibodies made by the hybridoma method (see e.g. Monoclonal Antibody Production Techniques and Applications, pp. 51-63 (Marcel Dekker, Inc., New York, 1987)). Human antibodies and human variable regions may also be prepared by administering an immunogen to a transgenic animal that has been modified to produce intact human antibodies or intact antibodies with human variable regions in response to antigenic challenge (see e.g. Lonberg, Nat Biotech 23, 1117-1125 (2005). Human antibodies and human variable regions may also be generated by isolating Fv clone variable region sequences selected from human-derived phage display libraries (see e.g., Hoogenboom et al. in Methods in Molecular Biology 178, 1-37 (O’Brien et al., ed., Human Press, Totowa, N.J., 2001); and McCafferty et al., Nature 348, 552-554; Clackson et al., Nature 352, 624-628 (1991)). Phage typically display antibody fragments, either as single-chain Fv (scFv) fragments or as Fab fragments.

In certain aspects, the moieties capable of specific binding to a target cell antigen (e.g., Fab fragments) comprised in the antigen binding molecules of the present invention are engineered to have enhanced binding affinity according to, for example, the methods disclosed in PCT publication WO 2012/020006 or U.S. Pat. Appl. Publ. No. 2004/0132066. The ability of the antigen binding molecules of the invention to bind to a specific antigenic determinant can be measured either through an enzyme-linked immunosorbent assay (ELISA) or other techniques familiar to one of skill in the art, e.g., surface plasmon resonance technique (Liljeblad, et al., Glyco J 17, 323-329 (2000)), and traditional binding assays (Heeley, Endocr Res 28, 217-229 (2002)). Competition assays may be used to identify an antigen binding molecule that competes with a reference antibody for binding to a particular antigen. In certain embodiments, such a competing antigen binding molecule binds to the same epitope (e.g., a linear or a conformational epitope) that is bound by the reference antigen binding molecule. Detailed exemplary methods for mapping an epitope to which an antigen binding molecule binds are provided in Morris (1996) "Epitope Mapping Protocols", in Methods in Molecular Biology vol. 66 (Humana Press, Totowa, N.J.). In an exemplary competition assay, immobilized antigen is incubated in a solution comprising a first labeled antigen binding molecule that binds to the antigen and a second unlabeled antigen binding molecule that is being tested for its ability to compete with the first antigen binding molecule for binding to the antigen. The second antigen binding molecule may be present in a hybridoma supernatant. As a control, immobilized antigen is incubated in a solution comprising the first labeled antigen binding molecule but not the second unlabeled antigen binding molecule. After incubation under conditions permissive for binding of the first antibody to the antigen, excess unbound antibody is removed, and the amount of label associated with immobilized antigen is measured. If the amount of label associated with immobilized antigen is substantially reduced in the test sample relative to the control sample, then that indicates that the second antigen binding molecule is competing with the first antigen binding molecule for binding to the antigen. See Harlow and Lane (1988) Antibodies: A Laboratory Manual ch. 14 (Cold Spring Harbor Laboratory, Cold Spring Harbor, N.Y.).

Antigen binding molecules of the invention prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification an antibody, ligand, receptor or antigen can be used to which the antigen binding molecule binds. For example, for affinity chromatography purification of fusion proteins of the invention, a matrix with protein A or protein G may be used. Sequential Protein A or G affinity chromatography and size exclusion chromatography can be used to isolate an antigen binding molecule essentially as described in the Examples. The purity of the antigen binding molecule or fragments thereof can be determined by any of a variety of well-known analytical methods including gel electrophoresis, high pressure liquid chromatography, and the like. For example, the antigen binding molecules expressed as described in the Examples were shown to be intact and properly assembled as demonstrated by reducing and non-reducing SDS-PAGE.

Assays

The antigen binding molecules provided herein may be identified, screened for, or characterized for their physical/chemical properties and/or biological activities by various assays known in the art.

1. Affinity Assays

The affinity of the antigen binding molecule provided herein for TnC and/or for the corresponding TNF receptor can be determined in accordance with the methods set forth in the Examples by surface plasmon resonance (SPR), using standard instrumentation such as a BIAcore instrument (GE Healthcare), and receptors or target proteins such as may be obtained by recombinant expression. The affinity of the TNF family ligand trimer-containing antigen binding molecule for the target cell antigen can also be determined by surface plasmon resonance (SPR), using standard instrumentation such as a BIAcore instrument (GE Healthcare), and receptors or target proteins such as may be obtained by recombinant expression. A specific illustrative and exemplary embodiment for measuring binding affinity is described in Example 4. According to one aspect, $K_D$ is measured by surface plasmon resonance using a BIACORE® T100 machine (GE Healthcare) at 25° C.

2. Binding Assays and Other Assays

Binding of the TNF family ligand trimer-containing antigen binding molecule provided herein to the corresponding receptor expressing cells may be evaluated using cell lines expressing the particular receptor or target cell antigen, for example by flow cytometry (FACS). In one aspect, fresh peripheral blood mononuclear cells (PBMCs) expressing the TNF receptor are used in the binding assay. These cells are used directly after isolation (naïve PMBCs) or after stimulation (activated PMBCs). In another aspect, activated mouse splenocytes (expressing the TNF receptor molecule) were used to demonstrate the binding of the TNF family ligand trimer-containing antigen binding molecule of the invention to the corresponding TNF receptor expressing cells.

In a further aspect, cancer cell lines expressing TnC, were used to demonstrate the binding of the antigen binding molecules to the target cell antigen.

In another aspect, competition assays may be used to identify an antigen binding molecule that competes with a specific antibody or antigen binding molecule for binding to the target or TNF receptor, respectively. In certain embodiments, such a competing antigen binding molecule binds to the same epitope (e.g., a linear or a conformational epitope) that is bound by a specific anti-target antibody or a specific anti-TNF receptor antibody. Detailed exemplary methods for mapping an epitope to which an antibody binds are provided in Morris (1996) "Epitope Mapping Protocols," in Methods in Molecular Biology vol. 66 (Humana Press, Totowa, N.J.).

3. Activity Assays

In one aspect, assays are provided for identifying TNF family ligand trimer-containing antigen binding molecules that bind to a specific target cell antigen and to a specific TNF receptor having biological activity. Biological activity may include, e.g., agonistic signalling through the TNF receptor on cells expressing the target cell antigen. TNF family ligand trimer-containing antigen binding molecules identified by the assays as having such biological activity in vitro are also provided.

In certain aspects, a TNF family ligand trimer-containing antigen binding molecule of the invention is tested for such biological activity. Assays for detecting the biological activity of the molecules of the invention are those described in Example 12. Furthermore, assays for detecting cell lysis (e.g. by measurement of LDH release), induced apoptosis kinetics (e.g. by measurement of Caspase 3/7 activity) or apoptosis (e.g. using the TUNEL assay) are well known in the art. In addition the biological activity of such complexes can be assessed by evaluating their effects on survival, proliferation and lymphokine secretion of various lymphocyte subsets such as NK cells, NKT-cells or 145 T-cells or assessing their capacity to modulate phenotype and function of antigen presenting cells such as dendritic cells, monocytes/macrophages or B-cells.

Pharmaceutical Compositions, Formulations and Routes of Administration

In a further aspect, the invention provides pharmaceutical compositions comprising any of the antigen binding molecules provided herein, e.g., for use in any of the below therapeutic methods. In one embodiment, a pharmaceutical composition comprises any of the antigen binding molecules provided herein and at least one pharmaceutically acceptable excipient. In another embodiment, a pharmaceutical composition comprises any of the antigen binding molecules provided herein and at least one additional therapeutic agent, e.g., as described below.

Pharmaceutical compositions of the present invention comprise a therapeutically effective amount of one or more antigen binding molecules dissolved or dispersed in a pharmaceutically acceptable excipient. The phrases "pharmaceutical or pharmacologically acceptable" refers to molecular entities and compositions that are generally non-toxic to recipients at the dosages and concentrations employed, i.e., do not produce an adverse, allergic or other untoward reaction when administered to an animal, such as, for example, a human, as appropriate. The preparation of a pharmaceutical composition that contains at least one antigen binding molecule and optionally an additional active ingredient will be known to those of skill in the art in light of the present disclosure, as exemplified by Remington's Pharmaceutical Sciences, 18th Ed. Mack Printing Company, 1990, incorporated herein by reference. In particular, the compositions are lyophilized formulations or aqueous solutions. As used herein, "pharmaceutically acceptable excipient" includes any and all solvents, buffers, dispersion media, coatings, surfactants, antioxidants, preservatives (e.g., antibacterial agents, antifungal agents), isotonic agents, salts, stabilizers and combinations thereof, as would be known to one of ordinary skill in the art.

Parenteral compositions include those designed for administration by injection, e.g., subcutaneous, intradermal, intralesional, intravenous, intraarterial intramuscular, intrathecal or intraperitoneal injection. For injection, the antigen binding molecules of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Alternatively, the fusion proteins may be in powder form for constitution with a suitable vehicle, e.g., sterile pyrogen-free water, before use. Sterile injectable solutions are prepared by incorporating the fusion proteins of the invention in the required amount in the appropriate solvent with various of the other ingredients enumerated below, as required. Sterility may be readily accomplished, e.g., by filtration through sterile filtration membranes. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein. Suitable pharmaceutically acceptable excipients include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions. Additionally, suspensions of the active compounds may be prepared as appropriate oily injection suspensions. Suitable lipophilic solvents or vehicles include fatty oils such as sesame oil, or synthetic fatty acid esters, such as ethyl cleats or triglycerides, or liposomes.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (18th Ed. Mack Printing Company, 1990). Sustained-release preparations may be prepared. Suitable examples of sustained-release preparations include semipermeable matrices of solid hydrophobic polymers containing the polypeptide, which matrices are in the form of shaped articles, e.g. films, or microcapsules. In particular embodiments, prolonged absorption of an injectable composition can be brought about by the use in the compositions of agents delaying absorption, such as, for example, aluminum monostearate, gelatin or combinations thereof.

Exemplary pharmaceutically acceptable excipients herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

In addition to the compositions described previously, the fusion proteins may also be formulated as a depot preparation. Such long acting formulations may be administered by implantation (for example subcutaneously or intramuscularly) or by intramuscular injection. Thus, for example, the fusion proteins may be formulated with suitable polymeric or hydrophobic materials (for example as an emulsion in an acceptable oil) or ion exchange resins, or as sparingly soluble derivatives, for example, as a sparingly soluble salt.

Pharmaceutical compositions comprising the fusion proteins of the invention may be manufactured by means of conventional mixing, dissolving, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations that can be used pharmaceutically. Proper formulation is dependent upon the route of administration chosen.

The antigen binding molecules may be formulated into a composition in a free acid or base, neutral or salt form. Pharmaceutically acceptable salts are salts that substantially retain the biological activity of the free acid or base. These include the acid addition salts, e.g. those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Pharmaceutical salts tend to be more soluble in aqueous and other protic solvents than are the corresponding free base forms.

The composition herein may also contain more than one active ingredients as necessary for the particular indication being treated, preferably those with complementary activities that do not adversely affect each other. Such active ingredients are suitably present in combination in amounts that are effective for the purpose intended.

The formulations to be used for in vivo administration are generally sterile. Sterility may be readily accomplished, e.g., by filtration through sterile filtration membranes.

Therapeutic Methods and Compositions

Any of the antigen binding molecules provided herein may be used in therapeutic methods. For use in therapeutic methods, antigen binding molecules of the invention can be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

In one aspect, antigen binding molecules of the invention for use as a medicament are provided. In further aspects, antigen binding molecules of the invention for use in treating a disease, in particular for use in the treatment of cancer, are provided. In certain aspects, antigen binding molecules of the invention for use in a method of treatment are provided. In one aspect, the invention provides an antigen binding molecule as described herein for use in the treatment of a disease in an individual in need thereof. In certain aspects, the invention provides an antigen binding molecule for use in a method of treating an individual having a disease comprising administering to the individual a therapeutically effective amount of the fusion protein. In certain aspects, the disease to be treated is cancer. Examples of cancers include solid tumors, bladder cancer, renal cell carcinoma, brain cancer, head and neck cancer, pancreatic cancer, lung cancer, breast cancer, ovarian cancer, uterine cancer, cervical cancer, endometrial cancer, esophageal cancer, colon cancer, colorectal cancer, rectal cancer, gastric cancer, prostate cancer, blood cancer, skin cancer, squamous cell carcinoma, bone cancer, and kidney cancer, melanoma, B-cell lymphoma, B-cell leukemia, non-Hodgkin lymphoma and acute lymphoblastic leukemia. Thus, an antigen binding molecule as described herein for use in the treatment of cancer is provided. The subject, patient, or "individual" in need of treatment is typically a mammal, more specifically a human.

In another aspect, provided is an antigen binding molecule as described herein for use in the treatment of infectious diseases, in particular for the treatment of viral infections. In a further aspect, provided is an antigen binding molecule as described herein for use in the treatment of autoimmune diseases such as for example Lupus disease.

In one aspect, provided is an antigen binding molecule according to the invention for use in treating head and neck squamous cell carcinoma (HNSCC), breast cancer, colorectal cancer (CRC), pancreatic cancer (PAC), gastric cancer, non-small-cell lung carcinoma (NSCLC) and Mesothelioma, wherein the target cell antigen is TnC.

In a further aspect, the invention relates to the use of an antigen binding molecule in the manufacture or preparation of a medicament for the treatment of a disease in an individual in need thereof. In one aspect, the medicament is for use in a method of treating a disease comprising administering to an individual having the disease a therapeutically effective amount of the medicament. In certain embodiments the disease to be treated is a proliferative disorder, particularly cancer. Thus, in one aspect, the invention relates to the use of an antigen binding molecule of the invention in the manufacture or preparation of a medicament for the treatment of cancer. Examples of cancers include solid tumors, bladder cancer, renal cell carcinoma, brain cancer, head and neck cancer, pancreatic cancer, lung cancer, breast cancer, ovarian cancer, uterine cancer, cervical cancer, endometrial cancer, esophageal cancer, colon cancer, colorectal cancer, rectal cancer, gastric cancer, prostate cancer, blood cancer, skin cancer, squamous cell carcinoma, bone cancer, and kidney cancer, melanoma, B-cell lymphoma, B-cell leukemia, non-Hodgkin lymphoma and acute lymphoblastic leukemia. Other cell proliferation disorders that can be treated using an antigen binding molecule of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system. Also included are pre-cancerous conditions or lesions and cancer metastases. In certain embodiments the cancer is chosen from the group consisting of renal cell cancer, skin cancer, lung cancer, colorectal cancer, breast cancer, brain cancer, head and neck cancer. A skilled artisan may recognize that in some cases the antigen binding molecule may not provide a cure but may only provide partial benefit. In some aspects, a physiological change having some benefit is also considered therapeutically beneficial. Thus, in some aspects, an amount of antigen binding molecule that provides a physiological change is considered an "effective amount" or a "therapeutically effective amount".

In a further aspect, the invention relates to the use of an antigen binding molecule as described herein in the manufacture or preparation of a medicament for the treatment of infectious diseases, in particular for the treatment of viral infections or for the treatment of autoimmune diseases, for example Lupus disease.

In a further aspect, the invention provides a method for treating a disease in an individual, comprising administering to said individual a therapeutically effective amount of an antigen binding molecule of the invention. In one aspect a composition is administered to said individual, comprising a fusion protein of the invention in a pharmaceutically acceptable form. In certain aspects, the disease to be treated is a proliferative disorder. In a particular aspect, the disease is cancer. In another aspect, the disease is an infectious disease or an autoimmune disease. In certain aspects, the method further comprises administering to the individual a therapeutically effective amount of at least one additional therapeutic agent, e.g. an anti-cancer agent if the disease to be treated is cancer. An "individual" according to any of the above embodiments may be a mammal, preferably a human.

For the prevention or treatment of disease, the appropriate dosage of an antigen binding molecule of the invention (when used alone or in combination with one or more other additional therapeutic agents) will depend on the type of disease to be treated, the route of administration, the body weight of the patient, the type of fusion protein, the severity and course of the disease, whether the fusion protein is administered for preventive or therapeutic purposes, previous or concurrent therapeutic interventions, the patient's clinical history and response to the fusion protein, and the discretion of the attending physician. The practitioner responsible for administration will, in any event, determine the concentration of active ingredient(s) in a composition and appropriate dose(s) for the individual subject. Various dosing schedules including but not limited to single or multiple administrations over various time-points, bolus administration, and pulse infusion are contemplated herein.

The antigen binding molecule is suitably administered to the patient at one time or over a series of treatments. Depending on the type and severity of the disease, about 1 μg/kg to 15 mg/kg (e.g., 0.1 mg/kg-10 mg/kg) of antigen binding molecule can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the antigen binding molecule would be in the range from about 0.005 mg/kg to about 10 mg/kg. In other examples, a dose may also comprise from about 1 μg/kg body weight, about 5 μg/kg body weight, about 10 μg/kg body weight, about 50 μg/kg body weight, about 100 μg/kg body weight, about 200 μg/kg body weight, about 350 μg/kg body weight, about 500 μg/kg body weight, about 1 mg/kg body weight, about 5 mg/kg body weight, about 10 mg/kg body weight, about 50 mg/kg body weight, about 100 mg/kg body weight, about 200 mg/kg body weight, about 350 mg/kg body weight, about 500 mg/kg body weight, to about 1000 mg/kg body weight or more per administration, and any range derivable therein. In examples of a derivable range from the numbers listed herein, a range of about 5 mg/kg body weight to about 100 mg/kg body weight, about 5 μg/kg body weight to about 500 mg/kg body weight etc., can be administered, based on the numbers described above. Thus, one or more doses of about 0.5 mg/kg, 2.0 mg/kg, 5.0 mg/kg or 10 mg/kg (or any combination thereof) may be administered to the patient. Such doses may be administered intermittently, e.g., every week or every three weeks (e.g., such that the patient receives from about two to about twenty, or e.g., about six doses of the fusion protein). An initial higher loading dose, followed by one or more lower doses may be administered. However, other dosage regimens may be useful. The progress of this therapy is easily monitored by conventional techniques and assays.

The antigen binding molecules of the invention will generally be used in an amount effective to achieve the intended purpose. For use to treat or prevent a disease condition, the antigen binding molecules of the invention, or pharmaceutical compositions thereof, are administered or applied in a therapeutically effective amount. Determination of a therapeutically effective amount is well within the capabilities of those skilled in the art, especially in light of the detailed disclosure provided herein.

For systemic administration, a therapeutically effective dose can be estimated initially from in vitro assays, such as cell culture assays. A dose can then be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the antigen binding molecules which are sufficient to maintain therapeutic effect. Usual patient dosages for administration by injection range from about 0.1 to 50 mg/kg/day, typically from about 0.5 to 1 mg/kg/day. Therapeutically effective plasma levels may be achieved by administering multiple doses each day. Levels in plasma may be measured, for example, by HPLC.

In cases of local administration or selective uptake, the effective local concentration of the antigen binding molecule may not be related to plasma concentration. One skilled in the art will be able to optimize therapeutically effective local dosages without undue experimentation.

A therapeutically effective dose of the antigen binding molecules described herein will generally provide therapeutic benefit without causing substantial toxicity. Toxicity and therapeutic efficacy of a fusion protein can be determined by standard pharmaceutical procedures in cell culture or experimental animals. Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. Antigen binding molecules that exhibit large therapeutic indices are preferred. In one embodiment, the antigen binding molecule according to the present invention exhibits a high therapeutic index. The data obtained from cell culture assays and animal studies can be used in formulating a range of dosages suitable for use in humans. The dosage lies preferably within a range of circulating concentrations that include the $ED_{50}$ with little or no toxicity. The dosage may vary within this range depending upon a variety of factors, e.g., the dosage form employed, the route of administration utilized, the condition of the subject, and the like. The exact formulation, route of administration and dosage can be chosen by the individual physician in view of the patient's condition (see, e.g., Fingl et al., 1975, in: The Pharmacological Basis of Therapeutics, Ch. 1, p. 1, incorporated herein by reference in its entirety).

The attending physician for patients treated with fusion proteins of the invention would know how and when to terminate, interrupt, or adjust administration due to toxicity, organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

Other Agents and Treatments

The antigen binding molecules of the invention may be administered in combination with one or more other agents in therapy. For instance, a fusion protein of the invention may be co-administered with at least one additional therapeutic agent. The term "therapeutic agent" encompasses any agent that can be administered for treating a symptom or disease in an individual in need of such treatment. Such additional therapeutic agent may comprise any active ingredients suitable for the particular indication being treated, preferably those with complementary activities that do not adversely affect each other. In certain embodiments, an additional therapeutic agent is another anti-cancer agent.

Such other agents are suitably present in combination in amounts that are effective for the purpose intended. The effective amount of such other agents depends on the amount of fusion protein used, the type of disorder or treatment, and other factors discussed above. The antigen binding molecules of the invention are generally used in the same dosages and with administration routes as described herein, or about from 1 to 99% of the dosages described herein, or in any dosage and by any route that is empirically/clinically determined to be appropriate.

Such combination therapies noted above encompass combined administration (where two or more therapeutic agents are included in the same or separate compositions), and separate administration, in which case, administration of the antigen binding molecule of the invention can occur prior to, simultaneously, and/or following, administration of the additional therapeutic agent and/or adjuvant.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper that is pierceable by a hypodermic injection needle). At least one active agent in the composition is an antigen binding molecule of the invention.

The label or package insert indicates that the composition is used for treating the condition of choice. Moreover, the article of manufacture may comprise (a) a first container with a composition contained therein, wherein the composition comprises an antigen binding molecule of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition.

Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

TABLE C (Sequences):

| SEQ ID NO: | Name | Sequence |
|---|---|---|
| 1 | Nucleotide sequence huTNC | Table 3 |
| 2 | Nucleotide sequence muTNC | Table 3 |
| 3 | Nucleotide sequence cynoTNC | Table 3 |
| 4 | huTNC | Table 3 |
| 5 | muTNC | Table 3 |
| 6 | cynoTNC | Table 3 |
| 7 | GST huTNC fn5 A1234 BC fn6 B | Table 4 |
| 8 | GST huTNCfn5 mu A124 BC hu fn6 B | Table 4 |
| 9 | GST TNC hu fn5 B-C fn6 B | Table 4 |
| 10 | GST huTNC fn5 A1234 fn6 B | Table 4 |
| 11 | huTNC A4 B | Table 4 |
| 12 | huTNC A1 B | Table 4 |

TABLE C-continued

| (Sequences): | | |
|---|---|---|
| SEQ ID NO: | Name | Sequence |
| 13 | Nucleotide sequence pRJH33 library template DP88-4 library | Table 6 |
| 14 | Nucleotide sequence Fab light chain V1_5 | Table 7 |
| 15 | Nucleotide sequence Fab heavy chain VH1_69 | Table 7 |
| 16 | Fab light chain Vk1_5 | Table 8 |
| 17 | Fab heavy chain VH1_69 (DP88) | Table 8 |
| 18 | Nucleotide sequence LMB3 | Table 9 |
| 19 | Nucleotide sequence Vk1_5_L3r_S | Table 9 |
| 20 | Nucleotide sequence Vk1_5_L3r_SY | Table 9 |
| 21 | Nucleotide sequence Vk1_5_L3r_SPY | Table 9 |
| 22 | Nucleotide sequence RJH31 | Table 9 |
| 23 | Nucleotide sequence RJH32 | Table 9 |
| 24 | Nucleotide sequence DP88-v4-4 | Table 9 |
| 25 | Nucleotide sequence DP88-v4-6 | Table 9 |
| 26 | Nucleotide sequence DP88-v4-8 | Table 9 |
| 27 | Nucleotide sequence fdseqlong | Table 9 |
| 28 | Nucleotide sequence pRJH53 library template of lambda-DP47 library Vl3_19/VH3_23 | Table 10 |
| 29 | Nucleotide sequence Fab light chain Vl3_19 | Table 11 |
| 30 | Nucleotide sequence Fab heavy chain VH3_23 | Table 11 |
| 31 | Fab light chain Vl3_19 | Table 12 |
| 32 | Fab heavy chain VH3_23 (DP47) | Table 12 |
| 33 | Nucleotide sequence Vl_3_19_L3r_V | Table 13 |
| 34 | Nucleotide sequence Vl_3_19_L3r_HV | Table 13 |
| 35 | Nucleotide sequence Vl_3_19_L3r_HLV | Table 13 |
| 36 | Nucleotide sequence RJH80 | Table 13 |
| 37 | Nucleotide sequence DP47CDR3_ba (mod.) | Table 13 |
| 38 | Nucleotide sequence DP47-v4-4 | Table 13 |

TABLE C-continued

| (Sequences): | | |
|---|---|---|
| SEQ ID NO: | Name | Sequence |
| 39 | Nucleotide sequence DP47-v4-6 | Table 13 |
| 40 | Nucleotide sequence DP47-v4-8 | Table 13 |
| 41 | Nucleotide sequence 18D4 VL | Table 14 |
| 42 | Nucleotide sequence 18D4 VH | Table 14 |
| 43 | Nucleotide sequence 11C7 VL | Table 14 |
| 44 | Nucleotide sequence 11C7 VH | Table 14 |
| 45 | 18D4 VL | Table 15 |
| 46 | 18D4 VH | Table 15 |
| 47 | 11C7 VL | Table 15 |
| 48 | 11C7 VH | Table 15 |
| 49 | Nucleotide sequence 18D4 LCDR1 | Table 16 |
| 50 | Nucleotide sequence 18D4 LCDR2 | Table 16 |
| 51 | Nucleotide sequence 18D4 LCDR3 | Table 16 |
| 52 | Nucleotide sequence 11C7 LCDR1 | Table 16 |
| 53 | Nucleotide sequence 11C7 LCDR2 | Table 16 |
| 54 | Nucleotide sequence 11C7 LCDR3 | Table 16 |
| 55 | 18D4 LCDR1 | Table 17 |
| 56 | 18D4 LCDR2 | Table 17 |
| 57 | 18D4 LCDR3 | Table 17 |
| 58 | 11C7 LCDR1 | Table 17 |
| 59 | 11C7 LCDR2 | Table 17 |
| 60 | 11C7 LCDR3 | Table 17 |
| 61 | Nucleotide sequence 18D4 HCDR1 | Table 18 |
| 62 | Nucleotide sequence 18D4 HCDR2 | Table 18 |
| 63 | Nucleotide sequence 18D4 HCDR3 | Table 18 |
| 64 | Nucleotide sequence 11C7 HCDR1 | Table 18 |
| 65 | Nucleotide sequence 11C7 HCDR2 | Table 18 |
| 66 | Nucleotide sequence 11C7 HCDR3 | Table 18 |

TABLE C-continued

| (Sequences): | | |
|---|---|---|
| SEQ ID NO: | Name | Sequence |
| 67 | 18D4 HCDR1 | Table 19 |
| 68 | 18D4 HCDR2 | Table 19 |
| 69 | 18D4 HCDR3 | Table 19 |
| 70 | 11C7 HCDR1 | Table 19 |
| 71 | 11C7 HCDR2 | Table 19 |
| 72 | 11C7 HCDR3 | Table 19 |
| 73 | Nucleotide sequence 18D4 Light chain | Table 20 |
| 74 | Nucleotide sequence 18D4 Heavy chain | Table 20 |
| 75 | Nucleotide sequence 11C7 Light chain | Table 20 |
| 76 | Nucleotide sequence 11C7 Heavy chain | Table 20 |
| 77 | 18D4 Light chain | Table 21 |
| 78 | 18D4 Heavy chain | Table 21 |
| 79 | 11C7 Light chain | Table 21 |
| 80 | 11C7 Heavy chain | Table 21 |
| 81 | Nucleotide sequence 18D4 Heavy chain PGLALA | Table 22 |
| 82 | Nucleotide sequence 11C7 Heavy chain PGLALA | Table 22 |
| 83 | 18D4 Heavy chain PGLALA | Table 23 |
| 84 | 11C7 Heavy chain PGLALA | Table 23 |
| 85 | Human 4-1BB Fc(kih) | Table 27 |
| 86 | Cynomolgus 4-1BB Fc(kih) | Table 27 |
| 87 | Murine 4-1BB Fc(kih) | Table 27 |
| 88 | nucleotide sequence Fc hole chain | Table 28 |
| 89 | nucleotide sequence Human 4-1BB Fc(kih) | Table 28 |
| 90 | nucleotide sequence Cynomolgus 4-1BB Fc(kih) | Table 28 |
| 91 | nucleotide sequence Murine 4-1BB Fc(kih) | Table 28 |
| 92 | Fc hole chain | Table 28 |
| 93 | human 4-1BB antigen Fc knob chain | Table 28 |
| 94 | Cynomolgus 4-1BB Fc(kih) | Table 28 |
| 95 | Murine 4-1BB Fc(kih) | Table 28 |
| 96 | nucleotide sequence Human 4-1BB His | Table 29 |

TABLE C-continued (Sequences):

| SEQ ID NO: | Name | Sequence |
|---|---|---|
| 97 | Human 4-1BB His | Table 29 |
| 98 | Nucleotide sequence dimeric ligand (71-254)-CL* Fc knob chain | Table 30 |
| 99 | Nucleotide sequence monomeric ligand (71-254)-CH1* | Table 30 |
| 100 | Nucleotide sequence anti-TnC(18D4) Fc hole chain | Table 30 |
| 101 | Randomized sequence 1 | NNNNNNNNNN |
| 102 | Dimeric ligand (71-254)-CL* Fc knob chain | Table 31 |
| 103 | Monomeric ligand (71-254)-CH1* | Table 31 |
| 104 | anti-TnC(18D4) Fc hole chain | Table 31 |
| 105 | Randomized sequence 2 | NNNNNNNNNNN |
| 106 | Nucleotide sequence dimeric ligand (71-254)-CL Fc knob chain | Table 32 |
| 107 | Nucleotide sequence monomeric ligand (71-254)-CH1 | Table 32 |
| 108 | Dimeric ligand (71-254)-CL Fc knob chain | Table 33 |
| 109 | Monomeric ligand (71-254)-CH1 | Table 33 |
| 110 | Nucleotide sequence anti-TnC(18D4) Fc hole dimeric ligand (71-254) chain | Table 34 |
| 111 | Nucleotide sequence anti-TnC(18D4) Fc knob monomeric ligand (71-254) chain | Table 34 |
| 112 | anti-TnC(18D4) Fc hole dimeric ligand (71-254) chain | Table 35 |
| 113 | anti-TnC(18D4) Fc knob monomeric ligand (71-254) chain | Table 35 |
| 114 | Nucleotide sequence dimeric ligand (71-248)-CL* Fc knob chain | Table 36 |
| 115 | Nuceotide sequence monomeric ligand (71-248)-CH1* | Table 36 |
| 116 | Dimeric ligand (71-248)-CL* Fc knob chain | Table 37 |
| 117 | Monomeric ligand (71-248)-CH1* | Table 37 |
| 118 | Nucleotide sequence dimeric ligand (71-248)-CL Fc knob chain | Table 38 |

TABLE C-continued (Sequences):

| SEQ ID NO: | Name | Sequence |
|---|---|---|
| 119 | Nucleotide sequence monomeric ligand (71-248)-CH1 | Table 38 |
| 120 | Dimeric ligand (71-248)-CL Fc knob chain | Table 39 |
| 121 | Monomeric ligand (71-248)-CH1 | Table 39 |
| 122 | Nucleotide sequence anti-TnC(18D4) Fc hole dimeric ligand (71-248) chain | Table 40 |
| 123 | Nucleotide sequence anti-TnC(18D4) Fc knob monomeric (71-248) ligand | Table 40 |
| 124 | anti-TnC(18D4) Fc hole dimeric ligand (71-248) chain | Table 41 |
| 125 | anti-TnC(18D4) Fc knob monomeric (71-248) ligand | Table 41 |
| 126 | Nucleotide sequence Fc hole dimeric ligand (71-248) chain | Table 42 |
| 127 | Fc hole dimeric ligand (71-248) chain | Table 43 |
| 128 | Nucleotide sequence Fc hole monomeric ligand (71-248) chain | Table 44 |
| 129 | Nucleotide sequence anti-TnC(18D4) Fc knob dimeric ligand (71-248) chain | Table 44 |
| 130 | Fc hole monomeric ligand (71-248) chain | Table 45 |
| 131 | anti-TnC(18D4) Fc knob dimeric ligand (71-248) chain | Table 45 |
| 132 | Nucleotide sequence Fc knob monomeric ligand (71-248) chain | Table 46 |
| 133 | Fc knob monomeric ligand (71-248) chain | Table 47 |
| 134 | Nucleotide sequence anti-TnC(18D4) Fc hole monomeric ligand (71-248) chain | Table 48 |
| 135 | Nucleotide sequence Fc knob dimeric ligand (71-248) chain | Table 48 |
| 136 | anti-TnC(18D4) Fc hole monomeric ligand (71-248) chain | Table 49 |
| 137 | Fc knob dimeric ligand (71-248) chain | Table 49 |
| 138 | nucleotide sequence DP47 Fc-hole chain | Table 50 |

TABLE C-continued (Sequences):

| SEQ ID NO: | Name | Sequence |
|---|---|---|
| 139 | nucleotide sequence DP47 light chain | Table 50 |
| 140 | DP47 Fc-hole chain | Table 50 |
| 141 | DP47 light chain | Table 50 |
| 142 | nucleotide sequence DP47 Fc hole chain fused to dimeric hu 4-1BBL (71-254) | Table 51 |
| 143 | nucleotide sequence DP47 Fc knob chain fused to monomeric hu 4-1BBL (71-254) | Table 51 |
| 144 | DP47 Fc hole chain fused to dimeric hu 4-1BBL (71-254) | Table 51 |
| 145 | DP47 Fc knob chain fused to monomeric hu 4-1BBL (71-254) | Table 51 |
| 146 | nucleotide sequence DP47 heavy chain (hu IgG1 PGLALA) | Table 54 |
| 147 | DP47 heavy chain (hu IgG1 PGLALA) | Table 54 |
| 148 | nucleotide sequence anti-TnC(18D4) heavy chain (huIgG1 PGLALA) | Table 55 |
| 149 | anti-TnC(18D4) heavy chain (huIgG1 PGLALA) | Table 55 |
| 150 | Peptide linker $(G4S)_2$ | GGGGSGGGGS |
| 151 | Peptide linker $(SG4)_2$ | SGGGGSGGGG |
| 152 | Peptide linker $G4(SG4)_2$ | GGGGSGGGGSGGGG |
| 153 | Peptide linker 1 | GSPGSSSSGS |
| 154 | Peptide linker $(G4S)_4$ | GGGGSGGGGSGGGGSGGGGS |
| 155 | Peptide linker 2 | GSGSGNGS |
| 156 | Peptide linker 3 | GGSGSGSG |
| 157 | Peptide linker 4 | GGSGSG |
| 158 | Peptide linker 5 | GGSG |
| 159 | Peptide linker 6 | GGSGNGSG |
| 160 | Peptide linker 7 | GGNGSGSG |
| 161 | Peptide linker 8 | GGNGSG |
| 162 | Peptide linker 9 | GGGGS |
| 163 | Leader Sequence 1 | MDWTWRILFLVAAATGAHS |
| 164 | Leader Sequence 1 (DNA1) | ATGGACTGGACCTGGAGAATCCTCTTCTTGGT GGCAGCAGCCACAGGAGCCCACTCC |
| 165 | Leader Sequence 1 (DNA2) | ATGGACTGGACCTGGAGGATCCTCTTCTTGGT GGCAGCAGCCACAGGAGCCCACTCC |
| 166 | Leader Sequence 2 | MDMRVPAQLLGLLLLWFPGA |

TABLE C-continued (Sequences):

| SEQ ID NO: | Name | Sequence |
|---|---|---|
| 167 | Leader Sequence 2 (DNA) | ATGGACATGAGGGTCCCCGCTCAGCTCCTGGG CCTCCTGCTGCTCTGGTTCCCAGGTGCCAGGT GT |
| 168 | Leader Sequence 3 | MGWSCIILFLVATATGVHS |
| 169 | Leader Sequence 3 (DNA 1) | ATGGGATGGAGCTGTATCATCCTCTTCTTGGT AGCAACAGCTACCGGTGTGCATTCG |
| 170 | Leader Sequence 3 (DNA 2) | ATGGGCTGGTCCTGCATCATCCTGTTTCTGGTG GCTACCGCCACTGGAGTGCATTCC |
| 171 | Leader Sequence 3 (DNA 3) | ATGGGCTGGTCCTGCATCATCCTGTTTCTGGTC GCCACAGCCACCGGCGTGCACTCT |
| 172 | Human (hu) 4-1BBL (71-254) | REGPELSPDDPAGLLDLRQGMFAQLVAQNVLLI DGPLSWYSDPGLAGVSLTGGLSYKEDTKELVVA KAGVYYVFFQLELRRVVAGEGSGSVSLALHLQP LRSAAGAAALALTVDLPPASSEARNSAFGFQGR LLHLSAGQRLGVHLHTEARARHAWQLTQGATV LGLFRVTPEIPAGLPSPRSE |
| 173 | hu 4-1BBL (85-254) | LDLRQGMFAQLVAQNVLLIDGPLSWYSDPGLA GVSLTGGLSYKEDTKELVVAKAGVYYVFFQLEL RRVVAGEGSGSVSLALHLQPLRSAAGAAALALT VDLPPASSEARNSAFGFQGRLLHLSAGQRLGVH LHTEARARHAWQLTQGATVLGLFRVTPEIPAGL PSPRSE |
| 174 | hu 4-1BBL (80-254) | DPAGLLDLRQGMFAQLVAQNVLLIDGPLSWYS DPGLAGVSLTGGLSYKEDTKELVVAKAGVYYV FFQLELRRVVAGEGSGSVSLALHLQPLRSAAGA AALALTVDLPPASSEARNSAFGFQGRLLHLSAG QRLGVHLHTEARARHAWQLTQGATVLGLFRVT PEIPAGLPSPRSE |
| 175 | hu 4-1BBL (52-254) | PWAVSGARASPGSAASPRLREGPELSPDDPAGLL DLRQGMFAQLVAQNVLLIDGPLSWYSDPGLAG VSLTGGLSYKEDTKELVVAKAGVYYVFFQLELR RVVAGEGSGSVSLALHLQPLRSAAGAAALALTV DLPPASSEARNSAFGFQGRLLHLSAGQRLGVHL HTEARARHAWQLTQGATVLGLFRVTPEIPAGLP SPRSE |
| 176 | dimeric hu 4-1BBL (71-254) connected by $(G4S)_2$ (SEQ ID NO: 150) linker | REGPELSPDDPAGLLDLRQGMFAQLVAQNVLLI DGPLSWYSDPGLAGVSLTGGLSYKEDTKELVVA KAGVYYVFFQLELRRVVAGEGSGSVSLALHLQP LRSAAGAAALALTVDLPPASSEARNSAFGFQGR LLHLSAGQRLGVHLHTEARARHAWQLTQGATV LGLFRVTPEIPAGLPSPRSEGGGGSGGGGSREGP ELSPDDPAGLLDLRQGMFAQLVAQNVLLIDGPL SWYSDPGLAGVSLTGGLSYKEDTKELVVAKAG VYYVFFQLELRRVVAGEGSGSVSLALHLQPLRS AAGAAALALTVDLPPASSEARNSAFGFQGRLLH LSAGQRLGVHLHTEARARHAWQLTQGATVLGL FRVTPEIPAGLPSPRSE |
| 177 | monomeric hu 4-1BBL (71-254) plus $(G4S)_2$ (SEQ ID NO: 150) linker | REGPELSPDDPAGLLDLRQGMFAQLVAQNVLLI DGPLSWYSDPGLAGVSLTGGLSYKEDTKELVVA KAGVYYVFFQLELRRVVAGEGSGSVSLALHLQP LRSAAGAAALALTVDLPPASSEARNSAFGFQGR LLHLSAGQRLGVHLHTEARARHAWQLTQGATV LGLFRVTPEIPAGLPSPRSEGGGGSGGGGS |
| 178 | dimeric hu 4-1BBL (71-254)-CH1 Fc knob chain | REGPELSPDDPAGLLDLRQGMFAQLVAQNVLLI DGPLSWYSDPGLAGVSLTGGLSYKEDTKELVVA KAGVYYVFFQLELRRVVAGEGSGSVSLALHLQP LRSAAGAAALALTVDLPPASSEARNSAFGFQGR LLHLSAGQRLGVHLHTEARARHAWQLTQGATV LGLFRVTPEIPAGLPSPRSEGGGGSGGGGSREGP ELSPDDPAGLLDLRQGMFAQLVAQNVLLIDGPL SWYSDPGLAGVSLTGGLSYKEDTKELVVAKAG VYYVFFQLELRRVVAGEGSGSVSLALHLQPLRS AAGAAALALTVDLPPASSEARNSAFGFQGRLLH |

TABLE C-continued (Sequences):

| SEQ ID NO: | Name | Sequence |
|---|---|---|
| | | LSAGQRLGVHLHTEARARHAWQLTQGATVLGL FRVTPEIPAGLPSPRSEGGGGSGGGGSASTKGPS VFPLAPSSKSTSGGTAALGCLVKDYFPEPVTVSW NSGALTSGVHTFPAVLQSSGLYSLSSVVTVPSSS LGTQTYICNVNHKPSNTKVDKKVEPKSCDKTHT CPPCPAPEAAGGPSVFLFPPKPKDTLMISRTPEVT CVVVDVSHEDPEVKFNWYVDGVEVHNAKTKPR EEQYNSTYRVVSVLTVLHQDWLNGKEYKCKVS NKALGAPIEKTISKAKGQPREPQVYTLPPCRDEL TKNQVSLWCLVKGFYPSDIAVEWESNGQPENN YKTTPPVLDSDGSFFLYSKLTVDKSRWQQGNVF SCSVMHEALHNHYTQKSLSLSPGK |
| 179 | monomeric hu 4-1BBL (71-254)-CL | REGPELSPDDPAGLLDLRQGMFAQLVAQNVLLI DGPLSWYSDPGLAGVSLTGGLSYKEDTKELVVA KAGVYYVFFQLELRRVVAGEGSGSVSLALHLQP LRSAAGAAALALTVDLPPASSEARNSAFGFQGR LLHLSAGQRLGVHLHTEARARHAWQLTQGATV LGLFRVTPEIPAGLPSPRSEGGGGSGGGGSRTVA APSVFIFPPSDEQLKSGTASVVCLLNNFYPREAK VQWKVDNALQSGNSQESVTEQDSKDSTYSLSST LTLSKADYEKHKVYACEVTHQGLSSPVTKSFNR GEC |
| 180 | hu 4-1BBL (50-254) | ACPWAVSGARASPGSAASPRLREGPELSPDDPA GLLDLRQGMFAQLVAQNVLLIDGPLSWYSDPGL AGVSLTGGLSYKEDTKELVVAKAGVYYVFFQL ELRRVVAGEGSGSVSLALHLQPLRSAAGAAALA LTVDLPPASSEARNSAFGFQGRLLHLSAGQRLG VHLHTEARARHAWQLTQGATVLGLFRVTPEIPA GLPSPRSE |
| 181 | hu OX40L (51-183) | QVSHRYPRIQSIKVQFTEYKKEKGFILTSQKEDEI MKVQNNSVIINCDGFYLISLKGYFSQEVNISLHY QKDEEPLFQLKKVRSVNSLMVASLTYKDKVYL NVTTDNTSLDDFHVNGGELILIHQNPGEFCVL |
| 182 | hu OX40L (52-183) | VSHRYPRIQSIKVQFTEYKKEKGFILTSQKEDEIM KVQNNSVIINCDGFYLISLKGYFSQEVNISLHYQ KDEEPLFQLKKVRSVNSLMVASLTYKDKVYLN VTTDNTSLDDFHVNGGELILIHQNPGEFCVL |
| 183 | Human (hu) 4-1BBL (71-248) | REGPELSPDDPAGLLDLRQGMFAQLVAQNVLLI DGPLSWYSDPGLAGVSLTGGLSYKEDTKELVVA KAGVYYVFFQLELRRVVAGEGSGSVSLALHLQP LRSAAGAAALALTVDLPPASSEARNSAFGFQGR LLHLSAGQRLGVHLHTEARARHAWQLTQGATV LGLFRVTPEIPAGL |
| 184 | dimeric hu 4-1BBL (71-248) connected by $(G4S)_2$ (SEQ ID NO: 150) linker | REGPELSPDDPAGLLDLRQGMFAQLVAQNVLLI DGPLSWYSDPGLAGVSLTGGLSYKEDTKELVVA KAGVYYVFFQLELRRVVAGEGSGSVSLALHLQP LRSAAGAAALALTVDLPPASSEARNSAFGFQGR LLHLSAGQRLGVHLHTEARARHAWQLTQGATV LGLFRVTPEIPAGLGGGGSGGGGSREGPELSPDD PAGLLDLRQGMFAQLVAQNVLLIDGPLSWYSDP GLAGVSLTGGLSYKEDTKELVVAKAGVYYVFF QLELRRVVAGEGSGSVSLALHLQPLRSAAGAAA LALTVDLPPASSEARNSAFGFQGRLLHLSAGQRL GVHLHTEARARHAWQLTQGATVLGLFRVTPEIP AGL |
| 185 | dimeric hu 4-1BBL (80-254) connected by $(G4S)_2$ (SEQ ID NO: 150) linker | DPAGLLDLRQGMFAQLVAQNVLLIDGPLSWYS DPGLAGVSLTGGLSYKEDTKELVVAKAGVYYV FFQLELRRVVAGEGSGSVSLALHLQPLRSAAGA AALALTVDLPPASSEARNSAFGFQGRLLHLSAG QRLGVHLHTEARARHAWQLTQGATVLGLFRVT PEIPAGLPSPRSEGGGGSGGGGSDPAGLLDLRQG MFAQLVAQNVLLIDGPLSWYSDPGLAGVSLTGG LSYKEDTKELVVAKAGVYYVFFQLELRRVVAG EGSGSVSLALHLQPLRSAAGAAALALTVDLPPA SSEARNSAFGFQGRLLHLSAGQRLGVHLHTEAR ARHAWQLTQGATVLGLFRVTPEIPAGLPSPRSE |

TABLE C-continued

| SEQ ID NO: | Name | Sequence |
|---|---|---|
| 186 | dimeric hu 4-1BBL (52-254) connected by $(G4S)_2$ (SEQ ID NO: 150) linker | PWAVSGARASPGSAASPRLREGPELSPDDPAGLL DLRQGMFAQLVAQNVLLIDGPLSWYSDPGLAG VSLTGGLSYKEDTKELVVAKAGVYYVFFQLELR RVVAGEGSGSVSLALHLQPLRSAAGAAALALTV DLPPASSEARNSAFGFQGRLLHLSAGQRLGVHL HTEARARHAWQLTQGATVLGLFRVTPEIPAGLP SPRSEGGGGSGGGGSPWAVSGARASPGSAASPR LREGPELSPDDPAGLLDLRQGMFAQLVAQNVLL IDGPLSWYSDPGLAGVSLTGGLSYKEDTKELVV AKAGVYYVFFQLELRRVVAGEGSGSVSLALHLQ PLRSAAGAAALALTVDLPPASSEARNSAFGFQG RLLHLSAGQRLGVHLHTEARARHAWQLTQGAT VLGLFRVTPEIPAGLPSPRSE |
| 187 | monomeric hu 4-1BBL (71-254) plus $(G4S)_1$ (SEQ ID NO: 162) linker | REGPELSPDDPAGLLDLRQGMFAQLVAQNVLLI DGPLSWYSDPGLAGVSLTGGLSYKEDTKELVVA KAGVYYVFFQLELRRVVAGEGSGSVSLALHLQP LRSAAGAAALALTVDLPPASSEARNSAFGFQGR LLHLSAGQRLGVHLHTEARARHAWQLTQGATV LGLFRVTPEIPAGLPSPRSEGGGGS |
| 188 | monomeric hu 4-1BBL (71-248) plus $(G4S)_2$ (SEQ ID NO: 150) linker | REGPELSPDDPAGLLDLRQGMFAQLVAQNVLLI DGPLSWYSDPGLAGVSLTGGLSYKEDTKELVVA KAGVYYVFFQLELRRVVAGEGSGSVSLALHLQP LRSAAGAAALALTVDLPPASSEARNSAFGFQGR LLHLSAGQRLGVHLHTEARARHAWQLTQGATV LGLFRVTPEIPAGLGGGGSGGGGS |
| 189 | monomeric hu 4-1BBL (71-248) plus $(G4S)_1$ (SEQ ID NO: 162) linker | REGPELSPDDPAGLLDLRQGMFAQLVAQNVLLI DGPLSWYSDPGLAGVSLTGGLSYKEDTKELVVA KAGVYYVFFQLELRRVVAGEGSGSVSLALHLQP LRSAAGAAALALTVDLPPASSEARNSAFGFQGR LLHLSAGQRLGVHLHTEARARHAWQLTQGATV LGLFRVTPEIPAGLGGGGS |
| 190 | dimeric huOX40L (51-183) connected by $(G4S)_2$ (SEQ ID NO: 150) linker | QVSHRYPRIQSIKVQFTEYKKEKGFILTSQKEDEI MKVQNNSVIINCDGFYLISLKGYFSQEVNISLHY QKDEEPLFQLKKVRSVNSLMVASLTYKDKVYL NVTTDNTSLDDFHVNGGELILIHQNPGEFCVLGG GGSGGGGSQVSHRYPRIQSIKVQFTEYKKEKGFI LTSQKEDEIMKVQNNSVIINCDGFYLISLKGYFS QEVNISLHYQKDEEPLFQLKKVRSVNSLMVASL TYKDKVYLNVTTDNTSLDDFHVNGGELILIHQN PGEFCVL |
| 191 | dimeric huOX40L (52-183) connected by (G4S)2 (SEQ ID NO: 150) linker | VSHRYPRIQSIKVQFTEYKKEKGFILTSQKEDEIM KVQNNSVIINCDGFYLISLKGYFSQEVNISLHYQ KDEEPLFQLKKVRSVNSLMVASLTYKDKVYLN VTTDNTSLDDFHVNGGELILIHQNPGEFCVLGGG GSGGGGSVSHRYPRIQSIKVQFTEYKKEKGFILTS QKEDEIMKVQNNSVIINCDGFYLISLKGYFSQEV NISLHYQKDEEPLFQLKKVRSVNSLMVASLTYK DKVYLNVTTDNTSLDDFHVNGGELILIHQNPGEF CVL |
| 192 | hu 4-1BBL (85-248) | LDLRQGMFAQLVAQNVLLIDGPLSWYSDPGLA GVSLTGGLSYKEDTKELVVAKAGVYYVFFQLEL RRVVAGEGSGSVSLALHLQPLRSAAGAAALALT VDLPPASSEARNSAFGFQGRLLHLSAGQRLGVH LHTEARARHAWQLTQGATVLGLFRVTPEIPAGL |
| 193 | hu 4-1BBL (80-248) | DPAGLLDLRQGMFAQLVAQNVLLIDGPLSWYS DPGLAGVSLTGGLSYKEDTKELVVAKAGVYYV FFQLELRRVVAGEGSGSVSLALHLQPLRSAAGA AALALTVDLPPASSEARNSAFGFQGRLLHLSAG QRLGVHLHTEARARHAWQLTQGATVLGLFRVT PEIPAGL |
| 194 | hu 4-1BBL (52-248) | PWAVSGARASPGSAASPRLREGPELSPDDPAGLL DLRQGMFAQLVAQNVLLIDGPLSWYSDPGLAG VSLTGGLSYKEDTKELVVAKAGVYYVFFQLELR RVVAGEGSGSVSLALHLQPLRSAAGAAALALTV DLPPASSEARNSAFGFQGRLLHLSAGQRLGVHL HTEARARHAWQLTQGATVLGLFRVTPEIPAGL |

TABLE C-continued

| SEQ ID NO: | Name | Sequence |
|---|---|---|
| | (Sequences): | |
| 195 | Dimeric hu OX40L (51-183)-CL* Fc knob chain | QVSHRYPRIQSIKVQFTEYKKEKGFILTSQKEDEIMKVQDNSVIINCDGFYLISLKGYFSQEVDISLHYQKDEEPLFQLKKVRSVNSLMVASLTYKDKVYLNVTTDNTSLDDFHVNGGELILIHQNPGEFCVLGGGGSGGGGSQVSHRYPRIQSIKVQFTEYKKEKGFILTSQKEDEIMKVQDNSVIINCDGFYLISLKGYFSQEVDISLHYQKDEEPLFQLKKVRSVNSLMVASLTYKDKVYLNVTTDNTSLDDFHVNGGELILIHQNPGEFCVLGGGGSGGGGSRTVAAPSVFIFPPSDRKLKSGTASVVCLLNNFYPREAKVQWKVDNALQSGNSQESVTEQDSKDSTYSLSSTLTLSKADYEKHKVYACEVTHQGLSSPVTKSFNRGECDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALGAPIEKTISKAKGQPREPQVYTLPPCRDELTKNQVSLWCLVKGFYPSDIAVEWESNGQPENNYKTTPPVLDSDGSFFLYSKLTVDKSRWQQGNVFSCSVMHEALHNHYTQKSLSLSPGK |
| 196 | Monomeric hu OX40L (51-183)-CH1* | QVSHRYPRIQSIKVQFTEYKKEKGFILTSQKEDEIMKVQDNSVIINCDGFYLISLKGYFSQEVDISLHYQKDEEPLFQLKKVRSVNSLMVASLTYKDKVYLNVTTDNTSLDDFHVNGGELILIHQNPGEFCVLGGGGSGGGGSASTKGPSVFPLAPSSKSTSGGTAALGCLVEDYFPEPVTVSWNSGALTSGVHTFPAVLQSSGLYSLSSVVTVPSSSLGTQTYICNVNHKPSNTKVDEKVEPKSC |
| 197 | human TnC | UniProt no. P24821 |
| 198 | human MCSP | UniProt no. Q6UVK1 |
| 199 | human EGFR | UniProt no. P00533 |
| 200 | human CD19 | UniProt no. P15391 |
| 201 | human CD20 | Uniprot no. P11836 |
| 202 | human CD33 | UniProt no. P20138 |
| 203 | human Lymphotoxin α | UniProt no. P01374 |
| 204 | human TNF | UniProt no. P01375 |
| 205 | human Lymphotoxin β | UniProt no. Q06643 |
| 206 | human OX40L | UniProt no. P23510 |
| 207 | human CD40L | UniProt no. P29965 |
| 208 | human FasL | UniProt no. P48023 |
| 209 | human CD27L | UniProt no. P32970 |
| 210 | human CD30L | UniProt no. P32971 |
| 211 | human 4-1BBL | UniProt no. P41273 |
| 212 | human TRAIL | UniProt no. P50591 |
| 213 | human RANKL | UniProt no. O14788 |
| 214 | human TWEAK | UniProt no. O43508 |
| 215 | human APRIL | UniProt no. O75888 |
| 216 | human BAFF | UniProt no. Q9Y275 |
| 217 | human LIGHT | UniProt no. O43557 |
| 218 | human TL1A | UniProt no. O95150 |

TABLE C-continued (Sequences):

| SEQ ID NO: | Name | Sequence |
|---|---|---|
| 219 | human GITRL | UniProt no. Q9UNG2 |
| 220 | human ectodysplasin A | UniProt no. Q92838 |

General information regarding the nucleotide sequences of human immunoglobulins light and heavy chains is given in: Kabat, E. A., et al., Sequences of Proteins of Immunological Interest, 5th ed., Public Health Service, National Institutes of Health, Bethesda, Md. (1991). Amino acids of antibody chains are numbered and referred to according to the EU numbering systems according to Kabat (Kabat, E. A., et al., Sequences of Proteins of Immunological Interest, 5th ed., Public Health Service, National Institutes of Health, Bethesda, Md. (1991)) as defined above.

Particular Embodiments

1. A TNF family ligand trimer-containing antigen binding molecule comprising
   (a) at least one moiety capable of specific binding to Tenascin-C (TnC) and
   (b) a first and a second polypeptide that are linked to each other by a disulfide bond,
   wherein the antigen binding molecule is characterized in that the first polypeptide comprises two ectodomains of a TNF ligand family member or a fragment thereof that are connected to each other by a peptide linker and in that the second polypeptide comprises only one ectodomain of said TNF ligand family member or a fragment thereof.

2. A TNF family ligand trimer-containing antigen binding molecule comprising
   (a) at least one antigen binding moiety capable of specific binding to Tenascin-C (TnC) and
   (b) a first and a second polypeptide that are linked to each other by a disulfide bond,
   wherein the antigen binding molecule is characterized in that the first polypeptide comprises two ectodomains of a TNF ligand family member or a fragment thereof that are connected to each other by a peptide linker and in that the second polypeptide comprises only one ectodomain of said TNF ligand family member or a fragment thereof.

3. The TNF family ligand trimer-containing antigen binding molecule of embodiment 1 or 2, further comprising
   (c) an Fc domain composed of a first and a second subunit capable of stable association.

4. The TNF family ligand trimer-containing antigen binding molecule of any one of embodiments 1 to 3, comprising
   (a) at least one moiety capable of specific binding to TnC and
   (b) a first and a second polypeptide that are linked to each other by a disulfide bond,
   wherein the antigen binding molecule is characterized in that
   (i) the first polypeptide contains a CH1 or CL domain and the second polypeptide contains a CL or CH1 domain, respectively, wherein the second polypeptide is linked to the first polypeptide by a disulfide bond between the CH1 and CL domain, and wherein the first polypeptide comprises two ectodomains of a TNF ligand family member or fragments thereof that are connected to each other and to the CH1 or CL domain by a peptide linker and wherein the second polypeptide comprises one ectodomain of said TNF ligand family member or a fragment thereof connected via a peptide linker to the CL or CH1 domain of said polypeptide, or
   (ii) the first polypeptide contains a CH3 domain and the second polypeptide contains a CH3 domain, respectively, and wherein the first polypeptide comprises two ectodomains of a TNF ligand family member or fragments thereof that are connected to each other and to the C-terminus of the CH3 domain by a peptide linker and wherein the second polypeptide comprises only one ectodomain of said TNF ligand family member or a fragment thereof connected via a peptide linker to C-terminus of the CH3 domain of said polypeptide, or
   (iii) the first polypeptide contains a VH-CL or a VL-CH1 domain and the second polypeptide contains a VL-CH1 domain or a VH-CL domain, respectively, wherein the second polypeptide is linked to the first polypeptide by a disulfide bond between the CH1 and CL domain, and wherein the first polypeptide comprises two ectodomains of a TNF ligand family member or fragments thereof that are connected to each other and to to VH or VL by a peptide linker and wherein the second polypeptide comprises one ectodomain of said TNF ligand family member or a fragment thereof connected via a peptide linker to VL or VH of said polypeptide.

5. The TNF family ligand trimer-containing antigen binding molecule of any one of embodiments 1 to 4, wherein the TNF ligand family member costimulates human T-cell activation.

6. The TNF family ligand trimer-containing antigen binding molecule of any one of embodiments 1 to 5, wherein the TNF ligand family member is selected from 4-1BBL and OX40L.

7. The TNF family ligand trimer-containing antigen binding molecule of any one of embodiments 1 to 6, wherein the TNF ligand family member is 4-1BBL.

8. The TNF family ligand trimer-containing antigen binding molecule of any one of embodiments 1 to 7, wherein the ectodomain of a TNF ligand family member comprises the amino acid sequence selected from the group consisting of SEQ ID NO: 172, SEQ ID NO: 173, SEQ ID NO: 174, SEQ ID NO: 175, SEQ ID NO: 183, SEQ ID NO: 192, SEQ ID NO: 193 and SEQ ID NO: 194, particularly the amino acid sequence of SEQ ID NO: 172 or SEQ ID NO: 183.

9. The TNF family ligand trimer-containing antigen binding molecule of any one of embodiments 1 to 8, wherein the ectodomain of a TNF ligand family member comprises the amino acid sequence of SEQ ID NO: 183.

10. The TNF family ligand trimer-containing antigen binding molecule of any one of embodiments 1 to 9, comprising
   (a) at least one moiety capable of specific binding to TnC and
   (b) a first and a second polypeptide that are linked to each other by a disulfide bond,
   wherein the antigen binding molecule is characterized in that the first polypeptide comprises the amino acid sequence selected from the group consisting of SEQ ID NO: 176, SEQ ID NO: 184, SEQ ID NO: 185 and SEQ ID NO: 186 and in that the second polypeptide comprises the amino acid sequence selected from the group consisting of SEQ ID NO: 172, SEQ ID NO: 174, SEQ ID NO: 175 and SEQ ID NO: 183.
11. The TNF family ligand trimer-containing antigen binding molecule of any one of embodiments 1 to 10, comprising
   (a) at least one moiety capable of specific binding to TnC, and
   (b) a first polypeptide containing a CH1 or CL domain and a second polypeptide containing a CL or CH1 domain, respectively, wherein the second polypeptide is linked to the first polypeptide by a disulfide bond between the CH1 and CL domain,
   and wherein the antigen binding molecule is characterized in that the first polypeptide comprises two ectodomains of a TNF ligand family member or fragments thereof that are connected to each other and to the CH1 or CL domain by a peptide linker and in that the second polypeptide comprises only one ectodomain of said TNF ligand family member or a fragment thereof connected via a peptide linker to the CL or CH1 domain of said polypeptide.
12. The TNF family ligand trimer-containing antigen binding molecule of any one of embodiments 1 to 11, wherein the moiety capable of specific binding to TnC is selected from the group consisting of an antibody fragment, a Fab molecule, a crossover Fab molecule, a single chain Fab molecule, a Fv molecule, a scFv molecule, a single domain antibody, an aVH and a scaffold antigen binding protein.
13. The TNF family ligand trimer-containing antigen binding molecule of any one of embodiments 1 to 12, wherein the molecule comprises one or two moieties capable of specific binding to TnC.
14. The TNF family ligand trimer-containing antigen binding molecule of any one of embodiments 1 to 13, wherein the moiety capable of specific binding to TnC is a Fab molecule capable of specific binding to TnC.
15. The TNF family ligand trimer-containing antigen binding molecule of any one of embodiments 1 to 14, wherein the moiety capable of specific binding to TnC comprises a VH domain comprising (i) CDR-H1 comprising the amino acid sequence of SEQ ID NO: 67 or SEQ ID NO: 70, (ii) CDR-H2 comprising the amino acid sequence of SEQ ID NO: 68 or SEQ ID NO: 71, and (iii) CDR-H3 comprising the amino acid sequence of SEQ ID NO: 69 or SEQ ID NO: 72, and a VL domain comprising (iv) CDR-L1 comprising the amino acid sequence of SEQ ID NO: 55 or SEQ ID NO: 58, (v) CDR-L2 comprising the amino acid sequence of SEQ ID NO: 56 or SEQ ID NO: 59, and (vi) CDR-L3 comprising the amino acid sequence of SEQ ID NO: 57 or SEQ ID NO: 60.
16. The TNF family ligand trimer-containing antigen binding molecule of any one of embodiments 1 to 15, wherein the moiety capable of specific binding to TnC comprises a variable heavy chain comprising an amino acid sequence of SEQ ID NO: 46 and a variable light chain comprising an amino acid sequence of SEQ ID NO: 45 or wherein the moiety capable of specific binding to TNC comprises a variable heavy chain comprising an amino acid sequence of SEQ ID NO: 48 and a variable light chain comprising an amino acid sequence of SEQ ID NO: 47.
17. The TNF family ligand trimer-containing antigen binding molecule of any one of embodiments 3 to 16, wherein the Fc domain is an IgG, particularly an IgG1 Fc domain or an IgG4 Fc domain.
18. The TNF family ligand trimer-containing antigen binding molecule of any one of embodiments 3 to 17, wherein the Fc domain is an IgG1 Fc domain comprising the amino acid substitutions at positions 234 and 235 (EU numbering) and/or 329 (EU numbering).
19. The TNF family ligand trimer-containing antigen binding molecule of any one of embodiments 1 to 18, wherein the antigen binding molecule comprises a first heavy chain and a first light chain, both comprising a Fab molecule capable of specific binding to TnC, a first peptide comprising two ectodomains of a TNF ligand family member or fragments thereof connected to each other by a first peptide linker fused at its C-terminus by a second peptide linker to a second heavy or light chain, and a second peptide comprising one ectodomain of said TNF ligand family member fused at its C-terminus by a third peptide linker to a second light or heavy chain, respectively.
20. The TNF family ligand trimer-containing antigen binding molecule of any one of embodiments 1 to 19, wherein the first peptide comprising two ectodomains of a TNF ligand family member or fragments thereof connected to each other by a first peptide linker is fused at its C-terminus by a second peptide linker to a CH1 domain that is part of a heavy chain, and the second peptide comprising one ectodomain of said TNF ligand family member or a fragment thereof is fused at its C-terminus by a third peptide linker to a CL domain that is part of a light chain.
21. The TNF family ligand trimer-containing antigen binding molecule of any one of embodiments 1 to 20, wherein the first peptide comprising two ectodomains of a TNF ligand family member or fragments thereof connected to each other by a first peptide linker is fused at its C-terminus by a second peptide linker to a CL domain that is part of a heavy chain, and the second peptide comprising one ectodomain of said TNF ligand family member or a fragment thereof is fused at its C-terminus by a third peptide linker to a CH1 domain that is part of a light chain.
22. The TNF family ligand trimer-containing antigen binding molecule of any one of embodiments 1 to 21, wherein the first peptide comprising two ectodomains of a TNF ligand family member or fragments thereof connected to each other by a first peptide linker is fused at its C-terminus by a second peptide linker to a VH domain that is part of a heavy chain, and the second peptide comprising one ectodomain of said TNF ligand family member or a fragment thereof is fused at its C-terminus by a third peptide linker to a VL domain that is part of a light chain.
23. The TNF family ligand trimer-containing antigen binding molecule of embodiments 20 or 21, wherein in the CL domain adjacent to the TNF ligand family member the amino acid at position 123 (EU numbering) has been replaced by arginine (R) and the amino acid at position 124 (EU numbering) has been substituted by lysine (K), and wherein in the CH1 domain adjacent to the TNF ligand family member the amino acids at position 147 (EU numbering) and at position 213 (EU numbering) have been substituted by glutamic acid (E).

24. The TNF family ligand trimer-containing antigen binding molecule of any one of embodiments 1 to 23, wherein the antigen binding molecule comprises
   (a) a first heavy chain and a first light chain, both comprising a Fab molecule capable of specific binding to TnC,
   (b) a second heavy chain comprising an amino acid sequence selected from the group consisting of SEQ ID NO: 176, SEQ ID NO: 184, SEQ ID NO: 185 and SEQ ID NO: 186, and a second light chain comprising an amino acid sequence selected from the group consisting of SEQ ID NO: 172, SEQ ID NO: 174, SEQ ID NO: 175 and SEQ ID NO: 183.

25. The TNF family ligand trimer-containing antigen binding molecule of any one of embodiments 1 to 20, wherein the antigen binding molecule comprises
   (i) a first heavy chain comprising the VH domain comprising the amino acid sequence of SEQ ID NO:46 and a first light chain comprising the VL domain comprising the amino acid sequence of SEQ ID NO: 45 or
   a first heavy chain comprising the VH domain comprising the amino acid sequence of SEQ ID NO: 48 and a first light chain comprising the VL domain comprising the amino acid sequence of SEQ ID NO: 47,
   (ii) a second heavy chain comprising the amino acid sequence of SEQ ID NO: 178, and
   (iii) a second light chain comprising the amino acid sequence of SEQ ID NO: 179.

26. The TNF family ligand trimer-containing antigen binding molecule of any one of embodiments 1 to 19 and 21, wherein the antigen binding molecule comprises
   (i) a first heavy chain comprising the VH domain comprising the amino acid sequence of SEQ ID NO: 46 and a first light chain comprising the VL domain comprising the amino acid sequence of SEQ ID NO: 45 or
   a first heavy chain comprising the VH domain comprising the amino acid sequence of SEQ ID NO: 48 and a first light chain comprising the VL domain comprising the amino acid sequence of SEQ ID NO: 47,
   (ii) a second heavy chain comprising the amino acid sequence selected from the group consisting of SEQ ID NO: 102, SEQ ID NO: 108, SEQ ID NO: 116 and SEQ ID NO: 120, and
   (iii) a second light chain comprising the amino acid sequence selected from the group consisting of SEQ ID NO: 103, SEQ ID NO: 109, SEQ ID NO: 117 and SEQ ID NO: 121.

27. The TNF family ligand trimer-containing antigen binding molecule of any one of embodiments 1 to 18, comprising
   (a) at least one moiety capable of specific binding TnC, and
   (b) a first and a second polypeptide that are linked to each other by a disulfide bond, wherein the antigen binding molecule is characterized in that the first polypeptide contains a CH3 domain and the second polypeptide contains a CH3 domain, respectively, and wherein the first polypeptide comprises two ectodomains of a TNF ligand family member or fragments thereof that are connected to each other and to the C-terminus of the CH3 domain by a peptide linker and wherein the second polypeptide comprises one ectodomain of said TNF ligand family member or a fragment thereof connected via a peptide linker to C-terminus of the CH3 domain of said polypeptide.

28. The TNF family ligand trimer-containing antigen binding molecule of embodiment 27, wherein the antigen binding molecule comprises
   (i) a first heavy chain comprising the amino acid sequence of SEQ ID NO: 127, a second heavy chain comprising the amino acid sequence of SEQ ID NO: 125, and one light chain comprising the amino acid sequence of SEQ ID NO: 77, or
   (ii) a first heavy chain comprising the amino acid sequence of SEQ ID NO: 130, a second heavy chain comprising the amino acid sequence of SEQ ID NO: 131, and one light chain comprising the amino acid sequence of SEQ ID NO: 77, or
   (ii) a first heavy chain comprising the amino acid sequence of SEQ ID NO: 124, a second heavy chain comprising the amino acid sequence of SEQ ID NO: 133, and one light chain comprising the amino acid sequence of SEQ ID NO: 77, or
   (ii) a first heavy chain comprising the amino acid sequence of SEQ ID NO: 136, a second heavy chain comprising the amino acid sequence of SEQ ID NO: 137, and one light chain comprising the amino acid sequence of SEQ ID NO: 77.

29. The TNF family ligand trimer-containing antigen binding molecule of embodiment 27, comprising two moieties capable of specific binding to a target cell antigen.

30. The TNF family ligand trimer-containing antigen binding molecule of any one of embodiments 27 or 29, wherein the antigen binding molecule comprises
   (i) a first heavy chain comprising the amino acid sequence of SEQ ID NO: 112, a second heavy chain comprising the amino acid sequence of SEQ ID NO: 113, and two light chains comprising the amino acid sequence of SEQ ID NO: 77, or
   (ii) a first heavy chain comprising the amino acid sequence of SEQ ID NO: 124, a second heavy chain comprising the amino acid sequence of SEQ ID NO: 125, and two light chains comprising the amino acid sequence of SEQ ID NO: 77.

31. The TNF family ligand trimer-containing antigen binding molecule of any one of embodiments 1 to 6, 11 to 23 and 27 to 29, wherein the TNF ligand family member is OX40L.

32. The TNF family ligand trimer-containing antigen binding molecule of any one of embodiments 1 to 6, 11 to 23 and 27 to 29, wherein the ectodomain of a TNF ligand family member comprises the amino acid sequence of SEQ ID NO: 181 or SEQ ID NO: 182, particularly the amino acid sequence of SEQ ID NO: 181.

33. The TNF family ligand trimer-containing antigen binding molecule of any one of embodiments 1 to 6, 11 to 23, 27 to 29, 31 and 32, comprising
   (a) at least one moiety capable of specific binding to a target cell antigen and
   (b) a first and a second polypeptide that are linked to each other by a disulfide bond,
   wherein the antigen binding molecule is characterized in that the first polypeptide comprises the amino acid sequence of SEQ ID NO: 190 or SEQ ID: 191 and in that the second polypeptide comprises the amino acid sequence of SEQ ID NO: 181 or SEQ ID NO: 182.

34. The TNF family ligand trimer-containing antigen binding molecule of any one of embodiments 1 to 6, 11 to 23, 27 to 29 and 31 to 33, wherein the target cell antigen is Tenascin-C (TnC) and the moiety capable of specific binding to TnC comprises a VH domain comprising (i) CDR-H1 comprising the amino acid sequence of SEQ ID NO: 67 or SEQ ID NO: 70, (ii) CDR-H2 comprising the amino acid sequence of SEQ ID NO: 68 or SEQ ID NO: 71, and (iii) CDR-H3 comprising the amino acid sequence of SEQ ID NO: 69 or SEQ ID NO: 72, and a VL domain comprising (iv) CDR-L1 comprising the amino acid sequence of SEQ ID NO: 55 or SEQ ID NO: 58, (v) CDR-L2 comprising the amino acid sequence of SEQ ID NO: 56 or SEQ ID NO: 59, and (vi) CDR-L3 comprising the amino acid sequence of SEQ ID NO: 57 or SEQ ID NO: 60.

35. The TNF family ligand trimer-containing antigen binding molecule of any one of embodiments 1 to 6, 11 to 23, 27 to 29 and 31 to 33, wherein the antigen binding moiety capable of specific binding to TnC comprises a VH domain comprising (i) CDR-H1 comprising the amino acid sequence of SEQ ID NO: 67, (ii) CDR-H2 comprising the amino acid sequence of SEQ ID NO: 68, and (iii) CDR-H3 comprising the amino acid sequence of SEQ ID NO: 69, and a VL domain comprising (iv) CDR-L1 comprising the amino acid sequence of SEQ ID NO: 55, (v) CDR-L2 comprising the amino acid sequence of SEQ ID NO: 56, and (vi) CDR-L3 comprising the amino acid sequence of SEQ ID NO: 57.

36. TNF family ligand trimer-containing antigen binding molecule of any one of embodiments 1 to 6, 11 to 23, 27 to 29 and 31 to 33, wherein the antigen binding moiety capable of specific binding to TnC comprises a VH domain comprising (i) CDR-H1 comprising the amino acid sequence of SEQ ID NO: 70, (ii) CDR-H2 comprising the amino acid sequence of SEQ ID NO: 71, and (iii) CDR-H3 comprising the amino acid sequence of SEQ ID NO: 72, and a VL domain comprising (iv) CDR-L1 comprising the amino acid sequence of SEQ ID NO: 58, (v) CDR-L2 comprising the amino acid sequence of SEQ ID NO: 59, and (vi) CDR-L3 comprising the amino acid sequence of SEQ ID NO: 60.

37. The TNF family ligand trimer-containing antigen binding molecule of any one of embodiments 1 to 6, 11 to 23, 27 to 29 and 31 to 36, wherein the antigen binding molecule comprises (i) a first heavy chain comprising the VH domain comprising the amino acid sequence of SEQ ID NO: 46 and a first light chain comprising the VL domain comprising the amino acid sequence of SEQ ID NO: 45 or a first heavy chain comprising the VH domain comprising the amino acid sequence of SEQ ID NO: 48 and a first light chain comprising the VL domain comprising the amino acid sequence of SEQ ID NO: 47, (ii) a second heavy chain comprising the amino acid sequence selected from the group consisting of SEQ ID NO: 195, and (iii) a second light chain comprising the amino acid sequence of SEQ ID NO: 196.

38. The TNF family ligand trimer-containing antigen binding molecule of any one of embodiments 1 to 37, wherein the antigen binding moiety has an improved affinity.

39. The TNF family ligand trimer-containing antigen binding molecule of any one of embodiments 1 to 38, wherein the antigen binding moiety binds to human TnC with a $K_D$ value lower than about 1 nM.

40. The TNF family ligand trimer-containing antigen binding molecule of any one of embodiments 1 to 39, wherein the antigen binding moiety has cross-species reactivity.

41. The TNF family ligand trimer-containing antigen binding molecule of any one of embodiments 1 to 40, wherein the antigen binding moiety binds to at least one of human, mouse and cynomolgus TnC with a $K_D$ value lower than about 2 nM.

42. The TNF family ligand trimer-containing antigen binding molecule of any one of embodiments 1 to 41, wherein the antigen binding moiety binds to human, mouse and cynomolgus TnC.

43. The TNF family ligand trimer-containing antigen binding molecule of any one of embodiments 40 to 42, wherein the antigen binding moiety binds to the target antigen from all indicated species with similar affinity.

44. The TNF family ligand trimer-containing antigen binding molecule of any one of embodiments 40 to 43, wherein the antigen binding moiety binds to the target antigen from all indicated species with similar affinity, in particular within a $K_D$ range of a factor of 100, within a $K_D$ range of a factor of 50, within a $K_D$ range of a factor of 20, within a $K_D$ range of a factor of 10, within a $K_D$ range of a factor of 5.

45. The TNF family ligand trimer-containing antigen binding molecule of any one of embodiments 40 to 44, wherein the antigen binding moiety binds to the target antigen from all indicated species with similar affinity within a $K_D$ range of a factor of 10.

46. An isolated polynucleotide encoding the TNF family ligand trimer-containing antigen binding molecule of any one of embodiments 1 to 45.

47. A vector, particularly an expression vector, comprising the isolated polynucleotide of embodiment 46.

48. A host cell comprising the isolated polynucleotide of embodiment 46 or the vector of embodiment 47.

49. A method for producing the TNF family ligand trimer-containing antigen binding molecule of any one of embodiments 1 to 45, comprising the steps of (i) culturing the host cell of embodiment 48 under conditions suitable for expression of the antigen binding molecule, and (ii) recovering the antigen binding molecule.

50. A pharmaceutical composition comprising the TNF family ligand trimer-containing antigen binding molecule of any one of embodiments 1 to 45 and at least one pharmaceutically acceptable excipient.

51. The TNF family ligand trimer-containing antigen binding molecule of any one of embodiments 1 to 45, or the pharmaceutical composition of embodiment 50, for use as a medicament.

52. The TNF family ligand trimer-containing antigen binding molecule of any one of embodiments 1 to 45, or the pharmaceutical composition of embodiment 50, for use in the treatment of cancer.

53. Use of the TNF family ligand trimer-containing antigen binding molecule of any one of embodiments 1 to 45 for the manufacture of a medicament for the treatment of cancer.

54. A method of treating a disease in an individual, comprising administering to said individual a therapeutically effective amount of a composition comprising a TNF family ligand trimer-containing antigen binding molecule of any one of embodiments 1 to 45 in a pharmaceutically acceptable form.

55. The method of embodiment 54, wherein said disease is cancer.

EXAMPLES

The following are examples of methods and compositions of the invention. It is understood that various other embodiments may be practiced, given the general description provided above.

Recombinant DNA Techniques

Standard methods were used to manipulate DNA as described in Sambrook, J. et al., Molecular cloning: A laboratory manual; Cold Spring Harbor Laboratory Press, Cold Spring Harbor, N.Y., 1989. The molecular biological reagents were used according to the manufacturer's instructions. DNA sequences were determined by double strand sequencing. In some cases desired gene segments were prepared by Geneart AG (Regensburg, Germany) from synthetic oligonucleotides and PCR products by automated gene synthesis. The gene segments which are flanked by singular restriction endonuclease cleavage sites were cloned into indicated plasmids. The plasmid DNA was purified from transformed bacteria and concentration determined by UV spectroscopy. The DNA sequence of the subcloned gene fragments was confirmed by DNA sequencing. Gene Segments were designed with suitable restriction sites to allow sub-cloning into the respective expression vectors.

General information regarding the nucleotide sequences of human immunoglobulin light and heavy chains is given in: Kabat, E. A. et al., (1991) Sequences of Proteins of Immunological Interest, Fifth Ed., NIH Publication No 91-3242. For expression, all constructs contained a 5'-end DNA sequence coding for a leader peptide which targets proteins for secretion in eukaryotic cells. Exemplary leader peptides and polynucleotide sequences encoding them are given in SEQ ID NO 163 to SEQ ID NO 171.

Cell Culture Techniques

Standard cell culture techniques were used as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

Protein Purification

Proteins were purified from filtered cell culture supernatants referring to standard protocols. In brief, antibodies were applied to a Protein A Sepharose column (GE healthcare) and washed with PBS. Elution of antibodies was achieved at pH 2.8 followed by immediate neutralization of the sample. Aggregated protein was separated from monomeric antibodies by size exclusion chromatography (Superdex 200, GE Healthcare) in PBS or in 20 mM Histidine, 150 mM NaCl pH 6.0. Monomeric antibody fractions were pooled, concentrated (if required) using e.g., a MILLIPORE Amicon Ultra (30 MWCO) centrifugal concentrator, frozen and stored at −20° C. or −80° C. Part of the samples were provided for subsequent protein analytics and analytical characterization e.g. by SDS-PAGE, size exclusion chromatography (SEC) or mass spectrometry.

SDS-PAGE

The NuPAGE® Pre-Cast gel system (Invitrogen) was used according to the manufacturer's instruction. In particular, 10% or 4-12% NuPAGE® Novex® Bis-TRIS Pre-Cast gels (pH 6.4) and a NuPAGE® MES (reduced gels, with NuPAGE® Antioxidant running buffer additive) or MOPS (non-reduced gels) running buffer was used.

Analytical Size Exclusion Chromatography

Size exclusion chromatography (SEC) for the determination of the aggregation and oligomeric state of antibodies was performed by HPLC chromatography. Briefly, Protein A purified antibodies were applied to a Tosoh TSKgel G3000SW column in 300 mM NaCl, 50 mM $KH_2PO_4$/$K_2HPO_4$, pH 7.5 on an Agilent HPLC 1100 system or to a Superdex 200 column (GE Healthcare) in 2×PBS on a Dionex HPLC-System. The eluted protein was quantified by UV absorbance and integration of peak areas. BioRad Gel Filtration Standard 151-1901 served as a standard.

Mass Spectrometry

This section describes the characterization of the multispecific antibodies with VH/VL exchange (VH/VL CrossMabs) with emphasis on their correct assembly. The expected primary structures were analyzed by electrospray ionization mass spectrometry (ESI-MS) of the deglycosylated intact CrossMabs and deglycosylated/plasmin digested or alternatively deglycosylated/limited LysC digested CrossMabs.

The VH/VL CrossMabs were deglycosylated with N-Glycosidase F in a phosphate or Tris buffer at 37° C. for up to 17 h at a protein concentration of 1 mg/ml. The plasmin or limited LysC (Roche) digestions were performed with 100 μg deglycosylated VH/VL CrossMabs in a Tris buffer pH 8 at room temperature for 120 hours and at 37° C. for 40 min, respectively. Prior to mass spectrometry the samples were desalted via HPLC on a Sephadex G25 column (GE Healthcare). The total mass was determined via ESI-MS on a maXis 4G UHR-QTOF MS system (Bruker Daltonik) equipped with a TriVersa NanoMate source (Advion).

Determination of Binding and Binding Affinity of Multispecific Antibodies to the Respective Antigens Using Surface Plasmon Resonance (SPR) (BIACORE)

Binding of the generated antibodies to the respective antigens is investigated by surface plasmon resonance using a BIACORE instrument (GE Healthcare Biosciences AB, Uppsala, Sweden). Briefly, for affinity measurements Goat-Anti-Human IgG, JIR 109-005-098 antibodies are immobilized on a CMS chip via amine coupling for presentation of the antibodies against the respective antigen. Binding is measured in HBS buffer (HBS-P (10 mM HEPES, 150 mM NaCl, 0.005% Tween 20, ph 7.4), 25° C. (or alternatively at 37° C.). Antigen (R&D Systems or in house purified) was added in various concentrations in solution. Association was measured by an antigen injection of 80 seconds to 3 minutes; dissociation was measured by washing the chip surface with HBS buffer for 3-10 minutes and a KD value was estimated using a 1:1 Langmuir binding model. Negative control data (e.g. buffer curves) are subtracted from sample curves for correction of system intrinsic baseline drift and for noise signal reduction. The respective Biacore Evaluation Software is used for analysis of sensorgrams and for calculation of affinity data.

Example 1

TnC Antigen Sequences and Production of Antigens

All constructs of Table 3 and Table 4 are fused to the C-term of GST and are expressed in *E. coli* BL21(DE3). For site specific biotinylation, the Avi-tag was added to the C-term of the Tenascin sequence, and the BirA biotin ligase was coexpressed on a separate plasmid (Avidity, Colo., USA). Growth medium was 2YT with 100 μg/ml ampicillin and 20 μg/ml chloramphenicol. Biotin was added to a final concentration of 50 μM. Protein Expression was induced with 1 mM IPTG at 22° C. overnight. Cells were harvested by centrifugation, and cell-lysis was performed by sonication in the presence of B-PER reagent (pierce 78260), and 1 mg/ml lysozyme (Sigma L6876). Lysate was centrifuged and cleared lysate was loaded on Glutathione Sepharose columns (GE Healthcare; Product No 17-0756-01). After washing, the TnC molecules were cleft from the GST via Thrombin (Sigma Aldrich; Product No 10602400001) over night at 4° C. Elution was performed in 50 mM Tris buffer pH 8.0; 200 mM NaCl, 5 mM MgCl2, 1 mM DTT and 10% glycerol. The final purification step was on a gelfiltration column (Superdex 75 16/60; GE Healthcare). Samples were flash frozen in liquid nitrogen until processing.

TABLE 3

Sequences of TnC antigens used for cross-species affinity determination (reference Table 26)

| Antigen | Sequence | SEQ ID NO |
|---|---|---|
| huTNC | ATGTCCCCTATACTAGGTTATTGGAAAATTAAGGGCCT<br>TGTGCAACCCACTCGACTTCTTTTGGAATATCTTGAAG<br>AAAAATATGAAGAGCATTTGTATGAGCGCGATGAAGG<br>TGATAAATGGCGAAACAAAAAGTTTGAATTGGGTTTG<br>GAGTTTCCCAATCTTCCTTATTATATTGATGGTGATGTT<br>AAATTAACACAGTCTATGGCCATCATACGTTATATAGC<br>TGACAAGCACAACATGTTGGGTGGTTGTCCAAAAGAG<br>CGTGCAGAGATTTCAATGCTTGAAGGAGCGGTTTTGGA<br>TATTAGATACGGTGTTTCGAGAATTGCATATAGTAAAG<br>ACTTTGAAACTCTCAAAGTTGATTTTCTTAGCAAGCTA<br>CCTGAAATGCTGAAAATGTTCGAAGATCGTTTATGTCA<br>TAAAACATATTTAAATGGTGATCATGTAACCCATCCTG<br>ACTTCATGTTGTATGACGCTCTTGATGTTGTTTTATACA<br>TGGACCCAATGTGCCTGGATGCGTTCCCAAAATTAGTT<br>TGTTTTAAAAAACGTATTGAAGCTATCCCACAAATTGA<br>TAAGTACTTGAAATCCAGCAAGTATATAGCATGGCCTT<br>TGCAGGGCTGGCAAGCCACGTTTGGTGGTGGCGACCAT<br>CCTCCAAAATCGGATGGTTCAACTAGTGGTTCTGGTCA<br>TCACCATCACCATCACTCCGCGGGTCTGGTGCCACGCG<br>GTAGTACTGCAATTGGTATGAAAGAAACCGCTGCTGCT<br>AAATTCGAACGCCAGCACATGGACAGCCCAGATCTGG<br>GTACCGGTGGTGGCTCCGGTATTGAGGGACGCGGGTCC<br>ATGGGATATCGGGGATCCGAGCTGGACACCCCCAAGG<br>ACCTGCAGGTGTCCGAGACAGCCGAGACAAGCCTGAC<br>CCTGCTGTGGAAAACCCCCCTGGCCAAGTTCGACCGGT<br>ACAGACTGAACTACAGCCTGCCCACTGGACAGTGGGT<br>CGGCGTGCAGCTGCCCCGGAACACCACCTCCTACGTGC<br>TGCGGGGCCTGGAACCCGGCCAGGAATACAACGTCCT<br>GCTGACGGCCGAGAAGGGCCGGCACAAGAGCAAGCCC<br>GCCAGAGTGAAGGCCAGCACCGAGCAGGCCCCCGAGC<br>TGGAAAACCTGACCGTGACCGAAGTGGGCTGGGACGG<br>CCTGCGGCTGAACTGGACCGCGGCTGACCAGGCCTATG<br>AGCACTTTATCATTCAGGTGCAGGAGGCCAACAAGGT<br>GGAGGCAGCTCGGAACCTCACCGTGCCTGGCAGCCTTC<br>GGGCTGTGGACATACCGGGCCTCAAGGCTGCTACGCCT<br>TATACAGTCTCCATCTATGGGGTGATCCAGGGCTATAG<br>AACACCAGTGCTCTCTGCTGAGGCCTCCACAGGCGAAA<br>CACCGAACCTGGGCGAAGTGGTGGTGGCGGAAGTGGG<br>TTGGGATGCGCTGAAACTGAACTGGACCGCGCCGGAA<br>GGCGCGTATGAATATTTTTTCATCCAGGTGCAGGAAGC<br>GGATACCGTTGAAGCGGCGCAGAACCTGACCGTTCCG<br>GGCGGTCTGCGTAGCACCGATCTGCCGGGCCTGAAAG<br>CGGCGACCCATTATACCATTACCATCCGTGGGGTGACC<br>CAGGACTTCTCTACCACCCCTCTGAGCGTGGAGGTGCT<br>GACCGAGGAGGTACCCGACATGGGCAACCTGACCGTG<br>ACCGAGGTGTCCTGGGACGCCCTGCGGCTGAACTGGA<br>CCACCCCCGACGGCACCTACGACCAGTTCACAATCCAG<br>GTGCAGGAAGCCGACCAGGTGGAAGAAGCACATAATC<br>TGACCGTTCCGGGTAGCCTGCGTAGCATGGAAATTCCG<br>GGTCTGCGTGCAGGCACCCCGTATACCGTTACCCTGCA<br>TGGTGAAGTTCGTGGTCATAGCACCCGTCCGCTGGCAG<br>TTGAAGTTGTTACCGAAGATCTGCCGCAGCTGGGTGAT<br>CTGGCAGTTAGCGAAGTTGGTTGGGATGGTCTGCGTCT<br>GAATTGGACCGCAGCAGATAATGCATATGAACATTTTG<br>TGATCCAGGTGCAAGAGGTGAATAAAGTTGAAGCAGC<br>CCAGAATCTGACCCTGCCTGGTTCACTGCGTGCAGTTG<br>ATATTCCGGGACTCGAGGCAGCAACCCCGTATCGTGTT<br>AGCATTTATGGTGTTATTCGCGGTTATCGTACACCGGT<br>TCTGAGCGCAGAAGCAAGCACCGCAAAAGAACCGGAA<br>ATTGGTAATCTGAACGTGAGCGATATTACACCGGAATC<br>ATTTAATCTGAGCTGGATGGCAACCGATGGTATTTTTG<br>AAACCTTTACCATCGAGATCATCGATAGCAATCGTCTG<br>CTGGAAACCGTGGAATATAATATTAGCGGTGCAGAAC<br>GTACCGCACATATTAGCGGTCTGCCTCCGAGCACCGAT<br>TTTATTGTTTATCTGAGCGGTCTGGCACCGAGCATTCGT<br>ACCAAAACCATTAGCGCAACCGCAACCACCGAAGCAC<br>TGCCGCTGCTGGAAAATCTGACCATTAGCGATATTAAC<br>CCGTATGGTTTTACCGTTTCATGGATGGCAAGCGAAAA<br>TGCATTTGATAGCTTTCTGGTTACAGTTGTGGATAGCG<br>GTAAACTGCTGGACCCGCAAGAATTTACCCTGAGCGGC | SEQ ID NO: 1 |

TABLE 3-continued

Sequences of TnC antigens used for cross-species affinity determination (reference Table 26)

| Antigen | Sequence | SEQ ID NO |
| --- | --- | --- |
| | ACCCAGCGCAAACTGGAACTGCGTGGTCTGATTACCGG<br>TATTGGTTATGAAGTTATGGTGAGCGGTTTTACCCAGG<br>GTCATCAGACCAAACCGCTGCGTGCAGAAATTGTTACC<br>GAAGCAATGGGTAGCCCGAAAGAAGTTATTTTTTCCGA<br>TATCACCGAGAATTCGGCAACCGTTAGCTGGCGTGCAC<br>CGACCGCACAGGTTGAAAGCTTTCGTATTACCTATGTT<br>CCGATTACCGGTGGCACCCCGAGCATGGTTACAGTTGA<br>TGGCACCAAAACCCAGACCCGTCTGGTTAAACTGATTC<br>CGGGTGTTGAATATCTGGTTAGCATTATTGCCATGAAA<br>GGCTTTGAAGAAAGCGAACCGGTTAGCGGTAGCTTTAC<br>CACAGCTAGCGGCCTGAACGACATCTTCGAGGCTCAG<br>AAAATCGAATGGCACGAAGGTACCCATCACCATCACC<br>ACCACTAA | |
| muTNC | TATGTCCCCTATACTAGGTTATTGGAAAATTAAGGGCC<br>TTGTGCAACCCACTCGACTTCTTTTGGAATATCTTGAA<br>GAAAAATATGAAGAGCATTTGTATGAGCGCGATGAAG<br>GTGATAAATGGCGAAACAAAAAGTTTGAATTGGGTTT<br>GGAGTTTCCCAATCTTCCTTATTATATTGATGGTGATGT<br>TAAATTAACACAGTCTATGGCCATCATACGTTATATAG<br>CTGACAAGCACAACATGTTGGGTGGTTGTCCAAAAGA<br>GCGTGCAGAGATTTCAATGCTTGAAGGAGCGGTTTTGG<br>ATATTAGATACGGTGTTTCGAGAATTGCATATAGTAAA<br>GACTTTGAAACTCTCAAAGTTGATTTTCTTAGCAAGCT<br>ACCTGAAATGCTGAAAATGTTCGAAGATCGTTTATGTC<br>ATAAAACATATTTAAATGGTGATCATGTAACCCATCCT<br>GACTTCATGTTGTATGACGCTCTTGATGTTGTTTTATAC<br>ATGGACCCAATGTGCCTGGATGCGTTCCCAAAATTAGT<br>TTGTTTTAAAAAACGTATTGAAGCTATCCCACAAATTG<br>ATAAGTACTTGAAATCCAGCAAGTATATAGCATGGCCT<br>TTGCAGGGCTGGCAAGCCACGTTTGGTGGTGGCGACCA<br>TCCTCCAAAATCGGATGGTTCAACTAGTGGTTCTGGTC<br>ATCACCATCACCATCACTCCGCGGGTCTGGTGCCACGC<br>GGTAGTACTGCAATTGGTATGAAAGAAACCGCTGCTGC<br>TAAATTCGAACGCCAGCACATGGACAGCCCAGATCTG<br>GGTACCGGTGGTGGCTCCGGTATTGAGGGACGCGGGT<br>CCATGGGATATCGGGGATCCGAGCTGGACACCCCCAA<br>GGACCTGCAGGTGTCCGAGACAGCCGAGACAAGCCTG<br>ACCCTGCTGTGGAAAACCCCCCTGGCCAAGTTCGACCG<br>GTACAGACTGAACTACAGCCTGCCCACTGGACAGTGG<br>GTCGGCGTGCAGCTGCCCCGGAACACCACCTCCTACGT<br>GCTGCGGGGCCTGGAACCCGGCCAGGAATACAACGTC<br>CTGCTGACGGCCGAGAAGGGCCGGCACAAGAGCAAGC<br>CCGCCAGAGTGAAGGCCAGCACCGAGGAAGTGCCCAG<br>CCTGGAAAACCTGACCGTGACCGAGGCCGGCTGGGAC<br>GGCCTGCGGCTGAACTGGACCGCCGACGACCTGGCCT<br>ACGAGTACTTCGTGATCCAGGTGCAGGAAGCCAACAA<br>CGTCGAGACAGCCCACAACTTCACCGTGCCCGGCAACC<br>TGAGAGCCGCCGACATCCCCGGCCTGAAGGTGGCCAC<br>ATCCTACCGGGTGTCCATCTACGGCGTGGCCAGGGGCT<br>ACCGGACCCCCGTGCTGTCCGCCGAGACAAGCACCGG<br>CACCACGCCGAACCTGGGCGAAGTGACCGTGGCGGAA<br>GTGGGTTGGGATGCGCTGACCCTGAATTGGACCGCACC<br>GGAAGGCGCGTATAAAAACTTTTTCATCCAGGTGCTGG<br>AAGCGGATACCACCCAGACCGTGCAGAACCTGACCGT<br>GCCGGGTGGTCTGCGTAGCGTAGATCTGCCTGGTCTGA<br>AAGCAGCAACCCGCTATTACATTACCCTGCGTGGTGTT<br>ACCCAGGATTTTGGCACCGCACCGCTGAGCGTTGAAGT<br>TCTGACCGAGGATCTGCCGCAGCTGGGTGGTCTGAGCG<br>TTACCGAAGTTAGTTGGGATGGTCTGACCCTGAATTGG<br>ACCACCGATGATCTGGCATATAAACATTTTGTGGTGCA<br>GGTTCAAGAGGCCAATAATGTTGAAGCAGCACAGAAT<br>CTGACCGTTCCGGGTAGCCTGCGTGCAGTTGATATTCC<br>GGGACTGAAAGCCGATACCCCGTATCGTGTTAGCATTT<br>ATGGTGTTATTCAGGGTTATCGTACCCCGATGCTGAGC<br>ACCGATGTTAGCACAGCACGTGAACCGGAAATTGGTA<br>ATCTGAATGTTAGTGATGTGACCCCGAAATCATTTAAT<br>CTGAGCTGGACCGCAACCGATGGTATTTTTGATATGTT<br>TACCATTGAAATTATTGATAGCAATCGCCTGCTGCAGA<br>CCGCAGAACATAACATTAGCGGTGCAGAACGTACCGC<br>ACATATTAGCGGTCTGCCTCCGAGCACCGATTTTATTG<br>TTTATCTGAGCGGTATTGCACCGAGCATTCGTACCAAA<br>ACCATTAGCACCACCGCAACCACCGAAGCACTGACCG<br>CAATGGGTAGCCCGAAAGAAGTGATTTTTAGCGATATT<br>ACCGAAAATAGCGCCACCGTTTCATGGCGTGCACCGAC | SEQ ID NO: 2 |

TABLE 3-continued

Sequences of TnC antigens used for cross-species affinity determination (reference Table 26)

| Antigen | Sequence | SEQ ID NO |
|---|---|---|
| | CGCACAGGTTGAAAGCTTTCGTATTACCTATGTTCCGA<br>TTACCGGTGGCACCCCGAGCATGGTTACCGTTGATGGC<br>ACCAAAACCCAGACCCGTCTGGTTAAACTGATTCCGGG<br>TGTTGAATATCTGGTTAGCATTATTGCCATGAAAGGCT<br>TTGAAGAAAGCGAACCGGTTAGCGGTAGCTTTACCAC<br>AGCTAGCGGCCTGAACGACATCTTCGAGGCTCAGAAA<br>ATCGAATGGCACGAAGGTACCCATCACCATCACCACC<br>ACTAA | |
| cynoTNC | ATGTCCCCTATACTAGGTTATTGGAAAATTAAGGGCCT<br>TGTGCAACCCACTCGACTTCTTTTGGAATATCTTGAAG<br>AAAAATATGAAGAGCATTTGTATGAGCGCGATGAAGG<br>TGATAAATGGCGAAACAAAAAGTTTGAATTGGGTTTG<br>GAGTTTCCCAATCTTCCTTATTATATTGATGGTGATGTT<br>AAATTAACACAGTCTATGGCCATCATACGTTATATAGC<br>TGACAAGCACAACATGTTGGGTGGTTGTCCAAAAGAG<br>CGTGCAGAGATTTCAATGCTTGAAGGAGCGGTTTTGGA<br>TATTAGATACGGTGTTTCGAGAATTGCATATAGTAAAG<br>ACTTTGAAACTCTCAAAGTTGATTTTCTTAGCAAGCTA<br>CCTGAAATGCTGAAAATGTTCGAAGATCGTTTATGTCA<br>TAAAACATATTTAAATGGTGATCATGTAACCCATCCTG<br>ACTTCATGTTGTATGACGCTCTTGATGTTGTTTTATACA<br>TGGACCCAATGTGCCTGGATGCGTTCCCAAAATTAGTT<br>TGTTTTAAAAAACGTATTGAAGCTATCCCACAAATTGA<br>TAAGTACTTGAAATCCAGCAAGTATATAGCATGGCCTT<br>TGCAGGGCTGGCAAGCCACGTTTGGTGGTGGCGACCAT<br>CCTCCAAAATCGGATGGTTCAACTAGTGGTTCTGGTCA<br>TCACCATCACCATCACTCCGCGGGTCTGGTGCCACGCG<br>GTAGTACTGCAATTGGTATGAAAGAAACCGCTGCTGCT<br>AAATTCGAACGCCAGCACATGGACAGCCCAGATCTGG<br>GTACCGGTGGTGGCTCCGGTATTGAGGGACGCGGGTCC<br>ATGGGATATCGGGGATCCGAACTGGATACCCCGAAAG<br>ATCTGCGTGTTAGCGAAACCGCAGAAACCAGCCTGAC<br>CCTGTTTTGGAAAACACCGCTGGCAAAATTTGATCGTT<br>ATCGTCTGAATTATAGCCTGCCGACCGGTCAGTGGGTT<br>GGTGTTCAGCTGCCTCGTAATACCACCAGTTATGTTCT<br>GCGTGGTCTGGAACCGGGTCAAGAATATAACGTTCTGC<br>TGACCGCAGAAAAAGGTCGTCATAAAAGCAAACCGGC<br>ACGTGTTAAAGCAAGCACCGAACAGGCACCGGAACTG<br>GAAAATCTGACCGTTACCGAAGTTGGCTGGGATGGCCT<br>GCGCCTGAACTGGACGGCTGCGGACCAGGCCTACGAA<br>CACTTCGTTATCCAGGTGCAAGAAGCCAACAAAGTAG<br>AAGCCGCTCAGAATCTGACGGTTCCGGGAAATCTGCGT<br>GCAGTTGATATTCCGGGTCTGAAAGCAGCAACCCCGTA<br>TACCGTTAGCATTTATGGTGTTATTCAGGGTTATCGTAC<br>ACCGGTTCTGAGTGCCGAAGCCAGCACCGGTGAAACC<br>CCGAATCTGGGTGAAGTTATGGTTAGCGAAGTGGGCTG<br>GGATGCACTGAAACTGAATTGGACAGTTCCGGAAGGT<br>GCCTATGAATACTTTTTCATTCAGGTTCAAGAAGCGGA<br>TACCGTTGAAGCCGCTCAGAATCATACCGTTCCGGGTG<br>GTCTGCGTAGCACCGATCTGCCTGGCCTGAAAGCCGCT<br>ACCCATTACACCATTACCATTCGTGGTGTTACCCAGGA<br>TTTTAGCACCACACCGCTGAGCGTTGAAGTTCTGACAG<br>AAGAACTGCCGCAGCTGGGTGATCTGGCAGTTAGCGA<br>AGTTGGTTGGGATGGTCTGCGTCTGAATTGGACCGCAG<br>CAGATCAGGCATATGAACATTTTGTTATCCAGGTGCAA<br>GAAGTGAACAAAGTTGAAGCAGCACAGAATCTGACCG<br>TTCCGGGTAGCCTGCGTGCAGTTGATATTCCGGGTCTG<br>AAAGCAGCAACCCCGTATACCGTTAGCATTTATGGTGT<br>TATTCGCGGTTATCGTACACCGGTTCTGAGCGCAGAAG<br>CAAGCACCGCAAAAGAACCGGAAATTGGTAATCTGAA<br>CGTGAGCGATATTACACCGGAAAGTTTTAGCCTGAGCT<br>GGACCGCAACCGATGGTATTTTTGAAACCTTTACCATC<br>GAGATCATCGATAGCAATCGTCTGCTGGAAATCGTGGA<br>ATATAACATTAGCGGTGCAGAACGTACCGCACATATTA<br>GCGGTCTGCCTCCGAGCACCGATTTTATTGTTTATCTGA<br>GCGGTCTGGCACCGAGCTTTCGTACCAAAACCATTAGC<br>GCAACCGCAACCACCGAAGCACTGACCGCAATGGGTA<br>GCCCGAAAGAAGTGATTTTTAGCGATATTACCGAAAAT<br>AGCGCCACCGTTTCATGGCGTGCACCGACCGCACAGGT<br>TGAAAGCTTTCGTATTACCTATGTTCCGATTACCGGTG<br>GCACCCCGAGCATGGTTACCGTGGATGGCACCAAAAC<br>CCAGACCCGTCTGGTTAAACTGGTTCCGGGTGTTGAAT<br>ATCTGGTGAATATCATTGCCATGAAAGGCTTTGAAGAA<br>AGCGAACCGGTTAGCGGTAGCTTTACCACCGCTAGCGG | SEQ ID NO: 3 |

TABLE 3-continued

Sequences of TnC antigens used for cross-species affinity determination (reference Table 26)

| Antigen | Sequence | SEQ ID NO |
|---|---|---|
| | CCTGAACGACATCTTCGAGGCTCAGAAAATCGAATGG<br>CACGAAGGTACCCATCACCATCACCACCACTAA | |
| huTNC | MSPILGYWKIKGLVQPTRLLLEYLEEKYEEHLYERDEGD<br>KWRNKKFELGLEFPNLPYYIDGDVKLTQSMAIIRYIADKH<br>NMLGGCPKERAEISMLEGAVLDIRYGVSRIAYSKDFETLK<br>VDFLSKLPEMLKMFEDRLCHKTYLNGDHVTHPDFMLYD<br>ALDVVLYMDPMCLDAFPKLVCFKKRIEAIPQIDKYLKSSK<br>YIAWPLQGWQATFGGGDHPPKSDGSTSGSGHHHHHHSA<br>GLVPRGSTAIGMKETAAAKFERQHMDSPDLGTGGGSGIE<br>GRGSMGYRGSELDTPKDLQVSETAETSLTLLWKTPLAKF<br>DRYRLNYSLPTGQWVGVQLPRNTTSYVLRGLEPGQEYN<br>VLLTAEKGRHKSKPARVKASTEQAPELENLTVTEVGWD<br>GLRLNWTAADQAYEHFIIQVQEANKVEAARNLTVPGSLR<br>AVDIPGLKAATPYTVSIYGVIQGYRTPVLSAEASTGETPN<br>LGEVVVAEVGWDALKLNWTAPEGAYEYFFIQVQEADTV<br>EAAQNLTVPGGLRSTDLPGLKAATHYTITIRGVTQDFSTT<br>PLSVEVLTEEVPDMGNLTVTEVSWDALRLNWTTPDGTY<br>DQFTIQVQEADQVEEAHNLTVPGSLRSMEIPGLRAGTPYT<br>VTLHGEVRGHSTRPLAVEVVTEDLPQLGDLAVSEVGWD<br>GLRLNWTAADNAYEHFVIQVQEVNKVEAAQNLTLPGSL<br>RAVDIPGLEAATPYRVSIYGVIRGYRTPVLSAEASTAKEPE<br>IGNLNVSDITPESFNLSWMATDGIFETFTIEIIDSNRLLETV<br>EYNISGAERTAHISGLPPSTDFIVYLSGLAPSIRTKTISATA<br>TTEALPLLENLTISDINPYGFTVSWMASENAFDSFLVTVV<br>DSGKLLDPQEFTLSGTQRKLELRGLITGIGYEVMVSGFTQ<br>GHQTKPLRAEIVTEAMGSPKEVIFSDITENSATVSWRAPT<br>AQVESFRITYVPITGGTPSMVTVDGTKTQTRLVKLIPGVE<br>YLVSIIAMKGFEESEPVSGSFTTASGLNDIFEAQKIEWHEG<br>THHHHHH | SEQ ID NO: 4 |
| muTNC | MSPILGYWKIKGLVQPTRLLLEYLEEKYEEHLYERDEGD<br>KWRNKKFELGLEFPNLPYYIDGDVKLTQSMAIIRYIADKH<br>NMLGGCPKERAEISMLEGAVLDIRYGVSRIAYSKDFETLK<br>VDFLSKLPEMLKMFEDRLCHKTYLNGDHVTHPDFMLYD<br>ALDVVLYMDPMCLDAFPKLVCFKKRIEAIPQIDKYLKSSK<br>YIAWPLQGWQATFGGGDHPPKSDGSTSGSGHHHHHHSA<br>GLVPRGSTAIGMKETAAAKFERQHMDSPDLGTGGGSGIE<br>GRGSMGYRGSELDTPKDLQVSETAETSLTLLWKTPLAKF<br>DRYRLNYSLPTGQWVGVQLPRNTTSYVLRGLEPGQEYN<br>VLLTAEKGRHKSKPARVKASTEEVPSLENLTVTEAGWDG<br>LRLNWTADDLAYEYFVIQVQEANNVETAHNFTVPGNLR<br>AADIPGLKVATSYRVSIYGVARGYRTPVLSAETSTGTTPN<br>LGEVTVAEVGWDALTLNWTAPEGAYKNFFIQVLEADTT<br>QTVQNLTVPGGLRSVDLPGLKAATRYYITLRGVTQDFGT<br>APLSVEVLTEDLPQLGGLSVTEVSWDGLTLNWTTDDLAY<br>KHFVVQVQEANNVEAAQNLTVPGSLRAVDIPGLKADTP<br>YRVSIYGVIQGYRTPMLSTDVSTAREPEIGNLNVSDVTPK<br>SFNLSWTATDGIFDMFTIEIIDSNRLLQTAEHNISGAERTA<br>HISGLPPSTDFIVYLSGIAPSIRTKTISTTATTEALTAMGSPK<br>EVIFSDITENSATVSWRAPTAQVESFRITYVPITGGTPSMV<br>TVDGTKTQTRLVKLIPGVEYLVSIIAMKGFEESEPVSGSFT<br>TASGLNDIFEAQKIEWHEGTHHHHHH | SEQ ID NO: 5 |
| cynoTNC | MSPILGYWKIKGLVQPTRLLLEYLEEKYEEHLYERDEGD<br>KWRNKKFELGLEFPNLPYYIDGDVKLTQSMAIIRYIADKH<br>NMLGGCPKERAEISMLEGAVLDIRYGVSRIAYSKDFETLK<br>VDFLSKLPEMLKMFEDRLCHKTYLNGDHVTHPDFMLYD<br>ALDVVLYMDPMCLDAFPKLVCFKKRIEAIPQIDKYLKSSK<br>YIAWPLQGWQATFGGGDHPPKSDGSTSGSGHHHHHHSA<br>GLVPRGSTAIGMKETAAAKFERQHMDSPDLGTGGGSGIE<br>GRGSMGYRGSELDTPKDLRVSETAETSLTLFWKTPLAKF<br>DRYRLNYSLPTGQWVGVQLPRNTTSYVLRGLEPGQEYN<br>VLLTAEKGRHKSKPARVKASTEQAPELENLTVTEVGWD<br>GLRLNWTAADQAYEHFVIQVQEANKVEAAQNLTVPGNL<br>RAVDIPGLKAATPYTVSIYGVIQGYRTPVLSAEASTGETP<br>NLGEVMVSEVGWDALKLNWTVPEGAYEYFFIQVQEADT<br>VEAAQNHTVPGGLRSTDLPGLKAATHYTITIRGVTQDFST<br>TPLSVEVLTEELPQLGDLAVSEVGWDGLRLNWTAADQA<br>YEHFVIQVQEVNKVEAAQNLTVPGSLRAVDIPGLKAATP<br>YTVSIYGVIRGYRTPVLSAEASTAKEPEIGNLNVSDITPESF<br>SLSWTATDGIFETFTIEIIDSNRLLEIVEYNISGAERTAHISG<br>LPPSTDFIVYLSGLAPSFRTKTISATATTEALTAMGSPKEVI | SEQ ID NO: 6 |

TABLE 3-continued

| Sequences of TnC antigens used for cross-species affinity determination (reference Table 26) | | |
|---|---|---|
| Antigen | Sequence | SEQ ID NO |
| | FSDITENSATVSWRAPTAQVESFRITYVPITGGTPSMVTVD GTKTQTRLVKLVPGVEYLVNIIAMKGFEESEPVSGSFTTA SGLNDIFEAQKIEWHEGTHHHHHH | |

TABLE 4

| Sequences of TnC antigens used for affinity determination (reference Table 5) | | |
|---|---|---|
| Antigen pETR # batch ID | Protein Sequence | SEQ ID NO |
| GST huTNC fn5 A1234 BC fn6 B | MSPILGYWKIKGLVQPTRLLLEYLEEKYEEHLYERDEGDK WRNKKFELGLEFPNLPYYIDGDVKLTQSMAIIRYIADKHN MLGGCPKERAEISMLEGAVLDIRYGVSRIAYSKDFETLKV DFLSKLPEMLKMFEDRLCHKTYLNGDHVTHPDFMLYDAL DVVLYMDPMCLDAFPKLVCFKKRIEAIPQIDKYLKSSKYI AWPLQGWQATFGGGDHPPKSDGSTSGSGHHHHHHSAGL VPRGSTAIGMKETAAAKFERQHMDSPDLGTGGGSGIEGR GSMGYRGSELDTPKDLQVSETAETSLTLLWKTPLAKFDR YRLNYSLPTGQWVGVQLPRNTTSYVLRGLEPGQEYNVLL TAEKGRHKSKPARVKASTEQAPELENLTVTEVGWDGLRL NWTAADQAYEHFIIQVQEANKVEAARNLTVPGSLRAVDI PGLKAATPYTVSIYGVIQGYRTPVLSAEASTGETPNLGEV VVAEVGWDALKLNWTAPEGAYEYFFIQVQEADTVEAAQ NLTVPGGLRSTDLPGLKAATHYTITIRGVTQDFSTTPLSVE VLTEEVPDMGNLTVTEVSWDALRLNWTTPDGTYDQFTIQ VQEADQVEEAHNLTVPGSLRSMEIPGLRAGTPYTVTLHGE VRGHSTRPLAVEVVTEDLPQLGDLAVSEVGWDGLRLNW TAADNAYEHFVIQVQEVNKVEAAQNLTLPGSLRAVDIPG LEAATPYRVSIYGVIRGYRTPVLSAEASTAKEPEIGNLNVS DITPESFNLSWMATDGIFETFTIEIIDSNRLLETVEYNISGAE RTAHISGLPPSTDFIVYLSGLAPSIRTKTISATATTEALPLLE NLTISDINPYGFTVSWMASENAFDSFLVTVVDSGKLLDPQ EFTLSGTQRKLELRGLITGIGYEVMVSGFTQGHQTKPLRA EIVTEAMGSPKEVIFSDITENSATVSWRAPTAQVESFRITY VPITGGTPSMVTVDGTKTQTRLVKLIPGVEYLVSIIAMKGF EESEPVSGSFTTASGLNDIFEAQKIEWHEGTHHHHHH | SEQ ID NO: 7 |
| GST huTNCfn5 mu A124 BC hu fn6 B | MSPILGYWKIKGLVQPTRLLLEYLEEKYEEHLYERDEGDK WRNKKFELGLEFPNLPYYIDGDVKLTQSMAIIRYIADKHN MLGGCPKERAEISMLEGAVLDIRYGVSRIAYSKDFETLKV DFLSKLPEMLKMFEDRLCHKTYLNGDHVTHPDFMLYDAL DVVLYMDPMCLDAFPKLVCFKKRIEAIPQIDKYLKSSKYI AWPLQGWQATFGGGDHPPKSDGSTSGSGHHHHHHSAGL VPRGSTAIGMKETAAAKFERQHMDSPDLGTGGGSGIEGR GSMGYRGSELDTPKDLQVSETAETSLTLLWKTPLAKFDR YRLNYSLPTGQWVGVQLPRNTTSYVLRGLEPGQEYNVLL TAEKGRHKSKPARVKASTEEVPSLENLTVTEAGWDGLRL NWTADDLAYEYFVIQVQEANNVETAHNFTVPGNLRAADI PGLKVATSYRVSIYGVARGYRTPVLSAETSTGTTPNLGEV TVAEVGWDALTLNWTAPEGAYKNFFIQVLEADTTQTVQ NLTVPGGLRSVDLPGLKAATRYYITLRGVTQDFGTAPLSV EVLTEDLPQLGGLSVTEVSWDGLTLNWTTDDLAYKHFVV QVQEANNVEAAQNLTVPGSLRAVDIPGLKADTPYRVSIY GVIQGYRTPMLSTDVSTAREPEIGNLNVSDVTPKSFNLSW TATDGIFDMFTIEIIDSNRLLQTAEHNISGAERTAHISGLPPS TDFIVYLSGIAPSIRTKTISTTATTEALTAMGSPKEVIFSDIT ENSATVSWRAPTAQVESFRITYVPITGGTPSMVTVDGTKT QTRLVKLIPGVEYLVSIIAMKGFEESEPVSGSFTTASGLNDI FEAQKIEWHEGTHHHHHH | SEQ ID NO: 8 |
| GST TNC hu fn5 B-C fn6 B | MSPILGYWKIKGLVQPTRLLLEYLEEKYEEHLYERDEGDK WRNKKFELGLEFPNLPYYIDGDVKLTQSMAIIRYIADKHN MLGGCPKERAEISMLEGAVLDIRYGVSRIAYSKDFETLKV DFLSKLPEMLKMFEDRLCHKTYLNGDHVTHPDFMLYDAL DVVLYMDPMCLDAFPKLVCFKKRIEAIPQIDKYLKSSKYI AWPLQGWQATFGGGDHPPKSDGSTSGSGHHHHHHSAGL VPRGSTAIGMKETAAAKFERQHMDSPDLGTGGGSGIEGR GSMGYRGSELDTPKDLQVSETAETSLTLLWKTPLAKFDR YRLNYSLPTGQWVGVQLPRNTTSYVLRGLEPGQEYNVLL | SEQ ID NO: 9 |

TABLE 4-continued

Sequences of TnC antigens used for affinity determination (reference Table 5)

| Antigen<br>pETR #<br>batch ID | Protein Sequence | SEQ ID NO |
|---|---|---|
| | TAEKGRHKSKPARVKASTAKEPEIGNLNVSDITPESFNLS<br>WMATDGIFETFTIEIIDSNRLLETVEYNISGAERTAHISGLP<br>PSTDFIVYLSGLAPSIRTKTISATATTEALPLLENLTISDINP<br>YGFTVSWMASENAFDSFLVTVVDSGKLLDPQEFTLSGTQ<br>RKLELRGLITGIGYEVMVSGFTQGHQTKPLRAEIVTAMGS<br>PKEVIFSDITENSATVSWRAPTAQVESFRITYVPITGGTPSM<br>VTVDGTKTQTRLVKLIPGVEYLVSIIAMKGFEESEPVSGSF<br>TTASGLNDIFEAQKIEWHEGTHHHHHH | |
| GST huTNC<br>fn5 A1234 fn6 B | MSPILGYWKIKGLVQPTRLLLEYLEEKYEEHLYERDEGDK<br>WRNKKFELGLEFPNLPYYIDGDVKLTQSMAIIRYIADKHN<br>MLGGCPKERAEISMLEGAVLDIRYGVSRIAYSKDFETLKV<br>DFLSKLPEMLKMFEDRLCHKTYLNGDHVTHPDFMLYDAL<br>DVVLYMDPMCLDAFPKLVCFKKRIEAIPQIDKYLKSSKYI<br>AWPLQGWQATFGGGDHPPKSDGSTSGSGHHHHHHSAGL<br>VPRGSTAIGMKETAAAKFERQHMDSPDLGTGGGSGIEGR<br>GSMGYRGSELDTPKDLQVSETAETSLTLLWKTPLAKFDR<br>YRLNYSLPTGQWVGVQLPRNTTSYVLRGLEPGQEYNVLL<br>TAEKGRHKSKPARVKASTEQAPELENLTVTEVGWDGLRL<br>NWTAADQAYEHFIIQVQEANKVEAARNLTVPGSLRAVDI<br>PGLKAATPYTVSIYGVIQGYRTPVLSAEASTGETPNLGEV<br>VVAEVGWDALKLNWTAPEGAYEYFFIQVQEADTVEAAQ<br>NLTVPGGLRSTDLPGLKAATHYTITIRGVTQDFSTTPLSVE<br>VLTEEVPDMGNLTVTEVSWDALRLNWTTPDGTYDQFTIQ<br>VQEADQVEEAHNLTVPGSLRSMEIPGLRAGTPYTVTLHGE<br>VRGHSTRPLAVEVVTEDLPQLGDLAVSEVGWDGLRLNW<br>TAADNAYEHFVIQVQEVNKVEAAQNLTLPGSLRAVDIPG<br>LEAATPYRVSIYGVIRGYRTPVLSAEASTAKEAMGSPKEVI<br>FSDITENSATVSWRAPTAQVESFRITYVPITGGTPSMVTVD<br>GTKTQTRLVKLIPGVEYLVSIIAMKGFEESEPVSGSFTTAS<br>GLNDIFEAQKIEWHEGTHHHHHH | SEQ ID NO: 10 |
| huTNC A4 B | MSPILGYWKIKGLVQPTRLLLEYLEEKYEEHLYERDEGDK<br>WRNKKFELGLEFPNLPYYIDGDVKLTQSMAIIRYIADKHN<br>MLGGCPKERAEISMLEGAVLDIRYGVSRIAYSKDFETLKV<br>DFLSKLPEMLKMFEDRLCHKTYLNGDHVTHPDFMLYDAL<br>DVVLYMDPMCLDAFPKLVCFKKRIEAIPQIDKYLKSSKYI<br>AWPLQGWQATFGGGDHPPKSDGSTSGSGHHHHHHSAGL<br>VPRGSTAIGMKETAAAKFERQHMDSPDLGTGGGSGIEGR<br>GSMGYRGSEDLPQLGDLAVSEVGWDGLRLNWTAADNA<br>YEHFVIQVQEVNKVEAAQNLTLPGSLRAVDIPGLEAATPY<br>RVSIYGVIRGYRTPVLSAEASTASGLNDIFEAQKIEWHEGT<br>HHHHHH | SEQ ID NO: 11 |
| huTNC A1 B | MSPILGYWKIKGLVQPTRLLLEYLEEKYEEHLYERDEGDK<br>WRNKKFELGLEFPNLPYYIDGDVKLTQSMAIIRYIADKHN<br>MLGGCPKERAEISMLEGAVLDIRYGVSRIAYSKDFETLKV<br>DFLSKLPEMLKMFEDRLCHKTYLNGDHVTHPDFMLYDAL<br>DVVLYMDPMCLDAFPKLVCFKKRIEAIPQIDKYLKSSKYI<br>AWPLQGWQATFGGGDHPPKSDGSTSGSGHHHHHHSAGL<br>VPRGSTAIGMKETAAAKFERQHMDSPDLGTGGGSGIEGR<br>GSMGYRGSEQAPELENLTVTEVGWDGLRLNWTAADQAY<br>EHFIIQVQEANKVEAARNLTVPGSLRAVDIPGLKAATPYT<br>VSIYGVIQGYRTPVLSAEASTASGLNDIFEAQKIEWHEGTH<br>HHHHH | SEQ ID NO: 12 |

Example 2

Selection of Anti-TnC Antibodies from Generic Fab Libraries

Anti-TnC antibodies were selected from two different generic phage display libraries: DP88-4 (clone 18D4) and lambda-DP47 (clone 11C7).

Library Construction

The DP88-4 library was constructed on the basis of human germline genes using the V-domain pairing Vk1_5 (kappa light chain) and VH1_69 (heavy chain) comprising randomized sequence space in CDR3 of the light chain (L3, 3 different lengths) and CDR3 of the heavy chain (H3, 3 different lengths). Library generation was performed by assembly of 3 PCR-amplified fragments applying splicing by overlapping extension (SOE) PCR. Fragment 1 comprises the 5' end of the antibody gene including randomized L3, fragment 2 is a central constant fragment spanning from L3 to H3 whereas fragment 3 comprises randomized H3 and the 3' portion of the antibody gene. The following primer combinations were used to generate these library fragments for DP88-4 library: fragment 1 (forward primer LMB3 combined with reverse primers Vk1_5_L3r_S or Vk1_5_L3r_SY or Vk1_5_L3r_SPY), fragment 2 (forward primer RJH31 combined with reverse primer RJH32) and fragment 3 (forward primers DP88-v4-4 or DP88-v4-6 or DP88-v4-8 combined with reverse primer fdseqlong), respectively. PCR parameters for production of library fragments were 5 min initial denaturation at 94° C., 25 cycles of 1 min 94° C., 1 min 58° C., 1 min 72° C. and terminal elongation for 10 min at 72° C. For assembly PCR, using equimolar ratios of the gel-purified single fragments as template, parameters were 3 min initial denaturation at 94° C. and 5 cycles of 30 s 94° C., 1 min 58° C., 2 min 72° C. At this stage, outer primers (LMB3 and fdseqlong) were added and additional 20 cycles were performed prior to a terminal elongation for 10 min at 72° C. After assembly of sufficient amounts of full length randomized Fab constructs, they were digested NcoI/NheI and ligated into similarly treated acceptor phagemid vector. Purified ligations were used for ~60 transformations into electrocompetent *E. coli* TG1. Phagemid particles displaying the Fab library were rescued and purified by PEG/NaCl purification to be used for selections. These library construction steps were repeated three times to obtain a final library size of $4.4\times10^9$. Percentages of functional clones, as determined by C-terminal tag detection in dot blot, were 92.6% for the light chain and 93.7% for the heavy chain, respectively.

The lambda-DP47 library was constructed on the basis of human germline genes using the following V-domain pairings: V13_19 lambda light chain with VH3_23 heavy chain. The library was randomized in CDR3 of the light chain (L3) and CDR3 of the heavy chain (H3) and was assembled from 3 fragments by "splicing by overlapping extension" (SOE) PCR. Fragment 1 comprises the 5' end of the antibody gene including randomized L3, fragment 2 is a central constant fragment spanning from the end of L3 to the beginning of H3 whereas fragment 3 comprises randomized H3 and the 3' portion of the Fab fragment. The following primer combinations were used to generate library fragments for library: fragment 1 (LMB3-V1_3_19_L3r_V/V1_3_19_L3r_HV/V1_3_19_L3r_HLV), fragment 2 (RJH80-DP47CDR3_ba (mod)) and fragment 3 (DP47-v4-4/DP47-v4-6/DP47-v4-8-fdseqlong). PCR parameters for production of library fragments were 5 min initial denaturation at 94° C., 25 cycles of 60 sec 94° C., 60 sec 55° C., 60 sec 72° C. and terminal elongation for 10 min at 72° C. For assembly PCR, using equimolar ratios of the 3 fragments as template, parameters were 3 min initial denaturation at 94° C. and 5 cycles of 60 s 94° C., 60 sec 55° C., 120 sec 72° C. At this stage, outer primers were added and additional 20 cycles were performed prior to a terminal elongation for 10 min at 72° C. After assembly of sufficient amounts of full length randomized Fab fragments, they were digested with NcoI/NheI alongside with similarly treated acceptor phagemid vector. 15 μg of Fab library insert were ligated with 13.3 μg of phagemid vector. Purified ligations were used for 60 transformations resulting in $1.5\times10^9$ transformants Phagemid particles displaying the Fab library were rescued and purified by PEG/NaCl purification to be used for selections.

Phage Display Selections & ELISA Screening

Human GST-fused TnC fn5 A1234 BC fn6 as antigen for the phage display selections was expressed in *E. coli* and in vivo site-specifically biotinylated via co-expression of BirA biotin ligase at the avi-tag recognition sequence located at the C-terminus of the fusion protein (production of antigens according to Example 1, sequences derived from Table 4). This antigen comprises the human TnC extra splice domains A1, A2, A3, A4, B, and C, located between the two fibronectin type III domains 5 and 6. The phage display selections aimed at selecting binders to any of these extra splice domains and determine the domain specificity in a subsequent step by surface plasmon resonance using additional antigen constructs comprising fewer extra splice domains.

Selection rounds (biopanning) were performed in solution according to the following pattern: 1. Pre-clearing of $\sim10^{12}$ phagemid particles with an unrelated GST-fusion protein that also carried an avi-tag and His6-tag similar to the TnC target cell antigen to deplete the libraries of antibodies recognizing the three different tags, 2. incubation of the pre-cleared phagemid particles in the supernatant with 100 nM biotinylated human GST-fused TnC fn5 A1234 BC fn6 for 0.5 hours in the presence of an unrelated non-biotinylated GST-fusion protein for further depletion of tag-binders in a total volume of 1 ml, 3. capture of biotinylated human GST-fused TnC fn5 A1234 BC fn6 and attached specifically binding phage by transfer to 4 wells of a neutravidin pre-coated microtiter plate for 10 minutes (in rounds 1 & 3), 4. washing of respective wells using 5×PBS/Tween20 and 5×PBS, 5. elution of phage particles by addition of 250 μl 100 mM TEA (triethylamine) per well for 10 minutes and neutralization by addition of 500 μl 1 M Tris/HCl pH 7.4 to the pooled eluates from 4 wells, 6. re-infection of log-phase *E. coli* TG1 cells with the supernatant of eluted phage particles, infection with helperphage VCSM13, incubation on a shaker at 30° C. over night and subsequent PEG/NaCl precipitation of phagemid particles to be used in the next selection round. Selections were carried out over 3 rounds using constant antigen concentrations of 100 nM. In round 2, in order to avoid enrichment of binders to neutravidin, capture of antigen: phage complexes was performed by addition of $5.4\times10^7$ streptavidin-coated magnetic beads. Specific binders were identified by ELISA after rounds 2 and 3 as follows: 100 μl of 100 nM biotinylated human GST-fused TnC fn5 A1234 BC fn6 were coated on neutravidin plates. Fab-containing bacterial supernatants were added and binding Fabs were detected via their Flag-tags using an anti-Flag/HRP secondary antibody. Clones exhibiting signals on human GST-fused TnC fn5 A1234 BC fn6 and being negative on an unrelated GST-fusion protein carrying the same tags as the target, were short-listed for further analyses. They were bacterially expressed in a 0.5 liter culture volume, affinity purified and further characterized by SPR-analysis using BioRad's ProteOn XPR36 biosensor to test cross-reactivity to murine TnC and to determine which extra splice domains the antibodies recognize.

SPR-Analysis Using BioRad's ProteOn XPR36 Biosensor

Affinities ($K_D$) of selected clones were measured by surface plasmon resonance (SPR) using a ProteOn XPR36 instrument (Biorad) at 25° C. with biotinylated human and murine TnC antigens immobilized on NLC chips by neutravidin capture. Immobilization of antigens (ligand): Recombinant antigens were diluted with PBST (10 mM phosphate, 150 mM sodium chloride pH 7.4, 0.005% Tween 20) to 10 μg/ml, then injected at 30 μl/minute in vertical orientation. Injection of analytes: For 'one-shot kinetics' measurements, injection direction was changed to horizontal orientation, two-fold dilution series of purified Fab were injected simultaneously along separate channels 1-5, with association times of 200 s, and dissociation times of 240 s, respectively. Buffer (PBST) was injected along the sixth channel to provide an "in-line" blank for referencing. Association rate constants ($k_{on}$) and dissociation rate constants ($k_{off}$) were calculated using a simple one-to-one Langmuir binding model in ProteOn Manager v3.1 software by simultaneously fitting the association and dissociation sensorgrams. The equilibrium dissociation constant ($K_D$) was calculated as the ratio $k_{off}/k_{on}$. Table 5 lists the equilibrium dissociation constants ($K_D$) of the two selected clones 18D4 and 11C7 for several TnC antigens differing in species and composition of the extra splice domains.

TABLE 5

Equilibrium dissociation constants ($K_D$) for clones 18D4 and 11C7

| antigen | clone 18D4 $K_D$ [nM] | clone 11C7 $K_D$ [nM] |
|---|---|---|
| GST huTNC fn5 A1234 BC fn6 B | 4.0 | 2.3 |
| GST huTNCfn5 mu A124 BC hu fn6 B | 11.2 | 1.9 |
| GST TNC hu fn5 B-C fn6 B | n.a. | 1.0 |
| GST huTNC fn5 A1234 fn6 B | 5.0 | n.a. |
| huTNC A4 B | 2.0 | n.a. |
| huTNC A1 B | 5.6 | n.a. |

TABLE 6

DNA sequence of generic phage-displayed DP88-4 library (Vk1_5/VH1_69) template used for PCRs

| Construct | Base pair sequence | SEQ ID NO |
|---|---|---|
| pRJH33 library template DP88-4 library; complete Fab coding region comprising PelB leader sequence + Vk1_5 kappa V-domain + CL constant domain for light chain and PelB + VH1_69 V-domain + CH1 constant domain for heavy chain) | ATGAAATACCTATTGCCTACGGCAGCCGCTGGATTGTTAT<br>TACTCGCGGCCCAGCCGGCCATGGCCGACATCCAGATGAC<br>CCAGTCTCCTTCCACCCTGTCTGCATCTGTAGGAGACCGTG<br>TCACCATCACTTGCCGTGCCAGTCAGAGTATTAGTAGCTG<br>GTTGGCCTGGTATCAGCAGAAACCAGGGAAAGCCCCTAA<br>GCTCCTGATCTATGATGCCTCCAGTTTGGAAAGTGGGGTC<br>CCATCACGTTTCAGCGGCAGTGGATCCGGGACAGAATTCA<br>CTCTCACCATCAGCAGCTTGCAGCCTGATGATTTTGCAACT<br>TATTACTGCCAACAGTATAATAGTTATTCTACGTTTGGCCA<br>GGGCACCAAAGTCGAGATCAAGCGTACGGTGGCTGCACC<br>ATCTGTCTTCATCTTCCCGCCATCTGATGAGCAGTTGAAAT<br>CTGGAACTGCCTCTGTTGTGTGCCTGCTGAATAACTTCTAT<br>CCCAGAGAGGCCAAAGTACAGTGGAAGGTGGATAACGCC<br>CTCCAATCGGGTAACTCCCAGGAGAGTGTCACAGAGCAG<br>GACAGCAAGGACAGCACCTACAGCCTCAGCAGCACCCTG<br>ACGCTGAGCAAAGCAGACTACGAGAAACACAAAGTCTAC<br>GCCTGCGAAGTCACCCATCAGGGCCTGAGCTCGCCCGTCA<br>CAAAGAGCTTCAACAGGGGAGAGTGTGGAGCCGCAGAAC<br>AAAAACTCATCTCAGAAGAGGATCTGAATGGAGCCGCAG<br>ACTACAAGGACGACGACGACAAGGGTGCCGCATAATAAG<br>GCGCGCCAATTCTATTTCAAGGAGACAGTCATATGAAATA<br>CCTGCTGCCGACCGCTGCTGCTGGTCTGCTGCTCCTCGCTG<br>CCCAGCCGGCGATGGCCCAGGTGCAATTGGTGCAGTCTGG<br>GGCTGAGGTGAAGAAGCCTGGGTCCTCGGTGAAGGTCTCC<br>TGCAAGGCCTCCGGAGGCACATTCAGCAGCTACGCTATAA<br>GCTGGGTGCGACAGGCCCCTGGACAAGGGCTCGAGTGGA<br>TGGGAGGGATCATCCCTATCTTTGGTACAGCAAACTACGC<br>ACAGAAGTTCCAGGGCAGGGTCACCATTACTGCAGACAA<br>ATCCACGAGCACAGCCTACATGGAGCTGAGCAGCCTGAG<br>ATCTGAGGACACCGCCGTGTATTACTGTGCGAGACTATCC<br>CCAGGCGGTTACTATGTTATGGATGCCTGGGGCCAAGGGA<br>CCACCGTGACCGTCTCCTCAGCTAGCACCAAAGGCCCATC<br>GGTCTTCCCCCTGGCACCCTCCTCCAAGAGCACCTCTGGG<br>GGCACAGCGGCCCTGGGCTGCCTGGTCAAGGACTACTTCC<br>CCGAACCGGTGACGGTGTCGTGGAACTCAGGCGCCCTGAC<br>CAGCGGCGTGCACACCTTCCCGGCTGTCCTACAGTCCTCA<br>GGACTCTACTCCCTCAGCAGCGTGGTGACCGTGCCCTCCA<br>GCAGCTTGGGCACCCAGACCTACATCTGCAACGTGAATCA<br>CAAGCCCAGCAACACCAAAGTGGACAAGAAAGTTGAGCC<br>CAAATCTTGTGACGCGGCCGCAAGCACTAGTGCCCATCAC<br>CATCACCATCACGCCGCGGCA | SEQ ID NO: 13 |

TABLE 7

Base pair sequence of DP88-4 library (Vk1_5/VH1_69) germline template

| Construct | Base pair sequence | SEQ ID NO |
|---|---|---|
| Fab light chain V1_5 | GACATCCAGATGACCCAGTCTCCTTCCACCCTGTCTGCATC<br>TGTAGGAGACCGTGTCACCATCACTTGCCGTGCCAGTCAG<br>AGTATTAGTAGCTGGTTGGCCTGGTATCAGCAGAAACCAG<br>GGAAAGCCCCTAAGCTCCTGATCTATGATGCCTCCAGTTT<br>GGAAAGTGGGGTCCCATCACGTTTCAGCGGCAGTGGATCC | SEQ ID NO: 14 |

TABLE 7-continued

| Base pair sequence of DP88-4 library (Vk1_5/VH1_69) germline template | | |
|---|---|---|
| Construct | Base pair sequence | SEQ ID NO |
| | GGGACAGAATTCACTCTCACCATCAGCAGCTTGCAGCCTG<br>ATGATTTTGCAACTTATTACTGCCAACAGTATAATAGTTAT<br>TCTACGTTTGGCCAGGGCACCAAAGTCGAGATCAAGCGTA<br>CGGTGGCTGCACCATCTGTCTTCATCTTCCCGCCATCTGAT<br>GAGCAGTTGAAATCTGGAACTGCCTCTGTTGTGTGCCTGC<br>TGAATAACTTCTATCCCAGAGAGGCCAAAGTACAGTGGAA<br>GGTGGATAACGCCCTCCAATCGGGTAACTCCCAGGAGAGT<br>GTCACAGAGCAGGACAGCAAGGACAGCACCTACAGCCTC<br>AGCAGCACCCTGACGCTGAGCAAAGCAGACTACGAGAAA<br>CACAAAGTCTACGCCTGCGAAGTCACCCATCAGGGCCTGA<br>GCTCGCCCGTCACAAAGAGCTTCAACAGGGGAGAGTGTG<br>GAGCCGCAGAACAAAAACTCATCTCAGAAGAGGATCTGA<br>ATGGAGCCGCAGACTACAAGGACGACGACGACAAGGGTG<br>CCGCA | |
| Fab heavy chain VH1_69 | CAGGTGCAATTGGTGCAGTCTGGGGCTGAGGTGAAGAAG<br>CCTGGGTCCTCGGTGAAGGTCTCCTGCAAGGCCTCCGGAG<br>GCACATTCAGCAGCTACGCTATAAGCTGGGTGCGACAGGC<br>CCCTGGACAAGGGCTCGAGTGGATGGGAGGGATCATCCCT<br>ATCTTTGGTACAGCAAACTACGCACAGAAGTTCCAGGGCA<br>GGGTCACCATTACTGCAGACAAATCCACGAGCACAGCCTA<br>CATGGAGCTGAGCAGCCTGAGATCTGAGGACACCGCCGT<br>GTATTACTGTGCGAGACTATCCCCAGGCGGTTACTATGTT<br>ATGGATGCCTGGGGCCAAGGGACCACCGTGACCGTCTCCT<br>CAGCTAGCACCAAAGGCCCATCGGTCTTCCCCCTGGCACC<br>CTCCTCCAAGAGCACCTCTGGGGGCACAGCGGCCCTGGGC<br>TGCCTGGTCAAGGACTACTTCCCCGAACCGGTGACGGTGT<br>CGTGGAACTCAGGCGCCCTGACCAGCGGCGTGCACACCTT<br>CCCGGCTGTCCTACAGTCCTCAGGACTCTACTCCCTCAGC<br>AGCGTGGTGACCGTGCCCTCCAGCAGCTTGGGCACCCAGA<br>CCTACATCTGCAACGTGAATCACAAGCCCAGCAACACCAA<br>AGTGGACAAGAAAGTTGAGCCCAAATCTTGTGACGCGGC<br>CGCAAGCACTAGTGCCCATCACCATCACCATCACGCCGCG<br>GCA | SEQ ID NO: 15 |

TABLE 8

| Amino acid sequence of DP88-4 library (Vk1_5/VH1_69) germline template | | |
|---|---|---|
| Construct | Base pair sequence | SEQ ID NO |
| Fab light chain Vk1_5 | DIQMTQSPSTLSASVGDRVTITCRASQSISSWLAWYQQKPGK<br>APKLLIYDASSLESGVPSRFSGSGSGTEFTLTISSLQPDDFATY<br>YCQQYNSYSTFGQGTKVEIKRTVAAPSVFIFPPSDEQLKSGTA<br>SVVCLLNNFYPREAKVQWKVDNALQSGNSQESVTEQDSKD<br>STYSLSSTLTLSKADYEKHKVYACEVTHQGLSSPVTKSFNRG<br>ECGAAEQKLISEEDLNGAADYKDDDDKGAA | SEQ ID NO: 16 |
| Fab heavy chain VH1_69 (DP88) | QVQLVQSGAEVKKPGSSVKVSCKASGGTFSSYAISWVRQAP<br>GQGLEWMGGIIPIFGTANYAQKFQGRVTITADKSTSTAYMEL<br>SSLRSEDTAVYYCARLSPGGYYVMDAWGQGTTVTVSSAST<br>KGPSVFPLAPSSKSTSGGTAALGCLVKDYFPEPVTVSWNSGA<br>LTSGVHTFPAVLQSSGLYSLSSVVTVPSSSLGTQTYICNVNHK<br>PSNTKVDKKVEPKSCDAAASTSAHHHHHHAAA | SEQ ID NO: 17 |

TABLE 9

| Primer sequences used for generation of DP88-4 library (Vk1_5/VH1_69) | | |
|---|---|---|
| Primer name | Primer sequence 5'-3' | SEQ ID NO |
| LMB3 | CAGGAAACAGCTATGACCATGATTAC | SEQ ID NO: 18 |
| Vk1_5_L3r_S | CTCGACTTTGGTGCCCTGGCCAAACGTSBAATA<br>CGAATTATACTGTTGGCAGTAATAAGTTGCAAAATCAT | SEQ ID NO: 19 |

TABLE 9-continued

Primer sequences used for generation of DP88-4 library (Vk1_5/VH1_69)

| Primer name | Primer sequence 5'-3' | SEQ ID NO |
|---|---|---|
| Vk1_5_L3r_SY | CTCGACTTTGGTGCCCTGGCCAAACGTMHRSGRATACGA ATTATACTGTTGGCAGTAATAAGTTGCAAAATCAT | SEQ ID NO: 20 |
| Vk1_5_L3r_SPY | CTCGACTTTGGTGCCCTGGCCAAACGTMHHMSSSGRATAC GAATTATACTGTTGGCAGTAATAAGTTGCAAAATCAT | SEQ ID NO: 21 |
| RJH31 | ACGTTTGGCCAGGGCACCAAAGTCGAG | SEQ ID NO: 22 |
| RJH32 | TCTCGCACAGTAATACACGGCGGTGTCC | SEQ ID NO: 23 |
| DP88-v4-4 | GGACACCGCCGTGTATTACTGTGCGAGA-1-2-2-3-4-GAC-TAC-TGGGGCCAAGGGACCACCGTGACCGTCTCC | SEQ ID NO: 24 |
| DP88-v4-6 | GGACACCGCCGTGTATTACTGTGCGAGA-1-2-2-2-2-3-4-GAC-TAC-TGGGGCCAAGGGACCACCGTGACCGTCTCC | SEQ ID NO: 25 |
| DP88-v4-8 | GGACACCGCCGTGTATTACTGTGCGAGA-1-2-2-2-2-2-2-3-4-GAC-TAC-TGGGGCCAAGGGACCACCGTGACCGTCTCC | SEQ ID NO: 26 |
| fdseqlong | GACGTTAGTAAATGAATTTTCTGTATGAGG | SEQ ID NO: 27 |

Underlined bases: 60% given sequence and 40% N; Bases in italics: 60% given sequence and 40% M.
1: G/D = 20%, E/V/S = 10%, A/P/R/L/T/Y = 5%;
2: G/Y/S = 15%, A/D/T/R/P/L/V/N/W/F/I/E = 4.6%;
3: G/A/Y = 20%, P/W/S/D/T = 8%;
4: F = 46%, L/M = 15%, G/I/Y = 8%.

TABLE 10

DNA sequence of generic phage-displayed lambda-DP47 library (Vl3_19/VH3_23) template used for PCRs

| Construct | Base pair sequence | SEQ ID NO |
|---|---|---|
| pRJH53 library template of lambda-DP47 library Vl3_19/VH3_23; complete Fab coding region comprising PelB leader sequence + Vl3_19 lambda V-domain + CL constant domain for light chain and PelB + VH3_23 V-domain + CH1 constant domain for heavy chain including tags | ATGAAATACCTATTGCCTACGGCAGCCGCTGGATTGTTAT<br>TACTCGCGGCCCAGCCGGCCATGGCCTCGTCTGAGCTGAC<br>TCAGGACCCTGCTGTGTCTGTGGCCTTGGGACAGACAGTC<br>AGGATCACATGCCAAGGAGACAGCCTCAGAAGTTATTATG<br>CAAGCTGGTACCAGCAGAAGCCAGGACAGGCCCCTGTAC<br>TTGTCATCTATGGTAAAAACAACCGGCCCTCAGGGATCCC<br>AGACCGATTCTCTGGCTCCAGCTCAGGAAACACAGCTTCC<br>TTGACCATCACTGGGGCTCAGGCGGAAGATGAGGCTGACT<br>ATTACTGTAACTCCCGTGATAGTAGCGGTAATCATGTGGT<br>ATTCGGCGGAGGGACCAAGCTGACCGTCCTAGGACAACC<br>CAAGGCTGCCCCCAGCGTGACCCTGTTCCCCCCCAGCAGC<br>GAGGAATTGCAGGCCAACAAGGCCACCCTGGTCTGCCTGA<br>TCAGCGACTTCTACCCAGGCGCCGTGACCGTGGCCTGGAA<br>GGCCGACAGCAGCCCCGTGAAGGCCGGCGTGGAGACCAC<br>CACCCCCAGCAAGCAGAGCAACAACAAGTACGCCGCCAG<br>CAGCTACCTGAGCCTGACCCCCGAGCAGTGGAAGAGCCA<br>CAGGTCCTACAGCTGCCAGGTGACCCACGAGGGCAGCAC<br>CGTGGAGAAAACCGTGGCCCCCACCGAGTGCAGCGGAGC<br>CGCAGAACAAAAACTCATCTCAGAAGAGGATCTGAATGG<br>AGCCGCAGACTACAAGGACGACGACGACAAGGGTGCCGC<br>ATAATAAGGCGCGCCAATTCTATTTCAAGGAGACAGTCAT<br>ATGAAATACCTGCTGCCGACCGCTGCTGCTGGTCTGCTGC<br>TCCTCGCTGCCCAGCCGGCGATGGCCGAGGTGCAATTGCT<br>GGAGTCTGGGGGAGGCTTGGTACAGCCTGGGGGGTCCCTG<br>AGACTCTCCTGTGCAGCCTCCGGATTCACCTTTAGCAGTTA<br>TGCCATGAGCTGGGTCCGCCAGGCTCCAGGGAAGGGGCT<br>GGAGTGGGTCTCAGCTATTAGTGGTAGTGGTGGTAGCACA<br>TACTACGCAGACTCCGTGAAGGGCCGGTTCACCATCTCCA<br>GAGACAATTCCAAGAACACGCTGTATCTGCAGATGAACA<br>GCCTGAGAGCCGAGGACACGGCCGTATATTACTGTGCGAA<br>ACCGTTTCCGTATTTTGACTACTGGGGCCAAGGAACCCTG<br>GTCACCGTCTCGAGTGCTAGCACCAAAGGCCCATCGGTCT<br>TCCCCCTGGCACCCTCCTCCAAGAGCACCTCTGGGGGCAC<br>AGCGGCCCTGGGCTGCCTGGTCAAGGACTACTTCCCCGAA<br>CCGGTGACGGTGTCGTGGAACTCAGGCGCCCTGACCAGCG<br>GCGTGCACACCTTCCCGGCTGTCCTACAGTCCTCAGGACT<br>CTACTCCCTCAGCAGCGTGGTGACCGTGCCCTCCAGCAGC | SEQ ID NO: 28 |

TABLE 10-continued

DNA sequence of generic phage-displayed lambda-DP47 library (Vl3_19/VH3_23) template used for PCRs

| Construct | Base pair sequence | SEQ ID NO |
|---|---|---|
| | TTGGGCACCCAGACCTACATCTGCAACGTGAATCACAAGC CCAGCAACACCAAAGTGGACAAGAAAGTTGAGCCCAAAT CTTGTGACGCGGCCGCAAGCACTAGTGCCCATCACCATCA CCATCACGCCGCGGCA | |

TABLE 11

Base pair sequence of lambda-DP47 library (Vl3_19/VH3_23) germline template

| Construct | Base pair sequence | SEQ ID NO |
|---|---|---|
| Fab light chain Vl3_19 | TCGTCTGAGCTGACTCAGGACCCTGCTGTGTCTGTGGCCTT GGGACAGACAGTCAGGATCACATGCCAAGGAGACAGCCT CAGAAGTTATTATGCAAGCTGGTACCAGCAGAAGCCAGG ACAGGCCCCTGTACTTGTCATCTATGGTAAAAACAACCGG CCCTCAGGGATCCCAGACCGATTCTCTGGCTCCAGCTCAG GAAACACAGCTTCCTTGACCATCACTGGGGCTCAGGCGGA AGATGAGGCTGACTATTACTGTAACTCCCGTGATAGTAGC GGTAATCATGTGGTATTCGGCGGAGGGACCAAGCTGACCG TCCTAGGACAACCCAAGGCTGCCCCCAGCGTGACCCTGTT CCCCCCCAGCAGCGAGGAATTGCAGGCCAACAAGGCCAC CCTGGTCTGCCTGATCAGCGACTTCTACCCAGGCGCCGTG ACCGTGGCCTGGAAGGCCGACAGCAGCCCCGTGAAGGCC GGCGTGGAGACCACCACCCCCAGCAAGCAGAGCAACAAC AAGTACGCCGCCAGCAGCTACCTGAGCCTGACCCCCGAGC AGTGGAAGAGCCACAGGTCCTACAGCTGCCAGGTGACCC ACGAGGGCAGCACCGTGGAGAAAACCGTGGCCCCCACCG AGTGCAGCGGAGCCGCAGAACAAAAACTCATCTCAGAAG AGGATCTGAATGGAGCCGCAGACTACAAGGACGACGACG ACAAGGGTGCCGCA | SEQ ID NO: 29 |
| Fab heavy chain VH3_23 | GAGGTGCAATTGCTGGAGTCTGGGGGAGGCTTGGTACAGC CTGGGGGGTCCCTGAGACTCTCCTGTGCAGCCTCCGGATT CACCTTTAGCAGTTATGCCATGAGCTGGGTCCGCCAGGCT CCAGGGAAGGGGCTGGAGTGGGTCTCAGCTATTAGTGGTA GTGGTGGTAGCACATACTACGCAGACTCCGTGAAGGGCCG GTTCACCATCTCCAGAGACAATTCCAAGAACACGCTGTAT CTGCAGATGAACAGCCTGAGAGCCGAGGACACGGCCGTA TATTACTGTGCGAAACCGTTTCCGTATTTTGACTACTGGGG CCAAGGAACCCTGGTCACCGTCTCGAGTGCTAGCACCAAA GGCCCATCGGTCTTCCCCCTGGCACCCTCCTCCAAGAGCA CCTCTGGGGGCACAGCGGCCCTGGGCTGCCTGGTCAAGGA CTACTTCCCCGAACCGGTGACGGTGTCGTGGAACTCAGGC GCCCTGACCAGCGGCGTGCACACCTTCCCGGCTGTCCTAC AGTCCTCAGGACTCTACTCCCTCAGCAGCGTGGTGACCGT GCCCTCCAGCAGCTTGGGCACCCAGACCTACATCTGCAAC GTGAATCACAAGCCCAGCAACACCAAAGTGGACAAGAAA GTTGAGCCCAAATCTTGTGACGCGGCCGCAAGCACTAGTG CCCATCACCATCACCATCACGCCGCGGCA | SEQ ID NO: 30 |

TABLE 12

Amino acid sequence of lambda-DP47 library (Vl3_19/VH3_23) germline template

| Construct | Base pair sequence | SEQ ID NO |
|---|---|---|
| Fab light chain Vl3_19 | SSELTQDPAVSVALGQTVRITCQGDSLRSYYASWYQQKPGQ APVLVIYGKNNRPSGIPDRFSGSSSGNTASLTITGAQAEDEAD YYCNSRDSSGNHVVFGGGTKLTVLGQPKAAPSVTLFPPSSEE LQANKATLVCLISDFYPGAVTVAWKADSSPVKAGVETTTPS KQSNNKYAASSYLSLTPEQWKSHRSYSCQVTHEGSTVEKTV APTECSGAAEQKLISEEDLNGAADYKDDDDKGAA | SEQ ID NO: 31 |

TABLE 12-continued

| Amino acid sequence of lambda-DP47 library (Vl3_19/VH3_23) germline template | | |
|---|---|---|
| Construct | Base pair sequence | SEQ ID NO |
| Fab heavy chain VH3_23 (DP47) | EVQLLESGGGLVQPGGSLRLSCAASGFTFSSYAMSWVRQAP<br>GKGLEWVSAISGSGGSTYYADSVKGRFTISRDNSKNTLYLQ<br>MNSLRAEDTAVYYCAKPFPYFDYWGQGTLVTVSSASTKGPS<br>VFPLAPSSKSTSGGTAALGCLVKDYFPEPVTVSWNSGALTSG<br>VHTFPAVLQSSGLYSLSSVVTVPSSSLGTQTYICNVNHKPSNT<br>KVDKKVEPKSCDAAASTSAHHHHHHAAA | SEQ ID NO: 32 |

TABLE 13

| Primer sequences used for generation of lambda-DP47 library (Vl3_19/VH3_23) | | |
|---|---|---|
| Primer name | Primer sequence 5'-3' | SEQ ID NO |
| LMB3 | See Table 9 | SEQ ID NO: 18 |
| Vl_3_19_L3r_V | GGACGGTCAGCTTGGTCCCTCCGCCGAATAC V***HV***A***TT***<br>A***CC***G***CT***A***CT*** A***TC***A***CG***<br>GGAGTTACAGTAATAGTCAGCCTCATCTTCCGC<br>underlined: 60% original base and 40% randomization as M<br>bold and italic: 60% original base and 40% randomization as N | SEQ ID NO: 33 |
| Vl_3_19_L3r_H V | GGACGGTCAGCTTGGTCCCTCCGCCGAATAC C***MM***A***TG***<br>A***TT*** A***CC*** G***CT*** A***CT*** A***TC*** A***CG***<br>GGAGTTACAGTAATAGTCAGCCTCATCTTCCGC<br>underlined: 60% original base and 40% randomization as M<br>bolded and italic: 60% original base and 40% randomization as N | SEQ ID NO: 34 |
| Vl_3_19_L3r_H LV | GGACGGTCAGCTTGGTCCCTCCGCCGAATAC R***HM***V***WG***<br>A***TG*** A***TT*** A***CC*** G***CT*** A***CT*** A***TC*** A***CG***<br>GGAGTTACAGTAATAGTCAGCCTCATCTTC CGC<br>underlined: 60% original base and 40% randomization as M<br>bolded and italic: 60% original base and 40% randomization as N | SEQ ID NO: 35 |
| RJH80 | TTCGGCGGAGGGACCAAGCTGACCGTCC | SEQ ID NO: 36 |
| DP47CDR3_ba (mod.) | CGCACAGTAATATACGGCCGTGTCC | SEQ ID NO: 37 |
| DP47-v4-4 | CGAGGACACGGCCGTATATTACTGTGCG-5-1-2-2-3-4-GAC-<br>TAC-TGGGGCCAAGGAACCCTGGTCACCGTCTCG | SEQ ID NO: 38 |
| DP47-v4-6 | CGAGGACACGGCCGTATATTACTGTGCG-5-1-2-2-2-2-3-4-<br>GAC-TAC-TGGGGCCAAGGAACCCTGGTCACCGTCTCG | SEQ ID NO: 39 |
| DP47-v4-8 | CGAGGACACGGCCGTATATTACTGTGCG-5-1-2-2-2-2-2-2-3-<br>4-GAC-TAC-TGGGGCCAAGGAACCCTGGTCACCGTCTCG | SEQ ID NO: 40 |
| fdseqlong | See Table 9 | SEQ ID NO: 27 |

Trinucleotide mixtures in randomized primers:
1 (G/D = 20%, E/V/S = 10%, A/P/R/L/T/Y = 5%);
2 (G/Y/S = 15%, A/D/T/R/P/L/V/N/W/F/I/E = 4.6%);
3 (G/A/Y = 20, P/W/S/D/T = 8%);
4 (F = 46%, L/M = 15%, G/I/Y = 8%);
5 (K = 70%, R = 30%)

Example 3

Cloning of Variable Antibody Domains into Expression Vectors

The variable regions of heavy and light chain DNA sequences of the selected anti-TnC binders (Table 14 to Table 19) were subcloned in frame with either the constant heavy chain or the constant light chain of human IgG1. The antibodies have been prepared either as wild type human IgG1 backbone or as variant containing Pro329Gly, Leu234Ala and Leu235Ala mutations, which have been introduced to abrogate binding to Fc gamma receptors according to the method described in International Patent Appl. Publ. No. WO 2012/130831 A1.

The CDR sequences of the anti-TnC binder are shown in Table 16 to Table 19. The base pair and amino acid sequences of the anti-TnC IgGs are shown in Table 20 and Table 21. The base pair and amino acid sequences of the anti-TnC P319GLALA IgGs are shown in Table 22 and Table 23. All antibody-encoding sequences were cloned into an expression vector, which drives transcription of the insert with a chimeric MPSV promoter and contains a synthetic polyA signal sequence located at the 3' end of the CDS. In addition, the vector contains an EBV OriP sequence for episomal maintenance of the plasmid.

LCDR3 of clone 11C7 (NSINSTRNEV (SEQ ID NO: 60)), as selected by phage display, contains a potential N-glycosylation site, i.e. NST, which can potentially be removed by amino acid substitutions to facilitate production of a homogeneous product. At the same time, binding to the target should be retained. N (position 1) could preferentially be substituted by Q, S or T. Alternatively, S (position 2) could be replaced by P. Alternatively, T (position 3) could be substituted preferentially by G or N or by any other proteinogenic amino acid except for S or C. Whichever substitution(s) would be the best, can be determined empirically by those skilled in the art.

TABLE 14

Variable region base pair sequences for phage-derived anti-TnC antibodies

| Clone | Chain | Base pair sequence | SEQ ID NO |
|---|---|---|---|
| 18D4 | VL | GACATCCAGATGACCCAGTCTCCATCCACCCTGTCTGCAT<br>CTGTAGGAGACCGTGTCACCATCACTTGCCGTGCCAGTCA<br>GAGTATTAGTAGCTGGTTGGCCTGGTATCAGCAGAAACC<br>AGGGAAAGCCCCTAAGCTCCTGATCTATGATGCCTCCAGT<br>TTGGAAAGTGGGGTCCCATCACGTTTCAGCGGCAGTGGAT<br>CCGGGACAGAATTCACTCTCACCATCAGCAGCTTGCAGCC<br>TGATGATTTTGCAACTTATTACTGCCAACAGAATAAGAAG<br>TTTCCTTCGGGGACGTTTGGCCAGGGCACCAAAGTCGAGA<br>TCAAG | SEQ ID NO: 41 |
| | VH | CAGGTGCAATTGGTGCAGTCTGGGGCTGAGGTGAAGAAG<br>CCTGGGTCCTCGGTGAAGGTCTCCTGCAAGGCCTCCGGAG<br>GCACATTCAGCAGCTACGCTATAAGCTGGGTGCGACAGG<br>CCCCTGGACAAGGGCTCGAGTGGATGGGAGGGATCATCC<br>CTATCTTTGGTACAGCAAACTACGCACAGAAGTTCCAGGG<br>CAGGGTCACCATTACTGCAGACAAATCCACGAGCACAGC<br>CTACATGGAGCTGAGCAGCCTGAGATCTGAGGACACCGC<br>CGTGTATTACTGTGCGAAAGGTAACTTCTACGGTGGTCTG<br>GACTACTGGGGCCAAGGGACCACCGTGACCGTCTCCTCA | SEQ ID NO: 42 |
| 11C7 | VL | TCGTCTGAGCTGACTCAGGACCCTGCTGTGTCTGTGGCCT<br>TGGGACAGACAGTCAGGGTCACATGCCAAGGAGACAGCC<br>TCAGAAGTTATTATGCAAGCTGGTACCAGCAGAAGCCAG<br>GACAGGCCCCTGTACTTGTCATCTATGGTAAAAACAACCG<br>GCCCTCAGGGATCCCAGACCGATTCTCTGGCTCCAGCTCA<br>GGAAACACAGCTTCCTTGACCATCACTGGGGCTCAGGCG<br>GAAGATGAGGCTGACTATTACTGTAACTCCATTAATAGTA<br>CTCGTAATGAGGTATTCGGCGGAGGGACCAAGCTGACCG<br>TCCTA | SEQ ID NO: 43 |
| | VH | GAGGTGCAATTGTTGGAGTCTGGGGGAGGCTTGGTACAG<br>CCTGGGGGGTCCCTGAGACTCTCCTGTGCAGCCTCCGGAT<br>TCACCTTTAGCAGTTATGCCATGAGCTGGGTCCGCCAGGC<br>TCCAGGGAAGGGGCTGGAGTGGGTCTCAGCTATTAGCGG<br>TAGTGGTGGTAGCACATACTACGCAGACTCCGTGAAGGG<br>CCGGTTCACCATCTCCAAAGACAATTCCAAGAACACGCTG<br>TATCTGCAGATGAACAGCCTGAGAGCCGAGGACACGGCC<br>GTATATTACTGTGCGAAAACTTCTCCGCGTGTTCCGCTGG<br>ACTACTGGGGCCAAGGAACCCTGGTCACCGTCTCGAGT | SEQ ID NO: 44 |

TABLE 15

Variable region polypeptide sequences for phage-derived anti-TnC antibodies

| Clone | Chain | Polypeptide sequence | |
|---|---|---|---|
| 18D4 | VL | DIQMTQSPSTLSASVGDRVTITCRASQSISSWLAWYQQKPGK<br>APKLLIYDASSLESGVPSRFSGSGSGTEFTLTISSLQPDDFATY<br>YCQQNKKFPSGTFGQGTKVEIK | SEQ ID NO: 45 |
| | VH | QVQLVQSGAEVKKPGSSVKVSCKASGGTFSSYAISWVRQAP<br>GQGLEWMGGIIPIFGTANYAQKFQGRVTITADKSTSTAYME<br>LSSLRSEDTAVYYCAKGNFYGGLDYWGQGTTVTVSS | SEQ ID NO: 46 |
| 11C7 | VL | SSELTQDPAVSVALGQTVRVTCQGDSLRSYYASWYQQKPG<br>QAPVLVIYGKNNRPSGIPDRFSGSSSGNTASLTITGAQAEDEA<br>DYYCNSINSTRNEVFGGGTKLTVL | SEQ ID NO: 47 |
| | VH | EVQLLESGGGLVQPGGSLRLSCAASGFTFSSYAMSWVRQAP<br>GKGLEWVSAISGSGGSTYYADSVKGRFTISKDNSKNTLYLQ<br>MNSLRAEDTAVYYCAKTSPRVPLDYWGQGTLVTVSS | SEQ ID NO: 48 |

TABLE 16

CDR base pairs sequences of the anti-TnC antibody light chains

| clone | SEQ ID NO | LCDR1 | SEQ ID NO | LCDR2 | SEQ ID NO | LCDR3 |
|---|---|---|---|---|---|---|
| 18D4 | SEQ ID NO: 49 | CGTGCCAGTCAGAGTATTAGTAGCTGGTTGGCC | SEQ ID NO: 50 | GATGCCTCCAGTTTGGAAAGT | SEQ ID NO: 51 | CAACAGAATAAGAAGTTTCCTTCGGGGACG |
| 11C7 | SEQ ID NO: 52 | CAAGGAGACAGCCTCAGAAGTTATTATGCAAGC | SEQ ID NO: 53 | GGTAAAAACAACCGGCCCTCA | SEQ ID NO: 54 | AACTCCATTAATAGTACTCGTAATGAGGTA |

TABLE 17

CDR polypeptides sequences of the anti-TnC antibody light chains

| clone | SEQ ID NO | LCDR1 | SEQ ID NO | LCDR2 | SEQ ID NO | LCDR3 |
|---|---|---|---|---|---|---|
| 18D4 | SEQ ID NO: 55 | RASQSISSWLA | SEQ ID NO: 56 | DASSLES | SEQ ID NO: 57 | QQNKKFPSGT |
| 11C7 | SEQ ID NO: 58 | QGDSLRSYYAS | SEQ ID NO: 59 | GKNNRPS | SEQ ID NO: 60 | NSINSTRNEV |

TABLE 18

CDR base pairs sequences of the anti-TnC antibody heavy chains

| clone | SEQ ID NO | HCDR1 | SEQ ID NO | HCDR2 | SEQ ID NO | HCDR3 |
|---|---|---|---|---|---|---|
| 18D4 | SEQ ID NO: 61 | AGCTACGCTATAAGC | SEQ ID NO: 62 | GGGATCATCCCTATCTTTGGTACAGCAAACTACGCACAGAAGTTCCAGGGC | SEQ ID NO: 63 | GGTAACTTCTACGGTGGTCTGGACTAC |
| 11C7 | SEQ ID NO: 64 | GGATTCACCTTTAGCAGTTATGCCATGAGC | SEQ ID NO: 65 | GCTATTAGCGGTAGTGGTGGTAGCACATACTACGCAGACTCCGTGAAGGGC | SEQ ID NO: 66 | ACTTCTCCGCGTGTTCCGCTGGACTAC |

TABLE 19

CDR polypeptide sequences of the anti-TnC antibody heavy chains

| clone | SEQ ID NO | HCDR1 | SEQ ID NO | HCDR2 | SEQ ID NO | HCDR3 |
|---|---|---|---|---|---|---|
| 18D4 | SEQ ID NO: 67 | SYAIS | SEQ ID NO: 68 | GIIPIFGTANYAQKFQG | SEQ ID NO: 69 | GNFYGGLDY |
| 11C7 | SEQ ID NO: 70 | GFTFSSYAMS | SEQ ID NO: 71 | AISGSGGSTYYADSVKG | SEQ ID NO: 72 | TSPRVPLDY |

TABLE 20

Base pair sequences of anti-TnC clones in wild type human IgG1 format

| Clone | Chain | Base pair sequence | SEQ ID NO |
|---|---|---|---|
| 18D4 | Light chain | GACATCCAGATGACCCAGTCTCCATCCACCCTGTCTGCATC<br>TGTAGGAGACCGTGTCACCATCACTTGCCGTGCCAGTCAGA<br>GTATTAGTAGCTGGTTGGCCTGGTATCAGCAGAAACCAGGG<br>AAAGCCCCTAAGCTCCTGATCTATGATGCCTCCAGTTTGGA<br>AAGTGGGGTCCCATCACGTTTCAGCGGCAGTGGATCCGGGA<br>CAGAATTCACTCTCACCATCAGCAGCTTGCAGCCTGATGAT<br>TTTGCAACTTATTACTGCCAACAGAATAAGAAGTTTCCTTC<br>GGGGACGTTTGGCCAGGGCACCAAAGTCGAGATCAAGCGT<br>ACGGTGGCTGCACCATCTGTCTTCATCTTCCCGCCATCTGAT<br>GAGCAGTTGAAATCTGGAACTGCCTCTGTTGTGTGCCTGCT<br>GAATAACTTCTATCCCAGAGAGGCCAAAGTACAGTGGAAG<br>GTGGATAACGCCCTCCAATCGGGTAACTCCCAGGAGAGTGT<br>CACAGAGCAGGACAGCAAGGACAGCACCTACAGCCTCAGC<br>AGCACCCTGACGCTGAGCAAAGCAGACTACGAGAAACACA<br>AAGTCTACGCCTGCGAAGTCACCCATCAGGGCCTGAGCTCG<br>CCCGTCACAAAGAGCTTCAACAGGGGAGAGTGT | SEQ ID NO: 73 |
| | Heavy chain | CAGGTGCAATTGGTGCAGTCTGGGGCTGAGGTGAAGAAGC<br>CTGGGTCCTCGGTGAAGGTCTCCTGCAAGGCCTCCGGAGGC<br>ACATTCAGCAGCTACGCTATAAGCTGGGTGCGACAGGCCCC<br>TGGACAAGGGCTCGAGTGGATGGGAGGGATCATCCCTATCT<br>TTGGTACAGCAAACTACGCACAGAAGTTCCAGGGCAGGGT<br>CACCATTACTGCAGACAAATCCACGAGCACAGCCTACATGG<br>AGCTGAGCAGCCTGAGATCTGAGGACACCGCCGTGTATTAC<br>TGTGCGAAAGGTAACTTCTACGGTGGTCTGGACTACTGGGG<br>CCAAGGGACCACCGTGACCGTCTCCTCAGCTAGCACCAAGG<br>GCCCATCGGTCTTCCCCCTGGCACCCTCCTCCAAGAGCACC<br>TCTGGGGGCACAGCGGCCCTGGGCTGCCTGGTCAAGGACTA<br>CTTCCCCGAACCGGTGACGGTGTCGTGGAACTCAGGCGCCC<br>TGACCAGCGGCGTGCACACCTTCCCGGCTGTCCTACAGTCC<br>TCAGGACTCTACTCCCTCAGCAGCGTGGTGACCGTGCCCTC<br>CAGCAGCTTGGGCACCCAGACCTACATCTGCAACGTGAATC<br>ACAAGCCCAGCAACACCAAGGTGGACAAGAAAGTTGAGCC<br>CAAATCTTGTGACAAAACTCACACATGCCCACCGTGCCCAG<br>CACCTGAACTCCTGGGGGGACCGTCAGTCTTCCTCTTCCCC<br>CCAAAACCCAAGGACACCCTCATGATCTCCCGGACCCCTGA<br>GGTCACATGCGTGGTGGTGGACGTGAGCCACGAAGACCCT<br>GAGGTCAAGTTCAACTGGTACGTGGACGGCGTGGAGGTGC<br>ATAATGCCAAGACAAAGCCGCGGGAGGAGCAGTACAACAG<br>CACGTACCGTGTGGTCAGCGTCCTCACCGTCCTGCACCAGG<br>ACTGGCTGAATGGCAAGGAGTACAAGTGCAAGGTCTCCAA<br>CAAAGCCCTCCCAGCCCCCATCGAGAAAACCATCTCCAAAG<br>CCAAAGGGCAGCCCCGAGAACCACAGGTGTACACCCTGCC<br>CCCATCCCGGGATGAGCTGACCAAGAACCAGGTCAGCCTG<br>ACCTGCCTGGTCAAAGGCTTCTATCCCAGCGACATCGCCGT<br>GGAGTGGGAGAGCAATGGGCAGCCGGAGAACAACTACAAG<br>ACCACGCCTCCCGTGCTGGACTCCGACGGCTCCTTCTTCCTC<br>TACAGCAAGCTCACCGTGGACAAGAGCAGGTGGCAGCAGG<br>GGAACGTCTTCTCATGCTCCGTGATGCATGAGGCTCTGCAC<br>AACCACTACACGCAGAAGAGCCTCTCCCTGTCTCCGGGTAAA | SEQ ID NO: 74 |
| 11C7 | Light chain | TCGTCTGAGCTGACTCAGGACCCTGCTGTGTCTGTGGCCTT<br>GGGACAGACAGTCAGGGTCACATGCCAAGGAGACAGCCTC<br>AGAAGTTATTATGCAAGCTGGTACCAGCAGAAGCCAGGAC<br>AGGCCCCTGTACTTGTCATCTATGGTAAAAACAACCGGCCC<br>TCAGGGATCCCAGACCGATTCTCTGGCTCCAGCTCAGGAAA<br>CACAGCTTCCTTGACCATCACTGGGGCTCAGGCGGAAGATG<br>AGGCTGACTATTACTGTAACTCCATTAATAGTACTCGTAAT<br>GAGGTATTCGGCGGAGGGACCAAGCTGACCGTCCTAGGTC<br>AACCCAAGGCTGCCCCCAGCGTGACCCTGTTCCCCCCCAGC<br>AGCGAGGAACTGCAGGCCAACAAGGCCACCCTGGTCTGCC<br>TGATCAGCGACTTCTACCCAGGCGCCGTGACCGTGGCCTGG<br>AAGGCCGACAGCAGCCCCGTGAAGGCCGGCGTGGAGACCA<br>CCACCCCCAGCAAGCAGAGCAACAACAAGTACGCCGCCAG<br>CAGCTACCTGAGCCTGACCCCCGAGCAGTGGAAGAGCCAC<br>AGGTCCTACAGCTGCCAGGTGACCCACGAGGGCAGCACCG<br>TGGAGAAAACCGTGGCCCCCACCGAGTGCAGC | SEQ ID NO: 75 |
| | Heavy chain | GAGGTGCAATTGTTGGAGTCTGGGGGAGGCTTGGTACAGCC<br>TGGGGGGTCCCTGAGACTCTCCTGTGCAGCCTCCGGATTCA<br>CCTTTAGCAGTTATGCCATGAGCTGGGTCCGCCAGGCTCCA<br>GGGAAGGGGCTGGAGTGGGTCTCAGCTATTAGCGGTAGTG<br>GTGGTAGCACATACTACGCAGACTCCGTGAAGGGCCGGTTC<br>ACCATCTCCAAAGACAATTCCAAGAACACGCTGTATCTGCA<br>GATGAACAGCCTGAGAGCCGAGGACACGGCCGTATATTAC<br>TGTGCGAAAACTTCTCCGCGTGTTCCGCTGGACTACTGGGG<br>CCAAGGAACCCTGGTCACCGTCTCGAGTGCTAGCACCAAGG | SEQ ID NO: 76 |

TABLE 20-continued

| Base pair sequences of anti-TnC clones in wild type human IgG1 format | | | |
|---|---|---|---|
| Clone | Chain | Base pair sequence | SEQ ID NO |
| | | GCCCATCGGTCTTCCCCCTGGCACCCTCCTCCAAGAGCACC<br>TCTGGGGGCACAGCGGCCCTGGGCTGCCTGGTCAAGGACTA<br>CTTCCCCGAACCGGTGACGGTGTCGTGGAACTCAGGCGCCC<br>TGACCAGCGGCGTGCACACCTTCCCGGCTGTCCTACAGTCC<br>TCAGGACTCTACTCCCTCAGCAGCGTGGTGACCGTGCCCTC<br>CAGCAGCTTGGGCACCCAGACCTACATCTGCAACGTGAATC<br>ACAAGCCCAGCAACACCAAGGTGGACAAGAAAGTTGAGCC<br>CAAATCTTGTGACAAAACTCACACATGCCCACCGTGCCCAG<br>CACCTGAACTCCTGGGGGGACCGTCAGTCTTCCTCTTCCCC<br>CCAAAACCCAAGGACACCCTCATGATCTCCCGGACCCCTGA<br>GGTCACATGCGTGGTGGTGGACGTGAGCCACGAAGACCCT<br>GAGGTCAAGTTCAACTGGTACGTGGACGGCGTGGAGGTGC<br>ATAATGCCAAGACAAAGCCGCGGGAGGAGCAGTACAACAG<br>CACGTACCGTGTGGTCAGCGTCCTCACCGTCCTGCACCAGG<br>ACTGGCTGAATGGCAAGGAGTACAAGTGCAAGGTCTCCAA<br>CAAAGCCCTCCCAGCCCCCATCGAGAAAACCATCTCCAAAG<br>CCAAAGGGCAGCCCCGAGAACCACAGGTGTACACCCTGCC<br>CCCATCCCGGGATGAGCTGACCAAGAACCAGGTCAGCCTG<br>ACCTGCCTGGTCAAAGGCTTCTATCCCAGCGACATCGCCGT<br>GGAGTGGGAGAGCAATGGGCAGCCGGAGAACAACTACAAG<br>ACCACGCCTCCCGTGCTGGACTCCGACGGCTCCTTCTTCCTC<br>TACAGCAAGCTCACCGTGGACAAGAGCAGGTGGCAGCAGG<br>GGAACGTCTTCTCATGCTCCGTGATGCATGAGGCTCTGCAC<br>AACCACTACACGCAGAAGAGCCTCTCCCTGTCTCCGGGTAAA | |

TABLE 21

| Polypeptide sequences of anti-TnC clones in wild type human IgG1 format | | | |
|---|---|---|---|
| Clone | Chain | Polypeptide sequence | SEQ ID NO |
| 18D4 | Light chain | DIQMTQSPSTLSASVGDRVTITCRASQSISSWLAWYQQKPGK<br>APKLLIYDASSLESGVPSRFSGSGSGTEFTLTISSLQPDDFATY<br>YCQQNKKFPSGTFGQGTKVEIKRTVAAPSVFIFPPSDEQLKSG<br>TASVVCLLNNFYPREAKVQWKVDNALQSGNSQESVTEQDSK<br>DSTYSLSSTLTLSKADYEKHKVYACEVTHQGLSSPVTKSFNR<br>GEC | SEQ ID NO: 77 |
| | Heavy chain | QVQLVQSGAEVKKPGSSVKVSCKASGGTFSSYAISWVRQAP<br>GQGLEWMGGIIPIFGTANYAQKFQGRVTITADKSTSTAYMEL<br>SSLRSEDTAVYYCAKGNFYGGLDYWGQGTTVTVSSASTKGP<br>SVFPLAPSSKSTSGGTAALGCLVKDYFPEPVTVSWNSGALTS<br>GVHTFPAVLQSSGLYSLSSVVTVPSSSLGTQTYICNVNHKPSN<br>TKVDKKVEPKSCDKTHTCPPCPAPELLGGPSVFLFPPKPKDTL<br>MISRTPEVTCVVVDVSHEDPEVKFNWYVDGVEVHNAKTKPR<br>EEQYNSTYRVVSVLTVLHQDWLNGKEYKCKVSNKALPAPIE<br>KTISKAKGQPREPQVYTLPPSRDELTKNQVSLTCLVKGFYPS<br>DIAVEWESNGQPENNYKTTPPVLDSDGSFFLYSKLTVDKSRW<br>QQGNVFSCSVMHEALHNHYTQKSLSLSPGK | SEQ ID NO: 78 |
| 11C7 | Light chain | SSELTQDPAVSVALGQTVRVTCQGDSLRSYYASWYQQKPGQ<br>APVLVIYGKNNRPSGIPDRFSGSSSGNTASLTITGAQAEDEAD<br>YYCNSINSTRNEVFGGGTKLTVLGQPKAAPSVTLFPPSSEELQ<br>ANKATLVCLISDFYPGAVTVAWKADSSPVKAGVETTTPSKQ<br>SNNKYAASSYLSLTPEQWKSHRSYSCQVTHEGSTVEKTVAPT<br>ECS | SEQ ID NO: 79 |
| | Heavy chain | EVQLLESGGGLVQPGGSLRLSCAASGFTFSSYAMSWVRQAP<br>GKGLEWVSAISGSGGSTYYADSVKGRFTISKDNSKNTLYLQ<br>MNSLRAEDTAVYYCAKTSPRVPLDYWGQGTLVTVSSASTKG<br>PSVFPLAPSSKSTSGGTAALGCLVKDYFPEPVTVSWNSGALT<br>SGVHTFPAVLQSSGLYSLSSVVTVPSSSLGTQTYICNVNHKPS<br>NTKVDKKVEPKSCDKTHTCPPCPAPELLGGPSVFLFPPKPKD<br>TLMISRTPEVTCVVVDVSHEDPEVKFNWYVDGVEVHNAKTK<br>PREEQYNSTYRVVSVLTVLHQDWLNGKEYKCKVSNKALPAP<br>IEKTISKAKGQPREPQVYTLPPSRDELTKNQVSLTCLVKGFYP<br>SDIAVEWESNGQPENNYKTTPPVLDSDGSFFLYSKLTVDKSR<br>WQQGNVFSCSVMHEALHNHYTQKSLSLSPGK | SEQ ID NO: 80 |

TABLE 22

Base pair sequences of anti-TnC clones in P329GLALA human IgG1 format

| Clone | Chain | Base pair sequence | |
|---|---|---|---|
| 18D4 | Light chain | See Table 20 | SEQ ID NO: 73 |
| | Heavy chain PGLALA | CAGGTGCAATTGGTGCAGTCTGGGGCTGAGGTGAAGAAG<br>CCTGGGTCCTCGGTGAAGGTCTCCTGCAAGGCCTCCGGAG<br>GCACATTCAGCAGCTACGCTATAAGCTGGGTGCGACAGG<br>CCCCTGGACAAGGGCTCGAGTGGATGGGAGGGATCATCC<br>CTATCTTTGGTACAGCAAACTACGCACAGAAGTTCCAGGG<br>CAGGGTCACCATTACTGCAGACAAATCCACGAGCACAGC<br>CTACATGGAGCTGAGCAGCCTGAGATCTGAGGACACCGC<br>CGTGTATTACTGTGCGAAAGGTAACTTCTACGGTGGTCTG<br>GACTACTGGGGCCAAGGGACCACCGTGACCGTCTCCTCA<br>GCTAGCACCAAGGGCCCATCGGTCTTCCCCCTGGCACCCT<br>CCTCCAAGAGCACCTCTGGGGGCACAGCGGCCCTGGGCT<br>GCCTGGTCAAGGACTACTTCCCCGAACCGGTGACGGTGTC<br>GTGGAACTCAGGCGCCCTGACCAGCGGCGTGCACACCTT<br>CCCGGCTGTCCTACAGTCCTCAGGACTCTACTCCCTCAGC<br>AGCGTGGTGACCGTGCCCTCCAGCAGCTTGGGCACCCAG<br>ACCTACATCTGCAACGTGAATCACAAGCCCAGCAACACC<br>AAGGTGGACAAGAAAGTTGAGCCCAAATCTTGTGACAAA<br>ACTCACACATGCCCACCGTGCCCAGCACCTGAAGCTGCA<br>GGGGGACCGTCAGTCTTCCTCTTCCCCCCAAAACCCAAGG<br>ACACCCTCATGATCTCCCGGACCCCTGAGGTCACATGCGT<br>GGTGGTGGACGTGAGCCACGAAGACCCTGAGGTCAAGTT<br>CAACTGGTACGTGGACGGCGTGGAGGTGCATAATGCCAA<br>GACAAAGCCGCGGGAGGAGCAGTACAACAGCACGTACCG<br>TGTGGTCAGCGTCCTCACCGTCCTGCACCAGGACTGGCTG<br>AATGGCAAGGAGTACAAGTGCAAGGTCTCCAACAAAGCC<br>CTCGGCGCCCCCATCGAGAAAACCATCTCCAAAGCCAAA<br>GGGCAGCCCCGAGAACCACAGGTGTACACCCTGCCCCCA<br>TCCCGGGATGAGCTGACCAAGAACCAGGTCAGCCTGACC<br>TGCCTGGTCAAAGGCTTCTATCCCAGCGACATCGCCGTGG<br>AGTGGGAGAGCAATGGGCAGCCGGAGAACAACTACAAG<br>ACCACGCCTCCCGTGCTGGACTCCGACGGCTCCTTCTTCC<br>TCTACAGCAAGCTCACCGTGGACAAGAGCAGGTGGCAGC<br>AGGGGAACGTCTTCTCATGCTCCGTGATGCATGAGGCTCT<br>GCACAACCACTACACGCAGAAGAGCCTCTCCCTGTCTCCG<br>GGTAAA | SEQ ID NO: 81 |
| 11C7 | Light chain | See Table 20 | SEQ ID NO: 75 |
| | Heavy chain PGLALA | GAGGTGCAATTGTTGGAGTCTGGGGGAGGCTTGGTACAG<br>CCTGGGGGGTCCCTGAGACTCTCCTGTGCAGCCTCCGGAT<br>TCACCTTTAGCAGTTATGCCATGAGCTGGGTCCGCCAGGC<br>TCCAGGGAAGGGGCTGGAGTGGGTCTCAGCTATTAGCGG<br>TAGTGGTGGTAGCACATACTACGCAGACTCCGTGAAGGG<br>CCGGTTCACCATCTCCAAAGACAATTCCAAGAACACGCTG<br>TATCTGCAGATGAACAGCCTGAGAGCCGAGGACACGGCC<br>GTATATTACTGTGCGAAAACTTCTCCGCGTGTTCCGCTGG<br>ACTACTGGGGCCAAGGAACCCTGGTCACCGTCTCGAGTG<br>CTAGCACCAAGGGCCCATCGGTCTTCCCCCTGGCACCCTC<br>CTCCAAGAGCACCTCTGGGGGCACAGCGGCCCTGGGCTG<br>CCTGGTCAAGGACTACTTCCCCGAACCGGTGACGGTGTCG<br>TGGAACTCAGGCGCCCTGACCAGCGGCGTGCACACCTTCC<br>CGGCTGTCCTACAGTCCTCAGGACTCTACTCCCTCAGCAG<br>CGTGGTGACCGTGCCCTCCAGCAGCTTGGGCACCCAGACC<br>TACATCTGCAACGTGAATCACAAGCCCAGCAACACCAAG<br>GTGGACAAGAAAGTTGAGCCCAAATCTTGTGACAAAACT<br>CACACATGCCCACCGTGCCCAGCACCTGAAGCTGCAGGG<br>GGACCGTCAGTCTTCCTCTTCCCCCCAAAACCCAAGGACA<br>CCCTCATGATCTCCCGGACCCCTGAGGTCACATGCGTGGT<br>GGTGGACGTGAGCCACGAAGACCCTGAGGTCAAGTTCAA<br>CTGGTACGTGGACGGCGTGGAGGTGCATAATGCCAAGAC<br>AAAGCCGCGGGAGGAGCAGTACAACAGCACGTACCGTGT<br>GGTCAGCGTCCTCACCGTCCTGCACCAGGACTGGCTGAAT<br>GGCAAGGAGTACAAGTGCAAGGTCTCCAACAAAGCCCTC<br>GGCGCCCCCATCGAGAAAACCATCTCCAAAGCCAAAGGG<br>CAGCCCCGAGAACCACAGGTGTACACCCTGCCCCCATCCC<br>GGGATGAGCTGACCAAGAACCAGGTCAGCCTGACCTGCC<br>TGGTCAAAGGCTTCTATCCCAGCGACATCGCCGTGGAGTG<br>GGAGAGCAATGGGCAGCCGGAGAACAACTACAAGACCA<br>CGCCTCCCGTGCTGGACTCCGACGGCTCCTTCTTCCTCTAC<br>AGCAAGCTCACCGTGGACAAGAGCAGGTGGCAGCAGGGG<br>AACGTCTTCTCATGCTCCGTGATGCATGAGGCTCTGCACA<br>ACCACTACACGCAGAAGAGCCTCTCCCTGTCTCCGGGTAAA | SEQ ID NO: 82 |

TABLE 23

Polypeptide sequences of anti-TnC clones in P329GLALA human IgG1 format

| Clone | Chain | Polypeptide sequence | |
|---|---|---|---|
| 18D4 | Light chain | See Table 21 | SEQ ID NO: 77 |
| | Heavy chain | QVQLVQSGAEVKKPGSSVKVSCKASGGTFSSYAISWVRQAP GQGLEWMGGIIPIFGTANYAQKFQGRVTITADKSTSTAYME LSSLRSEDTAVYYCAKGNFYGGLDYWGQGTTVTVSSASTK GPSVFPLAPSSKSTSGGTAALGCLVKDYFPEPVTVSWNSGAL TSGVHTFPAVLQSSGLYSLSSVVTVPSSSLGTQTYICNVNHK PSNTKVDKKVEPKSCDKTHTCPPCPAPEAAGGPSVFLFPPKP KDTLMISRTPEVTCVVVDVSHEDPEVKFNWYVDGVEVHNA KTKPREEQYNSTYRVVSVLTVLHQDWLNGKEYKCKVSNKA LGAPIEKTISKAKGQPREPQVYTLPPSRDELTKNQVSLTCLV KGFYPSDIAVEWESNGQPENNYKTTPPVLDSDGSFFLYSKLT VDKSRWQQGNVFSCSVMHEALHNHYTQKSLSLSPGK | SEQ ID NO: 83 |
| 11C7 | Light chain | See Table 21 | SEQ ID NO: 79 |
| | Heavy chain | EVQLLESGGGLVQPGGSLRLSCAASGFTFSSYAMSWVRQAP GKGLEWVSAISGSGGSTYYADSVKGRFTISKDNSKNTLYLQ MNSLRAEDTAVYYCAKTSPRVPLDYWGQGTLVTVSSASTK GPSVFPLAPSSKSTSGGTAALGCLVKDYFPEPVTVSWNSGAL TSGVHTFPAVLQSSGLYSLSSVVTVPSSSLGTQTYICNVNHK PSNTKVDKKVEPKSCDKTHTCPPCPAPEAAGGPSVFLFPPKP KDTLMISRTPEVTCVVVDVSHEDPEVKFNWYVDGVEVHNA KTKPREEQYNSTYRVVSVLTVLHQDWLNGKEYKCKVSNKA LGAPIEKTISKAKGQPREPQVYTLPPSRDELTKNQVSLTCLV KGFYPSDIAVEWESNGQPENNYKTTPPVLDSDGSFFLYSKLT VDKSRWQQGNVFSCSVMHEALHNHYTQKSLSLSPGK | SEQ ID NO: 84 |

Example 4

Purification of Anti-TnC IgGs

All genes were transiently expressed under control of a chimeric MPSV promoter consisting of the MPSV core promoter combined with the CMV promoter enhancer fragment. The expression vector also contains the oriP region for episomal replication in EBNA (Epstein Barr Virus Nuclear Antigen) containing host cells.

The anti-TnC IgGs were produced by co-transfecting HEK293-EBNA cells with the mammalian expression vectors using polyethylenimine. The cells were transfected with the corresponding expression vectors in a 1:1 ratio ("vector HC":"vector HLC").

For a 200 mL production in 500 mL shake flasks, 250 million HEK293 EBNA cells were seeded 24 hours before transfection in Excell media with supplements. For transfection, the cells were centrifuged for 5 minutes at 210×g, and supernatant was replaced by pre-warmed CD-CHO medium. Expression vectors were mixed in 20 mL CD-CHO medium to a final amount of 200 μg DNA. After addition of 540 μL PEI (1 mg/mL), the solution was vortexed for 15 seconds and incubated for 10 minutes at room temperature. Afterwards, cells were mixed with the DNA/PEI solution, transferred to a 500 mL shake flask and incubated for 3 hours at 37° C. in an incubator with a 5% $CO_2$ atmosphere and shaking at 165 rpm. After the incubation, 160 mL Excell medium with supplements was added and cells were cultured for 24 hours. At this point the valproic acid concentration is 1 mM (the media comprises additionally g/L PepSoy and 6 mM L-Glutamine) 24 hours after transfection the cells are supplement with an amino acid and glucose feed at 12% final volume (24 mL) and 3 g/L glucose (1.2 mL from 500 g/L stock). After culturing for 7 days, the cell supernatant was collected by centrifugation for 45 minutes at 2000-3000×g. The solution was sterile filtered (0.22 μm filter), supplemented with sodium azide to a final concentration of 0.01% (w/v), and kept at 4° C.

Purification of anti-TnC IgGs from cell culture supernatants was carried out by affinity chromatography using MabSelectSure. The protein was concentrated and filtered prior to loading on a HiLoad Superdex 200 column (GE Healthcare) equilibrated with 20 mM Histidine, 140 mM NaCl, 0.01% Tween-20 solution of pH 6.0.

For affinity chromatography, the supernatant was loaded on a ProtA MabSelect Sure column (CV=6 mL, GE Healthcare) equilibrated with 36 mL 20 mM Sodium Citrate, 20 mM Sodium Phosphate, pH 7.5. Unbound protein was removed by washing with 6-10 column volumes of a buffer containing 20 mM Sodium Citrate, 20 mM Sodium Phosphate, pH 7.5. The bound protein was eluted using a linear pH-gradient of 15 CVs of sodium chloride (from 20 to 100%) of 20 mM Sodium Citrate, 100 mM Sodium Chloride, 100 mM Glycine, 0.01% (v/v) Tween-20, pH 3.0. The column was then washed with 4 column volumes of a solution containing 20 mM Sodium Citrate, 100 mM Sodium Chloride, 100 mM Glycine, 0.01% (v/v) Tween-20, pH 3.0 followed by a re-equilibration step.

The pH of the collected fractions was adjusted by adding 1/10 (v/v) of 0.5 M $Na_2HPO_4$, pH 8.0. The protein was concentrated and filtered prior to loading on a HiLoad Superdex 200 column (GE Healthcare) equilibrated with 20 mM Histidine, 140 mM NaCl, pH 6.0, 0.01% Tween20.

The protein concentration of purified IgGs was determined by measuring the OD at 280 nm, using the molar extinction coefficient calculated on the basis of the amino acid sequence.

Purity and molecular weight of the IgGs were analyzed by CE-SDS in the presence and absence of a reducing agent (Invitrogen, USA) using a LabChipGXII (Caliper). The aggregate content of the purified protein was analyzed using a TSKgel G3000 SW XL analytical size-exclusion column (Tosoh) equilibrated in a 25 mM $K_2HPO_4$, 125 mM NaCl, 200 mM L-Arginine Monohydrocloride, 0.02% (w/v) $NaN_3$, pH 6.7 running buffer at 25° C. (Table 24).

TABLE 24

Biochemical analysis of anti-TnC IgG1

| Clone | Yield [mg/l] | Monomer [%] |
|---|---|---|
| a-TnC(18D4) huIgG1 | 6.8 | 98.3 |
| a-TnC(18D4) P329GLALA huIgG1 | 26.7 | 100 |

Example 5

Surface Plasmon Resonance (TnC Binding)

Binding of the anti-TnC IgGs 18D4, 11C7 and the Fab fragment of anti-TnC 18D4 to human, murine and cynomolgus TnC (antigens according to Table 4) was assessed by surface plasmon resonance (SPR). All SPR experiments were performed on a Biacore T200 at 25° C. with HBS-EP as running buffer (0.01 M HEPES pH 7.4, 0.15 M NaCl, 3 mM EDTA, 0.005% Surfactant P20, Biacore, Freiburg/Germany).

A 20 µg/ml stock solution of biotinylated human, murine or cynomolgus TnC was injected on a SA chip, with the aim to immobilize up to 100 RU using the immobilization wizard function. Final immobilization levels were between 79-400 RU.

The anti-TnC IgGs 18D4 (PGLALA and wtFc), 11C7 (rb IgG) and 18D4 Fab fragment were then immediately passed over the chip surface at a concentration ranging from 0.02-12.5 nM (IgGs) and 0.02-50 nM (Fab fragment) with a flow rate of 30 µl/min for 180 s followed by a dissociation step of 180s. An additional dissociation step of 1800s was performed for the highest concentration of IgG. After each step the surface was regenerated following two sequential injections of 10 mM glycine pH2.1 for 60 s. Bulk refractive index differences were corrected for by subtracting the response obtained in a reference flow cell without TNC. Affinity and avidity were calculated using the Langmuir 1:1 kinetic model. However, as the $K_D$ for the 1:1 fitting of bivalent interactions is an apparent value only, it should only be used for comparisons.

TABLE 26

KD values and species cross-reactivity

| Construct | hu TNC KD (nM) | cyno TNC KD (nM) | mu TNC KD (nM) |
|---|---|---|---|
| 18D4 IgG wt Fc | 0.093 | 0.036 | 0.061 |
| 18D4 IgG PG/LALA | 0.032 | 0.011 | 0.030 |
| llC7 rb IgG | 0.029 | nd | nd |
| 18D4 Fab fragment | 1.44 | 6.69 | 6.5 |

The anti-TnC binder 18D4 cross-reacts with mouse and cynomolgus TnC with similar avidity in the pM range. Monovalent binding of the 18D4 Fab fragment to TnC results in a $K_D$ in the low nM range. Anti-TNC binder 11C7 also binds human TnC in the pM range. Species cross-reactivity could not be assessed for binder 11C7 due to absence of the C domain in murine and cynomolgus TNC constructs used in this Biacore experiment (Table 26).

Thermal Stability

The thermal stability was monitored by Static Light Scattering (SLS) and by measuring the intrinsic protein fluorescence in response to applied temperature stress. 30 µg of filtered protein sample with a protein concentration of 1 mg/ml was applied in duplicate to an Optim 2 instrument (Avacta Analytical Ltd). The temperature was ramped from 25 to 85° C. at 0.1° C./min, with the radius and total scattering intensity being collected. For determination of intrinsic protein fluorescence the sample was excited at 266 nm and emission was collected between 275 nm and 460 nm. Both IgGs have an aggregation temperature of 62° C. (Table 26).

TABLE 26

Thermal stability

| Construct | Tagg (° C.) |
|---|---|
| 18D4 IgG PGLALA | 62 |
| 18D4 IgG wtFc | 62 |

Example 6

Results of TnC Staining in LS174T Xenograft Derived Tumor Tissue and Human Tissue Array Anti-TnC clones 18D4 and 11C7 as rabbit IgG antibodies were tested in LS174T xenograft derived tumor tissue and human tissue array for detection of TnC with an immunohistochemistry technique.

The LS174T colorectal carcinoma frozen tumor samples were sectioned in a Cryostat at 12 µm thickness, mounted on superfrost slides (Thermo Scientific, Germany). Frozen samples of human tissue array including paired normal and tumor samples were purchased from Biochain (San Francisco, USA). Tissue sections were allowed to thaw for 30 minutes. Slides were washed in PBS, fixed in cold acetone for 10 minutes and an incubation step with 0.03% hydrogen peroxidase in water was performed to block the endogeneous peroxidase. The sections were then incubated for 1 h with 5% goat serum in PBS followed by overnight incubation with 0.5 µg/ml anti-TnC clone 18D4 or 11C7 or an isotype control antibody (Serotec, Germany) at 4° C. Afterwards, the sections were washed with PBS three times for 5 minutes each and developed using the peroxidase Rabbit Vectastain ABC kit following the manufacturers' instructions (PK-6101, Vector laboratories, California, USA). Slides were then dehydrated in increasing concentration of ethanol and incubated 2 minutes in Xylene. One drop of Permount mounting medium (Fischer Chemical, Germany) was added to the sections and coverslip. Images were obtained with Olympus scanner VS120 (Olympus, Germany) and analyzed.

Figure 1B:
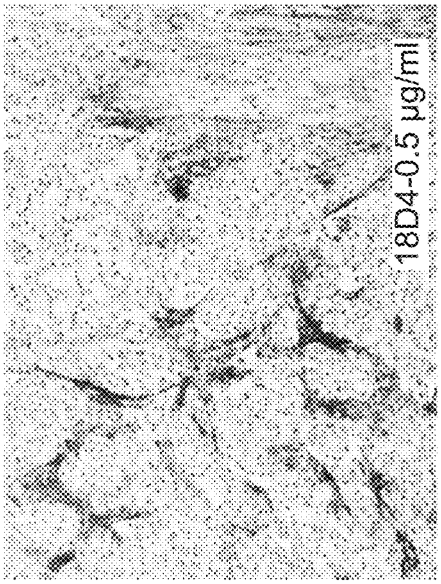
Figure 1C:
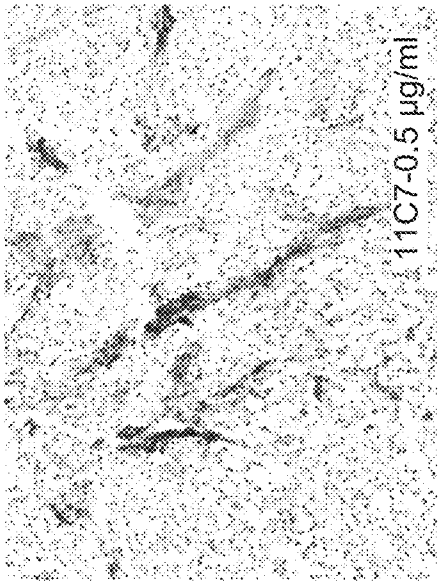

The pattern of histological staining in LS174T xenografts tumors corresponds to specific TnC stroma fibers (FIGS. 1A-1C). The TnC staining, for both clones 18D4 and 11C7, is overall expressed with moderate intensity. Negative isotype control signal validates the specificity of the technique. Specificity of the staining is validated by negative isotype control signals in the corresponding histological staining in with a rabbit isotype control (FIG. 2). Histological staining in human tumor array with anti-TnC clone 18D4 corresponds to specific TnC stroma fibers. The TnC staining is expressed at higher levels in most tumor tissues compared to control normal pair tissue (FIG. 3). Histological staining in human tumor array with anti-TnC clone 11C7 corresponds to specific TnC stroma fibers. The TnC staining is expressed at higher levels in most tumor tissues compared to control normal pair tissue (FIG. 4).

Example 7

Preparation, Purification and Characterization of 4-1BB

DNA sequences encoding the ectodomains of human, mouse or cynomolgus 4-1BB (Table 27) were subcloned in frame with the human IgG1 heavy chain CH2 and CH3 domains on the knob (Merchant et al., 1998). An AcTEV protease cleavage site was introduced between an antigen ectodomain and the Fc of human IgG1. An Avi tag for directed biotinylation was introduced at the C-terminus of the antigen-Fc knob. Combination of the antigen-Fc knob chain containing the S354C/T366W mutations, with a Fc hole chain containing the Y349C/T366S/L368A/Y407V mutations allows generation of a heterodimer which includes a single copy of 4-1BB ectodomain containing chain, thus creating a monomeric form of Fc-linked antigen. Table 28 shows the cDNA and amino acid sequences of the antigen Fc-fusion constructs.

TABLE 27

Amino acid numbering of antigen ectodomains (ECD) and their origin

| SEQ ID NO: | Construct | Origin | ECD |
|---|---|---|---|
| SEQ ID NO: 85 | human 4-1BB ECD | Synthetized according to Q07011 | aa 24-186 |
| SEQ ID NO: 86 | cynomolgus 4-1BB ECD | isolated from cynomolgus blood | aa 24-186 |
| SEQ ID NO: 87 | murine 4-1BB ECD | Synthetized according to P20334 | aa 24-187 |

TABLE 28 cDNA and Amino acid sequences of monomeric antigen Fc(kih) fusion molecules

| SEQ ID NO: | Antigen | Sequence |
|---|---|---|
| SEQ ID NO: 88 | Nucleotide sequence Fc hole chain | GACAAAACTCACACATGCCCACCGTGCCCAGCACC<br>TGAACTCCTGGGGGGACCGTCAGTCTTCCTCTTCC<br>CCCCAAAACCCAAGGACACCCTCATGATCTCCCGG<br>ACCCCTGAGGTCACATGCGTGGTGGTGGACGTGAG<br>CCACGAAGACCCTGAGGTCAAGTTCAACTGGTACG<br>TGGACGGCGTGGAGGTGCATAATGCCAAGACAAA<br>GCCGCGGGAGGAGCAGTACAACAGCACGTACCGT<br>GTGGTCAGCGTCCTCACCGTCCTGCACCAGGACTG<br>GCTGAATGGCAAGGAGTACAAGTGCAAGGTCTCC<br>AACAAAGCCCTCCCAGCCCCCATCGAGAAAACCAT<br>CTCCAAAGCCAAAGGGCAGCCCCGAGAACCACAG<br>GTGTGCACCCTGCCCCCATCCCGGGATGAGCTGAC<br>CAAGAACCAGGTCAGCCTCTCGTGCGCAGTCAAAG<br>GCTTCTATCCCAGCGACATCGCCGTGGAGTGGGAG<br>AGCAATGGGCAGCCGGAGAACAACTACAAGACCA<br>CGCCTCCCGTGCTGGACTCCGACGGCTCCTTCTTCC<br>TCGTGAGCAAGCTCACCGTGGACAAGAGCAGGTG<br>GCAGCAGGGGAACGTCTTCTCATGCTCCGTGATGC<br>ATGAGGCTCTGCACAACCACTACACGCAGAAGAG<br>CCTCTCCCTGTCTCCGGGTAAA |
| SEQ ID NO: 89 | Nucleotide sequence human 4-1BB antigen Fc knob chain | CTGCAGGACCCCTGCAGCAACTGCCCTGCCGGCAC<br>CTTCTGCGACAACAACCGGAACCAGATCTGCAGCC<br>CCTGCCCCCCCAACAGCTTCAGCTCTGCCGGCGGA<br>CAGCGGACCTGCGACATCTGCAGACAGTGCAAGG<br>GCGTGTTCAGAACCCGGAAAGAGTGCAGCAGCAC<br>CAGCAACGCCGAGTGCGACTGCACCCCCGGCTTCC<br>ATTGTCTGGGAGCCGGCTGCAGCATGTGCGAGCAG<br>GACTGCAAGCAGGGCCAGGAACTGACCAAGAAGG<br>GCTGCAAGGACTGCTGCTTCGGCACCTTCAACGAC<br>CAGAAGCGGGGCATCTGCCGGCCCTGGACCAACT<br>GTAGCCTGGACGGCAAGAGCGTGCTGGTCAACGG<br>CACCAAAGAACGGGACGTCGTGTGCGGCCCCAGC<br>CCTGCTGATCTGTCTCCTGGGGCCAGCAGCGTGAC<br>CCCTCCTGCCCCTGCCAGAGAGCCTGGCCACTCTC<br>CTCAGGTCGACGAACAGTTATATTTTCAGGGCGGC<br>TCACCCAAATCTGCAGACAAAACTCACACATGCCC<br>ACCGTGCCCAGCACCTGAACTCCTGGGGGGACCGT<br>CAGTCTTCCTCTTCCCCCCAAAACCCAAGGACACC<br>CTCATGATCTCCCGGACCCCTGAGGTCACATGCGT<br>GGTGGTGGACGTGAGCCACGAAGACCCTGAGGTC<br>AAGTTCAACTGGTACGTGGACGGCGTGGAGGTGC<br>ATAATGCCAAGACAAAGCCGCGGGAGGAGCAGTA<br>CAACAGCACGTACCGTGTGGTCAGCGTCCTCACCG<br>TCCTGCACCAGGACTGGCTGAATGGCAAGGAGTAC<br>AAGTGCAAGGTCTCCAACAAAGCCCTCCCAGCCCC<br>CATCGAGAAAACCATCTCCAAAGCCAAAGGGCAG<br>CCCCGAGAACCACAGGTGTACACCCTGCCCCCATG<br>CCGGGATGAGCTGACCAAGAACCAGGTCAGCCTG<br>TGGTGCCTGGTCAAAGGCTTCTATCCCAGCGACAT |

TABLE 28-continued

| cDNA and Amino acid sequences of monomeric antigen Fc(kih) fusion molecules | | |
|---|---|---|
| SEQ ID NO: | Antigen | Sequence |
| | | CGCCGTGGAGTGGGAGAGCAATGGGCAGCCGGAG<br>AACAACTACAAGACCACGCCTCCCGTGCTGGACTC<br>CGACGGCTCCTTCTTCCTCTACAGCAAGCTCACCG<br>TGGACAAGAGCAGGTGGCAGCAGGGGAACGTCTT<br>CTCATGCTCCGTGATGCATGAGGCTCTGCACAACC<br>ACTACACGCAGAAGAGCCTCTCCCTGTCTCCGGGT<br>AAATCCGGAGGCCTGAACGACATCTTCGAGGCCCA<br>GAAGATTGAATGGCACGAG |
| SEQ ID NO: 90 | Nucleotide sequence cynomolgus 4-1BB antigen Fc knob chain | TTGCAGGATCTGTGTAGTAACTGCCCAGCTGGTAC<br>ATTCTGTGATAATAACAGGAGTCAGATTTGCAGTC<br>CCTGTCCTCCAAATAGTTTCTCCAGCGCAGGTGGA<br>CAAAGGACCTGTGACATATGCAGGCAGTGTAAAG<br>GTGTTTTCAAGACCAGGAAGGAGTGTTCCTCCACC<br>AGCAATGCAGAGTGTGACTGCATTTCAGGGTATCA<br>CTGCCTGGGGGCAGAGTGCAGCATGTGTGAACAG<br>GATTGTAAACAAGGTCAAGAATTGACAAAAAAAG<br>GTTGTAAAGACTGTTGCTTTGGGACATTTAATGAC<br>CAGAAACGTGGCATCTGTCGCCCCTGGACAAACTG<br>TTCTTTGGATGGAAAGTCTGTGCTTGTGAATGGGA<br>CGAAGGAGAGGGACGTGGTCTGCGGACCATCTCC<br>AGCCGACCTCTCTCCAGGAGCATCCTCTGCGACCC<br>CGCCTGCCCCTGCGAGAGAGCCAGGACACTCTCCG<br>CAGGTCGACGAACAGTTATATTTTCAGGGCGGCTC<br>ACCCAAATCTGCAGACAAAACTCACACATGCCCAC<br>CGTGCCCAGCACCTGAACTCCTGGGGGGACCGTCA<br>GTCTTCCTCTTCCCCCCAAAACCCAAGGACACCCT<br>CATGATCTCCCGGACCCCTGAGGTCACATGCGTGG<br>TGGTGGACGTGAGCCACGAAGACCCTGAGGTCAA<br>GTTCAACTGGTACGTGGACGGCGTGGAGGTGCATA<br>ATGCCAAGACAAAGCCGCGGGAGGAGCAGTACAA<br>CAGCACGTACCGTGTGGTCAGCGTCCTCACCGTCC<br>TGCACCAGGACTGGCTGAATGGCAAGGAGTACAA<br>GTGCAAGGTCTCCAACAAAGCCCTCCCAGCCCCCA<br>TCGAGAAAACCATCTCCAAAGCCAAAGGGCAGCC<br>CCGAGAACCACAGGTGTACACCCTGCCCCCATGCC<br>GGGATGAGCTGACCAAGAACCAGGTCAGCCTGTG<br>GTGCCTGGTCAAAGGCTTCTATCCCAGCGACATCG<br>CCGTGGAGTGGGAGAGCAATGGGCAGCCGGAGAA<br>CAACTACAAGACCACGCCTCCCGTGCTGGACTCCG<br>ACGGCTCCTTCTTCCTCTACAGCAAGCTCACCGTG<br>GACAAGAGCAGGTGGCAGCAGGGGAACGTCTTCT<br>CATGCTCCGTGATGCATGAGGCTCTGCACAACCAC<br>TACACGCAGAAGAGCCTCTCCCTGTCTCCGGGTAA<br>ATCCGGAGGCCTGAACGACATCTTCGAGGCCCAGA<br>AGATTGAATGGCACGAG |
| SEQ ID NO: 91 | Nucleotide sequence murine 4-1BB antigen Fc knob chain | GTGCAGAACAGCTGCGACAACTGCCAGCCCGGCA<br>CCTTCTGCCGGAAGTACAACCCCGTGTGCAAGAGC<br>TGCCCCCCCAGCACCTTCAGCAGCATCGGCGGCCA<br>GCCCAACTGCAACATCTGCAGAGTGTGCGCCGGCT<br>ACTTCCGGTTCAAGAAGTTCTGCAGCAGCACCCAC<br>AACGCCGAGTGCGAGTGCATCGAGGGCTTCCACTG<br>CCTGGGCCCCCAGTGCACCAGATGCGAGAAGGAC<br>TGCAGACCCGGCCAGGAACTGACCAAGCAGGGCT<br>GTAAGACCTGCAGCCTGGGCACCTTCAACGACCAG<br>AACGGGACCGGCGTGTGCCGGCCTTGGACCAATTG<br>CAGCCTGGACGGGAGAAGCGTGCTGAAAACCGGC<br>ACCACCGAGAAGGACGTCGTGTGCGGCCCTCCCGT<br>GGTGTCCTTCAGCCCTAGCACCACCATCAGCGTGA<br>CCCCTGAAGGCGGCCCTGGCGGACACTCTCTGCAG<br>GTCCTGGTCGACGAACAGTTATATTTTCAGGGCGG<br>CTCACCCAAATCTGCAGACAAAACTCACACATGCC<br>CACCGTGCCCAGCACCTGAACTCCTGGGGGGACCG<br>TCAGTCTTCCTCTTCCCCCCAAAACCCAAGGACAC<br>CCTCATGATCTCCCGGACCCCTGAGGTCACATGCG<br>TGGTGGTGGACGTGAGCCACGAAGACCCTGAGGT<br>CAAGTTCAACTGGTACGTGGACGGCGTGGAGGTGC<br>ATAATGCCAAGACAAAGCCGCGGGAGGAGCAGTA<br>CAACAGCACGTACCGTGTGGTCAGCGTCCTCACCG<br>TCCTGCACCAGGACTGGCTGAATGGCAAGGAGTAC<br>AAGTGCAAGGTCTCCAACAAAGCCCTCCCAGCCCC<br>CATCGAGAAAACCATCTCCAAAGCCAAAGGGCAG<br>CCCCGAGAACCACAGGTGTACACCCTGCCCCCATG<br>CCGGGATGAGCTGACCAAGAACCAGGTCAGCCTG |

TABLE 28-continued cDNA and Amino acid sequences of monomeric antigen Fc(kih) fusion molecules

| SEQ ID NO: | Antigen | Sequence |
|---|---|---|
| | | TGGTGCCTGGTCAAAGGCTTCTATCCCAGCGACAT CGCCGTGGAGTGGGAGAGCAATGGGCAGCCGGAG AACAACTACAAGACCACGCCTCCCGTGCTGGACTC CGACGGCTCCTTCTTCCTCTACAGCAAGCTCACCG TGGACAAGAGCAGGTGGCAGCAGGGGAACGTCTT CTCATGCTCCGTGATGCATGAGGCTCTGCACAACC ACTACACGCAGAAGAGCCTCTCCCTGTCTCCGGGT AAATCCGGAGGCCTGAACGACATCTTCGAGGCCCA GAAGATTGAATGGCACGAG |
| SEQ ID NO: 92 | Fc hole chain | DKTHTCPPCPAPELLGGPSVFLFPPKPKDTLMISRTPE VTCVVVDVSHEDPEVKFNWYVDGVEVHNAKTKPRE EQYNSTYRVVSVLTVLHQDWLNGKEYKCKVSNKAL PAPIEKTISKAKGQPREPQVCTLPPSRDELTKNQVSLS CAVKGFYPSDIAVEWESNGQPENNYKTTPPVLDSDG SFFLVSKLTVDKSRWQQGNVFSCSVMHEALHNHYT QKSLSLSPGK |
| SEQ ID NO: 93 | human 4-1BB antigen Fc knob chain | LQDPCSNCPAGTFCDNNRNQICSPCPPNSFSSAGGQR TCDICRQCKGVFRTRKECSSTSNAECDCTPGFHCLGA GCSMCEQDCKQGQELTKKGCKDCCFGTFNDQKRGI CRPWTNCSLDGKSVLVNGTKERDVVCGPSPADLSPG ASSVTPPAPAREPGHSPQVDEQLYFQGGSPKSADKTH TCPPCPAPELLGGPSVFLFPPKPKDTLMISRTPEVTCV VVDVSHEDPEVKFNWYVDGVEVHNAKTKPREEQYN STYRVVSVLTVLHQDWLNGKEYKCKVSNKALPAPIE KTISKAKGQPREPQVYTLPPCRDELTKNQVSLWCLV KGFYPSDIAVEWESNGQPENNYKTTPPVLDSDGSFFL YSKLTVDKSRWQQGNVFSCSVMHEALHNHYTQKSL SLSPGKSGGLNDIFEAQKIEWHE |
| SEQ ID NO: 94 | cynomolgus 4-1BB antigen Fc knob chain | LQDLCSNCPAGTFCDNNRSQICSPCPPNSFSSAGGQR TCDICRQCKGVFKTRKECSSTSNAECDCISGYHCLGA ECSMCEQDCKQGQELTKKGCKDCCFGTFNDQKRGI CRPWTNCSLDGKSVLVNGTKERDVVCGPSPADLSPG ASSATPPAPAREPGHSPQVDEQLYFQGGSPKSADKTH TCPPCPAPELLGGPSVFLFPPKPKDTLMISRTPEVTCV VVDVSHEDPEVKFNWYVDGVEVHNAKTKPREEQYN STYRVVSVLTVLHQDWLNGKEYKCKVSNKALPAPIE KTISKAKGQPREPQVYTLPPCRDELTKNQVSLWCLV KGFYPSDIAVEWESNGQPENNYKTTPPVLDSDGSFFL YSKLTVDKSRWQQGNVFSCSVMHEALHNHYTQKSL SLSPGKSGGLNDIFEAQKIEWHE |
| SEQ ID NO: 95 | murine 4-1BB antigen Fc knob chain | VQNSCDNCQPGTFCRKYNPVCKSCPPSTFSSIGGQPN CNICRVCAGYFRFKKFCSSTHNAECECIEGFHCLGPQ CTRCEKDCRPGQELTKQGCKTCSLGTFNDQNGTGVC RPWTNCSLDGRSVLKTGTTEKDVVCGPPVVSFSPSTT ISVTPEGGPGGHSLQVLVDEQLYFQGGSPKSADKTHT CPPCPAPELLGGPSVFLFPPKPKDTLMISRTPEVTCVV VDVSHEDPEVKFNWYVDGVEVHNAKTKPREEQYNS TYRVVSVLTVLHQDWLNGKEYKCKVSNKALPAPIE KTISKAKGQPREPQVYTLPPCRDELTKNQVSLWCLV KGFYPSDIAVEWESNGQPENNYKTTPPVLDSDGSFFL YSKLTVDKSRWQQGNVFSCSVMHEALHNHYTQKSL SLSPGKSGGLNDIFEAQKIEWHE |

All 4-1BB-Fc-fusion molecule encoding sequences were cloned into a plasmid vector, which drives expression of the insert from an MPSV promoter and contains a synthetic polyA signal sequence located at the 3' end of the CDS. In addition, the vector contains an EBV OriP sequence for episomal maintenance of the plasmid.

For preparation of the biotinylated monomeric antigen/Fc fusion molecules, exponentially growing suspension HEK293 EBNA cells were co-transfected with three vectors encoding the two components of fusion protein (knob and hole chains) as well as BirA, an enzyme necessary for the biotinylation reaction. The corresponding vectors were used at a 2:1:0.05 ratio ("antigen ECD-AcTEV-Fc knob":"Fc hole":"BirA").

For protein production in 500 ml shake flasks, 400 million HEK293 EBNA cells were seeded 24 hours before transfection. For transfection cells were centrifuged for 5 minutes at 210 g, and the supernatant was replaced by pre-warmed CD CHO medium. Expression vectors were resuspended in 20 mL of CD CHO medium containing 200 μg of vector DNA. After addition of 540 μL of polyethylenimine (PEI), the solution was vortexed for 15 seconds and incubated for 10 minutes at room temperature. Afterwards, cells were mixed with the DNA/PEI solution, transferred to a 500 mL shake flask and incubated for 3 hours at 37° C. in an incubator with a 5% $CO_2$ atmosphere. After the incubation, 160 mL of F17 medium was added and cells were cultured for 24 hours. The production medium was supplemented with 5 mM kifunensine. One day after transfection, 1 mM valproic acid and 7% Feed 1 with supplements were added to the culture. After 7 days of culturing, the cell supernatant was collected by spinning down cells for 15 min at 210 g. The solution was sterile filtered (0.22 µm filter), supplemented with sodium azide to a final concentration of 0.01% (w/v), and kept at 4° C.

Secreted proteins were purified from cell culture supernatants by affinity chromatography using Protein A, followed by size exclusion chromatography. For affinity chromatography, the supernatant was loaded on a HiTrap ProteinA HP column (CV=5 mL, GE Healthcare) equilibrated with 40 mL 20 mM sodium phosphate, 20 mM sodium citrate pH 7.5. Unbound protein was removed by washing with at least 10 column volumes of 20 mM sodium phosphate, 20 mM sodium citrate, 0.5 M sodium chloride containing buffer (pH 7.5). The bound protein was eluted using a linear pH-gradient of sodium chloride (from 0 to 500 mM) created over 20 column volumes of 20 mM sodium citrate, 0.01% (v/v) Tween-20, pH 3.0. The column was then washed with 10 column volumes of 20 mM sodium citrate, 500 mM sodium chloride, 0.01% (v/v) Tween-20, pH 3.0.

The pH of collected fractions was adjusted by adding 1/40 (v/v) of 2M Tris, pH8.0. The protein was concentrated and filtered prior to loading on a HiLoad Superdex 200 column (GE Healthcare) equilibrated with 2 mM MOPS, 150 mM sodium chloride, 0.02% (w/v) sodium azide solution of pH 7.4.

For affinity determination to the human receptor, the ectodomain of human 4-1BB was also subcloned in frame with an avi (GLNDIFEAQKIEWHE (SEQ ID NO: 225)) and a hexahistidine tag.

Protein production was performed as described above for the Fc-fusion protein. Secreted proteins were purified from cell culture supernatants by chelating chromatography, followed by size exclusion chromatography. The first chromatographic step was performed on a NiNTA Superflow Cartridge (5 ml, Qiagen) equilibrated in 20 mM sodium phosphate, 500 nM sodium chloride, pH7.4. Elution was performed by applying a gradient over 12 column volume from 5% to 45% of elution buffer (20 mM sodium phosphate, 500 nM sodium chloride, 500 mM Imidazole, pH7.4). The protein was concentrated and filtered prior to loading on a HiLoad Superdex 75 column (GE Healthcare) equilibrated with 2 mM MOPS, 150 mM sodium chloride, 0.02% (w/v) sodium azide solution of pH 7.4 (Table 29).

TABLE 29

Sequences of monomeric human 4-1BB His molecule

| SEQ ID NO: | antigen | Sequence |
|---|---|---|
| SEQ ID NO: 96 | nucleotide sequence human 4-1BB His | CTGCAGGACCCCTGCAGCAACTGCCCTGCCGGCA CCTTCTGCGACAACAACCGGAACCAGATCTGCAG CCCCTGCCCCCCCAACAGCTTCAGCTCTGCCGGC GGACAGCGGACCTGCGACATCTGCAGACAGTGC AAGGGCGTGTTCAGAACCCGGAAAGAGTGCAGC AGCACCAGCAACGCCGAGTGCGACTGCACCCCC GGCTTCCATTGTCTGGGAGCCGGCTGCAGCATGT GCGAGCAGGACTGCAAGCAGGGCCAGGAACTGA CCAAGAAGGGCTGCAAGGACTGCTGCTTCGGCA CCTTCAACGACCAGAAGCGGGGCATCTGCCGGCC CTGGACCAACTGTAGCCTGGACGGCAAGAGCGT GCTGGTCAACGGCACCAAAGAACGGGACGTCGT GTGCGGCCCCAGCCCTGCTGATCTGTCTCCTGGG GCCAGCAGCGTGACCCCTCCTGCCCCTGCCAGAG AGCCTGGCCACTCTCCTCAGGTCGACGAACAGTT ATATTTTCAGGGCGGCTCAGGCCTGAACGACATC TTCGAGGCCCAGAAGATCGAGTGGCACGAGGCT CGAGCTCACCACCATCACCATCAC |
| SEQ ID NO: 97 | human 4-1BB His | LQDPCSNCPAGTFCDNNRNQICSPCPPNSFSSAGGQ RTCDICRQCKGVFRTRKECSSTSNAECDCTPGFHCL GAGCSMCEQDCKQGQELTKKGCKDCCFGTFNDQK RGICRPWTNCSLDGKSVLVNGTKERDVVCGPSPAD LSPGASSVTPPAPAREPGHSPQVDEQLYFQGGSGLN DIFEAQKIEWHEARAHHHHHH |

Example 8

Preparation of TnC Targeted Split Trimeric 4-1BB Ligand Fc Fusion Molecules

The DNA sequence encoding part of the ectodomain (amino acid 71-254 and 71-248) of human 4-1BB ligand was synthesized according to the P41273 sequence of Uniprot database. The TnC binder used to target the trimeric 4-1BB ligand was clone 18D4.

Figure 5A:
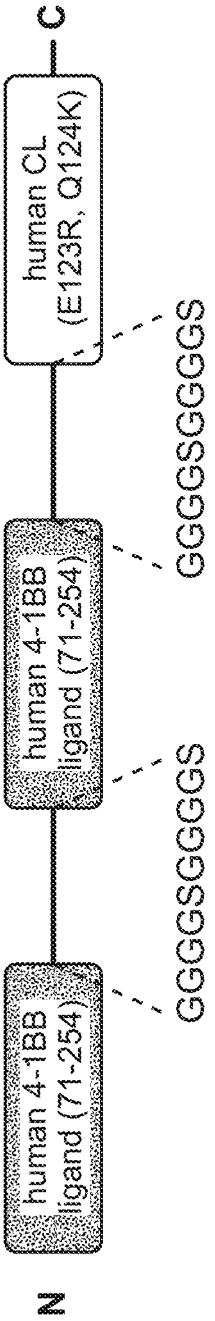
FIGS. 5A and 5B show components for the assembly of monovalent TnC targeted split trimeric human 4-1BB ligand (71-254) (construct 6.1).

Construct 6.1: Monovalent TnC (18D4) Targeted Split Trimeric 4-1BB Ligand (71-254) Fc (kih) Fusion with CH-CL Cross and Charged Residues A polypeptide containing two ectodomains of 4-1BB ligand (71-254), separated by (G4S)2 (SEQ ID NO: 150) linkers, and fused to the human IgG1-CL domain, was cloned as depicted in FIG. 5A: human 4-1BB ligand, (G4S)2 connector, human 4-1BB ligand, (G4S)2 connector, human CL.

Figure 5B:
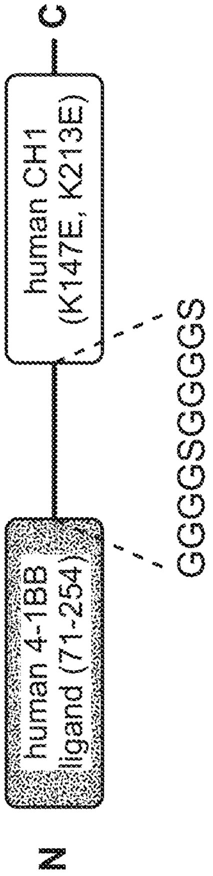
Figure 6:
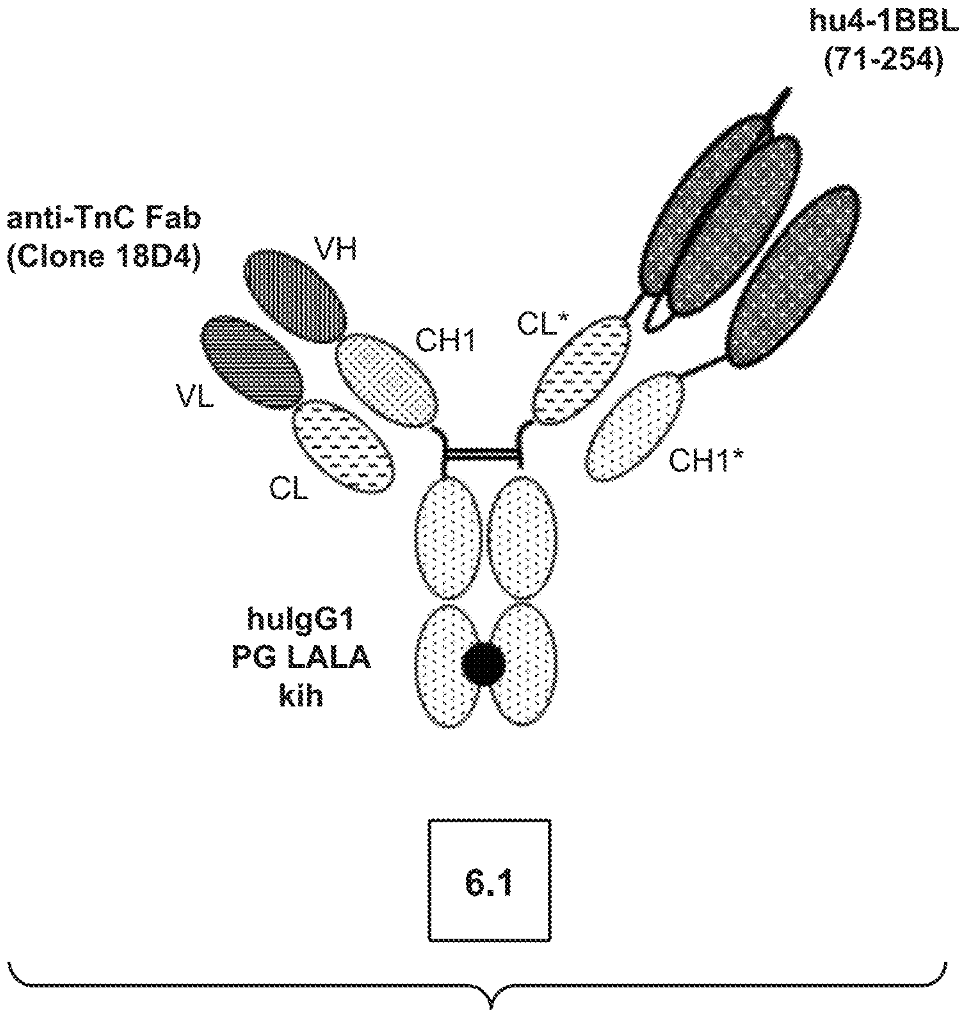
FIG. 6 shows the 4-1BBL-trimer-containing antigen binding molecule constructs 6.1 of the invention (monovalent TnC (18D4) targeted split trimeric 4-1BB ligand (71-254) Fc (kih) PGLALA fusion containing CH-CL cross with charged residues). The preparation and production of this construct is described in Example 1.1. The VH and VL domains are those of anti-TnC antibody 18D4, the thick black point stands for the knob-into-hole modification. * symbolizes amino acid modifications in the CH1 and CL domain (so-called charged residues).

A polypeptide containing one ectodomain of 4-1BB ligand (71-254) and fused to the human IgG1-CH domain, was cloned as described in FIG. 5B: human 4-1BB ligand, (G4S)2 connector, human CH.

To improve correct pairing the following mutations have been introduced in the crossed CH-CL. In the dimeric 4-1BB ligand fused to human CL, E123R and Q124K. In the monomeric 4-1BB ligand fused to human CH1, K147E and K213E.

The variable region of heavy and light chain DNA sequences encoding a binder specific for Tenescin (TnC), clone 18D4, were subcloned in frame with either the constant heavy chain of the hole or the constant light chain of human IgG1.

The Pro329Gly, Leu234Ala and Leu235Ala mutations have been introduced in the constant region of the knob and hole heavy chains to abrogate binding to Fc gamma receptors (as described in International Patent Appl. Publ. No. WO 2012/130831).

Combination of the dimeric ligand-Fc knob chain containing the S354C/T366W mutations, the monomeric CH1 fusion, the targeted anti-TnC-Fc hole chain containing the Y349C/T366S/L368A/Y407V mutations and the anti-TnC light chain (as described e.g. in U.S. Pat. Nos. 5,731,168; 7,695,936) allows generation of a heterodimer, which includes an assembled trimeric 4-1BB ligand and a TnC binding Fab (FIG. 2).

Table 30 and Table 31 show, respectively, the cDNA and amino acid sequences of the monovalent TnC (18D4) targeted split trimeric 4-1BB ligand (71-254) Fc (kih) fusion with CH-CL cross and charged residues (construct 6.1).

TABLE 30

Base pair sequences of monovalent TnC(18D4) targeted split trimeric 4-1BB ligand (71-254) Fc (kih) fusion containing CH-CL cross with charged residues (construct 6.1).

| SEQ ID NO | Construct | Sequence |
|---|---|---|
| SEQ ID NO: 98 | Dimeric ligand (71-254)-CL* Fc knob chain | AGAGAGGGCCCTGAGCTGAGCCCCGATGATCCTGC<br>TGGACTGCTGGACCTGCGGCAGGGCATGTTTGCTC<br>AGCTGGTGGCCCAGAACGTGCTGCTGATCGATGGC<br>CCCCTGTCCTGGTACAGCGATCCTGGACTGGCTGG<br>CGTGTCACTGACAGGCGGCCTGAGCTACAAAGAG<br>GACACCAAAGAACTGGTGGTGGCCAAGGCCGGCG<br>TGTACTACGTGTTCTTTCAGCTGGAACTGCGGAGA<br>GTGGTGGCCGGCGAAGGATCTGGCTCTGTGTCTCT<br>GGCCCTGCATCTGCAGCCTCTGAGAAGCGCTGCTG<br>GCGCTGCAGCTCTGGCACTGACAGTGGATCTGCCT<br>CCTGCCAGCTCCGAGGCCCGGAATAGCGCATTTGG<br>GTTTCAAGGCAGGCTGCTGCACCTGTCTGCCGGCC<br>AGAGGCTGGGAGTGCATCTGCACACAGAGGCCAG<br>GGCTAGACACGCCTGGCAGCTGACACAGGGCGCT<br>ACAGTGCTGGGCCTGTTCAGAGTGACCCCCGAGAT<br>TCCAGCCGGCCTGCCTTCTCCAAGAAGCGAAGGCG<br>GAGGCGGATCTGGCGGCGGAGGATCTAGAGAGGG<br>ACCCGAACTGTCCCCTGACGATCCAGCCGGGCTGC<br>TGGATCTGAGACAGGGAATGTTCGCCCAGCTGGTG<br>GCTCAGAATGTGCTGCTGATTGACGGACCTCTGAG<br>CTGGTACTCCGACCCAGGGCTGGCAGGGGTGTCCC<br>TGACTGGGGGACTGTCCTACAAAGAAGATACAAA<br>AGAACTGGTGGTGGCTAAAGCTGGGGTGTACTATG<br>TGTTTTTTCAGCTGGAACTGAGGCGGGTGGTGGCT<br>GGGGAGGGCTCAGGATCTGTGTCCCTGGCTCTGCA<br>TCTGCAGCCACTGCGCTCTGCTGCTGGCGCAGCTG<br>CACTGGCTCTGACTGTGGACCTGCCACCAGCCTCT<br>AGCGAGGCCAGAAACAGCGCCTTCGGGTTCCAAG<br>GACGCCTGCTGCATCTGAGCGCCGGACAGCGCCTG<br>GGAGTGCATCTGCATACTGAAGCCAGAGCCCGGC<br>ATGCTTGGCAGCTGACTCAGGGGGCAACTGTGCTG<br>GGACTGTTTCGCGTGACACCTGAGATCCCTGCCGG<br>ACTGCCAAGCCCTAGATCAGAAGGGGGCGGAGGT<br>TCCGGAGGGGGAGGATCTCGTACGGTGGCTGCACC<br>ATCTGTCTTTATCTTCCCACCCAGCGACCGGAAGC<br>TGAAGTCTGGCACAGCCAGCGTCGTGTGCCTGCTG<br>AATAACTTCTACCCCCGCGAGGCCAAGGTGCAGTG<br>GAAGGTGGACAATGCCCTGCAGAGCGGCAACAGC<br>CAGGAAAGCGTGACCGAGCAGGACAGCAAGGACT<br>CCACCTACAGCCTGAGCAGCACCCTGACCCTGAGC<br>AAGGCCGACTACGAGAAGCACAAGGTGTACGCCT<br>GCGAAGTGACCCACCAGGGCCTGTCTAGCCCCGTG<br>ACCAAGAGCTTCAACCGGGGCGAGTGCGACAAGA<br>CCCACACCTGTCCTCCATGCCCTGCCCCTGAAGCT<br>GCTGGCGGCCCTAGCGTGTTCCTGTTCCCCCCAAA<br>GCCCAAGGACACCCTGATGATCAGCCGGACCCCTG<br>AAGTGACCTGCGTGGTGGTGGATGTGTCCCACGAG<br>GACCCTGAAGTGAAGTTCAATTGGTACGTGGACGG<br>CGTGGAAGTGCACAATGCCAAGACCAAGCCGCGG<br>GAGGAGCAGTACAACAGCACGTACCGTGTGGTCA<br>GCGTCCTCACCGTCCTGCACCAGGACTGGCTGAAT<br>GGCAAGGAGTACAAGTGCAAGGTCTCCAACAAAG<br>CCCTCGGCGCCCCCATCGAGAAAACCATCTCCAAA<br>GCCAAAGGGCAGCCCCGAGAACCACAGGTGTACA<br>CCCTGCCCCCATGCCGGGATGAGCTGACCAAGAAC<br>CAGGTCAGCCTGTGGTGCCTGGTCAAAGGCTTCTA<br>TCCCAGCGACATCGCCGTGGAGTGGGAGAGCAAT<br>GGGCAGCCGGAGAACAACTACAAGACCACGCCTC<br>CCGTGCTGGACTCCGACGGCTCCTTCTTCCTCTACA<br>GCAAGCTCACCGTGGACAAGAGCAGGTGGCAGCA<br>GGGGAACGTCTTCTCATGCTCCGTGATGCATGAGG |

TABLE 30-continued

Base pair sequences of monovalent TnC(18D4) targeted split trimeric 4-1BB ligand (71-254) Fc (kih) fusion containing CH-CL cross with charged residues (construct 6.1).

| SEQ ID NO | Construct | Sequence |
|---|---|---|
| | | CTCTGCACAACCACTACACGCAGAAGAGCCTCTCC CTGTCTCCGGGTAAA |
| SEQ ID NO: 99 | Monomeric ligand (71-254)-CH1* | AGAGAGGGCCCTGAGCTGAGCCCCGATGATCCTGC TGGACTGCTGGACCTGCGGCAGGGCATGTTTGCTC AGCTGGTGGCCCAGAACGTGCTGCTGATCGATGGC CCCCTGTCCTGGTACAGCGATCCTGGACTGGCTGG CGTGTCACTGACAGGCGGCCTGAGCTACAAAGAG GACACCAAAGAACTGGTGGTGGCCAAGGCCGGCG TGTACTACGTGTTCTTTCAGCTGGAACTGCGGAGA GTGGTGGCCGGCGAAGGATCTGGCTCTGTGTCTCT GGCCCTGCATCTGCAGCCTCTGAGAAGCGCTGCTG GCGCTGCAGCTCTGGCTCTGACAGTGGATCTGCCT CCTGCCAGCTCCGAGGCCCGGAATAGCGCATTTGG GTTTCAAGGCCGGCTGCTGCACCTGTCTGCCGGCC AGAGACTGGGAGTGCATCTGCACACAGAGGCCAG AGCCAGGCACGCCTGGCAGCTGACACAGGGCGCT ACAGTGCTGGGCCTGTTCAGAGTGACCCCCGAGAT TCCTGCCGGCCTGCCTAGCCCTAGATCTGAAGGCG GCGGAGGTTCCGGAGGCGGAGGATCTGCTAGCAC AAAGGGCCCCAGCGTGTTCCCTCTGGCCCCTAGCA GCAAGAGCACATCTGGCGGAACAGCCGCCCTGGG CTGCCTGGTGGAAGATTACTTCCCCGAGCCCGTGA CCGTGTCCTGGAATTCTGGCGCCCTGACAAGCGGC GTGCACACCTTTCCAGCCGTGCTGCAGAGCAGCGG CCTGTACTCTCTGAGCAGCGTCGTGACAGTGCCCA GCAGCTCTCTGGGCACCCAGACCTACATCTGCAAC GTGAACCACAAGCCCAGCAACACCAAGGTGGACG AGAAGGTGGAACCCAAGTCCTGC |
| SEQ ID NO: 100 | anti-TnC(18D4) Fc hole chain | CAGGTGCAATTGGTGCAGTCTGGGGCTGAGGTGAA GAAGCCTGGGTCCTCGGTGAAGGTCTCCTGCAAGG CCTCCGGAGGCACATTCAGCAGCTACGCTATAAGC TGGGTGCGACAGGCCCCTGGACAAGGGCTCGAGT GGATGGGAGGGATCATCCCTATCTTTGGTACAGCA AACTACGCACAGAAGTTCCAGGGCAGGGTCACCA TTACTGCAGACAAATCCACGAGCACAGCCTACATG GAGCTGAGCAGCCTGAGATCTGAGGACACCGCCG TGTATTACTGTGCGAAAGGTAACTTCTACGGTGGT CTGGACTACTGGGGCCAAGGGACCACCGTGACCGT CTCCTCAGCTAGCACCAAGGGCCCCTCCGTGTTCC CCCTGGCCCCCAGCAGCAAGAGCACCAGCGGCGG CACAGCCGCTCTGGGCTGCCTGGTCAAGGACTACT TCCCCGAGCCCGTGACCGTGTCCTGGAACAGCGGA GCCCTGACCTCCGGCGTGCACACCTTCCCCGCCGT GCTGCAGAGTTCTGGCCTGTATAGCCTGAGCAGCG TGGTCACCGTGCCTTCTAGCAGCCTGGGCACCCAG ACCTACATCTGCAACGTGAACCACAAGCCCAGCAA CACCAAGGTGGACAAGAAGGTGGAGCCCAAGAGC TGCGACAAAACTCACACATGCCCACCGTGCCCAGC ACCTGAAGCTGCAGGGGGACCGTCAGTCTTCCTCT TCCCCCCAAAACCCAAGGACACCCTCATGATCTCC CGGACCCCTGAGGTCACATGCGTGGTGGTGGACGT GAGCCACGAAGACCCTGAGGTCAAGTTCAACTGGT ACGTGGACGGCGTGGAGGTGCATAATGCCAAGAC AAAGCCGCGGGAGGAGCAGTACAACAGCACGTAC CGTGTGGTCAGCGTCCTCACCGTCCTGCACCAGGA CTGGCTGAATGGCAAGGAGTACAAGTGCAAGGTC TCCAACAAAGCCCTCGGCGCCCCCATCGAGAAAAC CATCTCCAAAGCCAAAGGGCAGCCCCGAGAACCA CAGGTGTGCACCCTGCCCCCATCCCGGGATGAGCT GACCAAGAACCAGGTCAGCCTCTCGTGCGCAGTCA AAGGCTTCTATCCCAGCGACATCGCCGTGGAGTGG GAGAGCAATGGGCAGCCGGAGAACAACTACAAGA CCACGCCTCCCGTGCTGGACTCCGACGGCTCCTTC TTCCTCGTGAGCAAGCTCACCGTGGACAAGAGCAG GTGGCAGCAGGGGAACGTCTTCTCATGCTCCGTGA TGCATGAGGCTCTGCACAACCACTACACGCAGAAG AGCCTCTCCCTGTCTCCGGGTAAA |

TABLE 30-continued

Base pair sequences of monovalent TnC(18D4) targeted split trimeric 4-1BB ligand (71-254) Fc (kih) fusion containing CH-CL cross with charged residues (construct 6.1).

| SEQ ID NO | Construct | Sequence |
|---|---|---|
| SEQ ID NO: 73 | anti-TnC(18D4) light chain | See Table 20 |

*for charged residues

TABLE 31

Amino acid sequences of monovalent TnC(18D4) targeted split trimeric 4-1BB ligand (71-254) Fc (kih) fusion containing CH-CL cross with charged residues (construct 6.1).

| SEQ ID NO | Construct | Sequence |
|---|---|---|
| SEQ ID NO: 102 | Dimeric ligand (71-254)-CL* Fc knob chain | REGPELSPDDPAGLLDLRQGMFAQLVAQNVLLIDGP LSWYSDPGLAGVSLTGGLSYKEDTKELVVAKAGVY YVFFQLELRRVVAGEGSGSVSLALHLQPLRSAAGAA ALALTVDLPPASSEARNSAFGFQGRLLHLSAGQRLG VHLHTEARARHAWQLTQGATVLGLFRVTPEIPAGLP SPRSEGGGGSGGGGSREGPELSPDDPAGLLDLRQGM FAQLVAQNVLLIDGPLSWYSDPGLAGVSLTGGLSYK EDTKELVVAKAGVYYVFFQLELRRVVAGEGSGSVSL ALHLQPLRSAAGAAALALTVDLPPASSEARNSAFGF QGRLLHLSAGQRLGVHLHTEARARHAWQLTQGATV LGLFRVTPEIPAGLPSPRSEGGGGSGGGGSRTVAAPS VFIFPPSDRKLKSGTASVVCLLNNFYPREAKVQWKV DNALQSGNSQESVTEQDSKDSTYSLSSTLTLSKADYE KHKVYACEVTHQGLSSPVTKSFNRGECDKTHTCPPC PAPEAAGGPSVFLFPPKPKDTLMISRTPEVTCVVVDV SHEDPEVKFNWYVDGVEVHNAKTKPREEQYNSTYR VVSVLTVLHQDWLNGKEYKCKVSNKALGAPIEKTIS KAKGQPREPQVYTLPPCRDELTKNQVSLWCLVKGFY PSDIAVEWESNGQPENNYKTTPPVLDSDGSFFLYSKL TVDKSRWQQGNVFSCSVMHEALHNHYTQKSLSLSP GK |
| SEQ ID NO: 103 | Monomeric ligand (71-254)-CH1* | REGPELSPDDPAGLLDLRQGMFAQLVAQNVLLIDGP LSWYSDPGLAGVSLTGGLSYKEDTKELVVAKAGVY YVFFQLELRRVVAGEGSGSVSLALHLQPLRSAAGAA ALALTVDLPPASSEARNSAFGFQGRLLHLSAGQRLG VHLHTEARARHAWQLTQGATVLGLFRVTPEIPAGLP SPRSEGGGGSGGGGSASTKGPSVFPLAPSSKSTSGGT AALGCLVEDYFPEPVTVSWNSGALTSGVHTFPAVLQ SSGLYSLSSVVTVPSSSLGTQTYICNVNHKPSNTKVD EKVEPKSC |
| SEQ ID NO: 104 | anti-TnC(18D4) Fc hole chain | QVQLVQSGAEVKKPGSSVKVSCKASGGTFSSYAISW VRQAPGQGLEWMGGIIPIFGTANYAQKFQGRVTITA DKSTSTAYMELSSLRSEDTAVYYCAKGNFYGGLDY WGQGTTVTVSSASTKGPSVFPLAPSSKSTSGGTAALG CLVKDYFPEPVTVSWNSGALTSGVHTFPAVLQSSGL YSLSSVVTVPSSSLGTQTYICNVNHKPSNTKVDKKVE PKSCDKTHTCPPCPAPEAAGGPSVFLFPPKPKDTLMIS RTPEVTCVVVDVSHEDPEVKFNWYVDGVEVHNAKT KPREEQYNSTYRVVSVLTVLHQDWLNGKEYKCKVS NKALGAPIEKTISKAKGQPREPQVCTLPPSRDELTKN QVSLSCAVKGFYPSDIAVEWESNGQPENNYKTTPPV LDSDGSFFLVSKLTVDKSRWQQGNVFSCSVMHEALH NHYTQKSLSLSPGK |
| SEQ ID NO: 77 | anti-TnC(18D4) light chain | See Table 21 |

*for charged residues

Figure 7A:
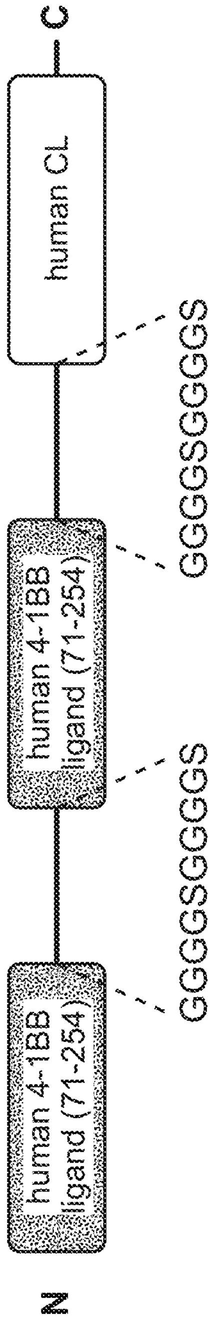
FIGS. 7A and 7B show the components for the assembly of monovalent TnC targeted split trimeric human 4-1BB ligand (71-254) (construct 6.2).

Construct 6.2: Monovalent TnC (18D4) Targeted Split Trimeric 4-1BB Ligand (71-254) Fc (kih) Fusion Containing CH-CL Cross without Charged Residues A polypeptide containing two ectodomains of 4-1BB ligand (71-254), separated by (G4S)2 (SEQ ID NO: 150) linkers, and fused to the human IgG1-CL domain, was cloned as depicted in FIG. 7A: human 4-1BB ligand, (G4S)2 connector, human 4-1BB ligand, (G4S)2 connector, human CL.

Figure 7B:
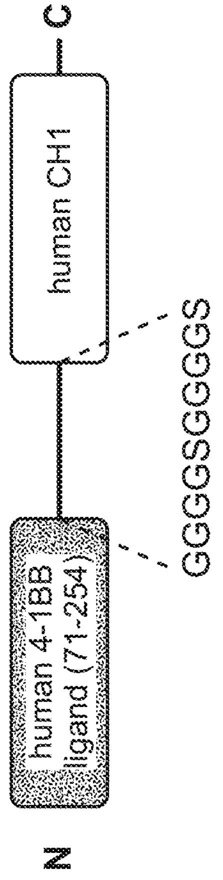

A polypeptide containing one ectodomain of 4-1BB ligand (71-254) and fused to the human IgG1-CH domain, was cloned as described in FIG. 7B: human 4-1BB ligand, (G4S)2 connector, human CH.

The variable region of heavy and light chain DNA sequences encoding a binder specific for TnC, clone 18D4, were subcloned in frame with either the constant heavy chain of the hole or the constant light chain of human IgG1.

The Pro329Gly, Leu234Ala and Leu235Ala mutations have been introduced in the constant region of the knob and hole heavy chains to abrogate binding to Fc gamma receptors (patent accession number).

Figure 8:
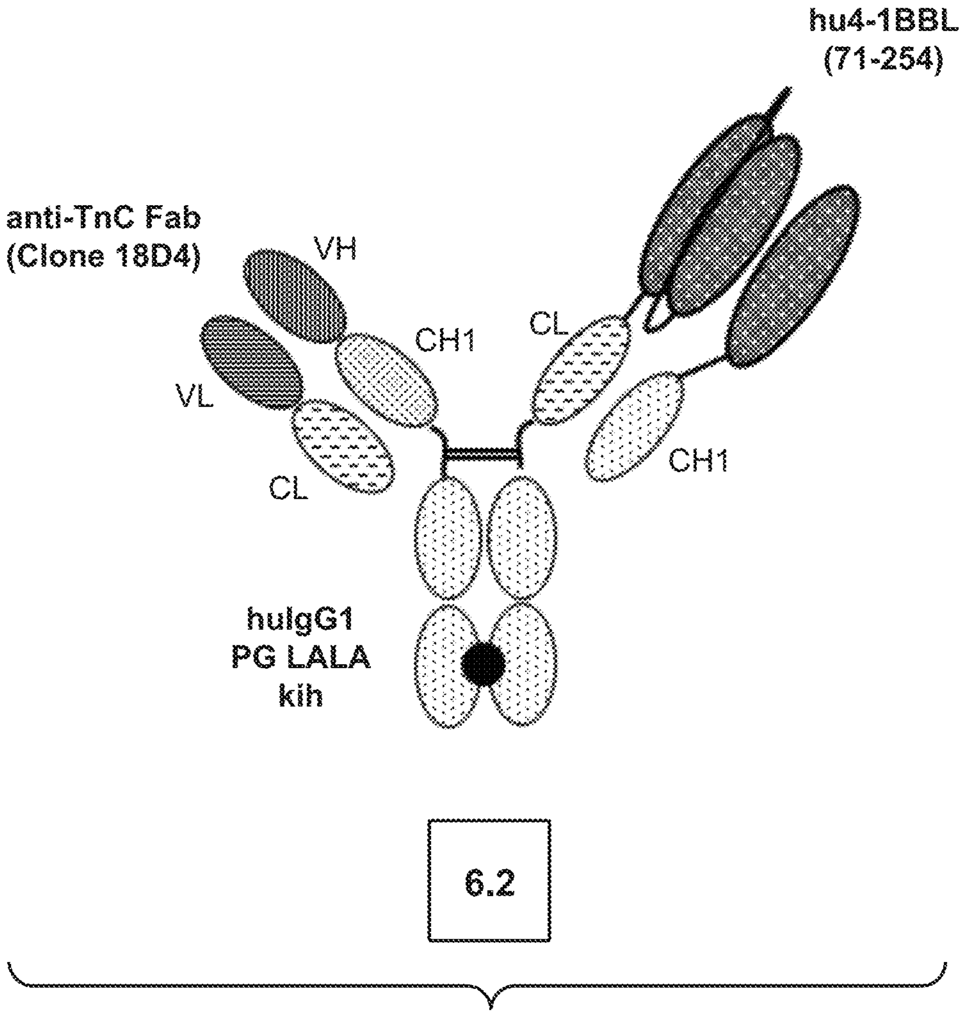
FIG. 8 shows monovalent TnC (18D4) targeted split trimeric 4-1BB ligand (71-254) Fc (kih) fusion containing CH-CL cross without charged residues (construct 6.2). The preparation and production of this construct is described in Example 1.2. The VH and VL domains are those of anti-TnC antibody 18D4, the thick black point stands for the knob-into-hole modification.

Combination of the dimeric ligand-Fc knob chain containing the S354C/T366W mutations, the monomeric CH1 fusion, the targeted anti-TnC-Fc hole chain containing the Y349C/T366S/L368A/Y407V mutations and the anti-TnC light chain allows generation of a heterodimer, which includes an assembled trimeric 4-1BB ligand and a TnC binding Fab (FIG. 8).

Table 32 and Table 33 show, respectively, the cDNA and amino acid sequences of the monovalent TnC (18D4) targeted split trimeric 4-1BB ligand (71-254) Fc (kih) fusion containing CH-CL cross without charged residues (construct 6.2).

TABLE 32

Base pair sequences of monovalent TnC(18D4) targeted split trimeric 4-1BB ligand (71-254) Fc (kih) fusion containing CH-CL cross without charged residues (construct 6.2).

| SEQ ID NO | Construct | Sequence |
|---|---|---|
| SEQ ID NO: 106 | Dimeric ligand (71-254)-CL Fc knob chain | AGAGAGGGCCCTGAGCTGAGCCCCGATGATCCTGCT<br>GGACTGCTGGACCTGCGGCAGGGCATGTTTGCTCAGC<br>TGGTGGCCCAGAACGTGCTGCTGATCGATGGCCCCCT<br>GTCCTGGTACAGCGATCCTGGACTGGCTGGCGTGTCA<br>CTGACAGGCGGCCTGAGCTACAAAGAGGACACCAAA<br>GAACTGGTGGTGGCCAAGGCCGGCGTGTACTACGTGT<br>TCTTTCAGCTGGAACTGCGGAGAGTGGTGGCCGGCGA<br>AGGATCTGGCTCTGTGTCTCTGGCCCTGCATCTGCAG<br>CCTCTGAGAAGCGCTGCTGGCGCTGCAGCTCTGGCAC<br>TGACAGTGGATCTGCCTCCTGCCAGCTCCGAGGCCCG<br>GAATAGCGCATTTGGGTTTCAAGGCAGGCTGCTGCAC<br>CTGTCTGCCGGCCAGAGGCTGGGAGTGCATCTGCACA<br>CAGAGGCCAGGGCTAGACACGCCTGGCAGCTGACAC<br>AGGGCGCTACAGTGCTGGGCCTGTTCAGAGTGACCCC<br>CGAGATTCCAGCCGGCCTGCCTTCTCCAAGAAGCGAA<br>GGCGGAGGCGGATCTGGCGGCGGAGGATCTAGAGAG<br>GGACCCGAACTGTCCCCTGACGATCCAGCCGGGCTGC<br>TGGATCTGAGACAGGGAATGTTCGCCCAGCTGGTGGC<br>TCAGAATGTGCTGCTGATTGACGGACCTCTGAGCTGG<br>TACTCCGACCCAGGGCTGGCAGGGGTGTCCCTGACTG<br>GGGGACTGTCCTACAAAGAAGATACAAAAGAACTGG<br>TGGTGGCTAAAGCTGGGGTGTACTATGTGTTTTTCA<br>GCTGGAACTGAGGCGGGTGGTGGCTGGGGAGGGCTC<br>AGGATCTGTGTCCCTGGCTCTGCATCTGCAGCCACTG<br>CGCTCTGCTGCTGGCGCAGCTGCACTGGCTCTGACTG<br>TGGACCTGCCACCAGCCTCTAGCGAGGCCAGAAACA<br>GCGCCTTCGGGTTCCAAGGACGCCTGCTGCATCTGAG<br>CGCCGGACAGCGCCTGGGAGTGCATCTGCATACTGA<br>AGCCAGAGCCCGGCATGCTTGGCAGCTGACTCAGGG<br>GGCAACTGTGCTGGGACTGTTTCGCGTGACACCTGAG<br>ATCCCTGCCGGACTGCCAAGCCCTAGATCAGAAGGG<br>GGCGGAGGTTCCGGAGGGGGAGGATCTCGTACGGTG<br>GCCGCTCCCTCCGTGTTTATCTTTCCCCCATCCGATGA<br>ACAGCTGAAAAGCGGCACCGCCTCCGTCGTGTGTCTG<br>CTGAACAATTTTTACCCTAGGGAAGCTAAAGTGCAGT<br>GGAAAGTGGATAACGCACTGCAGTCCGGCAACTCCC<br>AGGAATCTGTGACAGAACAGGACTCCAAGGACAGCA<br>CCTACTCCCTGTCCTCCACCCTGACACTGTCTAAGGCT<br>GATTATGAGAAACACAAAGTCTACGCCTGCGAAGTC<br>ACCCATCAGGGCCTGAGCTCGCCCGTCACAAAGAGCT<br>TCAACAGGGGAGAGTGTGACAAGACCCACACCTGTC<br>CCCCTTGTCCTGCCCCTGAAGCTGCTGGCGGCCCTTCT<br>GTGTTCCTGTTCCCCCCAAAGCCCAAGGACACCCTGA<br>TGATCAGCCGGACCCCCGAAGTGACCTGCGTGGTGGT<br>GGATGTGTCCCACGAGGACCCTGAAGTGAAGTTCAAT<br>TGGTACGTGGACGGCGTGGAAGTGCACAATGCCAAG<br>ACCAAGCCGCGGGAGGAGCAGTACAACAGCACGTAC<br>CGTGTGGTCAGCGTCCTCACCGTCCTGCACCAGGACT<br>GGCTGAATGGCAAGGAGTACAAGTGCAAGGTCTCCA<br>ACAAAGCCCTCGGCGCCCCCATCGAGAAAACCATCTC<br>CAAAGCCAAAGGGCAGCCCCGAGAACCACAGGTGTA<br>CACCCTGCCCCCATGCCGGGATGAGCTGACCAAGAA |

TABLE 32-continued

Base pair sequences of monovalent TnC(18D4) targeted split trimeric 4-1BB ligand (71-254) Fc (kih) fusion containing CH-CL cross without charged residues (construct 6.2).

| SEQ ID NO | Construct | Sequence |
|---|---|---|
| | | CCAGGTCAGCCTGTGGTGCCTGGTCAAAGGCTTCTAT<br>CCCAGCGACATCGCCGTGGAGTGGGAGAGCAATGGG<br>CAGCCGGAGAACAACTACAAGACCACGCCTCCCGTG<br>CTGGACTCCGACGGCTCCTTCTTCCTCTACAGCAAGC<br>TCACCGTGGACAAGAGCAGGTGGCAGCAGGGGAACG<br>TCTTCTCATGCTCCGTGATGCATGAGGCTCTGCACAA<br>CCACTACACGCAGAAGAGCCTCTCCCTGTCTCCGGGT<br>AAA |
| SEQ ID NO: 107 | Monomeric ligand (71-254)-CH1 | AGAGAGGGCCCTGAGCTGAGCCCCGATGATCCTGCT<br>GGACTGCTGGACCTGCGGCAGGGCATGTTTGCTCAGC<br>TGGTGGCCCAGAACGTGCTGCTGATCGATGGCCCCCT<br>GTCCTGGTACAGCGATCCTGGACTGGCTGGCGTGTCA<br>CTGACAGGCGGCCTGAGCTACAAAGAGGACACCAAA<br>GAACTGGTGGTGGCCAAGGCCGGCGTGTACTACGTGT<br>TCTTTCAGCTGGAACTGCGGAGAGTGGTGGCCGGCGA<br>AGGATCTGGCTCTGTGTCTCTGGCCCTGCATCTGCAG<br>CCTCTGAGAAGCGCTGCTGGCGCTGCAGCTCTGGCTC<br>TGACAGTGGATCTGCCTCCTGCCAGCTCCGAGGCCCG<br>GAATAGCGCATTTGGGTTTCAAGGCCGGCTGCTGCAC<br>CTGTCTGCCGGCCAGAGACTGGGAGTGCATCTGCACA<br>CAGAGGCCAGAGCCAGGCACGCCTGGCAGCTGACAC<br>AGGGCGCTACAGTGCTGGGCCTGTTCAGAGTGACCCC<br>CGAGATTCCTGCCGGCCTGCCTAGCCCTAGATCTGAA<br>GGCGGCGGAGGTTCCGGAGGCGGAGGATCTGCTAGC<br>ACCAAAGGCCCTTCCGTGTTTCCTCTGGCTCCTAGCTC<br>CAAGTCCACCTCTGGAGGCACCGCTGCTCTCGGATGC<br>CTCGTGAAGGATTATTTTCCTGAGCCTGTGACAGTGT<br>CCTGGAATAGCGGAGCACTGACCTCTGGAGTGCATAC<br>TTTCCCCGCTGTGCTGCAGTCCTCTGGACTGTACAGC<br>CTGAGCAGCGTGGTGACAGTGCCCAGCAGCAGCCTG<br>GGCACCCAGACCTACATCTGCAACGTGAACCACAAG<br>CCCAGCAACACCAAGGTGGACAAGAAGGTGGAACCC<br>AAGTCTTGT |
| SEQ ID NO: 98 | anti-TnC(18D4) Fc hole chain | See Table 30 |
| SEQ ID NO: 99 | anti-TnC(18D4) light chain | See Table 30 |

TABLE 33

Amino acid sequences of monovalent TnC(18D4) targeted split trimeric 4-1BB ligand (71-254) Fc (kih) fusion containing CH-CL cross without charged residues (construct 6.2).

| SEQ ID NO | Construct | Sequence |
|---|---|---|
| SEQ ID NO: 108 | Dimeric ligand (71-254)-CL Fc knob chain | REGPELSPDDPAGLLDLRQGMFAQLVAQNVLLIDGPLS<br>WYSDPGLAGVSLTGGLSYKEDTKELVVAKAGVYYVFF<br>QLELRRVVAGEGSGSVSLALHLQPLRSAAGAAALALTV<br>DLPPASSEARNSAFGFQGRLLHLSAGQRLGVHLHTEAR<br>ARHAWQLTQGATVLGLFRVTPEIPAGLPSPRSEGGGGS<br>GGGGSREGPELSPDDPAGLLDLRQGMFAQLVAQNVLLI<br>DGPLSWYSDPGLAGVSLTGGLSYKEDTKELVVAKAGV<br>YYVFFQLELRRVVAGEGSGSVSLALHLQPLRSAAGAAA<br>LALTVDLPPASSEARNSAFGFQGRLLHLSAGQRLGVHL<br>HTEARARHAWQLTQGATVLGLFRVTPEIPAGLPSPRSEG<br>GGGSGGGGSRTVAAPSVFIFPPSDEQLKSGTASVVCLLN<br>NFYPREAKVQWKVDNALQSGNSQESVTEQDSKDSTYS<br>LSSTLTLSKADYEKHKVYACEVTHQGLSSPVTKSFNRG<br>ECDKTHTCPPCPAPEAAGGPSVFLFPPKPKDTLMISRTPE<br>VTCVVVDVSHEDPEVKFNWYVDGVEVHNAKTKPREEQ<br>YNSTYRVVSVLTVLHQDWLNGKEYKCKVSNKALGAPI<br>EKTISKAKGQPREPQVYTLPPCRDELTKNQVSLWCLVK<br>GFYPSDIAVEWESNGQPENNYKTTPPVLDSDGSFFLYSK<br>LTVDKSRWQQGNVFSCSVMHEALHNHYTQKSLSLSPGK |

TABLE 33-continued

Amino acid sequences of monovalent TnC(18D4) targeted split trimeric 4-1BB ligand (71-254) Fc (kih) fusion containing CH-CL cross without charged residues (construct 6.2).

| SEQ ID NO | Construct | Sequence |
| --- | --- | --- |
| SEQ ID NO: 109 | Monomeric ligand (71-254)-CH1 | REGPELSPDDPAGLLDLRQGMFAQLVAQNVLLIDGPLS WYSDPGLAGVSLTGGLSYKEDTKELVVAKAGVYYVFF QLELRRVVAGEGSGSVSLALHLQPLRSAAGAAALALTV DLPPASSEARNSAFGFQGRLLHLSAGQRLGVHLHTEAR ARHAWQLTQGATVLGLFRVTPEIPAGLPSPRSEGGGGS GGGGSASTKGPSVFPLAPSSKSTSGGTAALGCLVKDYFP EPVTVSWNSGALTSGVHTFPAVLQSSGLYSLSSVVTVPS SSLGTQTYICNVNHKPSNTKVDKKVEPKSC |
| SEQ ID NO: 104 | anti-TnC(18D4) Fc hole chain | See Table 31 |
| SEQ ID NO: 77 | anti-TnC(18D4) light chain | See Table 21 |

Figure 9A:
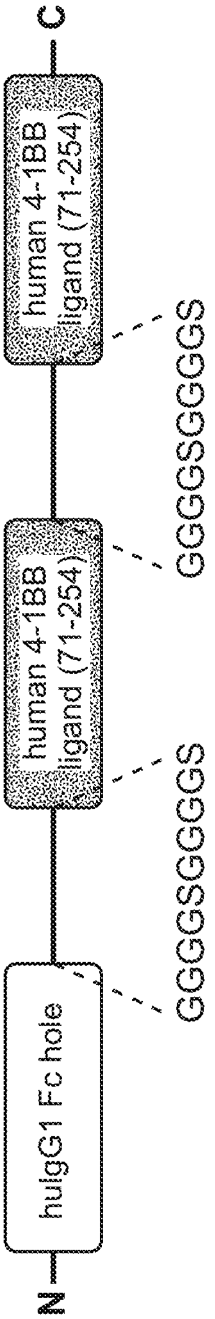
FIGS. 9A and 9B show components for the assembly of bivalent TnC targeted split trimeric human 4-1BB ligand (71-254) (construct 6.3).

Construct 6.3: Bivalent TnC (18D4) Targeted Split Trimeric 4-1BB Ligand (71-254) Fc (kih) Fusion A polypeptide containing two ectodomains of 4-1BB ligand (71-254), separated by (G4S)2 (SEQ ID NO: 150) linkers was fused to the C-terminus of human IgG1 Fc hole chain, as depicted in FIG. 9A: human IgG1 Fc hole, (G4S)2 connector, human 4-1BB ligand, (G4S)2 connector, human 4-1BB ligand.

Figure 9B:
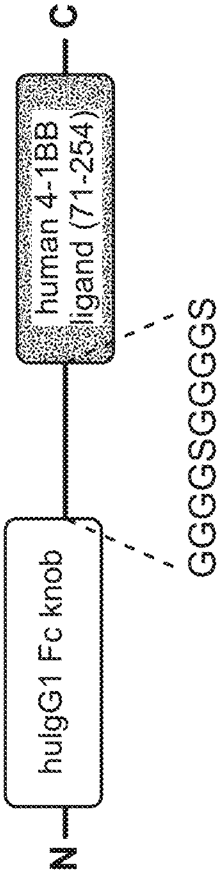

A polypeptide containing one ectodomain of 4-1BB ligand (71-254) and fused to the C-terminus of human IgG1 Fc knob chain as described in FIG. 9B: human IgG1 Fc knob, (G4S)2 connector, human 4-1BB ligand.

The variable region of heavy and light chain DNA sequences encoding a binder specific for TnC, clone 18D4, were subcloned in frame with either the constant heavy chain of the hole, the knob or the constant light chain of human IgG1.

The Pro329Gly, Leu234Ala and Leu235Ala mutations have been introduced in the constant region of the knob and hole heavy chains to abrogate binding to Fc gamma receptors (described in International Patent Appl. Publ. No. WO 2012/130831).

Figure 10:
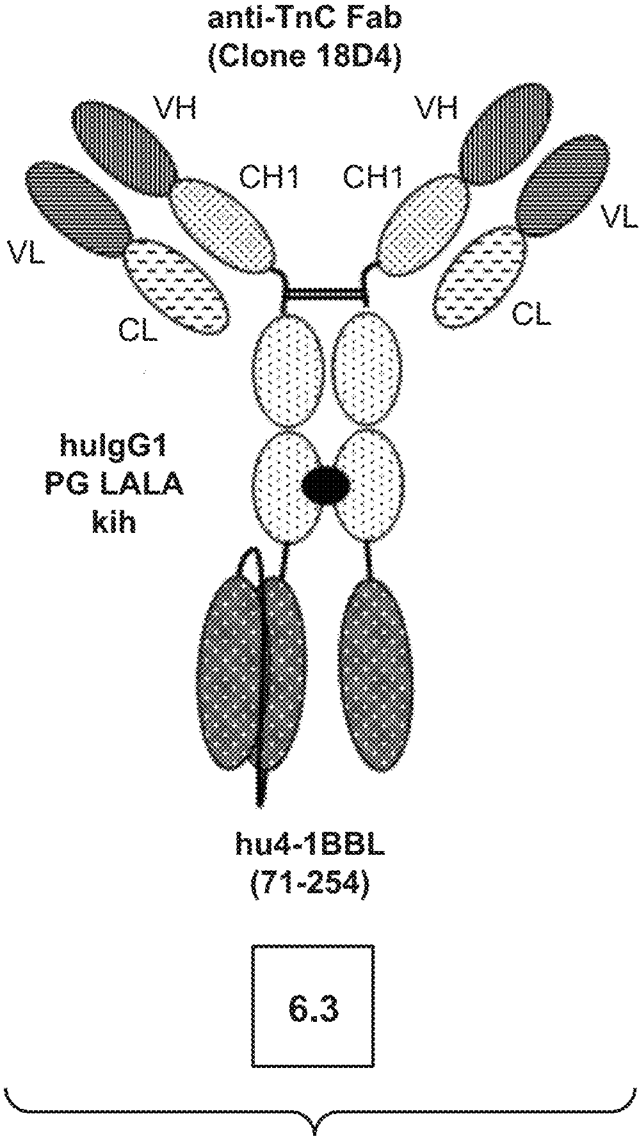
FIG. 10 shows bivalent TnC (18D4) targeted split trimeric 4-1BB ligand Fc (kih) PGLALA fusion (construct 6.3). The preparation and production of this construct is described in Example 1.3. The VH and VL domains are those of anti-TnC antibody 18D4, the thick black point stands for the knob-into-hole modification.

Combination of the anti-TnC huIgG1 hole dimeric ligand chain containing the Y349C/T366S/L368A/Y407V mutations, the anti-TnC huIgG1 knob monomeric ligand chain containing the S354C/T366W mutations and the anti-TnC light chain allows generation of a heterodimer, which includes an assembled trimeric 4-1BB ligand and two TnC binding Fabs (FIG. 10).

Table 34 and Table 35 show, respectively, the cDNA and amino acid sequences of the bivalent TnC (18D4)-targeted split trimeric 4-1BB ligand (71-254) Fc (kih) fusion (construct 6.3).

TABLE 34

Base pair sequences of bivalent TnC(18D4) targeted split trimeric 4-1BB ligand Fc (kih) PGLALA fusion (construct 6.3)

| SEQ IO NO | Construct | Sequence |
| --- | --- | --- |
| SEQ ID NO: 110 | anti-TnC(18D4) Fc hole dimeric ligand (71-254) chain | CAGGTGCAATTGGTGCAGTCTGGGGCTGAGGTGA AGAAGCCTGGGTCCTCGGTGAAGGTCTCCTGCAAG GCCTCCGGAGGCACATTCAGCAGCTACGCTATAAG CTGGGTGCGACAGGCCCCTGGACAAGGGCTCGAG TGGATGGGAGGGATCATCCCTATCTTTGGTACAGC AAACTACGCACAGAAGTTCCAGGGCAGGGTCACC ATTACTGCAGACAAATCCACGAGCACAGCCTACAT GGAGCTGAGCAGCCTGAGATCTGAGGACACCGCC GTGTATTACTGTGCGAAAGGTAACTTCTACGGTGG TCTGGACTACTGGGGCCAAGGGACCACCGTGACC GTCTCCTCAGCTAGCACCAAGGGCCCCTCCGTGTT CCCCCTGGCCCCCAGCAGCAAGAGCACCAGCGGC GGCACAGCCGCTCTGGGCTGCCTGGTCAAGGACTA CTTCCCCGAGCCCGTGACCGTGTCCTGGAACAGCG GAGCCCTGACCTCCGGCGTGCACACCTTCCCCGCC GTGCTGCAGAGTTCTGGCCTGTATAGCCTGAGCAG CGTGGTCACCGTGCCTTCTAGCAGCCTGGGCACCC AGACCTACATCTGCAACGTGAACCACAAGCCCAG CAACACCAAGGTGGACAAGAAGGTGGAGCCCAAG AGCTGCGACAAAACTCACACATGCCCACCGTGCCC AGCACCTGAAGCTGCAGGGGGACCGTCAGTCTTCC TCTTCCCCCCAAAACCCAAGGACACCCTCATGATC TCCCGGACCCCTGAGGTCACATGCGTGGTGGTGGA CGTGAGCCACGAAGACCCTGAGGTCAAGTTCAAC TGGTACGTGGACGGCGTGGAGGTGCATAATGCCA |

TABLE 34-continued

| Base pair sequences of bivalent TnC(18D4) targeted split trimeric 4-1BB ligand Fc (kih) PGLALA fusion (construct 6.3) | | |
|---|---|---|
| SEQ IO NO | Construct | Sequence |
| | | AGACAAAGCCGCGGGAGGAGCAGTACAACAGCAC GTACCGTGTGGTCAGCGTCCTCACCGTCCTGCACC AGGACTGGCTGAATGGCAAGGAGTACAAGTGCAA GGTCTCCAACAAAGCCCTCGGCGCCCCCATCGAGA AAACCATCTCCAAAGCCAAAGGGCAGCCCCGAGA ACCACAGGTGTGCACCCTGCCCCCATCCCGGGATG AGCTGACCAAGAACCAGGTCAGCCTCTCGTGCGC AGTCAAAGGCTTCTATCCCAGCGACATCGCCGTGG AGTGGGAGAGCAATGGGCAGCCGGAGAACAACTA CAAGACCACGCCTCCCGTGCTGGACTCCGACGGCT CCTTCTTCCTCGTGAGCAAGCTCACCGTGGACAAG AGCAGGTGGCAGCAGGGGAACGTCTTCTCATGCTC CGTGATGCATGAGGCTCTGCACAACCACTACACGC AGAAGAGCCTCTCCCTGTCTCCGGGTGGAGGCGGC GGAAGCGGAGGAGGAGGATCCAGAGAGGGCCCTG AGCTGAGCCCCGATGATCCTGCTGGACTGCTGGAC CTGCGGCAGGGCATGTTTGCTCAGCTGGTGGCCCA GAACGTGCTGCTGATCGATGGCCCCCTGTCCTGGT ACAGCGATCCTGGACTGGCTGGCGTGTCACTGACA GGCGGCCTGAGCTACAAAGAGGACACCAAAGAAC TGGTGGTGGCCAAGGCCGGCGTGTACTACGTGTTC TTTCAGCTGGAACTGCGGAGAGTGGTGGCCGGCG AAGGATCTGGCTCTGTGTCTCTGGCCCTGCATCTG CAGCCTCTGAGAAGCGCTGCTGGCGCTGCAGCTCT GGCACTGACAGTGGATCTGCCTCCTGCCAGCTCCG AGGCCCGGAATAGCGCATTTGGGTTTCAAGGCAG GCTGCTGCACCTGTCTGCCGGCCAGAGGCTGGGAG TGCATCTGCACACAGAGGCCAGGGCTAGACACGC CTGGCAGCTGACACAGGGCGCTACAGTGCTGGGC CTGTTCAGAGTGACCCCCGAGATTCCAGCCGGCCT GCCTTCTCCAAGAAGCGAAGGCGGAGGCGGATCT GGCGGCGGAGGATCTAGAGAGGGACCCGAACTGT CCCCTGACGATCCAGCCGGGCTGCTGGATCTGAGA CAGGGAATGTTCGCCCAGCTGGTGGCTCAGAATGT GCTGCTGATTGACGGACCTCTGAGCTGGTACTCCG ACCCAGGGCTGGCAGGGGTGTCCCTGACTGGGGG ACTGTCCTACAAAGAAGATACAAAAGAACTGGTG GTGGCTAAAGCTGGGGTGTACTATGTGTTTTTCA GCTGGAACTGAGGCGGGTGGTGGCTGGGGAGGGC TCAGGATCTGTGTCCCTGGCTCTGCATCTGCAGCC ACTGCGCTCTGCTGCTGGCGCAGCTGCACTGGCTC TGACTGTGGACCTGCCACCAGCCTCTAGCGAGGCC AGAAACAGCGCCTTCGGGTTCCAAGGACGCCTGCT GCATCTGAGCGCCGGACAGCGCCTGGGAGTGCAT CTGCATACTGAAGCCAGAGCCCGGCATGCTTGGCA GCTGACTCAGGGGGCAACTGTGCTGGGACTGTTTC GCGTGACACCTGAGATCCCTGCCGGACTGCCAAGC CCTAGATCAGAA |
| SEQ ID NO: 111 | anti-TnC(18D4) Fc knob monomeric ligand (71-254) chain | CAGGTGCAATTGGTGCAGTCTGGGGCTGAGGTGA AGAAGCCTGGGTCCTCGGTGAAGGTCTCCTGCAAG GCCTCCGGAGGCACATTCAGCAGCTACGCTATAAG CTGGGTGCGACAGGCCCCTGGACAAGGGCTCGAG TGGATGGGAGGGATCATCCCTATCTTTGGTACAGC AAACTACGCACAGAAGTTCCAGGGCAGGGTCACC ATTACTGCAGACAAATCCACGAGCACAGCCTACAT GGAGCTGAGCAGCCTGAGATCTGAGGACACCGCC GTGTATTACTGTGCGAAAGGTAACTTCTACGGTGG TCTGGACTACTGGGGCCAAGGGACCACCGTGACC GTCTCCTCAGCTAGCACCAAGGGCCCATCGGTCTT CCCCCTGGCACCCTCCTCCAAGAGCACCTCTGGGG GCACAGCGGCCCTGGGCTGCCTGGTCAAGGACTA CTTCCCCGAACCGGTGACGGTGTCGTGGAACTCAG GCGCCCTGACCAGCGGCGTGCACACCTTCCCGGCT GTCCTACAGTCCTCAGGACTCTACTCCCTCAGCAG CGTGGTGACCGTGCCCTCCAGCAGCTTGGGCACCC AGACCTACATCTGCAACGTGAATCACAAGCCCAG CAACACCAAGGTGGACAAGAAAGTTGAGCCCAAA TCTTGTGACAAAACTCACACATGCCCACCGTGCCC AGCACCTGAAGCTGCAGGGGGACCGTCAGTCTTCC TCTTCCCCCCAAAACCCAAGGACACCCTCATGATC TCCCGGACCCCTGAGGTCACATGCGTGGTGGTGGA CGTGAGCCACGAAGACCCTGAGGTCAAGTTCAAC TGGTACGTGGACGGCGTGGAGGTGCATAATGCCA AGACAAAGCCGCGGGAGGAGCAGTACAACAGCAC |

TABLE 34-continued

Base pair sequences of bivalent TnC(18D4) targeted split trimeric 4-1BB ligand Fc (kih) PGLALA fusion (construct 6.3)

| SEQ IO NO | Construct | Sequence |
|---|---|---|
| | | GTACCGTGTGGTCAGCGTCCTCACCGTCCTGCACC AGGACTGGCTGAATGGCAAGGAGTACAAGTGCAA GGTCTCCAACAAAGCCCTCGGCGCCCCCATCGAGA AAACCATCTCCAAAGCCAAAGGGCAGCCCCGAGA ACCACAGGTGTACACCCTGCCCCCCTGCAGAGATG AGCTGACCAAGAACCAGGTGTCCCTGTGGTGTCTG GTCAAGGGCTTCTACCCCAGCGATATCGCCGTGGA GTGGGAGAGCAACGGCCAGCCTGAGAACAACTAC AAGACCACCCCCCCTGTGCTGGACAGCGACGGCA GCTTCTTCCTGTACTCCAAACTGACCGTGGACAAG AGCCGGTGGCAGCAGGGCAACGTGTTCAGCTGCA GCGTGATGCACGAGGCCCTGCACAACCACTACAC CCAGAAGTCCCTGAGCCTGAGCCCCGGCGGAGGC GGCGGAAGCGGAGGAGGAGGATCCAGAGAGGGC CCTGAGCTGAGCCCCGATGATCCTGCTGGACTGCT GGACCTGCGGCAGGGCATGTTTGCTCAGCTGGTGG CCCAGAACGTGCTGCTGATCGATGGCCCCCTGTCC TGGTACAGCGATCCTGGACTGGCTGGCGTGTCACT GACAGGCGGCCTGAGCTACAAAGAGGACACCAAA GAACTGGTGGTGGCCAAGGCCGGCGTGTACTACG TGTTCTTTCAGCTGGAACTGCGGAGAGTGGTGGCC GGCGAAGGATCTGGCTCTGTGTCTCTGGCCCTGCA TCTGCAGCCTCTGAGAAGCGCTGCTGGCGCTGCAG CTCTGGCACTGACAGTGGATCTGCCTCCTGCCAGC TCCGAGGCCCGGAATAGCGCATTTGGGTTTCAAGG CAGGCTGCTGCACCTGTCTGCCGGCCAGAGGCTGG GAGTGCATCTGCACACAGAGGCCAGGGCTAGACA CGCCTGGCAGCTGACACAGGGCGCTACAGTGCTG GGCCTGTTCAGAGTGACCCCCGAGATTCCAGCCGG CCTGCCTTCTCCAAGAAGCGAA |
| SEQ ID NO: 77 | anti-TnC(18D4) light chain | See Table 21 |

TABLE 35

Amino acid sequences of bivalent TnC(18D4) targeted split trimeric 4-1BB ligand Fc (kih) PGLALA fusion (construct 6.3)

| SEQ ID NO | Construct | Sequence |
|---|---|---|
| SEQ ID NO: 112 | anti-TnC(18D4) Fc hole dimeric ligand (71-254) chain | QVQLVQSGAEVKKPGSSVKVSCKASGGTFSSYAIS WVRQAPGQGLEWMGGIIPIFGTANYAQKFQGRVTI TADKSTSTAYMELSSLRSEDTAVYYCAKGNFYGGL DYWGQGTTVTVSSASTKGPSVFPLAPSSKSTSGGTA ALGCLVKDYFPEPVTVSWNSGALTSGVHTFPAVLQ SSGLYSLSSVVTVPSSSLGTQTYICNVNHKPSNTKV DKKVEPKSCDKTHTCPPCPAPEAAGGPSVFLFPPKP KDTLMISRTPEVTCVVVDVSHEDPEVKFNWYVDG VEVHNAKTKPREEQYNSTYRVVSVLTVLHQDWLN GKEYKCKVSNKALGAPIEKTISKAKGQPREPQVCTL PPSRDELTKNQVSLSCAVKGFYPSDIAVEWESNGQP ENNYKTTPPVLDSDGSFFLVSKLTVDKSRWQQGNV FSCSVMHEALHNHYTQKSLSLSPGGGGGSGGGGSR EGPELSPDDPAGLLDLRQGMFAQLVAQNVLLIDGP LSWYSDPGLAGVSLTGGLSYKEDTKELVVAKAGV YYVFFQLELRRVVAGEGSGSVSLALHLQPLRSAAG AAALALTVDLPPASSEARNSAFGFQGRLLHLSAGQ RLGVHLHTEARARHAWQLTQGATVLGLFRVTPEIP AGLPSPRSEGGGGSGGGGSREGPELSPDDPAGLLDL RQGMFAQLVAQNVLLIDGPLSWYSDPGLAGVSLTG GLSYKEDTKELVVAKAGVYYVFFQLELRRVVAGE GSGSVSLALHLQPLRSAAGAAALALTVDLPPASSEA RNSAFGFQGRLLHLSAGQRLGVHLHTEARARHAW QLTQGATVLGLFRVTPEIPAGLPSPRSE |
| SEQ ID NO: 113 | anti-TnC(18D4) Fc knob monomeric ligand (71-254) | QVQLVQSGAEVKKPGSSVKVSCKASGGTFSSYAIS WVRQAPGQGLEWMGGIIPIFGTANYAQKFQGRVTI TADKSTSTAYMELSSLRSEDTAVYYCAKGNFYGGL DYWGQGTTVTVSSASTKGPSVFPLAPSSKSTSGGTA ALGCLVKDYFPEPVTVSWNSGALTSGVHTFPAVLQ |

TABLE 35-continued

Amino acid sequences of bivalent TnC(18D4) targeted split trimeric 4-1BB ligand Fc (kih) PGLALA fusion (construct 6.3)

| SEQ ID NO | Construct | Sequence |
|---|---|---|
| | chain | SSGLYSLSSVVTVPSSSLGTQTYICNVNHKPSNTKV<br>DKKVEPKSCDKTHTCPPCPAPEAAGGPSVFLFPPKP<br>KDTLMISRTPEVTCVVVDVSHEDPEVKFNWYVDG<br>VEVHNAKTKPREEQYNSTYRVVSVLTVLHQDWLN<br>GKEYKCKVSNKALGAPIEKTISKAKGQPREPQVYTL<br>PPCRDELTKNQVSLWCLVKGFYPSDIAVEWESNGQ<br>PENNYKTTPPVLDSDGSFFLYSKLTVDKSRWQQGN<br>VFSCSVMHEALHNHYTQKSLSLSPGGGGGSGGGGS<br>REGPELSPDDPAGLLDLRQGMFAQLVAQNVLLIDG<br>PLSWYSDPGLAGVSLTGGLSYKEDTKELVVAKAGV<br>YYVFFQLELRRVVAGEGSGSVSLALHLQPLRSAAG<br>AAALALTVDLPPASSEARNSAFGFQGRLLHLSAGQ<br>RLGVHLHTEARARHAWQLTQGATVLGLFRVTPEIP<br>AGLPSPRSE |
| SEQ ID NO: 77 | anti-TnC(18D4) light chain | See Table 21 |

Construct 6.4: Monovalent TnC (18D4) Targeted Split Trimeric 4-1BB Ligand (71-248) Fc (kih) Fusion Containing CH-CL Cross with Charged Residues A polypeptide containing two ectodomains of 4-1BB ligand (71-248), separated by (G4S)2 (SEQ ID NO: 150) linkers, and fused to the human IgG1-CL domain, was cloned as depicted in FIG. 11A: human 4-1BB ligand, (G4S)2 connector, human 4-1BB ligand, (G4S)2 connector, human CL.

Figures 11A, 11B:
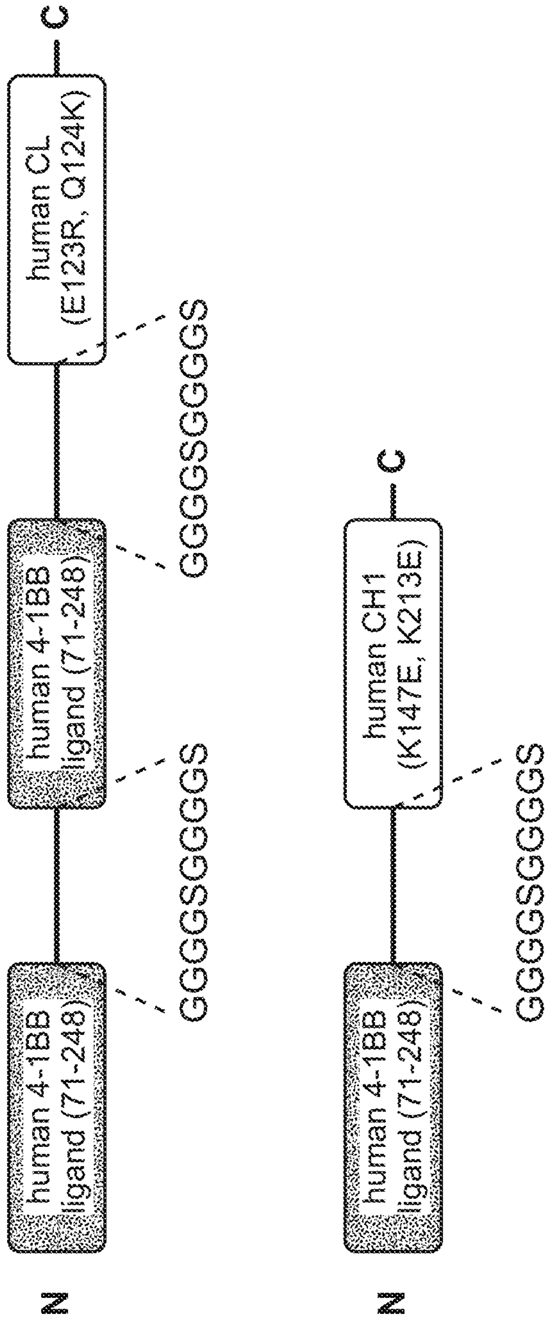
FIGS. 11A and 11B show components for the assembly of monovalent TnC targeted split trimeric human 4-1BB ligand (71-248) (construct 6.4).

A polypeptide containing one ectodomain of 4-1BB ligand (71-248) and fused to the human IgG1-CH domain, was cloned as described in FIG. 11B: human 4-1BB ligand, (G4S)2 connector, human CH.

To improve correct pairing the following mutations have been introduced in the crossed CH-CL. In the dimeric 4-1BB ligand fused to human CL, E123R and Q124K. In the monomeric 4-1BB ligand fused to human CH1, K147E and K213E.

The variable region of heavy and light chain DNA sequences encoding a binder specific for TnC, clone 18D4, were subcloned in frame with either the constant heavy chain of the hole, the knob or the constant light chain of human IgG1.

The Pro329Gly, Leu234Ala and Leu235Ala mutations have been introduced in the constant region of the knob and hole heavy chains to abrogate binding to Fc gamma receptors (patent accession number).

Figure 12:
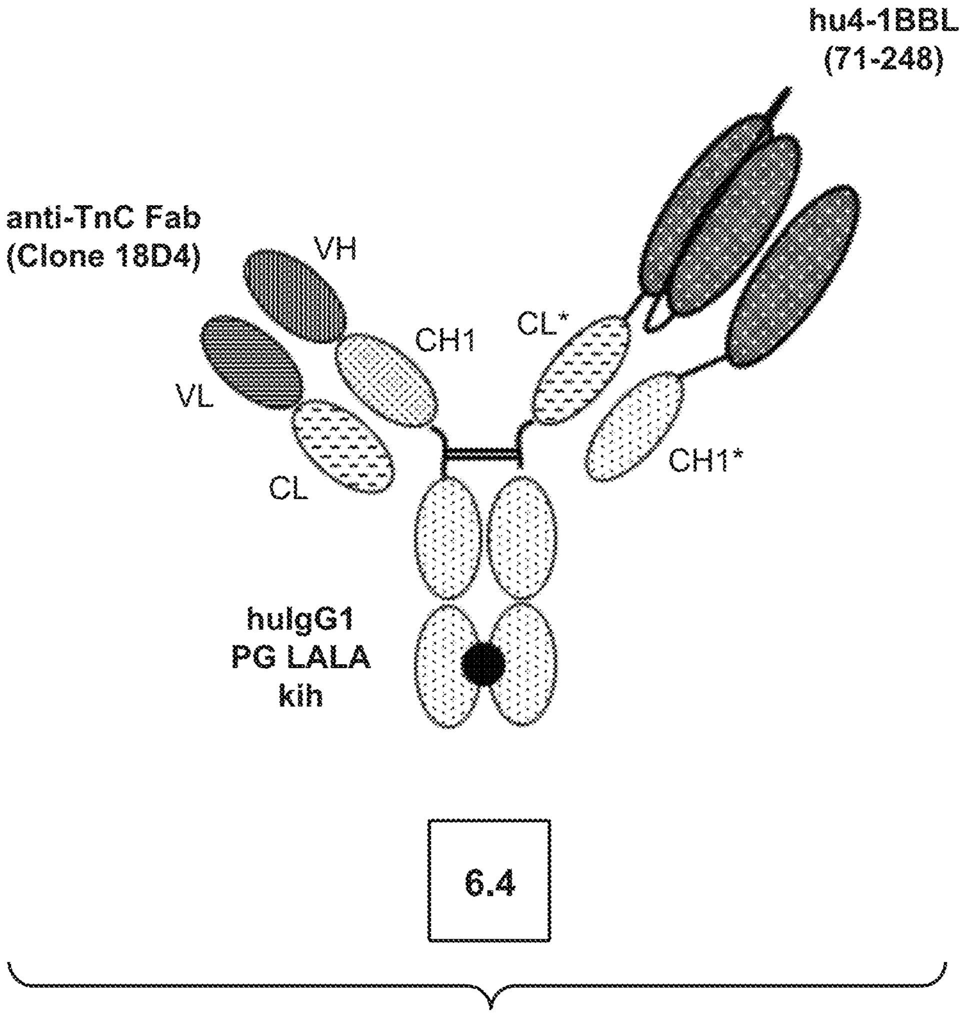
FIG. 12 monovalent TnC (18D4) targeted split trimeric 4-1BB ligand (71-248) Fc (kih) fusion containing CH-CL cross with charged residues (construct 6.4). The preparation and production of this construct is described in Example 1.4. The VH and VL domains are those of anti-TnC antibody 18D4, the thick black point stands for the knob-into-hole modification.

Combination of the dimeric ligand-Fc knob chain containing the S354C/T366W mutations, the monomeric CH1 fusion, the targeted anti-TnC-Fc hole chain containing the Y349C/T366S/L368A/Y407V mutations and the anti-TnC light chain allows generation of a heterodimer, which includes an assembled trimeric 4-1BB ligand and a TnC binding Fab (FIG. 12).

Table 36 and Table 37 show, respectively, the cDNA and amino acid sequences of the monovalent TnC targeted split trimeric 4-1BB ligand (71-248) Fc (kih) fusion containing CH-CL cross with charged residues (construct 6.4).

TABLE 36

Base pair sequences of monovalent TnC(18D4) targeted split trimeric 4-1BB ligand (71-248) Fc (kih) fusion containing CH-CL cross with charged residues (construct 6.4).

| SEQ ID NO | Construct | Sequence |
|---|---|---|
| SEQ ID NO: 114 | Dimeric ligand (71-248)-CL* Fc knob chain | AGAGAGGGCCCTGAGCTGAGCCCCGATGATCCTGCT<br>GGACTGCTGGACCTGCGGCAGGGCATGTTTGCTCAGC<br>TGGTGGCCCAGAACGTGCTGCTGATCGATGGCCCCCT<br>GTCCTGGTACAGCGATCCTGGACTGGCTGGCGTGTCA<br>CTGACAGGCGGCCTGAGCTACAAAGAGGACACCAAA<br>GAACTGGTGGTGGCCAAGGCCGGCGTGTACTACGTGT<br>TCTTTCAGCTGGAACTGCGGAGAGTGGTGGCCGGCGA<br>AGGATCTGGCTCTGTGTCTCTGGCCCTGCATCTGCAG<br>CCTCTGAGATCTGCTGCTGGCGCCGCTGCTCTGGCAC<br>TGACAGTGGATCTGCCTCCTGCCAGCAGCGAGGCCCG<br>GAATAGCGCATTTGGGTTTCAAGGCAGGCTGCTGCAC<br>CTGTCTGCCGGCCAGAGGCTGGGAGTGCATCTGCACA<br>CAGAGGCCAGGGCTAGACACGCCTGGCAGCTGACAC<br>AGGGCGCTACAGTGCTGGGCCTGTTCAGAGTGACCCC<br>CGAGATTCCAGCCGGACTGGGAGGCGGCGGATCTGG<br>CGGCGGAGGATCTAGAGAAGGACCCGAGCTGTCCCC<br>TGACGATCCAGCCGGGCTGCTGGATCTGAGACAGGG<br>AATGTTCGCCCAGCTGGTGGCTCAGAATGTGCTGCTG<br>ATTGACGGACCTCTGAGCTGGTACTCCGACCCAGGGC<br>TGGCAGGGGTGTCCCTGACTGGGGGACTGTCCTACAA<br>AGAAGATACAAAAGAACTGGTGGTGGCTAAAGCTGG |

TABLE 36-continued

Base pair sequences of monovalent TnC(18D4) targeted split trimeric 4-1BB ligand (71-248) Fc (kih) fusion containing CH-CL cross with charged residues (construct 6.4).

| SEQ ID NO | Construct | Sequence |
|---|---|---|
| | | GGTGTACTATGTGTTTTTCAGCTGGAACTGAGGCGG<br>GTGGTGGCTGGGGAGGGCTCAGGATCTGTGTCCCTGG<br>CTCTGCATCTGCAGCCACTGCGCTCTGCAGCAGGGGC<br>TGCAGCACTGGCCCTGACTGTGGACCTGCCCCCAGCT<br>TCTTCCGAGGCCAGAAACAGCGCCTTCGGGTTCCAAG<br>GACGCCTGCTGCATCTGAGCGCCGGACAGCGCCTGG<br>GAGTGCATCTGCATACTGAAGCCAGAGCCCGGCATG<br>CTTGGCAGCTGACTCAGGGGGCAACTGTGCTGGGACT<br>GTTTCGCGTGACACCTGAGATCCCCGCTGGACTGGGC<br>GGAGGCGGTTCCGGAGGGGGAGGATCTCGTACGGTG<br>GCTGCACCATCTGTCTTTATCTTCCCACCCAGCGACC<br>GGAAGCTGAAGTCTGGCACAGCCAGCGTCGTGTGCCT<br>GCTGAATAACTTCTACCCCCGCGAGGCCAAGGTGCAG<br>TGGAAGGTGGACAATGCCCTGCAGAGCGGCAACAGC<br>CAGGAAAGCGTGACCGAGCAGGACAGCAAGGACTCC<br>ACCTACAGCCTGAGCAGCACCCTGACCCTGAGCAAG<br>GCCGACTACGAGAAGCACAAGGTGTACGCCTGCGAA<br>GTGACCCACCAGGGCCTGTCTAGCCCCGTGACCAAGA<br>GCTTCAACCGGGGCGAGTGCGACAAGACCCACACCT<br>GTCCTCCATGCCCTGCCCCTGAAGCTGCTGGCGGCCC<br>TAGCGTGTTCCTGTTCCCCCCAAAGCCCAAGGACACC<br>CTGATGATCAGCCGGACCCCTGAAGTGACCTGCGTGG<br>TGGTGGATGTGTCCCACGAGGACCCTGAAGTGAAGTT<br>CAATTGGTACGTGGACGGCGTGGAAGTGCACAATGC<br>CAAGACCAAGCCGCGGGAGGAGCAGTACAACAGCAC<br>GTACCGTGTGGTCAGCGTCCTCACCGTCCTGCACCAG<br>GACTGGCTGAATGGCAAGGAGTACAAGTGCAAGGTC<br>TCCAACAAAGCCCTCGGCGCCCCCATCGAGAAAACC<br>ATCTCCAAAGCCAAAGGGCAGCCCCGAGAACCACAG<br>GTGTACACCCTGCCCCCATGCCGGGATGAGCTGACCA<br>AGAACCAGGTCAGCCTGTGGTGCCTGGTCAAAGGCTT<br>CTATCCCAGCGACATCGCCGTGGAGTGGGAGAGCAA<br>TGGGCAGCCGGAGAACAACTACAAGACCACGCCTCC<br>CGTGCTGGACTCCGACGGCTCCTTCTTCCTCTACAGC<br>AAGCTCACCGTGGACAAGAGCAGGTGGCAGCAGGGG<br>AACGTCTTCTCATGCTCCGTGATGCATGAGGCTCTGC<br>ACAACCACTACACGCAGAAGAGCCTCTCCCTGTCTCC<br>GGGTAAA |
| SEQ ID NO: 115 | Monomeric ligand (71-248)-CH1* | AGAGAGGGCCCTGAGCTGAGCCCCGATGATCCTGCT<br>GGACTGCTGGACCTGCGGCAGGGCATGTTTGCTCAGC<br>TGGTGGCCCAGAACGTGCTGCTGATCGATGGCCCCCT<br>GTCCTGGTACAGCGATCCTGGACTGGCTGGCGTGTCA<br>CTGACAGGCGGCCTGAGCTACAAAGAGGACACCAAA<br>GAACTGGTGGTGGCCAAGGCCGGCGTGTACTACGTGT<br>TCTTTCAGCTGGAACTGCGGAGAGTGGTGGCCGGCGA<br>AGGATCTGGCTCTGTGTCTCTGGCCCTGCATCTGCAG<br>CCTCTGAGATCTGCTGCTGGCGCCGCTGCTCTGGCAC<br>TGACAGTGGATCTGCCTCCTGCCAGCAGCGAGGCCCG<br>GAATAGCGCATTTGGGTTTCAAGGCAGGCTGCTGCAC<br>CTGTCTGCCGGCCAGAGGCTGGGAGTGCATCTGCACA<br>CAGAGGCCAGGGCTAGACACGCCTGGCAGCTGACAC<br>AGGGCGCTACAGTGCTGGGCCTGTTCAGAGTGACCCC<br>CGAGATTCCAGCCGGACTGGGAGGCGGAGGTTCCGG<br>AGGCGGAGGATCTGCTAGCACAAAGGGCCCCAGCGT<br>GTTCCCTCTGGCCCCTAGCAGCAAGAGCACATCTGGC<br>GGAACAGCCGCCCTGGGCTGCCTGGTGGAAGATTACT<br>TCCCCGAGCCCGTGACCGTGTCCTGGAATTCTGGCGC<br>CCTGACAAGCGGCGTGCACACCTTTCCAGCCGTGCTG<br>CAGAGCAGCGGCCTGTACTCTCTGAGCAGCGTCGTGA<br>CAGTGCCCAGCAGCTCTCTGGGCACCCAGACCTACAT<br>CTGCAACGTGAACCACAAGCCCAGCAACACCAAGGT<br>GGACGAGAAGGTGGAACCCAAGTCCTGC |
| SEQ ID NO: 100 | anti-TnC(18D4) Fc hole chain | See Table 30 |
| SEQ ID NO: 73 | anti-TnC(18D4) light chain | See Table 20 |

*charged residues

TABLE 37

Amino acid sequences of monovalent TnC(18D4) targeted split trimeric 4-1BB ligand (71-248) Fc (kih) fusion containing CH-CL cross with charged residues (construct 6.4).

| SEQ ID NO | Construct | Sequence |
|---|---|---|
| SEQ ID NO: 116 | Dimeric ligand (71-248)-CL* Fc knob chain | REGPELSPDDPAGLLDLRQGMFAQLVAQNVLLIDGPLS WYSDPGLAGVSLTGGLSYKEDTKELVVAKAGVYYVFF QLELRRVVAGEGSGSVSLALHLQPLRSAAGAAALALTV DLPPASSEARNSAFGFQGRLLHLSAGQRLGVHLHTEAR ARHAWQLTQGATVLGLFRVTPEIPAGLGGGGSGGGGSR EGPELSPDDPAGLLDLRQGMFAQLVAQNVLLIDGPLSW YSDPGLAGVSLTGGLSYKEDTKELVVAKAGVYYVFFQ LELRRVVAGEGSGSVSLALHLQPLRSAAGAAALALTVD LPPASSEARNSAFGFQGRLLHLSAGQRLGVHLHTEARA RHAWQLTQGATVLGLFRVTPEIPAGLGGGGSGGGGSRT VAAPSVFIFPPSDRKLKSGTASVVCLLNNFYPREAKVQ WKVDNALQSGNSQESVTEQDSKDSTYSLSSTLTLSKAD YEKHKVYACEVTHQGLSSPVTKSFNRGECDKTHTCPPC PAPEAAGGPSVFLFPPKPKDTLMISRTPEVTCVVVDVSH EDPEVKFNWYVDGVEVHNAKTKPREEQYNSTYRVVSV LTVLHQDWLNGKEYKCKVSNKALGAPIEKTISKAKGQP REPQVYTLPPCRDELTKNQVSLWCLVKGFYPSDIAVEW ESNGQPENNYKTTPPVLDSDGSFFLYSKLTVDKSRWQQ GNVFSCSVMHEALHNHYTQKSLSLSPGK |
| SEQ ID NO: 117 | Monomeric ligand (71-248)-CH1* | REGPELSPDDPAGLLDLRQGMFAQLVAQNVLLIDGPLS WYSDPGLAGVSLTGGLSYKEDTKELVVAKAGVYYVFF QLELRRVVAGEGSGSVSLALHLQPLRSAAGAAALALTV DLPPASSEARNSAFGFQGRLLHLSAGQRLGVHLHTEAR ARHAWQLTQGATVLGLFRVTPEIPAGLGGGGSGGGGS ASTKGPSVFPLAPSSKSTSGGTAALGCLVEDYFPEPVTV SWNSGALTSGVHTFPAVLQSSGLYSLSSVVTVPSSSLGT QTYICNVNHKPSNTKVDEKVEPKSC |
| SEQ ID NO: 104 | anti-TnC(18D4) Fc hole chain | See Table 31 |
| SEQ ID NO: 77 | anti-TnC(18D4) light chain | See Table 21 |

*charged residues

Figure 13A:
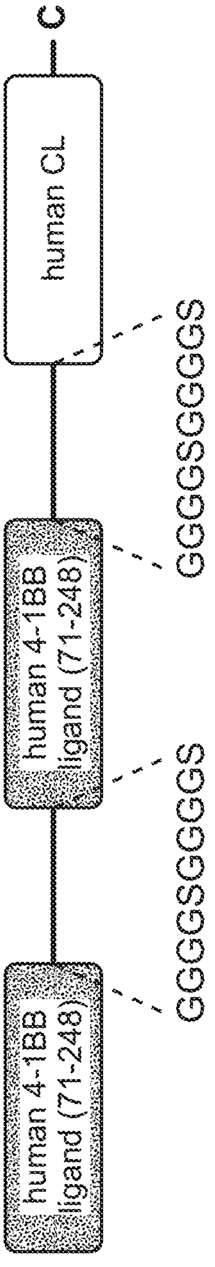
FIGS. 13A and 13B show components for the assembly of monovalent TnC targeted split trimeric human 4-1BB ligand (71-248) (construct 6.5).

Construct 6.5: Monovalent TnC (18D4) Targeted Split Trimeric 4-1BB Ligand (71-248) Fc (kih) Fusion Containing CH-CL Cross without Charged Residues A polypeptide containing two ectodomains of 4-1BB ligand (71-248), separated by (G4S)2 (SEQ ID NO: 150) linkers, and fused to the human IgG1-CL domain, was cloned as depicted in FIG. 13A: human 4-1BB ligand, (G4S)2 connector, human 4-1BB ligand, (G4S)2 connector, human CL.

Figure 13B:
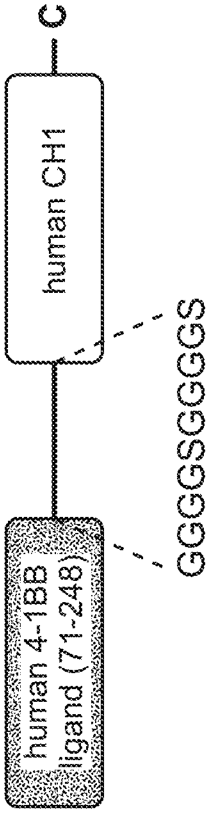

A polypeptide containing one ectodomain of 4-1BB ligand (71-248) and fused to the human IgG1-CH domain, was cloned as described in FIG. 13B: human 4-1BB ligand, (G4S)2 connector, human CH.

The variable region of heavy and light chain DNA sequences encoding a binder specific for TnC, clone 18D4, were subcloned in frame with either the constant heavy chain of the hole, the knob or the constant light chain of human IgG1.

The Pro329Gly, Leu234Ala and Leu235Ala mutations have been introduced in the constant region of the knob and hole heavy chains to abrogate binding to Fc gamma receptors (patent accession number).

Figure 14:
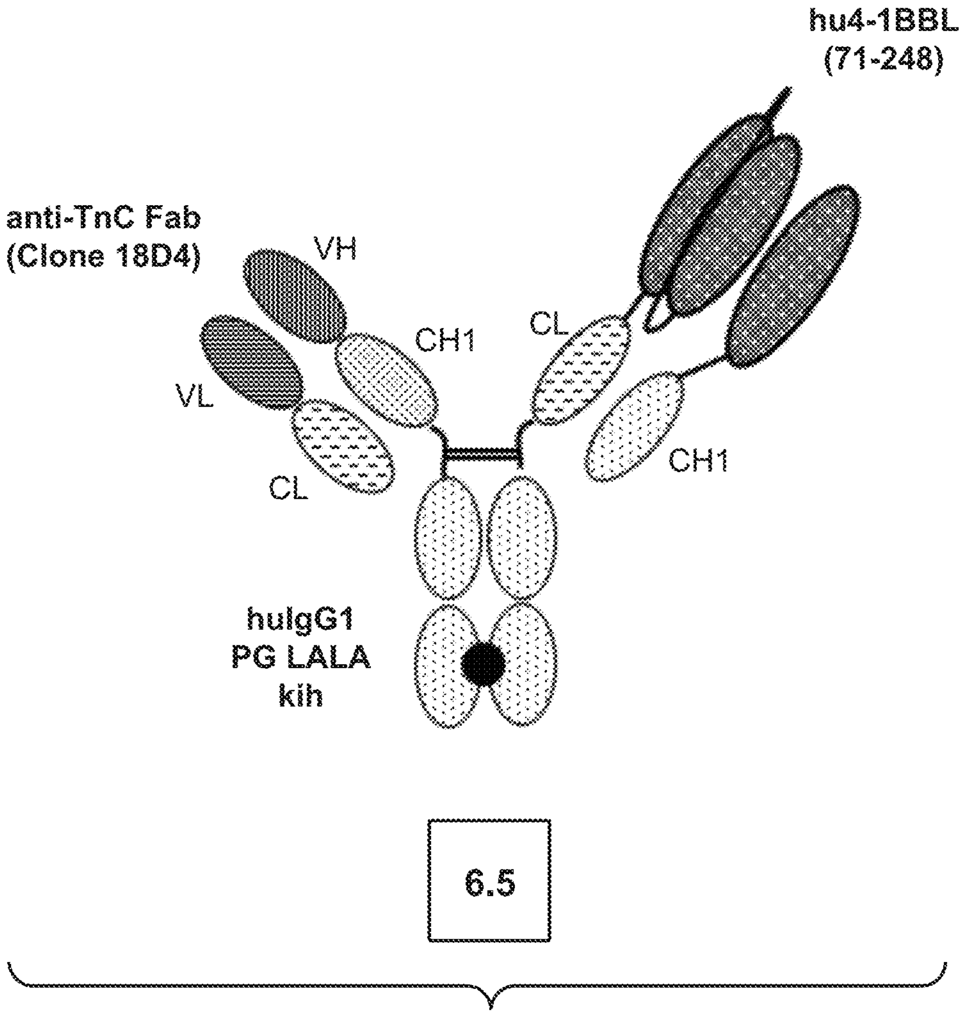
FIG. 14 shows monovalent TnC (18D4) targeted split trimeric 4-1BB ligand (71-248) Fc (kih) fusion containing CH-CL cross without charged residues (construct 6.5). The preparation and production of this construct is described in Example 1.5. The VH and VL domains are those of anti-TnC antibody 18D4, the thick black point stands for the knob-into-hole modification.

Combination of the dimeric ligand-Fc knob chain containing the S354C/T366W mutations, the monomeric CH1 fusion, the targeted anti-TnC-Fc hole chain containing the Y349C/T366S/L368A/Y407V mutations and the anti-TnC light chain allows generation of a heterodimer, which includes an assembled trimeric 4-1BB ligand and a TnC binding Fab (FIG. 14).

Table 38 and Table 39 show, respectively, the cDNA and amino acid sequences of the monovalent TnC (18D4) targeted split trimeric 4-1BB ligand (71-248) with charged residues in the CH-CL cross Fc (kih) fusion (construct 6.5).

TABLE 38

Base pair sequences of monovalent TnC(18D4) targeted split trimeric 4-1BB ligand (71-248) Fc (kih) fusion containing CH-CL cross without charged residues (construct 6.5).

| SEQ ID NO | Construct | Sequence |
|---|---|---|
| SEQ ID NO: 118 | Dimeric ligand (71-248)-CL Fc knob chain | AGAGAGGGCCCTGAGCTGAGCCCCGATGATCCTGCT GGACTGCTGGACCTGCGGCAGGGCATGTTTGCTCAG CTGGTGGCCCAGAACGTGCTGCTGATCGATGGCCCC |

TABLE 38-continued

Base pair sequences of monovalent TnC(18D4) targeted split trimeric 4-1BB ligand (71-248) Fc (kih) fusion containing CH-CL cross without charged residues (construct 6.5).

| SEQ ID NO | Construct | Sequence |
|---|---|---|
| | | CTGTCCTGGTACAGCGATCCTGGACTGGCTGGCGTG<br>TCACTGACAGGCGGCCTGAGCTACAAAGAGGACAC<br>CAAAGAACTGGTGGTGGCCAAGGCCGGCGTGTACT<br>ACGTGTTCTTTCAGCTGGAACTGCGGAGAGTGGTGG<br>CCGGCGAAGGATCTGGCTCTGTGTCTCTGGCCCTGC<br>ATCTGCAGCCTCTGAGATCTGCTGCTGGCGCCGCTG<br>CTCTGGCACTGACAGTGGATCTGCCTCCTGCCAGCA<br>GCGAGGCCCGGAATAGCGCATTTGGGTTTCAAGGCA<br>GGCTGCTGCACCTGTCTGCCGGCCAGAGGCTGGGAG<br>TGCATCTGCACACAGAGGCCAGGGCTAGACACGCCT<br>GGCAGCTGACACAGGGCGCTACAGTGCTGGGCCTGT<br>TCAGAGTGACCCCCGAGATTCCAGCCGGACTGGGA<br>GGCGGCGGATCTGGCGGCGGAGGATCTAGAGAAGG<br>ACCCGAGCTGTCCCCTGACGATCCAGCCGGGCTGCT<br>GGATCTGAGACAGGGAATGTTCGCCCAGCTGGTGGC<br>TCAGAATGTGCTGCTGATTGACGGACCTCTGAGCTG<br>GTACTCCGACCCAGGGCTGGCAGGGGTGTCCCTGAC<br>TGGGGGACTGTCCTACAAAGAAGATACAAAAGAAC<br>TGGTGGTGGCTAAAGCTGGGGTGTACTATGTGTTTT<br>TTCAGCTGGAACTGAGGCGGGTGGTGGCTGGGGAG<br>GGCTCAGGATCTGTGTCCCTGGCTCTGCATCTGCAG<br>CCACTGCGCTCTGCAGCAGGGGCTGCAGCACTGGCC<br>CTGACTGTGGACCTGCCCCCAGCTTCTTCCGAGGCC<br>AGAAACAGCGCCTTCGGGTTCCAAGGACGCCTGCTG<br>CATCTGAGCGCCGGACAGCGCCTGGGAGTGCATCTG<br>CATACTGAAGCCAGAGCCCGGCATGCTTGGCAGCTG<br>ACTCAGGGGGCAACTGTGCTGGGACTGTTTCGCGTG<br>ACACCTGAGATCCCCGCTGGACTGGGCGGAGGCGG<br>TTCCGGAGGGGGAGGATCTCGTACGGTGGCCGCTCC<br>CTCCGTGTTTATCTTTCCCCCATCCGATGAACAGCTG<br>AAAAGCGGCACCGCCTCCGTCGTGTGTCTGCTGAAC<br>AATTTTTACCCTAGGGAAGCTAAAGTGCAGTGGAAA<br>GTGGATAACGCACTGCAGTCCGGCAACTCCCAGGA<br>ATCTGTGACAGAACAGGACTCCAAGGACAGCACCT<br>ACTCCCTGTCCTCCACCCTGACACTGTCTAAGGCTG<br>ATTATGAGAAACACAAAGTCTACGCCTGCGAAGTCA<br>CCCATCAGGGCCTGAGCTCGCCCGTCACAAAGAGCT<br>TCAACAGGGGAGAGTGTGACAAGACCCACACCTGT<br>CCCCCTTGTCCTGCCCCTGAAGCTGCTGGCGGCCCTT<br>CTGTGTTCCTGTTCCCCCCAAAGCCCAAGGACACCC<br>TGATGATCAGCCGGACCCCCGAAGTGACCTGCGTGG<br>TGGTGGATGTGTCCCACGAGGACCCTGAAGTGAAGT<br>TCAATTGGTACGTGGACGGCGTGGAAGTGCACAATG<br>CCAAGACCAAGCCGCGGGAGGAGCAGTACAACAGC<br>ACGTACCGTGTGGTCAGCGTCCTCACCGTCCTGCAC<br>CAGGACTGGCTGAATGGCAAGGAGTACAAGTGCAA<br>GGTCTCCAACAAAGCCCTCGGCGCCCCCATCGAGAA<br>AACCATCTCCAAAGCCAAAGGGCAGCCCCGAGAAC<br>CACAGGTGTACACCCTGCCCCCATGCCGGGATGAGC<br>TGACCAAGAACCAGGTCAGCCTGTGGTGCCTGGTCA<br>AAGGCTTCTATCCCAGCGACATCGCCGTGGAGTGGG<br>AGAGCAATGGGCAGCCGGAGAACAACTACAAGACC<br>ACGCCTCCCGTGCTGGACTCCGACGGCTCCTTCTTCC<br>TCTACAGCAAGCTCACCGTGGACAAGAGCAGGTGG<br>CAGCAGGGGAACGTCTTCTCATGCTCCGTGATGCAT<br>GAGGCTCTGCACAACCACTACACGCAGAAGAGCCT<br>CTCCCTGTCTCCGGGTAAA |
| SEQ ID NO: 119 | Monomeric ligand (71-248)-CH1 | AGAGAGGGCCCTGAGCTGAGCCCCGATGATCCTGCT<br>GGACTGCTGGACCTGCGGCAGGGCATGTTTGCTCAG<br>CTGGTGGCCCAGAACGTGCTGCTGATCGATGGCCCC<br>CTGTCCTGGTACAGCGATCCTGGACTGGCTGGCGTG<br>TCACTGACAGGCGGCCTGAGCTACAAAGAGGACAC<br>CAAAGAACTGGTGGTGGCCAAGGCCGGCGTGTACT<br>ACGTGTTCTTTCAGCTGGAACTGCGGAGAGTGGTGG<br>CCGGCGAAGGATCTGGCTCTGTGTCTCTGGCCCTGC<br>ATCTGCAGCCTCTGAGATCTGCTGCTGGCGCCGCTG<br>CTCTGGCACTGACAGTGGATCTGCCTCCTGCCAGCA<br>GCGAGGCCCGGAATAGCGCATTTGGGTTTCAAGGCA<br>GGCTGCTGCACCTGTCTGCCGGCCAGAGGCTGGGAG<br>TGCATCTGCACACAGAGGCCAGGGCTAGACACGCCT<br>GGCAGCTGACACAGGGCGCTACAGTGCTGGGCCTGT<br>TCAGAGTGACCCCCGAGATTCCAGCCGGACTGGGA<br>GGCGGAGGTTCCGGAGGCGGAGGATCTGCTAGCAC |

TABLE 38-continued

Base pair sequences of monovalent TnC(18D4) targeted split trimeric 4-1BB ligand (71-248) Fc (kih) fusion containing CH-CL cross without charged residues (construct 6.5).

| SEQ ID NO | Construct | Sequence |
|---|---|---|
| | | CAAAGGCCCTTCCGTGTTTCCTCTGGCTCCTAGCTCC AAGTCCACCTCTGGAGGCACCGCTGCTCTCGGATGC CTCGTGAAGGATTATTTTCCTGAGCCTGTGACAGTG TCCTGGAATAGCGGAGCACTGACCTCTGGAGTGCAT ACTTTCCCCGCTGTGCTGCAGTCCTCTGGACTGTACA GCCTGAGCAGCGTGGTGACAGTGCCCAGCAGCAGC CTGGGCACCCAGACCTACATCTGCAACGTGAACCAC AAGCCCAGCAACACCAAGGTGGACAAGAAGGTGGA ACCCAAGTCTTGT |
| SEQ ID NO: 100 | anti-TnC(18D4) Fc hole chain | See Table 30 |
| SEQ ID NO: 73 | anti-TnC(18D4) light chain | See Table 20 |

TABLE 39

Amino acid sequences of monovalent TnC(18D4) targeted split trimeric 4-1BB ligand (71-248) Fc (kih) fusion containing CH-CL cross without charged residues (construct 6.5).

| SEQ ID NO | Construct | Sequence |
|---|---|---|
| SEQ ID NO: 120 | Dimeric ligand (71-248)-CL Fc knob chain | REGPELSPDDPAGLLDLRQGMFAQLVAQNVLLIDGPL SWYSDPGLAGVSLTGGLSYKEDTKELVVAKAGVYYV FFQLELRRVVAGEGSGSVSLALHLQPLRSAAGAAALA LTVDLPPASSEARNSAFGFQGRLLHLSAGQRLGVHLH TEARARHAWQLTQGATVLGLFRVTPEIPAGLGGGGSG GGGSREGPELSPDDPAGLLDLRQGMFAQLVAQNVLLI DGPLSWYSDPGLAGVSLTGGLSYKEDTKELVVAKAG VYYVFFQLELRRVVAGEGSGSVSLALHLQPLRSAAGA AALALTVDLPPASSEARNSAFGFQGRLLHLSAGQRLG VHLHTEARARHAWQLTQGATVLGLFRVTPEIPAGLGG GGSGGGGSRTVAAPSVFIFPPSDEQLKSGTASVVCLLN NFYPREAKVQWKVDNALQSGNSQESVTEQDSKDSTY SLSSTLTLSKADYEKHKVYACEVTHQGLSSPVTKSFNR GECDKTHTCPPCPAPEAAGGPSVFLFPPKPKDTLMISR TPEVTCVVVDVSHEDPEVKFNWYVDGVEVHNAKTKP REEQYNSTYRVVSVLTVLHQDWLNGKEYKCKVSNKA LGAPIEKTISKAKGQPREPQVYTLPPCRDELTKNQVSL WCLVKGFYPSDIAVEWESNGQPENNYKTTPPVLDSDG SFFLYSKLTVDKSRWQQGNVFSCSVMHEALHNHYTQ KSLSLSPGK |
| SEQ ID NO: 121 | Monomeric ligand (71-248)-CH1 | REGPELSPDDPAGLLDLRQGMFAQLVAQNVLLIDGPL SWYSDPGLAGVSLTGGLSYKEDTKELVVAKAGVYYV FFQLELRRVVAGEGSGSVSLALHLQPLRSAAGAAALA LTVDLPPASSEARNSAFGFQGRLLHLSAGQRLGVHLH TEARARHAWQLTQGATVLGLFRVTPEIPAGLGGGGSG GGGSASTKGPSVFPLAPSSKSTSGGTAALGCLVKDYFP EPVTVSWNSGALTSGVHTFPAVLQSSGLYSLSSVVTVP SSSLGTQTYICNVNHKPSNTKVDKKVEPKSC |
| SEQ ID NO: 104 | anti-TnC(18D4) Fc hole chain | See Table 31 |
| SEQ ID NO: 77 | anti-TnC(18D4) light chain | See Table 21 |

Figure 15A:
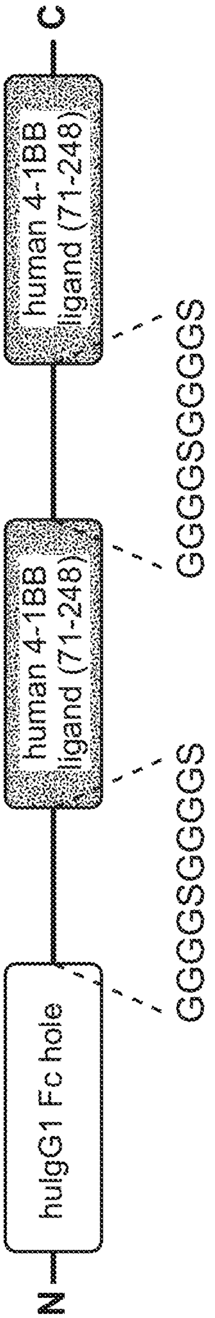
FIGS. 15A and 15B show components for the assembly of bivalent TnC targeted split trimeric human 4-1BB ligand (71-248) (construct 6.6).

Construct 6.6: Bivalent TnC (18D4) Targeted Split Trimeric 4-1BB Ligand (71-248) Fc (kih) Fusion A polypeptide containing two ectodomains of 4-1BB ligand (71-248), separated by (G4S)2 (SEQ ID NO: 150) linkers was fused to the C-terminus of human IgG1 Fc hole chain, as depicted in FIG. 15A: human IgG1 Fc hole, (G4S)2 connector, human 4-1BB ligand, (G4S)2 connector, human 4-1BB ligand.

Figure 15B:
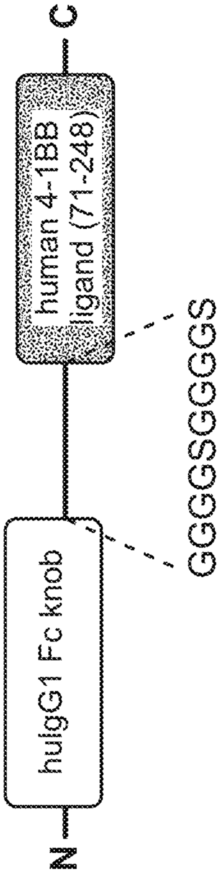

A polypeptide containing one ectodomain of 4-1BB ligand (71-248) and fused to the C-terminus of human IgG1 Fc knob chain as described in FIG. 15B: human IgG1 Fc knob, (G4S)2 connector, human 4-1BB ligand.

The variable region of heavy and light chain DNA sequences encoding a binder specific for TnC, clone 18D4, were subcloned in frame with either the constant heavy chain of the hole, the knob or the constant light chain of human IgG1.

The Pro329Gly, Leu234Ala and Leu235Ala mutations have been introduced in the constant region of the knob and hole heavy chains to abrogate binding to Fc gamma receptors (patent accession number).

Figure 16:
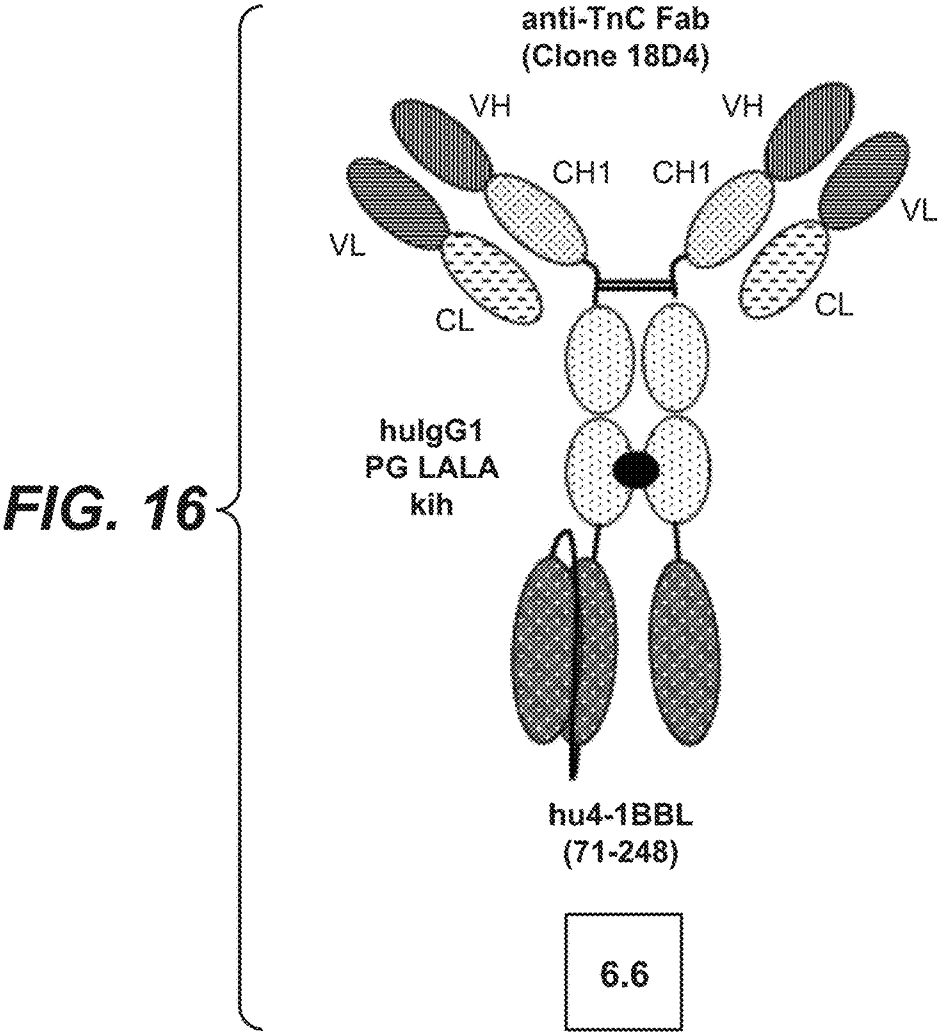
FIG. 16 shows bivalent TnC (18D4) targeted split trimeric 4-1BB ligand (71-248) Fc (kih) fusion (construct 6.6). The preparation and production of this construct is described in Example 1.6. The VH and VL domains are those of anti-TnC antibody 18D4, the thick black point stands for the knob-into-hole modification.

Combination of the anti-TnC huIgG1 hole dimeric ligand chain containing the Y349C/T366S/L368A/Y407V mutations, the anti-TnC huIgG1 knob monomeric ligand chain containing the S354C/T366W mutations and the anti-TnC light chain allows generation of a heterodimer, which includes an assembled trimeric 4-1BB ligand and two TnC binding Fabs (FIG. 16).

Table 40 and Table 41 show, respectively, the cDNA and amino acid sequences of the bivalent TnC (18D4) targeted split trimeric 4-1BB ligand (71-248) Fc (kih) fusion (construct 6.6).

TABLE 40

Base pair sequences of bivalent TnC(18D4) targeted split trimeric 4-1BB ligand (71-248) Fc (kih) fusion (construct 6.6)

| SEQ ID NO | Construct | Sequence |
|---|---|---|
| SEQ ID NO: 122 | anti-TnC(18D4) Fc hole dimeric ligand (71-248) chain | CAGGTGCAATTGGTGCAGTCTGGGGCTGAGGTGAAG AAGCCTGGGTCCTCGGTGAAGGTCTCCTGCAAGGCCT CCGGAGGCACATTCAGCAGCTACGCTATAAGCTGGG TGCGACAGGCCCCTGGACAAGGGCTCGAGTGGATGG GAGGGATCATCCCTATCTTTGGTACAGCAAACTACGC ACAGAAGTTCCAGGGCAGGGTCACCATTACTGCAGA CAAATCCACGAGCACAGCCTACATGGAGCTGAGCAG CCTGAGATCTGAGGACACCGCCGTGTATTACTGTGCG AAAGGTAACTTCTACGGTGGTCTGGACTACTGGGGCC AAGGGACCACCGTGACCGTCTCCTCAGCTAGCACCA AGGGCCCCTCCGTGTTCCCCCTGGCCCCCAGCAGCAA GAGCACCAGCGGCGGCACAGCCGCTCTGGGCTGCCT GGTCAAGGACTACTTCCCCGAGCCCGTGACCGTGTCC TGGAACAGCGGAGCCCTGACCTCCGGCGTGCACACC TTCCCCGCCGTGCTGCAGAGTTCTGGCCTGTATAGCC TGAGCAGCGTGGTCACCGTGCCTTCTAGCAGCCTGGG CACCCAGACCTACATCTGCAACGTGAACCACAAGCC CAGCAACACCAAGGTGGACAAGAAGGTGGAGCCCAA GAGCTGCGACAAAACTCACACATGCCCACCGTGCCC AGCACCTGAAGCTGCAGGGGGACCGTCAGTCTTCCTC TTCCCCCCAAAACCCAAGGACACCCTCATGATCTCCC GGACCCCTGAGGTCACATGCGTGGTGGTGGACGTGA GCCACGAAGACCCTGAGGTCAAGTTCAACTGGTACG TGGACGGCGTGGAGGTGCATAATGCCAAGACAAAGC CGCGGGAGGAGCAGTACAACAGCACGTACCGTGTGG TCAGCGTCCTCACCGTCCTGCACCAGGACTGGCTGAA TGGCAAGGAGTACAAGTGCAAGGTCTCCAACAAAGC CCTCGGCGCCCCCATCGAGAAAACCATCTCCAAAGC CAAAGGGCAGCCCCGAGAACCACAGGTGTGCACCCT GCCCCCATCCCGGGATGAGCTGACCAAGAACCAGGT CAGCCTCTCGTGCGCAGTCAAAGGCTTCTATCCCAGC GACATCGCCGTGGAGTGGGAGAGCAATGGGCAGCCG GAGAACAACTACAAGACCACGCCTCCCGTGCTGGAC TCCGACGGCTCCTTCTTCCTCGTGAGCAAGCTCACCG TGGACAAGAGCAGGTGGCAGCAGGGGAACGTCTTCT CATGCTCCGTGATGCATGAGGCTCTGCACAACCACTA CACGCAGAAGAGCCTCTCCCTGTCTCCGGGTGGAGG CGGCGGAAGCGGAGGAGGAGGATCCAGAGAGGGCC CTGAGCTGAGCCCTGATGATCCTGCCGGACTGCTGGA CCTGCGGCAGGGAATGTTTGCCCAGCTGGTGGCCCA GAACGTGCTGCTGATCGATGGCCCCCTGTCCTGGTAC AGCGATCCTGGACTGGCTGGCGTGTCACTGACAGGC GGCCTGAGCTACAAAGAGGACACCAAAGAACTGGTG GTGGCCAAGGCCGGCGTGTACTACGTGTTCTTTCAGC TGGAACTGCGGAGAGTGGTGGCCGGCGAAGGATCTG GCTCTGTGTCTCTGGCCCTGCATCTGCAGCCTCTGAG ATCTGCTGCTGGCGCCGCTGCTCTGGCACTGACAGTG GATCTGCCTCCTGCCAGCAGCGAGGCCCGGAATAGC GCATTTGGGTTTCAAGGCAGGCTGCTGCACCTGTCTG CCGGCCAGAGGCTGGGAGTGCATCTGCACACAGAGG CCAGGGCTAGACACGCCTGGCAGCTGACACAGGGCG CTACAGTGCTGGGCCTGTTCAGAGTGACCCCCGAGAT TCCAGCAGGCCTGGGAGGCGGCGGATCTGGCGGCGG AGGATCTAGAGAAGGACCCGAGCTGTCCCCCGACGA TCCCGCTGGGCTGCTGGATCTGAGACAGGGCATGTTC GCTCAGCTGGTGGCTCAGAATGTGCTGCTGATTGACG GACCTCTGAGCTGGTACTCCGACCCAGGGCTGGCAG GGGTGTCCCTGACTGGGGGACTGTCCTACAAAGAAG |

TABLE 40-continued

Base pair sequences of bivalent TnC(18D4) targeted split trimeric 4-1BB ligand (71-248) Fc (kih) fusion (construct 6.6)

| SEQ ID NO | Construct | Sequence |
|---|---|---|
| | | ATACAAAAGAACTGGTGGTGGCTAAAGCTGGGGTGT ACTATGTGTTTTTTCAGCTGGAACTGAGGCGGGTGGT GGCTGGGGAGGGCTCAGGATCTGTGTCCCTGGCTCTG CATCTGCAGCCACTGCGCTCTGCAGCAGGGGCTGCA GCACTGGCCCTGACTGTGGACCTGCCCCCAGCTTCTT CCGAGGCCAGAAACAGCGCCTTCGGGTTCCAAGGAC GCCTGCTGCATCTGAGCGCCGGACAGCGCCTGGGAG TGCATCTGCATACTGAAGCCAGAGCCCGGCATGCTTG GCAGCTGACTCAGGGGGCAACTGTGCTGGGACTGTTT CGCGTGACACCTGAGATCCCAGCCGGGCTC |
| SEQ ID NO: 123 | anti-TnC(18D4) Fc knob monomeric (71-248) ligand | CAGGTGCAATTGGTGCAGTCTGGGGCTGAGGTGAAG AAGCCTGGGTCCTCGGTGAAGGTCTCCTGCAAGGCCT CCGGAGGCACATTCAGCAGCTACGCTATAAGCTGGG TGCGACAGGCCCCTGGACAAGGGCTCGAGTGGATGG GAGGGATCATCCCTATCTTTGGTACAGCAAACTACGC ACAGAAGTTCCAGGGCAGGGTCACCATTACTGCAGA CAAATCCACGAGCACAGCCTACATGGAGCTGAGCAG CCTGAGATCTGAGGACACCGCCGTGTATTACTGTGCG AAAGGTAACTTCTACGGTGGTCTGGACTACTGGGGCC AAGGGACCACCGTGACCGTCTCCTCAGCTAGCACCA AGGGCCCATCGGTCTTCCCCCTGGCACCCTCCTCCAA GAGCACCTCTGGGGGCACAGCGGCCCTGGGCTGCCT GGTCAAGGACTACTTCCCCGAACCGGTGACGGTGTC GTGGAACTCAGGCGCCCTGACCAGCGGCGTGCACAC CTTCCCGGCTGTCCTACAGTCCTCAGGACTCTACTCC CTCAGCAGCGTGGTGACCGTGCCCTCCAGCAGCTTGG GCACCCAGACCTACATCTGCAACGTGAATCACAAGC CCAGCAACACCAAGGTGGACAAGAAAGTTGAGCCCA AATCTTGTGACAAAACTCACACATGCCCACCGTGCCC AGCACCTGAAGCTGCAGGGGGACCGTCAGTCTTCCTC TTCCCCCCAAAACCCAAGGACACCCTCATGATCTCCC GGACCCCTGAGGTCACATGCGTGGTGGTGGACGTGA GCCACGAAGACCCTGAGGTCAAGTTCAACTGGTACG TGGACGGCGTGGAGGTGCATAATGCCAAGACAAAGC CGCGGGAGGAGCAGTACAACAGCACGTACCGTGTGG TCAGCGTCCTCACCGTCCTGCACCAGGACTGGCTGAA TGGCAAGGAGTACAAGTGCAAGGTCTCCAACAAAGC CCTCGGCGCCCCCATCGAGAAAACCATCTCCAAAGC CAAAGGGCAGCCCCGAGAACCACAGGTGTACACCCT GCCCCCCTGCAGAGATGAGCTGACCAAGAACCAGGT GTCCCTGTGGTGTCTGGTCAAGGGCTTCTACCCCAGC GATATCGCCGTGGAGTGGGAGAGCAACGGCCAGCCT GAGAACAACTACAAGACCACCCCCCCTGTGCTGGAC AGCGACGGCAGCTTCTTCCTGTACTCCAAACTGACCG TGGACAAGAGCCGGTGGCAGCAGGGCAACGTGTTCA GCTGCAGCGTGATGCACGAGGCCCTGCACAACCACT ACACCCAGAAGTCCCTGAGCCTGAGCCCCGGCGGAG GCGGCGGAAGCGGAGGAGGAGGATCCAGAGAGGGC CCTGAGCTGAGCCCTGATGATCCTGCCGGACTGCTGG ACCTGCGGCAGGGAATGTTTGCCCAGCTGGTGGCCC AGAACGTGCTGCTGATCGATGGCCCCCTGTCCTGGTA CAGCGATCCTGGACTGGCTGGCGTGTCACTGACAGG CGGCCTGAGCTACAAAGAGGACACCAAAGAACTGGT GGTGGCCAAGGCCGGCGTGTACTACGTGTTCTTTCAG CTGGAACTGCGGAGAGTGGTGGCCGGCGAAGGATCT GGCTCTGTGTCTCTGGCCCTGCATCTGCAGCCTCTGA GATCTGCTGCTGGCGCCGCTGCTCTGGCACTGACAGT GGATCTGCCTCCTGCCAGCAGCGAGGCCCGGAATAG CGCATTTGGGTTTCAAGGCAGGCTGCTGCACCTGTCT GCCGGCCAGAGGCTGGGAGTGCATCTGCACACAGAG GCCAGGGCTAGACACGCCTGGCAGCTGACACAGGGC GCTACAGTGCTGGGCCTGTTCAGAGTGACCCCCGAG ATTCCTGCCGGGCTC |
| SEQ ID NO: 73 | anti-TnC(18D4) light chain | See Table 20 |

TABLE 41

Amino acid sequences of bivalent TnC(18D4) targeted split trimeric 4-1BB ligand (71-248) Fc (kih) fusion (construct 6.6)

| SEQ ID NO | Construct | Sequence |
|---|---|---|
| SEQ ID NO: 124 | anti-TnC(18D4) Fc hole dimeric ligand (71-248) chain | QVQLVQSGAEVKKPGSSVKVSCKASGGTFSSYAISWVR<br>QAPGQGLEWMGGIIPIFGTANYAQKFQGRVTITADKSTS<br>TAYMELSSLRSEDTAVYYCAKGNFYGGLDYWGQGTTV<br>TVSSASTKGPSVFPLAPSSKSTSGGTAALGCLVKDYFPE<br>PVTVSWNSGALTSGVHTFPAVLQSSGLYSLSSVVTVPSS<br>SLGTQTYICNVNHKPSNTKVDKKVEPKSCDKTHTCPPC<br>PAPEAAGGPSVFLFPPKPKDTLMISRTPEVTCVVVDVSH<br>EDPEVKFNWYVDGVEVHNAKTKPREEQYNSTYRVVSV<br>LTVLHQDWLNGKEYKCKVSNKALGAPIEKTISKAKGQP<br>REPQVCTLPPSRDELTKNQVSLSCAVKGFYPSDIAVEWE<br>SNGQPENNYKTTPPVLDSDGSFFLVSKLTVDKSRWQQG<br>NVFSCSVMHEALHNHYTQKSLSLSPGGGGGSGGGGSRE<br>GPELSPDDPAGLLDLRQGMFAQLVAQNVLLIDGPLSWY<br>SDPGLAGVSLTGGLSYKEDTKELVVAKAGVYYVFFQLE<br>LRRVVAGEGSGSVSLALHLQPLRSAAGAAALALTVDLP<br>PASSEARNSAFGFQGRLLHLSAGQRLGVHLHTEARARH<br>AWQLTQGATVLGLFRVTPEIPAGLGGGGSGGGGSREGP<br>ELSPDDPAGLLDLRQGMFAQLVAQNVLLIDGPLSWYSD<br>PGLAGVSLTGGLSYKEDTKELVVAKAGVYYVFFQLELR<br>RVVAGEGSGSVSLALHLQPLRSAAGAAALALTVDLPPA<br>SSEARNSAFGFQGRLLHLSAGQRLGVHLHTEARARHA<br>WQLTQGATVLGLFRVTPEIPAGL |
| SEQ ID NO: 125 | anti-TnC(18D4) Fc knob monomeric (71-248) ligand | QVQLVQSGAEVKKPGSSVKVSCKASGGTFSSYAISWVR<br>QAPGQGLEWMGGIIPIFGTANYAQKFQGRVTITADKSTS<br>TAYMELSSLRSEDTAVYYCAKGNFYGGLDYWGQGTTV<br>TVSSASTKGPSVFPLAPSSKSTSGGTAALGCLVKDYFPE<br>PVTVSWNSGALTSGVHTFPAVLQSSGLYSLSSVVTVPSS<br>SLGTQTYICNVNHKPSNTKVDKKVEPKSCDKTHTCPPC<br>PAPEAAGGPSVFLFPPKPKDTLMISRTPEVTCVVVDVSH<br>EDPEVKFNWYVDGVEVHNAKTKPREEQYNSTYRVVSV<br>LTVLHQDWLNGKEYKCKVSNKALGAPIEKTISKAKGQP<br>REPQVYTLPPCRDELTKNQVSLWCLVKGFYPSDIAVEW<br>ESNGQPENNYKTTPPVLDSDGSFFLYSKLTVDKSRWQQ<br>GNVFSCSVMHEALHNHYTQKSLSLSPGGGGGSGGGGS<br>REGPELSPDDPAGLLDLRQGMFAQLVAQNVLLIDGPLS<br>WYSDPGLAGVSLTGGLSYKEDTKELVVAKAGVYYVFF<br>QLELRRVVAGEGSGSVSLALHLQPLRSAAGAAALALTV<br>DLPPASSEARNSAFGFQGRLLHLSAGQRLGVHLHTEAR<br>ARHAWQLTQGATVLGLFRVTPEIPAGL |
| SEQ ID NO: 77 | anti-TnC(18D4) light chain | See Table 21 |

Figure 17A:
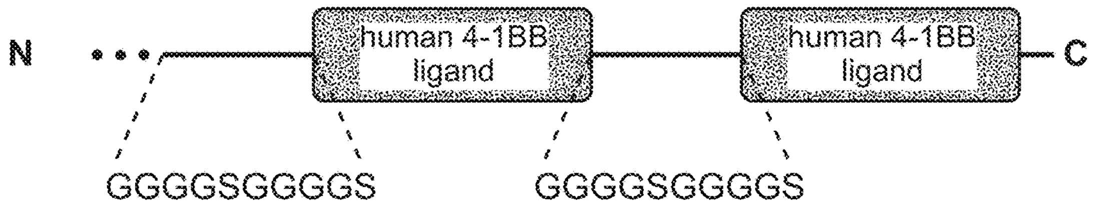
FIGS. 17A and 17B show components for the assembly of monovalent targeted split trimeric human 4-1BB ligand fused at the C-terminus of a human Fc.
Figure 17B:
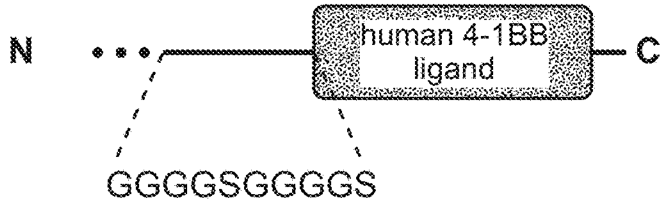

Constructs 6.11 and 6.12: Monovalent TnC (Knob) Targeted Trimeric C-Terminal 4-1BB Ligand Fc (kih) Fusion A polypeptide containing two ectodomains of 4-1BB ligand, separated by (G4S)2 (SEQ ID NO: 150) linkers was subcloned in frame to the C-terminus of human IgG1 Fc hole or knob chain (Merchant, Zhu et al. 1998), as depicted in FIG. 17A: human IgG1 Fc, (G4S)2 connector, human 4-1BB ligand, (G4S)2 connector, human 4-1BB ligand. A polypeptide containing one ectodomain of 4-1BB ligand was subcloned in frame to the C-terminus of human IgG1 Fc knob or hole chain as described in FIG. 17B: human IgG1 Fc, (G4S)2 connector, human 4-1BB ligand.

The variable region of heavy and light chain DNA sequences encoding a binder specific for TnC, clone 18D4, were subcloned in frame with either the constant heavy chain of the knob or the constant light chain of human IgG1.

The Pro329Gly, Leu234Ala and Leu235Ala mutations have been introduced in the constant region of the knob and hole heavy chains to abrogate binding to Fc gamma receptors (described in International Patent Appl. Publ. No. WO 2012/130831).

Figure 18A:
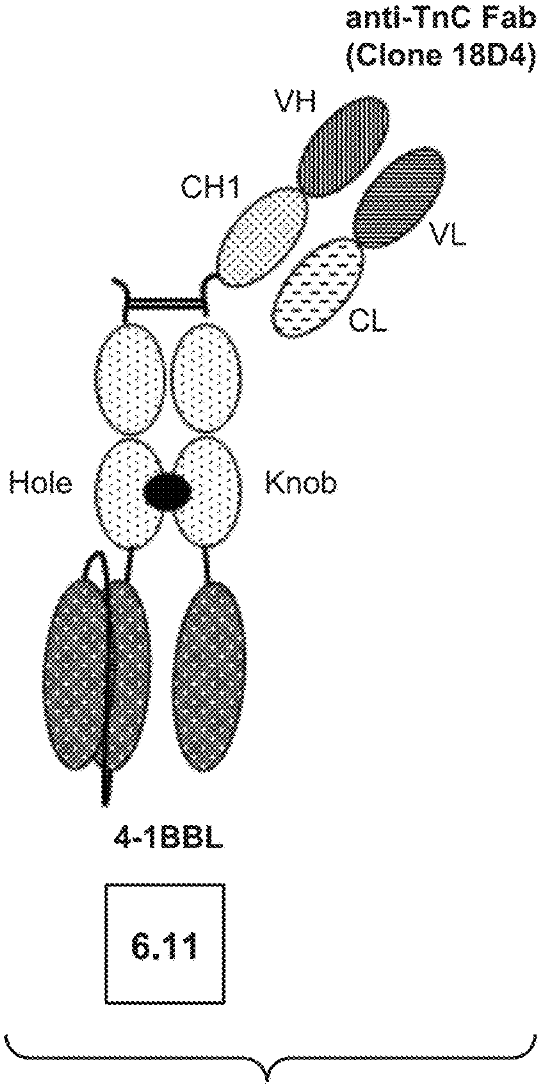
FIGS. 18A and 18B show monovalent targeted split trimeric C-terminal 4-1BB ligand Fc (kih) knob fusion.
Figure 18B:
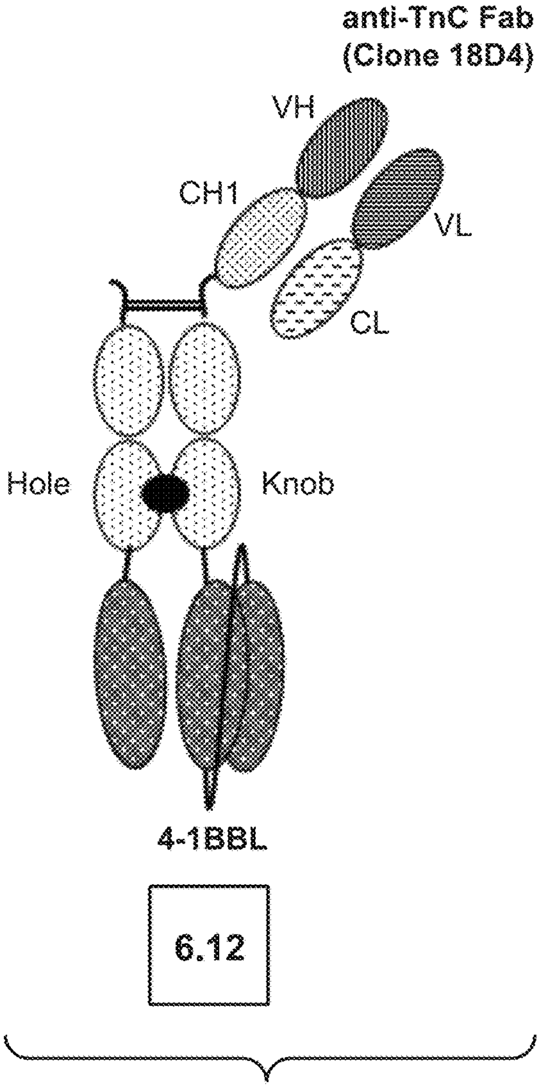

Combination of the huIgG1 Fc hole chain containing the Y349C/T366S/L368A/Y407V mutations, the anti-TnC huIgG1 knob chain containing the S354C/T366W mutations and the anti-TnC light chain allows generation of a heterodimer, which includes an assembled trimeric 4-1BB ligand and one TnC binding Fab (FIGS. 18A and 18B).

Table 42 and Table 43 show respectively, the cDNA and amino acid sequences of the monovalent targeted TnC (18D4) split trimeric C-terminal 4-1BB ligand (71-248) Fc (kih) fusion (construct 6.11).

TABLE 42

Base pair sequences of bivalent TnC(18D4) split trimeric C-terminal 4-1BB ligand (71-248) Fc (kih) fusion (construct 6.11)

| SEQ ID NO | Construct | Sequence |
|---|---|---|
| SEQ ID NO: 126 | Fc hole dimeric ligand (71-248) chain | GACAAAACTCACACATGCCCACCGTGCCCAGCACCT GAAGCTGCAGGGGGACCGTCAGTCTTCCTCTTCCCC CCAAAACCCAAGGACACCCTCATGATCTCCCGGACC CCTGAGGTCACATGCGTGGTGGTGGACGTGAGCCAC GAAGACCCTGAGGTCAAGTTCAACTGGTACGTGGAC GGCGTGGAGGTGCATAATGCCAAGACAAAGCCGCG GGAGGAGCAGTACAACAGCACGTACCGTGTGGTCA GCGTCCTCACCGTCCTGCACCAGGACTGGCTGAATG GCAAGGAGTACAAGTGCAAGGTCTCCAACAAAGCC CTCGGCGCCCCCATCGAGAAAACCATCTCCAAAGCC AAAGGGCAGCCCCGAGAACCACAGGTGTGCACCCT GCCCCCATCCCGGGATGAGCTGACCAAGAACCAGG TCAGCCTCTCGTGCGCAGTCAAAGGCTTCTATCCCA GCGACATCGCCGTGGAGTGGGAGAGCAATGGGCAG CCGGAGAACAACTACAAGACCACGCCTCCCGTGCTG GACTCCGACGGCTCCTTCTTCCTCGTGAGCAAGCTC ACCGTGGACAAGAGCAGGTGGCAGCAGGGGAACGT CTTCTCATGCTCCGTGATGCATGAGGCTCTGCACAA CCACTACACGCAGAAGAGCCTCTCCCTGTCTCCGGG TGGAGGCGGCGGAAGCGGAGGAGGAGGATCCAGAG AGGGCCCTGAGCTGAGCCCTGATGATCCTGCCGGAC TGCTGGACCTGCGGCAGGGAATGTTTGCCCAGCTGG TGGCCCAGAACGTGCTGCTGATCGATGGCCCCCTGT CCTGGTACAGCGATCCTGGACTGGCTGGCGTGTCAC TGACAGGCGGCCTGAGCTACAAAGAGGACACCAAA GAACTGGTGGTGGCCAAGGCCGGCGTGTACTACGTG TTCTTTCAGCTGGAACTGCGGAGAGTGGTGGCCGGC GAAGGATCTGGCTCTGTGTCTCTGGCCCTGCATCTG CAGCCTCTGAGATCTGCTGCTGGCGCCGCTGCTCTG GCACTGACAGTGGATCTGCCTCCTGCCAGCAGCGAG GCCCGGAATAGCGCATTTGGGTTTCAAGGCAGGCTG CTGCACCTGTCTGCCGGCCAGAGGCTGGGAGTGCAT CTGCACACAGAGGCCAGGGCTAGACACGCCTGGCA GCTGACACAGGGCGCTACAGTGCTGGGCCTGTTCAG AGTGACCCCCGAGATTCCAGCAGGCCTGGGAGGCG GCGGATCTGGCGGCGGAGGATCTAGAGAAGGACCC GAGCTGTCCCCCGACGATCCCGCTGGGCTGCTGGAT CTGAGACAGGGCATGTTCGCTCAGCTGGTGGCTCAG AATGTGCTGCTGATTGACGGACCTCTGAGCTGGTAC TCCGACCCAGGGCTGGCAGGGGTGTCCCTGACTGGG GGACTGTCCTACAAAGAAGATACAAAAGAACTGGT GGTGGCTAAAGCTGGGGTGTACTATGTGTTTTTTCA GCTGGAACTGAGGCGGGTGGTGGCTGGGGAGGGCT CAGGATCTGTGTCCCTGGCTCTGCATCTGCAGCCAC TGCGCTCTGCAGCAGGGGCTGCAGCACTGGCCCTGA CTGTGGACCTGCCCCCAGCTTCTTCCGAGGCCAGAA ACAGCGCCTTCGGGTTCCAAGGACGCCTGCTGCATC TGAGCGCCGGACAGCGCCTGGGAGTGCATCTGCATA CTGAAGCCAGAGCCCGGCATGCTTGGCAGCTGACTC AGGGGGCAACTGTGCTGGGACTGTTTCGCGTGACAC CTGAGATCCCAGCCGGGCTC |
| SEQ ID NO: 123 | anti-TnC(18D4) Fc knob monomeric ligand (71-248) chain | See Table 40 |
| SEQ ID NO: 73 | anti-TnC(18D4) light chain | See Table 20 |

TABLE 43

Amino acid sequences of bivalent TnC(18D4) split trimeric C-terminal 4-1BB ligand (71-248) Fc (kih) fusion (construct 6.11)

| SEQ ID NO | Construct | Sequence |
|---|---|---|
| SEQ ID NO: 127 | Fc hole dimeric ligand (71-248) chain | DKTHTCPPCPAPEAAGGPSVFLFPPKPKDTLMISRTPEV TCVVVDVSHEDPEVKFNWYVDGVEVHNAKTKPREEQ YNSTYRVVSVLTVLHQDWLNGKEYKCKVSNKALGAP IEKTISKAKGQPREPQVCTLPPSRDELTKNQVSLSCAV KGFYPSDIAVEWESNGQPENNYKTTPPVLDSDGSFFLV SKLTVDKSRWQQGNVFSCSVMHEALHNHYTQKSLSL SPGGGGGSGGGGSREGPELSPDDPAGLLDLRQGMFAQ LVAQNVLLIDGPLSWYSDPGLAGVSLTGGLSYKEDTK ELVVAKAGVYYVFFQLELRRVVAGEGSGSVSLALHLQ PLRSAAGAAALALTVDLPPASSEARNSAFGFQGRLLHL SAGQRLGVHLHTEARARHAWQLTQGATVLGLFRVTP EIPAGLGGGGSGGGGSREGPELSPDDPAGLLDLRQGM FAQLVAQNVLLIDGPLSWYSDPGLAGVSLTGGLSYKE DTKELVVAKAGVYYVFFQLELRRVVAGEGSGSVSLAL HLQPLRSAAGAAALALTVDLPPASSEARNSAFGFQGR LLHLSAGQRLGVHLHTEARARHAWQLTQGATVLGLF RVTPEIPAGL |
| SEQ ID NO: 125 | anti-TnC(18D4) Fc knob monomeric ligand (71-248) chain | See Table 41 |
| SEQ ID NO: 77 | anti-TnC(18D4) light chain | See Table 21 |

Table 44 and Table 45 show, respectively, the cDNA and amino acid sequences of the monovalent targeted TnC (18D4) split trimeric C-terminal 4-1BB ligand (71-248) Fc (kih) fusion (construct 6.12).

TABLE 44

Base pair sequences of monovalent targeted TnC(18D4) split trimeric C-terminal 4-1BB ligand (71-248) Fc (kih) fusion (construct 6.12)

| SEQ ID NO | Construct | Sequence |
|---|---|---|
| SEQ ID NO: 128 | Fc hole monomeric ligand (71-248) chain | GACAAAACTCACACATGCCCACCGTGCCCAGCACCT GAAGCTGCAGGGGGACCGTCAGTCTTCCTCTTCCCC CCAAAACCCAAGGACACCCTCATGATCTCCCGGACC CCTGAGGTCACATGCGTGGTGGTGGACGTGAGCCAC GAAGACCCTGAGGTCAAGTTCAACTGGTACGTGGAC GGCGTGGAGGTGCATAATGCCAAGACAAAGCCGCG GGAGGAGCAGTACAACAGCACGTACCGTGTGGTCA GCGTCCTCACCGTCCTGCACCAGGACTGGCTGAATG GCAAGGAGTACAAGTGCAAGGTCTCCAACAAAGCC CTCGGCGCCCCCATCGAGAAAACCATCTCCAAAGCC AAAGGGCAGCCCCGAGAACCACAGGTGTGCACCCT GCCCCCATCCCGGGATGAGCTGACCAAGAACCAGG TCAGCCTCTCGTGCGCAGTCAAAGGCTTCTATCCCA GCGACATCGCCGTGGAGTGGGAGAGCAATGGGCAG CCGGAGAACAACTACAAGACCACGCCTCCCGTGCTG GACTCCGACGGCTCCTTCTTCCTCGTGAGCAAGCTC ACCGTGGACAAGAGCAGGTGGCAGCAGGGGAACGT CTTCTCATGCTCCGTGATGCATGAGGCTCTGCACAA CCACTACACGCAGAAGAGCCTCTCCCTGTCTCCGGG TAGAGAGGGCCCTGAGCTGAGCCCTGATGATCCTGC CGGACTGCTGGACCTGCGGCAGGGAATGTTTGCCCA GCTGGTGGCCCAGAACGTGCTGCTGATCGATGGCCC CCTGTCCTGGTACAGCGATCCTGGACTGGCTGGCGT GTCACTGACAGGCGGCCTGAGCTACAAAGAGGACA CCAAAGAACTGGTGGTGGCCAAGGCCGGCGTGTAC TACGTGTTCTTTCAGCTGGAACTGCGGAGAGTGGTG GCCGGCGAAGGATCTGGCTCTGTGTCTCTGGCCCTG CATCTGCAGCCTCTGAGATCTGCTGCTGGCGCCGCT GCTCTGGCACTGACAGTGGATCTGCCTCCTGCCAGC AGCGAGGCCCGGAATAGCGCATTTGGGTTTCAAGGC |

TABLE 44-continued

Base pair sequences of monovalent targeted TnC(18D4) split trimeric C-terminal 4-1BB ligand (71-248) Fc (kih) fusion (construct 6.12)

| SEQ ID NO | Construct | Sequence |
|---|---|---|
| | | AGGCTGCTGCACCTGTCTGCCGGCCAGAGGCTGGGA GTGCATCTGCACACAGAGGCCAGGGCTAGACACGC CTGGCAGCTGACACAGGGCGCTACAGTGCTGGGCCT GTTCAGAGTGACCCCCGAGATTCCTGCCGGGCTC |
| SEQ ID NO: 129 | anti-TnC(18D4) Fc knob dimeric ligand (71-248) chain | CAGGTGCAATTGGTGCAGTCTGGGGCTGAGGTGAA GAAGCCTGGGTCCTCGGTGAAGGTCTCCTGCAAGGC CTCCGGAGGCACATTCAGCAGCTACGCTATAAGCTG GGTGCGACAGGCCCCTGGACAAGGGCTCGAGTGGA TGGGAGGGATCATCCCTATCTTTGGTACAGCAAACT ACGCACAGAAGTTCCAGGGCAGGGTCACCATTACTG CAGACAAATCCACGAGCACAGCCTACATGGAGCTG AGCAGCCTGAGATCTGAGGACACCGCCGTGTATTAC TGTGCGAAAGGTAACTTCTACGGTGGTCTGGACTAC TGGGGCCAAGGGACCACCGTGACCGTCTCCTCAGCT AGCACCAAGGGCCCATCGGTCTTCCCCCTGGCACCC TCCTCCAAGAGCACCTCTGGGGGCACAGCGGCCCTG GGCTGCCTGGTCAAGGACTACTTCCCCGAACCGGTG ACGGTGTCGTGGAACTCAGGCGCCCTGACCAGCGGC GTGCACACCTTCCCGGCTGTCCTACAGTCCTCAGGA CTCTACTCCCTCAGCAGCGTGGTGACCGTGCCCTCC AGCAGCTTGGGCACCCAGACCTACATCTGCAACGTG AATCACAAGCCCAGCAACACCAAGGTGGACAAGAA AGTTGAGCCCAAATCTTGTGACAAAACTCACACATG CCCACCGTGCCCAGCACCTGAAGCTGCAGGGGGAC CGTCAGTCTTCCTCTTCCCCCCAAAACCCAAGGACA CCCTCATGATCTCCCGGACCCCTGAGGTCACATGCG TGGTGGTGGACGTGAGCCACGAAGACCCTGAGGTC AAGTTCAACTGGTACGTGGACGGCGTGGAGGTGCAT AATGCCAAGACAAAGCCGCGGGAGGAGCAGTACAA CAGCACGTACCGTGTGGTCAGCGTCCTCACCGTCCT GCACCAGGACTGGCTGAATGGCAAGGAGTACAAGT GCAAGGTCTCCAACAAAGCCCTCGGCGCCCCCATCG AGAAAACCATCTCCAAAGCCAAAGGGCAGCCCCGA GAACCACAGGTGTACACCCTGCCCCCCTGCAGAGAT GAGCTGACCAAGAACCAGGTGTCCCTGTGGTGTCTG GTCAAGGGCTTCTACCCCAGCGATATCGCCGTGGAG TGGGAGAGCAACGGCCAGCCTGAGAACAACTACAA GACCACCCCCCCTGTGCTGGACAGCGACGGCAGCTT CTTCCTGTACTCCAAACTGACCGTGGACAAGAGCCG GTGGCAGCAGGGCAACGTGTTCAGCTGCAGCGTGAT GCACGAGGCCCTGCACAACCACTACACCCAGAAGT CCCTGAGCCTGAGCCCCGGCAGAGAGGGCCCTGAG CTGAGCCCTGATGATCCTGCCGGACTGCTGGACCTG CGGCAGGGAATGTTTGCCCAGCTGGTGGCCCAGAAC GTGCTGCTGATCGATGGCCCCCTGTCCTGGTACAGC GATCCTGGACTGGCTGGCGTGTCACTGACAGGCGGC CTGAGCTACAAAGAGGACACCAAAGAACTGGTGGT GGCCAAGGCCGGCGTGTACTACGTGTTCTTTCAGCT GGAACTGCGGAGAGTGGTGGCCGGCGAAGGATCTG GCTCTGTGTCTCTGGCCCTGCATCTGCAGCCTCTGAG ATCTGCTGCTGGCGCCGCTGCTCTGGCACTGACAGT GGATCTGCCTCCTGCCAGCAGCGAGGCCCGGAATAG CGCATTTGGGTTTCAAGGCAGGCTGCTGCACCTGTC TGCCGGCCAGAGGCTGGGAGTGCATCTGCACACAG AGGCCAGGGCTAGACACGCCTGGCAGCTGACACAG GGCGCTACAGTGCTGGGCCTGTTCAGAGTGACCCCC GAGATTCCAGCAGGCCTGGGAGGCGGCGGATCTGG CGGCGGAGGATCTAGAGAAGGACCCGAGCTGTCCC CCGACGATCCCGCTGGGCTGCTGGATCTGAGACAGG GCATGTTCGCTCAGCTGGTGGCTCAGAATGTGCTGC TGATTGACGGACCTCTGAGCTGGTACTCCGACCCAG GGCTGGCAGGGGTGTCCCTGACTGGGGGACTGTCCT ACAAAGAAGATACAAAAGAACTGGTGGTGGCTAAA GCTGGGGTGTACTATGTGTTTTTTCAGCTGGAACTG AGGCGGGTGGTGGCTGGGGAGGGCTCAGGATCTGT GTCCCTGGCTCTGCATCTGCAGCCACTGCGCTCTGC AGCAGGGGCTGCAGCACTGGCCCTGACTGTGGACCT GCCCCCAGCTTCTTCCGAGGCCAGAAACAGCGCCTT CGGGTTCCAAGGACGCCTGCTGCATCTGAGCGCCGG ACAGCGCCTGGGAGTGCATCTGCATACTGAAGCCAG AGCCCGGCATGCTTGGCAGCTGACTCAGGGGGCAA CTGTGCTGGGACTGTTTCGCGTGACACCTGAGATCC CAGCCGGGCTC |

TABLE 44-continued

Base pair sequences of monovalent targeted TnC(18D4) split trimeric C-terminal 4-1BB ligand (71-248) Fc (kih) fusion (construct 6.12)

| SEQ ID NO | Construct | Sequence |
|---|---|---|
| SEQ ID NO: 73 | anti-TnC(18D4) light chain | See Table 20 |

TABLE 45

Amino acid sequences of monovalent targeted TnC(18D4) split trimeric C-terminal 4-1BB ligand (71-248) Fc (kih) fusion (construct 6.12)

| SEQ ID NO | Construct | Sequence |
|---|---|---|
| SEQ ID NO: 130 | Fc hole monomeric ligand (71-248) chain | DKTHTCPPCPAPEAAGGPSVFLFPPKPKDTLMISRTPEV<br>TCVVVDVSHEDPEVKFNWYVDGVEVHNAKTKPREEQ<br>YNSTYRVVSVLTVLHQDWLNGKEYKCKVSNKALGAP<br>IEKTISKAKGQPREPQVCTLPPSRDELTKNQVSLSCAV<br>KGFYPSDIAVEWESNGQPENNYKTTPPVLDSDGSFFLV<br>SKLTVDKSRWQQGNVFSCSVMHEALHNHYTQKSLSL<br>SPGREGPELSPDDPAGLLDLRQGMFAQLVAQNVLLID<br>GPLSWYSDPGLAGVSLTGGLSYKEDTKELVVAKAGV<br>YYVFFQLELRRVVAGEGSGSVSLALHLQPLRSAAGAA<br>ALALTVDLPPASSEARNSAFGFQGRLLHLSAGQRLGV<br>HLHTEARARHAWQLTQGATVLGLFRVTPEIPAGL |
| SEQ ID NO: 131 | anti-TnC(18D4) Fc knob dimeric ligand (71-248) chain | QVQLVQSGAEVKKPGSSVKVSCKASGGTFSSYAISWV<br>RQAPGQGLEWMGGIIPIFGTANYAQKFQGRVTITADKS<br>TSTAYMELSSLRSEDTAVYYCAKGNFYGGLDYWGQG<br>TTVTVSSASTKGPSVFPLAPSSKSTSGGTAALGCLVKD<br>YFPEPVTVSWNSGALTSGVHTFPAVLQSSGLYSLSSVV<br>TVPSSSLGTQTYICNVNHKPSNTKVDKKVEPKSCDKT<br>HTCPPCPAPEAAGGPSVFLFPPKPKDTLMISRTPEVTCV<br>VVDVSHEDPEVKFNWYVDGVEVHNAKTKPREEQYNS<br>TYRVVSVLTVLHQDWLNGKEYKCKVSNKALGAPIEK<br>TISKAKGQPREPQVYTLPPCRDELTKNQVSLWCLVKG<br>FYPSDIAVEWESNGQPENNYKTTPPVLDSDGSFFLYSK<br>LTVDKSRWQQGNVFSCSVMHEALHNHYTQKSLSLSP<br>GREGPELSPDDPAGLLDLRQGMFAQLVAQNVLLIDGP<br>LSWYSDPGLAGVSLTGGLSYKEDTKELVVAKAGVYY<br>VFFQLELRRVVAGEGSGSVSLALHLQPLRSAAGAAAL<br>ALTVDLPPASSEARNSAFGFQGRLLHLSAGQRLGVHL<br>HTEARARHAWQLTQGATVLGLFRVTPEIPAGLGGGGS<br>GGGGSREGPELSPDDPAGLLDLRQGMFAQLVAQNVLL<br>IDGPLSWYSDPGLAGVSLTGGLSYKEDTKELVVAKAG<br>VYYVFFQLELRRVVAGEGSGSVSLALHLQPLRSAAGA<br>AALALTVDLPPASSEARNSAFGFQGRLLHLSAGQRLG<br>VHLHTEARARHAWQLTQGATVLGLFRVTPEIPAGL |
| SEQ ID NO: 77 | anti-TnC(18D4) light chain | See Table 21 |

Constructs 6.13 and 6.14: Monovalent TnC (Hole) Targeted Trimeric C-Terminal 4-1BB Ligand Fc (kih) Fusion A polypeptide containing two ectodomains of 4-1BB ligand, separated by (G4S)2 (SEQ ID NO: 150) linkers was subcloned in frame to the C-terminus of human IgG1 Fc hole or knob chain (Merchant, Zhu et al. 1998), as depicted in FIG. 17A: human IgG1 Fc, (G4S)2 connector, human 4-1BB ligand, (G4S)2 connector, human 4-1BB ligand. A polypeptide containing one ectodomain of 4-1BB ligand was subcloned in frame to the C-terminus of human IgG1 Fc knob or hole chain as described in FIG. 17B: human IgG1 Fc, (G4S)2 connector, human 4-1BB ligand.

The variable region of heavy and light chain DNA sequences encoding a binder specific for TnC, clone 18D4, were subcloned in frame with either the constant heavy chain of the hole or the constant light chain of human IgG1.

The Pro329Gly, Leu234Ala and Leu235Ala mutations have been introduced in the constant region of the knob and hole heavy chains to abrogate binding to Fc gamma receptors (described in International Patent Appl. Publ. No. WO 2012/130831).

Figure 19A:
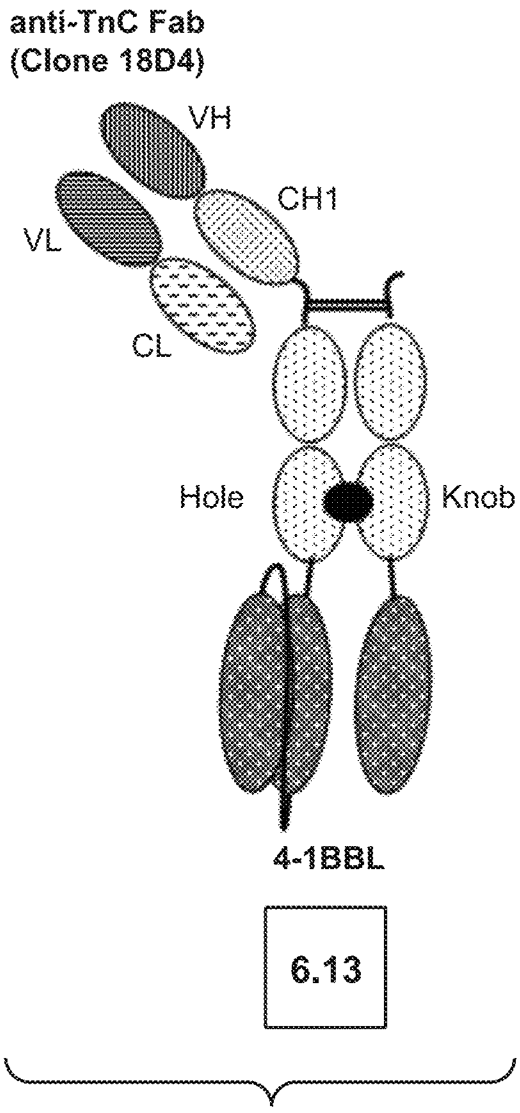
FIGS. 19A and 19B show monovalent targeted (hole chain) split trimeric C-terminal 4-1BB ligand Fc (kih) fusion.
Figure 19B:
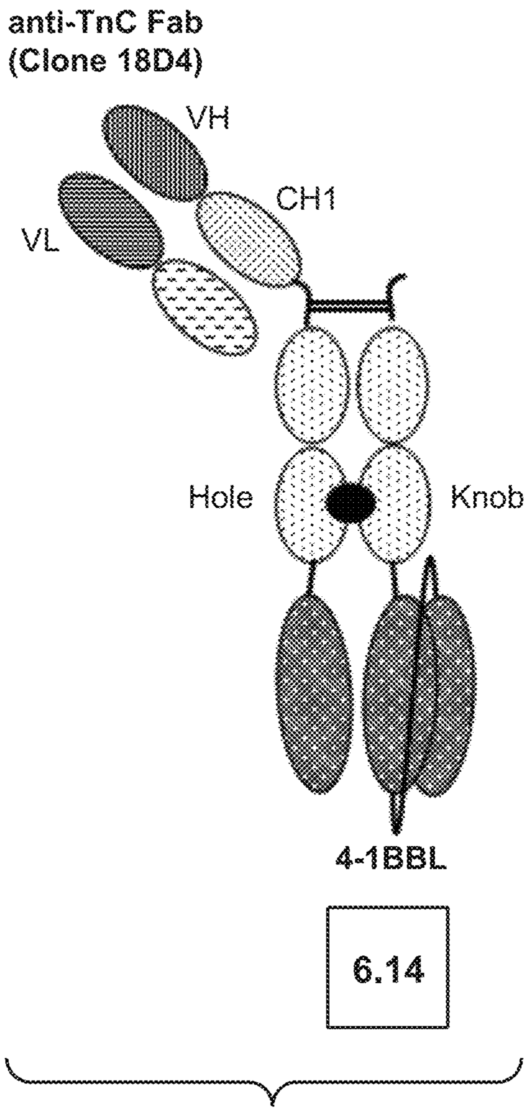

Combination of the anti-TnC huIgG1 Fc hole chain containing the Y349C/T366S/L368A/Y407V mutations, the huIgG1 knob chain containing the S354C/T366W mutations and the anti-TnC light chain allows generation of a heterodimer, which includes an assembled trimeric 4-1BB ligand and one TnC binding Fab (FIGS. 19A and 19B).

Table 46 and Table 47 show, respectively, the cDNA and amino acid sequences of the monovalent targeted TnC (18D4) split trimeric C-terminal 4-1BB ligand (71-248) Fc (kih) fusion (construct 6.13).

TABLE 46

Base pair sequences of monovalent targeted TnC(18D4) split trimeric C-terminal 4-1BB ligand (71-248) Fc (kih) fusion (construct 6.13).

| SEQ ID NO | Construct | Sequence |
|---|---|---|
| SEQ ID NO: 122 | anti-TnC(18D4) Fc hole dimeric ligand (71-248) chain | See Table 40 |
| SEQ ID NO: 132 | Fc knob monomeric ligand (71-248) chain | GACAAAACTCACACATGCCCACCGTGCCCAGCACCT GAAGCTGCAGGGGGACCGTCAGTCTTCCTCTTCCCC CCAAAACCCAAGGACACCCTCATGATCTCCCGGACC CCTGAGGTCACATGCGTGGTGGTGGACGTGAGCCAC GAAGACCCTGAGGTCAAGTTCAACTGGTACGTGGAC GGCGTGGAGGTGCATAATGCCAAGACAAAGCCGCG GGAGGAGCAGTACAACAGCACGTACCGTGTGGTCA GCGTCCTCACCGTCCTGCACCAGGACTGGCTGAATG GCAAGGAGTACAAGTGCAAGGTCTCCAACAAAGCC CTCGGCGCCCCCATCGAGAAAACCATCTCCAAAGCC AAAGGGCAGCCCCGAGAACCACAGGTGTACACCCT GCCCCCCTGCAGAGATGAGCTGACCAAGAACCAGG TGTCCCTGTGGTGTCTGGTCAAGGGCTTCTACCCCA GCGATATCGCCGTGGAGTGGGAGAGCAACGGCCAG CCTGAGAACAACTACAAGACCACCCCCCCTGTGCTG GACAGCGACGGCAGCTTCTTCCTGTACTCCAAACTG ACCGTGGACAAGAGCCGGTGGCAGCAGGGCAACGT GTTCAGCTGCAGCGTGATGCACGAGGCCCTGCACAA CCACTACACCCAGAAGTCCCTGAGCCTGAGCCCCGG CGGAGGCGGCGGAAGCGGAGGAGGAGGATCCAGA GAGGGCCCTGAGCTGAGCCCTGATGATCCTGCCGGA CTGCTGGACCTGCGGCAGGGAATGTTTGCCCAGCTG GTGGCCCAGAACGTGCTGCTGATCGATGGCCCCCTG TCCTGGTACAGCGATCCTGGACTGGCTGGCGTGTCA CTGACAGGCGGCCTGAGCTACAAAGAGGACACCAA AGAACTGGTGGTGGCCAAGGCCGGCGTGTACTACGT GTTCTTTCAGCTGGAACTGCGGAGAGTGGTGGCCGG CGAAGGATCTGGCTCTGTGTCTCTGGCCCTGCATCT GCAGCCTCTGAGATCTGCTGCTGGCGCCGCTGCTCT GGCACTGACAGTGGATCTGCCTCCTGCCAGCAGCGA GGCCCGGAATAGCGCATTTGGGTTTCAAGGCAGGCT GCTGCACCTGTCTGCCGGCCAGAGGCTGGGAGTGCA TCTGCACACAGAGGCCAGGGCTAGACACGCCTGGC AGCTGACACAGGGCGCTACAGTGCTGGGCCTGTTCA GAGTGACCCCCGAGATTCCTGCCGGGCTC |
| SEQ ID NO: 73 | anti-TnC(18D4) light chain | See Table 20 |

TABLE 47

Amino acid sequences of monovalent targeted TnC(18D4) split trimeric C-terminal 4-1BB ligand (71-248) Fc (kih) fusion (construct 6.13).

| SEQ ID NO | Construct | Sequence |
|---|---|---|
| SEQ ID NO: 124 | anti-TnC(18D4) Fc hole dimeric ligand (71-248) chain | See Table 41 |
| SEQ ID NO: 133 | Fc knob monomeric ligand (71-248) chain | DKTHTCPPCPAPEAAGGPSVFLFPPKPKDTLMISRTPEV TCVVVDVSHEDPEVKFNWYVDGVEVHNAKTKPREEQ YNSTYRVVSVLTVLHQDWLNGKEYKCKVSNKALGAP IEKTISKAKGQPREPQVYTLPPCRDELTKNQVSLWCLV KGFYPSDIAVEWESNGQPENNYKTTPPVLDSDGSFFLY SKLTVDKSRWQQGNVFSCSVMHEALHNHYTQKSLSL |

TABLE 47-continued

Amino acid sequences of monovalent targeted TnC(18D4) split trimeric C-terminal 4-1BB ligand (71-248) Fc (kih) fusion (construct 6.13).

| SEQ ID NO | Construct | Sequence |
|---|---|---|
| | | SPGGGGGSGGGGSREGPELSPDDPAGLLDLRQGMFAQ LVAQNVLLIDGPLSWYSDPGLAGVSLTGGLSYKEDTK ELVVAKAGVYYVFFQLELRRVVAGEGSGSVSLALHLQ PLRSAAGAAALALTVDLPPASSEARNSAFGFQGRLLHL SAGQRLGVHLHTEARARHAWQLTQGATVLGLFRVTP EIPAGL |
| SEQ ID NO: 77 | anti-TnC(18D4) light chain | See Table 21 |

Table 48 and Table 49 show, respectively, the cDNA and amino acid sequences of the monovalent targeted TnC (18D4) split trimeric C-terminal 4-1BB ligand (71-248) Fc (kih) fusion (construct 6.14).

TABLE 48

Base pair sequences of monovalent targeted TnC(18D4) split trimeric C-terminal 4-1BB ligand (71-248) Fc (kih) fusion (construct 6.14).

| SEQ ID NO | Construct | Sequence |
|---|---|---|
| SEQ ID NO: 134 | anti-TnC(18D4) Fc hole monomeric ligand (71-248) chain | CAGGTGCAATTGGTGCAGTCTGGGGCTGAGGTGAA GAAGCCTGGGTCCTCGGTGAAGGTCTCCTGCAAGGC CTCCGGAGGCACATTCAGCAGCTACGCTATAAGCTG GGTGCGACAGGCCCCTGGACAAGGGCTCGAGTGGA TGGGAGGGATCATCCCTATCTTTGGTACAGCAAACT ACGCACAGAAGTTCCAGGGCAGGGTCACCATTACTG CAGACAAATCCACGAGCACAGCCTACATGGAGCTG AGCAGCCTGAGATCTGAGGACACCGCCGTGTATTAC TGTGCGAAAGGTAACTTCTACGGTGGTCTGGACTAC TGGGGCCAAGGGACCACCGTGACCGTCTCCTCAGCT AGCACCAAGGGCCCCTCCGTGTTCCCCCTGGCCCCC AGCAGCAAGAGCACCAGCGGCGGCACAGCCGCTCT GGGCTGCCTGGTCAAGGACTACTTCCCCGAGCCCGT GACCGTGTCCTGGAACAGCGGAGCCCTGACCTCCGG CGTGCACACCTTCCCCGCCGTGCTGCAGAGTTCTGG CCTGTATAGCCTGAGCAGCGTGGTCACCGTGCCTTC TAGCAGCCTGGGCACCCAGACCTACATCTGCAACGT GAACCACAAGCCCAGCAACACCAAGGTGGACAAGA AGGTGGAGCCCAAGAGCTGCGACAAAACTCACACA TGCCCACCGTGCCCAGCACCTGAAGCTGCAGGGGG ACCGTCAGTCTTCCTCTTCCCCCCAAAACCCAAGGA CACCCTCATGATCTCCCGGACCCCTGAGGTCACATG CGTGGTGGTGGACGTGAGCCACGAAGACCCTGAGG TCAAGTTCAACTGGTACGTGGACGGCGTGGAGGTGC ATAATGCCAAGACAAAGCCGCGGGAGGAGCAGTAC AACAGCACGTACCGTGTGGTCAGCGTCCTCACCGTC CTGCACCAGGACTGGCTGAATGGCAAGGAGTACAA GTGCAAGGTCTCCAACAAAGCCCTCGGCGCCCCCAT CGAGAAAACCATCTCCAAAGCCAAAGGGCAGCCCC GAGAACCACAGGTGTGCACCCTGCCCCCATCCCGGG ATGAGCTGACCAAGAACCAGGTCAGCCTCTCGTGCG CAGTCAAAGGCTTCTATCCCAGCGACATCGCCGTGG AGTGGGAGAGCAATGGGCAGCCGGAGAACAACTAC AAGACCACGCCTCCCGTGCTGGACTCCGACGGCTCC TTCTTCCTCGTGAGCAAGCTCACCGTGGACAAGAGC AGGTGGCAGCAGGGGAACGTCTTCTCATGCTCCGTG ATGCATGAGGCTCTGCACAACCACTACACGCAGAA GAGCCTCTCCCTGTCTCCGGGTGGAGGCGGCGGAAG CGGAGGAGGAGGATCCAGAGAGGGCCCTGAGCTGA GCCCTGATGATCCTGCCGGACTGCTGGACCTGCGGC AGGGAATGTTTGCCCAGCTGGTGGCCCAGAACGTGC TGCTGATCGATGGCCCCCTGTCCTGGTACAGCGATC CTGGACTGGCTGGCGTGTCACTGACAGGCGGCCTGA GCTACAAAGAGGACACCAAAGAACTGGTGGTGGCC AAGGCCGGCGTGTACTACGTGTTCTTTCAGCTGGAA CTGCGGAGAGTGGTGGCCGGCGAAGGATCTGGCTCT GTGTCTCTGGCCCTGCATCTGCAGCCTCTGAGATCT |

TABLE 48-continued

Base pair sequences of monovalent targeted TnC(18D4) split trimeric C-terminal 4-1BB ligand (71-248) Fc (kih) fusion (construct 6.14).

| SEQ ID NO | Construct | Sequence |
|---|---|---|
| | | GCTGCTGGCGCCGCTGCTCTGGCACTGACAGTGGAT<br>CTGCCTCCTGCCAGCAGCGAGGCCCGGAATAGCGCA<br>TTTGGGTTTCAAGGCAGGCTGCTGCACCTGTCTGCC<br>GGCCAGAGGCTGGGAGTGCATCTGCACACAGAGGC<br>CAGGGCTAGACACGCCTGGCAGCTGACACAGGGCG<br>CTACAGTGCTGGGCCTGTTCAGAGTGACCCCCGAGA<br>TTCCTGCCGGGCTC |
| SEQ ID NO: 135 | Fc knob dimeric ligand (71-248) chain | GACAAAACTCACACATGCCCACCGTGCCCAGCACCT<br>GAAGCTGCAGGGGGACCGTCAGTCTTCCTCTTCCCC<br>CCAAAACCCAAGGACACCCTCATGATCTCCCGGACC<br>CCTGAGGTCACATGCGTGGTGGTGGACGTGAGCCAC<br>GAAGACCCTGAGGTCAAGTTCAACTGGTACGTGGAC<br>GGCGTGGAGGTGCATAATGCCAAGACAAAGCCGCG<br>GGAGGAGCAGTACAACAGCACGTACCGTGTGGTCA<br>GCGTCCTCACCGTCCTGCACCAGGACTGGCTGAATG<br>GCAAGGAGTACAAGTGCAAGGTCTCCAACAAAGCC<br>CTCGGCGCCCCCATCGAGAAAACCATCTCCAAAGCC<br>AAAGGGCAGCCCCGAGAACCACAGGTGTACACCCT<br>GCCCCCCTGCAGAGATGAGCTGACCAAGAACCAGG<br>TGTCCCTGTGGTGTCTGGTCAAGGGCTTCTACCCCA<br>GCGATATCGCCGTGGAGTGGGAGAGCAACGGCCAG<br>CCTGAGAACAACTACAAGACCACCCCCCCTGTGCTG<br>GACAGCGACGGCAGCTTCTTCCTGTACTCCAAACTG<br>ACCGTGGACAAGAGCCGGTGGCAGCAGGGCAACGT<br>GTTCAGCTGCAGCGTGATGCACGAGGCCCTGCACAA<br>CCACTACACCCAGAAGTCCCTGAGCCTGAGCCCCGG<br>CGGAGGCGGCGGAAGCGGAGGAGGAGGATCCAGA<br>GAGGGCCCTGAGCTGAGCCCTGATGATCCTGCCGGA<br>CTGCTGGACCTGCGGCAGGGAATGTTTGCCCAGCTG<br>GTGGCCCAGAACGTGCTGCTGATCGATGGCCCCCTG<br>TCCTGGTACAGCGATCCTGGACTGGCTGGCGTGTCA<br>CTGACAGGCGGCCTGAGCTACAAAGAGGACACCAA<br>AGAACTGGTGGTGGCCAAGGCCGGCGTGTACTACGT<br>GTTCTTTCAGCTGGAACTGCGGAGAGTGGTGGCCGG<br>CGAAGGATCTGGCTCTGTGTCTCTGGCCCTGCATCT<br>GCAGCCTCTGAGATCTGCTGCTGGCGCCGCTGCTCT<br>GGCACTGACAGTGGATCTGCCTCCTGCCAGCAGCGA<br>GGCCCGGAATAGCGCATTTGGGTTTCAAGGCAGGCT<br>GCTGCACCTGTCTGCCGGCCAGAGGCTGGGAGTGCA<br>TCTGCACACAGAGGCCAGGGCTAGACACGCCTGGC<br>AGCTGACACAGGGCGCTACAGTGCTGGGCCTGTTCA<br>GAGTGACCCCCGAGATTCCAGCAGGCCTGGGAGGC<br>GGCGGATCTGGCGGCGGAGGATCTAGAGAAGGACC<br>CGAGCTGTCCCCCGACGATCCCGCTGGGCTGCTGGA<br>TCTGAGACAGGGCATGTTCGCTCAGCTGGTGGCTCA<br>GAATGTGCTGCTGATTGACGGACCTCTGAGCTGGTA<br>CTCCGACCCAGGGCTGGCAGGGGTGTCCCTGACTGG<br>GGGACTGTCCTACAAAGAAGATACAAAAGAACTGG<br>TGGTGGCTAAAGCTGGGGTGTACTATGTGTTTTTTC<br>AGCTGGAACTGAGGCGGGTGGTGGCTGGGGAGGGC<br>TCAGGATCTGTGTCCCTGGCTCTGCATCTGCAGCCA<br>CTGCGCTCTGCAGCAGGGGCTGCAGCACTGGCCCTG<br>ACTGTGGACCTGCCCCCAGCTTCTTCCGAGGCCAGA<br>AACAGCGCCTTCGGGTTCCAAGGACGCCTGCTGCAT<br>CTGAGCGCCGGACAGCGCCTGGGAGTGCATCTGCAT<br>ACTGAAGCCAGAGCCCGGCATGCTTGGCAGCTGACT<br>CAGGGGGCAACTGTGCTGGGACTGTTTCGCGTGACA<br>CCTGAGATCCCAGCCGGGCTC |
| SEQ ID NO: 73 | anti-TnC(18D4) light chain | See Table 20 |

TABLE 49

Amino acid sequences of monovalent targeted TnC(18D4) split trimeric C-terminal 4-1BB ligand (71-248) Fc (kih) fusion (construct 6.14).

| SEQ ID NO | Construct | Sequence |
|---|---|---|
| SEQ ID NO: 136 | anti-TnC(18D4) Fc hole monomeric ligand (71-248) chain | QVQLVQSGAEVKKPGSSVKVSCKASGGTFSSYAISWV RQAPGQGLEWMGGIIPIFGTANYAQKFQGRVTITADKS TSTAYMELSSLRSEDTAVYYCAKGNFYGGLDYWGQG TTVTVSSASTKGPSVFPLAPSSKSTSGGTAALGCLVKD YFPEPVTVSWNSGALTSGVHTFPAVLQSSGLYSLSSVV TVPSSSLGTQTYICNVNHKPSNTKVDKKVEPKSCDKT HTCPPCPAPEAAGGPSVFLFPPKPKDTLMISRTPEVTCV VVDVSHEDPEVKFNWYVDGVEVHNAKTKPREEQYNS TYRVVSVLTVLHQDWLNGKEYKCKVSNKALGAPIEK TISKAKGQPREPQVCTLPPSRDELTKNQVSLSCAVKGF YPSDIAVEWESNGQPENNYKTTPPVLDSDGSFFLVSKL TVDKSRWQQGNVFSCSVMHEALHNHYTQKSLSLSPG GGGGSGGGGSREGPELSPDDPAGLLDLRQGMFAQLV AQNVLLIDGPLSWYSDPGLAGVSLTGGLSYKEDTKEL VVAKAGVYYVFFQLELRRVVAGEGSGSVSLALHLQPL RSAAGAAALALTVDLPPASSEARNSAFGFQGRLLHLS AGQRLGVHLHTEARARHAWQLTQGATVLGLFRVTPEI PAGL |
| SEQ ID NO: 137 | Fc knob dimeric ligand (71-248) chain | DKTHTCPPCPAPEAAGGPSVFLFPPKPKDTLMISRTPEV TCVVVDVSHEDPEVKFNWYVDGVEVHNAKTKPREEQ YNSTYRVVSVLTVLHQDWLNGKEYKCKVSNKALGAP IEKTISKAKGQPREPQVYTLPPCRDELTKNQVSLWCLV KGFYPSDIAVEWESNGQPENNYKTTPPVLDSDGSFFLY SKLTVDKSRWQQGNVFSCSVMHEALHNHYTQKSLSL SPGGGGGSGGGGSREGPELSPDDPAGLLDLRQGMFAQ LVAQNVLLIDGPLSWYSDPGLAGVSLTGGLSYKEDTK ELVVAKAGVYYVFFQLELRRVVAGEGSGSVSLALHLQ PLRSAAGAAALALTVDLPPASSEARNSAFGFQGRLLHL SAGQRLGVHLHTEARARHAWQLTQGATVLGLFRVTP EIPAGLGGGGSGGGGSREGPELSPDDPAGLLDLRQGM FAQLVAQNVLLIDGPLSWYSDPGLAGVSLTGGLSYKE DTKELVVAKAGVYYVFFQLELRRVVAGEGSGSVSLAL HLQPLRSAAGAAALALTVDLPPASSEARNSAFGFQGR LLHLSAGQRLGVHLHTEARARHAWQLTQGATVLGLF RVTPEIPAGL |
| SEQ ID NO: 77 | anti-TnC(18D4) light chain | See Table 21 |

Preparation of Untargeted Split Trimeric 4-1BB Ligand Fc Fusion and Human IgG as Control Molecules These control molecules were prepared as described above for the TnC targeted construct 6.1 (termed control B), 6.3 (termed control C), 6.4 (termed control D) and 6.5 (termed control E) with the only difference that the anti-TnC binder (VH-VL) was replaced by a germline control, termed DP47, not binding to the antigen).

Table 50 shows, respectively, the cDNA and amino acid sequences of the monovalent DP47-untargeted split trimeric 4-1BB ligand (71-254) Fc (kih) fusion containing crossed CH-CL with charged residues, control B.

Table 51 shows, respectively, the cDNA and amino acid sequences of the bivalent DP47-untargeted split trimeric 4-1BB ligand (71-254) Fc (kih) fusion, control C.

Table 52 shows, respectively, the cDNA and amino acid sequences of the monovalent DP47-untargeted split trimeric 4-1BB ligand (71-248) Fc (kih) fusion containing CH-CL cross with charged residues, control D.

Table 53 shows, respectively, the cDNA and amino acid sequences of the monovalent DP47-untargeted split trimeric 4-1BB ligand (71-248) Fc (kih) fusion without charged residues in the CH-CL cross, control E.

TABLE 50 cDNA and amino acid sequences of monovalent DP47 untargeted split trimeric human 4-1BB ligand (71-254) Fc (kih) fusion with CH-CL cross and with charged residues (control B).

| SEQ ID NO: | Description | Sequence |
|---|---|---|
| SEQ ID NO: 98 | nucleotide sequence dimeric hu 4-1BBL (71-254)-CL* Fc knob chain | see above |

TABLE 50-continued cDNA and amino acid sequences of monovalent DP47 untargeted split trimeric human 4-1BB ligand (71-254) Fc (kih) fusion with CH-CL cross and with charged residues (control B).

| SEQ ID NO: | Description | Sequence |
|---|---|---|
| SEQ ID NO: 99 | nucleotide sequence monomeric hu 4-1BBL (71-254)-CH1* | see above |
| SEQ ID NO: 138 | nucleotide sequence DP47 Fc hole chain | GAGGTGCAATTGTTGGAGTCTGGGGGAGGCTTGGT<br>ACAGCCTGGGGGGTCCCTGAGACTCTCCTGTGCAG<br>CCTCCGGATTCACCTTTAGCAGTTATGCCATGAGC<br>TGGGTCCGCCAGGCTCCAGGGAAGGGGCTGGAGT<br>GGGTCTCAGCTATTAGTGGTAGTGGTGGTAGCACA<br>TACTACGCAGACTCCGTGAAGGGCCGGTTCACCAT<br>CTCCAGAGACAATTCCAAGAACACGCTGTATCTGC<br>AGATGAACAGCCTGAGAGCCGAGGACACGGCCGT<br>ATATTACTGTGCGAAAGGCAGCGGATTTGACTACT<br>GGGGCCAAGGAACCCTGGTCACCGTCTCGAGTGCT<br>AGCACCAAGGGCCCATCGGTCTTCCCCCTGGCACC<br>CTCCTCCAAGAGCACCTCTGGGGGCACAGCGGCCC<br>TGGGCTGCCTGGTCAAGGACTACTTCCCCGAACCG<br>GTGACGGTGTCGTGGAACTCAGGCGCCCTGACCAG<br>CGGCGTGCACACCTTCCCGGCTGTCCTACAGTCCT<br>CAGGACTCTACTCCCTCAGCAGCGTGGTGACCGTG<br>CCCTCCAGCAGCTTGGGCACCCAGACCTACATCTG<br>CAACGTGAATCACAAGCCCAGCAACACCAAGGTG<br>GACAAGAAAGTTGAGCCCAAATCTTGTGACAAAA<br>CTCACACATGCCCACCGTGCCCAGCACCTGAAGCT<br>GCAGGGGGACCGTCAGTCTTCCTCTTCCCCCCAAA<br>ACCCAAGGACACCCTCATGATCTCCCGGACCCCTG<br>AGGTCACATGCGTGGTGGTGGACGTGAGCCACGA<br>AGACCCTGAGGTCAAGTTCAACTGGTACGTGGACG<br>GCGTGGAGGTGCATAATGCCAAGACAAAGCCGCG<br>GGAGGAGCAGTACAACAGCACGTACCGTGTGGTC<br>AGCGTCCTCACCGTCCTGCACCAGGACTGGCTGAA<br>TGGCAAGGAGTACAAGTGCAAGGTCTCCAACAAA<br>GCCCTCGGCGCCCCCATCGAGAAAACCATCTCCAA<br>AGCCAAAGGGCAGCCCCGAGAACCACAGGTGTGC<br>ACCCTGCCCCCATCCCGGGATGAGCTGACCAAGAA<br>CCAGGTCAGCCTCTCGTGCGCAGTCAAAGGCTTCT<br>ATCCCAGCGACATCGCCGTGGAGTGGGAGAGCAA<br>TGGGCAGCCGGAGAACAACTACAAGACCACGCCT<br>CCCGTGCTGGACTCCGACGGCTCCTTCTTCCTCGTG<br>AGCAAGCTCACCGTGGACAAGAGCAGGTGGCAGC<br>AGGGGAACGTCTTCTCATGCTCCGTGATGCATGAG<br>GCTCTGCACAACCACTACACGCAGAAGAGCCTCTC<br>CCTGTCTCCGGGTAAA |
| SEQ ID NO: 139 | nucleotide sequence DP47 light chain | GAAATCGTGTTAACGCAGTCTCCAGGCACCCTGTC<br>TTTGTCTCCAGGGGAAAGAGCCACCCTCTCTTGCA<br>GGGCCAGTCAGAGTGTTAGCAGCAGCTACTTAGCC<br>TGGTACCAGCAGAAACCTGGCCAGGCTCCCAGGCT<br>CCTCATCTATGGAGCATCCAGCAGGGCCACTGGCA<br>TCCCAGACAGGTTCAGTGGCAGTGGATCCGGGACA<br>GACTTCACTCTCACCATCAGCAGACTGGAGCCTGA<br>AGATTTTGCAGTGTATTACTGTCAGCAGTATGGTA<br>GCTCACCGCTGACGTTCGGCCAGGGGACCAAAGTG<br>GAAATCAAACGTACGGTGGCTGCACCATCTGTCTT<br>CATCTTCCCGCCATCTGATGAGCAGTTGAAATCTG<br>GAACTGCCTCTGTTGTGTGCCTGCTGAATAACTTCT<br>ATCCCAGAGAGGCCAAAGTACAGTGGAAGGTGGA<br>TAACGCCCTCCAATCGGGTAACTCCCAGGAGAGTG<br>TCACAGAGCAGGACAGCAAGGACAGCACCTACAG<br>CCTCAGCAGCACCCTGACGCTGAGCAAAGCAGACT<br>ACGAGAAACACAAAGTCTACGCCTGCGAAGTCAC<br>CCATCAGGGCCTGAGCTCGCCCGTCACAAAGAGCT<br>TCAACAGGGGAGAGTGT |
| SEQ ID NO: 102 | Dimeric hu 4-1BBL (71-254)-CL* Fc knob chain | see Table 31 |

TABLE 50-continued cDNA and amino acid sequences of monovalent DP47 untargeted split trimeric human 4-1BB ligand (71-254) Fc (kih) fusion with CH-CL cross and with charged residues (control B).

| SEQ ID NO: | Description | Sequence |
|---|---|---|
| SEQ ID NO: 103 | Monomeric hu 4-1BBL (71-254)-CH1* | see Table 31 |
| SEQ ID NO: 140 | DP47 Fc hole chain | EVQLLESGGGLVQPGGSLRLSCAASGFTFSSYAMSW VRQAPGKGLEWVSAISGSGGSTYYADSVKGRFTISR DNSKNTLYLQMNSLRAEDTAVYYCAKGSGFDYWG QGTLVTVSSASTKGPSVFPLAPSSKSTSGGTAALGCL VKDYFPEPVTVSWNSGALTSGVHTFPAVLQSSGLYS LSSVVTVPSSSLGTQTYICNVNHKPSNTKVDKKVEPK SCDKTHTCPPCPAPEAAGGPSVFLFPPKPKDTLMISRT PEVTCVVVDVSHEDPEVKFNWYVDGVEVHNAKTKP REEQYNSTYRVVSVLTVLHQDWLNGKEYKCKVSNK ALGAPIEKTISKAKGQPREPQVCTLPPSRDELTKNQV SLSCAVKGFYPSDIAVEWESNGQPENNYKTTPPVLDS DGSFFLVSKLTVDKSRWQQGNVFSCSVMHEALHNH YTQKSLSLSPGK |
| SEQ ID NO: 141 | DP47 light chain | EIVLTQSPGTLSLSPGERATLSCRASQSVSSSYLAWY QQKPGQAPRLLIYGASSRATGIPDRFSGSGSGTDFTLT ISRLEPEDFAVYYCQQYGSSPLTFGQGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |

*charges residues

TABLE 51 cDNA and amino acid sequences of bivalent DP47 untargeted split trimeric human 4-1BB ligand (71-254) Fc (kih) fusion (control C).

| SEQ ID NO: | Description | Sequence |
|---|---|---|
| SEQ ID NO: 142 | nucleotide sequence DP47 Fc hole chain fused to dimeric hu 4-1BBL (71-254) | GAGGTGCAATTGTTGGAGTCTGGGGGAGGCTTGGT ACAGCCTGGGGGGTCCCTGAGACTCTCCTGTGCAG CCTCCGGATTCACCTTTAGCAGTTATGCCATGAGC TGGGTCCGCCAGGCTCCAGGGAAGGGGCTGGAGT GGGTCTCAGCTATTAGTGGTAGTGGTGGTAGCACA TACTACGCAGACTCCGTGAAGGGCCGGTTCACCAT CTCCAGAGACAATTCCAAGAACACGCTGTATCTGC AGATGAACAGCCTGAGAGCCGAGGACACGGCCGT ATATTACTGTGCGAAAGGCAGCGGATTTGACTACT GGGGCCAAGGAACCCTGGTCACCGTCTCGAGTGCT AGCACCAAGGGCCCCTCCGTGTTCCCCCTGGCCCC CAGCAGCAAGAGCACCAGCGGCGGCACAGCCGCT CTGGGCTGCCTGGTCAAGGACTACTTCCCCGAGCC CGTGACCGTGTCCTGGAACAGCGGAGCCCTGACCT CCGGCGTGCACACCTTCCCCGCCGTGCTGCAGAGT TCTGGCCTGTATAGCCTGAGCAGCGTGGTCACCGT GCCTTCTAGCAGCCTGGGCACCCAGACCTACATCT GCAACGTGAACCACAAGCCCAGCAACACCAAGGT GGACAAGAAGGTGGAGCCCAAGAGCTGCGACAAA ACTCACACATGCCCACCGTGCCCAGCACCTGAAGC TGCAGGGGGACCGTCAGTCTTCCTCTTCCCCCCAA AACCCAAGGACACCCTCATGATCTCCCGGACCCCT GAGGTCACATGCGTGGTGGTGGACGTGAGCCACG AAGACCCTGAGGTCAAGTTCAACTGGTACGTGGAC GGCGTGGAGGTGCATAATGCCAAGACAAAGCCGC GGGAGGAGCAGTACAACAGCACGTACCGTGTGGT CAGCGTCCTCACCGTCCTGCACCAGGACTGGCTGA ATGGCAAGGAGTACAAGTGCAAGGTCTCCAACAA AGCCCTCGGCGCCCCCATCGAGAAAACCATCTCCA AAGCCAAAGGGCAGCCCCGAGAACCACAGGTGTG CACCCTGCCCCCATCCCGGGATGAGCTGACCAAGA ACCAGGTCAGCCTCTCGTGCGCAGTCAAAGGCTTC TATCCCAGCGACATCGCCGTGGAGTGGGAGAGCA ATGGGCAGCCGGAGAACAACTACAAGACCACGCC TCCCGTGCTGGACTCCGACGGCTCCTTCTTCCTCGT GAGCAAGCTCACCGTGGACAAGAGCAGGTGGCAG |

TABLE 51-continued cDNA and amino acid sequences of bivalent DP47 untargeted split trimeric human 4-1BB ligand (71-254) Fc (kih) fusion (control C).

| SEQ ID NO: | Description | Sequence |
|---|---|---|
| | | CAGGGGAACGTCTTCTCATGCTCCGTGATGCATGA<br>GGCTCTGCACAACCACTACACGCAGAAGAGCCTCT<br>CCCTGTCTCCGGGTGGAGGCGGCGGAAGCGGAGG<br>AGGAGGATCCAGAGAGGGCCCTGAGCTGAGCCCC<br>GATGATCCTGCTGGACTGCTGGACCTGCGGCAGGG<br>CATGTTTGCTCAGCTGGTGGCCCAGAACGTGCTGC<br>TGATCGATGGCCCCCTGTCCTGGTACAGCGATCCT<br>GGACTGGCTGGCGTGTCACTGACAGGCGGCCTGAG<br>CTACAAAGAGGACACCAAAGAACTGGTGGTGGCC<br>AAGGCCGGCGTGTACTACGTGTTCTTTCAGCTGGA<br>ACTGCGGAGAGTGGTGGCCGGCGAAGGATCTGGC<br>TCTGTGTCTCTGGCCCTGCATCTGCAGCCTCTGAGA<br>AGCGCTGCTGGCGCTGCAGCTCTGGCACTGACAGT<br>GGATCTGCCTCCTGCCAGCTCCGAGGCCCGGAATA<br>GCGCATTTGGGTTTCAAGGCAGGCTGCTGCACCTG<br>TCTGCCGGCCAGAGGCTGGGAGTGCATCTGCACAC<br>AGAGGCCAGGGCTAGACACGCCTGGCAGCTGACA<br>CAGGGCGCTACAGTGCTGGGCCTGTTCAGAGTGAC<br>CCCCGAGATTCCAGCCGGCCTGCCTTCTCCAAGAA<br>GCGAAGGCGGAGGCGGATCTGGCGGCGGAGGATC<br>TAGAGAGGGACCCGAACTGTCCCCTGACGATCCAG<br>CCGGGCTGCTGGATCTGAGACAGGGAATGTTCGCC<br>CAGCTGGTGGCTCAGAATGTGCTGCTGATTGACGG<br>ACCTCTGAGCTGGTACTCCGACCCAGGGCTGGCAG<br>GGGTGTCCCTGACTGGGGGACTGTCCTACAAAGAA<br>GATACAAAAGAACTGGTGGTGGCTAAAGCTGGGG<br>TGTACTATGTGTTTTTTCAGCTGGAACTGAGGCGG<br>GTGGTGGCTGGGGAGGGCTCAGGATCTGTGTCCCT<br>GGCTCTGCATCTGCAGCCACTGCGCTCTGCTGCTG<br>GCGCAGCTGCACTGGCTCTGACTGTGGACCTGCCA<br>CCAGCCTCTAGCGAGGCCAGAAACAGCGCCTTCGG<br>GTTCCAAGGACGCCTGCTGCATCTGAGCGCCGGAC<br>AGCGCCTGGGAGTGCATCTGCATACTGAAGCCAGA<br>GCCCGGCATGCTTGGCAGCTGACTCAGGGGGCAAC<br>TGTGCTGGGACTGTTTCGCGTGACACCTGAGATCC<br>CTGCCGGACTGCCAAGCCCTAGATCAGAA |
| SEQ ID NO: 143 | nucleotide sequence DP47 Fc knob chain fused to monomeric hu 4-1BBL (71-254) | GAGGTGCAATTGTTGGAGTCTGGGGGAGGCTTGGT<br>ACAGCCTGGGGGGTCCCTGAGACTCTCCTGTGCAG<br>CCTCCGGATTCACCTTTAGCAGTTATGCCATGAGC<br>TGGGTCCGCCAGGCTCCAGGGAAGGGGCTGGAGT<br>GGGTCTCAGCTATTAGTGGTAGTGGTGGTAGCACA<br>TACTACGCAGACTCCGTGAAGGGCCGGTTCACCAT<br>CTCCAGAGACAATTCCAAGAACACGCTGTATCTGC<br>AGATGAACAGCCTGAGAGCCGAGGACACGGCCGT<br>ATATTACTGTGCGAAAGGCAGCGGATTTGACTACT<br>GGGGCCAAGGAACCCTGGTCACCGTCTCGAGTGCT<br>AGCACCAAGGGCCCATCGGTCTTCCCCCTGGCACC<br>CTCCTCCAAGAGCACCTCTGGGGGCACAGCGGCCC<br>TGGGCTGCCTGGTCAAGGACTACTTCCCCGAACCG<br>GTGACGGTGTCGTGGAACTCAGGCGCCCTGACCAG<br>CGGCGTGCACACCTTCCCGGCTGTCCTACAGTCCT<br>CAGGACTCTACTCCCTCAGCAGCGTGGTGACCGTG<br>CCCTCCAGCAGCTTGGGCACCCAGACCTACATCTG<br>CAACGTGAATCACAAGCCCAGCAACACCAAGGTG<br>GACAAGAAAGTTGAGCCCAAATCTTGTGACAAAA<br>CTCACACATGCCCACCGTGCCCAGCACCTGAAGCT<br>GCAGGGGGACCGTCAGTCTTCCTCTTCCCCCCAAA<br>ACCCAAGGACACCCTCATGATCTCCCGGACCCCTG<br>AGGTCACATGCGTGGTGGTGGACGTGAGCCACGA<br>AGACCCTGAGGTCAAGTTCAACTGGTACGTGGACG<br>GCGTGGAGGTGCATAATGCCAAGACAAAGCCGCG<br>GGAGGAGCAGTACAACAGCACGTACCGTGTGGTC<br>AGCGTCCTCACCGTCCTGCACCAGGACTGGCTGAA<br>TGGCAAGGAGTACAAGTGCAAGGTCTCCAACAAA<br>GCCCTCGGCGCCCCCATCGAGAAAACCATCTCCAA<br>AGCCAAAGGGCAGCCCCGAGAACCACAGGTGTAC<br>ACCCTGCCCCCCTGCAGAGATGAGCTGACCAAGAA<br>CCAGGTGTCCCTGTGGTGTCTGGTCAAGGGCTTCT<br>ACCCCAGCGATATCGCCGTGGAGTGGGAGAGCAA<br>CGGCCAGCCTGAGAACAACTACAAGACCACCCCC<br>CCTGTGCTGGACAGCGACGGCAGCTTCTTCCTGTA<br>CTCCAAACTGACCGTGGACAAGAGCCGGTGGCAG<br>CAGGGCAACGTGTTCAGCTGCAGCGTGATGCACGA |

TABLE 51-continued cDNA and amino acid sequences of bivalent DP47 untargeted split trimeric human 4-1BB ligand (71-254) Fc (kih) fusion (control C).

| SEQ ID NO: | Description | Sequence |
|---|---|---|
| | | GGCCCTGCACAACCACTACACCCAGAAGTCCCTGA<br>GCCTGAGCCCCGGCGGAGGCGGCGGAAGCGGAGG<br>AGGAGGATCCAGAGAGGGCCCTGAGCTGAGCCCC<br>GATGATCCTGCTGGACTGCTGGACCTGCGGCAGGG<br>CATGTTTGCTCAGCTGGTGGCCCAGAACGTGCTGC<br>TGATCGATGGCCCCCTGTCCTGGTACAGCGATCCT<br>GGACTGGCTGGCGTGTCACTGACAGGCGGCCTGAG<br>CTACAAAGAGGACACCAAAGAACTGGTGGTGGCC<br>AAGGCCGGCGTGTACTACGTGTTCTTTCAGCTGGA<br>ACTGCGGAGAGTGGTGGCCGGCGAAGGATCTGGC<br>TCTGTGTCTCTGGCCCTGCATCTGCAGCCTCTGAGA<br>AGCGCTGCTGGCGCTGCAGCTCTGGCACTGACAGT<br>GGATCTGCCTCCTGCCAGCTCCGAGGCCCGGAATA<br>GCGCATTTGGGTTTCAAGGCAGGCTGCTGCACCTG<br>TCTGCCGGCCAGAGGCTGGGAGTGCATCTGCACAC<br>AGAGGCCAGGGCTAGACACGCCTGGCAGCTGACA<br>CAGGGCGCTACAGTGCTGGGCCTGTTCAGAGTGAC<br>CCCCGAGATTCCAGCCGGCCTGCCTTCTCCAAGAA<br>GCGAA |
| SEQ ID NO: 139 | nucleotide sequence DP47 light chain | See Table 50 |
| SEQ ID NO: 144 | DP47 Fc hole chain fused to dimeric hu 4-1BBL (71-254) | EVQLLESGGGLVQPGGSLRLSCAASGFTFSSYAMSW<br>VRQAPGKGLEWVSAISGSGGSTYYADSVKGRFTISR<br>DNSKNTLYLQMNSLRAEDTAVYYCAKGSGFDYWG<br>QGTLVTVSSASTKGPSVFPLAPSSKSTSGGTAALGCL<br>VKDYFPEPVTVSWNSGALTSGVHTFPAVLQSSGLYS<br>LSSVVTVPSSSLGTQTYICNVNHKPSNTKVDKKVEPK<br>SCDKTHTCPPCPAPEAAGGPSVFLFPPKPKDTLMISRT<br>PEVTCVVVDVSHEDPEVKFNWYVDGVEVHNAKTKP<br>REEQYNSTYRVVSVLTVLHQDWLNGKEYKCKVSNK<br>ALGAPIEKTISKAKGQPREPQVCTLPPSRDELTKNQV<br>SLSCAVKGFYPSDIAVEWESNGQPENNYKTTPPVLDS<br>DGSFFLVSKLTVDKSRWQQGNVFSCSVMHEALHNH<br>YTQKSLSLSPGGGGGSGGGGSREGPELSPDDPAGLLD<br>LRQGMFAQLVAQNVLLIDGPLSWYSDPGLAGVSLTG<br>GLSYKEDTKELVVAKAGVYYVFFQLELRRVVAGEG<br>SGSVSLALHLQPLRSAAGAAALALTVDLPPASSEARN<br>SAFGFQGRLLHLSAGQRLGVHLHTEARARHAWQLT<br>QGATVLGLFRVTPEIPAGLPSPRSEGGGGSGGGGSRE<br>GPELSPDDPAGLLDLRQGMFAQLVAQNVLLIDGPLS<br>WYSDPGLAGVSLTGGLSYKEDTKELVVAKAGVYYV<br>FFQLELRRVVAGEGSGSVSLALHLQPLRSAAGAAAL<br>ALTVDLPPASSEARNSAFGFQGRLLHLSAGQRLGVH<br>LHTEARARHAWQLTQGATVLGLFRVTPEIPAGLPSPR<br>SE |
| SEQ ID NO: 145 | DP47 Fc knob chain fused to monomeric hu 4-1BBL (71-254) | EVQLLESGGGLVQPGGSLRLSCAASGFTFSSYAMSW<br>VRQAPGKGLEWVSAIIGSGASTYYADSVKGRFTISRD<br>NSKNTLYLQMNSLRAEDTAVYYCAKGWFGGFNYW<br>GQGTLVTVSSASTKGPSVFPLAPSSKSTSGGTAALGC<br>LVKDYFPEPVTVSWNSGALTSGVHTFPAVLQSSGLY<br>SLSSVVTVPSSSLGTQTYICNVNHKPSNTKVDKKVEP<br>KSCDKTHTCPPCPAPEAAGGPSVFLFPPKPKDTLMIS<br>RTPEVTCVVVDVSHEDPEVKFNWYVDGVEVHNAKT<br>KPREEQYNSTYRVVSVLTVLHQDWLNGKEYKCKVS<br>NKALGAPIEKTISKAKGQPREPQVYTLPPCRDELTKN<br>QVSLWCLVKGFYPSDIAVEWESNGQPENNYKTTPPV<br>LDSDGSFFLYSKLTVDKSRWQQGNVFSCSVMHEALH<br>NHYTQKSLSLSPGGGGGSGGGGSREGPELSPDDPAG<br>LLDLRQGMFAQLVAQNVLLIDGPLSWYSDPGLAGVS<br>LTGGLSYKEDTKELVVAKAGVYYVFFQLELRRVVA<br>GEGSGSVSLALHLQPLRSAAGAAALALTVDLPPASSE<br>ARNSAFGFQGRLLHLSAGQRLGVHLHTEARARHAW<br>QLTQGATVLGLFRVTPEIPAGLPSPRSE |
| SEQ ID NO: 141 | DP47 light chain | See Table 50 |

TABLE 52 cDNA and amino acid sequences of monovalent DP47 untargeted split trimeric human 4-1BB ligand (71-248) Fc (kih) fusion with CH-CL cross and with charged residues (control D).

| SEQ ID NO: | Description | Sequence |
|---|---|---|
| SEQ ID NO: 114 | nucleotide sequence dimeric hu 4-1BBL (71-248) – CL* Fc knob chain | see Table 36 |
| SEQ ID NO: 115 | nucleotide sequence monomeric hu 4-1BBL (71-248) – CH1* | see Table 36 |
| SEQ ID NO: 138 | nucleotide sequence DP47 Fc hole chain | see Table 50 |
| SEQ ID NO: 139 | nucleotide sequence DP47 light chain | see Table 50 |
| SEQ ID NO: 116 | Dimeric hu 4-1BBL (71-248) – CL* Fc knob chain | see Table 37 |
| SEQ ID NO: 117 | Monomeric hu 4-1BBL (71-248) – CH1* | see Table 37 |
| SEQ ID NO: 140 | DP47 Fc hole chain | see Table 50 |
| SEQ ID NO: 141 | DP47 light chain | see Table 50 |

*charged residues

TABLE 53 cDNA and amino acid sequences of monovalent DP47 untargeted split trimeric human 4-1BB ligand (71-248) Fc (kih) fusion with CH-CL cross and without charged residues (control E).

| SEQ ID NO: | Description | Sequence |
|---|---|---|
| SEQ ID NO: 118 | nucleotide sequence dimeric hu 4-1BBL (71-248) – CL Fc knob chain | see Table 38 |
| SEQ ID NO: 119 | nucleotide sequence monomeric hu 4-1BBL (71-248) – CH1 | see Table 38 |
| SEQ ID NO: 138 | nucleotide sequence DP47 Fc hole chain | see Table 50 |
| SEQ ID NO: 139 | nucleotide sequence DP47 light chain | see Table 50 |
| SEQ ID NO: 120 | Dimeric hu 4-1BBL (71-248) – CL Fc knob chain | see Table 39 |
| SEQ ID NO: 121 | Monomeric hu 4-1BBL (71-248) – CH1 | see Table 39 |
| SEQ ID NO: 140 | DP47 Fc hole chain | see Table 50 |
| SEQ ID NO: 141 | DP47 light chain | see Table 50 |

Two control human IgG1 molecules containing PGLALA were prepared. Table 54 shows the cDNA and amino acid sequences of germline control DP47 huIgG1 PGLALA (control F). Table 55 shows the cDNA and amino acid sequences of the anti-TnC (18D4) heavy chain (huIgG1 PGLALA, i.e. control L).

TABLE 54 cDNA and amino acid sequences of germline control DP47 huIgG1 PGLALA (control F)

| SEQ ID NO: | Description | Sequence |
|---|---|---|
| SEQ ID NO: 146 | nucleotide sequence DP47 heavy chain (hu IgG1 PGLALA) | GAGGTGCAATTGTTGGAGTCTGGGGGAGGCTTGGT ACAGCCTGGGGGGTCCCTGAGACTCTCCTGTGCAG CCTCCGGATTCACCTTTAGCAGTTATGCCATGAGCT GGGTCCGCCAGGCTCCAGGGAAGGGGCTGGAGTG GGTCTCAGCTATTAGTGGTAGTGGTGGTAGCACAT ACTACGCAGACTCCGTGAAGGGCCGGTTCACCATC TCCAGAGACAATTCCAAGAACACGCTGTATCTGCA GATGAACAGCCTGAGAGCCGAGGACACGGCCGTA TATTACTGTGCGAAAGGCAGCGGATTTGACTACTG GGGCCAAGGAACCCTGGTCACCGTCTCGAGTGCTA GCACCAAGGGCCCATCGGTCTTCCCCCTGGCACCC TCCTCCAAGAGCACCTCTGGGGGCACAGCGGCCCT GGGCTGCCTGGTCAAGGACTACTTCCCCGAACCGG TGACGGTGTCGTGGAACTCAGGCGCCCTGACCAGC GGCGTGCACACCTTCCCGGCTGTCCTACAGTCCTCA GGACTCTACTCCCTCAGCAGCGTGGTGACCGTGCC CTCCAGCAGCTTGGGCACCCAGACCTACATCTGCA ACGTGAATCACAAGCCCAGCAACACCAAGGTGGA CAAGAAAGTTGAGCCCAAATCTTGTGACAAAACTC ACACATGCCCACCGTGCCCAGCACCTGAAGCTGCA GGGGGACCGTCAGTCTTCCTCTTCCCCCCAAAACC CAAGGACACCCTCATGATCTCCCGGACCCCTGAGG TCACATGCGTGGTGGTGGACGTGAGCCACGAAGAC CCTGAGGTCAAGTTCAACTGGTACGTGGACGGCGT GGAGGTGCATAATGCCAAGACAAAGCCGCGGGAG GAGCAGTACAACAGCACGTACCGTGTGGTCAGCGT CCTCACCGTCCTGCACCAGGACTGGCTGAATGGCA AGGAGTACAAGTGCAAGGTCTCCAACAAAGCCCTC GGCGCCCCCATCGAGAAAACCATCTCCAAAGCCAA AGGGCAGCCCCGAGAACCACAGGTGTACACCCTGC |

TABLE 54-continued

| cDNA and amino acid sequences of germline control DP47 huIgG1 PGLALA (control F) | | |
|---|---|---|
| SEQ ID NO: | Description | Sequence |
| | | CCCCATCCCGGGATGAGCTGACCAAGAACCAGGTC AGCCTGACCTGCCTGGTCAAAGGCTTCTATCCCAG CGACATCGCCGTGGAGTGGGAGAGCAATGGGCAG CCGGAGAACAACTACAAGACCACGCCTCCCGTGCT GGACTCCGACGGCTCCTTCTTCCTCTACAGCAAGCT CACCGTGGACAAGAGCAGGTGGCAGCAGGGGAAC GTCTTCTCATGCTCCGTGATGCATGAGGCTCTGCAC AACCACTACACGCAGAAGAGCCTCTCCCTGTCTCC GGGTAAA |
| SEQ ID NO: 139 | DP47 light chain | see Table 50 |
| SEQ ID NO: 147 | DP47 heavy chain (hu IgG1 PGLALA) | EVQLLESGGGLVQPGGSLRLSCAASGFTFSSYAMSW VRQAPGKGLEWVSAISGSGGSTYYADSVKGRFTISRD NSKNTLYLQMNSLRAEDTAVYYCAKGSGFDYWGQG TLVTVSSASTKGPSVFPLAPSSKSTSGGTAALGCLVK DYFPEPVTVSWNSGALTSGVHTFPAVLQSSGLYSLSS VVTVPSSSLGTQTYICNVNHKPSNTKVDKKVEPKSCD KTHTCPPCPAPEAAGGPSVFLFPPKPKDTLMISRTPEV TCVVVDVSHEDPEVKFNWYVDGVEVHNAKTKPREE QYNSTYRVVSVLTVLHQDWLNGKEYKCKVSNKALG APIEKTISKAKGQPREPQVYTLPPSRDELTKNQVSLTC LVKGFYPSDIAVEWESNGQPENNYKTTPPVLDSDGSF FLYSKLTVDKSRWQQGNVFSCSVMHEALHNHYTQK SLSLSPGK |
| SEQ ID NO: 141 | DP47 light chain | see Table 50 |

TABLE 55

| cDNA and amino acid sequences of anti-TnC(18D4) heavy chain (huIgG1 PGLALA) (control L) | | |
|---|---|---|
| SEQ ID NO: | Description | Sequence |
| SEQ ID NO: 148 | Nucleotide sequence anti-TnC(18D4) heavy chain (huIgG1 PGLALA) | CAGGTGCAATTGGTGCAGTCTGGGGCTGAGGTGAA GAAGCCTGGGTCCTCGGTGAAGGTCTCCTGCAAGG CCTCCGGAGGCACATTCAGCAGCTACGCTATAAGC TGGGTGCGACAGGCCCCTGGACAAGGGCTCGAGTG GATGGGAGGGATCATCCCTATCTTTGGTACAGCAA ACTACGCACAGAAGTTCCAGGGCAGGGTCACCATT ACTGCAGACAAATCCACGAGCACAGCCTACATGGA GCTGAGCAGCCTGAGATCTGAGGACACCGCCGTGT ATTACTGTGCGAAAGGTAACTTCTACGGTGGTCTG GACTACTGGGGCCAAGGGACCACCGTGACCGTCTC CTCAGCTAGCACCAAGGGCCCATCGGTCTTCCCCC TGGCACCCTCCTCCAAGAGCACCTCTGGGGGCACA GCGGCCCTGGGCTGCCTGGTCAAGGACTACTTCCC CGAACCGGTGACGGTGTCGTGGAACTCAGGCGCCC TGACCAGCGGCGTGCACACCTTCCCGGCTGTCCTA CAGTCCTCAGGACTCTACTCCCTCAGCAGCGTGGT GACCGTGCCCTCCAGCAGCTTGGGCACCCAGACCT ACATCTGCAACGTGAATCACAAGCCCAGCAACACC AAGGTGGACAAGAAAGTTGAGCCCAAATCTTGTGA CAAAACTCACACATGCCCACCGTGCCCAGCACCTG AAGCTGCAGGGGGACCGTCAGTCTTCCTCTTCCCC CCAAAACCCAAGGACACCCTCATGATCTCCCGGAC CCCTGAGGTCACATGCGTGGTGGTGGACGTGAGCC ACGAAGACCCTGAGGTCAAGTTCAACTGGTACGTG GACGGCGTGGAGGTGCATAATGCCAAGACAAAGC CGCGGGAGGAGCAGTACAACAGCACGTACCGTGT GGTCAGCGTCCTCACCGTCCTGCACCAGGACTGGC TGAATGGCAAGGAGTACAAGTGCAAGGTCTCCAAC AAAGCCCTCGGCGCCCCCATCGAGAAAACCATCTC CAAAGCCAAAGGGCAGCCCCGAGAACCACAGGTG TACACCCTGCCCCCATCCCGGGATGAGCTGACCAA GAACCAGGTCAGCCTGACCTGCCTGGTCAAAGGCT TCTATCCCAGCGACATCGCCGTGGAGTGGGAGAGC AATGGGCAGCCGGAGAACAACTACAAGACCACGC CTCCCGTGCTGGACTCCGACGGCTCCTTCTTCCTCT ACAGCAAGCTCACCGTGGACAAGAGCAGGTGGCA GCAGGGGAACGTCTTCTCATGCTCCGTGATGCATG |

TABLE 55-continued cDNA and amino acid sequences of anti-TnC(18D4) heavy chain (huIgG1 PGLALA) (control L)

| SEQ ID NO: | Description | Sequence |
|---|---|---|
| | | AGGCTCTGCACAACCACTACACGCAGAAGAGCCTC TCCCTGTCTCCGGGTAAA |
| SEQ ID NO: 73 | Nucleotide sequence 18D4 Light chain | see Table 20 |
| SEQ ID NO: 149 | anti-TnC(18D4) heavy chain (huIgG1 PGLALA) | QVQLVQSGAEVKKPGSSVKVSCKASGGTFSSYAISW VRQAPGQGLEWMGGIIPIFGTANYAQKFQGRVTITAD KSTSTAYMELSSLRSEDTAVYYCAKGNFYGGLDYW GQGTTVTVSSASTKGPSVFPLAPSSKSTSGGTAALGC LVKDYFPEPVTVSWNSGALTSGVHTFPAVLQSSGLYS LSSVVTVPSSSLGTQTYICNVNHKPSNTKVDKKVEPK SCDKTHTCPPCPAPEAAGGPSVFLFPPKPKDTLMISRT PEVTCVVVDVSHEDPEVKFNWYVDGVEVHNAKTKP REEQYNSTYRVVSVLTVLHQDWLNGKEYKCKVSNK ALGAPIEKTISKAKGQPREPQVYTLPPSRDELTKNQVS LTCLVKGFYPSDIAVEWESNGQPENNYKTTPPVLDSD GSFFLYSKLTVDKSRWQQGNVFSCSVMHEALHNHYT QKSLSLSPGK |
| SEQ ID NO: 77 | 18D4 Light chain | see Table 21 |

Example 9

Production of TnC-Targeted Split Trimeric C-Terminal 4-1BB Ligand Fc Fusion and their Controls The targeted and untargeted trimeric 4-1BB ligand C-terminal Fc (kih) fusion encoding sequences were cloned into a plasmid vector, which drives expression of the insert from an MPSV promoter and contains a synthetic polyA sequence located at the 3' end of the CDS. In addition, the vector contains an EBV OriP sequence for episomal maintenance of the plasmid. The split trimeric 4-1BB ligand Fc (kih) fusion molecules were produced by co-transfecting HEK293-EBNA cells with the mammalian expression vectors using polyethylenimine. The cells were transfected with the corresponding expression vectors. For constructs 6.1, 6.2, 6.4, 6.6 and it's control B, D and E, at a 1:1:1:1 ratio ("vector Fc hole chain":"vector PD1 light chain":"vector Fc knob chain":"vector 4-1BBL light chain"). For constructs 6.3, 6.6, 6.11, 6.12, 6.13, 6.14 and it's control C, at a 1:1:1 ratio ("vector Fc hole chain":"vector Fc knob chain":"vector anti-PD1 light chain"). Human IgGs, used as control in the assay, were produced as for the bispecific construct (for transfection only a vector for light and a vector for heavy chain were used at a 1:1 ratio).

For production in 500 mL shake flasks, 300 million HEK293 EBNA cells were seeded 24 hours before transfection. For transfection cells were centrifuged for 10 minutes at 210×g, and the supernatant was replaced by 20 mL pre-warmed CD CHO medium. Expression vectors (200 μg of total DNA) were mixed in 20 mL CD CHO medium. After addition of 540 μL PEI, the solution was vortexed for 15 seconds and incubated for 10 minutes at room temperature. Afterwards, cells were mixed with the DNA/PEI solution, transferred to a 500 mL shake flask and incubated for 3 hours at 37° C. in an incubator with a 5% $CO_2$ atmosphere. After the incubation, 160 mL of Excell medium supplemented with 6 mM L-Glutamine, 5 g/L PEPSOY and 1.2 mM valproic acid was added and cells were cultured for 24 hours. One day after transfection 12% Feed were added. After culturing for 7 days, the supernatant was collected by centrifugation for 30-40 minutes at least 400×g. The solution was sterile filtered (0.22 μm filter), supplemented with sodium azide to a final concentration of 0.01% (w/v), and kept at 4° C.

Secreted proteins were purified from cell culture supernatants by affinity chromatography using Protein A, followed by size exclusion chromatography. For affinity chromatography, the supernatant was loaded on a MabSelect Sure column (CV=5-15 mL, resin from GE Healthcare) equilibrated with Sodium Phosphate (20 mM), Sodium Citrate (20 mM) buffer (pH 7.5). Unbound protein was removed by washing with at least 6 column volumes of the same buffer. The bound protein was eluted using either a linear gradient (20 CV) or a step elution (8 CV) with 20 mM sodium citrate, 100 mM Sodium chloride, 100 mM Glycine buffer (pH 2.5). For the linear gradient an additional 4 column volumes step elution was applied.

The pH of collected fractions was adjusted by adding 1/10 (v/v) of 0.5M sodium phosphate, pH8.0. The protein was concentrated prior to loading on a HiLoad Superdex 200 column (GE Healthcare) equilibrated with 20 mM Histidine, 140 mM sodium chloride, 0.01% (v/v) Tween20 solution of pH 6.0.

The protein concentration was determined by measuring the optical density (OD) at 280 nm, using a molar extinction coefficient calculated on the basis of the amino acid sequence. Purity and molecular weight of the targeted trimeric 4-1BB ligand Fc (kih) fusion was analyzed by SDS-PAGE in the presence and absence of a reducing agent (5 mM 1,4-dithiotreitol) and staining with Coomassie SimpleBlue™ SafeStain (Invitrogen USA) or CE-SDS using Caliper LabChip GXII (Perkin Elmer). The aggregate content of samples was analyzed using a TSKgel G3000 SW XL analytical size-exclusion column (Tosoh) equilibrated in 25 mM K2HPO4, 125 mM NaCl, 200 mM L-Arginine Monohydrocloride, 0.02% (w/v) NaN3, pH 6.7 running buffer at 25° C.

Table 56 summarizes the yield and final monomer content of the TnC targeted split trimeric 4-1BB ligand Fc (kih) fusion.

TABLE 56

Biochemical analysis of TnC targeted split trimeric 4-1BB ligand Fc (kih) fusion

| Construct | Monomer [%] (SEC) | Yield [mg/l] |
|---|---|---|
| monovalent TnC(18D4) targeted split trimeric 4-1BB ligand (71-248) Fc (kih) fusion containing CH-CL cross without charged residues (construct 6.5) | 91.5 | 3.7 |
| bivalent TnC(18D4) targeted split trimeric 4-1BB ligand (71-248) Fc (kih) fusion (construct 6.6) | 97 | 9.9 |

Example 10

Simultaneous Binding of TnC Targeted 4-1BB Split Trimeric Ligand Fc Fusion Antigen Binding Molecule by Surface Plasmon Resonance The capacity of binding simultaneously human 4-1BB Fc(kih) and human TnC was assessed by surface plasmon resonance (SPR). All SPR experiments were performed on a Biacore T200 at 25° C. with HBS-EP as running buffer (0.01 M HEPES pH 7.4, 0.15 M NaCl, 3 mM EDTA, 0.005% Surfactant P20, Biacore, Freiburg/Germany).

Figure 20A:
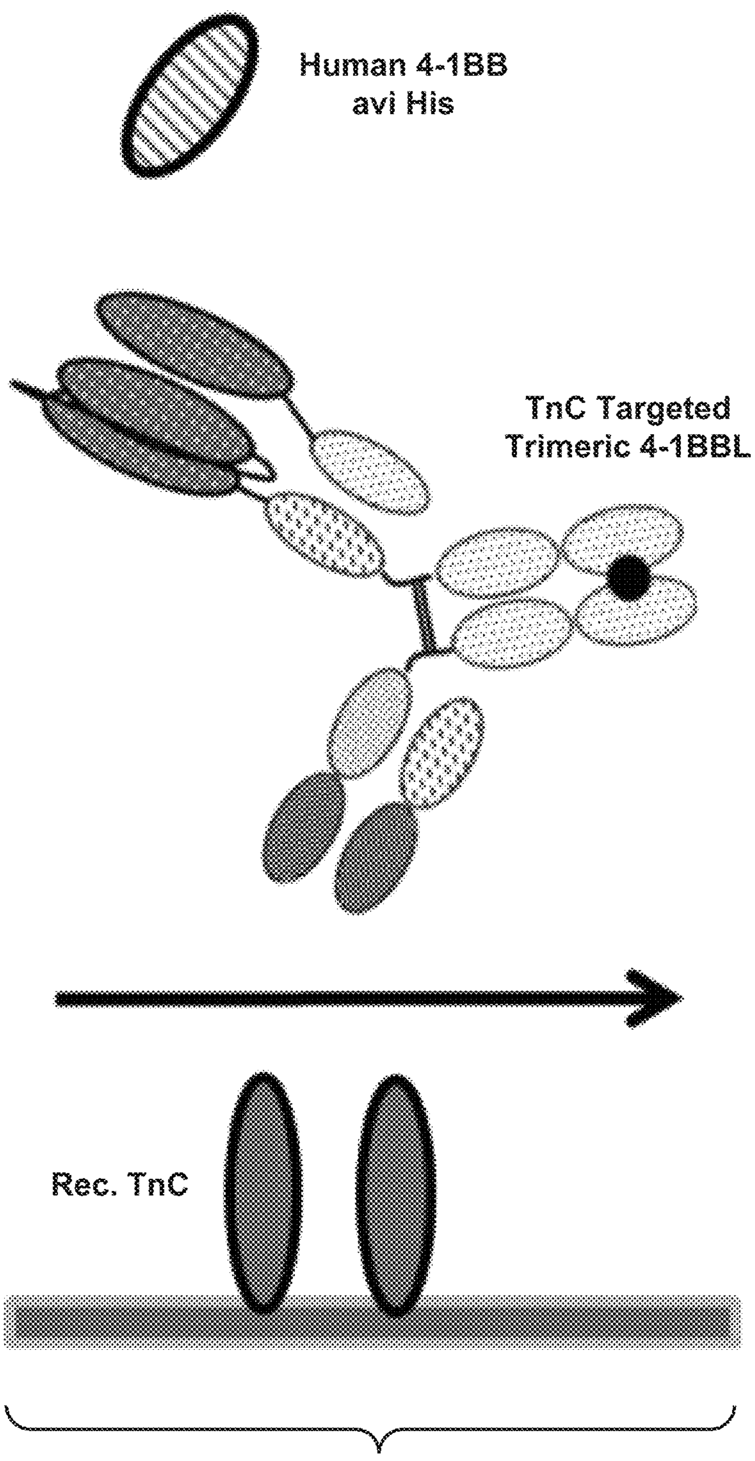
FIGS. 20A, 20B, and 20C relate to simultaneous binding of targeted split trimeric C-terminal 4-1BB ligand (71-248) Fc (kih) fusion molecules.
Figure 20B:
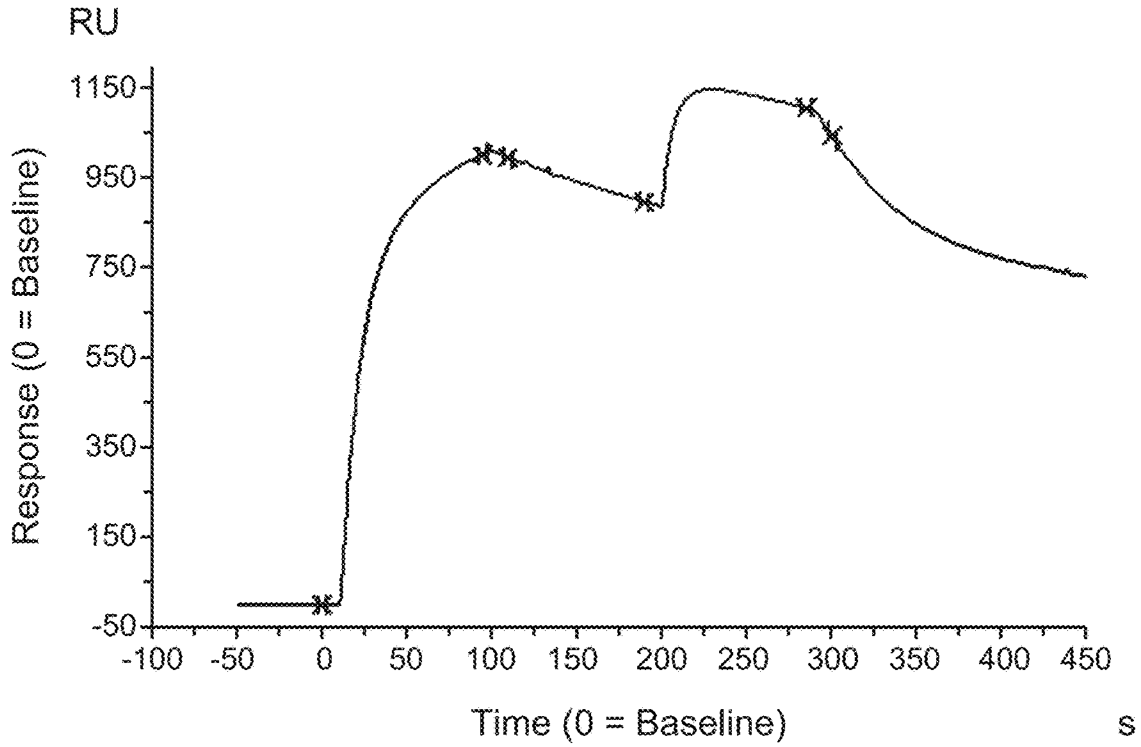
Figure 20C:
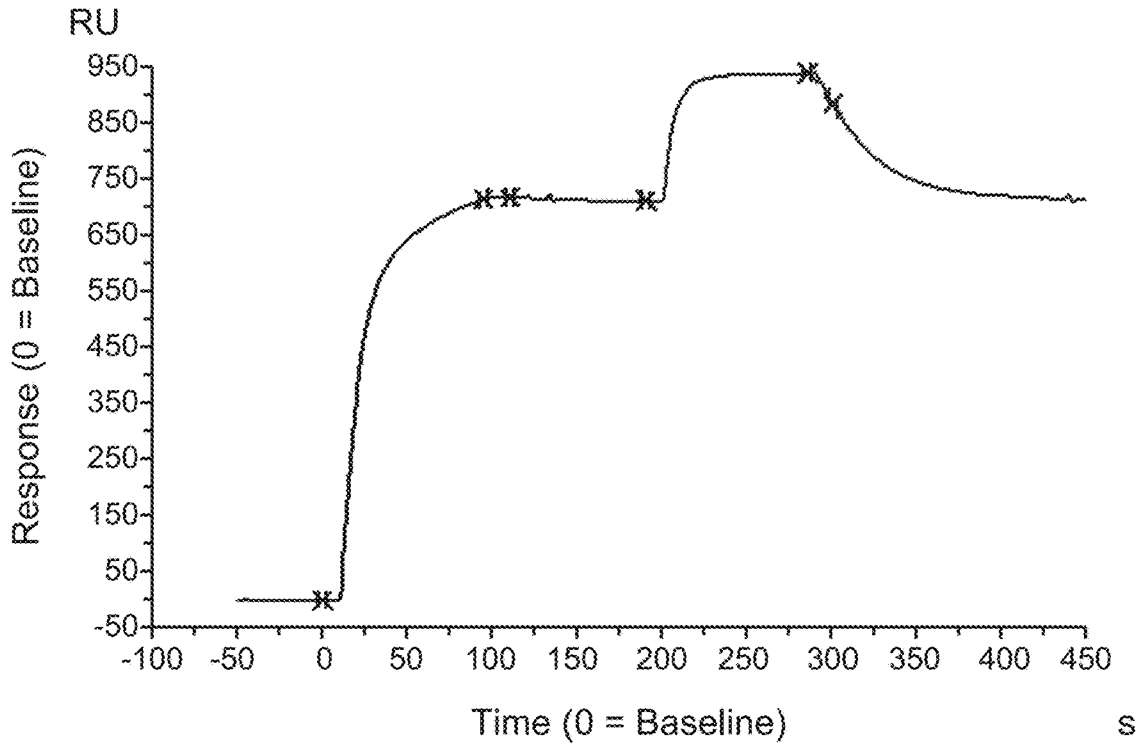
Figure 21A:
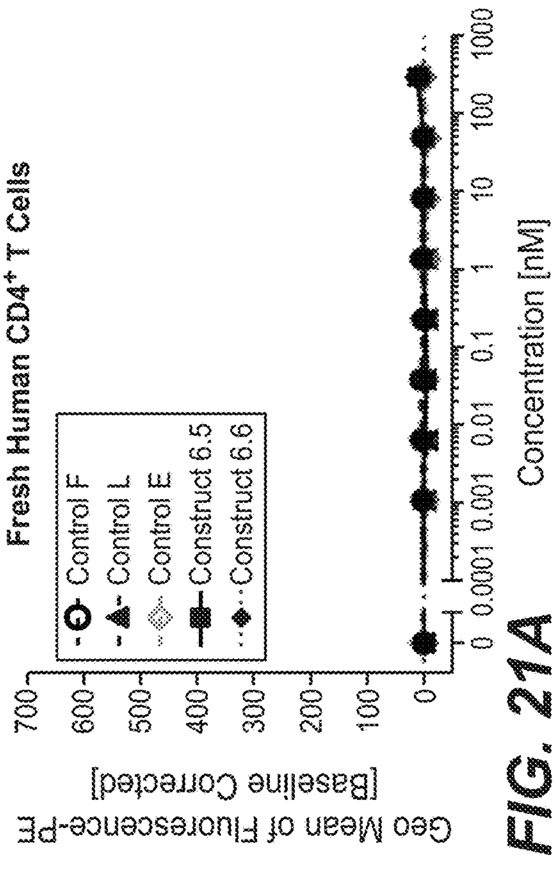
FIGS. 21A, 21B, 21C, and 21D show binding of TnC-targeted 4-1BB split trimeric ligand Fc fusion antigen binding molecules to freshly isolated PBMCs. Shown is the geo mean of fluorescence intensity of PE-conjugated secondary detection antibody (y-axis) versus the concentration of tested constructs (x-axis). Binding was monitored on fresh human CD45+CD3+ CD8neg CD4+ T cells (FIG. 21A), fresh human CD45+ CD3+ CD4neg CD8+ T cells (FIG. 21), fresh human CD45+ CD3neg CD19+ B cells (FIG. 21C) and CD45+ CD3+ CD4neg CD8neg γδT cells (FIG. 21D).
Figure 21B:
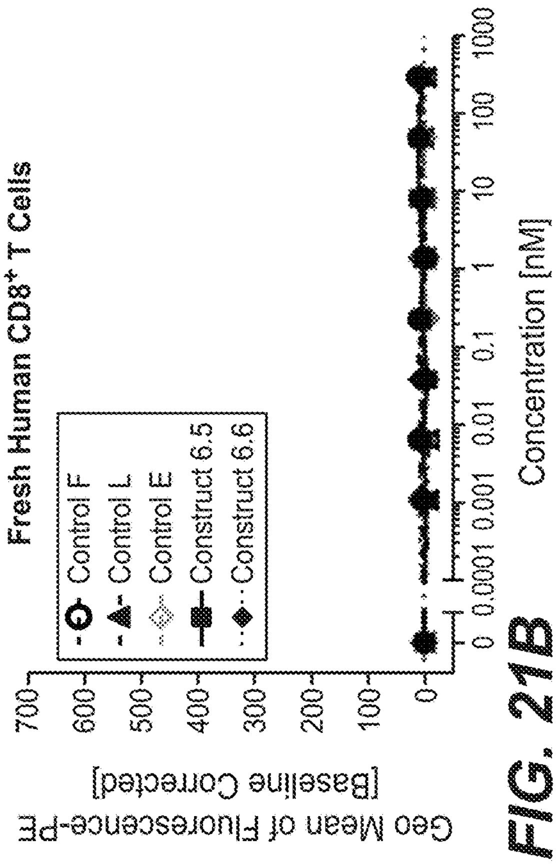
Figure 21C:
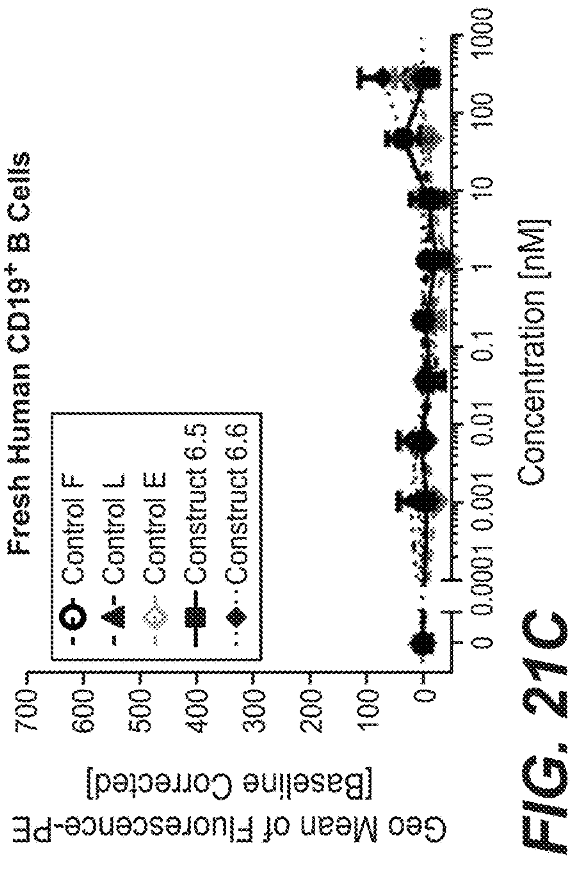
Figure 21D:
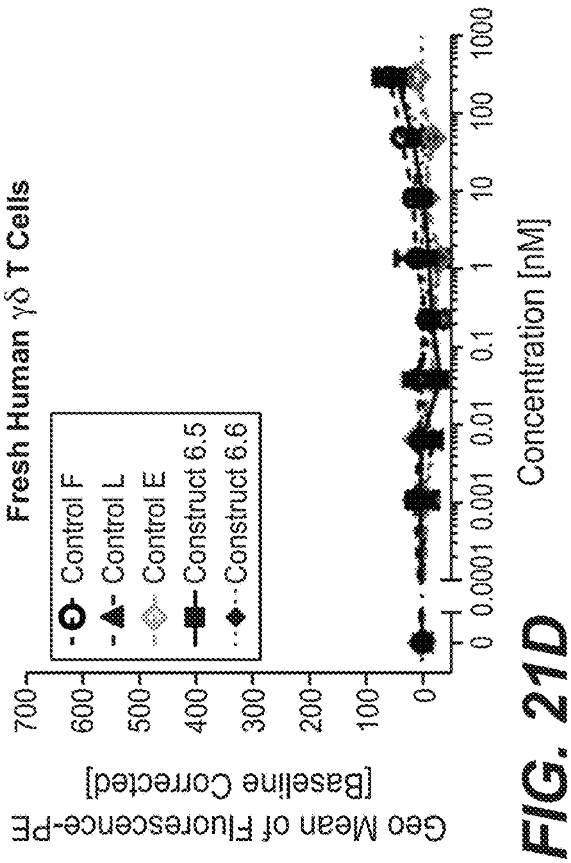
Figure 22A:
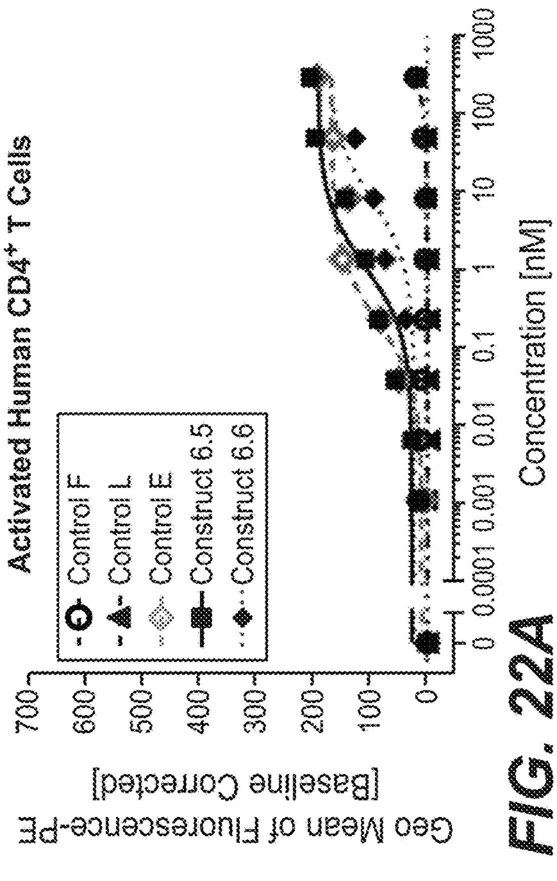
FIGS. 22A, 22B, 22C, and 22D show binding of TnC-targeted 4-1BB split trimeric ligand Fc fusion antigen binding molecules to activated PBMCs. Shown is the geo mean of fluorescence intensity of PE-conjugated secondary detection antibody (y-axis) versus the concentration of tested constructs (x-axis). Binding was monitored on activated human CD45+ CD3+ CD8neg CD4+ T cells (FIG. 22A), activated human CD45+ CD3+ CD4neg CD8+ T cells (FIG. 22B), CD45+ CD3neg CD19+ B cells (FIG. 22C) and activated human CD45+ CD3+ CD4neg CD8neg γδT cells (FIG. 22D).
Figure 22B:
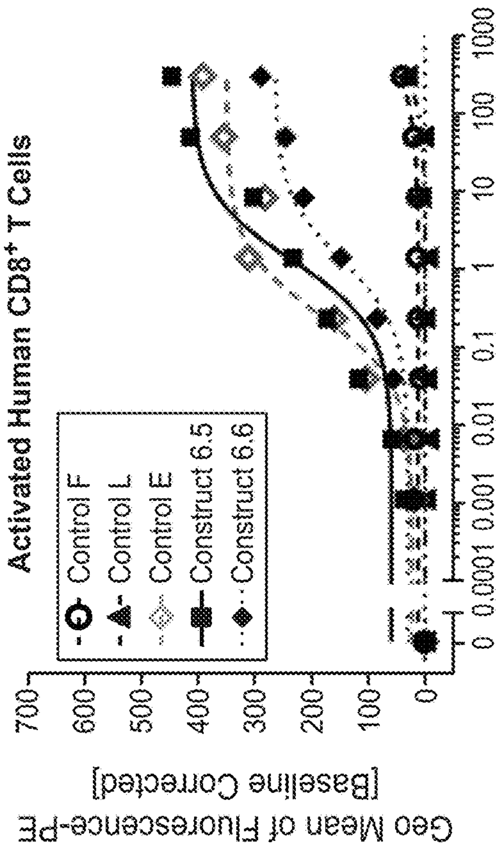
Figure 22C:
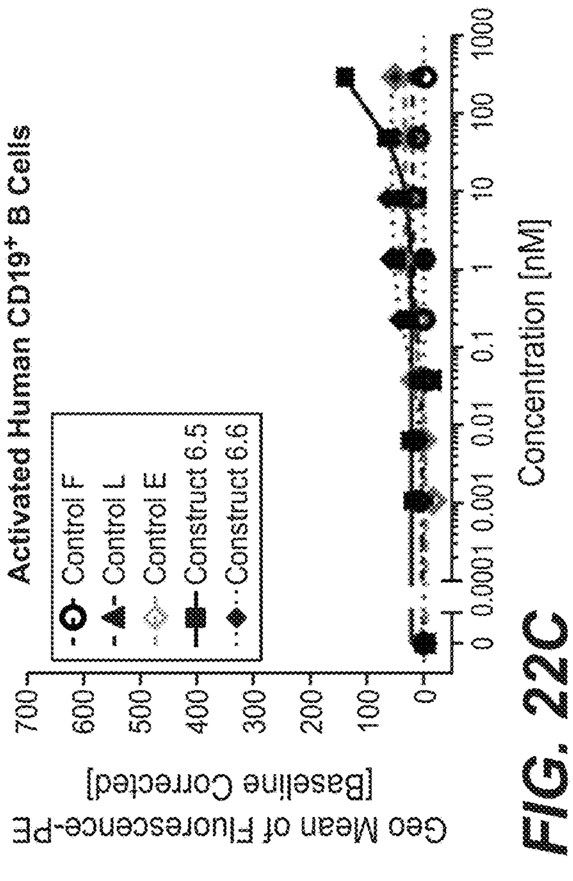
Figure 22D:
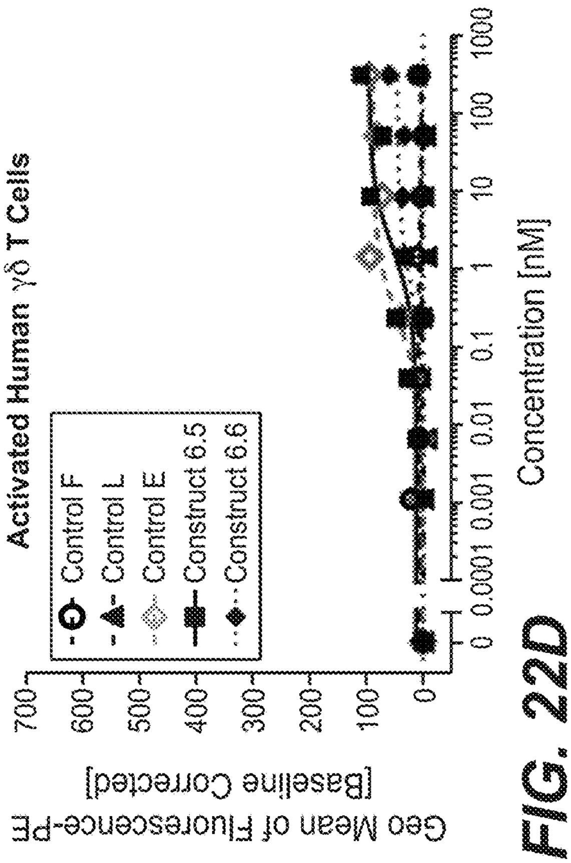

Biotinylated TnC-antigen was directly coupled to a flow cell of a streptavidin (SA) sensor chip. Immobilization levels up to 500 resonance units (RU) were used. The TnC-targeted 4-1BB ligand Fc (kih) fusion molecules were passed at a concentration range of 100 nM with a flow of 30 μL/minute through the flow cells over 90 seconds and dissociation was set to zero sec. Human 4-1BB avi His was injected as second analyte with a flow of 30 μL/minute through the flow cells over 90 seconds at a concentration of 1000 nM (FIGS. 20A and 20B). The dissociation was monitored for 120 sec. Bulk refractive index differences were corrected for by subtracting the response obtained in a reference flow cell, where no protein was immobilized. All bispecific constructs could bind simultaneously human 4-1BB and human TnC (FIGS. 20A and 20B).

Example 11

Affinity Determination of Monovalent TnC Targeted 4-1BB Split Trimeric Ligand Fc Fusion Antigen Binding Molecule by Surface Plasmon Resonance The binding of TnC-targeted 4-1BB ligand trimer-containing Fc (kih) fusion antigen binding molecules to recombinant TnC was assessed by surface plasmon resonance (SPR). All SPR experiments were performed on a Biacore T100 at 25° C. with HBS-EP as a running buffer (0.01 M HEPES pH 7.4, 0.15 M NaCl, 3 mM EDTA, 0.005% Surfactant P20, Biacore, Freiburg/Germany).

For affinity measurement, direct coupling of around 500 resonance units (RU) of recombinant human, cynomolgus and murine TnC was performed on a CM5 chip at pH 5.0 using the standard amine coupling kit (GE Healthcare). A dilution series (0.05-50 nM) of TnC-targeted 4-1BB ligand trimer-containing Fc (kih) fusion antigen binding molecule was passed on both flow cells at 30 μl/min for 120 sec to record the association phase. The dissociation phase was monitored for 180 s and triggered by switching from the sample solution to HBS-EP. The chip surface was regenerated after every cycle using a double injection of 60 sec 10 mM Glycine-HCl pH 2.1. Bulk refractive index differences were corrected for by subtracting the response obtained on reference flow cell 1. For the interaction between the TnC-targeted 4-1BB ligand trimer-containing Fc (kih) fusion antigen binding molecule and recombinant TnC, the affinity constants were derived from the rate constants by fitting to a 1:1 Langmuir binding curve using the Biaeval software (GE Healthcare) (Table 57).

TABLE 57

Fittings to 1:1 Langmuir binding and Affinity constants

| Ligand | Analyte | ka (1/Ms) | kd (1/s) | KD (M) |
|---|---|---|---|---|
| monovalent TnC(18D4) targeted split trimeric 4-1BB ligand (71-248) Fc (kih) fusion containing CH-CL cross without charged residues (construct 6.5) | Human TnC | 2.9E+06 | 2.0E−03 | 6.8E−10 |
| | Cynomolgus TnC | 1.5E+06 | 6.9E−03 | 4.7E−09 |
| | Murine TnC | 5.9E+05 | 2.9E−03 | 5.0E−09 |
| bivalent TnC(18D4) targeted split trimeric 4-1BB ligand (71-248) Fc (kih) fusion (construct 6.6) | Human TnC | 5.3E+06 | 1.1E−04 | 2.1E−11 |
| | Cynomolgus TnC | 4.1E+06 | 1.1E−04 | 2.7E−11 |
| | Murine TnC | 1.2E+06 | 3.0E−04 | 2.5E−10 |

Example 12

Functional Characterization of TnC-Targeted 4-1BB Split Trimeric Ligand Fc Fusion Antigen Binding Molecules A) Binding on Fresh and Activated Human PBMCs of TnC-Targeted Split Trimeric 4-1BB Ligand Buffy coats were obtained from the Zurich blood donation center. To isolate fresh peripheral blood mononuclear cells (PBMCs) the buffy coat was diluted with the same volume of DPBS (Gibco by Life Technologies, Cat. No. 14190 326). 50 mL polypropylene centrifuge tubes (TPP, Cat.-No. 91050) were supplied with 15 mL Histopaque 1077 (SIGMA Life Science, Cat.-No. 10771, polysucrose and sodium diatrizoate, adjusted to a density of 1.077 g/mL) and the diluted buffy coat contents were layered above the Histopaque 1077. The tubes were centrifuged for 30 min at 450×g. PBMCs were then collected from the interface, washed three times with DPBS and resuspended in T cell medium consisting of RPMI 1640 medium (Gibco by Life Technology, Cat. No. 42401-042) supplied with 10% (v/v) Fetal Bovine Serum (FBS, US-origin, PAN biotech, P30-2009, Lot P150307GI, gamma irradiated *mycoplasma* free, heat inactivated 35 min 56° C.), 1% (v/v) GlutaMAX I (GIBCO by Life Technologies, Cat. No. 35050 038), 1 mM Sodium-Pyruvat (SIGMA, Cat. No. S8636), 1% (v/v) MEM non-essential amino acids (SIGMA, Cat.-No. M7145) and 50 μM β-Mercaptoethanol (SIGMA, M3148).

PBMCs were used directly after isolation (binding on fresh human PBMCs) or they were stimulated to induce 4-1BB expression on the cell surface of T cells (binding on activated human PBMCs). To induce 4-1BB upregulation on human T cells, PBMCs were cultured for 3 days in RPMI 1640 supplied with 10% FBS, 1 mM Sodium-Pyruvat (SIGMA, Cat.-No. S8636), 1% Gluta-MAX-I, 1% MEM-non essential amino acid Solution (SIGMA, Cat.-No. M7145), 50 μM beta-Mercaptoethanol (Sigma M3148), 200 U/mL Proleukin (Novartis Pharma Schweiz AG) and 2 μg/mL PHA-L (SIGMA, Cat.-No. L2769) to a final concentration of $1\times10^6$ cells/mL. After pre-activation cells were harvested and resuspended in RPMI 1640 supplied with 10% PBS, 1 mM Sodium-Pyruvat (SIGMA, Cat.-No. S8636), 1% Gluta-MAX-I, 1% MEM-non essential amino acid solution (SIGMA, Cat.-No. M7145), 50 μM beta-Mercaptoethanol (Sigma M3148) and seeded in 6-well tissue culture plates (TTP, Cat.-No. 92006), which had been coated overnight at 4° C. with 10 μg/mL anti-human CD3 (clone OKT3, Mouse IgG2a, BioLegend, Cat.-No. 317315) and 2 ug/mL anti-human CD28 (clone CD28.2, Mouse IgG1, BioLegend, Cat.-No. 302923). Cells were further incubated for 3 days at 37° C. and 5% $CO_2$.

For binding assay $0.1\times10^6$ fresh or activated PBMCs were added to each well of round-bottom suspension cell 96-well plates (greiner bio-one, cellstar, Cat. No. 650185). Plates were centrifuged 5 minutes with 350×g and at 4° C. and supernatant were discarded. Afterwards cells were stained in 100 μL/well DPBS containing 1:5000 diluted fixable viability dye eF660 (eBioscience, Cat.-No. 65-0864-18) for 30 minutes at 4° C. in the dark. Cells were washed once with 200 μL cold DPBS buffer. Next, 50 μL/well of 4° C. cold FACS buffer (DPBS supplied with 2% FBS, 5 mM EDTA pH8 (Amresco, Cat. No. E177) and 7.5 mM Sodium azide (Sigma-Aldrich, Cat.-No. S2002)) containing titrated concentrations of construct 6.5 and construct 6.6 and as controls control E, control F and control L were added and cells were incubated for 60 minutes at 4° C. and washed three times with 200 μL/well 4° C. FACS buffer. Cells were further resuspended in 50 μL/well of 4° C. cold FACS buffer containing 0.67 μg/mL anti-human CD45-AF488 (clone HI30, mouse igG1k, BioLegend, Cat.-No. 304019), 0.33 μg/mL anti-human CD8a-B V510 (clone SK1, mouse IgG1k, BioLegend, Cat.-No. 344732), 0.23 μg/mL anti-human CD4-BV421 (clone OKT4, mouse IgG2bκ, BioLegend, Cat.-No. 317434), 0.67 μg/mL anti-human CD3-PerCP-Cy5.5 (clone UCHT1, mouse IgG1k, BioLegend, Cat.-No. 300430), 0.67 μg/mL anti-human CD19-PE/Cy7 (clone HIB19, mouse IgG1k, BioLegend, Cat.-No. 302216), 5 μg/mL PE-conjugated AffiniPure anti-human IgG F(ab')2-fragment-specific goat F(ab')2 fragment (Jackson ImmunoResearch, Cat. No. 109 116 098) and incubated for 30 min at 4° C. Cells were washed twice with 200 μL/well 4° C. FACS buffer and then fixed with DPBS supplied with 1% Formaldehyde (Sigma, HT501320-9.5L). Cells were resuspended in 100 μL/well FACS-buffer and acquired using the MACS Quant Analyzer 10 (Miltenyi Biotech). Data was analyzed using FlowJo V10 (FlowJo, LLC) and GraphPad Prism 6.04 (GraphPad Software, Inc).

Gates were set on living CD45+ CD3+ CD4+ T cells, CD45+ CD3+ CD8+ T cells, CD45+ CD3+ CD4neg CD8neg γδ T cells and CD45+ CD3neg CD19+ B cells and geo means of fluorescence intensity of PE-conjugated AffiniPure anti-human IgG IgG Fcγ-fragment-specific goat F(ab')2 fragment were blotted against the titrated concentration of TnC-targeted or DP47-untargeted 4-1BB split trimeric ligand Fc fusion antigen binding molecules and their controls. As shown in FIGS. 21A, 21B, 21C, and 21D, none of the tested TnC-targeted split trimeric 4-1BB ligand fusion molecules or their controls bind to cells of freshly isolated PBMC.

As shown in FIGS. 22A, 22B, 22C, and 22D, after activation living CD45+ CD3+CD4+ T cells, CD45+ CD3+ CD8+ T cells and CD45+ CD3+ CD4neg CD8neg γδ T cells express human 4-1BB. The anti-TnC huIgG1 P329G LALA control L and the DP47 huIgG1 P329G LALA control F did not bind to the activated human PBMCs. All molecules containing a 4-1BB split trimeric ligand as construct 6.5, construct 6.6 and control E bind to activated CD8+ T cells, CD4+ T cells and γδ T cells. In Table 58 the EC50 values are summarized for the binding curves to activated human PBMCs.

TABLE 58

EC50 values of binding curves to activated human PBMCs

| | Control E | construct 6.5 | construct 6.6 |
|---|---|---|---|
| EC50 [nM] on activated CD4 T cells | 0.23 | 1.11 | 8.56 |
| EC50 [nM] on activated CD8 T cells | 0.26 | 1.28 | 1.29 |
| EC50 [nM] on activated γδ T cells | 0.23 | 1.79 | 0.80 |

B) Binding of Human TnC Expressing Tumor Cells

For binding assays on TnC expressing tumor cells the human glioblastoma cell line U87-MG (ATCC HTB-14) was used.

$0.2\times10^6$ tumor cells resuspended in cold DPBS (Gibco by Life Technologies, Cat. No. 14190 326) were added to each well of a round-bottom suspension cell 96-well plates (greiner bio-one, cellstar, Cat. No. 650185). Cells were washed once with 200 μL DPBS. Cells were resuspended in 100 μL/well of 4° C. cold DPBS buffer containing 1:5000 diluted Fixable Viability Dye eFluor 660 (eBioscience, Cat. No. 65-0864-18) and plates were incubated for 30 minutes at 4° C. Cells were washed once with 200 μL/well 4° C. cold DPBS buffer and resuspended in 50 μL/well of 4° C. cold FACS buffer (DPBS supplied with 2% FBS, 5 mM EDTA pH8 (Amresco, Cat. No. E177) and 7.5 mM Sodium azide (Sigma-Aldrich S2002)) containing TnC-targeted 4-1BB split trimeric ligand Fc fusion antigen binding molecules or their controls at a series of concentrations, followed by incubation for 1 hour at 4° C. After extensive washing, cells were further stained with 50 μL/well of 4° C. cold FACS buffer containing 5 μg/mL PE-conjugated AffiniPure anti-human IgG F(ab')2-fragment-specific goat F(ab')2 fragment (Jackson ImmunoResearch, Cat. No. 109 116 098) for 30 minutes at 4° C. Cells were washed twice with 200 μL/well 4° C. FACS buffer and cells were fixed in 50 μL/well DPBS containing 1% Formaldehyde (Sigma, HT501320-9.5L). Cells were resuspended in 100 μL/well FACS-buffer and acquired using the MACS Quant Analyzer 10 (Miltenyi Biotech). Data was analyzed using FlowJo V10 (FlowJo, LLC) and GraphPad Prism 6.04 (GraphPad Software, Inc).

Figure 23:
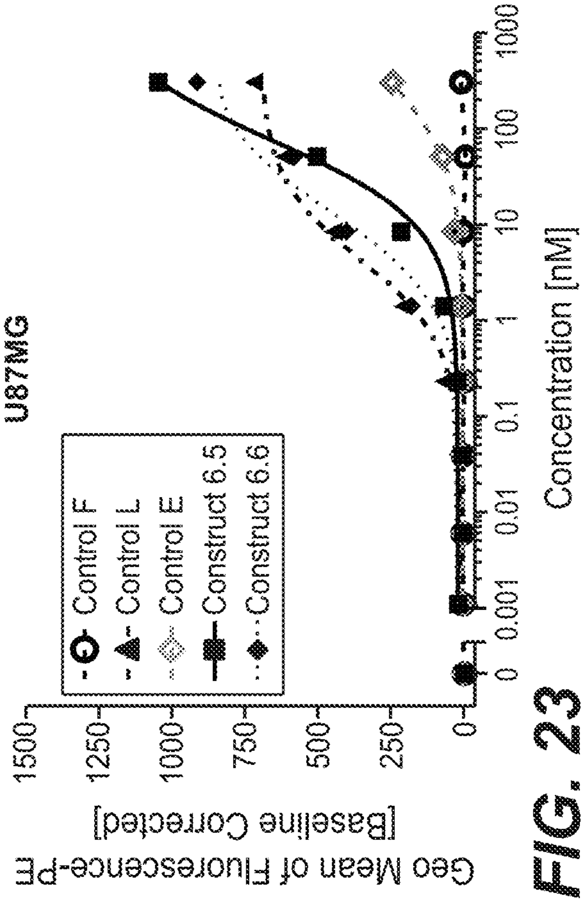
FIG. 23 shows binding of TnC-targeted or untargeted split trimeric human 4-1BB ligand Fc (kih) fusion molecules to human-TnC expressing U87-MG tumor cell line. Binding was detected with R-Phycoerythrin-fluorochrome conjugated anti-human IgG Fcγ-specific goat IgG F(ab')2 fragment and the geo mean measured by flow cytometry is shown on the y-axis. On the x-axis the used concentration of TnC-targeted 4-1BB split trimeric ligand Fc fusion antigen binding molecules and their controls are shown.
Figure 24:
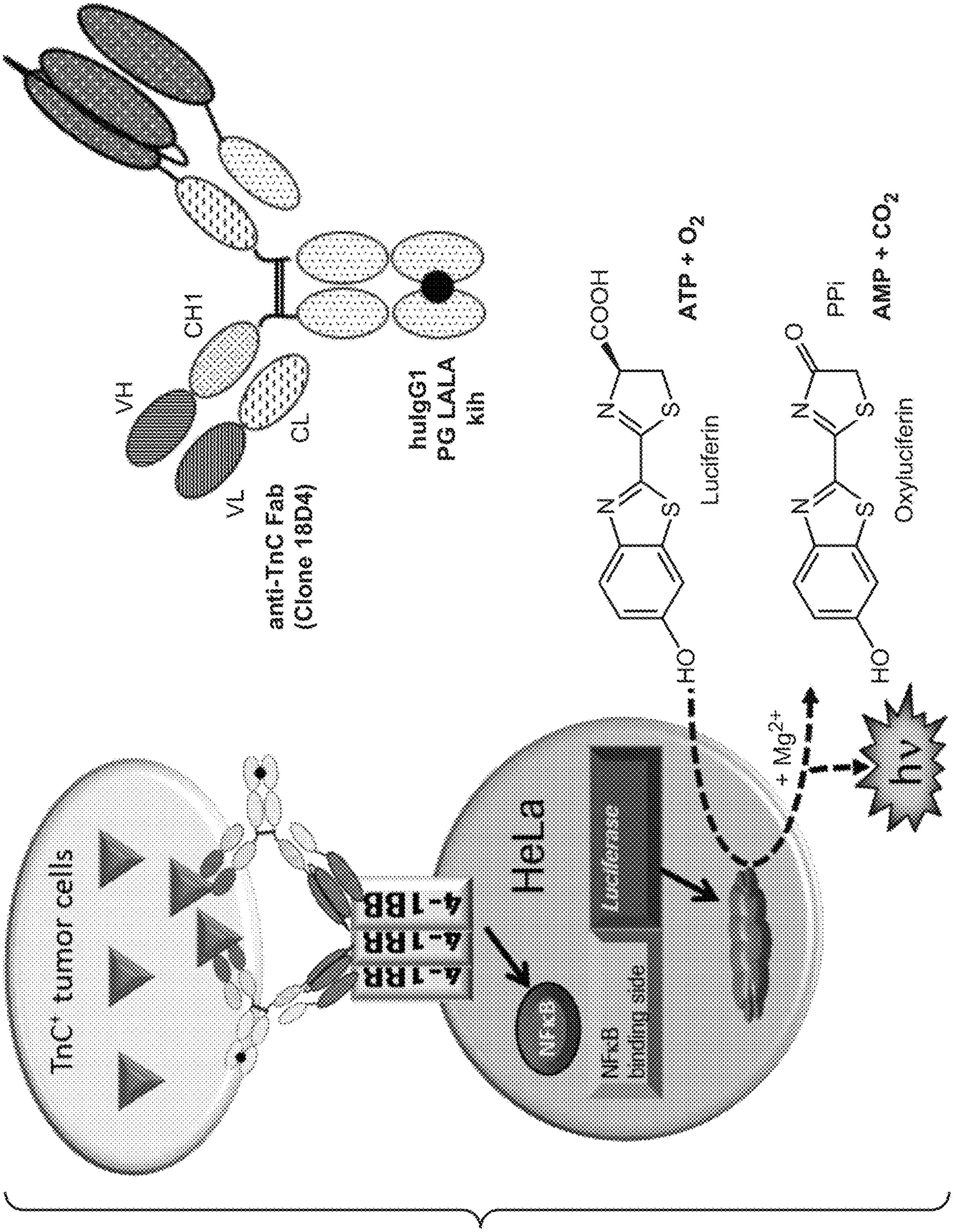
FIG. 24 shows an illustration of an activation assay set up with human 4-1BB expressing HeLa reporter cell line. A crosslinking of 4-1BB, expressed on the reporter cells, induces NFκB activation and NFκB-mediated Luciferase expression. After lysis of the cells, luciferase can catalyze the oxidation of Luciferin to Oxyluciferin. This chemical reaction correlates positively with the strength of NFκB-mediated luciferase expression and can be measured by the strength of light emission (units of released light).
Figure 25A:
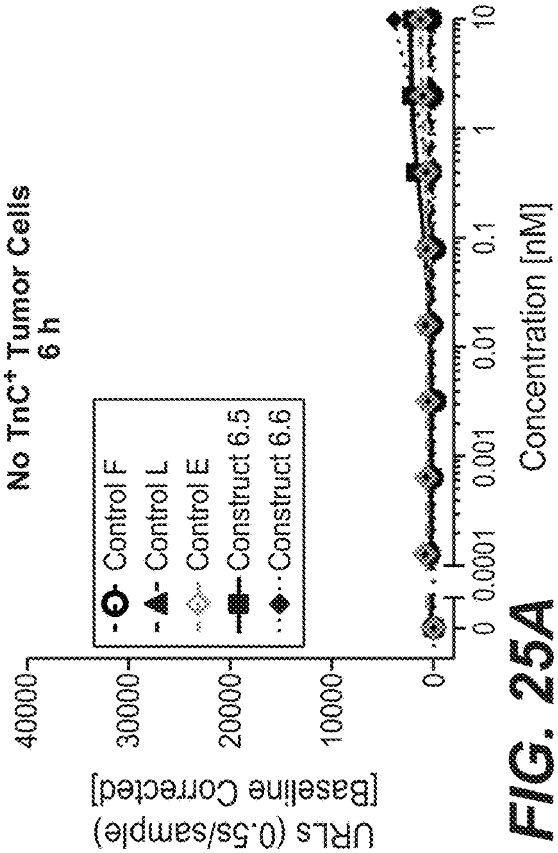
FIGS. 25A and 25B show the NFκB-activation-induced luciferase activity. Units of released light (URL) are measured for 0.5 s/well and plotted against the used concentration of split trimeric 4-1BB ligand containing fusion molecules and controls. Human 4-1BB-expressing HeLa-reporter cells were incubated for 6 h in the absence (FIG. 25A) or presence of crosslinking via human-TnC expressing U87MG cells (FIG. 25B). The cell ratio of 4-1BB-expressing HeLa reporter cell to TnC-expressing tumor cells was 1:5.
Figure 25B:
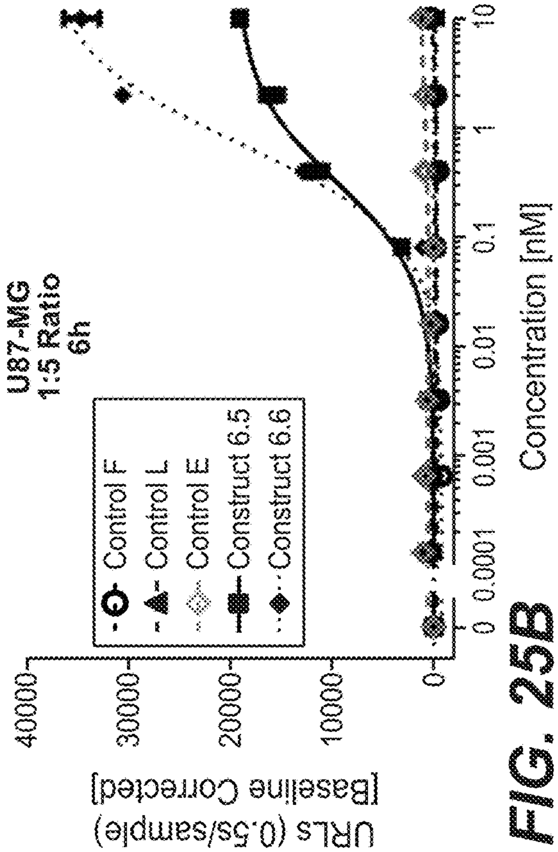
Figure 26:
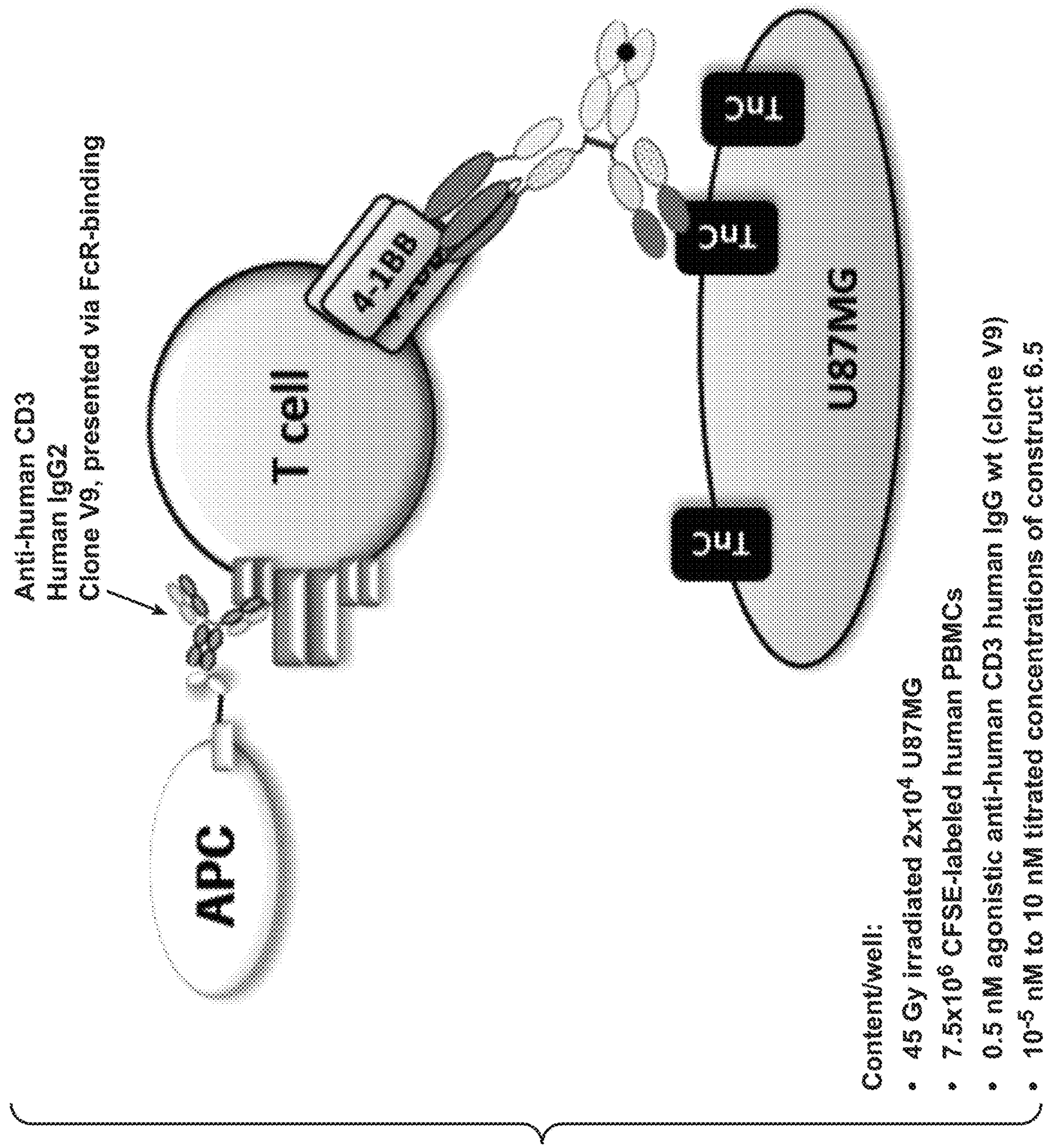
FIG. 26 shows an illustration of the Schematic set-up of the human PBMC activation in the presence of TnC-expressing U87MG, agonistic anti-human CD3 antibody and bispecific anti-TnC split trimeric 4-1BBL fusion molecule construct 6.5.

Gates were set on living tumor cells and geo means of fluorescence intensity of PE-conjugated AffiniPure anti-human IgG IgG Fcγ-fragment-specific goat F(ab')2 fragment were blotted against the titrated concentration of TnC-targeted 4-1BB split trimeric ligand Fc fusion antigen binding molecules or their controls. As shown in FIG. 23 only the TnC-targeted molecules construct 6.5, construct 6.6 and control L bound to TnC-expressing U87-MG whereas the not TnC-targeted controls control E and control F did not bind to the tumor cells. In Table 59 the EC50 values of the curves are listed.

TABLE 59

EC50 values of binding curves to TnC-expressing tumor cells

| | Construct 6.5 | Construct 6.6 | Control L |
|---|---|---|---|
| EC50 [nM] on U87MG | 73.99 | 12.75 | 4.24 |

C) Biological Activity: NF-κB Activation of Human 4-1BB Expressing HeLa Reporter Cell Line Generation of HeLa Reporter Cells Expressing Human 4-1BB and NF-κB-Luciferase The human-papilloma-virus-18-induced cervix carcinoma cell line HeLa (ATCC CCL-2) was transduced with a plasmid based on the expression vector pETR10829, which contains the sequence of human 4-1BB (Uniprot accession Q07011) under control of a CMV-promoter and a puromycin resistance gene. Cells were cultured in DMEM-medium (Gibco by Life Technologies Cat. No. 42430-025) supplied with 10% Fetal Bovine Serum (FBS, GIBCO by Life Technologies, Cat. No. 16000-044, Lot. No. 941273, gamma-irradiated *mycoplasma* free, heat inactivated at 56° C. for 35 minutes), 1% GlutaMAX-I (GIBCO by Life Technologies, Cat.-No. 35050-038) and 3 μg/mL Puromycin (InvivoGen, Cat-No. ant-pr). 4-1BB-transduced HeLa cells were tested for 4-1BB expression by flow cytometry: 0.2×$10^6$ living cells were resuspended in 100 μL FACS buffer (DPBS supplied with 2% FBS, 5 mM EDTA pH 8 (Amresco, Cat. No. E177) and 7.5 mM Sodium Azide (Sigma-Aldrich, Cat. No. S2002)) containing 0.1 μg PerCP/Cy5.5 conjugated anti-human 4-1BB mouse IgG1K clone 4B4-1 (BioLegend Cat. No. 309814) or its isotype control (PerCP/Cy5.5 conjugated mouse IgG1K isotype control antibody clone MOPC 21, BioLegend Cat. No. 400150) and incubated for 30 minutes at 4° C. Cells were washed twice with FACS buffer, resuspended in 300 μL FACS buffer containing 0.06 μg DAPI (Santa Cruz Biotec, Cat. No. Sc-3598) and acquired using a 5-laser LSR-Fortessa (BD Bioscience, DIVA software). Limited dilutions were performed to generate single clones as following: Human-4-1BB transduced HeLa cells were resuspended in medium to a concentration of 10, 5 and 2.5 cells/mL and 200 μL, of cell suspensions were transferred to round bottom tissue-culture treated 96-well plates (6 plates/cell concentration, TPP Cat. No. 92697). Single clones were harvested, expanded and tested for 4-1BB expression as described above. The clone with the highest expression of 4-1BB (clone 5) was chosen for subsequent transfection with the NFκB-luciferase expression-vector 5495p Tranlucent HygB. The vector confers transfected cells both with resistance to hygromycin B and capacity to express luciferase under control of NFkB-response element (Panomics, Cat. No. LR0051). Human-4-1BB HeLa clone 5 cells were cultured to 70% confluence. 50 μg (40 μL) linearized (restriction enzymes AseI and SalI) 5495p Tranlucent HygB expression vector were added to a sterile 0.4 cm Gene Pulser/MicroPulser Cuvette (Biorad, Cat.-No, 165-2081). 2.5×$10^6$ human-4-1BB HeLa clone 5 cells in 400 μl supplement-free DMEM were added and mixed carefully with the plasmid solution. Transfection of cells was performed using a Gene Pulser Xcell total system (Biorad, Cat No. 165 2660) under the following settings: exponential pulse, capacitance 500 μF, voltage 160 V, resistance ∞. Immediately after the pulse transfected cells were transferred to a tissue culture flask 75 $cm^2$ (TPP, Cat. No. 90075) with 15 mL 37° C. warm DMEM-Medium (Gibco by Life Technologies Cat. No. 42430-025) supplied with 10% FBS and 1% GlutaMAX I (GIBCO by Life Technologies, Cat. No. 35050 038). Next day, culture medium containing 3 μg/mL Puromycin (InvivoGen, Cat No. ant pr) and 200 μg/mL Hygromycin B (Roche, Cat. No. 10843555001) was added. Surviving cells were expanded and limited dilution was performed as described above to generate single clones. Clones were tested for 4-1BB expression as described above and for NFκB-Luciferase activity as following: Clones were harvested in selection medium and counted using a Cell Counter Vi-cell xr 2.03 (Beckman Coulter, Cat. No. 731050). Cells were set to a cell density of 0.33×$10^6$ cells/mL and 150 μL of this cell suspension were transferred to each well of a sterile white 96-well flat bottom tissue culture plate with lid (greiner bio one, Cat. No. 655083) and as a control to normal 96 well flat bottom tissue culture plate (TPP Cat. No. 92096) to test survival and cell density the next day. Cells were incubated at 37° C. and 5% $CO_2$ overnight. The next day 50 μL of medium containing different concentrations of recombinant human tumor necrosis factor alpha (rhTNF α, PeproTech, Cat.-No. 300 01A) were added to each well of a 96-well plate resulting in final concentration of rhTNF α of 100, 50, 25, 12.5, 6.25 and 0 ng/well. Cells were incubated for 6 hours at 37° C. and 5% $CO_2$ and then washed three times with 200 μL/well DPBS. Reporter Lysis Buffer (Promega, Cat-No: E3971) was added to each well (30 μl) and the plates were stored over night at −20° C. The next day frozen cell plates and Detection Buffer (Luciferase 1000 Assay System, Promega, Cat. No. E4550) were thawed to room temperature. 100 uL of detection buffer were added to each well and the plate was measured as fast as possible using a SpectraMax M5/M5e microplate reader and the SoftMax Pro Software (Molecular Devices). Measured URLs above control (no rhTNF-α added) were taken as luciferase activity. The NFκB-luc-4-1BB-HeLa clone 26 was chosen for further use exhibiting the highest luciferase activity and a considerable level of 4-1BB-expression.

NF-κB Activation of HeLa Reporter Cells Expressing Human 4-1BB Co-Cultured with TnC-Expressing U87MG and SkK-Me15 Cells Adherent human glioblastoma cell line U87MG (ATCC HTB-14) were washed with DPBS (Gibco by Life Technologies, Cat. No. 14190 326) and treated with enzyme-free, PBS-based cell dissociation buffer (Gibco by Life Technologies, Cat.-No. 13151-014) for 10 minutes at 37° C. Afterwards cell were harvested and counted using Cell Counter Vi-cell xr 2.03. Cells were resuspended in DMEM medium (Gibco by Life Technologies Cat. No. 42430 025) supplied with 10% Fetal Calf Serum (FBS, US-origin, PAN biotech, P30-2009, Lot P150307GI, gamma irradiated *mycoplasma* free, heat inactivated 35 min 56° C.) and 1% GlutaMAX-I (GIBCO by Life Technologies, Cat. No. 35050 038) to 1×$10^6$ cells/mL and 100 μL were added/well of sterile white 96-well flat bottom tissue culture plates with lid (greiner bio one, Cat. No. 655083). For negative controls 100 μL medium were added. Plates were incubated overnight at 37° C. and 5% $CO_2$.

The next day different titrated split trimeric 4-1BB ligand containing fusion molecules and their controls were added. Afterwards NFκB-luc-4-1BB-HeLa clone 26 cells were washed with DPBS and treated with 0.05% Trypsin EDTA (Gibco by Life Technologies Cat. No. 25300 054) for 5 min at 37° C. Cells were harvested and resuspended in DMEM medium supplied with 10% Fetal Calf Serum and 1% GlutaMAX-I. Cells were counted using Cell Counter Vi-cell xr 2.03 (Beckman Coulter, Cat. No. 731050) and set to a cell density of $0.4\times10^6$ cells/mL. 50 μL ($2\times10^4$ cells) of this cell suspension were transferred to each well. Plates were incubated for 6 hours at 37° C. and 5% $CO_2$. White flat bottom 96-well plates were washed three times with 200 μL/well DPBS. 40 μl fresh prepared Reporter Lysis Buffer (Promega, Cat-No: E3971) were added to each well and the plate were stored over night at −20° C. The next day frozen plates and detection buffer (Luciferase 1000 Assay System, Promega, Cat. No. E4550) were thawed to room temperature. 100 uL of detection buffer were added to each well and plates were measured as fast as possible using the SpectraMax M5/M5e microplate reader and SoftMax Pro Software (Molecular Devices) with following settings: for luciferase (RLUs), 500 ms integration time, no filter, collecting all wave length and top reading.

TABLE 60

| EC50 values of NFκB-activation-induced Luciferase activity-curves | | |
|---|---|---|
| | construct 6.5 | construct 6.6 |
| U87MG EC50 [nM] | 0.33 | 0.70 |

D) Activation Assay of Human PBMCs in the Presence of TnC-Expressing Tumor Cells For TnC-binding-mediated crosslinking the TnC-expressing adherent human glioblastoma cell line U87MG (ATCC HTB-14) was used. U87MG cells were washed with DPBS (Gibco by Life Technologies, Cat. No. 14190 326) and treated with enzyme-free, PBS-based Cell Dissociation Buffer (Gibco by Life Technologies, Cat.-No. 13151-014) for 10 minutes at 37° C. Cells were harvested and resuspended in T cell medium consisting of RPMI 1640 (GIBCO by Life Technologies, Cat.-No. 42401-042) supplied with 10% fetal bovine serum (FBS, US-origin, PAN biotech, P30-2009, Lot P150307GI, gamma irradiated *mycoplasma* free, heat inactivated 35 min 56° C.), 1% L-GlutaMAX-I (GIBCO by Life Technologies, Cat-No. 35050-038), 1 mM Sodium-Pyruvat (SIGMA-Aldrich, Cat.-No. S8636), 1% MEM-Non essential Aminoacid Solution (SIGMA-Aldrich, Cat.-No. M7145), 50 μM β-Mercaptoethanol (Sigma-Aldrich, Cyt.-No. M3148) and irradiated with 50 Gy (X-Ray Irradiator RS 2000, Rad source). $2\times10^4$ U87MG cells in 50 μL T cell medium were seeded to each well of a round bottom tissue culture 96-well plate (TTP, Cat.-No. 92697). 50 μL, of T cell medium containing different titrated concentrations of construct 6.5 and 6.6 or the fitting controls (control F, control L and control E) were added. Human PBMCs were labeled in 37° C. warm DPBS containing 40 nM CFDA-SE (SIGMA-Aldrich, Cat.-No. 21888-25MG-F) for 15 min at 37° C. CFSE-labeling was stopped by adding FBS, PBMCs were washed twice and resuspended in T cell medium to a final concentration of $1.5\times10^6$ cells/mL. 50 μL of this PBMC cell solution were seeded to each well e.g. $7.5\times10^4$ CFSE-labeled PBMCs were added to each well. Finally a stock solution of T cell medium containing 8 nM agonistic anti-human CD3 human IgG1 clone V9 was prepared and 50 μL/well were added to each well giving a final concentration of 2 nM anti-human CD3 human IgG1 clone V9.

Plates were incubated for 4 days at 37° C. Cells were washed with DPBS and stained with 100 μL/well DPBS containing 1:1000 diluted LIVE/DEAD Fixable Aqua Dead Cell Stain Kit (Molecular Probes by Life Technology, Cat.-No. L34957) for 30 min at 4° C. Cells were washed once with 200 μL/well DPBS and stained with 50 μL FACS buffer (DPBS supplied with 2% FBS, 5 mM EDTA pH8 (Amresco, Cat. No. E177) and 7.5 mM Sodium azide (Sigma-Aldrich S2002)) containing 0.1 μg/mL PerCP-Cy5.5-conjugated anti-human CD137 mouse IgG1 κ (clone 4B4-1, BioLegend, Cat.-No. 309814), 0.1 μg/mL PE/Cy7-conjugated anti-human PD-1 mouse IgG1 κ (clone EH12.2H7, BioLegend, Cat.-No. 329918), 0.03 μg/mL APC-conjugated anti-human CD25 mouse IgG1 κ (clone BC96, BioLegend, Cat.-No. 302610), 0.06 μg/mL APC/Cy7-conjugated anti-human CD8 Mouse IgG1 κ (clone RPA-T8, BioLegend, Cat.-No. 3301016), BV421-conjugated anti-human CD4 Mouse IgG1 κ (clone RPA-T4, BioLegend, Cat.-No. 300532) for 30 min at 4° C. Cells were washed twice with 200 μL/well DPBS and incubated for 30 min at 4° C. with 50 μL/well freshly prepared FoxP3 Perm/Fix buffer (eBioscience Cat.-No. 00-5123). Cells were washed twice with 200 μL/well DPBS, resuspended in 50 μL/well freshly prepared Perm-buffer (eBioscience Cat.-No 00-8333) supplied with PE-conjugated 1:250 diluted anti-human Granzyme B mouse IgG1 κ (clone GB11, Lot 4269803, BD Pharmingen, Cat.-No. 561142) and incubated for 1 h at 4° C. Plates were washed twice with 200 μL/well DPBS and cells were fixed for 15 min with DPBS containing 1% Formaldehyde (Sigma, HT501320-9.5L). Cells were resuspended in 100 μL/well FACS-buffer and acquired using the MACS Quant Analyzer 10 (Miltenyi Biotech). Data was analyzed using FlowJo V10 (FlowJo, LLC) and GraphPad Prism 6.04 (GraphPad Software, Inc).

Figure 27B:
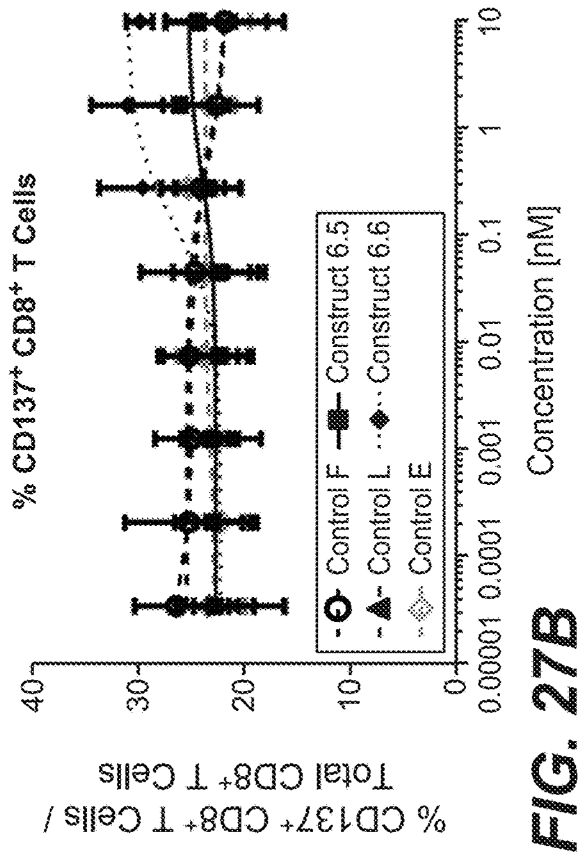
FIGS. 27A and 27B shows the human PBMC activation assay in the presence of TnC+U87MG, agonistic CD3 antibody and TnC-targeted split trimeric 4-1BBL fusion molecules.
Figure 27A:
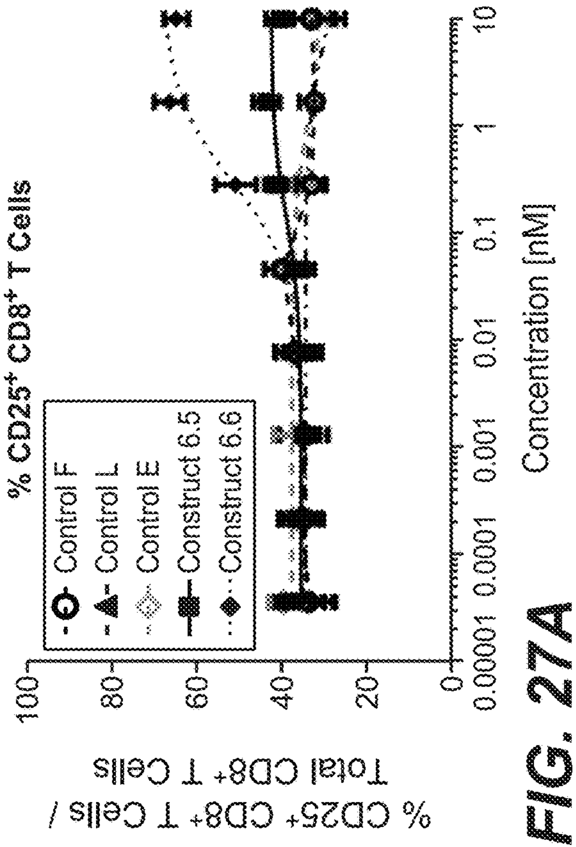

As shown in FIGS. 27A and 27B only the TnC-targeted split trimeric 4-1BBL fusion molecules construct 6.6 and to a less extent construct 6.5 induced a concentration-dependent increased surface expressed of CD25 and 4-1BB on CD8+ T cells. The negative control molecules (control F, control L and control E) did not induce this upregulation of activation markers. The correlating EC50 values are listed in Table 61.

TABLE 61

| EC50 values of upregulation of CD25 and 4-1BB (CD137) on activated CD8+ T cells | | |
|---|---|---|
| | Construct 6.5 | Construct 6.6 |
| % CD25+ CD8 EC50 [nM] | 0.13 | 0.29 |
| % CD137 (4-1BB)+ CD8 EC50 [nM] | 0.36 | 0.13 |

CITATIONS

Ascierto, P. A., E. Simeone, M. Sznol, Y. X. Fu, and I. Melero (2010), Clinical experiences with anti-CD137 and anti-PD1 therapeutic antibodies. Semin Oncol 37:508-516.

Aggarwal B. B. (2003), Signalling pathways of the TNF superfamily: a double-edged sword. Nat. Rev. Immunol. 3(9), 745-56.

Banner D. et al (1993), Crystal structure of the soluble human 55 kd TNF receptor-human TNF beta complex: implications for TNF receptor activation. Cell 73, 431-445.

Berg et al. (2007), Enforced covalent trimerization increases the activity of the TNF ligand family members TRAIL and CD95L. Cell Deatch and Differentiation 14(12), 2021-2034.
Bodmer J., Schneider P. and Tschopp, J. (2002), The molecular architecture of the TNF superfamily Trends in Biochemical Sciences 27(1), 19-26.
Broll, K., Richter, G., Pauly, S., Hofstaedter, F., and Schwarz, H. (2001). CD137 expression in tumor vessel walls. High correlation with malignant tumors. Am J Clin Pathol 115, 543-549.
Buechele, C., Baessler, T., Schmiedel, B. J., Schumacher, C. E., Grosse-Hovest, L., Rittig, K., and Salih, H. R. (2012). 4-1BB ligand modulates direct and Rituximab-induced NK-cell reactivity in chronic lymphocytic leukemia. Eur J Immunol 42, 737-748.
Choi, B. K., Kim, Y. H., Kwon, P. M., Lee, S. C., Kang, S. W., Kim, M. S., Lee, M. J., and Kwon, B. S. (2009). 4-1BB functions as a survival factor in dendritic cells. J Immunol 182, 4107-4115.
Cuadros, C., Dominguez, A. L., Lollini, P. L., Croft, M., Mittler, R. S., Borgstrom, P., and Lustgarten, J. (2005). Vaccination with dendritic cells pulsed with apoptotic tumors in combination with anti-OX40 and anti-4-1BB monoclonal antibodies induces T cell-mediated protective immunity in Her-2/neu transgenic mice. Int J Cancer 116, 934-943.
Curran, M. A., Kim, M., Montalvo, W., A1-Shamkhani, A., and Allison, J. P. (2011). Combination CTLA-4 blockade and 4-1BB activation enhances tumor rejection by increasing T-cell infiltration, proliferation, and cytokine production. PLoS One 6, e19499.
Diehl, L., van Mierlo, G. J., den Boer, A. T., van der Voort, E., Fransen, M., van Bostelen, L., Krimpenfort, P., Melief, C. J., Mittler, R., Toes, R. E., and Offringa, R. (2002). In vivo triggering through 4-1BB enables Th-independent priming of CTL in the presence of an intact CD28 costimulatory pathway. J Immunol 168, 3755-3762.
Dubrot, J., Milheiro, F., Alfaro, C., Palazon, A., Martinez-Forero, I., Perez-Gracia, J. L., Morales-Kastresana, A., Romero-Trevejo, J. L., Ochoa, M. C., Hervas-Stubbs, S., et al. (2010). Treatment with anti-CD137 mAbs causes intense accumulations of liver T cells without selective antitumor immunotherapeutic effects in this organ. Cancer Immunol Immunother 59, 1223-1233.
Futagawa, T., Akiba, H., Kodama, T., Takeda, K., Hosoda, Y., Yagita, H., and Okumura, K. (2002). Expression and function of 4-1BB and 4-1BB ligand on murine dendritic cells. Int Immunol 14, 275-286.
Guo, Z., Cheng, D., Xia, Z., Luan, M., Wu, L., Wang, G., and Zhang, S. (2013). Combined TIM-3 blockade and CD137 activation affords the long-term protection in a murine model of ovarian cancer. J Transl Med 11, 215.
Heinisch, I. V., Daigle, I., Knopfli, B., and Simon, H. U. (2000). CD137 activation abrogates granulocyte-macrophage colony-stimulating factor-mediated anti-apoptosis in neutrophils. Eur J Immunol 30, 3441-3446.
Hornig, N., Kermer, V., Frey, K., Diebolder, P., Kontermann, R. E., Mueller, D. (2012), Combination of a bispecific antibody and costimulatory antibody-ligand fusion proteins for targeted cancer immunotherapy. J. Immunother. 35, 418-429.
Ju, S. A., Cheon, S. H., Park, S. M., Tam, N. Q., Kim, Y. M., An, W. G., and Kim, B. S. (2008). Eradication of established renal cell carcinoma by a combination of 5-fluorouracil and anti-4-1BB monoclonal antibody in mice. Int J Cancer 122, 2784-2790.
Kienzle, G., and von Kempis, J. (2000). CD137 (ILA/4-1BB), expressed by primary human monocytes, induces monocyte activation and apoptosis of B lymphocytes. Int Immunol 12, 73-82.
Kim, D. H., Chang, W. S., Lee, Y. S., Lee, K. A., Kim, Y. K., Kwon, B. S., and Kang, C. Y. (2008). 4-1BB engagement costimulates NKT cell activation and exacerbates NKT cell ligand-induced airway hyperresponsiveness and inflammation. J Immunol 180, 2062-2068.
Kim, Y. H., Choi, B. K., Oh, H. S., Kang, W. J., Mittler, R. S., and Kwon, B. S. (2009). Mechanisms involved in synergistic anticancer effects of anti-4-1BB and cyclophosphamide therapy. Mol Cancer Ther 8, 469-478.
Kwon, B. S., and Weissman, S. M. (1989). cDNA sequences of two inducible T-cell genes. Proc Natl Acad Sci USA 86, 1963-1967.
Lee, H., Park, H. J., Sohn, H. J., Kim, J M, and Kim, S. J. (2011). Combinatorial therapy for liver metastatic colon cancer: dendritic cell vaccine and low-dose agonistic anti-4-1BB antibody co-stimulatory signal. J Surg Res 169, e43-50.
Levitsky, V., de Campos-Lima, P. O., Frisan, T., and Masucci, M. G. (1998). The clonal composition of a peptide-specific oligoclonal CTL repertoire selected in response to persistent EBV infection is stable over time. J Immunol 161, 594-601.
Li, F., and Ravetch, J. V. (2011). Inhibitory Fcgamma receptor engagement drives adjuvant and anti-tumor activities of agonistic CD40 antibodies. Science 333, 1030-1034.
Lin, W., Voskens, C. J., Zhang, X., Schindler, D. G., Wood, A., Burch, E., Wei, Y., Chen, L., Tian, G., Tamada, K., et al. (2008). Fc-dependent expression of CD137 on human NK cells: insights into "agonistic" effects of anti-CD137 monoclonal antibodies. Blood 112, 699-707.
Melero, I., Johnston, J. V., Shufford, W. W., Mittler, R. S., and Chen, L. (1998). NK1.1 cells express 4-1BB (CDw137) costimulatory molecule and are required for tumor immunity elicited by anti-4-1BB monoclonal antibodies. Cell Immunol 190, 167-172.
Melero, I., Shuford, W. W., Newby, S. A., Aruffo, A., Ledbetter, J. A., Hellstrom, K. E., Mittler, R. S., and Chen, L. (1997). Monoclonal antibodies against the 4-1BB T-cell activation molecule eradicate established tumors. Nat Med 3, 682-685.
Merchant, A. M., Zhu, Z., Yuan, J. Q., Goddard, A., Adams, C. W., Presta, L. G., and Carter, P. (1998). An efficient route to human bispecific IgG. Nat Biotechnol 16, 677-681.
Morales-Kastresana, A., Sanmamed, M. F., Rodriguez, I., Palazon, A., Martinez-Forero, I., Labiano, S., Hervas-Stubbs, S., Sangro, B., Ochoa, C., Rouzaut, A., et al. (2013). Combined immunostimulatory monoclonal antibodies extend survival in an aggressive transgenic hepatocellular carcinoma mouse model. Clin Cancer Res 19, 6151-6162.
Mueller, D., Frey, K., Kontermann, R. E. (2008), A novel antibody-4-1BB1 fusion protein for targeted costimulation in cancer immunotherapy, J. Immunother. 31, 714-722.
Murillo, O., Dubrot, J., Palazon, A., Arina, A., Azpilikueta, A., Alfaro, C., Solano, S., Ochoa, M. C., Berasain, C., Gabari, I., et al. (2009). In vivo depletion of DC impairs the anti-tumor effect of agonistic anti-CD137 mAb. Eur J Immunol 39, 2424-2436.
Narazaki, H., Zhu, Y., Luo, L., Zhu, G., and Chen, L. (2010). CD137 agonist antibody prevents cancer recurrence: contribution of CD137 on both hematopoietic and nonhematopoietic cells. Blood 115, 1941-1948.

Nishimoto, H., Lee, S. W., Hong, H., Potter, K. G., Maeda-Yamamoto, M., Kinoshita, T., Kawakami, Y., Mittler, R. S., Kwon, B. S., Ware, C. F., et al. (2005). Costimulation of mast cells by 4-1BB, a member of the tumor necrosis factor receptor superfamily, with the high-affinity IgE receptor. Blood 106, 4241-4248.

Olofsson, P. S., Soderstrom, L. A., Wagsater, D., Sheikine, Y., Ocaya, P., Lang, F., Rabu, C., Chen, L., Rudling, M., Aukrust, P., et al. (2008). CD137 is expressed in human atherosclerosis and promotes development of plaque inflammation in hypercholesterolemic mice. Circulation 117, 1292-1301.

Palazon, A., Teijeira, A., Martinez-Forero, I., Hervas-Stubbs, S., Roncal, C., Penuelas, I., Dubrot, J., Morales-Kastresana, A., Perez-Gracia, J. L., Ochoa, M. C., et al. (2011). Agonist anti-CD137 mAb act on tumor endothelial cells to enhance recruitment of activated T lymphocytes. Cancer Res 71, 801-811.

Schwarz, H., Valbracht, J., Tuckwell, J., von Kempis, J., and Lotz, M. (1995). ILA, the human 4-1BB homologue, is inducible in lymphoid and other cell lineages. Blood 85, 1043-1052.

Shao, Z., and Schwarz, H. (2011). CD137 ligand, a member of the tumor necrosis factor family, regulates immune responses via reverse signal transduction. J Leukoc Biol 89, 21-29.

Shi, W., and Siemann, D. W. (2006). Augmented antitumor effects of radiation therapy by 4-1BB antibody (BMS-469492) treatment. Anticancer Res 26, 3445-3453.

Simeone, E., and Ascierto, P. A. (2012) Immunomodulating antibodies in the treatment of metastatic melanoma: the experience with anti-CTLA-4, anti-CD137, and anti-PD1. J Immunotoxicol 9, 241-247.

Snell, L. M., Lin, G. H., McPherson, A. J., Moraes, T. J., and Watts, T. H. (2011). T-cell intrinsic effects of GITR and 4-1BB during viral infection and cancer immunotherapy Immunol Rev 244, 197-217.

Stagg, J., Loi, S., Divisekera, U., Ngiow, S. F., Duret, H., Yagita, H., Teng, M. W., and Smyth, M. J. (2011). Anti-ErbB-2 mAb therapy requires type I and II interferons and synergizes with anti-PD-1 or anti-CD137 mAb therapy. Proc Natl Acad Sci USA 108, 7142-7147.

Teng, M. W., Sharkey, J., McLaughlin, N. M., Exley, M. A., and Smyth, M. J. (2009). CD1d-based combination therapy eradicates established tumors in mice. J Immunol 183, 1911-1920.

von Kempis, J., Schwarz, H., and Lotz, M. (1997). Differentiation-dependent and stimulus-specific expression of ILA, the human 4-1BB-homologue, in cells of mesenchymal origin. Osteoarthritis Cartilage 5, 394-406.

Wei, H., Zhao, L., Li, W., Fan, K., Qian, W., Hou, S., Wang, H., Dai, M., Hellstrom, I., Hellstrom, K. E., and Guo, Y. (2013). Combinatorial PD-1 blockade and CD137 activation has therapeutic efficacy in murine cancer models and synergizes with cisplatin. PLoS One 8, e84927.

Wilcox, R. A., Chapoval, A. I., Gorski, K. S., Otsuji, M., Shin, T., Flies, D. B., Tamada, K., Mittler, R. S., Tsuchiya, H., Pardoll, D. M., and Chen, L. (2002). Cutting edge: Expression of functional CD137 receptor by dendritic cells. J Immunol 168, 4262-4267.

Wilcox, R. A., Tamada, K., Flies, D. B., Zhu, G., Chapoval, A. I., Blazar, B. R., Kast, W. M., and Chen, L. (2004). Ligation of CD137 receptor prevents and reverses established anergy of CD8+ cytolytic T lymphocytes in vivo. Blood 103, 177-184.

Wyzgol. A., Müller. N., Fick, A., Munkel, S., Grigoleit, G. U., Pfizenmaier, K. and Wajant, H. (2009). Trimer Stabilization, Oligomerization, and Antibody-Mediated Cell Surface Immobilization Improve the Activity of Soluble Trimers of CD27L, CD40L, 41BBL, and Glucocorticoid-Induced TNF Receptor Ligand J Immunol 183, 1851-1861

Zhang, N., Sadun, R. E., Arias, R. S., Flanagan, M. L., Sachsman, S. M., Nien, Y, Khawli, L. A., Hu, P., Epstein, A. L. (2007). Targeted and untargeted CD137L fusion proteins for the immunotherapy of experimental solid tumors. Clin. Cancer Res. 13, 2758-2767.

Zhang, X., Voskens, C. J., Sallin, M., Maniar, A., Montes, C. L., Zhang, Y., Lin, W., Li, G., Burch, E., Tan, M., et al. (2010). CD137 promotes proliferation and survival of human B cells. J Immunol 184, 787-795.

The invention claimed is:

1. A TNF (tumor necrosis factor) family ligand trimer-containing antigen binding molecule comprising (a) at least one antigen binding moiety capable of specific binding to Tenascin-C(TnC) and (b) a first and a second polypeptide that are linked to each other by a disulfide bond, wherein the antigen binding molecule is characterized in that the first polypeptide comprises two ectodomains of a TNF ligand family member or a fragment thereof that are connected to each other by a peptide linker and in that the second polypeptide comprises only one ectodomain of said TNF ligand family member or a fragment thereof.

2. The TNF family ligand trimer-containing antigen binding molecule of claim 1, further comprising (c) an Fc domain composed of a first and a second subunit capable of stable association.

3. The TNF family ligand trimer-containing antigen binding molecule of claim 1, wherein the antigen binding molecule is further characterized in that (i) the first polypeptide contains a CH1 or CL domain and the second polypeptide contains a CL or CH1 domain, respectively, wherein the second polypeptide is linked to the first polypeptide by a disulfide bond between the CH1 and CL domain, or (ii) the first polypeptide contains a CH3 domain and the second polypeptide contains a CH3 domain, respectively, or (iii) the first polypeptide contains a VH-CL or a VL-CH1 domain and the second polypeptide contains a VL-CH1 domain or a VH-CL domain, respectively, wherein the second polypeptide is linked to the first polypeptide by a disulfide bond between the CH1 and CL domain.

4. The TNF family ligand trimer-containing antigen binding molecule of claim 1, wherein the TNF ligand family member costimulates human T-cell activation.

5. The TNF family ligand trimer-containing antigen binding molecule of claim 1, wherein the TNF ligand family member is selected from 4-1BBL and OX40L.

6. The TNF family ligand trimer-containing antigen binding molecule of claim 1, wherein the TNF ligand family member is 4-1BBL.

7. The TNF family ligand trimer-containing antigen binding molecule of claim 1, wherein the moiety capable of specific binding to TnC is selected from the group consisting of an antibody fragment, a Fab molecule, a crossover Fab molecule, a single chain Fab molecule, a Fv molecule, a scFv molecule, a single domain antibody, an aVH and a scaffold antigen binding protein.

8. The TNF family ligand trimer-containing antigen binding molecule of claim 1, wherein the molecule comprises one or two moieties capable of specific binding to TnC.

9. The TNF family ligand trimer-containing antigen binding molecule of claim 1, wherein the antigen binding moiety capable of specific binding to TnC is a Fab molecule capable of specific binding to TnC.

10. The TNF family ligand trimer-containing antigen binding molecule of claim 1, wherein the antigen binding moiety capable of specific binding to TnC comprises a VH domain comprising (i) CDR-H1 comprising the amino acid sequence of SEQ ID NO: 67, (ii) CDR-H2 comprising the amino acid sequence of SEQ ID NO: 68, and (iii) CDR-H3 comprising the amino acid sequence of SEQ ID NO: 69, and a VL domain comprising (iv) CDR-L1 comprising the amino acid sequence of SEQ ID NO: 55, (v) CDR-L2 comprising the amino acid sequence of SEQ ID NO: 56, and (vi) CDR-L3 comprising the amino acid sequence of SEQ ID NO: 57.

11. The TNF family ligand trimer-containing antigen binding molecule of claim 1, wherein the antigen binding moiety capable of specific binding to TnC comprises a VH domain comprising (i) CDR-H1 comprising the amino acid sequence of SEQ ID NO: 70, (ii) CDR-H2 comprising the amino acid sequence of SEQ ID NO: 71, and (iii) CDR-H3 comprising the amino acid sequence of SEQ ID NO: 72, and a VL domain comprising (iv) CDR-L1 comprising the amino acid sequence of SEQ ID NO: 58, (v) CDR-L2 comprising the amino acid sequence of SEQ ID NO: 59, and (vi) CDR-L3 comprising the amino acid sequence of SEQ ID NO: 60.

12. The TNF family ligand trimer-containing antigen binding molecule of claim 2, wherein the Fc domain is an IgG1 Fc domain comprising the amino acid substitutions at positions 234 and 235 (EU numbering) and/or 329 (EU numbering).

13. The TNF family ligand trimer-containing antigen binding molecule of claim 1, wherein the antigen binding molecule comprises a first heavy chain and a first light chain, both comprising a Fab molecule capable of specific binding to TnC, a first peptide comprising two ectodomains of a TNF ligand family member or fragments thereof connected to each other by a first peptide linker fused at its C-terminus by a second peptide linker to a second heavy or light chain, and a second peptide comprising one ectodomain of said TNF ligand family member fused at its C-terminus by a third peptide linker to a second light or heavy chain, respectively.

14. The TNF family ligand trimer-containing antigen binding molecule of claim 1, wherein the first peptide comprising two ectodomains of a TNF ligand family member or fragments thereof connected to each other by a first peptide linker is fused at its C-terminus by a second peptide linker to a CH1 domain that is part of a heavy chain, and the second peptide comprising one ectodomain of said TNF ligand family member or a fragment thereof is fused at its C-terminus by a third peptide linker to a CL domain that is part of a light chain.

15. The TNF family ligand trimer-containing antigen binding molecule of claim 1, wherein the first peptide comprising two ectodomains of a TNF ligand family member or fragments thereof connected to each other by a first peptide linker is fused at its C-terminus by a second peptide linker to a CL domain that is part of a heavy chain, and the second peptide comprising one ectodomain of said TNF ligand family member or a fragment thereof is fused at its C-terminus by a third peptide linker to a CH1 domain that is part of a light chain.

16. The TNF family ligand trimer-containing antigen binding molecule of claim 1, wherein the first peptide comprising two ectodomains of a TNF ligand family member or fragments thereof connected to each other by a first peptide linker is fused at its C-terminus by a second peptide linker to a VH domain that is part of a heavy chain, and the second peptide comprising one ectodomain of said TNF ligand family member or a fragment thereof is fused at its C-terminus by a third peptide linker to a VL domain that is part of a light chain.

17. The TNF family ligand trimer-containing antigen binding molecule of claim 1, wherein the antigen binding moiety binds to human TnC, and cross-reacts to mouse and cynomolgus TnC.

18. The TNF family ligand trimer-containing antigen binding molecule of claim 1, wherein the antigen binding moiety binds to at least one of human, mouse and cynomolgus TnC with a $K_D$ range of about 1 μM to about 0.001 nM.

19. The TNF family ligand trimer-containing antigen binding molecule of claim 17, wherein the antigen binding moiety binds to human TnC with a $K_D$ range of about 1 μM to about 0.001 nM, and cross-reacts to mouse and cynomolgus TnC with a binding affinity within the $K_D$ range of a factor of 20 relative to the $K_D$ for binding human TnC.

20. The TNF family ligand trimer-containing antigen binding molecule of claim 1, for use as a medicament.

21. The TNF family ligand trimer-containing antigen binding molecule of claim 1, for use in the treatment of cancer.

22. The TNF family ligand trimer-containing antigen binding molecule of claim 1, wherein the antigen binding moiety binds to human TnC with a $K_D$ range of about 1 μM to about 0.001 nM, and cross-reacts to mouse and cynomolgus TnC with a binding affinity within the $K_D$ range of a factor of 20 relative to the $K_D$ for binding human TnC.

23. A pharmaceutical composition comprising the TNF family ligand trimer-containing antigen binding molecule of and at least one pharmaceutically acceptable excipient wherein the TNF family ligand trimer-containing antigen binding molecule comprises:

(a) at least one antigen binding moiety capable of specific binding to Tenascin-C(TnC) and (b) a first and a second polypeptide that are linked to each other by a disulfide bond, wherein the antigen binding molecule is characterized in that the first polypeptide comprises two ectodomains of a TNF ligand family member or a fragment thereof that are connected to each other by a peptide linker and in that the second polypeptide comprises only one ectodomain of said TNF ligand family member or a fragment thereof.

24. The TNF family ligand trimer-containing antigen binding molecule of the pharmaceutical composition of claim 23, for use as a medicament.

25. The pharmaceutical composition of claim 23 for use in the treatment of cancer.

* * * * *